US009187544B2

(12) United States Patent
Popel et al.

(10) Patent No.: US 9,187,544 B2

(45) Date of Patent: Nov. 17, 2015

(54) PEPTIDE MODULATORS OF ANGIOGENESIS AND USE THEREOF

(71) Applicant: The Johns Hopkins University, Baltimore, MD (US)

(72) Inventors: Aleksander S. Popel, Lutherville, MD (US); Emmanouil D. Karagiannis, Cambridge, MA (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 13/962,383

(22) Filed: Aug. 8, 2013

(65) Prior Publication Data

US 2014/0100164 A1 Apr. 10, 2014

Related U.S. Application Data

(62) Division of application No. 12/522,042, filed as application No. PCT/US2008/000036 on Jan. 3, 2008, now Pat. No. 8,507,434.

(60) Provisional application No. 60/878,579, filed on Jan. 3, 2007.

(51) Int. Cl.

| | |
|---|---|
| ***A61K 38/00*** | (2006.01) |
| ***A61K 38/10*** | (2006.01) |
| ***C07K 7/00*** | (2006.01) |
| ***C07K 7/08*** | (2006.01) |
| ***C07K 14/575*** | (2006.01) |
| ***C07K 14/00*** | (2006.01) |

(52) U.S. Cl.

CPC ........... *C07K 14/57518* (2013.01); *C07K 14/00* (2013.01); *A61K 38/00* (2013.01)

(58) Field of Classification Search

CPC ......... A61K 38/00; A61K 38/10; C07K 7/00; C07K 7/08

USPC ........................ 514/13.3, 19.3, 21.5; 530/327

See application file for complete search history.

(56) References Cited

U.S. PATENT DOCUMENTS

| | | | | |
|---|---|---|---|---|
| 4,966,848 | A * | 10/1990 | Smith et al. | 435/193 |
| 5,223,421 | A * | 6/1993 | Smith et al. | 435/193 |
| 5,837,218 | A * | 11/1998 | Peers et al. | 424/1.69 |
| 5,889,148 | A | 3/1999 | Lee et al. | |
| 6,559,160 | B1 | 5/2003 | Schall et al. | |
| 6,833,248 | B2 | 12/2004 | Kletzien et al. | |
| 2002/0169127 | A1 | 11/2002 | Charmley et al. | |
| 2003/0100510 | A1 | 5/2003 | Hudson et al. | |
| 2004/0047861 | A1 | 3/2004 | Kehrel et al. | |
| 2005/0026169 | A1* | 2/2005 | Cargill et al. | 435/6 |
| 2005/0118586 | A1* | 6/2005 | Bejanin et al. | 435/6 |
| 2006/0018418 | A1 | 1/2006 | Ichiyama et al. | |
| 2006/0241067 | A1 | 10/2006 | Varner et al. | |
| 2012/0114759 | A1* | 5/2012 | Green et al. | 424/491 |

FOREIGN PATENT DOCUMENTS

WO 2006/018418 2/2006

OTHER PUBLICATIONS

Seq ID No. 956 from US 2005/0026169, 2005.*

Water is naturally occurring from www.biology-online.org/dictionary/Water, pp. 1-3. Accessed Apr. 24, 2014.*

Lee, et al., "Inhibition of Lymphangiogenesis and Angiogenesis in Breast Tumor Xenografts and Lymph Nodes by a Peptide Derived from Transmembrane Protein 45A1,2.", Neoplasia (2012) vol. 15, No. 2, 112-124.

Lee, et al., "Small Peptides Derived form Somatotropin Domain-Containing Proteins Inhibit Blood and Lymphatic Endothelial Cell Proliferation, Migration, Adhesion and Tube Formation", The International Journal of Biochemistry & Cell Biology, 43 (2011) 1812-1821.

* cited by examiner

*Primary Examiner* — Julie Ha

(74) *Attorney, Agent, or Firm* — Mintz Levin Cohn Ferris Glovsky and Popeo, P.C.; Peter F. Corless; Richard B. Emmons

(57) ABSTRACT

Compositions and methods that are useful for modulating blood vessel formation, as well as methods that provide for the systematic and efficient identification of angiogenesis modulators, are described. As described in more detail below, a systematic computational methodology based on bioinformatics was used to identify novel peptide modulators of angiogenesis that have been characterized in vitro and/or in vivo.

7 Claims, 22 Drawing Sheets

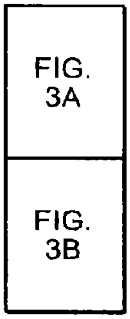

| | |
|---|---|
| *ADAMTS-01/1-20* | G P W G D C S R T C G G G V Q Y T M R - |
| *ADAMTS-02/1-18* | G P W S Q C S V T C G N G T Q E R - - - |
| *ADAMTS-03/1-18* | G P W S E C S V T C G E G T E V R - - - |
| *ADAMTS-04(a)/1-15* | G P W G D C S R T C G G G V - - - - - - |
| *ADAMTS-04(b)/1-20* | G P W G D C S R T C G G G V Q F S S R - |
| *ADAMTS-05/1-18* | G P W L A C S R T C D T G W H T R - - - |
| *ADAMTS-06(a)/1-15* | Q P W S E C S A T C A G G V - - - - - - |
| *ADAMTS-06(b)/1-18* | Q P W S E C S A T C A G G V Q R Q - - - |
| *ADAMTS-07(a)/1-18* | G P W G Q C S G P C G G G V Q R R - - - |
| *ADAMTS-07(b)1-15* | G P W T K C T V T C G R G V - - - - - - |
| *ADAMTS-08(a)1-15* | G P W G E C S R T C G G G V - - - - - - |
| *ADAMTS-08(b)1-20* | G P W G E C S R T C G G G V Q F S H R - |
| *ADAMTS-09(a)1-16* | - - W S S C S V T C G Q G R A T R - - - |
| *ADAMTS-09(b)1-18* | G P W G A C S S T C A G G S Q R R - - - |
| *ADAMTS-10/1-20* | T P W G D C S R T C G G G V S S S S R - |
| *ADAMTS-12(a)/1-16* | - - W D L C S T S C G G G F Q K R - - - |
| *ADAMTS-12(b)/1-15* | S P W S H C S R T C G A G V - - - - - - |
| *ADAMTS-13/1-16* | - - W M E C S V S C G D G I Q R R - - - |
| *ADAMTS-14/1-16* | - - W S Q C S A T C G E G I Q Q R - - - |
| *ADAMTS-15/1-18* | S A W S P C S K S C G R G F Q R R - - - |
| *ADAMTS-16(a)/1-18* | S P W S Q C T A S C G G G V Q T R - - - |
| *ADAMTS-16(b)/1-19* | S P W S Q C T A S C G G G V Q T R S - - |
| *ADAMTS-18(a)/1-17* | - P W Q Q C T V T C G G G V Q T R - - - |
| *ADAMTS-18(b)/1-18* | - P W Q Q C T V T C G G G V Q T R S - - |

FIG. 3A

A less common motif within the sequences of collagen derived peptide fragments.

| | Collagen IV Derived Peptide | TSP1 Derived Peptide | CXC Derived Peptide |
|---|---|---|---|
| Human Sequence | LRRFSTMPFMFCNINNVCNF | GPWEPCSVTCSKGTRTRRR | NGRKACLNPASPIVKKIIEKMLNS |
| Mouse Sequence | LRRFSTMPFMFCNINNVCNF | GPWGPCSVTCSKGTQIRQR | NGREACLDPEAPLVQKIVQKMLKG |

*Modifications*

| | |
|---|---|
| Disulfide Bond Formation | **C** substituted by **Abu, S, A** |
| Pegylation | **M** substituted by **I**<br>**K** substituted by **R** |

FIG. 14

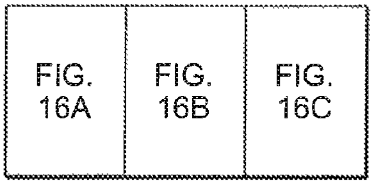
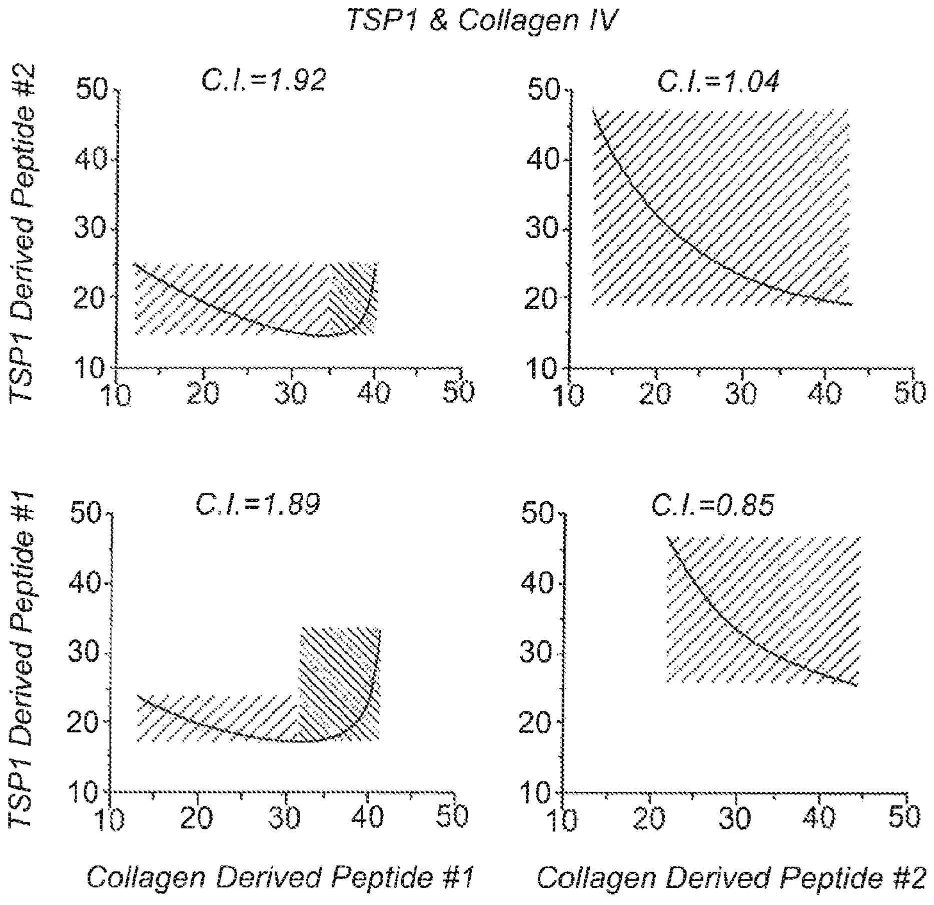
FIG. 16A

PEPTIDE MODULATORS OF ANGIOGENESIS AND USE THEREOF

CROSS-REFERENCE TO RELATED APPLICATION

This application is a divisional of U.S. application Ser. No. 12/522,042, filed Sep. 22, 2010 which is the U.S. national phase application, pursuant to 35 U.S.C. §371 of PCT International Application Ser. No. PCT/US2008/000036, filed Jan. 3, 2008, designating the United States and published in English, which claims priority to U.S. provisional patent application Ser. No. 60/878,579, filed on Jan. 3, 2007, the entire contents of the aforementioned patent applications are incorporated herein by this reference.

STATEMENT OF RIGHTS TO INVENTIONS MADE UNDER FEDERALLY SPONSORED RESEARCH

This work was supported by the following grant from the National Institutes of Health, Grant No.: HL079653 and CA103175. The government may have certain rights in the invention.

SEQUENCE LISTING

The instant application contains a Sequence Listing which has been submitted in ASCII format via EFS-Web and is hereby incorporated by reference in its entirety. Said ASCII copy, created on Aug. 8, 2013, is named 67101DIV_71699_ST25.txt and is 376,832 bytes in size.

BACKGROUND OF THE INVENTION

Angiogenesis, the process of developing a novel vascular network from a pre-existing one, is tightly controlled by various endogenous regulators. These regulatory elements include both pro- and anti-angiogenic proteins that finely modulate the neovascular morphological and functional characteristics. Where the regulation of such processes is disrupted a variety of pathological conditions can ensue, including neoplasia, hematologic malignancies, rheumatoid arthritis, diabetic retinopathy, age-related macular degeneration, atherosclerosis, endometriosis, pathologic obesity, and ischemic heart and limb disease. An urgent need exists for angiogenesis modulators that can be used as therapeutics for these and other numerous angiogenesis related diseases and conditions. While some promising angiogenesis modulators have been identified, to date, the quest for the experimental identification of such agents has been an empirical time-consuming process. Improved angiogenesis modulators and methods for systematically identifying and assessing the biological activity of such agents are urgently required.

SUMMARY OF THE INVENTION

As described below, the present invention generally features angiogenesis modulators, related prophylactic and therapeutic methods, as well as screening methods for the identification of such agents.

The invention generally provides peptides that reduce blood vessel formation in a cell, tissue, or organ. Accordingly, in one aspect the invention features an isolated peptide or analog thereof containing one of the following amino acid sequences:

| | | |
|---|---|---|
| TSP Motif: | W-X(2)-C-X(3)-C-X(2)-G | (SEQ ID NO: 2287) |
| CXC Motif: | G-X(3)-C-L | |
| Collagen Motif: | C-N-X(3)-V-C | (SEQ ID NO: 2288) |
| Collagen Motif: | P-F-X(2)-C | |
| Somatotropin Motif: | L-X(3)-L-L-X(3)-S-X-L | (SEQ ID NO: 2289) |
| Serpin Motif: | L-X(2)-E-E-X-P; | (SEQ ID NO: 2290) |

where X denotes a variable amino acid and the number in parentheses denotes the number of variable amino acids; W denotes tryptophan; C denotes cysteine, G denotes glycine, V denotes valine; L denotes leucine, P is proline, and where the peptide reduces blood vessel formation in a cell, tissue or organ. In one embodiment, the peptide contains an amino acid sequence shown in Table 1-6, 8 and 9. In yet another embodiment, the peptide further contains at least 5, 10, 15, or 20 amino acids flanking the naturally occurring sequence.

In another aspect, the invention features an isolated peptide or analog thereof having at least 85%, 90%, 95%, or 100% identity to an amino acid sequence shown in Table 1-10 or otherwise disclosed herein. In one embodiment, the peptide contains an amino acid sequence shown in Table 1-10. In another embodiment, the peptide consists essentially of an amino acid sequence shown in Table 1-10. In yet another embodiment, the peptide further contains at least 5, 10, 15, or 20 amino acids flanking the naturally occurring sequence.

In yet another aspect, the invention features an isolated peptide or analog thereof containing or consisting essentially of a sequence having at least 85% 90%, 95%, or 100% amino acid sequence identity to an amino acid sequence selected from the group consisting of:

| | | |
|---|---|---|
| Placental Lactogen | LLRISLLLIESWLE | (SEQ ID NO: 2291) |
| hGH-V | LLRISLLLTQSWLE | (SEQ ID NO: 2292) |
| GH2 | LLHISLLLIQSWLE | (SEQ ID NO: 2293) |
| Chorionic somatomammotropin | LLRLLLLIESWLE | (SEQ ID NO: 2294) |
| Chorionic somatomammotropin hormone-like 1 | LLHISLLLIESRLE | (SEQ ID NO: 2295) |
| Transmembrane protein 45A | LLRSSLILLQGSWF | (SEQ ID NO: 2296) |
| IL-17 receptor C | RLRLLTLQSWLL | (SEQ ID NO: 2297) |
| Neuropeptide FF receptor 2 | LLIVALLFILSWL | (SEQ ID NO: 2298) |
| Brush border myosin-I | LMRKSQILISSWF | (SEQ ID NO: 2299) |

where the peptide reduces blood vessel formation in a cell, tissue or organ.

In yet another aspect, the invention features an isolated peptide or analog thereof containing or consisting essentially of a sequence having at least 85%, 90%, 95%, or 100% amino acid sequence identity to an amino acid sequence selected from the group consisting of:

| | | |
|---|---|---|
| DEAH box polypeptide 8 | EIELVEEEPPF | (SEQ ID NO: 2300) (SEQ ID NO: 2301) |
| Caspase 10 | AEDLLSEEDPF | (SEQ ID NO: 2302) |
| CKIP-1 | TLDLIQEEDPS | (SEQ ID NO: 2303) |

where the peptide reduces blood vessel formation in a cell, tissue or organ.

In yet another aspect, the invention features an isolated peptide or analog thereof containing or consisting essentially of a sequence having at least 85% amino acid sequence identity to an amino acid sequence selected from the group consisting of:

| | | |
|---|---|---|
| Collagen type IV, alpha6 fibril | LPRFSTMPFIYCNINEVCHY | (SEQ ID NO: 2304) |

where the peptide reduces blood vessel formation in a cell, tissue or organ.

In another aspect, the invention features a pharmaceutical composition containing an effective amount of an isolated peptide containing an amino acid sequence shown in Table 1-10 or a peptide analog thereof in a pharmacologically acceptable excipient. In one embodiment, the composition contains at least one peptide that is a TSP, CXC, Collagen IV, Somatotropin, or Serpin derived peptide. In another embodiment, the composition contains at least two, three, four, or five peptides selected from the group consisting of TSP, CXC, Collagen IV, Somatotropin, and Serpin derived peptides. In one embodiment, the composition contains at least a CXC derived peptide and a TSP1 derived peptide. In another embodiment, the CXC derived peptide contains the amino acid sequence NGRKACLNPASPIVKKIIEKMLNS (SEQ ID NO: 2305). In yet another embodiment, the TSP1 repeat-containing protein contains the amino acid sequence GPWEPCSVTCSKGTRTRRR (SEQ ID NO: 2306).

In a related aspect, the invention features an isolated nucleic acid molecule encoding the peptide of any previous aspect.

In another related aspect, the invention features an expression vector containing the nucleic acid molecule of the previous aspect, where the nucleic acid molecule is positioned for expression. In one embodiment, the vector includes a promoter suitable for expressing the nucleic acid molecule in a mammalian cell.

In yet another related aspect, the invention features a host cell containing the peptide of any previous aspect or a nucleic acid molecule encoding the peptide. In one embodiment, the cell is a prokaryotic or eukaryotic cell (e.g., mammalian, human). In another embodiment, the cell is in vitro or in vivo.

In another aspect, the invention features a method of reducing blood vessel formation in a tissue or organ, the method involving contacting an endothelial cell, or a tissue or organ containing an endothelial cell with an effective amount of a peptide of any previous aspect, thereby reducing blood vessel formation in the tissue or organ.

In yet another aspect, the invention features a method of reducing endothelial cell proliferation, migration, survival, or stability in a tissue or organ, the method involving contacting tissue or organ containing an endothelial cell with an effective amount of a peptide of any previous aspect.

In still another aspect, the invention features a method of increasing endothelial cell death in a tissue or organ, the method involving contacting a tissue or organ containing an endothelial cell with an effective amount of a peptide of any o previous aspect, thereby increasing endothelial cell death in the tissue or organ.

In another aspect, the invention features a method of reducing blood vessel formation in a tissue or organ the method involving contacting the tissue, or organ with a vector encoding a peptide of any previous aspect; and expressing the peptide in a cell of the tissue or organ, thereby reducing blood vessel formation in the tissue or organ.

In another aspect, the invention features a method of modulating angiogenesis in a cell, tissue, or organ, the method involving contacting the cell, tissue, or organ with an effective amount of an agent that binds CD36, CD47 or CXCR3.

In another aspect, the invention features a method for treating a neoplasia in a subject in need thereof, the method involving administering an effective amount of a peptide of any previous aspect. In one embodiment, at least one peptide binds CD36, CD47 or CXCR3. In another embodiment, the method involves administering two peptides, one that binds CD36 or CD47 and one that binds CXCR3. In yet another embodiment, the method reduces angiogenesis in a neoplastic tissue. In yet another embodiment, the neoplasia is lung carcinoma.

In another aspect, the invention features a kit containing an effective amount of a peptide of any previous aspect, and directions for using the peptide to treat a disease characterized by undesirable or excess angiogenesis.

In various embodiments of any of the above aspects, the peptide contains a motif delineated herein or an amino acid sequence delineated herein. In various embodiments of the above aspects, the peptide contains an alteration in one amino acid relative to a reference sequence shown in Tables 1-10. In various embodiments of the above aspects, the peptide contains at least one modification (e.g., a sequence alteration or post-translational modification that increases protease resistance, biodistribution, or therapeutic efficacy). In various embodiments of the above aspects, the peptide is cyclized or pegylated. In other embodiments delineated herein, the sequence alteration replaces a cysteine with aminobutyric acid (Abu), serine or alanine, replaces methionine with isoleucine, or replaces lysine with arginine. In various embodiments of the above aspects, the peptide contains at least 10, 20, 30, 40, or 50 amino acids of a naturally occurring amino acid sequence described by an NCBI reference number listed in Table 1-10. In various embodiments of the above aspects, the tissue or organ is in vitro or in vivo. In other embodiments, the cell is a human cell, tissue, or organ. In yet other embodiments, the cell is a neoplastic cell (lung carcinoma cell). In another embodiment, the method treats a neoplasia (e.g., lung carcinoma). In another embodiment, the method treats corneal or choroidal neovascularization. In another embodiment, the number or volume of blood vessels in the tissue or organ (e.g., mammalian tissue or organ) are reduced by at least 10%, 25%, 30%, 50%, 75% or more relative to a control condition. In another embodiment, the peptide acts on an endothelial cell. In various embodiments of the above aspects, the method involves contacting the cell tissue or organ with two agents, one that binds CD36 or CD47 and one that binds CXCR3 (e.g., a CXC derived peptide or a TSP1 derived peptide). In another embodiment, the method involves administering at least two peptides, such as a CXC derived peptide and a TSP1 derived peptide; a peptide that binds CD36 or CD47 and a peptide that binds BetaI or BetaIII integrin; a TSP derived peptide and a collagen IV derived peptide. In various embodiments of the above aspects, the method involves administering a combination of two, three, four, or more peptides shown in Table 1-10.

Definitions

By "analog" is meant a chemical compounds having a structure that is different from the general structure of a reference agent, but that functions in a manner similar to the reference agent. For example, a peptide analog having a variation in sequence or having a modified amino acid.

By "thrombospondin (TSP) derived peptide" is meant a peptide comprising a TSP motif: W-X(2)-C-X(3)-C-X(2)-G (SEQ ID NO: 2287). Exemplary TSP derived peptides are shown in Tables 1 and 2. If desired, the peptide includes at least about 5, 10, 20, 30, 40, 50 or more amino acids that flank the carboxy or amino terminus of the motif in the naturally occurring amino acid sequence of the peptide. TSP1 derived peptides include, for example, those derived from proteins WISP-1 (SPWSPCSTSCGLGVSTRI (SEQ ID NO: 2307)), NOVH (TEWTACSKSCGMGFSTRV (SEQ ID NO: 2308)) and UNC5C (TEWSVCNSRCGRGYQKRTR (SEQ ID NO: 2309)).

By "CXC derived peptide" is meant a peptide comprising a CXC Motif: G-X(3)-C-L. Exemplary CXC derived peptides are shown in Table 3. If desired, the peptide includes at least about 5, 10, 20, 30, 40, 50 or more amino acids that flank the carboxy or amino terminus of the motif in the naturally occurring amino acid sequence. CXC derived peptides include, for example, those derived from proteins GRO-α/CXCL1 (NGRKACLNPASPIVKKIIEKMLNS (SEQ ID NO: 2305)), GRO-γ/MIP-2β/CXCL3 (NGKKACLNPASPMVQKIIEKIL (SEQ ID NO: 2310)), and ENA-78/CXCL5 (NGKEICLDPEAPFLKKVIQKILD (SEQ ID NO: 2311)).

By "Collagen IV derived peptide" is meant a peptide comprising a C-N-X(3)-V-C (SEQ ID NO: 2288) or P-F-X(2)-C collagen motif. Exemplary collagen IV derived peptides are shown in Table 5. If desired, the peptide includes at least about 5, 10, 20, 30, 40, 50 or more amino acids that flank the carboxy or amino terminus of the motif in the naturally occurring amino acid sequence. Type IV collagen derived peptides include, for example, LRRFSTMPFMFCNINNVCNF (SEQ ID NO: 2312) and FCNINNVCNFASRNDYSYWL (SEQ ID NO: 2313), and LPRFSTMPFIYCNINEVCHY (SEQ ID NO: 2304).

By "Somatotropin derived peptide" is meant a peptide comprising a Somatotropin Motif: L-X(3)-L-L-X(3)-S-X-L (SEQ ID NO: 2289). Exemplary somatotropin derived peptides are shown in Table 8. If desired, the peptide includes at least about 5, 10, 20, 30, 40, 50 or more amino acids that flank the carboxy or amino terminus of the motif in the naturally occurring amino acid sequence. Somatotropin derived peptides include, for example, those shown in FIG. 10A.

By "Serpin derived peptide" is meant a peptide comprising a Serpin Motif: L-X(2)-E-E-X-P. Exemplary serpin derived peptides are shown in Table 9. If desired, the peptide includes at least about 5, 10, 20, 30, 40, 50 or more amino acids that flank the carboxy or amino terminus of the motif in the naturally occurring amino acid sequence. Serpin derived peptides include, for example, those shown in FIG. 10B.

By "Beta 1 integrin" is meant a polypeptide that binds a collagen IV derived peptide or that has at least about 85% identity to NP_596867 or a fragment thereof.

By "Beta 3 integrin" is meant a polypeptide that binds a collagen IV derived peptide or that has at least about 85% identity to P05106 or a fragment thereof.

By "CD36" is meant a CD36 glycoprotein that binds to a thrombospondin-derived peptide or that has at least about 85% identity to NP_001001548 or a fragment thereof. CD36 is described, for example, by Oquendo et al., "CD36 directly mediates cytoadherence of *Plasmodium falciparum* parasitized erythrocytes," Cell 58: 95-101, 1989.

By "CD47" is meant a CD47 glycoprotein that binds to a thrombospondin-derived peptides or that has at least about 85% identity to NP_000315 or a fragment thereof. CD47 is described, for example, by Han et al., "CD47, a ligand for the macrophage fusion receptor, participates in macrophage multinucleation." J. Biol. Chem. 275: 37984-37992, 2000.

By "CXCR3" is meant a G protein coupled receptor or fragment thereof having at least about 85% identity to NP_001495. CXCR3 is described, for example, by Trentin et al., "The chemokine receptor CXCR3 is expressed on malignant B cells and mediates chemotaxis." J. Clin. Invest. 104: 115-121, 1999.

By "blood vessel formation" is meant the dynamic process that includes one or more steps of blood vessel development and/or maturation, such as angiogenesis, vasculogenesis, formation of an immature blood vessel network, blood vessel remodeling, blood vessel stabilization, blood vessel maturation, blood vessel differentiation, or establishment of a functional blood vessel network.

By "angiogenesis" is meant the growth of new blood vessels originating from existing blood vessels. Angiogenesis can be assayed by measuring the total length of blood vessel segments per unit area, the functional vascular density (total length of perfused blood vessel per unit area), or the vessel volume density (total of blood vessel volume per unit volume of tissue).

By "vasculogenesis" is meant the development of new blood vessels originating from stem cells, angioblasts, or other precursor cells.

By "blood vessel stability" is meant the maintenance of a blood vessel network.

By "alteration" is meant a change in the sequence or in a modification (e.g., a post-translational modification) of a gene or polypeptide relative to an endogeneous wild-type reference sequence.

By "ameliorate" is meant decrease, suppress, attenuate, diminish, arrest, or stabilize the development or progression of a disease.

By "antibody" is meant any immunoglobulin polypeptide, or fragment thereof, having immunogen binding ability.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

A "cancer" in an animal refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells.

By "disease" is meant any condition or disorder that damages or interferes with the normal function of a cell, tissue, or organ.

By "an effective amount" is meant the amount required to ameliorate the symptoms of a disease relative to an untreated patient. The effective amount of active compound(s) used to practice the present invention for therapeutic treatment of an angiogenesis-associated disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "isolated nucleic acid molecule" is meant a nucleic acid (e.g., a DNA) that is free of the genes, which, in the naturally occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule which is transcribed from a DNA molecule, as well as a recombinant DNA which is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

"By "neoplasia" is meant a disease that is caused by or results in inappropriately high levels of cell division, inappropriately low levels of apoptosis, or both. Solid tumors, hematological disorders, and cancers are examples of neoplasias.

By "operably linked" is meant that a first polynucleotide is positioned adjacent to a second polynucleotide that directs transcription of the first polynucleotide when appropriate molecules (e.g., transcriptional activator proteins) are bound to the second polynucleotide.

By "peptide" is meant any fragment of a polypeptide. Typically peptide lengths vary between 5 and 1000 amino acids (e.g., 5, 10, 15, 20, 25, 50, 100, 200, 250, 500, 750, and 1000).

By "polypeptide" is meant any chain of amino acids, regardless of length or post-translational modification.

By "promoter" is meant a polynucleotide sufficient to direct transcription.

By "reduce" is meant a decrease in a parameter (e.g., blood vessel formation) as detected by standard art known methods, such as those described herein. As used herein, reduce includes a 10% change, preferably a 25% change, more preferably a 40% change, and even more preferably a 50% or greater change.

By "reference" is meant a standard or control condition.

By "subject" is meant a mammal, including, but not limited to, a human or non-human mammal, such as a bovine, equine, canine, ovine, or feline.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and even more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

"Sequence identity" or "identity" in the context of two nucleic acid or polypeptide sequences includes reference to the residues in the two sequences which are the same when aligned for maximum correspondence over a specified comparison window, and can take into consideration additions, deletions and substitutions. When percentage of sequence identity is used in reference to proteins it is recognized that residue positions which are not identical often differ by conservative amino acid substitutions, where amino acid residues are substituted for other amino acid residues with similar chemical properties (for example, charge or hydrophobicity) and therefore do not deleteriously change the functional properties of the molecule. Where sequences differ in conservative substitutions, the percent sequence identity may be adjusted upwards to correct for the conservative nature of the substitution. Sequences which differ by such conservative substitutions are said to have sequence similarity. Approaches for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, for example, according to the algorithm of Meyers and Miller, *Computer*

*Applic. Biol. Sci.,* 4: 11-17, 1988, for example, as implemented in the program PC/GENE (Intelligenetics, Mountain View, Calif., USA).

"Percentage of sequence identity" means the value determined by comparing two optimally aligned sequences over a comparison window, wherein the portion of the polynucleotide sequence in the comparison window may comprise additions, substitutions, or deletions (i.e., gaps) as compared to the reference sequence (which does not comprise additions, substitutions, or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "homologous" in their various grammatical forms in the context of polynucleotides means that a polynucleotide comprises a sequence that has a desired identity, for example, at least 60% identity, preferably at least 70% sequence identity, more preferably at least 80%, still more preferably at least 90% and even more preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 85%, 90%, and even more preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, for example, when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid, although such cross-reactivity is not required for two polypeptides to be deemed substantially identical.

An "expression vector" is a nucleic acid construct, generated recombinantly or synthetically, bearing a series of specified nucleic acid elements that enable transcription of a particular gene in a host cell. Typically, gene expression is placed under the control of certain regulatory elements, including constitutive or inducible promoters, tissue-preferred regulatory elements, and enhancers.

A "recombinant host" may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

The term "operably linked" is used to describe the connection between regulatory elements and a gene or its coding region. That is, gene expression is typically placed under the control of certain regulatory elements, including constitutive or inducible promoters, tissue-specific regulatory elements, and enhancers. Such a gene or coding region is said to be "operably linked to" or "operatively linked to" or "operably associated with" the regulatory elements, meaning that the gene or coding region is controlled or influenced by the regulatory element.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 5, 10, or 15 amino acids, preferably at least about 20 amino acids, more preferably at least about 25 amino acids, and even more preferably about 35 amino acids, about 50 amino acids, about 100 amino acids, or about 150 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides about 300 nucleotides or about 450 nucleotides or any integer thereabout or therebetween.

Methods of alignment of sequences for comparison are well-known in the art. Optimal alignment of sequences for comparison may be conducted by the local homology algorithm of Smith and Waterman, *Adv. Appl. Math.,* 2: 482, 1981; by the homology alignment algorithm of Needleman and Wunsch, *J. Mol. Biol.,* 48: 443, 1970; by the search for similarity method of Pearson and Lipman, *Proc. Natl. Acad. Sci. USA,* 8: 2444, 1988; by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 7 Science Dr., Madison, Wis., USA; the CLUSTAL program is well described by Higgins and Sharp, *Gene,* 73: 237-244, 1988; Corpet, et al., *Nucleic Acids Research,* 16:881-90, 1988; Huang, et al., *Computer Applications in the Biosciences,* 8:1-6, 1992; and Pearson, et al., *Methods in Molecular Biology,* 24:7-331, 1994. The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York, 1995. New versions of the above programs or new programs altogether will undoubtedly become available in the future, and can be used with the present invention.

Unless otherwise stated, sequence identity/similarity values provided herein refer to the value obtained using the BLAST 2.0 suite of programs, or their successors, using default parameters (Altschul et al., *Nucleic Acids Res,* 2:3389-3402, 1997). It is to be understood that default settings of these parameters can be readily changed as needed in the future.

As those ordinary skilled in the art will understand, BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.,* 17:149-163, 1993) and XNU (Clayerie and States, *Comput. Chem.,* 17:191-1, 1993) low-complexity filters can be employed alone or in combination.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

A "tumor," as used herein, refers to all neoplastic cell growth and proliferation, whether malignant or benign, and all precancerous and cancerous cells and tissues.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

BRIEF DESCRIPTION OF THE DRAWINGS

FIG. 6B discloses SEQ ID NOS 2408-2409, 2312, 2410, 2418-2419 and 2415-2416, respectively, in order of appearance; & FIG. 6C discloses SEQ ID NOS 2313, 2313, 2408, 2410, 2418, 2412, 2419, 2414-2415 and 2320, respectively, in order of appearance). Novel motifs occur when the abundant 7-mer is shifted downstream (FIG. 6B) or upstream (FIG. 6C).

FIG. 14 shows exemplary amino acid sequence modifications (SEQ ID NOS 2442, 2444-2445 and 2439-2441, respectively, in order of appearance).

FIG. 15A shows the effect of β- and αvβ3 integrin-neutralizing antibodies on the activity of three collagen IV-derived peptides (red). The collagen derived peptides used in the experiment are derived from the alpha5 fibrils of type IV collagen (LRRFSTMPFMFCNINNVCNF (SEQ ID NO: 2312) and FCNINNVCNFASRNDYSYWL (SEQ ID NO: 2313)), and from alpha6 fibrils of type IV collagen (LPRFSTMPFIYCNINEVCHY (SEQ ID NO: 2304)). FIG. 15B shows the effect of two different concentrations of the CXCR3 receptor-neutralizing antibody on the activity of three CXC chemokine-derived peptides (green). The CXC derived peptides used in this experiment are derived from proteins GRO-α/CXCL1 (NGRKACLNPASPIVKKIIEKMLNS (SEQ ID NO: 2305)), GRO-γ/MIP-2β/CXCL3 (NGKKACLNPASPMVQKIIEKIL (SEQ ID NO: 2310)), and ENA-78/CXCL5 (NGKEICLDPEAPFLKKVIQKILD (SEQ ID NO: 2311)).

FIG. 15C shows the effect of CD36 and CD47 receptor-neutralizing antibodies on the activity of three thrombospondin-derived peptides (blue). The TSP1 repeat-containing protein derived peptides used in the experiment are derived from proteins WISP-1 (SPWSPCSTSCGLGVSTRI (SEQ ID NO: 2307)), NOVH (TEWTACSKSCGMGFSTRV (SEQ ID NO: 2308)) and UNC5C (TEWSVCNSRCGRGYQKRTR (SEQ ID NO: 2309)).

FIGS. 16A-C depict graphs showing the evaluation of peptide combinations from different protein families. Two peptides from each of three different protein families were combined serially in the proliferation assay, and the efficiency of the peptide combinations was evaluated after calculating the isobolograms and Combination Index for each of the combinations. FIG. 16A depicts data for TSP1 and Collagen IV. FIG. 16B depicts data for CXC and Collagen IV. FIG. 16C depicts data for TSP1 and CXC.

FIG. 18A shows the results of the administration of collagen IV, TSP1 and CXC derived peptides, as well as the combination of the TSP1 derived peptide and the CXC derived peptide. Each of the peptides was administered at 20 mg/kg/day i.p. (n=3 per condition). For the combination, the peptides were administered alternately every other day. PBS was administered as a positive control. FIG. 18B shows the effect of the administration of the collagen IV derived peptide on tumor volume. The peptide was administered in an i.p. injection at 10 mg/kg/day for 12 days. Control (n=6); peptide application (green, n=6; red, n=5). These results for n=5 do not include one animal in which the tumor started growing after day 9. FIG. 18C shows the tumor growth rate (% volume change per day) on day 14 after inoculation (day 0 at panel C). Once the tumors reached a volume of approximately 800 $mm^3$ treatment with a TSP1 derived and CXC derived peptides was started. The peptides were administered alternately every other day at a dose of 10 mg/kg. The tumor growth rate dropped to zero after 3 injections.

DETAILED DESCRIPTION OF THE INVENTION

Figure 1:
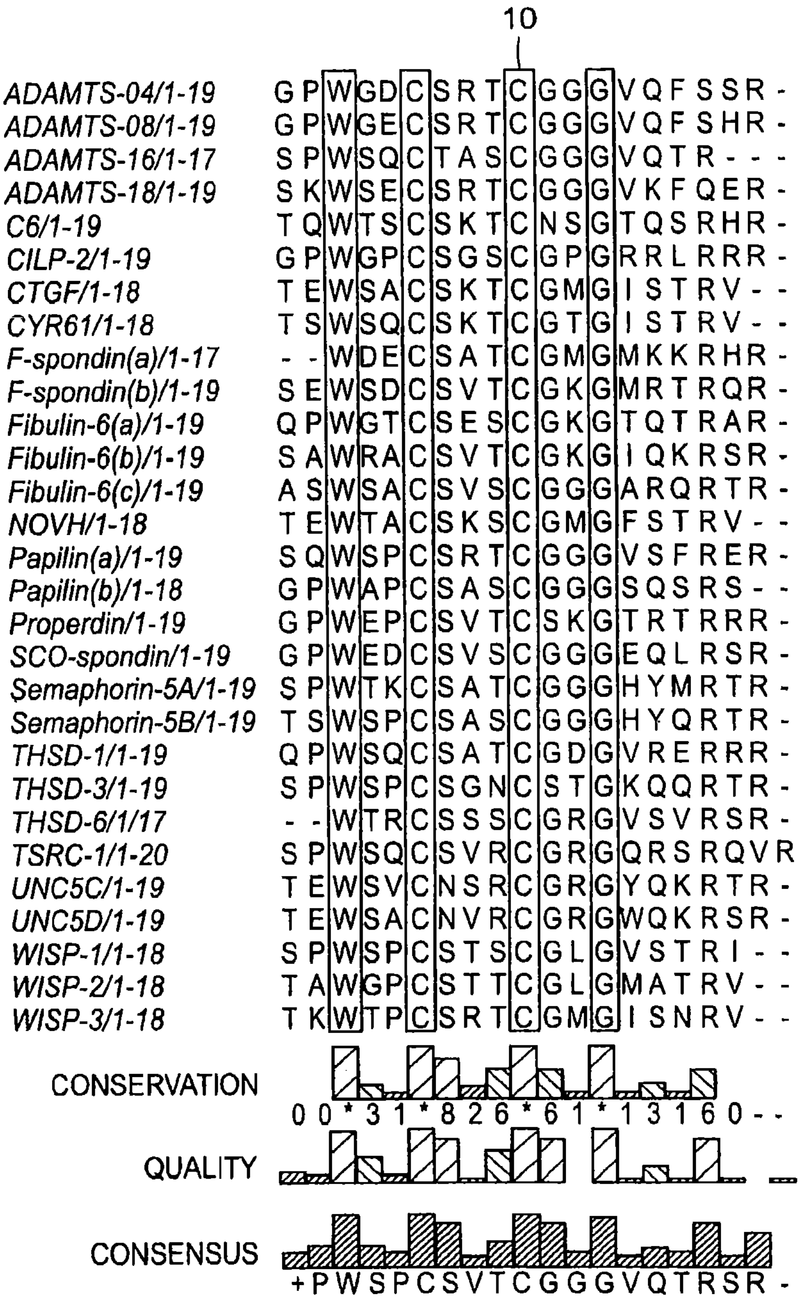
FIG. 1 shows a set of amino acid sequences that include a shaded 4-letter motif common in all the experimentally tested TSP-1 containing proteins (SEQ ID NOS 2324-2352, respectively, in order of appearance). At the bottom of the figure is the consensus sequence.

The invention features compositions and methods that are useful for modulating angiogenesis. The invention is based, at least in part, on the discovery of general peptide motifs that are associated with anti-angiogenic properties of peptides.

Angiogenesis

Angiogenesis, which involves the growth or sprouting of new microvessels from pre-existing vasculature, and vasculogenesis, which involves de novo vascular growth, is essential to many physiological and pathological conditions, including embryogenesis, cancer, rheumatoid arthritis, diabetic retinopathy, obesity, atherosclerosis, ischemic heart and limb disease, and wound healing. Over 70 diseases have been identified as angiogenesis dependent (Carmeliet, *Nature,* 438:932-6, 2005). Under physiological conditions, the growth of new microvessels is tightly regulated and orchestrated by maintaining a balance between endogenous pro- and anti-angiogenic factors. Tipping the balance of this regulation may lead to either excessive neovascularization, as in cancer, age-related macular degeneration, and rheumatoid arthritis, or insufficient vascularization, as in ischemic heart and limb disease, ischemic brain, and neural degeneration.

Angiogenesis is a complex multistep process that involves interactions between endothelial cells (EC), pericytes, vascular smooth muscle cells, and stromal cells (e.g., stem cells and parenchymal cells). These interactions occur through secreted factors, such as vascular endothelial growth factor (VEGF), platelet-derived growth factor (PDGF), basic fibroblast growth factor (bFGF or FGF-2) and angiopoietins, as well as through cell-cell and cell-extracellular matrix (ECM) interactions. Endothelial cell-ECM interactions regulate numerous processes that are critical for angiogenesis, including endothelial cell migration, proliferation, differentiation and apoptosis. Angiogenic processes include network stabilization and remodeling that may involve the recruitment of stromal cells, as well as the pruning of some vessels. In many cases, angiogenesis occurs as a response to hypoxia. A transcription factor called hypoxia-inducible factor, HIF1$\alpha$, has been demonstrated to act as an oxygen sensor whose activity leads to upregulation of VEGF in parenchymal and stromal cells (Semenza, *Physiology* (*Bethesda*), 19:176-82, 2004). VEGF is secreted as a homodimer in the form of several heparin-binding and non-heparin-binding splice-variant isoforms; it diffuses through the interstitial space and can bind to the endothelial cell receptors VEGFR1 and VEGFR2, as well as co-receptors such as Neuropilin-1, thus initiating a signal transduction cascade that leads to endothelial cell proliferation and migration. The production of endothelial cell matrix metalloproteinases, MMPs, increases as a result of endothelial cell activation; MMPs are necessary for selectively clipping the capillary basement membrane and the ECM, which constitute physical barriers to endothelial cell migration and capillary sprouting. MMPs and their associated molecules also play a crucial role in uncovering cryptic sites of the ECM proteins, a number of which have been identified as anti-angiogenic (Davis et al., *Anat Rec,* 268:252-75, 2002; Folkman, *Annu Rev Med,* 57:1-18, 2006; Rundhaug, *J Cell Mol Med,* 9:267-85, 2005; Schenk and Quaranta, *Trends Cell Biol,* 13:366-75, 2003), and in processing cell-surface receptors (Mott and Werb, *Curr Opin Cell Biol,* 16:558-64, 2004).

Diseases Associated with Undesirable Angiogenesis

Where the processes regulating angiogenesis are disrupted, pathology may result. Such pathology affects a wide variety of tissues and organ systems. Diseases characterized by excess or undesirable angiogenesis are susceptible to treatment with therapeutic agents described herein.

Excess angiogenesis in numerous organs is associated with cancer and metastasis, including neoplasia and hematologic malignancies.

Angiogenesis-related diseases and disorders are commonly observed in the eye where they may result in blindness. Such disease include, but are not limited to, age-related macular degeneration, choroidal neovascularization, persistent hyperplastic vitreous syndrome, diabetic retinopathy, and retinopathy of prematurity (ROP).

A number of angiogenesis-related diseases are associated with the blood and lymph vessels including transplant arteriopathy and atherosclerosis, where plaques containing blood and lymph vessels form, vascular malformations, DiGeorge syndrome, hereditary hemorrhagic telangiectasia, cavernous hemangioma, cutaneous hemangioma, and lymphatic malformations.

Other angiogenesis diseases and disorders affect the bones, joints, and/or cartilage include, but are not limited to, arthritis, synovitis, osteomyelitis, osteophyte formation, and HIV-induced bone marrow angiogenesis.

The gastro-intestinal tract is also susceptible to angiogenesis diseases and disorders. These include, but are not limited to, inflammatory bowel disease, ascites, peritoneal adhesions, and liver cirrhosis.

Angiogenesis diseases and disorders affecting the kidney include, but are not limited to, diabetic nephropathy (early stage: enlarged glomerular vascular tufts).

Excess angiogenesis in the reproductive system is associated with endometriosis, uterine bleeding, ovarian cysts, ovarian hyperstimulation.

In the lung, excess angiogenesis is associated with primary pulmonary hypertension, asthma, nasal polyps, rhinitis, chronic airway inflammation, cystic fibrosis.

Diseases and disorders characterized by excessive or undesirable angiogenesis in the skin include psoriasis, warts, allergic dermatitis, scar keloids, pyogenic granulomas, blistering disease, Kaposi's sarcoma in AIDS patients, systemic sclerosis.

Obesity is also associated with excess angiogenesis (e.g., angiogenesis induced by fatty diet). Adipose tissue may be reduced by the administration of angiogenesis inhibitors.

Excess angiogenesis is associated with a variety of autoimmune disorders, such as systemic sclerosis, multiple sclerosis, Sjögren's disease (in part by activation of mast cells and leukocytes). Undesirable angiogenesis is also associated with a number of infectious diseases, including those associated with pathogens that express (lymph)-angiogenic genes, that induce a (lymph)-angiogenic program or that transform endothelial cells. Such infectious disease include those bacterial infections that increase HIF-1 levels, HIV-Tat levels, antimicrobial peptides, levels, or those associated with tissue remodeling.

Infectious diseases, such as viral infections, can cause excessive angiogenesis which is susceptible to treatment with agents of the invention. Examples of viruses that have been found in humans include, but are not limited to, Retroviridae (e.g. human immunodeficiency viruses, such as HIV-1 (also referred to as HDTV-III, LAVE or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

The present invention provides methods of treating diseases and/or disorders or symptoms thereof associated with excess or undesired angiogenesis, which comprise administering a therapeutically effective amount of a pharmaceutical composition comprising a compound of the formulae herein to a subject (e.g., a mammal, such as a human). Thus, one embodiment is a method of treating a subject suffering from or susceptible to an angiogenesis-related disease or disorder or symptom thereof. The method includes the step of administering to the mammal a therapeutic amount of an amount of a compound herein sufficient to treat the disease or disorder or symptom thereof (e.g., to prevent or reduce angiogenesis) under conditions such that the disease or disorder is treated.

The methods herein include administering to the subject (including a subject identified as in need of such treatment) an effective amount of a compound described herein (e.g., a peptide described herein, or mimetic, or analog thereof), or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which angiogenesis may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with angiogenesis, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Treatment of Neoplasia

The methods of the invention are particularly well suited for the treatment of neoplasias. By "neoplasia" is meant a disease that is caused by or results in inappropriately high levels of cell division, inappropriately low levels of apoptosis, or both. For example, cancer is an example of a proliferative disease. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors, such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

Peptides of the Invention

The present invention utilizes powerful computational and bioinformatic approaches to identify therapeutic agents (e.g., polypeptides, peptides, analogs, and fragments thereof) having anti-angiogenic activity. The amino acid sequences of such agents are provided herein. The Tables and Figures provide sequences of peptides of the invention, GenBank Accession Nos., and the amino acid positions of the sequences. Amino acids are referred to herein by their commonly known one-letter symbols recommended by the IUPAC-IUB Biochemical Nomenclature Commission; they can also be referred to by their commonly known three letter symbols.

Angiogenesis Assays

The biological activity of therapeutic agents of the invention is characterized using any method for assaying angiogenic activity known in the art. In vitro angiogenesis assays have been described in detail in recent reviews (Akhtar et al., *Angiogenesis,* 5:75-80, 2002; Auerbach et al., *Cancer Metastasis Rev,* 19:167-72, 2000; Auerbach et al., *Clin Chem,* 49:32-40, 2003; Staton et al., *Int J Exp Pathol,* 85:233-48, 2004; Vailhe et al., *Lab Invest,* 81:439-52, 2001). There are a number of different endothelial cell lineages that have been used in angiogenesis assays: bovine aortic, bovine retinal, rat and mouse microvascular, human aortic, human bladder microvascular, human cardiac microvascular, human dermal microvascular, human lung microvascular and human umbilical vein endothelial cells. All of these endothelial cells are capable of differentiating in vitro and forming capillary-like structures. This process occurs when the cells are cultured in a monolayer of extracellular matrix components, such as the Matrigel (extracellular matrix material similar to basement membrane), type I collagen, fibronectin or laminin. An endothelial cell lineage that is commonly used for testing the angiogenic response is the human umbilical vein endothelial cells (HUVECs). The National Cancer Institute (NCI) has issued guidelines for testing the anti-angiogenic efficacy of novel agents; they include proliferation, migration and tube formation assays using HUVECs.

Initially the anti-angiogenic effect of selected standard agents is assessed as a positive control by adding them into the wells containing cultured endothelial cells. Such standard anti-angiogenic agents include the fumigillin analog TNP-470 that is available by request from NCI. The standard cell culture medium is usually used as a negative control. The experiments described below are repeated several times as required to obtain statistically significant and reproducible results. Once the platform is calibrated and tested for the known agents, the novel inhibitors are tested.

Cell Proliferation Assay

In these assays anti-angiogenic agents are tested for their ability to alter endothelial cell proliferation. A reduction in endothelial cell proliferation identifies an agent that inhibits angiogenesis. The viability and metabolic activity of the cells is measured in the presence of the anti-angiogenic peptides at different concentrations and various time steps. In one example, a cell proliferation reagent, MTT, is used in a substrate/assay that measures the metabolic activity of viable cells. The assay is based on the reduction of the yellow tetrazolium salt, MTT, by viable, metabolically active cells to form the insoluble purple formazan crystals, which are solubilized by the addition of a detergent. MTT is a colorimetric, non-radioactive assay that can be performed in a microplate. It is suitable for measuring cell proliferation, cell viability or cytotoxicity. The procedure involves three steps. First, the cells are cultured in a multi-well plate and then incubated with the yellow MTT for approximately 2 to 4 hours. During this incubation period, viable cells convert, in their mitochondria, the yellow MTT to the purple formazan crystals. The second step involves the solubilization of the crystals. A detergent solution is added to lyse the cells and solubilize the colored crystals. The final step of the assay involves quantifying changes in proliferation by measuring the changes in the color after lysing the cells. The samples are read using an ELISA plate reader at a wavelength of 570 nm. The amount of color produced is directly proportional to the number of viable cells present in a particular well. Other proliferation assays include WST-1, XTT, Trypan Blue, Alamar Blue and BrdU. In contrast to the MTT assay, in the WST-1 assay the formazan crystals do not need to be solubilized by the addition of a detergent; they are soluble to the cell medium.

In another example, cell proliferation is assayed by quantitating bromodeoxyuridine (BrdU) incorporation into the newly synthesized DNA of replicating cells. The assay is a cellular immunoassay that uses a mouse monoclonal antibody directed against BrdU. The procedure involves four steps. First, the cells are cultured in a microtiterplate and pulse-labeled with BrdU. Only proliferating cells incorporate BrdU into their DNA. The cells are then fixed in a denaturing solution. The genomic DNA is denatured, exposing the incorporated BrdU to immunodetection. The BrdU label is located in the DNA with a peroxidase-conjugated anti-BrdU antibody. The antibody is quantitated using a peroxidase substrate. To test anti-proliferative effects of the selected peptides, the endothelial cells are incubated in the presence of varying amounts of the peptides for different time intervals. After labeling of the cells with BrdU the cell proliferation reagent WST-1 is added, and the cells are reincubated. The formazan product is quantified at 450 nm with an absorbance reader. Subsequently, BrdU incorporation is determined using the colorimetric cell proliferation ELISA, BrdU. The results of this assay indicate the effects of the anti-angiogenic peptides either on DNA synthesis (anti-proliferative) or the metabolic activity (pro-apoptotic) of the cell. Kits for implementing these techniques are commercially available.

Preferably, an agent of the invention reduces cell proliferation by at least about 5%, 10%, 20% or 25%. More preferably, cell proliferation is reduced by at least 50%, 75%, or even by 100%.

Cell Apoptosis and Cell Cycle Assay

Agents having anti-angiogenic activity can also be identified in assay that measures the effect of a candidate agent on cell proliferation and survival using a mitogenic assay (incorporation of thymidine, or 5-bromodeoxyuridine) that measures alterations in cell number (direct counts or indirect colorimetric evaluation). Agents that reduce cell proliferation, cell survival, or that increase cell death are identified as having anti-angiogenic activity. Cell death by apoptosis can be measured using a TUNEL assay or by analyzing the expression of apoptosis markers, such as the caspases and annexin V (Fennell et al., *J Biomol Screen,* 11:296-302, 2006;

Loo and Rillema, *Methods Cell Biol,* 57:251-64, 1998; Otsuki et al., *Prog Histochem Cytochem,* 38:275-339, 2003).

A number of methods have been developed to study apoptosis in cell populations. Apoptosis is a form of cell death that is characterized by cleavage of the genomic DNA into discrete fragments prior to membrane disintegration. Because DNA cleavage is a hallmark for apoptosis, assays that measure prelytic DNA fragmentation are especially attractive for the determination of apoptotic cell death. DNA fragments obtained from cell populations are assayed on agarose gels to identify the presence of absence of "DNA ladders" or bands of 180 bp multiples, which form the rungs of the ladders, or by quantifying the presence of histone complexed DNA fragments by ELISA.

Other indicators of apoptosis include assaying for the presence caspases that are involved in the early stages of apoptosis. The appearance of caspases sets off a cascade of events that disable a multitude of cell functions. Caspase activation can be analyzed in vitro by utilizing an enzymatic assay. Activity of a specific caspase, for instance caspase 3, can be determined in cellular lysates by capturing of the caspase and measuring proteolytic cleavage of a suitable substrate that is sensitive to the specific protease (Fennell et al., *J Biomol Screen,* 11:296-302, 2006; Loo and Rillema, *Methods Cell Biol,* 57:251-64, 1998; Otsuki et al., *Prog Histochem Cytochem,* 38:275-339, 2003). Agents that increase caspase activity or DNA fragmentation in endothelial cells are identified as useful in the methods of the invention.

In addition to in vitro techniques, apoptosis can be measured using flow cytometry. One of the simplest methods is to use propidium iodide (PI) to stain the DNA and look for sub-diploid cells (Fennell et al., *J Biomol Screen,* 11:296-302, 2006; Loo and Rillema, *Methods Cell Biol,* 57:251-64, 1998; Otsuki et al., *Prog Histochem Cytochem,* 38:275-339, 2003).

The most commonly used dye for DNA content/cell cycle analysis is propidium iodide (PI). PI intercalates into the major groove of double-stranded DNA and produces a highly fluorescent adduct that can be excited at 488 nm with a broad emission centered around 600 nm. Since PI can also bind to double-stranded RNA, it is necessary to treat the cells with RNase for optimal DNA resolution. Other flow cytometric-based methods include the TUNEL assay, which measures DNA strand breaks and Annexin V binding, which detects relocation of membrane phosphatidyl serine from the intracellular surface to the extracellular surface.

Cell Migration and Invasion Assay

Another anti-angiogenic activity is the ability to reduce endothelial cell migration towards an attractant that is present in a chemotactic gradient, such as a growth factor gradient. Endothelial cell motility or migration can be assessed using the Boyden chamber technique (Auerbach et al., *Cancer Metastasis Rev,* 19:167-72, 2000; Auerbach et al., *Clin Chem,* 49:32-40, 2003; Taraboletti and Giavazzi, *Eur J Cancer,* 40:881-9, 2004). In one example, a Boyden chamber assay is used to test endothelial cell migration from one side of the chamber in the presence of an activator. In brief, the lower compartment of the Boyden chamber is separated from the upper (containing the endothelial cells) by a matrix-coated polycarbonate filter with pores small enough to allow only the active passage of the cells (3-8 μm pore size). The matrix may include, for example, extracellular matrix proteins, such as collagen, laminin and fibronectin. Activators include but are not limited to growth factors, such as vascular endothelial growth factor and fibroblast growth factor-2 or conditioned medium (e.g. from tumor cells or NIH-3T3 fibroblasts). Migration typically occurs rapidly typically within 4-20 hours cells have migrated through the filter. The number of migrating cells is quantified using a cell-permeable fluorescent dye in the presence or absence of an inhibitor; it can also be quantified by any means of cell counting. A fluorescence plate reader is used to quantify the migrating cells by measuring the amount of fluorescence and directly correlating it to cell number. A decrease in cell migration identifies a peptide that inhibits angiogenesis. Preferably, cell migration or motility is reduced by at least about 5%, 10%, 20% or 25%. More preferably, cell migration or motility is reduced by at least about 50%, 75%, or even by 100%.

In other embodiments, anti-angiogenic agents of the invention alter the invasiveness of an endothelial cell, for example, by reducing the ability of an endothelial cell to degrade an extracellular matrix component. In one example, an anti-angiogenic inhibitor acts by reducing the proteolytic activity of a matrix metalloproteinase. Methods for assaying protease activity are known in the art. Quantification of the matrix metalloproteinase activity can be accomplished using a zymographic or gelatinase activity assay (Frederiks and Mook, *J Histochem Cytochem.* 52:711-22, 2004). Preferably, protease activity is reduced by at least about 5%, 10%, 20% or 25%. More preferably, protease activity is reduced by at least about 50%, 75%, or even by 100%.

In another example, the invasive activity of an endothelial cell is measured using a Boyden chamber invasion assay or by measuring phagokinetic tracks. The invasion assay is essentially as described above for the Boyden motility assay, except that the filter is coated with a layer of a matrix several microns thick, usually Matrigel or other basement membrane extracts, which the cells must degrade before migrating through the filter (Auerbach et al., *Cancer Metastasis Rev,* 19:167-72, 2000; Auerbach et al., *Clin Chem,* 49:32-40, 2003; Taraboletti and Giavazzi, *Eur J Cancer,* 40:881-9, 2004). Compounds that reduce extracellular matrix degradation or endothelial cell invasiveness are identified as useful in the methods of the invention.

Tube Formation Assay

Another method of identifying an agent having anti-angiogenic activity involves measuring the agent's ability to reduce or disrupt capillary tube formation. Various types of endothelial cells (e.g., HUVECs, HMVECs (human microvascular endothelial cells)) form tubes when cultured in wells uniformly coated with Matrigel, an extracellular matrix protein, or other substrates. Therefore the assay characterizes endothelial cell differentiation. The endothelial cells are cultured in the presence or the absence of a candidate agent. The agent may be added to the culture media or may be present or applied to the gel. Typically, the effect on tube formation is measured by incubating the cells for a period of time (e.g., one to four days) at 37° C. in 5% $CO_2$ atmosphere. Kits for implementing these techniques are commercially available.

The output of the experiments are images of capillary networks formed. A common metric used for the morphological characteristics of a capillary network is the angiogenic index. This index is calculated as the ratio of the total length of the connected tubes over the total monitored surface of the well. The change of the angiogenic index as a function of the concentration of the anti-angiogenic peptide will be the determinant for the effectiveness of the tested novel angiogenesis inhibitors.

Aortic Ring Assay

The aortic ring assay integrates the advantages of both in vivo and in vitro systems. It is a useful assay to test angiogenic factors or inhibitors in a controlled environment. More importantly, it recapitulates all of the necessary steps involved in angiogenesis (Staton et al., *Int J Exp Pathol,* 85:233-48, 2004).

In this quantitative method of studying angiogenesis, ring segments of aortas from various animals such as rats and mice are embedded in a three-dimensional matrix composed of fibrin or collagen, and cultured in a defined medium devoid of serum and growth factors. Microvessels sprout spontaneously from the surface of the aortic rings. This angiogenic process is mediated by endogenous growth factors produced from the aorta or can be assisted by applying exogenously specific concentrations of growth factors. The embedded aortas are incubated for 10-12 days and after the incubation period the newly formed vessels are quantified. Microvessels can be counted manually or quantified using computer-assisted image analysis. Test agents can be added to the culture medium to assay for angiogenic or anti-angiogenic activity. Also aortas from animals with different genetic background (e.g., knockout mice) can be used in order to assess specific mechanisms of the effect of the anti-angiogenic peptides on the neovessel formation process.

In Vivo Angiogenesis Assays

A recent review identified over 70 disease conditions that involve angiogenesis, about half of those characterized by abnormal or excessive angiogenesis or lymphangiogenesis (Carmeliet, *Nature,* 438:932-6, 2005). Agents identified as having anti-angiogenic activity are optionally tested in in vivo assays using animal models that exhibit abnormal or excessive angiogenesis or lymphangiogenesis.

Matrigel Plug Assay

In one in vivo approach, a candidate agent of the invention is tested for anti-angiogenic activity by implanting a polymer matrix subcutaneously in an animal and assaying the matrix for signs of neovascularization. In one embodiment, a Matrigel plug or a similar substrate containing tumor cells and an anti-angiogenic factor is used to study in vivo angiogenesis (Auerbach et al., *Cancer Metastasis Rev,* 19:167-72, 2000; Staton et al., *Int J Exp Pathol,* 85:233-48, 2004). Matrigel is a liquid at 4° C., but forms a solid gel at 37° C. A candidate agent is suspended together with an attractant, such as a growth factor, in the gel. The Matrigel is then injected subcutaneously where it forms a solid plug allowing for the prolonged local release of pro- or anti-angiogenic agents present in the gel. The plug is subsequently removed and neovascularization is assessed by any standard methods, including but not limited to, identifying the presence of endothelial cells or endothelial cell tubules in the plug using microscopy. In some embodiments, this approach is combined with an immuno-histological identification of endothelium specific proteins (e.g., CD-31/34 or integrins) on the newly formed vessels.

The Matrigel plug assay can be applied for testing the efficacy of the novel anti-angiogenic peptides identified herein. In one example, Matrigel is mixed with heparin (usually 20 U/ml) and a vascular endothelial growth factor at about 50 ng/ml in the presence or absence of a candidate peptide, which is supplied at a variety of concentrations (e.g., at the $IC_{50}$). A control animal receives the gel without the anti-angiogenic fragment. The Matrigel is injected into the mice subcutaneously and after one week the animals are sacrificed. The Matrigel plugs are then removed and fixed with 4% paraformaldehyde. The plugs are then embedded in paraffin, sectioned and stained with hematoxylin and eosin. The number of blood vessels as well as any other angiogenic indexes are estimated.

Directed In Vivo Angiogenesis Assay (DIVAA)

Directed in vivo angiogenesis assay (DIVAA) is a reproducible and quantitative in vivo method of assaying angiogenesis. It involves the preparation of silicon cylinders that are closed on one side filled with some type of extracellular matrix (for example Matrigel) with or without premixed angiogenic factors (Guedez et al., *Am J Pathol,* 162:1431-9, 2003) to form an angioreactor. The angioreactors are then implanted subcutaneously in mice. Vascular endothelial cells migrate into the extracellular matrix and form vessels in the angioreactor. As early as nine days post-implantation, there are enough cells present in the angioreactor to assay the effect of an angiogenic modulating factors. A candidate agent may be included in the matrix together with the angiogenic factors. The design of the angioreactor provides a standardized platform for reproducible and quantifiable in vivo angiogenesis assays.

Advantageously, the angioreactor prevents assay errors due to absorption of the basement membrane extract or the diffusion of the anti-angiogenic agent into the surrounding tissue; may be carried out using only a fraction of the materials required in the plug assay described above; and up to four angioreactors may be implanted in a single animal (e.g., mouse), providing more data for analysis. Vascularization response can be measured by intravenous injection of fluorescein isothiocyanate (FITC)-dextran before the recovery of the angioreactor, followed by spectrofluorimetry. Alternatively, to obtain a quantitative assessment of the angiogenic invasion, the content of the angioreactors, can be removed and the endothelial cells stained using FITC-Lectin. Fluorescence of the FITC-Lectin solution can be quantitated by measuring the fluorescence at 485 nm excitation and 510 nm emission using a fluorescence plate reader e.g., Victor 3V (Perkin Elmer). The intensity of the signal is directly proportional to the number of endothelial cells that are present in the angioreactors. The technique allows dose response analysis and identification of effective doses of angiogenesis-modulating factors in vivo.

Chorioallantoic Membrane Assay

The chorioallantoic membrane assay (CAM) is widely used as an angiogenesis assay Auerbach et al., *Cancer Metastasis Rev* 19:167-172, 2000; Staton et al., *Int J Exp Pathol* 85: 233-248, 2004; D'Amato, In: Voest, E. E., and D'Amore, P. A. (eds). *Tumor Angiogenesis Microcirculation,* 2001, Marcel Dekker, New York-Base1). In one embodiment, the chorioallantoic membrane of a 7-9 day old chick embryos is exposed by making a window in the egg shell. A candidate agent is provided in a formulation that provides for its extended release (e.g., in a slow-release polymer pellets, absorbed on a gelatin sponge, or air-dried onto a plastic disc). The candidate agent formulation is implanted onto the chorioallantoic membrane through a window in the shell. The window is sealed and the egg is re-incubated. The lack of mature immune system in the 7 day old chick embryos allows the study of angiogenesis without any immunological interference. In the modified version of the in ovo assay, the entire egg content is transferred to a plastic culture dish. After 3-6 days of incubation the testing agents are applied and angiogenesis is monitored using various angiogenesis indexes.

In the case of testing the angiostatic peptides, polymer pellets can be loaded both with the growth factors and the anti-angiogenic fragments and be implanted in the chorioallantoic membrane. The modified version of the assay allows the application of a candidate agent using different strategies to identify effective therapeutic regimens. For example, a candidate agent is applied in a single bolus at a particular concentration; at different time points at lower concentrations; or in different formulations that provide for the extended release of an agent. This provides for the temporal control of candidate agent release and the delineation of temporal variations in drug administration on the angiostatic activity of the candidate agents.

Ocular Angiogenesis Models

Corneal Micropocket:

The cornea is an avascular site and presumably any vessels penetrating from the limbus into the cornea stroma can be identified as newly formed. In this assay a pocket is created in the cornea stroma of the animal. An angiogenic response is usually initiated by implantation of a slow release pellet or polymer containing growth factors (Auerbach et al., *Cancer Metastasis Rev,* 19:167-72, 2000; Auerbach et al., *Clin Chem,* 49:32-40, 2003; D'Amato, *Tumor Angiogenesis and Microcirculation,* 103-110, 2001; Staton et al., *Int J Exp Pathol,* 85:233-48, 2004).

In order to test an angiogenesis inhibitor, the effect of a candidate agent on an angiogenic response in the cornea is assayed after the implantation of a pellet comprising an angiogenic agent in combination with a candidate inhibitor in the cornea pockets. Also the efficacy of an anti-angiogenic agent can be evaluated using the mouse model of ocular ischemic retinopathy to quantitatively assess anti-angiogenic effects on retinal neovascularization. In addition, a mouse model of laser induced choroidal neovascularization can be used in order to quantitatively assess the anti-angiogenic effects of candidate agents on choroidal neovascularization. The tested peptides can be administered with a bolus injection or any other scheduled administration.

Mouse Model of Choroidal Neovascularization (CNV):

Laser photocoagulation is used on normal mice to rupture Bruch's membrane at three locations in each eye (e.g., To be et al., *Am J Pathol* 153:1641-1646, 1998); this procedure leads to neovascularization arising from the choroidal circulation. On the day of laser treatment, the mice are injected intravitreously with the peptide being evaluated. The injections are repeated a week later. One eye is injected with peptide, the contralateral eye receives the vehicle or scrambled peptide as control. Two weeks following laser treatment the mice are sacrificed and quantitative assessment of choroidal neovascularization is performed. The eyes are removed and fixed overnight in phosphate-buffered formalin. The cornea and lens are removed and the entire retina is dissected from the eyecup. Radial cuts are made from the edge to the equator and the eyecup is flat mounted with the sclera facing down. Flat mounts are examined by fluorescence microscopy. The area of the CNV lesions in the peptide injected eyes are compared to the area of neovascularization of CNV in the paired vehicle injected eyes.

Mouse Model of Ischemic Retinopathy:

Seven-day-old (P7) mice and their mothers are placed in an airtight incubator and exposed to an atmosphere of 75% oxygen for 5 day (Smith et al., *Invest Ophthalmol Vis Sci.* 35:101-111, 1994). The incubator temperature is maintained at 23° C., and oxygen is continuously monitored with an oxygen controller. At P12 the litters are returned to room air. One day following removal from oxygen and return to room air intravitreous injection of peptide into the right eye of each pup and vehicle into the left is carried out. On P17 pups are euthanized, and the eyes are rapidly removed, positioned and frozen in an embedding compound. Ocular sections are then stained with Griffonia Simplicifolia lectin that labels vascular endothelial cells. Histopathological sections demonstrating the presence, extent and location of normal and abnormal blood vessels are then analyzed following preparation of a standardized series of sections in each eye. The area of retinal neovascularization in the peptide injected eye is compared to the area of retinal neovascularization in the vehicle injected eye.

Chamber Assays

Other methods for studying the effect of a candidate agent in vivo on chronic angiogenesis involve the use of an implanted transparent chamber. The chamber is implanted in an accessible site (e.g., the rabbit ear, the dorsal skinfold and the cranial window chamber (Auerbach et al., *Clin Chem,* 49:32-40, 2003; Staton et al., *Int J Exp Pathol,* 85:233-48, 2004). In each of these systems a piece of skin (the ear or skinfold chamber) or part of the skull (cranial chamber) is removed from an anesthetized animal. Tumor cells or a pellet containing an angiogenesis stimulus is then placed on the exposed surface and covered by a glass. The animals are allowed to recover, and angiogenesis is subsequently monitored. The models allow for the continuous measurement of various angiogenesis as well as tissue parameters, such as pH or blood flow. Similarly to the corneal pocket assay, the angiostatic agents are administered orally, locally, or systemically using a predefined drug administration schedule. Agents that reduce angiogenesis in a chamber assay are identified as useful in the methods of the invention.

Tumor Models

Many different in vivo models have been developed to test the activity of potential anti-angiogenic or anti-cancer treatments, specifically on tumor vasculature. Tumors are implanted and can be grown syngeneically; i.e., subcutaneously, orthotopically in a tissue of origin, or as xenografts in immunodeficient mice (Auerbach et al., *Clin Chem,* 49:32-40, 2003; Staton et al., *Int J Exp Pathol,* 85:233-48, 2004). Any number of histological analyses may be used to examine the effect of a candidate agent on a blood vessel supplying the tumor. In one embodiment, the blood vessel density of a newly formed vasculature in the tumor is monitored; in another embodiment, the vascular architecture is monitored, for example, by counting the number of vascular branches per vessel unit length. In another embodiment, blood flow through the vasculature is measured.

The tumor models provide a variety of different conditions that can be analyzed to assay the efficacy of a candidate anti-angiogenic agent. For example, the effects of a candidate agent on the stability of a well vascularized vs. a poorly vascularized tumor can be assayed; the effect of a candidate agent on tumors of different origin, for example prostate and breast cancer, renal cell carcinoma, and including those of vascular origin such as the chemically induced hemangiosarcomas and Kaposi's sarcomas, can be analyzed. The study of in vivo tumor models provide the closest approximation of human tumor angiogenesis. Moreover, such models provide the opportunity to study the pharmacokinetics of the candidate drug as well as its efficacy simultaneously in a large scale model and under different administration carriers and strategies.

Anti-Angiogenic Peptides and Analogs

The invention is not limited to conventional therapeutic peptides having anti-angiogenic activity, but comprises a variety of modified peptides having properties that enhance their biodistribution, selectivity, or half-life. In particular, the invention provides peptides that are modified in ways that enhance their ability to inhibit angiogenesis in a cell, tissue, or organ in a subject in need thereof.

The invention provides methods for optimizing a transcription factor or protein transduction domain amino acid sequence or nucleic acid sequence by producing an alteration in the sequence. Such alterations may include certain mutations, deletions, insertions, or post-translational modifications. The invention further includes analogs of any naturally-occurring polypeptide of the invention. Analogs can differ from a naturally-occurring polypeptide of the invention by amino acid sequence differences, by post-translational modifications, or by both. Analogs of the invention will generally exhibit at least 85%, more preferably 90%, and most preferably 95% or even 99% identity with all or part of a naturally-occurring amino, acid sequence of the invention. The length of sequence comparison is at least about 5, 10, 15 or 20 amino acid residues, at least about 25, 50, or 75 amino acid residues, or at least about 100 amino acid residues. Again, in an exemplary approach to determining the degree of identity, a BLAST program may be used, with a probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example, hydroxyproline, gamma-carboxyglutamate, and O-phosphoserine, phosphothreonine. "Amino acid analogs" refer to compounds that have the same basic chemical structure as a naturally occurring amino acid, i.e., a carbon that is bound to a hydrogen, a carboxyl group, an amino group, and an R group, for example, homoserine, norleucine, methionine sulfoxide, methionine methyl sulfonium. Such analogs have modified R groups (for example, norleucine) or modified peptide backbones, but retain the same basic chemical structure as a naturally occurring amino acid. "Amino acid mimetics" refers to chemical compounds that have a structure that is different from the general chemical structure of an amino acid, but that function in a manner similar to a naturally occurring amino acid. Amino acids and analogs are well known in the art. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" apply to both amino acid and nucleic acid sequences. With respect to particular nucleic acid sequences, conservatively modified variants refers to those nucleic acids which encode identical or similar amino acid sequences and include degenerate sequences. For example, the codons GCA, GCC, GCG and GCU all encode alanine. Thus, at every amino acid position where an alanine is specified, any of these codons can be used interchangeably in constructing a corresponding nucleotide sequence. The resulting nucleic acid variants are conservatively modified variants, since they encode the same protein (assuming that is the only alternation in the sequence). One skilled in the art recognizes that each codon in a nucleic acid, except for AUG (sole codon for methionine) and UGG (tryptophan), can be modified conservatively to yield a functionally-identical peptide or protein molecule. As to amino acid sequences, one skilled in the art will recognize that substitutions, deletions, or additions to a polypeptide or protein sequence which alter, add or delete a single amino acid or a small number (typically less than about ten) of amino acids is a "conservatively modified variant" where the alteration results in the substitution of an amino acid with a chemically similar amino acid. Conservative substitutions are well known in the art and include, for example, the changes of alanine to serine; arginine to lysine; asparigine to glutamine or histidine; aspartate to glutamate; cysteine to serine; glutamine to asparigine; glutamate to aspartate; glycine to proline; histidine to asparigine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine. Other conservative and semi-conservative substitutions are known in the art and can be employed in practice of the present invention.

The terms "protein", "peptide" and "polypeptide" are used herein to describe any chain of amino acids, regardless of length or post-translational modification (for example, glycosylation or phosphorylation). Thus, the terms can be used interchangeably herein to refer to a polymer of amino acid residues. The terms also apply to amino acid polymers in which one or more amino acid residue is an artificial chemical mimetic of a corresponding naturally occurring amino acid. Thus, the term "polypeptide" includes full-length, naturally occurring proteins as well as recombinantly or synthetically produced polypeptides that correspond to a full-length naturally occurring protein or to particular domains or portions of a naturally occurring protein. The term also encompasses mature proteins which have an added amino-terminal methionine to facilitate expression in prokaryotic cells.

The polypeptides and peptides of the invention can be chemically synthesized or synthesized by recombinant DNA methods; or, they can be purified from tissues in which they are naturally expressed, according to standard biochemical methods of purification. Also included in the invention are "functional polypeptides," which possess one or more of the biological functions or activities of a protein or polypeptide of the invention. These functions or activities include the ability to inhibit angiogenesis (e.g., by reducing endothelial cell proliferation, migration, survival, or tube formation). The functional polypeptides may contain a primary amino acid sequence that has been modified from that considered to be the standard sequence of a peptide described herein. Preferably these modifications are conservative amino acid substitutions, as described herein.

In addition to full-length polypeptides, the invention also includes fragments of any one of the polypeptides of the invention. As used herein, the term "a fragment" means at least 5, 10, 13, or 15 amino acids. In other embodiments a fragment is at least 20 contiguous amino acids, at least 21, 22, 23, 24, or 25 contiguous amino acids, or at least 30, 35, 40, or 50 contiguous amino acids, and in other embodiments at least 60 to 80 or more contiguous amino acids. Fragments of the invention can be generated by methods known to those skilled in the art or may result from normal protein processing (e.g., removal of amino acids from the nascent polypeptide that are not required for biological activity or removal of amino acids by alternative mRNA splicing or alternative protein processing events).

Non-protein transcription factor/protein transduction domain fusion analogs have a chemical structure designed to mimic the fusion proteins functional activity. Such analogs are administered according to methods of the invention. Fusion protein analogs may exceed the physiological activity of the original fusion polypeptide. Methods of analog design are well known in the art, and synthesis of analogs can be carried out according to such methods by modifying the chemical structures such that the resultant analogs increase the reprogramming or regenerative activity of a reference transcription factor/protein transduction domain fusion polypeptide. These chemical modifications include, but are not limited to, substituting alternative R groups and varying the degree of saturation at specific carbon atoms of a reference fusion polypeptide. Preferably, the fusion protein analogs are relatively resistant to in vivo degradation, resulting in a more prolonged therapeutic effect upon administration. Assays for measuring functional activity include, but are not limited to, those described in the Examples below.

Peptide-Design Approaches

Iterative design approaches (DeFreest et al., *J Pept Res,* 63:409-19, 2004) offer unique opportunities to optimize the structure and function of the candidate anti-angiogenic peptides. During iterative design an initial set of amino acids is substituted and the effect of the resulting agent on angiogenesis is assayed. The exploration of the structure-function relationships, but most importantly the conservation of the biophysical and biochemical characteristics of the peptides, during the iterative design and synthesis, is expected to contribute to the optimization of the anti-angiogenic activity. To determine which residues are essential to the bioactivity of the predicted peptide a series of analogs is prepared and evaluated.

In order to assess the types of substitutions within the amino acid sequence of the candidate peptide one can initially use computational methods. The most straightforward method for deciphering the importance of each amino acid is to investigate the conservation of these amino acids at multiple orthologues (same locus in different organisms). Amino acids that are conserved among different organisms are identified as functionally significant. From a biophysical point of view electrostatic interactions and hydrophobic partitioning act in concert to promote the interactions of the peptides with their receptors. In this sense, any point substitution should comply with the conservation of the net charge and hydrophobicity of the agent (DeFreest et al., *J Pept Res,* 63:409-19, 2004). Phage display technology can also be used for performing random substitutions at expressed peptides of 20-25 amino acids length (Scott and Smith, *Science,* 249:386-90, 1990). In each of the cases the resultant peptide is tested for its effect on angiogenesis using any of the assays described herein.

Design optimization of the activity of the predicted peptides can also be performed by altering specific structural characteristics of the agents. For example, it has been shown (DeFreest et al., *J Pept Res,* 63:409-19, 2004) that head-to-tail cyclization of the molecules confers an active dose range broader than the linear form of the molecules, and the peptide stability and shelf life are not compromised. The head-to-tail conjunction can occur either by a disulfide bond or by a peptide bond formation. The use of a peptide bond may be advantageous for purposes of shelf life, and elimination of dimers, trimers, and higher-order aggregates formation that can sometimes develop when peptides are stored or used in conditions where the redox state cannot be fully controlled. The cyclization approaches are discussed in the following section.

Cyclization of Linear Peptides

Cyclization of peptides has been shown to be a useful approach to developing diagnostically and therapeutically useful peptidic and peptidomimetic agents. Cyclization of peptides reduces the conformational freedom of these flexible, linear molecules, and often results in higher receptor binding affinities by reducing unfavorable entropic effects. Because of the more constrained structural framework, these agents are more selective in their affinity to specific receptor cavities. By the same reasoning, structurally constrained cyclic peptides confer greater stability against the action of proteolytic enzymes.

Methods for cyclization can be classified into the so called "backbone to backbone" cyclization by the formation of the amide bond between the N-terminal and the C-terminal amino acid residues, and cyclizations involving the side chains of individual amino acids (Li and Roller, *Curr Top Med Chem,* 2:325-41, 2002). Although many novel approaches have been developed to accomplish the head-to-tail cyclization of linear peptides and peptidomimetics, the most commonly used method is still the solution phase macro-cyclization using peptide coupling reagents. The results of the peptide cyclization are mainly influenced by the conformation of the linear peptide precursors in solution. Synthesis design is affected by the strategy of the ring disconnection, and the rational selection of peptide coupling reagents. A reasonable ring disconnection will significantly facilitate the peptide macro-cyclization reaction, while a poor selection of cyclization site may result in slow reaction speed and low yield accompanied by various side reactions such as racemization, dimerization, and oligomerization.

Cyclization involving the side chains of individual amino acids includes the formation of disulfide bridges between omega-thio amino acid residues (cysteine, homocysteine), the formation of lactam bridges between glutamic/aspartic acid and lysine residues, the formation of lactone or thiolactone bridges between amino acid residues containing carboxyl, hydroxyl or mercapto functional groups, and the formation of thio-ether or ether bridges between the amino acids containing hydroxyl or mercapto functional groups.

Recombinant Polypeptide Expression

The invention provides therapeutic peptides that are most commonly generated by routine methods for peptide synthesis. Such methods are known in the art and are described herein. If an alternative approach is desired, the peptides are expressed recombinantly, either alone, or as part of a larger fusion protein that includes an anti-angiogenic peptide operably linked to a polypeptide that facilitates expression. If desired, the peptide can subsequently be cleaved (e.g., enzymatically) from the fusion protein. Where the fusion protein does not interfere with the anti-angiogenic activity of the peptide such cleavage may not be necessary or even desirable. When the therapeutic peptide or fusion protein comprising the peptide contacts an endothelial cell, tissue, or organ comprising such a cell it reduces angiogenesis. Recombinant polypeptides of the invention are produced using virtually any method known to the skilled artisan. Typically, recombinant polypeptides are produced by transformation of a suitable host cell with all or part of a polypeptide-encoding nucleic acid molecule or fragment thereof in a suitable expression vehicle.

Those skilled in the field of molecular biology will understand that any of a wide variety of expression systems may be used to provide the recombinant protein. The precise host cell used is not critical to the invention. A polypeptide of the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, or preferably COS cells). Such cells are available from a wide range of sources (e.g., the American Type Culture Collection, Rockland, Md.; also, see, e.g., Ausubel et al., *Current Protocol in Molecular Biology*, New York: John Wiley and Sons, 1997). The method of transformation or transfection and the choice of expression vehicle will depend on the host system selected. Transformation and transfection methods are described, e.g., in Ausubel et al. (supra); expression vehicles may be chosen from those provided, e.g., in *Cloning Vectors: A Laboratory Manual* (P. H. Pouwels et al., 1985, Supp. 1987).

A variety of expression systems exist for the production of the polypeptides of the invention. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

One particular bacterial expression system for polypeptide production is the *E. coli* pET expression system (e.g., pET-28) (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains that express T7 RNA polymerase in response to IPTG induction. Once produced, recombinant polypeptide is then isolated according to standard methods known in the art, for example, those described herein.

Another bacterial expression system for polypeptide production is the pGEX expression system (Pharmacia). This system employs a GST gene fusion system that is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

Alternatively, recombinant polypeptides of the invention are expressed in *Pichia pastoris*, a methylotrophic yeast. *Pichia* is capable of metabolizing methanol as the sole carbon source. The first step in the metabolism of methanol is the oxidation of methanol to formaldehyde by the enzyme, alcohol oxidase. Expression of this enzyme, which is coded for by the AOX1 gene is induced by methanol. The AOX1 promoter can be used for inducible polypeptide expression or the GAP promoter for constitutive expression of a gene of interest.

Once the recombinant polypeptide of the invention is expressed, it is isolated, for example, using affinity chromatography. In one example, an antibody (e.g., produced as described herein) raised against a polypeptide of the invention may be attached to a column used to isolate the recombinant polypeptide. Lysis and fractionation of polypeptide-harboring cells prior to affinity chromatography may be performed by standard methods (see, e.g., Ausubel et al., supra). Alternatively, the polypeptide is isolated using a sequence tag, such as a hexahistidine tag (SEQ ID NO: 2314), that binds to nickel column.

Once isolated, the recombinant protein can, if desired, be further purified, e.g., by high performance liquid chromatography (see, e.g., Fisher, *Laboratory Techniques In Biochemistry and Molecular Biology*, eds., Work and Burdon, Elsevier, 1980). Polypeptides of the invention, particularly short peptide fragments, can also be produced by chemical synthesis (e.g., by the methods described in *Solid Phase Peptide Synthesis,* 2nd ed., 1984 The Pierce Chemical Co., Rockford, Ill.). These general techniques of polypeptide expression and purification can also be used to produce and isolate useful peptide fragments or analogs (described herein).

Combinatorial Peptide Libraries

In addition to the synthetic solid state production of small peptides, the amino acid sequences of predicted fragments can be expressed and produced recombinantly using a variety of genetically modified organisms following insertion of the relevant DNA into their genome. One such widely used organism is *Escherichia coli.* Combinatorial biology depends on the ability to link peptides to their encoding DNA and create large libraries of encoded peptides. The methods for generating DNA-encoded peptide libraries can be divided into two groups. In vitro methods use libraries in which the peptides are accessible to exogenous ligands or cells. These libraries can be used in direct in vitro binding selections with cell cultures to enrich for peptides that induce particular phenotypes. In contrast, in vivo methods use peptide libraries that are expressed inside living cells. An interaction between a particular library member and the target protein is detected by virtue of an effect on the host cell, such as a selective growth advantage, or changes to a physical property of the host cell (Pelletier and Sidhu, *Curr Opin Biotechnol,* 12:340-7, 2001).

To optimize a set of peptides, such as those peptides identified herein, in vitro methods for creating and testing peptide libraries are suitable. In one embodiment, oligonucleotide directed mutagenesis of initial sequence is used. In another embodiment, a phage is used to display libraries of peptides.

Oligonucleotide Directed Mutagenesis

Oligonucleotide directed mutagenesis can be used in order to modify a single or multiple amino acids that compose the maternal sequence of the predicted anti-angiogenic fragments (Ryu and Nam, *Biotechnol Prog,* 16:2-16, 2000). Directed mutagenesis is based on the concept that an oligonucleotide encoding a desired mutation is annealed to one strand of a DNA of interest and serves as a primer for initiation of DNA synthesis. In this manner, the mutagenic oligonucleotide is incorporated into the newly synthesized strand. Mutagenic oligonucleotides incorporate at least one base change but can be designed to generate multiple substitutions, insertions or deletions.

Oligonucleotides can also encode a library of mutations by randomizing the base composition at sites during chemical synthesis resulting in degenerate oligonucleotides. The ability to localize and specify mutations is greatly enhanced by the use of synthetic oligonucleotides hybridized to the DNA insert-containing plasmid vector. The general format for site-directed mutagenesis includes several steps. Plasmid DNA containing the template of interest (cDNA) is denatured to produce single-stranded regions. A synthetic mutant oligonucleotide is annealed to the target strand. DNA polymerase is used to synthesize a new complementary strand, and finally DNA ligase is used to seal the resulting nick between the end of the new strand and the oligonucleotide. The resulting heteroduplex is propagated by transformation in *E. coli*.

Phage-Displayed Peptide Library Screening

Phage display is one method for in vitro combinatorial biology. The method stems from the observation that peptides fused to certain bacteriophage coat proteins are displayed on the surfaces of phage particles that also contain the cognate DNA (Landon et al., *Curr Drug Discov Technol,* 1:113-32, 2004).

Phage display describes a selection technique in which a library of variants of an initial peptide (e.g., a peptide described herein), is expressed on the outside of a phage virion, while the genetic material encoding each variant resides on the inside. This creates a physical linkage between each variant protein sequence and the DNA encoding it, which allows rapid partitioning based on binding affinity to a given target molecule by an in vitro selection process called panning. In its simplest form, panning is carried out by incubating a library of phage-displayed peptides with a plate containing a culture of cells, such as endothelial cells, washing away the unbound phage, and eluting the specifically bound phage. The eluted phage is then amplified and taken through additional binding/amplification cycles to enrich the pool in favor of specific phenotypes, such as suppression of proliferation, of the cells that are cultured. After 3-4 rounds, individual clones are characterized by DNA sequencing and ELISA.

Libraries of "fusion phages" are rapidly sorted to obtain clones with desired properties and phages can be readily amplified by passage through a bacterial host. Phage display was first demonstrated with the *Escherichia-coli*-specific M13 bacteriophage and this remains the most popular platform. Several other *E. coli* phages have also been adapted for phage display and eukaryotic systems have also been developed.

Screening Assays

Polypeptides and fragments of the invention are useful as targets for the identification of agents that modulate angiogenesis. In particular, the peptides identified herein are typically polypeptide fragments that are hidden within hydrophobic regions of a larger polypeptide. While the entire polypeptide may be pro-angiogenic, the peptides of the invention are typically anti-angiogenic. As such, the activity of these peptides, when exposed to the cellular or extracellular milleau, may reduce the pro-angiogenic function of the larger polypeptide. Where this antagonistic function is undesirable, agents that bind and/or inhibit the biological activity of these peptides are sought. Once identified, such agents are used to enhance angiogenesis. In another approach, anti-angiogenic agents are identified by screening for agents that bind to and enhance the activity of a peptide of the invention. Once identified, such agents are used to reduce angiogenesis.

Alternatively, or in addition, candidate agents may be identified that specifically bind to and inhibit a peptide of the invention. The efficacy of such a candidate compound is dependent upon its ability to interact with the peptide. Such an interaction can be readily assayed using any number of standard binding techniques and functional assays (e.g., those described in Ausubel et al., supra). For example, a candidate compound may be tested in vitro for interaction and binding with a polypeptide of the invention and its ability to modulate angiogenesis may be assayed by any standard assays (e.g., those described herein).

Potential antagonists include organic molecules, peptides, peptide mimetics, polypeptides, nucleic acid ligands, aptamers, and antibodies that bind to a peptide of the invention and thereby inhibit or extinguish its activity. Potential antagonists also include small molecules that bind to and occupy the binding site of the polypeptide thereby preventing binding to cellular binding molecules, such that normal biological activity is prevented.

In one particular example, a candidate compound that binds to a pathogenicity polypeptide may be identified using a chromatography-based technique. For example, a recombinant polypeptide of the invention may be purified by standard techniques from cells engineered to express the polypeptide, or may be chemically synthesized, once purified the peptide is immobilized on a column. A solution of candidate compounds is then passed through the column, and a compound specific for the peptide is identified on the basis of its ability to bind to the peptide and be immobilized on the column. To isolate the compound, the column is washed to remove non-specifically bound molecules, and the compound of interest is then released from the column and collected. Compounds isolated by this method (or any other appropriate method) may, if desired, be further purified (e.g., by high performance liquid chromatography). In addition, these candidate compounds may be tested for their ability to modulate angiogenesis (e.g., as described herein). Compounds isolated by this approach may also be used, for example, as therapeutics to treat or prevent the onset of a disease or disorder characterized by excess or undesirable angiogenesis. Compounds that are identified as binding to peptides with an affinity constant less than or equal to 1 nM, 5 nM, 10 nM, 100 nM, 1 mM or 10 mM are considered particularly useful in the invention.

Methods of the invention are useful for the high-throughput low-cost screening of polypeptides, biologically active fragments or analogs thereof that can be used to modulate angiogenesis. One skilled in the art appreciates that the effects of a candidate peptide on a cell (e.g., an endothelial cell) are typically compared to a corresponding control cell not contacted with the candidate peptide. Thus, the screening methods include comparing the expression profile, phenotype, or biological activity of a cell modulated by a candidate peptide to a reference value of an untreated control cell.

In one example, candidate peptides are added at varying concentrations to the culture medium of an endothelial cell. The survival, tube formation, apoptosis, proliferation, migration of the cell are assayed as indicators of angiogenesis. Peptides that reduce the survival, tube formation, proliferation, or migration of an endothelial cell are identified as useful anti-angiogenic agents. Alternatively, peptides that enhance the survival, tube formation, proliferation, or migration of an endothelial cell are identified as useful angiogenic agents. In another embodiment, the expression of a nucleic acid molecule or polypeptide characteristic of the vasculature is monitored. Typical cell surface markers include the fibronectin extra-domain B, large tenascin-C isoforms, various integrins, VEGF receptors, prostate specific membrane antigen, endoglin and CD44 isoforms and tumor endothelium marker (TEM). Peptides or other agents that alter the expression of such markers are identified as useful modulators of angiogenesis. An agent that reduces the expression of a characteristic polypeptide expressed in the vasculature is considered useful in the invention; such an agent may be used, for example, as a therapeutic to prevent, delay, ameliorate, stabilize, or treat an injury, disease or disorder characterized by an undesirable increase in neovascularization. In other embodiments, agents that increase the expression or activity of a marker characteristically expressed in an endothelial cell are used to prevent, delay, ameliorate, stabilize, or treat an injury, disease or disorder characterized by a reduction in angiogenesis. Agents identified according to the methods described herein maybe administered to a patient in need of angiogenesis modulation. Where such agents are peptides, such as those described herein, one skilled in the art appreciates that the invention further provides nucleic acid sequences encoding such peptides (e.g., a peptide shown in Tables 1-10).

Test Compounds and Extracts

In general, peptides are identified from large libraries of natural product or synthetic (or semi-synthetic) extracts or chemical libraries or from polypeptide or nucleic acid libraries, according to methods known in the art. Such candidate polypeptides or the nucleic acid molecules encoding them may be modified to enhance biodistribution, protease resistance, or specificity. The modified peptides are then screened for a desired activity (e.g., angiogenesis modulating activity). Those skilled in the field of drug discovery and development will understand that the precise source of test extracts or compounds is not critical to the screening procedure(s) of the invention. Agents used in screens may include known compounds (for example, known polypeptide therapeutics used for other diseases or disorders). Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as the modification of existing polypeptides.

Libraries of natural polypeptides in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Such polypeptides can be modified to include a protein transduction domain using methods known in the art and described herein. In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994. Furthermore, if desired, any library or compound is readily modified using standard chemical, physical, or biochemical methods.

Numerous methods are also available for generating random or directed synthesis (e.g., semi-synthesis or total synthesis) of any number of polypeptides, chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2nd ed., John Wiley and Sons (1991); L. Fieser and M. Fieser, Fieser and Fieser's *Reagents for Organic Synthesis*, John Wiley and Sons (1994); and L. Paquette, ed., *Encyclopedia of Reagents for Organic Synthesis*, John Wiley and Sons (1995), and subsequent editions thereof.

Libraries of compounds may be presented in solution (e.g., Houghten, *Biotechniques* 13:412-421, 1992), or on beads (Lam, *Nature* 354:82-84, 1991), chips (Fodor, *Nature* 364: 555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222:301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is found to have angiogenesis modulating activity further fractionation of the positive lead extract is necessary to isolate molecular constituents responsible for the observed effect. Thus, the goal of the extraction, fractionation, and purification process is the careful characterization and identification of a chemical entity within the crude extract that alters angiogenesis (increases or decreases). Methods of fractionation and purification of such heterogeneous extracts are known in the art. If desired, compounds shown to be useful as therapeutics are chemically modified according to methods known in the art.

Therapeutic Methods

Therapeutic polypeptides, peptides, or analogs or fragments thereof, as well as the nucleic acid molecules encoding such molecules are useful for preventing or ameliorating a disease or injury associated with an undesirable increase or decrease in angiogenesis. Diseases and disorders characterized by excess angiogenesis may be treated using the methods and compositions of the invention. Such diseases and disorders include, but are not limited to, neoplasia, hematologic malignancies, rheumatoid arthritis, diabetic retinopathy, age-related macular degeneration, atherosclerosis, and pathologic obesity. In one embodiment, a peptide of the invention is delivered to one or more endothelial cells at a site of angiogenesis-associated disease or injury.

In other embodiments, a nucleic acid molecule encoding a peptide of the invention is administered to a cell, tissue, or organ in need of a reduction in angiogenesis. If desired, the peptide is expressed as a fusion with a longer polypeptide. The peptide may then be cleaved from the polypeptide to achieve its desired therapeutic effect. Such cleavage is not required where the fusion protein does not interfere with the peptide's biological activity.

Transducing viral (e.g., retroviral, adenoviral, and adeno-associated viral) vectors can be used for somatic cell gene therapy, especially because of their high efficiency of infection and stable integration and expression (see, e.g., Cayouette et al., *Human Gene Therapy* 8:423-430, 1997; Kido et al., *Current Eye Research* 15:833-844, 1996; Bloomer et al., *Journal of Virology* 71:6641-6649, 1997; Naldini et al., *Science* 272:263-267, 1996; and Miyoshi et al., *Proc. Natl. Acad. Sci. U.S.A.* 94:10319, 1997). For example, a full length gene sialidase gene, or a portion thereof, can be cloned into a retroviral vector and expression can be driven from its endogenous promoter, from the retroviral long terminal repeat, or from a promoter specific for a target cell type of interest (e.g. endothelial cell). Other viral vectors that can be used include, for example, a vaccinia virus, a bovine papilloma virus, or a herpes virus, such as Epstein-Barr Virus (also see, for example, the vectors of Miller, *Human Gene Therapy* 15-14, 1990; Friedman, *Science* 244:1275-1281, 1989; Eglitis et al., *BioTechniques* 6:608-614, 1988; Tolstoshev et al., *Current Opinion in Biotechnology* 1:55-61, 1990; Sharp, *The Lancet* 337:1277-1278, 1991; Cornetta et al., *Nucleic Acid Research and Molecular Biology* 36:311-322, 1987; Anderson, *Science* 226:401-409, 1984; Moen, *Blood Cells* 17:407-416, 1991; Miller et al., *Biotechnology* 7:980-990, 1989; Le Gal La Salle et al., *Science* 259:988-990, 1993; and Johnson, *Chest* 107:77 S-83S, 1995). Retroviral vectors are particularly well developed and have been used in clinical settings (Rosenberg et al., *N. Engl. J. Med* 323:370, 1990; Anderson et al., U.S. Pat. No. 5,399,346). Most preferably, a viral vector is used to administer the gene of interest systemically or to a cell at the site of neovascularization.

Non-viral approaches can also be employed for the introduction of therapeutic to a cell of a patient having an angiogenesis related disease. For example, a nucleic acid molecule can be introduced into a cell by administering the nucleic acid in the presence of lipofectin (Feigner et al., *Proc. Natl. Acad. Sci. U.S.A.* 84:7413, 1987; Ono et al., *Neuroscience Letters* 17:259, 1990; Brigham et al., *Am. J. Med. Sci.* 298:278, 1989; Staubinger et al., *Methods in Enzymology* 101:512, 1983), asialoorosomucoid-polylysine conjugation (Wu et al., *Journal of Biological Chemistry* 263:14621, 1988; Wu et al., *Journal of Biological Chemistry* 264:16985, 1989), or by micro-injection under surgical conditions (Wolff et al., *Science* 247:1465, 1990). Preferably the nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of normal genes into the affected tissues of a patient can also be accomplished by transferring a normal nucleic acid into a cultivatable cell type ex vivo (e.g., an autologous or heterologous primary cell or progeny thereof), after which the cell (or its descendants) are injected into a targeted tissue at the site of disease or injury.

cDNA expression for use in such methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types, such as an intestinal epithelial cell, can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Another therapeutic approach included in the invention involves administration of a recombinant therapeutic, such as a sialidase polypeptide, biologically active fragment, or variant thereof, either directly to the site of a potential or actual disease-affected tissue (for example, by administration to the intestine) or systemically (for example, by any conventional recombinant protein administration technique). The dosage of the administered protein depends on a number of factors, including the size and health of the individual patient. For any particular subject, the specific dosage regimes should be adjusted over time according to the individual need and the professional judgment of the person administering or supervising the administration of the compositions. Generally, between 0.1 mg and 100 mg, is administered per day to an adult in any pharmaceutically acceptable formulation.

Pharmaceutical Therapeutics

The invention provides a simple means for identifying compositions (including nucleic acids, peptides, small molecule inhibitors, and mimetics) capable of acting as therapeutics for the treatment of a disease associated with altered levels of angiogenesis. Accordingly, a chemical entity discovered to have medicinal value using the methods described herein is useful as a drug or as information for structural modification of existing compounds, e.g., by rational drug design. Such methods are useful for screening compounds having an effect on a variety of conditions characterized by undesired angiogenesis.

For therapeutic uses, the compositions or agents identified using the methods disclosed herein may be administered systemically, for example, formulated in a pharmaceutically-acceptable buffer such as physiological saline. Preferable routes of administration include, for example, subcutaneous, intravenous, interperitoneally, intramuscular, or intradermal injections that provide continuous, sustained levels of the drug in the patient. Treatment of human patients or other animals will be carried out using a therapeutically effective amount of a therapeutic agent described herein in a physiologically-acceptable carrier. Suitable carriers and their formulation are described, for example, in *Remington's Pharmaceutical Sciences* by E. W. Martin. The amount of the therapeutic agent to be administered varies depending upon the manner of administration, the age and body weight of the patient, and with the clinical symptoms of the disease or disorder. Generally, amounts will be in the range of those used for other agents used in the treatment of other diseases associated with alterations in angiogenesis, although in certain instances lower amounts will be needed because of the increased specificity of the compound. A compound is administered at a dosage that controls the clinical or physiological symptoms associated with angiogenesis as determined by a diagnostic method known to one skilled in the art.

It would be advantageous to administer therapeutic peptides in a formulation that would slow their elimination from the circulation through renal filtration, enzymatic degradation, uptake by the reticulo-endothelial system (RES), and accumulation in non-targeted organs and tissues. In addition, methods for administering agents that limits their widespread distribution in non-targeted organs and tissues allows lower concentrations of the agent to be administered reducing adverse side-effects and providing economic benefits. A variety of methods are available to slow the elimination of agents of the invention. In one embodiment, an implantable device is used to provide for the controlled release of an agent described herein. Such devices are known in the art and include, but are not limited to, polymeric gels and microfabricated chips. Some of these devices are already used in the clinic or are being tested in clinical trials (Moses et al., *Cancer Cell,* 4:337-41, 2003). Various delivery methods for anti-angiogenic agents are tissue specific, e.g., intraocular and periocular injection or gene transfer in the eye (Akiyama et al., *J Cell Physiol,* 2006; Saishin et al., *Hum Gene Ther,* 16:473-8, 2005). Numerous reviews on the subject of anti-angiogenic drug delivery are available.

Enhanced Permeability and Retention Effect

For the treatment of neoplasia or sites of neovascularization, the "enhanced permeability and retention effect" (EPR) constitutes a natural mechanism through which high molecular weight (40 kDa or higher) macromolecules with long circulation half-lives, including peptides and proteins conjugated with water-soluble polymers, accumulate (Shukla and Krag, *Expert Opin Biol Ther,* 6:39-54, 2006; Torchilin and Lukyanov, *Drug Discov Today,* 8:259-66, 2003). This effect occurs because of certain characteristics of those tissues. The first is that tumor or newly formed vasculature, unlike the vasculature of healthy tissues, is permeable to macromolecules with a MW up to 50 kDa or even higher. This allows macromolecules to enter into the interstitial space. Another characteristic is that in the case of many tumors the lymphatic system, which is responsible for the drainage of macromolecules from normal tissues, is impaired. Because of this, macromolecules that have entered a neo-vascularized tissue are retained there for a prolonged time. To enhance the retention of a low MW peptide described herein, the peptide may be conjugated to a suitable polymer or delivered using a micro-reservoir system.

Peptide and Protein Polymer Conjugation

Mechanisms that increase the MW of a peptide, such as conjugation with polymer chains or concentration of the drug in micro-reservoir systems tend to increase the retention time of the peptide in the tissue (Duncan, *Nat Rev Drug Discov,* 2:347-60, 2003). Moreover, renal filtration and excretion are mainly responsible for the rapid clearance from the systemic circulation of proteins with molecular weights (MW) of 40 kDa or lower. Rapid clearance and increased retention of a peptide of interest can be achieved by conjugating the peptides with water-soluble polymers. Preferably, the peptide-polymer conjugate has a molecular weight of at least about 30 kDA, 35 kDa, 40 kDa, 50 kDa, 75 kDa, or 100 kDa. Additional benefits of peptide and protein-polymer conjugation include increased resistance to enzymatic degradation and reduced immunogenicity.

Even endogenous proteins can be susceptible to protease degradation in the bloodstream and interstitial space or induce an immune response. Enzymatic degradation and an immune response against a protein result in its rapid elimination from the systemic circulation. In addition, the development of an immune response is potentially dangerous because of the possibility of allergic reactions and anaphylactic shock upon repetitive administrations. The mechanism of protein protection by polymer attachment is similar in both cases. Polymer molecules attached to the protein create steric hindrances, which interfere with binding to the active sites of proteases, and antigen-processing cells. Examples of peptide/protein-polymer conjugation include conjugates with poly(ethylene glycol) and conjugates with poly(styrene-co-maleic acid anhydride).

Conjugates with Poly(Ethylene Glycol)

Several polymers have been used for protein stabilization with varying degrees of success. Poly(ethylene glycol) (PEG) is one widely used polymer for the modification of proteins with therapeutic potential (Thanou and Duncan, *Curr Opin Investig Drugs,* 4:701-9, 2003; Vicent and Duncan, *Trends Biotechnol,* 24:39-47, 2006). This polymer is inexpensive, has low toxicity and has been approved for internal applications by drug regulatory agencies. PEG is commercially available in a variety of molecular weights and in chemically activated, ready-for-use forms for covalent attachment to proteins.

Conjugates with Poly(Styrene-Co-Maleic Acid Anhydride)

In some cases, the circulation time of drugs can be increased by conjugating with polymers that are not large enough to prevent renal clearance themselves, but which can attach themselves, with their conjugated drug, to natural long-circulating blood plasma components, such as serum albumin or lipoproteins (Thanou and Duncan, *Curr Opin Investig Drugs,* 4:701-9, 2003; Vicent and Duncan, *Trends Biotechnol,* 24:39-47, 2006).

Because of the small size and low molecular weight of the identified anti-angiogenic peptides and the high probability that the conjugated polymers, which are orders of magnitude larger than the peptides, may sterically hinder the activity of the fragments the method of protein conjugation may not be the most efficient method for increasing the retention of the agent in the neo-vascular site. A more attractive scenario is the administration of the peptide in a micro-reservoir delivery system.

Formulation of Pharmaceutical Compositions

The administration of a compound for the treatment of a disease or disorder associated with altered levels of angiogenesis may be by any suitable means that results in a concentration of the therapeutic that, combined with other components, is effective in ameliorating, reducing, or stabilizing a disease or disorder associated with altered levels of angiogenesis (e.g., an amount sufficient to reduce neovascularization). The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., *Remington: The Science and Practice of Pharmacy* (20th ed.), ed. A. R. Gennaro, Lippincott Williams & Wilkins, 2000 and *Encyclopedia of Pharmaceutical Technology*, eds. J. Swarbrick and J. C. Boylan, 1988-1999, Marcel Dekker, New York).

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in the central nervous system or cerebrospinal fluid; (v) formulations that allow for convenient dosing, such that doses are administered, for example, once every one or two weeks; and (vi) formulations that allow for convenient dosing for metronomic therapy that would require taking small doses of the drug several times a week; (vii) formulations that target a disease or disorder associated with altered levels of angiogenesis by using carriers or chemical derivatives to deliver the therapeutic agent to a particular cell type (e.g., endothelial cell) whose function is perturbed in a disease or disorder associated with altered levels of angiogenesis.

For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question.

In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Micro-Reservoir Delivery Systems

For some applications, micro-reservoir or micro-particulate carriers are used to deliver a peptide of the invention. Such systems include, but are not limited to, liposomes, micelles, polymer micro-particles, and cell ghosts. The use of such carriers results in a much higher ratio of active agent over carrier compared with direct molecular conjugates. They also provide a higher degree of protection against enzymatic degradation and other destructive factors upon parenteral administration because the carrier wall completely isolates drug molecules from the environment. An additional advantage of these carriers is that a single carrier can deliver multiple drug species so that they can be used in combination therapies. All micro-particulates are too large to be lost by renal filtration (Thanou and Duncan, *Curr Opin Investig Drugs,* 4:701-9, 2003). Exemplary micro-particulate delivery systems include, but are not limited to, liposomes and micelles.

Liposomes

Among particulate drug carriers, liposomes are the most extensively studied and possess suitable characteristics for peptide and protein encapsulation. Liposomes are vesicles formed by concentric spherical phospholipid bilayers encapsulating an aqueous space (Moses et al., *Cancer Cell,* 4:337-41, 2003). These particles are biocompatible, biologically inert and cause little toxic or antigenic reactions. Their inner aqueous compartment can be used for encapsulation of peptides and proteins. Many techniques for liposome preparation require only manipulations that are compatible with peptide and protein integrity (Allen and Cullis, *Science,* 303:1818-22, 2004). As with other micro-particulate delivery systems, cells of the RES rapidly eliminate conventional liposomes.

In one embodiment, surface-modified long-circulating liposomes grafted with a flexible hydrophilic polymer, such as PEG, are used. This approach prevents plasma protein adsorption to the liposome surface and the subsequent recognition and uptake of liposomes by the RES. Liposomes, in common with protein conjugated macromolecules, can accumulate in tumors of various origins via the EPR effect. Currently, liposomal forms of at least two conventional anticancer drugs, daunorubicin and doxorubicin, are used in the clinic (Torchilin and Lukyanov, *Drug Discov Today,* 8:259-66, 2003).

Micelles

In another approach, micelles or polymeric micelles, including those prepared from amphiphilic PEG-phospholipid conjugates, may be used to deliver an agent of the invention. Such formulations are of special interest because of their stability (Torchilin and Lukyanov, *Drug Discov Today,* 8:259-66, 2003). These particles are smaller than liposomes and lack the internal aqueous space. To load micelles, peptides can be attached to the surface of these particles or incorporated into them via a chemically attached hydrophobic anchor. An example of a biodegradable micelle developed for delivery of pharmacological agents are the poly{[(cholesteryl oxocarbonylamido ethyl) methyl bis(ethylene) ammonium iodide]ethyl phosphate} (PCEP) micelles (Wen, Mao et al., *J Pharm Sci.* 93:2142-57, 2004). Carrying a positive charge in its backbone and a lipophilic cholesterol structure in the side chain, PCEP self-assembles into micelles in aqueous buffer at room temperature with an average size of 60-100 nm. PCEP is an excellent platform for delivering ant-angiogenic agents as by itself shows lower cytotoxicity for endothelial cells than for poly-L-lysine and Lipofectamine.

Nanoparticles

An increasing number of agents are delivered with colloidal nanoparticles. Such formulations overcome non-cellular and cellular based mechanisms of resistance and increase the selectivity of agents to target cells while reducing their toxicity in normal tissues. Nanoparticles are typically submicron (<1 μm) colloidal systems. In some embodiments, nanoparticles are made of polymers (biodegradable or not). According to the process used for the preparation of the nanoparticles, nanospheres or nanocapsules can be obtained. Unlike nanospheres (matrix systems in which the drug is dispersed throughout the particles), nanocapsules are vesicular systems in which an agent is confined to an aqueous or oily cavity surrounded by a single polymeric membrane. Nanocapsules are one form of 'reservoir' system.

In some embodiments, nanoparticles are generated using hydrophilic polymers, (poly(ethylene glycol) (PEG), poloxamines, poloxamers, polysaccharides) to efficiently coat a nanoparticle surface. These coatings provide a dynamic 'cloud' of hydrophilic and neutral chains at the particle surface that repels plasma proteins. Hydrophilic polymers are introduced at the surface in two ways, either by adsorption of surfactants or by use of block or branched copolymers.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active therapeutic(s), the composition may include suitable parenterally acceptable carriers and/or excipients. The active therapeutic(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active angiogenic modulating therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug may be incorporated in biocompatible carriers, liposomes, nanoparticles, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Solid Dosage Forms for Oral Use

Formulations for oral use include tablets containing the active ingredient(s) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate may be employed.

The solid tablet compositions may include a coating adapted to protect the composition from unwanted chemical changes, (e.g., chemical degradation prior to the release of the active angiogenic modulating therapeutic). The coating may be applied on the solid dosage form in a similar manner as that described in *Encyclopedia of Pharmaceutical Technology*, supra.

At least two active angiogenic modulating therapeutics may be mixed together in the tablet, or may be partitioned. In one example, the first active in angiogenic modulating therapeutic is contained on the inside of the tablet, and the second active angiogenic modulating therapeutic is on the outside, such that a substantial portion of the second angiogenic modulating therapeutic is released prior to the release of the first angiogenic modulating therapeutic.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms

Controlled release compositions for oral use are constructed to release the active angiogenic modulating therapeutic by controlling the dissolution and/or the diffusion of the active substance. Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more therapeutic compounds may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the compound(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Polymeric Controlled-Release Implants

In another embodiment, an agent of the invention is delivered by implanting a biodegradable polymeric controlled-release device that stores the pharmaceutical agent and allows its delivery via diffusion into the surrounding tissue. Controlled release devices include Norplant and Gliadel, which are used clinically for the prevention of pregnancy and for brain tumor therapy, respectively. Local delivery of pro- or anti-angiogenic factors can be accomplished by encapsulating the agent within a biocompatible polymer matrix. The controlled-release polymer system is then implanted at the desired tissue site, where it releases the soluble factor directly into the interstitial space of the tissue. The diffusible agent can influence the survival or function of damaged cells within the local tissue, or provide a signal that elicits cell proliferation and migration or apoptosis and suppression of migration within the tissue region.

Controlled release implants are typically composed of inert, biocompatible polymers, such as poly(ethylene-co-vinyl acetate) (EVAc), or biodegradable polymers, such as poly (lactide-co-glycolide) (PLGA) (Torchilin and Lukyanov, *Drug Discov Today,* 8:259-66, 2003). EVAc-matrix systems have been used to release protein hormones, growth factors, antibodies, antigens and DNA. EVAc matrices allow a high degree of control over agent release, versatility in allowing the release of a wide range of agents, and good retention of biological activity. Biodegradable polymers have also been used to release growth factors, protein hormones, antibodies, antigens and DNA. Biodegradable materials disappear from the implant site after protein release. Polymer gels might also be useful for topical or localized protein delivery. Systems that release multiple protein factors are also possible (Saltzman and Olbricht, *Nat Rev Drug Discov,* 1:177-86, 2002; Torchilin and Lukyanov, *Drug Discov Today,* 8:259-66, 2003).

Biodegradable polymers include non-water-soluble polymers that are degraded by surface or bulk erosion in addition to water-soluble gels that dissolve and are cleared from the body without undergoing a decrease in molecular weight. There are many different types of biodegradable polymers that can potentially be used in the preparation of peptide delivery systems. They include both naturally derived and synthetic materials.

Biocompatibility of Polymeric Systems

Polymers used as drug delivery systems for protein pharmaceuticals need to exhibit biocompatible characteristics in terms of both the polymer's effect on the organism receiving the drug delivery system and the polymer's effect on the protein to be delivered. Several aspects of a polymeric delivery system ultimately contribute to its overall biocompatibility, or lack thereof. The polymer itself, which consists of a repeating monomeric species, may potentially be antigenic, carcinogenic, or toxic or have some inherent incompatibility with organisms. The shape of an implanted material has been implicated in its biocompatibility as well, smooth surfaces being less irritating and more biocompatible than rough surfaces (Saltzman and Olbricht, *Nat Rev Drug Discov,* 1:177-86, 2002).

Pharmaceutical Stability

Interactions between proteins and polymeric materials appear to be protein and polymer specific. At issue are the protein molecular weight, which is an important parameter with regard to diffusion characteristics and the iso-electric point of the protein (and polymer as well in some cases), which governs charge-charge interactions (protein-polymer and protein-protein). Moreover the presence of cysteines on the protein may facilitate the formation of intermolecular (i.e., protein-polymer) disulfide bonds. Furthermore, the primary amino acid sequence of the protein may be rendered susceptible to chemical modification in association with a polymeric material. The presence or absence of carbohydrates on the protein may enhance or prevent interaction with polymeric materials and affect the protein's hydrodynamic volume. The relative hydrophobicity of a protein could interact with hydrophobic sites on a polymer. Finally the heterogeneity of protein pharmaceuticals often exists for proteins produced by recombinant methods (Bilati et al., *Eur J Pharm Biopharm,* 59:375-88, 2005; Gombotz and Pettit, *Bioconjug Chem,* 6:332-51, 1995; Saltzman and Olbricht, *Nat Rev Drug Discov,* 1:177-86, 2002).

Bulk Erosion Polymers

Poly(Lactic-Co-Glycolic Acid)

Poly(lactic-co-glycolic acid) (PLGA) has been used successfully for several decades in biodegradable structures and more recently as drug delivery micro-carriers, and as a result of the extended use, much is known about their biocompatibility and physicochemical characteristics. PLGA copolymers are well suited for use in delivery systems since they can be fabricated into a variety of morphologies including films, rods, spheres by solvent casting, compression molding and solvent evaporation techniques. Examples of peptide drug delivery systems made from PLGA copolymers, have successfully met FDA approval and they are available as marketed products are Lupron Depot, Zoladex and Decapeptyl (Frokjaer and Otzen, *Nat Rev Drug Discov,* 4:298-306, 2005).

Block Copolymers of PEG and PLA

Copolymers of PEG and PLA have been synthesized for use in delivery systems. The net result is a biodegradable polymer with a reduced amount of hydrophobicity that is an inherent property of PLA systems. These copolymer systems can be composed of random blocks of the two polymers, two blocks in which case the molecules are amphiphilic, or triblocks in which hydrophilic microphases are present. Peptides that are incorporated into devices made from these copolymers are less likely to adsorb to the delivery system through hydrophobic interactions. The polymers were shown to swell very rapidly due to microphase separation, and degradation occurred over 2-3 weeks (Bilati et al., *Eur J Pharm Biopharm,* 59:375-88, 2005; Gombotz and Pettit, *Bioconjug Chem,* 6:332-51, 1995).

Poly(Cyanoacrylates)

Poly(cyanoacrylates) have received attention as delivery systems for proteins and peptides. They undergo spontaneous polymerization at room temperature in the presence of water, and their erosion has been shown to be controlled by the length of the monomer chain and the pH. Once formed, the polymer is slowly hydrolyzed, leading to a chain scission and liberation of formaldehyde. While the polymers are not toxic, the formaldehyde released as the degradation byproduct does create a toxicity concern. A characteristic example of their use are delivery systems for insulin prepared by the interfacial emulsion polymerization of alkyl cyanoacrylate (Gombotz and Pettit, *Bioconjug Chem,* 6:332-51, 1995).

Surface Erosion Polymers

Poly(Anhydrides)

Poly(anhydrides) represent a class of surface eroding polymers. Hydrolysis of the anhydride bond is suppressed by acid, which results in an inhibition of bulk erosion by the acidity of the carboxylic acid products of the polymer hydrolysis process. By varying the ratio of their hydrophobic components, one can control degradation rates ranging from days to years. Several proteins have been successfully incorporated into, and released, from poly-(anhydride) delivery systems. The incorporation of insulin and myoglobin has successfully been achieved in poly(anhydride) microspheres using both a hot-melt microencapsulation technique or microencapsulation by solvent removal (Gombotz and Pettit, *Bioconjug Chem,* 6:332-51, 1995).

Poly(Ortho Esters)

Poly(ortho esters) are another example of surface-eroding polymers that have been developed for drug delivery systems. Several proteins and peptides have been incorporated into poly(ortho-ester) delivery systems including the LHRH analog nafarelin, insulin and lysozyme.

Hydrogels

The use of biodegradable hydrogels as delivery systems for proteins is of particular interest due to their biocompatibility and their relative inertness toward protein drugs (Gombotz and Pettit, *Bioconjug Chem,* 6:332-51, 1995). Hydrogels are the only class of polymer that can enable a protein to permeate through the continuum of the carrier. The initial release rate of proteins from biodegradable hydrogels is therefore generally diffusion controlled through the aqueous channels of the gel and is inversely proportional to the molecular weight of the protein. Once polymer degradation occurs, and if protein still remains in the hydrogel, erosion-controlled release may contribute to the system. Several disadvantages must be considered when using a biodegradable hydrogel system for the release of proteins. Their ability to rapidly swell with water can lead to very fast release rates and polymer degradation rates. In addition, hydrogels can rapidly decrease in mechanical strength upon swelling with water. Examples of hydrogels include, pluronic polyols, poly(vinyl alcohol), poly(vinylpyrrolidone), malein anhydride, callulose, hyaluronic acid derivatives, alginate, collagens, gelatin, starches and dextrans.

Selective Drug Delivery

Selective delivery of therapeutic agents includes any methodology by which the functional concentration of drug is higher at the target site than in normal tissue. A wide variety of methods may fall under the category of "selective delivery," including interventions as simple and mechanical as selective vascular administration in which the drug is physically isolated in a neovascularized area. An example of that type of mechanical selectivity is also the EPR effect.

Most strategies, however, are pharmaceutical. In these approaches, the differences in the biochemical and physiological nature of normal and the targeted cells and their microenvironment are exploited for selective delivery. In one embodiment, a carrier is used to deliver a peptide of the invention that because of its physical properties, accumulates preferentially at a target site. In another embodiment, a ligand is conjugated to a peptide of the invention that binds to a tissue-associated antigen. In another embodiment, an agent of the invention is maintained in an inactive form that can be activated preferentially at the tissue site. In yet another embodiment, external energy irradiation is used to release a peptide at the delivery site.

A variety of technologies using combinations of different approaches are constantly being developed for selective delivery of therapeutics. These delivery systems employ different targets such as cancer cell and neovascular antigens, hypoxia, or high osmotic pressure; targeting agents such as monoclonal antibodies (mAbs), single chain variable fragments (scFvs), peptides and oligonucleotides; effectors like chemical or biological toxins, radioisotopes, genes, enzymes, immunomodulators, oligonucleotides, imaging and diagnostic agents; vehicles the already mentioned colloidal systems, including liposomes, emulsions, micelles, nanoparticles, polymer conjugates or implants; and drug-releasing switches such as systems that utilize thermal, radiation, ultrasound or magnetic fields (Allen and Cullis, *Science,* 303:1818-22, 2004; Gombotz and Pettit, *Bioconjug Chem,* 6:332-51, 1995; Moses et al., *Cancer Cell,* 4:337-41, 2003; Neri and Bicknell, *Nat Rev Cancer,* 5:436-46, 2005; Saltzman and Olbricht, *Nat Rev Drug Discov,* 1:177-86, 2002).

Tumor Marker Targeting

The advent of aptamer and antibody technology has facilitated the use of cancer-specific monoclonal antibodies and aptamers to deliver peptides of the invention to a selected target tissue. Of special interest are antibodies and aptamers that target, in vivo, tumor endothelium. Those targets include, but are not limited to, the fibronectin extra-domain B, large tenascin-C isoforms, various integrins, VEGF receptors, prostate specific membrane antigen, endoglin and CD44 isoforms (Shukla and Krag, *Expert Opin Biol Ther,* 6:39-54, 2006). Alternatively, the tumor itself may be targeted, exemplary tumor markers include CA-125, gangliosides G(D2), G(M2) and G(D3), CD20, CD52, CD33, Ep-CAM, CEA, bombesin-like peptides, PSA, HER2/neu, epidermal growth factor receptor, erbB2, erbB3, erbB4, CD44v6, Ki-67, cancer-associated mucin, VEGF, VEGFRs (e.g., VEGFR3), estrogen receptors, Lewis-Y antigen, TGF$\beta$1, IGF-1 receptor, EGF$\alpha$, c-Kit receptor, transferrin receptor, IL-2R and CO17-1A. Aptamers and antibodies of the invention can recognize tumors derived from a wide variety of tissue types, including, but not limited to, breast, prostate, colon, lung, pharynx, thyroid, lymphoid, lymphatic, larynx, esophagus, oral mucosa, bladder, stomach, intestine, liver, pancreas, ovary, uterus, cervix, testes, dermis, bone, blood and brain. In the context of the present invention, a tumor cell is a neoplastic (e.g., cancer) cell or a mass of cancer cells, which can also encompass cells that support the growth and/or propagation of a cancer cell, such as vasculature and/or stroma, but not necessarily macrophages. For instance, therefore, the present invention envisages compositions and methods for reducing growth of a tumor cell in a subject, wherein antibodies or aptamers bind with specificity to cell surface epitopes (or epitopes of receptor-binding molecules) of a cancer cell or a cell that is involved in the growth and/or propagation of a cancer cell such as a cell comprising the vasculature of a tumor or blood vessels that supply tumors and/or stromal cells. Methods of this invention are particularly suitable for administration to humans with neoplastic diseases.

Antibodies

Antibodies are well known to those of ordinary skill in the science of immunology. Particularly useful in the methods of the invention are antibodies that specifically bind a polypeptide that is expressed in a tumor or endothelial cell. As used herein, the term "antibody" means not only intact antibody molecules, but also fragments of antibody molecules that retain immunogen binding ability. Such fragments are also well known in the art and are regularly employed both in vitro and in vivo. Accordingly, as used herein, the term "antibody" means not only intact immunoglobulin molecules but also the well-known active fragments $F(ab')_2$, and Fab. $F(ab')_2$, and Fab fragments which lack the Fc fragment of intact antibody, clear more rapidly from the circulation, and may have less non-specific tissue binding of an intact antibody (Wahl et al., *J. Nucl. Med.* 24:316-325, 1983). The antibodies of the invention comprise whole native antibodies, bispecific antibodies; chimeric antibodies; Fab, Fab', single chain V region fragments (scFv) and fusion polypeptides.

In one embodiment, an antibody that binds polypeptide is monoclonal. Alternatively, the antibody is a polyclonal antibody. The preparation and use of polyclonal antibodies are also known to the skilled artisan. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "$F(ab')_2$" fragment, retains both of the antigen binding sites of the intact antibody. Similarly, an antibody from which the Fc region has been enzymatically cleaved, or which has been produced without the Fc region, designated an "Fab" fragment, retains one of the antigen binding sites of the intact antibody. Fab' fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Antibodies can be made by any of the methods known in the art utilizing a peptide of the invention (e.g., a peptide shown in Tables 1-10), or immunogenic fragments thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding a polypeptide described herein, or immunogenic fragments thereof, can be provided to the host in a delivery vehicle that is taken up by immune cells of the host. The cells will in turn express the receptor on the cell surface generating an immunogenic response in the host. Alternatively, nucleic acid sequences encoding a peptide of the invention (e.g., a peptide shown in Tables 1-10), or immunogenic fragments thereof, can be expressed in cells in vitro, followed by isolation of the polypeptide and administration of the receptor to a suitable host in which antibodies are raised.

Using either approach, antibodies can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition; e.g., Pristane.

Monoclonal antibodies (Mabs) produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

Aptamers

Nucleic acid aptamers are single-stranded nucleic acid (DNA or RNA) ligands that function by folding into a specific globular structure that dictates binding to target proteins or other molecules with high affinity and specificity, as described by Osborne et al., *Curr. Opin. Chem. Biol.* 1:5-9, 1997; and Cerchia et al., *FEBS Letters* 528:12-16, 2002. By "aptamer" is meant a single-stranded polynucleotide that binds to a protein. Desirably, the aptamers are small, approximately ~15 KD. The aptamers are isolated from libraries consisting of some $10^{14}$-$10^{15}$ random oligonucleotide sequences by a procedure termed SELEX (systematic evolution of ligands by exponential enrichment). See Tuerk et al., *Science,* 249:505-510, 1990; Green et al., *Methods Enzymology.* 75-86, 1991; Gold et al., *Annu. Rev. Biochem.,* 64: 763-797, 1995; Uphoff et al., *Curr. Opin. Struct. Biol.,* 6: 281-288, 1996. Methods of generating aptamers are known in the art and are described, for example, in U.S. Pat. Nos. 6,344,318, 6,331,398, 6,110,900, 5,817,785, 5,756,291, 5,696,249, 5,670,637, 5,637,461, 5,595,877, 5,527,894, 5,496,938, 5,475,096, 5,270,163, and in U.S. Patent Application Publication Nos. 20040241731, 20030198989, 20030157487, and 20020172962.

An aptamer of the invention is capable of binding with specificity to a polypeptide expressed by a cell of interest (e.g., a tumor cell or an endothelial cell supplying a tumor). "Binding with specificity" means that non-tumor polypeptides are either not specifically bound by the aptamer or are only poorly bound by the aptamer. In general, aptamers typically have binding constants in the picomolar range. Particularly useful in the methods of the invention are aptamers having apparent dissociation constants of 1, 10, 15, 25, 50, 75, or 100 nM.

In one embodiment, an antigen expressed on a blood vessel supplying a tumor is the molecular target of the aptamer. Because aptamers can act as direct antagonists of the biological function of proteins, aptamers that target such polypeptide can be used to modulate angiogenesis, vasculogenesis, blood vessel stabilization or remodeling. The therapeutic benefit of such aptamers derives primarily from the biological antagonism caused by aptamer binding.

The invention encompasses stabilized aptamers having modifications that protect against 3' and 5' exonucleases as well as endonucleases. Such modifications desirably maintain target affinity while increasing aptamer stability in vivo. In various embodiments, aptamers of the invention include chemical substitutions at the ribose and/or phosphate and/or base positions of a given nucleobase sequence. For example, aptamers of the invention include chemical modifications at the 2' position of the ribose moiety, circularization of the aptamer, 3' capping and 'spiegelmer' technology. Aptamers having A and G nucleotides sequentially replaced with their 2'-OCH3 modified counterparts are particularly useful in the methods of the invention. Such modifications are typically well tolerated in terms of retaining aptamer affinity and specificity. In various embodiments, aptamers include at least 10%, 25%, 50%, or 75% modified nucleotides. In other embodiments, as many as 80-90% of the aptamer's nucleotides contain stabilizing substitutions. In other embodiments, 2'-OMe aptamers are synthesized. Such aptamers are desirable because they are inexpensive to synthesize and natural polymerases do not accept 2'-OMe nucleotide triphosphates as substrates so that 2'-OMe nucleotides cannot be recycled into host DNA. A fully 2'-O-methyl aptamer, named ARC245, was reported to be so stable that degradation could not be detected after 96 hours in plasma at 37° C. or after autoclaving at 125° C. Using methods described herein, aptamers will be selected for reduced size and increased stability. In one embodiment, aptamers having 2'-F and 2'-$OCH_3$ modifications are used to generate nuclease resistant aptamers. Other modifications that stabilize aptamers are known in the art and are described, for example, in U.S. Pat. No. 5,580,737; and in U.S. Patent Application Publication Nos. 20050037394, 20040253679, 20040197804, and 20040180360.

Using standard methods tumor markers or endothelial call-specific aptamers can be selected that bind virtually any tumor marker or endothelial cell-expressed polypeptide known in the art.

The Fibronectin Extra-Domain B (EDB)

Fibronectin is a large glycoprotein that is present in large amounts in the plasma and tissues. EDB is a 91-amino-acid type III homology domain that becomes inserted into the fibronectin molecule under tissue-remodeling conditions by a mechanism of alternative splicing at the level of the primary transcript. EDB is essentially undetectable in healthy adult individuals. EDB-containing fibronectin is abundant in many aggressive solid tumors and in neo-vascularized endothelium, and displays either predominantly vascular or diffuse stromal patterns of expression, depending on the tissue.

Large Tenascin-C Isoforms

Tenascins are a family of four extracellular matrix glycoproteins that are found in vertebrates. They are typically present in many different connective tissues. Tenascins contribute to matrix structure and influence the behavior of cells that are in contact with the extracellular matrix. Several isoforms of tenascin-C can be generated as a result of different patterns of alternative splicing in the region between domains A1 and D. It has been known for some time that spliced isoforms containing extra domains are tumor-associated antigens, which show a more restricted pattern of expression in normal tissues compared with the "small" tenascin isoforms. The C domain of tenascin-C is the extra domain that shows the most restricted pattern of expression. In normal adult tissue it is undetectable by immunohistochemistry and northern-blot analysis, but it is strongly expressed in aggressive brain tumors and some lung tumors, with a prominent perivascular pattern of staining.

Integrins

During vascular remodeling and angiogenesis, endothelial cells show increased expression of several cell-surface molecules that potentiate cell invasion and proliferation. One such molecule is the integrin αv-β3, which has a key role in endothelial cell survival during angiogenesis in vivo and which might serve as a target for therapeutic molecules, particularly those that require internalization in endothelial cells. Monoclonal antibodies to the αv-β3 have been shown to display anti-angiogenic activities and to preferentially stain tumor blood vessels.

VEGFs and their Receptors

VEGFs represent a class of proteins that promote angiogenesis, increase vascular permeability and contribute to endothelial-cell survival in blood and lymphatic vessels. The contribution of VEGFA to cancer progression has been highlighted by the recent approval of the humanized anti-VEGF monoclonal antibody bevacizumab (Avastin; Genentech) for first-line cancer treatment. The overexpression of VEGFs and VEGF receptors in tumors is well documented. The selective tumor localization of monoclonal antibodies to VEGFA, VEGF receptor 2 and the VEGFA-VEGF receptor 2 complex can be used as an excellent selectivity mechanism for targeting the angiogenic vasculature.

Prostate-Specific Membrane Antigen

Prostate-specific membrane antigen (PSMA) is a membrane glycoprotein with proteolytic activity. PSMA is predominantly expressed in the prostate and serum concentrations are often increased in patients with prostate cancer. Several studies have reported overexpression of PSMA in the neo-vasculature of different solid tumors, whereas expression in normal vasculature is limited to some vessels of the breast, duodenum, kidney and prostate.

Endoglin

Endoglin (CD105) is a transforming growth factor-beta (TGF) co-receptor that is overexpressed in tumor neo-vasculature and is used as a marker for the tumor endothelium.

CD44 Isoforms

CD44 is a cell-surface receptor of great molecular heterogeneity, which is due to both alternative splicing and extensive post-translational modification. The radio-labeled monoclonal antibody TES-23, which is specific to an isoform of CD44, has shown impressive performance in tumor-targeting experiments in animal models. TES-23 recognizes a widely distributed form of CD44 that lacks variant exons, known as CD44H.

Tumor Endothelial Markers (TEMs)

TEMs is a family of genes encoding proteins that serve as tumor endothelial markers (Carson-Walter, Watkins, et al, *Cancer Res.* 61:6649-55, 2001). These genes display elevated expression during tumor angiogenesis. From both biological and clinical points of view, TEMs associated with the cell surface membrane are of particular interest. Accordingly, four such genes are characterized, TEM1, TEM5, TEM7, and TEM8, all of which contain putative transmembrane domains. TEM5 appears to be a seven-pass transmembrane receptor, whereas TEM1, TEM7, and TEM8 span the membrane once. Three of these TEMs (TEM1, TEM5, and TEM8) are abundantly expressed in tumor vessels in mouse tumors, embryos, and adult tissues as well as in the vasculature of the developing mouse embryo. The expression of these TEMs in normal adult mice tissues is undetectable.

Selective Delivery Through Pro-Drug Activation

Selective delivery of agents of the invention can be achieved by administering a pro-drug form that is converted into an active drug at the target site. Most pro-drugs are designed to have a "trigger," "linker" and "effector." The "trigger," following the tissue-specific metabolism, modifies the "linker," resulting in an activation of the "effector." There are several mechanisms potentially exploitable for selective activation. Some utilize unique aspects of the tissue physiology, such as selective enzyme expression or hypoxia in the case of tumors, whereas others are based on tissue antigen-specific delivery techniques.

Targeting Secreted Enzymes from Cells

The approach uses pro-drugs that are "hidden" from the cells until cleaved by an enzyme produced and secreted preferentially by the cells. A typical example of an enzyme used for pro-drug activation is MMP-9.

Targeting Tumor Hypoxia

Advances in the chemistry of bio-reductive drug activation have led to the design of hypoxia-selective drug delivery systems. These pro-drugs initially undergo one-electron reduction by reductases to give the radical anion, which in normal cells are re-oxidized to the parent compound, but in hypoxic tumor cells they are further reduced to more hydrophilic species and trapped inside. These drugs can be selectively delivered to tumors with defined hypoxic fractions rich in the required activating enzymes.

Antibody-Directed Enzyme Pro-Drug Therapy

Antibody-directed pro-drug therapy (ADEPT) is a 2-step approach in which first the antibody-enzyme construct is administered intravenously. This is composed of an antibody against a tissue-specific target linked to an enzyme that activates a pro-drug. In the second step, after the unbound antibody-enzyme conjugate construct is cleared from the circulation, a pro-drug is administered intravenously. The pro-drug is an agent that has been rendered less active by chemical addition of enzyme-cleavable moieties. The pro-drug is converted to an active form by the tumor-bound antibody-enzyme, which results in local accumulation of the fully active form of the agent.

External Energy-Controlled Delivery

Some selective delivery strategies involve focusing external energy for concentrating or delivering therapeutics at the tissue site. A variety of delivery systems in this category are in the experimental stage, although some have been used in clinical trials as well. Those strategies include selective delivery through photodynamic therapy, magnetically targeted delivery, selective delivery through X-ray exposure, radiation-induced selective delivery and ultrasound-guided delivery.

Methods of Ocular Delivery

The compositions of the invention (e.g., a peptide of the invention shown in Tables 1-10) are also particularly suitable for treating ocular diseases, such as age-related macular degeneration, choroidal neovascularization, persistent hyperplastic vitreous syndrome, diabetic retinopathy, and retinopathy of prematurity that are characterized by excess angiogenesis.

In one approach, the compositions of the invention are administered through an ocular device suitable for direct implantation into the vitreous of the eye. The compositions of the invention may be provided in sustained release compositions, such as those described in, for example, U.S. Pat. Nos. 5,672,659 and 5,595,760. Such devices are found to provide sustained controlled release of various compositions to treat the eye without risk of detrimental local and systemic side effects. An object of the present ocular method of delivery is to maximize the amount of drug contained in an intraocular device or implant while minimizing its size in order to prolong the duration of the implant. See, e.g., U.S. Pat. Nos. 5,378,475; 6,375,972, and 6,756,058 and U.S. Publications 20050096290 and 200501269448. Such implants may be biodegradable and/or biocompatible implants, or may be non-biodegradable implants. Biodegradable ocular implants are described, for example, in U.S. Patent Publication No. 20050048099. The implants may be permeable or impermeable to the active agent, and may be inserted into a chamber of the eye, such as the anterior or posterior chambers or may be implanted in the schlera, transchoroidal space, or an avascularized region exterior to the vitreous. Alternatively, a contact lens that acts as a depot for compositions of the invention may also be used for drug delivery.

In a preferred embodiment, the implant may be positioned over an avascular region, such as on the sclera, so as to allow for transcleral diffusion of the drug to the desired site of treatment, e.g. the intraocular space and macula of the eye. Furthermore, the site of transcleral diffusion is preferably in proximity to the macula. Examples of implants for delivery of a composition include, but are not limited to, the devices described in U.S. Pat. Nos. 3,416,530; 3,828,777; 4,014,335; 4,300,557; 4,327,725; 4,853,224; 4,946,450; 4,997,652; 5,147,647; 5,164,188; 5,178,635; 5,300,114; 5,322,691; 5,403,901; 5,443,505; 5,466,466; 5,476,511; 5,516,522; 5,632,984; 5,679,666; 5,710,165; 5,725,493; 5,743,274; 5,766,242; 5,766,619; 5,770,592; 5,773,019; 5,824,072; 5,824,073; 5,830,173; 5,836,935; 5,869,079, 5,902,598; 5,904,144; 5,916,584; 6,001,386; 6,074,661; 6,110,485; 6,126,687; 6,146,366; 6,251,090; and 6,299,895, and in WO 01/30323 and WO 01/28474, all of which are incorporated herein by reference.

Examples include, but are not limited to the following: a sustained release drug delivery system comprising an inner reservoir comprising an effective amount of an agent effective in obtaining a desired local or systemic physiological or pharmacological effect, an inner tube impermeable to the passage of the agent, the inner tube having first and second ends and covering at least a portion of the inner reservoir, the inner tube sized and formed of a material so that the inner tube is capable of supporting its own weight, an impermeable member positioned at the inner tube first end, the impermeable member preventing passage of the agent out of the reservoir through the inner tube first end, and a permeable member positioned at the inner tube second end, the permeable member allowing diffusion of the agent out of the reservoir through the inner tube second end; a method for administering a compound of the invention to a segment of an eye, the method comprising the step of implanting a sustained release device to deliver the compound of the invention to the vitreous of the eye or an implantable, sustained release device for administering a compound of the invention to a segment of an eye; a sustained release drug delivery device comprising: a) a drug core comprising a therapeutically effective amount of at least one first agent effective in obtaining a diagnostic effect or effective in obtaining a desired local or systemic physiological or pharmacological effect; b) at least one unitary cup essentially impermeable to the passage of the agent that surrounds and defines an internal compartment to accept the drug core, the unitary cup comprising an open top end with at least one recessed groove around at least some portion of the open top end of the unitary cup; c) a permeable plug which is permeable to the passage of the agent, the permeable plug is positioned at the open top end of the unitary cup wherein the groove interacts with the permeable plug holding it in position and closing the open top end, the permeable plug allowing passage of the agent out of the drug core, through the permeable plug, and out the open top end of the unitary cup; and d) at least one second agent effective in obtaining a diagnostic effect or effective in obtaining a desired local or systemic physiological or pharmacological effect; or a sustained release drug delivery device comprising: an inner core comprising an effective amount of an agent having a desired solubility and a polymer coating layer, the polymer layer being permeable to the agent, wherein the polymer coating layer completely covers the inner core.

Other approaches for ocular delivery include the use of liposomes to target a compound of the present invention to the eye, and preferably to retinal pigment epithelial cells and/or Bruch's membrane. For example, the compound may be complexed with liposomes in the manner described above, and this compound/liposome complex injected into patients with an ocular disease, using intravenous injection to direct the compound to the desired ocular tissue or cell. Directly injecting the liposome complex into the proximity of the retinal pigment epithelial cells or Bruch's membrane can also provide for targeting of the complex with some forms of ocular disease. In a specific embodiment, the compound is administered via intra-ocular sustained delivery (such as VITRASERT or ENVISION). In a specific embodiment, the compound is delivered by posterior subtenons injection. In another specific embodiment, microemulsion particles containing the compositions of the invention are delivered to ocular tissue to take up lipid from Bruch's membrane, retinal pigment epithelial cells, or both.

For optical applications, nanoparticles are a colloidal carrier system that has been shown to improve the efficacy of the encapsulated drug by prolonging the serum half-life. Polyalkylcyanoacrylates (PACAs) nanoparticles are a polymer colloidal drug delivery system that is in clinical development, as described by Stella et al., *J. Pharm. Sci.,* 2000. 89: p. 1452-1464; Brigger et al., *Int. J. Pharm.,* 2001. 214: p. 37-42; Calvo et al., *Pharm. Res.,* 2001. 18: p. 1157-1166; and Li et al., *Biol. Pharm. Bull.,* 2001. 24: p. 662-665. Biodegradable poly(hydroxyl acids), such as the copolymers of poly(lactic acid) (PLA) and poly(lactic-co-glycolide) (PLGA) are being extensively used in biomedical applications and have received FDA approval for certain clinical applications. In addition, PEG-PLGA nanoparticles have many desirable carrier features including (i) that the agent to be encapsulated comprises a reasonably high weight fraction (loading) of the total carrier system; (ii) that the amount of agent used in the first step of the encapsulation process is incorporated into the final carrier (entrapment efficiency) at a reasonably high level; (iii) that the carrier have the ability to be freeze-dried and reconstituted in solution without aggregation; (iv) that the carrier be biodegradable; (v) that the carrier system be of small size; and (vi) that the carrier enhance the particles persistence.

Nanoparticles are synthesized using virtually any biodegradable shell known in the art. In one embodiment, a polymer, such as poly(lactic-acid) (PLA) or poly(lactic-co-glycolic acid) (PLGA) is used. Such polymers are biocompatible and biodegradable, and are subject to modifications that desirably increase the photochemical efficacy and circulation lifetime of the nanoparticle. In one embodiment, the polymer is modified with a terminal carboxylic acid group (COOH) that increases the negative charge of the particle and thus limits the interaction with negatively charge nucleic acid aptamers. Nanoparticles are also modified with polyethylene glycol (PEG), which also increases the half-life and stability of the particles in circulation. Alternatively, the COOH group is converted to an N-hydroxysuccinimide (NHS) ester for covalent conjugation to amine-modified aptamers.

Biocompatible polymers useful in the composition and methods of the invention include, but are not limited to, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexlmethacrylate), poly(isodecylmethacrylate), poly (lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene, polyvinylpryrrolidone, polyhyaluronic acids, casein, gelatin, glutin, polyanhydrides, polyacrylic acid, alginate, chitosan, poly(methyl methacrylates), poly(ethyl methacrylates), poly(butylmethacrylate), poly (isobutylmethacrylate), poly(hexlmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) and combinations of any of these. In one embodiment, the nanoparticles of the invention include PEG-PLGA polymers.

Compositions of the invention may also be delivered topically. For topical delivery, the compositions are provided in any pharmaceutically acceptable excipient that is approved for ocular delivery. Preferably, the composition is delivered in drop form to the surface of the eye. For some application, the delivery of the composition relies on the diffusion of the compounds through the cornea to the interior of the eye.

Those of skill in the art will recognize that the best treatment regimens for using compounds of the present invention to treat an ocular disease can be straightforwardly determined. This is not a question of experimentation, but rather one of optimization, which is routinely conducted in the medical arts. In vivo studies in nude mice often provide a starting point from which to begin to optimize the dosage and delivery regimes. The frequency of injection will initially be once a week, as has been done in some mice studies. However, this frequency might be optimally adjusted from one day to every two weeks to monthly, depending upon the results obtained from the initial clinical trials and the needs of a particular patient.

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 mg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, 5000 mg/Kg body weight. In other embodiments, it is envisaged that higher doses may be used, such doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

Combination Therapies

Optionally, an angiogenic modulating therapeutic as described herein may be administered in combination with any other standard active angiogenic modulating therapeutics; such methods are known to the skilled artisan and described in *Remington's Pharmaceutical Sciences* by E. W. Martin. For example, an anti-angiogenic peptide of the invention may be administered in combination with any other anti-angiogenic peptide, or with known anti-angiogenic agent. Such agents are listed below (Folkman, *Annu Rev Med.* 57:1-18, 2006).

| Agent | Clinical Trials |
|---|---|
| 1. Alphastatin | |
| 2. Angiostatin | |
| 3. Arresten | |
| 4. Anti-thrombin III (truncated) | |
| 5. Canstatin | |
| 6. Endostatin | Phase II |
| 7. Fibulin-5 | |
| 8. Fragment of histidine-rich glycoprotein | |
| 9. Interferon-β | Phase III |
| 10. Maspin | |
| 11. 2-methoxyestradiol | Phase II |
| 12. PEX | |
| 13. Pigment epithelial-derived factor (PEDF) | |
| 14. Platelet factor 4 (PF4) | |
| 15. Semaphorin 3F | |
| 16. sFlt-1 | |
| 17. Tetrahydrocortisol | Phase III |
| 18. Thrombospondin-1 (and -2) | Phase II |
| 19. TIMP-2 | |
| 20. Troponin I | |
| 21. Tumstatin | |
| 22. Vasostatin | |

For the treatment of a neoplasia, a peptide of the invention is administered in combination with any conventional treatment (e.g., chemotherapy, radiotherapy, hormonal therapy, surgery, cryosurgery). A pharmaceutical composition of the invention may, if desired, include one or more chemotherapeutics typically used in the treatment of a neoplasm, such as abiraterone acetate, altretamine, anhydrovinblastine, auristatin, bexarotene, bicalutamide, BMS184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvin-caleukoblastine, docetaxol, doxetaxel, cyclophosphamide, carboplatin, carmustine (BCNU), cisplatin, cryptophycin, cyclophosphamide, cytarabine, dacarbazine (DTIC), dactinomycin, daunorubicin, dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), mechlorethamine (nitrogen mustard), melphalan, mivobulin isethionate, rhizoxin, sertenef, streptozocin, mitomycin, methotrexate, 5-fluorouracil, nilutamide, onapristone, paclitaxel, prednimustine, procarbazine, RPR109881, stramustine phosphate, tamoxifen, tasonermin, taxol, thalidomide, tretinoin, vinblastine, vincristine, vindesine sulfate, and vinflunine. Other examples of chemotherapeutic agents can be found in *Cancer Principles and Practice of Oncology* by V. T. Devita and S. Hellman (editors), 6th edition (Feb. 15, 2001), Lippincott Williams & Wilkins Publishers.

Kits

The invention provides kits for the treatment or prevention of diseases or disorders characterized by excess or undesirable angiogenesis. In one embodiment, the kit includes a therapeutic or prophylactic composition containing an effective amount of one or more peptides described herein in unit dosage form. In some embodiments, the kit comprises a sterile container that contains a therapeutic or prophylactic vaccine; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired a peptide of the invention is provided together with instructions for administering it to a subject having or at risk of developing excess or undesired angiogenesis. The instructions will generally include information about the use of the composition for the treatment or prevention of ischemia or for enhancing angiogenesis to a tissue in need thereof. In other embodiments, the instructions include at least one of the following: description of the expression vector; dosage schedule and administration for treatment or prevention of ischemia or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

METHODS OF THE INVENTION

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "*Molecular Cloning: A Laboratory Manual*", second edition (Sambrook, 1989); "*Oligonucleotide Synthesis*" (Gait, 1984); "*Animal Cell Culture*" (Freshney, 1987); "*Handbook of Experimental Immunology*" (Weir, 1996); "*Gene Transfer Vectors for Mammalian Cells*" (Miller and Calos, 1987); "*Current Protocols in Molecular Biology*" (Ausubel, 1987); "*PCR: The Polymerase Chain Reaction*", (Mullis, 1994); "*Current Protocols in Immunology*" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

EXAMPLES

Example 1

Analysis of Peptide Motifs

Using bioinformatic analysis 156 peptides with anti-angiogenic properties were identified based on their sequence similarity with known anti-angiogenic peptides. A number of these peptides were screened for anti-angiogenic activity using an endothelial cell proliferation assay to identify peptide motifs associated with anti-angiogenic activity. Multiple sequence alignments were used to identify peptides having conserved motifs that are common in a variety of sequences. Multiple sequence alignment was performed using the ClustalW algorithm to align sequences of peptides that belong to different protein families including type I thrombospondin repeat-containing proteins, C-X-C chemokines, collagen type IV, somatotropins and serpins. In order to perform the alignment a critical number of peptide sequences were required. The motifs were represented using the single letter abbreviations of the amino acids that are common and the letter "X" to denote a non-common amino acid that intervenes the common letters. If there is more than one non-common amino acid in between, the letter "X" followed by the number of the non-common amino acids was used. For example if there are three non-common amino acids between two conserved letters, we notify it as "a-X3-b", where a and b is the conserved motif. This notation is commonly used to represent motifs.

Initially multiple sequence alignments to the experimentally tested peptides were performed. The calculation was generalized to all the theoretically predicted fragments. To determine whether the motifs calculated for the experimentally tested fragments were conserved and reproduced in all of the anti-angiogenic predictions. The results obtained were organized by protein family. As described in more detail below, general peptide motifs associated with anti-angiogenic activity were identified for three families of human proteins: Type I thrombospondin (TSP) domain containing proteins, CXC chemokines, and collagens. Using these motifs, 2286 peptides each containing one of the identified motifs were identified in 1977 different proteins present in the human proteome (166 peptides from 54 different proteins listed in Table 2; 1337 peptides from 1170 proteins listed in Table 4; 24 peptides from 24 proteins listed in Table 5; 306 peptides from 288 proteins listed in Table 6; 139 peptides from 139 proteins listed in Table 8; and 314 peptides from 302 different proteins listed in Table 9.

In addition, 12 novel peptide sequences from the Somatotropin, Serpin, and Type IV Collagen families obtained based on the similarity criteria with known anti-angiogenic peptides are listed in Tables 7A, 7B, and 10, respectively.

Example 2

Thrombospondin-1 (TSP-1) Repeat-Containing Proteins Derived Peptides

From the 31 predicted and experimentally tested TSP-1 containing short peptides 29 share a global 4 letter common motif which is the X2-W-X2-C-X3-C-X2-G-X7 (SEQ ID NO: 2353), or W-X2-C-X3-C-X2-G (SEQ ID NO: 2287) after removing the uncommon edges, resulting in the generic TSP-1 containing 20-mer (FIG. 1). The first amino acid that succeeds the first cysteine of the motif, or the seventh amino acid of the sequence can alternate between T, S and N. Thus a more generic description of this motif is X2-W-X2-C-(T/S/N)-X2-C-X2-G-X7 (SEQ ID NO: 2354) with threonine or serine the most abundant alteration for the seventh amino acid position.

Figure 2B:
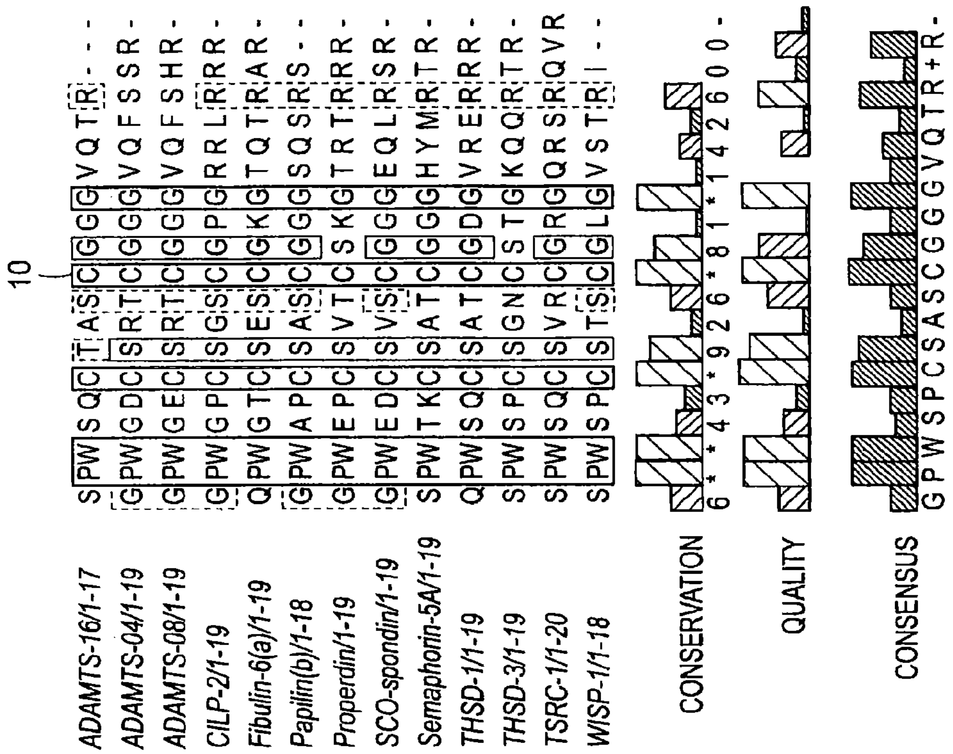
FIGS. 2A and 2B show a set of amino acid sequences that included shaded common motifs of the TSP-1 containing peptides using a threshold of 60% (FIG. 2A, SEQ ID NOS 2329-2331, 2333-2337, 2339, 2338, 2341-2344, 2347 and 2350-2352, respectively, in order of appearance) and 45% (FIG. 2B, SEQ ID NOS 2326, 2324-2325, 2329, 2334, 2339-2342, 2344-2345, 2347 and 2350, respectively, in order of appearance).
Figure 2A:
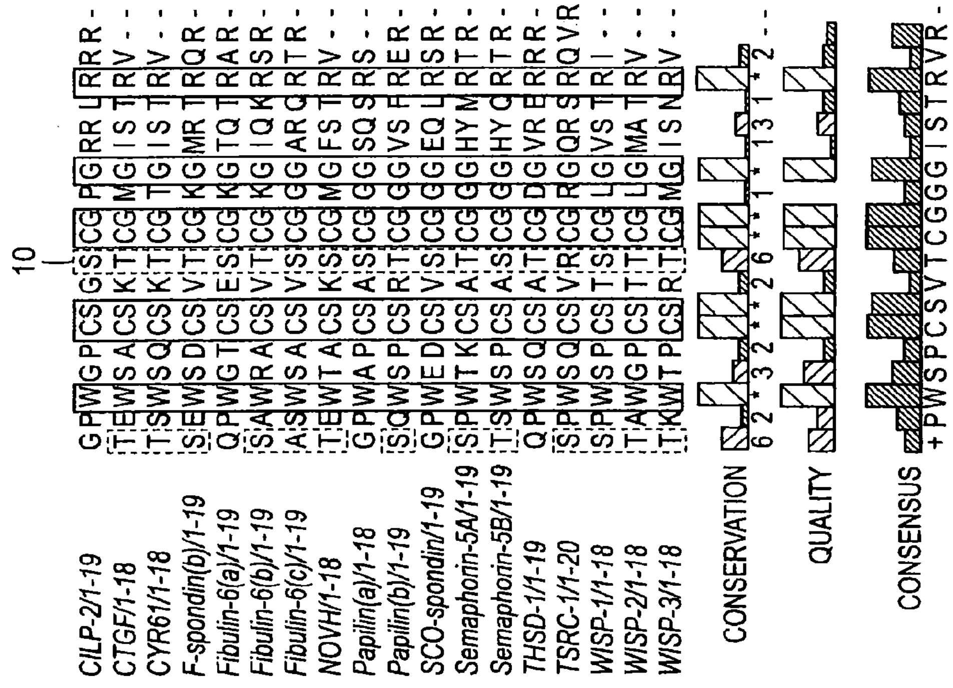

By altering the threshold of the conserved amino acids that are common among the sequences of the predicted peptides we can create subsets of peptide families with individual common motifs of greater length than the global 4-letter motif. The threshold here is defined as the percentage of the peptides that share a common motif. Such a subgroup of peptides is one that consists of 18 TSP-1 containing predictions (threshold 60%) that share a seven amino acid long common motif. The motif is the X2-W-X2-C-S-X2-C-G-X1-G-X3-R-X3 (SEQ ID NO: 2355). A common alteration occurs in the $19^{th}$ amino acid, which can be either an arginine or a valine with arginine the most abundant amino acid. In that case the motif is written X2-W-X2-C-S-X2-C-G-X1-G-X3-R-X1-(R/V)-X1 (SEQ ID NO: 2387). Similarly the ninth amino acid can be altered by either arginine, serine or threonine. In that case the motif can be represented as X2-W-X2-C-S-X1-(S/R/T)-C-G-X1-G-X3-R-X1-(R/V)-X1 (SEQ ID NO: 2391) with threonine the most abundant amino acid (FIG. 2A). Similarly another motif with 45% threshold, common in 13 sequences, is the 5 letter motif X1-P-W-X2-C-X3-C-X2-G-X7 (SEQ ID NO: 2407). The common alterations of this motif can be described as (S/G/Q)-P-W-X2-C-(T/S)-X2-C-(G/S)-X1-G-X3-(R/S)-X3 (FIG. 2B) (SEQ ID NO: 2417).

In addition to calculating the motifs that are present within the sequences of the predicted fragments one can analyze all the possible amino acids that are present within the 29 peptide sequences from which the motifs were calculated. This 20-mer with all the possible substitutions is presented in Table 1 along with the frequencies that each amino acid is present in the 29 sequences.

TABLE 1

The TSP-1 containing 20-mer with all the possible amino acid substitutions (SEQ ID NO: 2420)

| AA#1 | AA#2 | AA#3 | AA#4 | AA#5 | AA#6 | AA#7 | AA#8 | AA#9 | AA#10 |
|---|---|---|---|---|---|---|---|---|---|
| S(9) | P(13) | W(29) | S(14) | P(9) | C(29) | S(26) | V(7) | T(15) | C(29) |
| T(9) | E(5) | | T(5) | A(5) | | N(2) | A(6) | S(10) | |
| G(6) | S(3) | | G(5) | Q(4) | | T(1) | R(5) | R(3) | |
| Q(2) | A(2) | | E(2) | D(3) | | | K(4) | N(1) | |
| A(1) | Q(1) | | D(1) | E(3) | | | G(2) | | |
| | K(1) | | R(1) | K(1) | | | S(2) | | |
| | | | A(1) | R(1) | | | T(2) | | |
| | | | | V(1) | | | E(1) | | |

| AA#11 | AA#12 | AA#13 | AA#14 | AA#15 | AA#16 | AA#17 | AA#18 | AA#19 | AA#20 |
|---|---|---|---|---|---|---|---|---|---|
| G(26) | G(10) | G(29) | V(8) | Q(11) | T(10) | R(26) | S(5) | R(15) | R(1) |
| S(2) | K(4) | | I(4) | S(7) | F(4) | S(2) | T(5) | V(1) | |
| N(1) | R(4) | | M(3) | R(6) | K(3) | Q(1) | V(5) | | |
| | M(4) | | T(3) | K(2) | Q(3) | | R(3) | | |
| | T(2) | | H(2) | Y(2) | S(3) | | H(3) | | |
| | L(2) | | A(1) | A(1) | L(2) | | E(2) | | |
| | D(1) | | E(1) | | E(1) | | Q(2) | | |
| | S(1) | | F(1) | | M(1) | | A(1) | | |
| | P(1) | | K(1) | | N(1) | | I(1) | | |
| | | | R(1) | | V(1) | | | | |
| | | | S(1) | | | | | | |
| | | | Q(1) | | | | | | |
| | | | W(1) | | | | | | |
| | | | Y(1) | | | | | | |

The above motifs, for both the TSP-1 containing proteins were identified from the sequences of the peptide fragments that have already been experimentally tested in proliferation assay. The specific approach for identification of motifs within groups of sequences can be generalized for the case of all the theoretically predicted anti-angiogenic fragments. For the TSP-1 repeat-containing protein derived fragments the multiple sequence alignment calculations are repeated, but now all of the theoretically predicted fragments are included. The same approach is also utilized for the case of collagens where only the experimentally tested pool of sequences is not sufficient to yield statistically significant results. In that case after including all the theoretically predicted fragments we are able to identify common motifs.

Figure 3B:
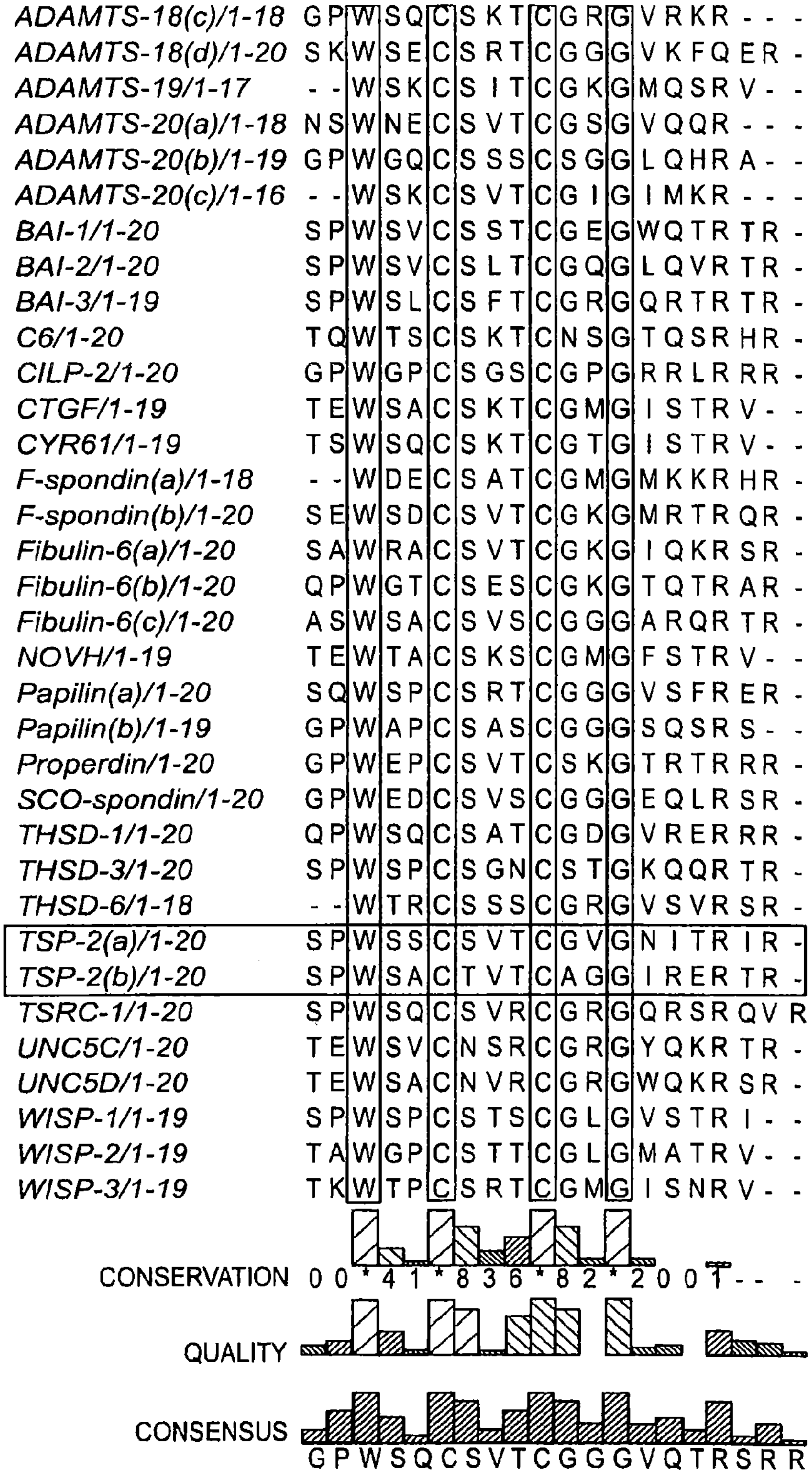
FIG. 3 shows a set of amino acid sequences that include a shaded 4-letter motif common in all the theoretically predicted TSP-1 containing proteins (FIG. 3A discloses SEQ ID NOS 2356-2359, 2324, 2360-2365, 2325, 2366-2373, 2326 and 2374-2376, respectively, in order of appearance & FIG. 3B discloses SEQ ID NOS 2377, 2327, 2378-2384, 2328-2333, 2335, 2334, 2336-2341, 2344-2346, 2385-2386 and 2347-2352, respectively, in order of appearance). In the red insert the predicted motif is identified within TSP-2 domains as well.

For the cases of all the theoretically predicted TSP-1 containing proteins, multiple sequence alignment yields a common motif within 97% of all the tested sequences. This motif is the already identified W-X2-C-X3-C-X2-G (SEQ ID NO: 2287) (FIG. 3) and a generic 20-mer can be expressed as X2-W-X2-C-X3-C-X2-G-X7 (SEQ ID NO: 2353). It is interesting that this motif is not a characteristic of only the TSP-1 domains, in other words in not a signature for TSP-1. When its presence was tested for all the TSP-1 containing proteins it was identified only within a subset of this family. Moreover, it is present within the type-2 thrombospondin containing proteins (TSP-2), which have already been shown to be associated with anti-angiogenic activity. In other words we claim that the motif W-X2-C-X3-C-X2-G (SEQ ID NO: 2287), although present within a large portion of the TSP-1 containing proteins, is not a signature for a generic TSP-1 containing protein but only for those proteins with putative anti-angiogenic activity that may or may not belong to the specific protein family. Moreover, as observed within the sequences of the experimentally tested fragments and is also reproduced in the case of all the theoretically predicted fragments, the amino acid following the first cysteine of the motif can alternate between T, S and N. Thus a more specific description of the motif is the W-X2-C-(T/S/N)-X2-C-X2-G (SEQ ID NO: 2421) with serine and threonine being the predominant amino acids in the position following the first cysteine.

A common alteration occurs in the $19^{th}$ amino acid of the 20-mer which can be either an arginine or a valine with arginine the most abundant amino acid. In that case the motif is written X2-W-X2-C-(T/S/N)-X2-C-X2-G-X5-(R/V)-X (SEQ ID NO: 2427).

The most generic 4-common letter motif identified within the peptide sequences is W-X2-C-X3-C-X2-G (SEQ ID NO: 2287). The ScanProsite tool can be used to search the human proteome Prosite database at the Swiss Institute of Bioinformatics. Using the aforementioned motif as a query identified this motif in 166 locations of 54 different proteins listed in Table 2 (SEQ ID Nos. 1-166).

TABLE 2

TSPs
Motif: W-X(2)-C-X(3)-C-X(2)-G (SEQ ID NO: 2287)
Number of Locations: 166
Number of Different Proteins: 54

| # | Accession Number\|Protein Name | First Amino acid | Last Amino acid | Sequence |
|---|---|---|---|---|
| 1 | O00622\|CYR61_HUMAN | 236 | 246 | WsqCsktCgtG |
| 2 | O14514\|BAI1_HUMAN | 270 | 280 | WgeCtrdCggG |
| 3 | O14514\|BAI1_HUMAN | 363 | 373 | WsvCsstCgeG |
| 4 | O14514\|BAI1_HUMAN | 418 | 428 | WslCsstCgrG |
| 5 | O14514\|BAI1_HUMAN | 476 | 486 | WsaCsasCsqG |
| 6 | O14514\|BAI1_HUMAN | 531 | 541 | WgsCsvtCgaG |
| 7 | O15072\|ATS3_HUMAN | 975 | 985 | WseCsvtCgeG |
| 8 | O60241\|BAI2_HUMAN | 306 | 316 | WsvCsltCgqG |
| 9 | O60241\|BAI2_HUMAN | 361 | 371 | WslCsrsCgrG |
| 10 | O60241\|BAI2_HUMAN | 416 | 426 | WgpCstsCanG |
| 11 | O60241\|BAI2_HUMAN | 472 | 482 | WslCsktCdtG |
| 12 | O60242\|BAI3_HUMAN | 300 | 310 | WstCsvtCgqG |
| 13 | O60242\|BAI3_HUMAN | 354 | 364 | WslCsftCgrG |
| 14 | O60242\|BAI3_HUMAN | 409 | 419 | WsqCsvtCsnG |
| 15 | O60242\|BAI3_HUMAN | 464 | 474 | WsgCsksCdgG |
| 16 | O75173\|ATS4_HUMAN | 529 | 539 | WgdCsrtCggG |
| 17 | O76076\|WISP2_HUMAN | 201 | 211 | WgpCsttCglG |
| 18 | O95185\|UNC5C_HUMAN | 269 | 279 | WsvCnsrCgrG |
| 19 | O95388\|WISP1_HUMAN | 223 | 233 | WspCstsCglG |
| 20 | O95389\|WISP3_HUMAN | 216 | 226 | WtpCsrtCgmG |
| 21 | O95450\|ATS2_HUMAN | 863 | 873 | WspCskpCggG |
| 22 | O95450\|ATS2_HUMAN | 984 | 994 | WsqCsvtCgnG |
| 23 | P07996\|TSP1_HUMAN | 388 | 398 | WtsCstsCgnG |
| 24 | P07996\|TSP1_HUMAN | 444 | 454 | WssCsvtCgdG |
| 25 | P07996\|TSP1_HUMAN | 501 | 511 | WdiCsvtCggG |
| 26 | P13671\|CO6_HUMAN | 32 | 42 | WtsCsktCnsG |
| 27 | P13671\|CO6_HUMAN | 75 | 85 | WqrCpinCllG |
| 28 | P14222\|PERF_HUMAN | 374 | 384 | WrdCsrpCppG |
| 29 | P27918\|PROP_HUMAN | 86 | 96 | WapCsvtCseG |
| 30 | P27918\|PROP_HUMAN | 145 | 155 | WepCsvtCskG |
| 31 | P27918\|PROP_HUMAN | 202 | 212 | WtpCsasChgG |
| 32 | P29279\|CTGF_HUMAN | 206 | 216 | WsaCsktCgmG |
| 33 | P35442\|TSP2_HUMAN | 390 | 400 | WtqCsvtCgsG |
| 34 | P35442\|TSP2_HUMAN | 446 | 456 | WssCsvtCgvG |
| 35 | P35442\|TSP2_HUMAN | 503 | 513 | WsaCtvtCagG |
| 36 | P48745\|NOV_HUMAN | 213 | 223 | WtaCsksCgmG |
| 37 | P49327\|FAS_HUMAN | 627 | 637 | WeeCkqrCppG |
| 38 | P58397\|ATS12_HUMAN | 551 | 561 | WshCsrtCgaG |
| 39 | P58397\|ATS12_HUMAN | 832 | 842 | WteCsvtCgtG |
| 40 | P58397\|ATS12_HUMAN | 952 | 962 | WseCsvsCggG |
| 41 | P58397\|ATS12_HUMAN | 1321 | 1331 | WseCsttCglG |
| 42 | P58397\|ATS12_HUMAN | 1372 | 1382 | WskCsrnCsgG |
| 43 | P58397\|ATS12_HUMAN | 1431 | 1441 | WsqCsrsCggG |
| 44 | P58397\|ATS12_HUMAN | 1479 | 1489 | WdlCstsCggG |
| 45 | P59510\|ATS20_HUMAN | 976 | 986 | WsqCsrsCggG |
| 46 | P59510\|ATS20_HUMAN | 1031 | 1041 | WseClvtCgkG |
| 47 | P59510\|ATS20_HUMAN | 1086 | 1096 | WgpCtttCghG |

TABLE 2-continued

TSPs
Motif: W-X(2)-C-X(3)-C-X(2)-G (SEQ ID NO: 2287)
Number of Locations: 166
Number of Different Proteins: 54

| # | Accession Number\|Protein Name | First Amino acid | Last Amino acid | Sequence |
|---|---|---|---|---|
| 48 | P59510\|ATS20_HUMAN | 1162 | 1172 | WtpCsvsCgrG |
| 49 | P59510\|ATS20_HUMAN | 1217 | 1227 | WspCsasCghG |
| 50 | P59510\|ATS20_HUMAN | 1314 | 1324 | WgsCsssCsgG |
| 51 | P59510\|ATS20_HUMAN | 1368 | 1378 | WgeCsqtCggG |
| 52 | P59510\|ATS20_HUMAN | 1427 | 1437 | WtsCsasCgkG |
| 53 | P59510\|ATS20_HUMAN | 1483 | 1493 | WneCsvtCgsG |
| 54 | P59510\|ATS20_HUMAN | 1664 | 1674 | WskCsvtCgiG |
| 55 | P82987\|ATL3_HUMAN | 84 | 94 | WsdCsrtCggG |
| 56 | P82987\|ATL3_HUMAN | 427 | 437 | WtaCsvsCggG |
| 57 | P82987\|ATL3_HUMAN | 487 | 497 | WsqCtvtCgrG |
| 58 | P82987\|ATL3_HUMAN | 573 | 583 | WsaCsttCgpG |
| 59 | P82987\|ATL3_HUMAN | 712 | 722 | WgpCsatCgvG |
| 60 | P82987\|ATL3_HUMAN | 768 | 778 | WqqCsrtCggG |
| 61 | P82987\|ATL3_HUMAN | 828 | 838 | WskCsvsCgvG |
| 62 | P82987\|ATL3_HUMAN | 1492 | 1502 | WsqCsvsCgeG |
| 63 | P82987\|ATL3_HUMAN | 1606 | 1616 | WkpCtaaCgrG |
| 64 | Q13591\|SEM5A_HUMAN | 604 | 614 | WspCsttCgiG |
| 65 | Q13591\|SEM5A_HUMAN | 662 | 672 | WerCtaqCggG |
| 66 | Q13591\|SEM5A_HUMAN | 793 | 803 | WsqCsrdCsrG |
| 67 | Q13591\|SEM5A_HUMAN | 850 | 860 | WtkCsatCggG |
| 68 | Q496M8\|CI094_HUMAN | 259 | 269 | WsaCtrsCggG |
| 69 | Q6S8J7\|POTE8_HUMAN | 27 | 37 | WccCcfpCcrG |
| 70 | Q6UXZ4\|UNC5D_HUMAN | 261 | 271 | WsaCnvrCgrG |
| 71 | Q6UY14\|ATL4_HUMAN | 53 | 63 | WasCsqpCgvG |
| 72 | Q6UY14\|ATL4_HUMAN | 732 | 742 | WtsCsrsCgpG |
| 73 | Q6UY14\|ATL4_HUMAN | 792 | 802 | WsqCsvrCgrG |
| 74 | Q6UY14\|ATL4_HUMAN | 919 | 929 | WgeCsseCgsG |
| 75 | Q6UY14\|ATL4_HUMAN | 979 | 989 | WspCsrsCqgG |
| 76 | Q6ZMM2\|ATL5_HUMAN | 44 | 54 | WtrCsssCgrG |
| 77 | Q76LX8\|ATS13_HUMAN | 1081 | 1091 | WmeCsvsCgdG |
| 78 | Q86TH1\|ATL2_HUMAN | 56 | 66 | WtaCsrsCggG |
| 79 | Q86TH1\|ATL2_HUMAN | 631 | 641 | WseCsrtCgeG |
| 80 | Q86TH1\|ATL2_HUMAN | 746 | 756 | WgpCsgsCgqG |
| 81 | Q86TH1\|ATL2_HUMAN | 803 | 813 | WerCnttCgrG |
| 82 | Q86TH1\|ATL2_HUMAN | 862 | 872 | WseCtktCgvG |
| 83 | Q8IUL8\|CILP2_HUMAN | 155 | 165 | WgpCsgsCgpG |
| 84 | Q8IZJ1\|UNC5B_HUMAN | 255 | 265 | WspCsnrCgrG |
| 85 | Q8N6G6\|ATL1_HUMAN | 42 | 52 | WseCsrtCggG |
| 86 | Q8N6G6\|ATL1_HUMAN | 385 | 395 | WtaCsssCggG |
| 87 | Q8N6G6\|ATL1_HUMAN | 445 | 455 | WspCtvtCgqG |
| 88 | Q8TE56\|ATS17_HUMAN | 552 | 562 | WsmCsrtCgtG |
| 89 | Q8TE56\|ATS17_HUMAN | 809 | 819 | WegCsvqCggG |
| 90 | Q8TE56\|ATS17_HUMAN | 870 | 880 | WspCsatCekG |
| 91 | Q8TE56\|ATS17_HUMAN | 930 | 940 | WsqCsasCgkG |
| 92 | Q8TE56\|ATS17_HUMAN | 981 | 991 | WstCsstCgkG |
| 93 | Q8TE57\|ATS16_HUMAN | 595 | 605 | WspCsrtCggG |
| 94 | Q8TE57\|ATS16_HUMAN | 936 | 946 | WsaCsrtCggG |
| 95 | Q8TE57\|ATS16_HUMAN | 995 | 1005 | WaeCshtCgkG |
| 96 | Q8TE57\|ATS16_HUMAN | 1060 | 1070 | WsqCsvtCerG |
| 97 | Q8TE57\|ATS16_HUMAN | 1135 | 1145 | WsqCtasCggG |
| 98 | Q8TE58\|ATS15_HUMAN | 848 | 858 | WgpCsasCgsG |
| 99 | Q8TE58\|ATS15_HUMAN | 902 | 912 | WspCsksCgrG |
| 100 | Q8TE59\|ATS19_HUMAN | 642 | 652 | WspCsrtCsaG |
| 101 | Q8TE59\|ATS19_HUMAN | 924 | 934 | WedCdatCggG |
| 102 | Q8TE59\|ATS19_HUMAN | 985 | 995 | WtpCsrtCgkG |
| 103 | Q8TE59\|ATS19_HUMAN | 1096 | 1106 | WskCsitCgkG |
| 104 | Q8TE60\|ATS18_HUMAN | 598 | 608 | WseCsrtCggG |
| 105 | Q8TE60\|ATS18_HUMAN | 940 | 950 | WstCskaCagG |
| 106 | Q8TE60\|ATS18_HUMAN | 1000 | 1010 | WsqCsktCgrG |
| 107 | Q8TE60\|ATS18_HUMAN | 1061 | 1071 | WseCsatCglG |
| 108 | Q8TE60\|ATS18_HUMAN | 1132 | 1142 | WqqCtvtCggG |
| 109 | Q8WXS8\|ATS14_HUMAN | 856 | 866 | WapCskaCggG |
| 110 | Q8WXS8\|ATS14_HUMAN | 977 | 987 | WsqCsatCgeG |
| 111 | Q92947\|GCDH_HUMAN | 225 | 235 | WarCedgCirG |
| 112 | Q96RW7\|HMCN1_HUMAN | 4538 | 4548 | WraCsvtCgkG |
| 113 | Q96RW7\|HMCN1_HUMAN | 4595 | 4605 | WeeCtrsCgrG |
| 114 | Q96RW7\|HMCN1_HUMAN | 4652 | 4662 | WgtCsesCgkG |
| 115 | Q96RW7\|HMCN1_HUMAN | 4709 | 4719 | WsaCsvsCggG |
| 116 | Q96RW7\|HMCN1_HUMAN | 4766 | 4776 | WgtCsrtCngG |
| 117 | Q96RW7\|HMCN1_HUMAN | 4823 | 4833 | WsqCsasCggG |
| 118 | Q99732\|LITAF_HUMAN | 116 | 126 | WlsCgslCllG |

TABLE 2-continued

TSPs
Motif: W-X(2)-C-X(3)-C-X(2)-G (SEQ ID NO: 2287)
Number of Locations: 166
Number of Different Proteins: 54

| # | Accession Number\|Protein Name | First Amino acid | Last Amino acid | Sequence |
|---|---|---|---|---|
| 119 | Q9C0I4\|THS7B_HUMAN | 49 | 59 | WgrCtgdCgpG |
| 120 | Q9C0I4\|THS7B_HUMAN | 345 | 355 | WspCsktCrsG |
| 121 | Q9C0I4\|THS7B_HUMAN | 746 | 756 | WtpCprmCqaG |
| 122 | Q9C0I4\|THS7B_HUMAN | 1009 | 1019 | WgsCsssCgiG |
| 123 | Q9C0I4\|THS7B_HUMAN | 1258 | 1268 | WteCsqtCghG |
| 124 | Q9C0I4\|THS7B_HUMAN | 1381 | 1391 | WstCeltCidG |
| 125 | Q9H324\|ATS10_HUMAN | 530 | 540 | WgdCsrtCggG |
| 126 | Q9H324\|ATS10_HUMAN | 808 | 818 | WtkCsaqCagG |
| 127 | Q9H324\|ATS10_HUMAN | 867 | 877 | WslCsrsCdaG |
| 128 | Q9H324\|ATS10_HUMAN | 927 | 937 | WseCtpsCgpG |
| 129 | Q9H324\|ATS10_HUMAN | 986 | 996 | WgeCsaqCgvG |
| 130 | Q9HCB6\|SPON1_HUMAN | 510 | 520 | WspCsisCgmG |
| 131 | Q9HCB6\|SPON1_HUMAN | 567 | 577 | WdeCsatCgmG |
| 132 | Q9HCB6\|SPON1_HUMAN | 623 | 633 | WsdCsvtCgkG |
| 133 | Q9HCB6\|SPON1_HUMAN | 677 | 687 | WseCnksCgkG |
| 134 | Q9HCB6\|SPON1_HUMAN | 763 | 773 | WseCtklCggG |
| 135 | Q9NS62\|THSD1_HUMAN | 349 | 359 | WsqCsatCgdG |
| 136 | Q9P283\|SEM5B_HUMAN | 615 | 625 | WalCstsCgiG |
| 137 | Q9P283\|SEM5B_HUMAN | 673 | 683 | WskCssnCggG |
| 138 | Q9P283\|SEM5B_HUMAN | 804 | 814 | WssCsrdCelG |
| 139 | Q9P283\|SEM5B_HUMAN | 861 | 871 | WspCsasCggG |
| 140 | Q9P2N4\|ATS9_HUMAN | 1006 | 1016 | WteCsksCdgG |
| 141 | Q9P2N4\|ATS9_HUMAN | 1061 | 1071 | WseClvtCgkG |
| 142 | Q9P2N4\|ATS9_HUMAN | 1116 | 1126 | WvqCsvtCgqG |
| 143 | Q9P2N4\|ATS9_HUMAN | 1191 | 1201 | WtpCsatCgkG |
| 144 | Q9P2N4\|ATS9_HUMAN | 1247 | 1257 | WssCsvtCgqG |
| 145 | Q9P2N4\|ATS9_HUMAN | 1337 | 1347 | WgaCsstCagG |
| 146 | Q9P2N4\|ATS9_HUMAN | 1391 | 1401 | WgeCtklCggG |
| 147 | Q9P2N4\|ATS9_HUMAN | 1450 | 1460 | WssCsvsCgrG |
| 148 | Q9P2N4\|ATS9_HUMAN | 1506 | 1516 | WsqCsvsCgrG |
| 149 | Q9P2N4\|ATS9_HUMAN | 1564 | 1574 | WqeCtktCgeG |
| 150 | Q9P2N4\|ATS9_HUMAN | 1621 | 1631 | WseCsvtCgkG |
| 151 | Q9P2N4\|ATS9_HUMAN | 1686 | 1696 | WgsCsvsCgvG |
| 152 | Q9UHI8\|ATS1_HUMAN | 568 | 578 | WgdCsrtCggG |
| 153 | Q9UHI8\|ATS1_HUMAN | 863 | 873 | WgeCsksCelG |
| 154 | Q9UHI8\|ATS1_HUMAN | 917 | 927 | WssCsktCgkG |
| 155 | Q9UKP4\|ATS7_HUMAN | 547 | 557 | WsiCsrsCgmG |
| 156 | Q9UKP4\|ATS7_HUMAN | 924 | 934 | WtkCtvtCgrG |
| 157 | Q9UKP5\|ATS6_HUMAN | 519 | 529 | WgeCsrtCggG |
| 158 | Q9UKP5\|ATS6_HUMAN | 801 | 811 | WseCsatCagG |
| 159 | Q9UNA0\|ATS5_HUMAN | 576 | 586 | WgqCsrsCggG |
| 160 | Q9UNA0\|ATS5_HUMAN | 884 | 894 | WlaCsrtCdtG |
| 161 | Q9UP79\|ATS8_HUMAN | 536 | 546 | WgeCsrtCggG |
| 162 | Q9UP79\|ATS8_HUMAN | 842 | 852 | WseCsstCgaG |
| 163 | Q9UPZ6\|THS7A_HUMAN | 203 | 213 | WseCsktCgsG |
| 164 | Q9UPZ6\|THS7A_HUMAN | 780 | 790 | WtsCpssCkeG |
| 165 | Q9UPZ6\|THS7A_HUMAN | 1044 | 1054 | WsrCsksCgsG |
| 166 | Q9UPZ6\|THS7A_HUMAN | 1423 | 1433 | WslCqltCvnG |

These peptides are likely to have anti-angiogenic activity. Methods for testing for such activity are described herein.

Example 3

Peptides Derived from C-X-C Chemokines

Figure 4:
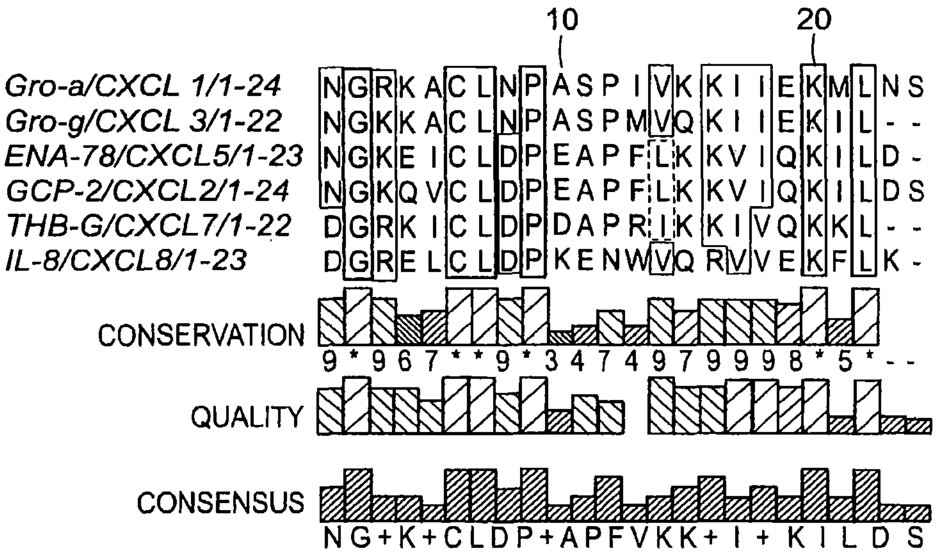
FIG. 4 shows a set of amino acid sequences that include a shaded 6-letter motif common in all the experimentally tested C-X-C containing proteins (SEQ ID NOS 2305, 2310-2311 and 2388-2390, respectively, in order of appearance).

For the six predicted and experimentally tested C-X-C chemokines, all of them contain a six amino acid common motif. Following the thus far used notation this motif can be described as X-G-X3-C-L-X-P-X10-K-X-L (SEQ ID NO: 2432) (FIG. 4). There are few common alterations that occur within the sequences of the predicted fragments. For all those cases the motif can be re-written as (N/D)-G-(R/K)-X2-C-L-(N/D)-P-X2-(P/N)-X2-(K/Q)-(K/Q)-(I/V)-(I/V)-(E/Q)-K-X-L (SEQ ID NO: 2436).

TABLE 3

The C-X-C chemokine 22-mer with
all the possible amino acid substitutions (SEQ ID NO: 2437)

| AA#1 | AA#2 | AA#3 | AA#4 | AA#5 | AA#6 | AA#7 | AA#8 | AA#9 | AA#10 | AA#11 |
|---|---|---|---|---|---|---|---|---|---|---|
| N(4) | G(6) | R(3) | K(3) | A(2) | C(6) | L(6) | D(4) | P(6) | A(2) | A(3) |
| D(2) |  | K(3) | E(2) | I(2) |  |  | N(2) |  | E(2) | S(2) |
|  |  |  | Q(1) | L(1) |  |  |  |  | D(1) | E(1) |
|  |  |  |  | V(1) |  |  |  |  | K(1) |  |

| AA#12 | AA#13 | AA#14 | AA#15 | AA#16 | AA#17 | AA#18 | AA#19 | AA#20 | AA#21 | AA#22 |
|---|---|---|---|---|---|---|---|---|---|---|
| P(6) | F(2) | V(3) | K(4) | K(5) | I(3) | I(4) | E(3) | K(6) | I(3) | L(6) |
|  | I(1) | L(2) | Q(2) | R(1) | V(3) | V(2) | Q(3) |  | F(1) |  |
|  | M(1) | I(1) |  |  |  |  |  |  | K(1) |  |
|  | R(1) |  |  |  |  |  |  |  | M(1) |  |
|  | W(1) |  |  |  |  |  |  |  |  |  |

The generic 22-mer of the predicted C-X-C chemokines including all the possible substitutions is presented in Table 3.

The case of the motif calculation for the theoretically predicted C-X-C chemokines is extremely interesting as in this calculation both short and long fragments are included. If the motifs that were identified within the experimentally tested short fragments are present in the longer ones as well, this might help localize possible anti-angiogenic activity within the longer fragments.

Figure 5:
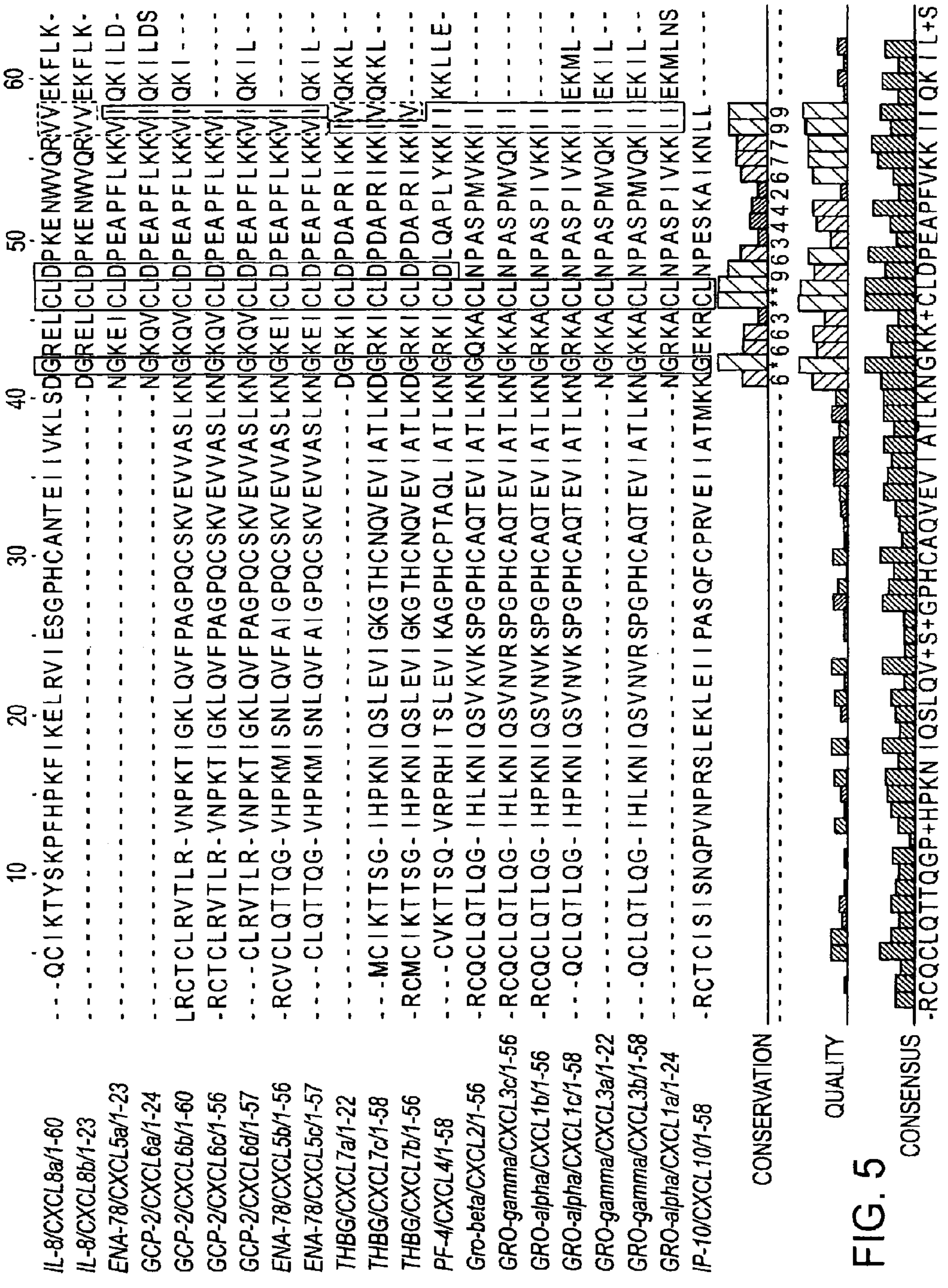
FIG. 5 shows a set of amino acid sequences that include a shaded common motif in all the theoretically predicted anti-angiogenic C-X-C containing proteins (SEQ ID NOS 2392, 2390, 2311, 2388, 2393-2397, 2389, 2398-2404, 2310, 2405, 2305 and 2406, respectively, in order of appearance).

When repeating the calculations with all the theoretically predicted C-X-C chemokines this reproduced the X-G-X3-C-L-X-P-X10-K-X-L motif (SEQ ID NO: 2432) as predicted when the motifs were calculated in the experimentally tested short fragments, but with minimal alterations (FIG. 5).

For the case of all the theoretically predicted C-X-C chemokines a more generic 22-mer can be described as (N/D/K)-G-X3-C-L-(D/N)-(P/L)-X5-(K/Q)-(K/R/N)-(I/V/L)-(I/V/L)-X6. From the above analysis it also becomes obvious that we can localize the activity of the longer predicted fragments at the sites where the predominant motif from the experimentally tested peptides resides.

Similarly to the type I thrombospondin containing proteins one can consider the most generic 3-common letter motif that is identified within the peptide sequences: G-X3-C-L, and search for its existence within the proteome and identify novel peptides that may contain it. Using as a query the aforementioned motif we utilize the ScanProsite tool to search the Prosite database at the Swiss Institute of Bioinformatics in order to identify protein location that may contain it. The G-X3-C-L motif is identified in 1337 locations of 1170 proteins listed in Table 4 (SEQ ID Nos. 167-1503).

TABLE 4

CXCs
Motif: G-X(3)-C-L
Number of Locations: 1337
Number of Different Proteins: 1170

| # | Accession Number\|Protein Name | First Amino acid | Last Amino acid | Sequence |
|---|---|---|---|---|
| 167 | O00142\|KITM_HUMAN | 62 | 67 | GkttCL |
| 168 | O00167\|EYA2_HUMAN | 361 | 366 | GanlCL |
| 169 | O00220\|TR10A_HUMAN | 332 | 337 | GeaqCL |
| 170 | O00291\|HIP1_HUMAN | 699 | 704 | GattCL |
| 171 | O00409\|FOXN3_HUMAN | 465 | 470 | GirsCL |
| 172 | O00444\|PLK4_HUMAN | 775 | 780 | GhriCL |
| 173 | O00462\|MANBA_HUMAN | 744 | 749 | GeavCL |
| 174 | O00468\|AGRIN_HUMAN | 1549 | 1554 | GdhpCL |
| 175 | O00468\|AGRIN_HUMAN | 2012 | 2017 | GfvgCL |
| 176 | O00476\|NPT4_HUMAN | 144 | 149 | GcvcCL |
| 177 | O00488\|ZN593_HUMAN | 41 | 46 | GlhrCL |
| 178 | O00501\|CLD5_HUMAN | 10 | 15 | GlvlCL |
| 179 | O00624\|NPT3_HUMAN | 220 | 225 | GcvcCL |
| 180 | O14514\|BAI1_HUMAN | 243 | 248 | GpenCL |
| 181 | O14522\|PTPRT_HUMAN | 736 | 741 | GtplCL |
| 182 | O14548\|COX7R_HUMAN | 97 | 102 | GtiyCL |
| 183 | O14617\|AP3D1_HUMAN | 1113 | 1118 | GhhvCL |
| 184 | O14628\|ZN195_HUMAN | 51 | 56 | GlitCL |
| 185 | O14772\|FPGT_HUMAN | 515 | 520 | GnktCL |
| 186 | O14773\|TPP1_HUMAN | 2 | 7 | GlqaCL |
| 187 | O14792\|OST1_HUMAN | 261 | 266 | GrdrCL |
| 188 | O14817\|TSN4_HUMAN | 68 | 73 | GfvgCL |
| 189 | O14841\|OPLA_HUMAN | 1240 | 1245 | GdvfCL |
| 190 | O14842\|FFAR1_HUMAN | 166 | 171 | GspvCL |
| 191 | O14894\|T4S5_HUMAN | 100 | 105 | GaiyCL |
| 192 | O14981\|BTAF1_HUMAN | 608 | 613 | GawlCL |
| 193 | O15021\|MAST4_HUMAN | 1534 | 1539 | GsheCL |
| 194 | O15031\|PLXB2_HUMAN | 308 | 313 | GaglCL |
| 195 | O15056\|SYNJ2_HUMAN | 27 | 32 | GrddCL |
| 196 | O15060\|ZBT39_HUMAN | 272 | 277 | GtnsCL |
| 197 | O15063\|K0355_HUMAN | 244 | 249 | GcdgCL |
| 198 | O15067\|PUR4_HUMAN | 914 | 919 | GlvtCL |
| 199 | O15067\|PUR4_HUMAN | 1040 | 1045 | GpsyCL |
| 200 | O15084\|ANR28_HUMAN | 449 | 454 | GnleCL |
| 201 | O15084\|ANR28_HUMAN | 549 | 554 | GhrlCL |
| 202 | O15084\|ANR28_HUMAN | 661 | 666 | GhseCL |
| 203 | O15105\|SMAD7_HUMAN | 293 | 298 | GngfCL |
| 204 | O15146\|MUSK_HUMAN | 648 | 653 | GkpmCL |
| 205 | O15229\|KMO_HUMAN | 320 | 325 | GfedCL |
| 206 | O15230\|LAMA5_HUMAN | 1933 | 1938 | GrtqCL |
| 207 | O15296\|LX15B_HUMAN | 157 | 162 | GwphCL |
| 208 | O15305\|PMM2_HUMAN | 5 | 10 | GpalCL |
| 209 | O15354\|GPR37_HUMAN | 448 | 453 | GcyfCL |
| 210 | O15379\|HDAC3_HUMAN | 214 | 219 | GryyCL |
| 211 | O15397\|IPO8_HUMAN | 148 | 153 | GsllCL |
| 212 | O15554\|KCNN4_HUMAN | 263 | 268 | GkivCL |

TABLE 4-continued

CXCs
Motif: G-X(3)-C-L
Number of Locations: 1337
Number of Different Proteins: 1170

| # | Accession Number\|Protein Name | First Amino acid | Last Amino acid | Sequence |
|---|---|---|---|---|
| 213 | O43156\|K0406_HUMAN | 642 | 647 | GkdfCL |
| 214 | O43175\|SERA_HUMAN | 111 | 116 | GmimCL |
| 215 | O43175\|SERA_HUMAN | 416 | 421 | GfgeCL |
| 216 | O43184\|ADA12_HUMAN | 407 | 412 | GmgvCL |
| 217 | O43283\|M3K13_HUMAN | 133 | 138 | GlfgCL |
| 218 | O43396\|TXNL1_HUMAN | 32 | 37 | GcgpCL |
| 219 | O43396\|TXNL1_HUMAN | 144 | 149 | GfdnCL |
| 220 | O43405\|COCH_HUMAN | 10 | 15 | GlgvCL |
| 221 | O43541\|SMAD6_HUMAN | 363 | 368 | GsgfCL |
| 222 | O43609\|SPY1_HUMAN | 219 | 224 | GtcmCL |
| 223 | O43638\|FREA_HUMAN | 315 | 320 | GltpCL |
| 224 | O43747\|AP1G1_HUMAN | 65 | 70 | GqleCL |
| 225 | O43820\|HYAL3_HUMAN | 12 | 17 | GvalCL |
| 226 | O43837\|IDH3B_HUMAN | 181 | 186 | GvieCL |
| 227 | O43889\|CREB3_HUMAN | 330 | 335 | GntsCL |
| 228 | O60244\|CRSP2_HUMAN | 447 | 452 | GnseCL |
| 229 | O60266\|ADCY3_HUMAN | 44 | 49 | GsclCL |
| 230 | O60266\|ADCY3_HUMAN | 944 | 949 | GgieCL |
| 231 | O60292\|SI1L3_HUMAN | 658 | 663 | GekvCL |
| 232 | O60423\|AT8B3_HUMAN | 238 | 243 | GdvvCL |
| 233 | O60504\|VINEX_HUMAN | 478 | 483 | GehiCL |
| 234 | O60508\|PRP17_HUMAN | 320 | 325 | GerrCL |
| 235 | O60613\|SEP15_HUMAN | 4 | 9 | GpsgCL |
| 236 | O60656\|UD19_HUMAN | 510 | 515 | GyrkCL |
| 237 | O60662\|KBTBA_HUMAN | 447 | 452 | GmiyCL |
| 238 | O60669\|MOT2_HUMAN | 93 | 98 | GllcCL |
| 239 | O60673\|DPOLZ_HUMAN | 47 | 52 | GqktCL |
| 240 | O60704\|TPST2_HUMAN | 229 | 234 | GkekCL |
| 241 | O60706\|ABCC9_HUMAN | 1046 | 1051 | GiflCL |
| 242 | O60883\|ETBR2_HUMAN | 315 | 320 | GcyfCL |
| 243 | O75037\|KI21B_HUMAN | 1454 | 1459 | GpvmCL |
| 244 | O75037\|KI21B_HUMAN | 1617 | 1622 | GltpCL |
| 245 | O75052\|CAPON_HUMAN | 420 | 425 | GrrdCL |
| 246 | O75077\|ADA23_HUMAN | 487 | 492 | GggaCL |
| 247 | O75078\|ADA11_HUMAN | 429 | 434 | GggsCL |
| 248 | O75094\|SLIT3_HUMAN | 1428 | 1433 | GepyCL |
| 249 | O75095\|MEGF6_HUMAN | 695 | 700 | GaclCL |
| 250 | O75173\|ATS4_HUMAN | 19 | 24 | GaqpCL |
| 251 | O75173\|ATS4_HUMAN | 419 | 424 | GyghCL |
| 252 | O75311\|GLRA3_HUMAN | 387 | 392 | GmgpCL |
| 253 | O75326\|SEM7A_HUMAN | 499 | 504 | GchgCL |
| 254 | O75342\|LX12B_HUMAN | 299 | 304 | GegtCL |
| 255 | O75342\|LX12B_HUMAN | 552 | 557 | GfprCL |
| 256 | O75346\|ZN253_HUMAN | 131 | 136 | GlnqCL |
| 257 | O75426\|FBX24_HUMAN | 119 | 124 | GrrrCL |
| 258 | O75436\|VP26A_HUMAN | 169 | 174 | GiedCL |
| 259 | O75443\|TECTA_HUMAN | 1687 | 1692 | GdgyCL |
| 260 | O75445\|USH2A_HUMAN | 1668 | 1673 | GfvgCL |
| 261 | O75445\|USH2A_HUMAN | 4401 | 4406 | GqglCL |
| 262 | O75446\|SAP30_HUMAN | 64 | 69 | GqlcCL |
| 263 | O75508\|CLD11_HUMAN | 164 | 169 | GavlCL |
| 264 | O75569\|PRKRA_HUMAN | 268 | 273 | GqyqCL |
| 265 | O75592\|MYCB2_HUMAN | 1087 | 1092 | GfgvCL |
| 266 | O75636\|FCN3_HUMAN | 16 | 21 | GgpaCL |
| 267 | O75678\|RFPL2_HUMAN | 117 | 122 | GcavCL |
| 268 | O75679\|RFPL3_HUMAN | 56 | 61 | GctvCL |
| 269 | O75689\|CENA1_HUMAN | 37 | 42 | GvfiCL |
| 270 | O75691\|UTP20_HUMAN | 2132 | 2137 | GalqCL |
| 271 | O75694\|NU155_HUMAN | 230 | 235 | GkdgCL |
| 272 | O75843\|AP1G2_HUMAN | 67 | 72 | GqmeCL |
| 273 | O75886\|STAM2_HUMAN | 42 | 47 | GakdCL |
| 274 | O75911\|DHRS3_HUMAN | 168 | 173 | GhivCL |
| 275 | O75916\|RGS9_HUMAN | 642 | 647 | GsgtCL |
| 276 | O75923\|DYSF_HUMAN | 378 | 383 | GahfCL |
| 277 | O75923\|DYSF_HUMAN | 1574 | 1579 | GpqeCL |
| 278 | O75925\|PIAS1_HUMAN | 431 | 436 | GvdgCL |
| 279 | O75954\|TSN9_HUMAN | 4 | 9 | GclcCL |
| 280 | O75954\|TSN9_HUMAN | 68 | 73 | GflgCL |
| 281 | O76000\|OR2B3_HUMAN | 108 | 113 | GateCL |
| 282 | O76013\|K1H6_HUMAN | 58 | 63 | GlgsCL |
| 283 | O76064\|RNF8_HUMAN | 15 | 20 | GrswCL |

TABLE 4-continued

CXCs
Motif: G-X(3)-C-L
Number of Locations: 1337
Number of Different Proteins: 1170

| # | Accession Number\|Protein Name | First Amino acid | Last Amino acid | Sequence |
|---|---|---|---|---|
| 284 | O76075\|DFFB_HUMAN | 43 | 48 | GsrlCL |
| 285 | O94759\|TRPM2_HUMAN | 272 | 277 | GnltCL |
| 286 | O94759\|TRPM2_HUMAN | 713 | 718 | GkttCL |
| 287 | O94761\|RECQ4_HUMAN | 543 | 548 | GlppCL |
| 288 | O94779\|CNTN5_HUMAN | 169 | 174 | GhyqCL |
| 289 | O94779\|CNTN5_HUMAN | 265 | 270 | GsyiCL |
| 290 | O94779\|CNTN5_HUMAN | 454 | 459 | GmyqCL |
| 291 | O94829\|IPO13_HUMAN | 159 | 164 | GqgrCL |
| 292 | O94856\|NFASC_HUMAN | 312 | 317 | GeyfCL |
| 293 | O94887\|FARP2_HUMAN | 192 | 197 | GqqhCL |
| 294 | O94900\|TOX_HUMAN | 22 | 27 | GpspCL |
| 295 | O94907\|DKK1_HUMAN | 107 | 112 | GvqiCL |
| 296 | O94919\|ENDD1_HUMAN | 371 | 376 | GiesCL |
| 297 | O94933\|SLIK3_HUMAN | 898 | 903 | GfvdCL |
| 298 | O94955\|RHBT3_HUMAN | 386 | 391 | GkinCL |
| 299 | O94956\|SO2B1_HUMAN | 449 | 454 | GmllCL |
| 300 | O95071\|EDD1_HUMAN | 531 | 536 | GtqvCL |
| 301 | O95153\|RIMB1_HUMAN | 79 | 84 | GaeaCL |
| 302 | O95153\|RIMB1_HUMAN | 1485 | 1490 | GlasCL |
| 303 | O95163\|IKAP_HUMAN | 472 | 477 | GfkvCL |
| 304 | O95202\|LETM1_HUMAN | 43 | 48 | GlrnCL |
| 305 | O95210\|GET1_HUMAN | 285 | 290 | GdheCL |
| 306 | O95239\|KIF4A_HUMAN | 27 | 32 | GcqmCL |
| 307 | O95248\|MTMR5_HUMAN | 159 | 164 | GlnvCL |
| 308 | O95248\|MTMR5_HUMAN | 381 | 386 | GyrwCL |
| 309 | O95255\|MRP6_HUMAN | 845 | 850 | GalvCL |
| 310 | O95255\|MRP6_HUMAN | 943 | 948 | GtplCL |
| 311 | O95255\|MRP6_HUMAN | 992 | 997 | GllgCL |
| 312 | O95256\|I18RA_HUMAN | 447 | 452 | GyslCL |
| 313 | O95279\|KCNK5_HUMAN | 122 | 127 | GvplCL |
| 314 | O95294\|RASL1_HUMAN | 130 | 135 | GqgrCL |
| 315 | O95342\|ABCBB_HUMAN | 327 | 332 | GfvwCL |
| 316 | O95373\|IPO7_HUMAN | 147 | 152 | GillCL |
| 317 | O95396\|MOCS3_HUMAN | 250 | 255 | GvlgCL |
| 318 | O95405\|ZFYV9_HUMAN | 137 | 142 | GnlaCL |
| 319 | O95477\|ABCA1_HUMAN | 2120 | 2125 | GrfrCL |
| 320 | O95500\|CLD14_HUMAN | 178 | 183 | GtllCL |
| 321 | O95551\|TTRAP_HUMAN | 217 | 222 | GnelCL |
| 322 | O95602\|RPA1_HUMAN | 1556 | 1561 | GitrCL |
| 323 | O95620\|DUS4L_HUMAN | 125 | 130 | GygaCL |
| 324 | O95633\|FSTL3_HUMAN | 88 | 93 | GlvhCL |
| 325 | O95671\|ASML_HUMAN | 588 | 593 | GeyqCL |
| 326 | O95714\|HERC2_HUMAN | 717 | 722 | GsthCL |
| 327 | O95714\|HERC2_HUMAN | 3265 | 3270 | GalhCL |
| 328 | O95714\|HERC2_HUMAN | 4047 | 4052 | GgkhCL |
| 329 | O95715\|SCYBE_HUMAN | 68 | 73 | GqehCL |
| 330 | O95780\|ZN682_HUMAN | 132 | 137 | GlnqCL |
| 331 | O95803\|NDST3_HUMAN | 815 | 820 | GktkCL |
| 332 | O95858\|TSN15_HUMAN | 285 | 290 | GtgcCL |
| 333 | O95873\|CF047_HUMAN | 171 | 176 | GpeeCL |
| 334 | O95886\|DLGP3_HUMAN | 284 | 289 | GgpfCL |
| 335 | O95967\|FBLN4_HUMAN | 76 | 81 | GgylCL |
| 336 | O95977\|EDG6_HUMAN | 333 | 338 | GpgdCL |
| 337 | O96006\|ZBED1_HUMAN | 221 | 226 | GapnCL |
| 338 | O96008\|TOM40_HUMAN | 72 | 77 | GacgCL |
| 339 | O96009\|NAPSA_HUMAN | 350 | 355 | GvrlCL |
| 340 | P00505\|AATM_HUMAN | 268 | 273 | GinvCL |
| 341 | P00750\|TPA_HUMAN | 515 | 520 | GplvCL |
| 342 | P00751\|CFAB_HUMAN | 288 | 293 | GakkCL |
| 343 | P01130\|LDLR_HUMAN | 314 | 319 | GtneCL |
| 344 | P01133\|EGF_HUMAN | 741 | 746 | GadpCL |
| 345 | P01266\|THYG_HUMAN | 2020 | 2025 | GevtCL |
| 346 | P01375\|TNFA_HUMAN | 26 | 31 | GsrrCL |
| 347 | P01730\|CD4_HUMAN | 366 | 371 | GmwqCL |
| 348 | P01833\|PIGR_HUMAN | 437 | 442 | GfywCL |
| 349 | P02775\|SCYB7_HUMAN | 101 | 106 | GrkiCL |
| 350 | P02776\|PLF4_HUMAN | 37 | 42 | GdlqCL |
| 351 | P02776\|PLF4_HUMAN | 79 | 84 | GrkiCL |
| 352 | P02778\|SCYBA_HUMAN | 70 | 75 | GekrCL |
| 353 | P02787\|TRFE_HUMAN | 209 | 214 | GafkCL |
| 354 | P02787\|TRFE_HUMAN | 538 | 543 | GafrCL |

TABLE 4-continued

CXCs
Motif: G-X(3)-C-L
Number of Locations: 1337
Number of Different Proteins: 1170

| # | Accession Number\|Protein Name | First Amino acid | Last Amino acid | Sequence |
|---|---|---|---|---|
| 355 | P02788\|TRFL_HUMAN | 213 | 218 | GafkCL |
| 356 | P02788\|TRFL_HUMAN | 549 | 554 | GafrCL |
| 357 | P03986\|TCC_HUMAN | 28 | 33 | GtylCL |
| 358 | P04350\|TBB4_HUMAN | 235 | 240 | GvttCL |
| 359 | P04920\|B3A2_HUMAN | 751 | 756 | GvvfCL |
| 360 | P05108\|CP11A_HUMAN | 458 | 463 | GvrqCL |
| 361 | P05141\|ADT2_HUMAN | 155 | 160 | GlgdCL |
| 362 | P05549\|AP2A_HUMAN | 371 | 376 | GiqsCL |
| 363 | P06401\|PRGR_HUMAN | 484 | 489 | GasgCL |
| 364 | P06756\|ITAV_HUMAN | 905 | 910 | GvaqCL |
| 365 | P07202\|PERT_HUMAN | 819 | 824 | GgfqCL |
| 366 | P07339\|CATD_HUMAN | 362 | 367 | GktlCL |
| 367 | P07357\|CO8A_HUMAN | 117 | 122 | GdqdCL |
| 368 | P07437\|TBB5_HUMAN | 235 | 240 | GvttCL |
| 369 | P07686\|HEXB_HUMAN | 483 | 488 | GgeaCL |
| 370 | P07814\|SYEP_HUMAN | 261 | 266 | GhscCL |
| 371 | P07942\|LAMB1_HUMAN | 1052 | 1057 | GqclCL |
| 372 | P07988\|PSPB_HUMAN | 244 | 249 | GicqCL |
| 373 | P08151\|GLI1_HUMAN | 14 | 19 | GepcCL |
| 374 | P08151\|GLI1_HUMAN | 828 | 833 | GlapCL |
| 375 | P08243\|ASNS_HUMAN | 8 | 13 | GsddCL |
| 376 | P08319\|ADH4_HUMAN | 241 | 246 | GatdCL |
| 377 | P08582\|TRFM_HUMAN | 212 | 217 | GafrCL |
| 378 | P08582\|TRFM_HUMAN | 558 | 563 | GafrCL |
| 379 | P08686\|CP21A_HUMAN | 424 | 429 | GarvCL |
| 380 | P08697\|A2AP_HUMAN | 139 | 144 | GsgpCL |
| 381 | P08709\|FA7_HUMAN | 14 | 19 | GlqgCL |
| 382 | P08922\|ROS_HUMAN | 2248 | 2253 | GdviCL |
| 383 | P09001\|RM03_HUMAN | 291 | 296 | GhknCL |
| 384 | P09326\|CD48_HUMAN | 5 | 10 | GwdsCL |
| 385 | P09341\|GROA_HUMAN | 81 | 86 | GrkaCL |
| 386 | P09848\|LPH_HUMAN | 1846 | 1851 | GphaCL |
| 387 | P10071\|GLI3_HUMAN | 1359 | 1364 | GpesCL |
| 388 | P10109\|ADX_HUMAN | 151 | 156 | GcqiCL |
| 389 | P10145\|IL8_HUMAN | 73 | 78 | GrelCL |
| 390 | P10635\|CP2D6_HUMAN | 439 | 444 | GrraCL |
| 391 | P10646\|TFPI1_HUMAN | 213 | 218 | GpswCL |
| 392 | P10720\|PF4V_HUMAN | 40 | 45 | GdlqCL |
| 393 | P10720\|PF4V_HUMAN | 82 | 87 | GrkiCL |
| 394 | P10745\|IRBP_HUMAN | 328 | 333 | GvvhCL |
| 395 | P11047\|LAMC1_HUMAN | 903 | 908 | GqceCL |
| 396 | P11362\|FGFR1_HUMAN | 337 | 342 | GeytCL |
| 397 | P11717\|MPRI_HUMAN | 231 | 236 | GtaaCL |
| 398 | P12236\|ADT3_HUMAN | 155 | 160 | GlgdCL |
| 399 | P13473\|LAMP2_HUMAN | 228 | 233 | GndtCL |
| 400 | P13498\|CY24A_HUMAN | 45 | 50 | GvfvCL |
| 401 | P13569\|CFTR_HUMAN | 124 | 129 | GiglCL |
| 402 | P13686\|PPA5_HUMAN | 215 | 220 | GpthCL |
| 403 | P13804\|ETFA_HUMAN | 49 | 54 | GevsCL |
| 404 | P13807\|GYS1_HUMAN | 185 | 190 | GvglCL |
| 405 | P13861\|KAP2_HUMAN | 354 | 359 | GdvkCL |
| 406 | P14222\|PERF_HUMAN | 530 | 535 | GggtCL |
| 407 | P14543\|NID1_HUMAN | 24 | 29 | GpvgCL |
| 408 | P14867\|GBRA1_HUMAN | 6 | 11 | GlsdCL |
| 409 | P15151\|PVR_HUMAN | 119 | 124 | GnytCL |
| 410 | P15538\|C11B1_HUMAN | 446 | 451 | GmrqCL |
| 411 | P15692\|VEGFA_HUMAN | 168 | 173 | GarcCL |
| 412 | P16109\|LYAM3_HUMAN | 271 | 276 | GnmiCL |
| 413 | P16112\|PGCA_HUMAN | 2183 | 2188 | GhviCL |
| 414 | P16581\|LYAM2_HUMAN | 376 | 381 | GymnCL |
| 415 | P17038\|ZNF43_HUMAN | 127 | 132 | GfnqCL |
| 416 | P17040\|ZNF31_HUMAN | 184 | 189 | GnsvCL |
| 417 | P17936\|IBP3_HUMAN | 66 | 71 | GcgcCL |
| 418 | P18510\|IL1RA_HUMAN | 87 | 92 | GgkmCL |
| 419 | P18564\|ITB6_HUMAN | 674 | 679 | GeneCL |
| 420 | P18577\|RHCE_HUMAN | 306 | 311 | GgakCL |
| 421 | P19099\|C11B2_HUMAN | 446 | 451 | GmrqCL |
| 422 | P19224\|UD16_HUMAN | 512 | 517 | GyrkCL |
| 423 | P19367\|HXK1_HUMAN | 713 | 718 | GdngCL |
| 424 | P19835\|CEL_HUMAN | 96 | 101 | GdedCL |
| 425 | P19875\|MIP2A_HUMAN | 81 | 86 | GqkaCL |

TABLE 4-continued

CXCs
Motif: G-X(3)-C-L
Number of Locations: 1337
Number of Different Proteins: 1170

| # | Accession Number\|Protein Name | First Amino acid | Last Amino acid | Sequence |
|---|---|---|---|---|
| 426 | P19876\|MIP2B_HUMAN | 81 | 86 | GkkaCL |
| 427 | P19883\|FST_HUMAN | 252 | 257 | GgkkCL |
| 428 | P20062\|TCO2_HUMAN | 79 | 84 | GyqqCL |
| 429 | P20273\|CD22_HUMAN | 691 | 696 | GlgsCL |
| 430 | P20648\|ATP4A_HUMAN | 108 | 113 | GglqCL |
| 431 | P20701\|ITAL_HUMAN | 76 | 81 | GtghCL |
| 432 | P20701\|ITAL_HUMAN | 1150 | 1155 | GdpgCL |
| 433 | P20813\|CP2B6_HUMAN | 432 | 437 | GkriCL |
| 434 | P20916\|MAG_HUMAN | 301 | 306 | GvyaCL |
| 435 | P20929\|NEBU_HUMAN | 4517 | 4522 | GvvhCL |
| 436 | P21554\|CNR1_HUMAN | 427 | 432 | GdsdCL |
| 437 | P21580\|TNAP3_HUMAN | 99 | 104 | GdgnCL |
| 438 | P21802\|FGFR2_HUMAN | 5 | 10 | GrfiCL |
| 439 | P21802\|FGFR2_HUMAN | 338 | 343 | GeytCL |
| 440 | P21817\|RYR1_HUMAN | 840 | 845 | GpsrCL |
| 441 | P21860\|ERBB3_HUMAN | 513 | 518 | GpgqCL |
| 442 | P21964\|COMT_HUMAN | 30 | 35 | GwglCL |
| 443 | P22064\|LTB1S_HUMAN | 938 | 943 | GsfrCL |
| 444 | P22064\|LTB1S_HUMAN | 1359 | 1364 | GsykCL |
| 445 | P22105\|TENX_HUMAN | 565 | 570 | GrgqCL |
| 446 | P22309\|UD11_HUMAN | 276 | 281 | GginCL |
| 447 | P22309\|UD11_HUMAN | 513 | 518 | GyrkCL |
| 448 | P22310\|UD14_HUMAN | 514 | 519 | GyrkCL |
| 449 | P22314\|UBE1_HUMAN | 230 | 235 | GvvtCL |
| 450 | P22455\|FGFR4_HUMAN | 97 | 102 | GrylCL |
| 451 | P22455\|FGFR4_HUMAN | 220 | 225 | GtytCL |
| 452 | P22455\|FGFR4_HUMAN | 329 | 334 | GeytCL |
| 453 | P22607\|FGFR3_HUMAN | 335 | 340 | GeytCL |
| 454 | P22680\|CP7A1_HUMAN | 330 | 335 | GnpiCL |
| 455 | P22732\|GTR5_HUMAN | 348 | 353 | GfsiCL |
| 456 | P23142\|FBLN1_HUMAN | 269 | 274 | GihnCL |
| 457 | P23142\|FBLN1_HUMAN | 547 | 552 | GgfrCL |
| 458 | P23416\|GLRA2_HUMAN | 376 | 381 | GmghCL |
| 459 | P23759\|PAX7_HUMAN | 466 | 471 | GqseCL |
| 460 | P24386\|RAE1_HUMAN | 395 | 400 | GgiyCL |
| 461 | P24557\|THAS_HUMAN | 475 | 480 | GprsCL |
| 462 | P24592\|IBP6_HUMAN | 100 | 105 | GrgrCL |
| 463 | P24593\|IBP5_HUMAN | 96 | 101 | GrgvCL |
| 464 | P24821\|TENA_HUMAN | 143 | 148 | GagcCL |
| 465 | P24903\|CP2F1_HUMAN | 432 | 437 | GrrlCL |
| 466 | P25205\|MCM3_HUMAN | 239 | 244 | GtyrCL |
| 467 | P25874\|UCP1_HUMAN | 21 | 26 | GiaaCL |
| 468 | P25940\|CO5A3_HUMAN | 1581 | 1586 | GgetCL |
| 469 | P26374\|RAE2_HUMAN | 397 | 402 | GgiyCL |
| 470 | P26951\|IL3RA_HUMAN | 363 | 368 | GleeCL |
| 471 | P27487\|DPP4_HUMAN | 335 | 340 | GrwnCL |
| 472 | P27540\|ARNT_HUMAN | 332 | 337 | GskfCL |
| 473 | P27987\|IP3KB_HUMAN | 284 | 289 | GtrsCL |
| 474 | P28332\|ADH6_HUMAN | 237 | 242 | GateCL |
| 475 | P28340\|DPOD1_HUMAN | 709 | 714 | GklpCL |
| 476 | P29274\|AA2AR_HUMAN | 162 | 167 | GqvaCL |
| 477 | P29353\|SHC1_HUMAN | 570 | 575 | GselCL |
| 478 | P29459\|IL12A_HUMAN | 33 | 38 | GmfpCL |
| 479 | P30040\|ERP29_HUMAN | 153 | 158 | GmpgCL |
| 480 | P30530\|UFO_HUMAN | 106 | 111 | GqyqCL |
| 481 | P30532\|ACHA5_HUMAN | 279 | 284 | GekiCL |
| 482 | P30566\|PUR8_HUMAN | 169 | 174 | GkrcCL |
| 483 | P31323\|KAP3_HUMAN | 368 | 373 | GtvkCL |
| 484 | P32004\|L1CAM_HUMAN | 308 | 313 | GeyrCL |
| 485 | P32004\|L1CAM_HUMAN | 493 | 498 | GryfCL |
| 486 | P32314\|FOXN2_HUMAN | 319 | 324 | GirtCL |
| 487 | P32418\|NAC1_HUMAN | 414 | 419 | GtyqCL |
| 488 | P32929\|CGL_HUMAN | 80 | 85 | GakyCL |
| 489 | P32970\|TNFL7_HUMAN | 29 | 34 | GlviCL |
| 490 | P33402\|GCYA2_HUMAN | 284 | 289 | GncsCL |
| 491 | P34913\|HYES_HUMAN | 258 | 263 | GpavCL |
| 492 | P34981\|TRFR_HUMAN | 94 | 99 | GyvgCL |
| 493 | P34998\|CRFR1_HUMAN | 83 | 88 | GyreCL |
| 494 | P35227\|PCGF2_HUMAN | 316 | 321 | GslnCL |
| 495 | P35251\|RFC1_HUMAN | 402 | 407 | GaenCL |
| 496 | P35270\|SPRE_HUMAN | 6 | 11 | GravCL |
| 497 | P35367\|HRH1_HUMAN | 96 | 101 | GrplCL |
| 498 | P35452\|HXD12_HUMAN | 176 | 181 | GvasCL |
| 499 | P35498\|SCN1A_HUMAN | 964 | 969 | GqamCL |
| 500 | P35499\|SCN4A_HUMAN | 774 | 779 | GqamCL |
| 501 | P35503\|UD13_HUMAN | 514 | 519 | GyrkCL |
| 502 | P35504\|UD15_HUMAN | 514 | 519 | GyrkCL |
| 503 | P35555\|FBN1_HUMAN | 1259 | 1264 | GeyrCL |
| 504 | P35555\|FBN1_HUMAN | 1385 | 1390 | GsyrCL |
| 505 | P35555\|FBN1_HUMAN | 1416 | 1421 | GngqCL |
| 506 | P35555\|FBN1_HUMAN | 1870 | 1875 | GsfyCL |
| 507 | P35555\|FBN1_HUMAN | 2034 | 2039 | GsfkCL |
| 508 | P35556\|FBN2_HUMAN | 1303 | 1308 | GeyrCL |
| 509 | P35556\|FBN2_HUMAN | 1952 | 1957 | GsynCL |
| 510 | P35556\|FBN2_HUMAN | 1994 | 1999 | GsfkCL |
| 511 | P35556\|FBN2_HUMAN | 2076 | 2081 | GgfqCL |
| 512 | P35590\|TIE1_HUMAN | 280 | 285 | GltfCL |
| 513 | P35916\|VGFR3_HUMAN | 4 | 9 | GaalCL |
| 514 | P35968\|VGFR2_HUMAN | 638 | 643 | GdyvCL |
| 515 | P36509\|UD12_HUMAN | 510 | 515 | GyrkCL |
| 516 | P36888\|FLT3_HUMAN | 99 | 104 | GnisCL |
| 517 | P37058\|DHB3_HUMAN | 13 | 18 | GllvCL |
| 518 | P38398\|BRCA1_HUMAN | 949 | 954 | GsrfCL |
| 519 | P38571\|LICH_HUMAN | 7 | 12 | GlvvCL |
| 520 | P38571\|LICH_HUMAN | 58 | 63 | GyilCL |
| 521 | P38606\|VATA1_HUMAN | 390 | 395 | GrvkCL |
| 522 | P38607\|VATA2_HUMAN | 388 | 393 | GrvkCL |
| 523 | P39059\|COFA1_HUMAN | 8 | 13 | GqcwCL |
| 524 | P40205\|NCYM_HUMAN | 100 | 105 | GrppCL |
| 525 | P40939\|ECHA_HUMAN | 709 | 714 | GfppCL |
| 526 | P41217\|OX2G_HUMAN | 117 | 122 | GcymCL |
| 527 | P42331\|RHG25_HUMAN | 4 | 9 | GqsaCL |
| 528 | P42345\|FRAP_HUMAN | 1479 | 1484 | GrnrCL |
| 529 | P42785\|PCP_HUMAN | 339 | 344 | GqvkCL |
| 530 | P42830\|SCYB5_HUMAN | 87 | 92 | GkeiCL |
| 531 | P42892\|ECE1_HUMAN | 79 | 84 | GlvaCL |
| 532 | P43378\|PTN9_HUMAN | 334 | 339 | GdvpCL |
| 533 | P43403\|ZAP70_HUMAN | 113 | 118 | GvfdCL |
| 534 | P43403\|ZAP70_HUMAN | 245 | 250 | GliyCL |
| 535 | P46379\|BAT3_HUMAN | 872 | 877 | GlfeCL |
| 536 | P46531\|NOTC1_HUMAN | 1354 | 1359 | GslrCL |
| 537 | P47775\|GPR12_HUMAN | 166 | 171 | GtsiCL |
| 538 | P47804\|RGR_HUMAN | 275 | 280 | GiwqCL |
| 539 | P48048\|IRK1_HUMAN | 204 | 209 | GgklCL |
| 540 | P48052\|CBPA2_HUMAN | 12 | 17 | GhiyCL |
| 541 | P48059\|PINC_HUMAN | 176 | 181 | GelyCL |
| 542 | P48067\|SC6A9_HUMAN | 457 | 462 | GtqfCL |
| 543 | P48230\|T4S4_HUMAN | 5 | 10 | GcarCL |
| 544 | P48745\|NOV_HUMAN | 60 | 65 | GcscCL |
| 545 | P49247\|RPIA_HUMAN | 100 | 105 | GgggCL |
| 546 | P49327\|FAS_HUMAN | 1455 | 1460 | GlvnCL |
| 547 | P49588\|SYAC_HUMAN | 897 | 902 | GkitCL |
| 548 | P49640\|EVX1_HUMAN | 345 | 350 | GpcsCL |
| 549 | P49641\|MA2A2_HUMAN | 862 | 867 | GwrgCL |
| 550 | P49646\|YYY1_HUMAN | 393 | 398 | GetpCL |
| 551 | P49753\|ACOT2_HUMAN | 296 | 301 | GgelCL |
| 552 | P49903\|SPS1_HUMAN | 323 | 328 | GlliCL |
| 553 | P49910\|ZN165_HUMAN | 32 | 37 | GqdtCL |
| 554 | P50851\|LRBA_HUMAN | 2736 | 2741 | GpenCL |
| 555 | P51151\|RAB9A_HUMAN | 79 | 84 | GsdcCL |
| 556 | P51168\|SCNNB_HUMAN | 532 | 537 | GsvlCL |
| 557 | P51589\|CP2J2_HUMAN | 444 | 449 | GkraCL |
| 558 | P51606\|RENBP_HUMAN | 37 | 42 | GfftCL |
| 559 | P51674\|GPM6A_HUMAN | 170 | 175 | GanlCL |
| 560 | P51685\|CCR8_HUMAN | 150 | 155 | GttlCL |
| 561 | P51790\|CLCN3_HUMAN | 520 | 525 | GaaaCL |
| 562 | P51790\|CLCN3_HUMAN | 723 | 728 | GlrqCL |
| 563 | P51793\|CLCN4_HUMAN | 520 | 525 | GaaaCL |
| 564 | P51793\|CLCN4_HUMAN | 721 | 726 | GlrqCL |
| 565 | P51795\|CLCN5_HUMAN | 506 | 511 | GaaaCL |
| 566 | P51795\|CLCN5_HUMAN | 707 | 712 | GlrqCL |
| 567 | P51800\|CLCKA_HUMAN | 613 | 618 | GhqqCL |

TABLE 4-continued

CXCs
Motif: G-X(3)-C-L
Number of Locations: 1337
Number of Different Proteins: 1170

| # | Accession Number\|Protein Name | First Amino acid | Last Amino acid | Sequence |
|---|---|---|---|---|
| 568 | P51801\|CLCKB_HUMAN | 613 | 618 | GhqqCL |
| 569 | P51957\|NEK4_HUMAN | 322 | 327 | GegkCL |
| 570 | P52306\|GDS1_HUMAN | 25 | 30 | GcldCL |
| 571 | P52306\|GDS1_HUMAN | 265 | 270 | GlveCL |
| 572 | P52429\|DGKE_HUMAN | 411 | 416 | GtkdCL |
| 573 | P52744\|ZN138_HUMAN | 48 | 53 | GlnqCL |
| 574 | P52789\|HXK2_HUMAN | 713 | 718 | GdngCL |
| 575 | P52803\|EFNA5_HUMAN | 147 | 152 | GrrsCL |
| 576 | P52823\|STC1_HUMAN | 55 | 60 | GafaCL |
| 577 | P52848\|NDST1_HUMAN | 824 | 829 | GktkCL |
| 578 | P52849\|NDST2_HUMAN | 302 | 307 | GkrlCL |
| 579 | P52849\|NDST2_HUMAN | 823 | 828 | GktrCL |
| 580 | P52961\|NAR1_HUMAN | 220 | 225 | GiwtCL |
| 581 | P53355\|DAPK1_HUMAN | 1326 | 1331 | GkdwCL |
| 582 | P54132\|BLM_HUMAN | 891 | 896 | GiiyCL |
| 583 | P54277\|PMS1_HUMAN | 837 | 842 | GmanCL |
| 584 | P54750\|PDE1A_HUMAN | 32 | 37 | GilrCL |
| 585 | P54753\|EPHB3_HUMAN | 297 | 302 | GegpCL |
| 586 | P54826\|GAS1_HUMAN | 19 | 24 | GawlCL |
| 587 | P55160\|NCKPL_HUMAN | 938 | 943 | GpieCL |
| 588 | P55268\|LAMB2_HUMAN | 501 | 506 | GcdrCL |
| 589 | P55268\|LAMB2_HUMAN | 1063 | 1068 | GqcpCL |
| 590 | P56192\|SYMC_HUMAN | 8 | 13 | GvpgCL |
| 591 | P56749\|CLD12_HUMAN | 63 | 68 | GssdCL |
| 592 | P57077\|TAK1L_HUMAN | 68 | 73 | GflkCL |
| 593 | P57679\|EVC_HUMAN | 683 | 688 | GssqCL |
| 594 | P58215\|LOXL3_HUMAN | 13 | 18 | GlllCL |
| 595 | P58397\|ATS12_HUMAN | 447 | 452 | GwgfCL |
| 596 | P58418\|USH3A_HUMAN | 69 | 74 | GscgCL |
| 597 | P58512\|CU067_HUMAN | 166 | 171 | GfpaCL |
| 598 | P59047\|NALP5_HUMAN | 64 | 69 | GlqwCL |
| 599 | P59510\|ATS20_HUMAN | 458 | 463 | GygeCL |
| 600 | P60370\|KR105_HUMAN | 32 | 37 | GtapCL |
| 601 | P60371\|KR106_HUMAN | 16 | 21 | GsrvCL |
| 602 | P60409\|KR107_HUMAN | 16 | 21 | GsrvCL |
| 603 | P60413\|KR10C_HUMAN | 11 | 16 | GsrvCL |
| 604 | P60602\|CT052_HUMAN | 38 | 43 | GtfsCL |
| 605 | P61011\|SRP54_HUMAN | 129 | 134 | GwktCL |
| 606 | P61550\|ENT1_HUMAN | 343 | 348 | GnasCL |
| 607 | P61619\|S61A1_HUMAN | 143 | 148 | GagiCL |
| 608 | P62072\|TIM10_HUMAN | 46 | 51 | GesvCL |
| 609 | P62312\|LSM6_HUMAN | 32 | 37 | GvlaCL |
| 610 | P62714\|PP2AB_HUMAN | 161 | 166 | GqifCL |
| 611 | P67775\|PP2AA_HUMAN | 161 | 166 | GqifCL |
| 612 | P68371\|TBB2C_HUMAN | 235 | 240 | GvttCL |
| 613 | P69849\|NOMO3_HUMAN | 507 | 512 | GkvsCL |
| 614 | P78310\|CXAR_HUMAN | 219 | 224 | GsdqCL |
| 615 | P78324\|SHPS1_HUMAN | 12 | 17 | GpllCL |
| 616 | P78325\|ADAM8_HUMAN | 101 | 106 | GqdhCL |
| 617 | P78346\|RPP30_HUMAN | 253 | 258 | GdedCL |
| 618 | P78357\|CNTP1_HUMAN | 1205 | 1210 | GfsgCL |
| 619 | P78423\|X3CL1_HUMAN | 350 | 355 | GllfCL |
| 620 | P78504\|JAG1_HUMAN | 898 | 903 | GprpCL |
| 621 | P78509\|RELN_HUMAN | 2862 | 2867 | GhgdCL |
| 622 | P78524\|ST5_HUMAN | 127 | 132 | GvaaCL |
| 623 | P78549\|NTHL1_HUMAN | 286 | 291 | GqqtCL |
| 624 | P78559\|MAP1A_HUMAN | 2433 | 2438 | GpqgCX |
| 625 | P80162\|SCYB6_HUMAN | 87 | 92 | GkqvCL |
| 626 | P82279\|CRUM1_HUMAN | 1092 | 1097 | GlqgCL |
| 627 | P83105\|HTRA4_HUMAN | 10 | 15 | GlgrCL |
| 628 | P98088\|MUC5A_HUMAN | 853 | 858 | GcprCL |
| 629 | P98095\|FBLN2_HUMAN | 1047 | 1052 | GsfrCL |
| 630 | P98153\|IDD_HUMAN | 289 | 294 | GddpCL |
| 631 | P98160\|PGBM_HUMAN | 3181 | 3186 | GtyvCL |
| 632 | P98161\|PKD1_HUMAN | 649 | 654 | GaniCL |
| 633 | P98164\|LRP2_HUMAN | 1252 | 1257 | GhpdCL |
| 634 | P98164\|LRP2_HUMAN | 3819 | 3824 | GsadCL |
| 635 | P98173\|FAM3A_HUMAN | 83 | 88 | GpkiCL |
| 636 | P98194\|AT2C1_HUMAN | 158 | 163 | GdtvCL |
| 637 | Q00872\|MYPC1_HUMAN | 447 | 452 | GkeiCL |
| 638 | Q00973\|B4GN1_HUMAN | 408 | 413 | GlgnCL |
| 639 | Q01064\|PDE1B_HUMAN | 243 | 248 | GmvhCL |
| 640 | Q01433\|AMPD2_HUMAN | 103 | 108 | GpapCL |
| 641 | Q02246\|CNTN2_HUMAN | 107 | 112 | GvyqCL |
| 642 | Q02246\|CNTN2_HUMAN | 203 | 208 | GnysCL |
| 643 | Q02318\|CP27A_HUMAN | 472 | 477 | GvraCL |
| 644 | Q02985\|FHR3_HUMAN | 188 | 193 | GsitCL |
| 645 | Q03923\|ZNF85_HUMAN | 133 | 138 | GlnqCL |
| 646 | Q03923\|ZNF85_HUMAN | 184 | 189 | GmisCL |
| 647 | Q03924\|ZN117_HUMAN | 103 | 108 | GlnqCL |
| 648 | Q03936\|ZNF92_HUMAN | 132 | 137 | GlnqCL |
| 649 | Q03938\|ZNF90_HUMAN | 132 | 137 | GlnqCL |
| 650 | Q04721\|NOTC2_HUMAN | 476 | 481 | GgftCL |
| 651 | Q05469\|LIPS_HUMAN | 716 | 721 | GeriCL |
| 652 | Q06730\|ZN33A_HUMAN | 530 | 535 | GktfCL |
| 653 | Q06732\|ZN11B_HUMAN | 531 | 536 | GktfCL |
| 654 | Q07325\|SCYB9_HUMAN | 70 | 75 | GvqtCL |
| 655 | Q07617\|SPAG1_HUMAN | 133 | 138 | GsnsCL |
| 656 | Q07954\|LRP1_HUMAN | 875 | 880 | GdndCL |
| 657 | Q07954\|LRP1_HUMAN | 3001 | 3006 | GsykCL |
| 658 | Q08629\|TICN1_HUMAN | 178 | 183 | GpcpCL |
| 659 | Q09428\|ABCC8_HUMAN | 1073 | 1078 | GivlCL |
| 660 | Q10471\|GALT2_HUMAN | 535 | 540 | GsnlCL |
| 661 | Q12796\|PNRC1_HUMAN | 63 | 68 | GdgpCL |
| 662 | Q12805\|FBLN3_HUMAN | 66 | 71 | GgylCL |
| 663 | Q12809\|KCNH2_HUMAN | 719 | 724 | GfpeCL |
| 664 | Q12841\|FSTL1_HUMAN | 48 | 53 | GeptCL |
| 665 | Q12852\|M3K12_HUMAN | 90 | 95 | GlfgCL |
| 666 | Q12860\|CNTN1_HUMAN | 110 | 115 | GiyyCL |
| 667 | Q12882\|DPYD_HUMAN | 988 | 993 | GctlCL |
| 668 | Q12933\|TRAF2_HUMAN | 387 | 392 | GykmCL |
| 669 | Q12986\|NFX1_HUMAN | 537 | 542 | GdfsCL |
| 670 | Q13077\|TRAF1_HUMAN | 302 | 307 | GyklCL |
| 671 | Q13129\|RLF_HUMAN | 48 | 53 | GlrpCL |
| 672 | Q13200\|PSMD2_HUMAN | 135 | 140 | GereCL |
| 673 | Q13224\|NMDE2_HUMAN | 584 | 589 | GynrCL |
| 674 | Q13224\|NMDE2_HUMAN | 1392 | 1397 | GddqCL |
| 675 | Q13255\|MGR1_HUMAN | 136 | 141 | GinrCL |
| 676 | Q13275\|SEM3F_HUMAN | 305 | 310 | GghcCL |
| 677 | Q13308\|PTK7_HUMAN | 429 | 434 | GyldCL |
| 678 | Q13309\|SKP2_HUMAN | 107 | 112 | GifsCL |
| 679 | Q13322\|GRB10_HUMAN | 219 | 224 | GlerCL |
| 680 | Q13370\|PDE3B_HUMAN | 253 | 258 | GgagCL |
| 681 | Q13371\|PHLP_HUMAN | 200 | 205 | GcmiCL |
| 682 | Q13387\|JIP2_HUMAN | 594 | 599 | GlfsCL |
| 683 | Q13410\|BT1A1_HUMAN | 8 | 13 | GlprCL |
| 684 | Q13444\|ADA15_HUMAN | 405 | 410 | GmgsCL |
| 685 | Q13470\|TNK1_HUMAN | 105 | 110 | GglkCL |
| 686 | Q13485\|SMAD4_HUMAN | 359 | 364 | GdrfCL |
| 687 | Q13554\|KCC2B_HUMAN | 472 | 477 | GpppCL |
| 688 | Q13591\|SEM5A_HUMAN | 819 | 824 | GgmpCL |
| 689 | Q13591\|SEM5A_HUMAN | 876 | 881 | GgdiCL |
| 690 | Q13639\|5HT4R_HUMAN | 89 | 94 | GevfCL |
| 691 | Q13642\|FHL1_HUMAN | 23 | 28 | GhhcCL |
| 692 | Q13686\|ALKB1_HUMAN | 300 | 305 | GlphCL |
| 693 | Q13698\|CAC1S_HUMAN | 1210 | 1215 | GglyCL |
| 694 | Q13751\|LAMB3_HUMAN | 449 | 454 | GrclCL |
| 695 | Q13772\|NCOA4_HUMAN | 97 | 102 | GqfnCL |
| 696 | Q13772\|NCOA4_HUMAN | 364 | 369 | GnlkCL |
| 697 | Q13795\|ARFRP_HUMAN | 159 | 164 | GrrdCL |
| 698 | Q13822\|ENPP2_HUMAN | 21 | 26 | GvniCL |
| 699 | Q13885\|TBB2A_HUMAN | 235 | 240 | GvttCL |
| 700 | Q14008\|CKAP5_HUMAN | 109 | 114 | GieiCL |
| 701 | Q14008\|CKAP5_HUMAN | 1237 | 1242 | GvigCL |
| 702 | Q14114\|LRP8_HUMAN | 175 | 180 | GnrsCL |
| 703 | Q14114\|LRP8_HUMAN | 336 | 341 | GlneCL |
| 704 | Q14159\|K0146_HUMAN | 513 | 518 | GtraCL |
| 705 | Q14264\|ENR1_HUMAN | 358 | 363 | GeltCL |
| 706 | Q14315\|FLNC_HUMAN | 1649 | 1654 | GlgaCL |
| 707 | Q14344\|GNA13_HUMAN | 314 | 319 | GdphCL |
| 708 | Q14392\|LRC32_HUMAN | 360 | 365 | GslpCL |
| 709 | Q14393\|GAS6_HUMAN | 138 | 143 | GnffCL |

TABLE 4-continued

CXCs
Motif: G-X(3)-C-L
Number of Locations: 1337
Number of Different Proteins: 1170

| # | Accession Number\|Protein Name | First Amino acid | Last Amino acid | Sequence |
|---|---|---|---|---|
| 710 | Q14393\|GAS6_HUMAN | 217 | 222 | GsysCL |
| 711 | Q14435\|GALT3_HUMAN | 93 | 98 | GerpCL |
| 712 | Q14435\|GALT3_HUMAN | 513 | 518 | GqplCL |
| 713 | Q14451\|GRB7_HUMAN | 517 | 522 | GilpCL |
| 714 | Q14520\|HABP2_HUMAN | 121 | 126 | GrgqCL |
| 715 | Q14524\|SCN5A_HUMAN | 911 | 916 | GqslCL |
| 716 | Q14566\|MCM6_HUMAN | 154 | 159 | GtflCL |
| 717 | Q14593\|ZN273_HUMAN | 100 | 105 | GlnqCL |
| 718 | Q14656\|ITBA1_HUMAN | 197 | 202 | GvlsCL |
| 719 | Q14669\|TRIPC_HUMAN | 562 | 567 | GladCL |
| 720 | Q14669\|TRIPC_HUMAN | 1136 | 1141 | GgaeCL |
| 721 | Q14703\|MBTP1_HUMAN | 845 | 850 | GdsnCL |
| 722 | Q14714\|SSPN_HUMAN | 91 | 96 | GiivCL |
| 723 | Q14766\|LTB1L_HUMAN | 1139 | 1144 | GsfrCL |
| 724 | Q14766\|LTB1L_HUMAN | 1560 | 1565 | GsykCL |
| 725 | Q14767\|LTBP2_HUMAN | 990 | 995 | GsytCL |
| 726 | Q14767\|LTBP2_HUMAN | 1156 | 1161 | GsyqCL |
| 727 | Q14767\|LTBP2_HUMAN | 1197 | 1202 | GsffCL |
| 728 | Q14767\|LTBP2_HUMAN | 1238 | 1243 | GsfnCL |
| 729 | Q14767\|LTBP2_HUMAN | 1324 | 1329 | GsfrCL |
| 730 | Q14767\|LTBP2_HUMAN | 1366 | 1371 | GsflCL |
| 731 | Q14774\|HLX1_HUMAN | 483 | 488 | GalgCL |
| 732 | Q14916\|NPT1_HUMAN | 110 | 115 | GfalCL |
| 733 | Q14916\|NPT1_HUMAN | 207 | 212 | GcavCL |
| 734 | Q14940\|SL9A5_HUMAN | 576 | 581 | GsgaCL |
| 735 | Q14957\|NMDE3_HUMAN | 941 | 946 | GpspCL |
| 736 | Q15021\|CND1_HUMAN | 730 | 735 | GtiqCL |
| 737 | Q15034\|HERC3_HUMAN | 145 | 150 | GnwhCL |
| 738 | Q15048\|LRC14_HUMAN | 281 | 286 | GrftCL |
| 739 | Q15058\|KIF14_HUMAN | 438 | 443 | GfntCL |
| 740 | Q15061\|WDR43_HUMAN | 103 | 108 | GtctCL |
| 741 | Q15147\|PLCB4_HUMAN | 987 | 992 | GgsnCL |
| 742 | Q15155\|NOMO1_HUMAN | 507 | 512 | GkvsCL |
| 743 | Q15274\|NADC_HUMAN | 92 | 97 | GpahCL |
| 744 | Q15303\|ERBB4_HUMAN | 516 | 521 | GpdqCL |
| 745 | Q15334\|L2GL1_HUMAN | 722 | 727 | GvvrCL |
| 746 | Q15399\|TLR1_HUMAN | 663 | 668 | GmqiCL |
| 747 | Q15413\|RYR3_HUMAN | 229 | 234 | GhdeCL |
| 748 | Q15413\|RYR3_HUMAN | 1656 | 1661 | GlrtCL |
| 749 | Q15418\|KS6A1_HUMAN | 548 | 553 | GnpeCL |
| 750 | Q15546\|PAQRB_HUMAN | 185 | 190 | GliyCL |
| 751 | Q15633\|TRBP2_HUMAN | 321 | 326 | GlcqCL |
| 752 | Q15650\|TRIP4_HUMAN | 196 | 201 | GsgpCL |
| 753 | Q15652\|JHD2C_HUMAN | 1864 | 1869 | GfvvCL |
| 754 | Q15735\|PI5PA_HUMAN | 379 | 384 | GpgrCL |
| 755 | Q15746\|MYLK_HUMAN | 229 | 234 | GvytCL |
| 756 | Q15746\|MYLK_HUMAN | 579 | 584 | GtytCL |
| 757 | Q15858\|SCN9A_HUMAN | 940 | 945 | GqamCL |
| 758 | Q15911\|ATBF1_HUMAN | 3527 | 3532 | GsyhCL |
| 759 | Q16342\|PDCD2_HUMAN | 121 | 126 | GesvCL |
| 760 | Q16363\|LAMA4_HUMAN | 1001 | 1006 | GfvgCL |
| 761 | Q16549\|PCSK7_HUMAN | 16 | 21 | GlptCL |
| 762 | Q16617\|NKG7_HUMAN | 15 | 20 | GlmfCL |
| 763 | Q16647\|PTGIS_HUMAN | 437 | 442 | GhnhCL |
| 764 | Q16787\|LAMA3_HUMAN | 1526 | 1531 | GvssCL |
| 765 | Q30KQ9\|DB111_HUMAN | 60 | 65 | GthcCL |
| 766 | Q32MQ0\|ZN750_HUMAN | 121 | 126 | GthrCL |
| 767 | Q3KNT7\|NSN5B_HUMAN | 134 | 139 | GaehCL |
| 768 | Q3LI83\|KR241_HUMAN | 153 | 158 | GqlnCL |
| 769 | Q3SYG4\|PTHB1_HUMAN | 822 | 827 | GgrlCL |
| 770 | Q3T8J9\|GON4L_HUMAN | 1740 | 1745 | GcadCL |
| 771 | Q495M9\|USH1G_HUMAN | 76 | 81 | GhlhCL |
| 772 | Q496M8\|CI094_HUMAN | 170 | 175 | GefsCL |
| 773 | Q499Z4\|ZN672_HUMAN | 40 | 45 | GrfrCL |
| 774 | Q4G0F5\|VP26B_HUMAN | 167 | 172 | GiedCL |
| 775 | Q4KMG0\|CDON_HUMAN | 93 | 98 | GyyqCL |
| 776 | Q53G59\|KLH12_HUMAN | 426 | 431 | GviyCL |
| 777 | Q53H47\|SETMR_HUMAN | 72 | 77 | GtcsCL |
| 778 | Q53R12\|T4S20_HUMAN | 213 | 218 | GflgCL |
| 779 | Q58EX2\|SDK2_HUMAN | 469 | 474 | GtytCL |
| 780 | Q5HYK3\|COQ5_HUMAN | 240 | 245 | GrflCL |
| 781 | Q5IJ48\|CRUM2_HUMAN | 243 | 248 | GsfrCL |
| 782 | Q5JPE7\|NOMO2_HUMAN | 507 | 512 | GkvsCL |
| 783 | Q5JQC9\|AKAP4_HUMAN | 242 | 247 | GkskCL |
| 784 | Q5JVG8\|ZN506_HUMAN | 132 | 137 | GlkqCL |
| 785 | Q5JWF2\|GNAS1_HUMAN | 2 | 7 | GvrnCL |
| 786 | Q5JWF2\|GNAS1_HUMAN | 584 | 589 | GtsgCL |
| 787 | Q5JWF8\|CT134_HUMAN | 111 | 116 | GccvCL |
| 788 | Q5MJ68\|SPDYC_HUMAN | 138 | 143 | GkdwCL |
| 789 | Q5NUL3\|GP120_HUMAN | 72 | 77 | GataCL |
| 790 | Q5SRN2\|CF010_HUMAN | 117 | 122 | GsikCL |
| 791 | Q5T2D3\|OTUD3_HUMAN | 72 | 77 | GdgnCL |
| 792 | Q5T5C0\|STXB5_HUMAN | 322 | 327 | GrrpCL |
| 793 | Q5T751\|LCE1C_HUMAN | 72 | 77 | GggcCL |
| 794 | Q5T752\|LCE1D_HUMAN | 68 | 73 | GggcCL |
| 795 | Q5T753\|LCE1E_HUMAN | 72 | 77 | GggcCL |
| 796 | Q5T754\|LCE1F_HUMAN | 72 | 77 | GggcCL |
| 797 | Q5T7P2\|LCE1A_HUMAN | 64 | 69 | GggcCL |
| 798 | Q5T7P3\|LCE1B_HUMAN | 72 | 77 | GggcCL |
| 799 | Q5TA78\|LCE4A_HUMAN | 55 | 60 | GggcCL |
| 800 | Q5TA79\|LCE2A_HUMAN | 64 | 69 | GggcCL |
| 801 | Q5TA82\|LCE2D_HUMAN | 68 | 73 | GggcCL |
| 802 | Q5TCM9\|LCE5A_HUMAN | 64 | 69 | GggcCL |
| 803 | Q5TEA3\|CT194_HUMAN | 465 | 470 | GgngCL |
| 804 | Q5TEJ8\|ICB1_HUMAN | 39 | 44 | GnecCL |
| 805 | Q5THJ4\|VP13D_HUMAN | 1215 | 1220 | GslgCL |
| 806 | Q5VST9\|OBSCN_HUMAN | 3315 | 3320 | GdryCL |
| 807 | Q5VST9\|OBSCN_HUMAN | 4189 | 4194 | GvqwCL |
| 808 | Q5VST9\|OBSCN_HUMAN | 5195 | 5200 | GvyrCL |
| 809 | Q5VST9\|OBSCN_HUMAN | 6425 | 6430 | GvytCL |
| 810 | Q5VT25\|MRCKA_HUMAN | 1325 | 1330 | GaltCL |
| 811 | Q5VUA4\|ZN318_HUMAN | 1984 | 1989 | GpspCL |
| 812 | Q5VZ18\|SHE_HUMAN | 8 | 13 | GasaCL |
| 813 | Q5VZM2\|RRAGB_HUMAN | 366 | 371 | GpkqCL |
| 814 | Q5W111\|CLLD6_HUMAN | 50 | 55 | GtggCL |
| 815 | Q5XUX1\|FBXW9_HUMAN | 184 | 189 | GgslCL |
| 816 | Q5ZPR3\|CD276_HUMAN | 216 | 221 | GtysCL |
| 817 | Q5ZPR3\|CD276_HUMAN | 434 | 439 | GtysCL |
| 818 | Q5ZPR3\|CD276_HUMAN | 472 | 477 | GlsvCL |
| 819 | Q63ZY6\|NSN5C_HUMAN | 216 | 221 | GaehCL |
| 820 | Q63ZY6\|NSN5C_HUMAN | 293 | 298 | GkgrCL |
| 821 | Q68CP9\|ARID2_HUMAN | 566 | 571 | GfykCL |
| 822 | Q6BDS2\|URFB1_HUMAN | 549 | 554 | GnlfCL |
| 823 | Q6GQQ9\|OTU7B_HUMAN | 190 | 195 | GdgnCL |
| 824 | Q6GTX8\|LAIR1_HUMAN | 10 | 15 | GlvlCL |
| 825 | Q6IS24\|GLTL3_HUMAN | 564 | 569 | GtgrCL |
| 826 | Q6ISS4\|LAIR2_HUMAN | 10 | 15 | GlvlCL |
| 827 | Q6ISS4\|LAIR2_HUMAN | 97 | 102 | GlyrCL |
| 828 | Q6N022\|TEN4_HUMAN | 139 | 144 | GrssCL |
| 829 | Q6NUM9\|RETST_HUMAN | 366 | 371 | GnarCL |
| 830 | Q6P1M0\|S27A4_HUMAN | 297 | 302 | GigqCL |
| 831 | Q6P1R4\|DUS1L_HUMAN | 209 | 214 | GniqCL |
| 832 | Q6P587\|FAHD1_HUMAN | 96 | 101 | GyalCL |
| 833 | Q6P656\|CO026_HUMAN | 144 | 149 | GqdfCL |
| 834 | Q6PCB7\|S27A1_HUMAN | 300 | 305 | GvgqCL |
| 835 | Q6PCT2\|FXL19_HUMAN | 222 | 227 | GgdaCL |
| 836 | Q6Q0C0\|TRAF7_HUMAN | 397 | 402 | GpvwCL |
| 837 | Q6Q4G3\|LAEVR_HUMAN | 794 | 799 | GledCL |
| 838 | Q6TGC4\|PADI6_HUMAN | 22 | 27 | GteiCL |
| 839 | Q6UB99\|ANR11_HUMAN | 498 | 503 | GssgCL |
| 840 | Q6UWJ8\|C16L2_HUMAN | 15 | 20 | GgccCL |
| 841 | Q6UWN5\|LYPD5_HUMAN | 15 | 20 | GaalCL |
| 842 | Q6UX01\|LMBRL_HUMAN | 394 | 399 | GncvCL |
| 843 | Q6UX53\|MET7B_HUMAN | 199 | 204 | GdgcCL |
| 844 | Q6UX65\|TMM77_HUMAN | 99 | 104 | GilsCL |
| 845 | Q6UXV0\|GFRAL_HUMAN | 127 | 132 | GmwsCL |
| 846 | Q6UY09\|CEA20_HUMAN | 226 | 231 | GlyrCL |
| 847 | Q6V0L0\|CP26C_HUMAN | 455 | 460 | GarsCL |
| 848 | Q6V0L0\|CP26C_HUMAN | 517 | 522 | GnglCL |
| 849 | Q6VVB1\|NHLC1_HUMAN | 47 | 52 | GhvvCL |
| 850 | Q6VVX0\|CP2R1_HUMAN | 444 | 449 | GrrhCL |
| 851 | Q6W4X9\|MUC6_HUMAN | 1095 | 1100 | GdceCL |

TABLE 4-continued

CXCs
Motif: G-X(3)-C-L
Number of Locations: 1337
Number of Different Proteins: 1170

| # | Accession Number\|Protein Name | First Amino acid | Last Amino acid | Sequence |
|---|---|---|---|---|
| 852 | Q6WN34\|CRDL2_HUMAN | 54 | 59 | GlmyCL |
| 853 | Q6ZN16\|M3K15_HUMAN | 82 | 87 | GarqCL |
| 854 | Q6ZN17\|LN28B_HUMAN | 103 | 108 | GgspCL |
| 855 | Q6ZRI6\|CO039_HUMAN | 141 | 146 | GlstCL |
| 856 | Q6ZRQ5\|CF167_HUMAN | 1116 | 1121 | GilkCL |
| 857 | Q6ZSY5\|PPR3F_HUMAN | 647 | 652 | GaevCL |
| 858 | Q6ZV89\|SH2D5_HUMAN | 195 | 200 | GghsCL |
| 859 | Q6ZVD8\|PHLPL_HUMAN | 5 | 10 | GsrnCL |
| 860 | Q6ZW76\|ANKS3_HUMAN | 632 | 637 | GqalCL |
| 861 | Q75N90\|FBN3_HUMAN | 551 | 556 | GsfsCL |
| 862 | Q75N90\|FBN3_HUMAN | 1217 | 1222 | GghrCL |
| 863 | Q75N90\|FBN3_HUMAN | 1826 | 1831 | GsymCL |
| 864 | Q75N90\|FBN3_HUMAN | 1866 | 1871 | GsynCL |
| 865 | Q75N90\|FBN3_HUMAN | 1908 | 1913 | GsfhCL |
| 866 | Q75N90\|FBN3_HUMAN | 1990 | 1995 | GsfqCL |
| 867 | Q7L099\|RUFY3_HUMAN | 37 | 42 | GewlCL |
| 868 | Q7L0J3\|SV2A_HUMAN | 230 | 235 | GrrqCL |
| 869 | Q7L3T8\|SYPM_HUMAN | 149 | 154 | GkeyCL |
| 870 | Q7L622\|K1333_HUMAN | 310 | 315 | GitdCL |
| 871 | Q7LBC6\|JHD2B_HUMAN | 1049 | 1054 | GfgvCL |
| 872 | Q7LBC6\|JHD2B_HUMAN | 1388 | 1393 | GrllCL |
| 873 | Q7RTN6\|STRAD_HUMAN | 294 | 299 | GtvpCL |
| 874 | Q7RTP0\|NIPA1_HUMAN | 122 | 127 | GklgCL |
| 875 | Q7RTU9\|STRC_HUMAN | 1077 | 1082 | GacsCL |
| 876 | Q7RTX0\|TS1R3_HUMAN | 20 | 25 | GaplCL |
| 877 | Q7Z2W7\|TRPM8_HUMAN | 652 | 657 | GgsnCL |
| 878 | Q7Z333\|SETX_HUMAN | 1106 | 1111 | GekkCL |
| 879 | Q7Z3K3\|POGZ_HUMAN | 749 | 754 | GrqtCL |
| 880 | Q7Z3T1\|OR2W3_HUMAN | 108 | 113 | GgveCL |
| 881 | Q7Z401\|MYCPP_HUMAN | 948 | 953 | GsadCL |
| 882 | Q7Z460\|CLAP1_HUMAN | 146 | 151 | GiclCL |
| 883 | Q7Z4S6\|KI21A_HUMAN | 1493 | 1498 | GpvmCL |
| 884 | Q7Z5G4\|GOGA7_HUMAN | 68 | 73 | GclaCL |
| 885 | Q7Z5K2\|WAPL_HUMAN | 850 | 855 | GaerCL |
| 886 | Q7Z713\|ANR37_HUMAN | 75 | 80 | GsleCL |
| 887 | Q7Z7E8\|UB2Q1_HUMAN | 36 | 41 | GpgpCL |
| 888 | Q7Z7M0\|MEGF8_HUMAN | 403 | 408 | GcgwCL |
| 889 | Q7Z7M1\|GP144_HUMAN | 343 | 348 | GselCL |
| 890 | Q86SG6\|NEK8_HUMAN | 418 | 423 | GsngCL |
| 891 | Q86SQ6\|GP123_HUMAN | 1058 | 1063 | GraaCL |
| 892 | Q86SQ6\|GP123_HUMAN | 1091 | 1096 | GhasCL |
| 893 | Q86T20\|CF001_HUMAN | 75 | 80 | GvldCL |
| 894 | Q86T65\|DAAM2_HUMAN | 570 | 575 | GappCL |
| 895 | Q86TX2\|ACOT1_HUMAN | 234 | 239 | GgelCL |
| 896 | Q86U44\|MTA70_HUMAN | 479 | 484 | GkehCL |
| 897 | Q86UE6\|LRTM1_HUMAN | 19 | 24 | GvvlCL |
| 898 | Q86UK0\|ABCAC_HUMAN | 1251 | 1256 | GwlcCL |
| 899 | Q86UK5\|LBN_HUMAN | 26 | 31 | GgrgCL |
| 900 | Q86UQ4\|ABCAD_HUMAN | 4056 | 4061 | GppfCL |
| 901 | Q86UQ4\|ABCAD_HUMAN | 4932 | 4937 | GsfkCL |
| 902 | Q86UU1\|PHLB1_HUMAN | 119 | 124 | GcmlCL |
| 903 | Q86UU1\|PHLB1_HUMAN | 1245 | 1250 | GvdtCL |
| 904 | Q86UV5\|UBP48_HUMAN | 50 | 55 | GnpnCL |
| 905 | Q86UW9\|DTX2_HUMAN | 347 | 352 | GlpvCL |
| 906 | Q86V24\|ADR2_HUMAN | 190 | 195 | GailCL |
| 907 | Q86V71\|ZN429_HUMAN | 132 | 137 | GlnqCL |
| 908 | Q86VH4\|LRTM4_HUMAN | 271 | 276 | GtfkCL |
| 909 | Q86WB7\|UN93A_HUMAN | 178 | 183 | GasdCL |
| 910 | Q86WG5\|MTMRD_HUMAN | 369 | 374 | GyrsCL |
| 911 | Q86WK7\|AMGO3_HUMAN | 348 | 353 | GlfvCL |
| 912 | Q86WR7\|CJ047_HUMAN | 84 | 89 | GgvcCL |
| 913 | Q86X76\|NIT1_HUMAN | 288 | 293 | GpglCL |
| 914 | Q86XN8\|RKHD1_HUMAN | 192 | 197 | GtdvCL |
| 915 | Q86Y01\|DTX1_HUMAN | 345 | 350 | GlpvCL |
| 916 | Q86Y56\|HEAT2_HUMAN | 271 | 276 | GwllCL |
| 917 | Q86YC3\|LRC33_HUMAN | 396 | 401 | GlasCL |
| 918 | Q8IU80\|TMPS6_HUMAN | 503 | 508 | GqpdCL |
| 919 | Q8IUK8\|CBLN2_HUMAN | 27 | 32 | GcgsCL |
| 920 | Q8IUL8\|CILP2_HUMAN | 464 | 469 | GcqkCL |
| 921 | Q8IVF6\|ANR18_HUMAN | 706 | 711 | GykkCL |
| 922 | Q8IVH4\|MMAA_HUMAN | 96 | 101 | GqraCL |

TABLE 4-continued

CXCs
Motif: G-X(3)-C-L
Number of Locations: 1337
Number of Different Proteins: 1170

| # | Accession Number\|Protein Name | First Amino acid | Last Amino acid | Sequence |
|---|---|---|---|---|
| 923 | Q8IWB7\|WDFY1_HUMAN | 200 | 205 | GsvaCL |
| 924 | Q8IWN6\|CX052_HUMAN | 89 | 94 | GskrCL |
| 925 | Q8IWV2\|CNTN4_HUMAN | 380 | 385 | GmyqCL |
| 926 | Q8IWY4\|SCUB1_HUMAN | 342 | 347 | GsfqCL |
| 927 | Q8IX30\|SCUB3_HUMAN | 337 | 342 | GsfqCL |
| 928 | Q8IXI1\|MIRO2_HUMAN | 515 | 520 | GqtpCL |
| 929 | Q8IXW0\|CK035_HUMAN | 268 | 273 | GslpCL |
| 930 | Q8IY26\|PPAC2_HUMAN | 149 | 154 | GtlyCL |
| 931 | Q8IY49\|PAQRA_HUMAN | 216 | 221 | GvfyCL |
| 932 | Q8IYB9\|ZN595_HUMAN | 132 | 137 | GvyqCL |
| 933 | Q8IYG6\|LRC56_HUMAN | 194 | 199 | GnlvCL |
| 934 | Q8IZ96\|CKLF1_HUMAN | 112 | 117 | GgslCL |
| 935 | Q8IZD0\|SAM14_HUMAN | 95 | 100 | GgsfCL |
| 936 | Q8IZE3\|PACE1_HUMAN | 322 | 327 | GetpCL |
| 937 | Q8IZF4\|GP114_HUMAN | 521 | 526 | GkllCL |
| 938 | Q8IZJ1\|UNC5B_HUMAN | 547 | 552 | GtfgCL |
| 939 | Q8IZL8\|PELP1_HUMAN | 317 | 322 | GlarCL |
| 940 | Q8IZY2\|ABCA7_HUMAN | 2001 | 2006 | GrfrCL |
| 941 | Q8N122\|RPTOR_HUMAN | 549 | 554 | GqeaCL |
| 942 | Q8N122\|RPTOR_HUMAN | 1302 | 1307 | GaisCL |
| 943 | Q8N1F7\|NUP93_HUMAN | 518 | 523 | GdppCL |
| 944 | Q8N1G0\|ZN687_HUMAN | 1133 | 1138 | GaqqCL |
| 945 | Q8N283\|ANR35_HUMAN | 65 | 70 | GlteCL |
| 946 | Q8N283\|ANR35_HUMAN | 703 | 708 | GlwdCL |
| 947 | Q8N357\|CB018_HUMAN | 57 | 62 | GefsCL |
| 948 | Q8N3C7\|RSNL2_HUMAN | 201 | 206 | GavkCL |
| 949 | Q8N3V7\|SYNPO_HUMAN | 28 | 33 | GsyrCL |
| 950 | Q8N441\|FGRL1_HUMAN | 334 | 339 | GmyiCL |
| 951 | Q8N442\|GUF1_HUMAN | 334 | 339 | GdtlCL |
| 952 | Q8N4B4\|FBX39_HUMAN | 114 | 119 | GllsCL |
| 953 | Q8N5D0\|WDTC1_HUMAN | 48 | 53 | GcvnCL |
| 954 | Q8N5D6\|GBGT1_HUMAN | 9 | 14 | GlgfCL |
| 955 | Q8N655\|CJ012_HUMAN | 468 | 473 | GdvkCL |
| 956 | Q8N6F8\|WBS27_HUMAN | 160 | 165 | GglvCL |
| 957 | Q8N6T3\|ARFG1_HUMAN | 38 | 43 | GiwiCL |
| 958 | Q8N6V9\|TEX9_HUMAN | 3 | 8 | GrslCL |
| 959 | Q8N6Y1\|PCD20_HUMAN | 27 | 32 | GpfsCL |
| 960 | Q8N6Y1\|PCD20_HUMAN | 881 | 886 | GiyiCL |
| 961 | Q8N726\|CD2A2_HUMAN | 160 | 165 | GrarCL |
| 962 | Q8N813\|CC056_HUMAN | 42 | 47 | GsctCL |
| 963 | Q8N895\|ZN366_HUMAN | 695 | 700 | GrdeCL |
| 964 | Q8N8A2\|ANR44_HUMAN | 543 | 548 | GhrqCL |
| 965 | Q8N8A2\|ANR44_HUMAN | 645 | 650 | GhtlCL |
| 966 | Q8N8Q9\|NIPA2_HUMAN | 112 | 117 | GkigCL |
| 967 | Q8N8R3\|MCATL_HUMAN | 133 | 138 | GsldCL |
| 968 | Q8N9B4\|ANR42_HUMAN | 142 | 147 | GrlgCL |
| 969 | Q8N9B4\|ANR42_HUMAN | 281 | 286 | GhieCL |
| 970 | Q8N9L9\|ACOT4_HUMAN | 234 | 239 | GadiCL |
| 971 | Q8NB46\|ANR52_HUMAN | 434 | 439 | GnveCL |
| 972 | Q8NB46\|ANR52_HUMAN | 732 | 737 | GcedCL |
| 973 | Q8NB46\|ANR52_HUMAN | 802 | 807 | GhedCL |
| 974 | Q8NB49\|AT11C_HUMAN | 110 | 115 | GyedCL |
| 975 | Q8NBJ9\|SIDT2_HUMAN | 296 | 301 | GmlfCL |
| 976 | Q8NBV4\|PPAC3_HUMAN | 128 | 133 | GtilCL |
| 977 | Q8NCL4\|GALT6_HUMAN | 505 | 510 | GtnqCL |
| 978 | Q8NCL4\|GALT6_HUMAN | 593 | 598 | GsgtCL |
| 979 | Q8NCN4\|RN169_HUMAN | 67 | 72 | GcagCL |
| 980 | Q8NDX1\|PSD4_HUMAN | 183 | 188 | GlkcCL |
| 981 | Q8NDX1\|PSD4_HUMAN | 821 | 826 | GedhCL |
| 982 | Q8NEN9\|PDZD8_HUMAN | 724 | 729 | GgliCL |
| 983 | Q8NFP4\|MDGA1_HUMAN | 622 | 627 | GsaaCL |
| 984 | Q8NFP9\|NBEA_HUMAN | 2819 | 2824 | GpenCL |
| 985 | Q8NFU7\|CXXC6_HUMAN | 1660 | 1665 | GvtaCL |
| 986 | Q8NG94\|O11H1_HUMAN | 112 | 117 | GtseCL |
| 987 | Q8NG99\|OR7G2_HUMAN | 109 | 114 | GlenCL |
| 988 | Q8NGC9\|O11H4_HUMAN | 118 | 123 | GtteCL |
| 989 | Q8NGH6\|O52L2_HUMAN | 96 | 101 | GytvCL |
| 990 | Q8NGH7\|O52L1_HUMAN | 96 | 101 | GyivCL |
| 991 | Q8NGI2\|O52N4_HUMAN | 95 | 100 | GfdeCL |
| 992 | Q8NGJ0\|OR5A1_HUMAN | 111 | 116 | GlseCL |
| 993 | Q8NGK5\|O52M1_HUMAN | 95 | 100 | GldaCL |

TABLE 4-continued

CXCs
Motif: G-X(3)-C-L
Number of Locations: 1337
Number of Different Proteins: 1170

| # | Accession Number\|Protein Name | First Amino acid | Last Amino acid | Sequence |
|---|---|---|---|---|
| 994 | Q8NGR9\|OR1N2_HUMAN | 112 | 117 | GldnCL |
| 995 | Q8NGS6\|O13C3_HUMAN | 108 | 113 | GsteCL |
| 996 | Q8NGT2\|O13J1_HUMAN | 108 | 113 | GsteCL |
| 997 | Q8NGT5\|OR9A2_HUMAN | 247 | 252 | GygsCL |
| 998 | Q8NGT9\|O2A42_HUMAN | 107 | 112 | GhseCL |
| 999 | Q8NGU2\|OR9A4_HUMAN | 251 | 256 | GygsCL |
| 1000 | Q8NGZ9\|O2T10_HUMAN | 109 | 114 | GaecCL |
| 1001 | Q8NH09\|OR8S1_HUMAN | 109 | 114 | GteaCL |
| 1002 | Q8NH19\|O10AG_HUMAN | 99 | 104 | GgteCL |
| 1003 | Q8NH40\|OR6S1_HUMAN | 66 | 71 | GnlsCL |
| 1004 | Q8NHA8\|OR1FC_HUMAN | 50 | 55 | GsdhCL |
| 1005 | Q8NHU2\|CT026_HUMAN | 158 | 163 | GnipCL |
| 1006 | Q8NHU2\|CT026_HUMAN | 582 | 587 | GfksCL |
| 1007 | Q8NHW6\|OTOSP_HUMAN | 8 | 13 | GlalCL |
| 1008 | Q8NHX4\|SPTA3_HUMAN | 175 | 180 | GsrsCL |
| 1009 | Q8NHY2\|RFWD2_HUMAN | 628 | 633 | GkpyCL |
| 1010 | Q8NHY3\|GA2L2_HUMAN | 463 | 468 | GpaeCL |
| 1011 | Q8TB24\|RIN3_HUMAN | 31 | 36 | GmrlCL |
| 1012 | Q8TB24\|RIN3_HUMAN | 971 | 976 | GsppCL |
| 1013 | Q8TCB7\|METL6_HUMAN | 89 | 94 | GvgnCL |
| 1014 | Q8TCN5\|ZN507_HUMAN | 142 | 147 | GmyrCL |
| 1015 | Q8TCT7\|PSL1_HUMAN | 262 | 267 | GlysCL |
| 1016 | Q8TCT7\|PSL1_HUMAN | 329 | 334 | GiafCL |
| 1017 | Q8TCT8\|PSL2_HUMAN | 321 | 326 | GiafCL |
| 1018 | Q8TD26\|CHD6_HUMAN | 1627 | 1632 | GnlcCL |
| 1019 | Q8TD43\|TRPM4_HUMAN | 238 | 243 | GthgCL |
| 1020 | Q8TD43\|TRPM4_HUMAN | 306 | 311 | GaadCL |
| 1021 | Q8TD43\|TRPM4_HUMAN | 650 | 655 | GdatCL |
| 1022 | Q8TD43\|TRPM4_HUMAN | 764 | 769 | GgrrCL |
| 1023 | Q8TDJ6\|DMXL2_HUMAN | 188 | 193 | GkddCL |
| 1024 | Q8TDM6\|DLG5_HUMAN | 1672 | 1677 | GvkdCL |
| 1025 | Q8TDN4\|CABL1_HUMAN | 135 | 140 | GsgpCL |
| 1026 | Q8TDU6\|GPBAR_HUMAN | 81 | 86 | GywsCL |
| 1027 | Q8TDU9\|RL3R2_HUMAN | 187 | 192 | GvrlCL |
| 1028 | Q8TDV0\|GP151_HUMAN | 183 | 188 | GvemCL |
| 1029 | Q8TDX9\|PK1L1_HUMAN | 317 | 322 | GealCL |
| 1030 | Q8TDY2\|RBCC1_HUMAN | 897 | 902 | GelvCL |
| 1031 | Q8TDZ2\|MICA1_HUMAN | 743 | 748 | GhfyCL |
| 1032 | Q8TE49\|OTU7A_HUMAN | 206 | 211 | GdgnCL |
| 1033 | Q8TE58\|ATS15_HUMAN | 418 | 423 | GhgdCL |
| 1034 | Q8TE85\|GRHL3_HUMAN | 429 | 434 | GvkgCL |
| 1035 | Q8TEM1\|PO210_HUMAN | 1489 | 1494 | GdvlCL |
| 1036 | Q8TF62\|AT8B4_HUMAN | 282 | 287 | GfliCL |
| 1037 | Q8TF76\|HASP_HUMAN | 190 | 195 | GtsaCL |
| 1038 | Q8WTV0\|SCRB1_HUMAN | 319 | 324 | GfcpCL |
| 1039 | Q8WUB8\|PHF10_HUMAN | 320 | 325 | GhpsCL |
| 1040 | Q8WUM0\|NU133_HUMAN | 112 | 117 | GgwaCL |
| 1041 | Q8WWQ8\|STAB2_HUMAN | 1358 | 1363 | GngiCL |
| 1042 | Q8WWQ8\|STAB2_HUMAN | 2026 | 2031 | GsgqCL |
| 1043 | Q8WWX0\|ASB5_HUMAN | 179 | 184 | GhheCL |
| 1044 | Q8WWZ1\|IL1FA_HUMAN | 63 | 68 | GgsrCL |
| 1045 | Q8WXI2\|CNKR2_HUMAN | 22 | 27 | GlddCL |
| 1046 | Q8WXI7\|MUC16_HUMAN | 22110 | 22115 | GlitCL |
| 1047 | Q8WXK4\|ASB12_HUMAN | 75 | 80 | GhlsCL |
| 1048 | Q8WXS8\|ATS14_HUMAN | 489 | 494 | GyqtCL |
| 1049 | Q8WXS8\|ATS14_HUMAN | 587 | 592 | GgrpCL |
| 1050 | Q8WYB5\|MYST4_HUMAN | 244 | 249 | GhpsCL |
| 1051 | Q8WYP5\|AHTF1_HUMAN | 112 | 117 | GsvlCL |
| 1052 | Q8WYP5\|AHTF1_HUMAN | 318 | 323 | GnrkCL |
| 1053 | Q8WYP5\|AHTF1_HUMAN | 526 | 531 | GynrCL |
| 1054 | Q8WZ42\|TITIN_HUMAN | 4919 | 4924 | GkytCL |
| 1055 | Q8WZ42\|TITIN_HUMAN | 5147 | 5152 | GsavCL |
| 1056 | Q8WZ42\|TITIN_HUMAN | 7829 | 7834 | GdysCL |
| 1057 | Q8WZ42\|TITIN_HUMAN | 16742 | 16747 | GaqdCL |
| 1058 | Q8WZ42\|TITIN_HUMAN | 20237 | 20242 | GtnvCL |
| 1059 | Q8WZ73\|RFFL_HUMAN | 81 | 86 | GprlCL |
| 1060 | Q8WZ74\|CTTB2_HUMAN | 924 | 929 | GfknCL |
| 1061 | Q92481\|AP2B_HUMAN | 379 | 384 | GiqsCL |
| 1062 | Q92496\|FHR4_HUMAN | 130 | 135 | GsitCL |
| 1063 | Q92520\|FAM3C_HUMAN | 82 | 87 | GpkiCL |
| 1064 | Q92527\|ANKR7_HUMAN | 148 | 153 | GeppCL |
| 1065 | Q92529\|SHC3_HUMAN | 581 | 586 | GselCL |
| 1066 | Q92546\|K0258_HUMAN | 248 | 253 | GtvaCL |
| 1067 | Q92583\|CCL17_HUMAN | 30 | 35 | GrecCL |
| 1068 | Q92621\|NU205_HUMAN | 950 | 955 | GfveCL |
| 1069 | Q92636\|FAN_HUMAN | 824 | 829 | GtdgCL |
| 1070 | Q92673\|SORL_HUMAN | 1415 | 1420 | GpstCL |
| 1071 | Q92750\|TAF4B_HUMAN | 410 | 415 | GaaiCL |
| 1072 | Q92752\|TENR_HUMAN | 293 | 298 | GqrqCL |
| 1073 | Q92782\|DPF1_HUMAN | 256 | 261 | GhpsCL |
| 1074 | Q92783\|STAM1_HUMAN | 41 | 46 | GpkdCL |
| 1075 | Q92785\|REQU_HUMAN | 302 | 307 | GhpsCL |
| 1076 | Q92794\|MYST3_HUMAN | 237 | 242 | GhpsCL |
| 1077 | Q92832\|NELL1_HUMAN | 618 | 623 | GgfdCL |
| 1078 | Q92854\|SEM4D_HUMAN | 620 | 625 | GvyqCL |
| 1079 | Q92900\|RENT1_HUMAN | 370 | 375 | GdeiCL |
| 1080 | Q92932\|PTPR2_HUMAN | 35 | 40 | GrlgCL |
| 1081 | Q92932\|PTPR2_HUMAN | 634 | 639 | GliyCL |
| 1082 | Q92947\|GCDH_HUMAN | 285 | 290 | GpfgCL |
| 1083 | Q92947\|GCDH_HUMAN | 346 | 351 | GlhaCL |
| 1084 | Q92952\|KCNN1_HUMAN | 361 | 366 | GkgvCL |
| 1085 | Q92956\|TNR14_HUMAN | 89 | 94 | GlskCL |
| 1086 | Q92968\|PEX13_HUMAN | 216 | 221 | GtvaCL |
| 1087 | Q93038\|TNR25_HUMAN | 66 | 71 | GnstCL |
| 1088 | Q969L2\|MAL2_HUMAN | 37 | 42 | GafvCL |
| 1089 | Q969P0\|IGSF8_HUMAN | 402 | 407 | GtyrCL |
| 1090 | Q96A54\|ADR1_HUMAN | 179 | 184 | GavlCL |
| 1091 | Q96AP0\|ACD_HUMAN | 269 | 274 | GalvCL |
| 1092 | Q96AQ2\|TM125_HUMAN | 71 | 76 | GtvlCL |
| 1093 | Q96B26\|EXOS8_HUMAN | 230 | 235 | GklcCL |
| 1094 | Q96B86\|RGMA_HUMAN | 311 | 316 | GlylCL |
| 1095 | Q96BD0\|SO4A1_HUMAN | 698 | 703 | GletCL |
| 1096 | Q96CE8\|T4S18_HUMAN | 8 | 13 | GclsCL |
| 1097 | Q96CW5\|GCP3_HUMAN | 190 | 195 | GvgdCL |
| 1098 | Q96D59\|RN183_HUMAN | 95 | 100 | GhqlCL |
| 1099 | Q96DN5\|WDR67_HUMAN | 52 | 57 | GtgdCL |
| 1100 | Q96DZ5\|CLR59_HUMAN | 212 | 217 | GaakCL |
| 1101 | Q96EP1\|CHFR_HUMAN | 528 | 533 | GcygCL |
| 1102 | Q96EY5\|F125A_HUMAN | 51 | 56 | GyflCL |
| 1103 | Q96EZ4\|MYEOV_HUMAN | 232 | 237 | GrraCL |
| 1104 | Q96F46\|I17RA_HUMAN | 628 | 633 | GsqaCL |
| 1105 | Q96GC6\|ZN274_HUMAN | 256 | 261 | GttcCL |
| 1106 | Q96H40\|ZN486_HUMAN | 132 | 137 | GlnqCL |
| 1107 | Q96H96\|COQ2_HUMAN | 172 | 177 | GvllCL |
| 1108 | Q96I82\|KAZD1_HUMAN | 249 | 254 | GtyrCL |
| 1109 | Q96IV0\|NGLY1_HUMAN | 70 | 75 | GaveCL |
| 1110 | Q96IW7\|SC22A_HUMAN | 234 | 239 | GtaaCL |
| 1111 | Q96J02\|ITCH_HUMAN | 160 | 165 | GvslCL |
| 1112 | Q96J94\|PIWL1_HUMAN | 674 | 679 | GlkvCL |
| 1113 | Q96JH7\|VCIP1_HUMAN | 215 | 220 | GdghCL |
| 1114 | Q96JK2\|WDR22_HUMAN | 178 | 183 | GepfCL |
| 1115 | Q96JT2\|S45A3_HUMAN | 27 | 32 | GlevCL |
| 1116 | Q96JT2\|S45A3_HUMAN | 485 | 490 | GrgiCL |
| 1117 | Q96K31\|CH076_HUMAN | 98 | 103 | GqarCL |
| 1118 | Q96KC8\|DNJC1_HUMAN | 228 | 233 | GiwfCL |
| 1119 | Q96KM6\|K1196_HUMAN | 782 | 787 | GkyrCL |
| 1120 | Q96LC7\|SIG10_HUMAN | 373 | 378 | GqslCL |
| 1121 | Q96LD4\|TRI47_HUMAN | 25 | 30 | GhnfCL |
| 1122 | Q96LQ0\|CN050_HUMAN | 366 | 371 | GeprCL |
| 1123 | Q96ME1\|FXL18_HUMAN | 352 | 357 | GcvhCL |
| 1124 | Q96ME7\|ZN512_HUMAN | 320 | 325 | GqpeCL |
| 1125 | Q96ME7\|ZN512_HUMAN | 438 | 443 | GkykCL |
| 1126 | Q96MU7\|YTDC1_HUMAN | 485 | 490 | GtqlCL |
| 1127 | Q96MU8\|KREM1_HUMAN | 53 | 58 | GgkpCL |
| 1128 | Q96NL3\|ZN599_HUMAN | 373 | 378 | GktfCL |
| 1129 | Q96NX9\|DACH2_HUMAN | 585 | 590 | GnyyCL |
| 1130 | Q96P11\|NSUN5_HUMAN | 400 | 405 | GaehCL |
| 1131 | Q96PH1\|NOX5_HUMAN | 272 | 277 | GcgqCL |
| 1132 | Q96PL5\|ERMAP_HUMAN | 122 | 127 | GsyrCL |
| 1133 | Q96PP9\|GBP4_HUMAN | 321 | 326 | GavpCL |
| 1134 | Q96Q04\|LMTK3_HUMAN | 676 | 681 | GacsCL |
| 1135 | Q96Q15\|SMG1_HUMAN | 2809 | 2814 | GnvtCL |

TABLE 4-continued

CXCs
Motif: G-X(3)-C-L
Number of Locations: 1337
Number of Different Proteins: 1170

| # | Accession Number\|Protein Name | First Amino acid | Last Amino acid | Sequence |
|---|---|---|---|---|
| 1136 | Q96Q27\|ASB2_HUMAN | 101 | 106 | GqvgCL |
| 1137 | Q96Q27\|ASB2_HUMAN | 135 | 140 | GhldCL |
| 1138 | Q96Q91\|B3A4_HUMAN | 455 | 460 | GaafCL |
| 1139 | Q96QG7\|MTMR9_HUMAN | 85 | 90 | GmeeCL |
| 1140 | Q96QS1\|TSN32_HUMAN | 258 | 263 | GpthCL |
| 1141 | Q96QU8\|XPO6_HUMAN | 413 | 418 | GyfsCL |
| 1142 | Q96R30\|OR2V2_HUMAN | 103 | 108 | GlfvCL |
| 1143 | Q96RV3\|PCX1_HUMAN | 696 | 701 | GtvaCL |
| 1144 | Q96RW7\|HMCN1_HUMAN | 677 | 682 | GiygCL |
| 1145 | Q96RW7\|HMCN1_HUMAN | 2546 | 2551 | GrytCL |
| 1146 | Q96RW7\|HMCN1_HUMAN | 3595 | 3600 | GrytCL |
| 1147 | Q96SM3\|CPXM1_HUMAN | 262 | 267 | GgapCL |
| 1148 | Q96SQ9\|CP2S1_HUMAN | 436 | 441 | GkrvCL |
| 1149 | Q96SU4\|OSBL9_HUMAN | 542 | 547 | GcvsCL |
| 1150 | Q99250\|SCN2A_HUMAN | 955 | 960 | GqtmCL |
| 1151 | Q99466\|NOTC4_HUMAN | 216 | 221 | GsfqCL |
| 1152 | Q99466\|NOTC4_HUMAN | 375 | 380 | GsfsCL |
| 1153 | Q99466\|NOTC4_HUMAN | 414 | 419 | GstlCL |
| 1154 | Q99466\|NOTC4_HUMAN | 457 | 462 | GsfnCL |
| 1155 | Q99466\|NOTC4_HUMAN | 609 | 614 | GaffCL |
| 1156 | Q99466\|NOTC4_HUMAN | 787 | 792 | GtfsCL |
| 1157 | Q99466\|NOTC4_HUMAN | 1121 | 1126 | GgpdCL |
| 1158 | Q99466\|NOTC4_HUMAN | 1872 | 1877 | GggaCL |
| 1159 | Q99558\|M3K14_HUMAN | 536 | 541 | GhavCL |
| 1160 | Q99611\|SPS2_HUMAN | 373 | 378 | GlliCL |
| 1161 | Q99678\|GPR20_HUMAN | 115 | 120 | GargCL |
| 1162 | Q99741\|CDC6_HUMAN | 207 | 212 | GktaCL |
| 1163 | Q99758\|ABCA3_HUMAN | 1590 | 1595 | GqfkCL |
| 1164 | Q99797\|PMIP_HUMAN | 277 | 282 | GqlkCL |
| 1165 | Q99848\|EBP2_HUMAN | 52 | 57 | GlkqCL |
| 1166 | Q99867\|TBB4Q_HUMAN | 235 | 240 | GvttCL |
| 1167 | Q99884\|SC6A7_HUMAN | 543 | 548 | GllsCL |
| 1168 | Q99973\|TEP1_HUMAN | 1464 | 1469 | GpfaCL |
| 1169 | Q99973\|TEP1_HUMAN | 1486 | 1491 | GarlCL |
| 1170 | Q99973\|TEP1_HUMAN | 1720 | 1725 | GisaCL |
| 1171 | Q99973\|TEP1_HUMAN | 2595 | 2600 | GsvsCL |
| 1172 | Q99996\|AKAP9_HUMAN | 3063 | 3068 | GllnCL |
| 1173 | Q9BQ08\|RSNB_HUMAN | 2 | 7 | GpssCL |
| 1174 | Q9BQG2\|NUD12_HUMAN | 348 | 353 | GmftCL |
| 1175 | Q9BQR3\|PRS27_HUMAN | 231 | 236 | GplvCL |
| 1176 | Q9BQS2\|SYT15_HUMAN | 23 | 28 | GascCL |
| 1177 | Q9BRB3\|PIGQ_HUMAN | 373 | 378 | GlsaCL |
| 1178 | Q9BRP4\|WDR71_HUMAN | 206 | 211 | GrsaCL |
| 1179 | Q9BRZ2\|TRI56_HUMAN | 343 | 348 | GpapCL |
| 1180 | Q9BS86\|ZPBP1_HUMAN | 346 | 351 | GaktCL |
| 1181 | Q9BT40\|SKIP_HUMAN | 131 | 136 | GvniCL |
| 1182 | Q9BT51\|CU122_HUMAN | 6 | 11 | GfshCL |
| 1183 | Q9BTF0\|THUM2_HUMAN | 407 | 412 | GikkCL |
| 1184 | Q9BTX1\|NDC1_HUMAN | 310 | 315 | GsdeCL |
| 1185 | Q9BUY5\|ZN426_HUMAN | 14 | 19 | GdpvCL |
| 1186 | Q9BUY5\|ZN426_HUMAN | 430 | 435 | GypsCL |
| 1187 | Q9BV38\|WDR18_HUMAN | 81 | 86 | GpvtCL |
| 1188 | Q9BV38\|WDR18_HUMAN | 139 | 144 | GgkdCL |
| 1189 | Q9BV73\|CP250_HUMAN | 806 | 811 | GevrCL |
| 1190 | Q9BV99\|LRC61_HUMAN | 113 | 118 | GqlqCL |
| 1191 | Q9BVA1\|TBB2B_HUMAN | 235 | 240 | GvttCL |
| 1192 | Q9BVH7\|SIA7E_HUMAN | 8 | 13 | GlavCL |
| 1193 | Q9BVK2\|ALG8_HUMAN | 361 | 366 | GflrCL |
| 1194 | Q9BWT7\|CAR10_HUMAN | 916 | 921 | GkkhCL |
| 1195 | Q9BWU0\|NADAP_HUMAN | 185 | 190 | GtsyCL |
| 1196 | Q9BWU0\|NADAP_HUMAN | 196 | 201 | GcdvCL |
| 1197 | Q9BWV1\|BOC_HUMAN | 1053 | 1058 | GppcCL |
| 1198 | Q9BXC9\|BBS2_HUMAN | 26 | 31 | GthpCL |
| 1199 | Q9BXL6\|CAR14_HUMAN | 850 | 855 | GfkkCL |
| 1200 | Q9BXM7\|PINK1_HUMAN | 408 | 413 | GgngCL |
| 1201 | Q9BXR0\|TGT_HUMAN | 50 | 55 | GcriCL |
| 1202 | Q9BXS4\|TMM59_HUMAN | 229 | 234 | GflrCL |
| 1203 | Q9BXT5\|TEX15_HUMAN | 1099 | 1104 | GekkCL |
| 1204 | Q9BXU8\|FHL17_HUMAN | 78 | 83 | GghiCL |
| 1205 | Q9BY15\|EMR3_HUMAN | 562 | 567 | GctwCL |
| 1206 | Q9BY41\|HDAC8_HUMAN | 283 | 288 | GigkCL |
| 1207 | Q9BYB4\|GNB1L_HUMAN | 163 | 168 | GmpmCL |
| 1208 | Q9BYE0\|HES7_HUMAN | 95 | 100 | GfreCL |
| 1209 | Q9BYJ1\|LOXE3_HUMAN | 309 | 314 | GqdtCL |
| 1210 | Q9BYK8\|PR285_HUMAN | 1908 | 1913 | GfslCL |
| 1211 | Q9BYT1\|CT059_HUMAN | 398 | 403 | GswtCL |
| 1212 | Q9BYX4\|IFIH1_HUMAN | 265 | 270 | GsvsCL |
| 1213 | Q9BZ11\|ADA33_HUMAN | 400 | 405 | GggaCL |
| 1214 | Q9BZ76\|CNTP3_HUMAN | 509 | 514 | GfqgCL |
| 1215 | Q9BZ76\|CNTP3_HUMAN | 1163 | 1168 | GftgCL |
| 1216 | Q9BZC7\|ABCA2_HUMAN | 2262 | 2267 | GrlrCL |
| 1217 | Q9BZF3\|OSBL6_HUMAN | 554 | 559 | GrraCL |
| 1218 | Q9BZF9\|UACA_HUMAN | 79 | 84 | GnleCL |
| 1219 | Q9BZF9\|UACA_HUMAN | 112 | 117 | GhalCL |
| 1220 | Q9BZH6\|BRWD2_HUMAN | 79 | 84 | GspyCL |
| 1221 | Q9BZS1\|FOXP3_HUMAN | 228 | 233 | GraqCL |
| 1222 | Q9BZY9\|TRI31_HUMAN | 32 | 37 | GhnfCL |
| 1223 | Q9BZZ2\|SN_HUMAN | 1507 | 1512 | GmyhCL |
| 1224 | Q9C004\|SPY4_HUMAN | 197 | 202 | GtcmCL |
| 1225 | Q9C0A0\|CNTP4_HUMAN | 1163 | 1168 | GftgCL |
| 1226 | Q9C0C6\|K1737_HUMAN | 47 | 52 | GsseCL |
| 1227 | Q9GZK3\|OR2B2_HUMAN | 108 | 113 | GsteCL |
| 1228 | Q9GZR3\|CFC1_HUMAN | 144 | 149 | GalhCL |
| 1229 | Q9GZY1\|PBOV1_HUMAN | 118 | 123 | GlecCL |
| 1230 | Q9H013\|ADA19_HUMAN | 400 | 405 | GggmCL |
| 1231 | Q9H093\|NUAK2_HUMAN | 587 | 592 | GpgsCL |
| 1232 | Q9H0A0\|NAT10_HUMAN | 654 | 659 | GrfpCL |
| 1233 | Q9H0B3\|K1683_HUMAN | 578 | 583 | GkirCL |
| 1234 | Q9H0J9\|PAR12_HUMAN | 272 | 277 | GdqiCL |
| 1235 | Q9H0M4\|ZCPW1_HUMAN | 249 | 254 | GfgqCL |
| 1236 | Q9H172\|ABCG4_HUMAN | 588 | 593 | GdltCL |
| 1237 | Q9H195\|MUC3B_HUMAN | 545 | 550 | GqcaCL |
| 1238 | Q9H1B7\|CN004_HUMAN | 294 | 299 | GgpaCL |
| 1239 | Q9H1D0\|TRPV6_HUMAN | 10 | 15 | GlilCL |
| 1240 | Q9H1K4\|GHC2_HUMAN | 47 | 52 | GmidCL |
| 1241 | Q9H1M3\|DB129_HUMAN | 23 | 28 | GlrrCL |
| 1242 | Q9H1M4\|DB127_HUMAN | 50 | 55 | GrycCL |
| 1243 | Q9H1P6\|CT085_HUMAN | 107 | 112 | GlnkCL |
| 1244 | Q9H1R3\|MYLK2_HUMAN | 240 | 245 | GqalCL |
| 1245 | Q9H1V8\|S6A17_HUMAN | 421 | 426 | GldpCL |
| 1246 | Q9H221\|ABCG8_HUMAN | 421 | 426 | GaeaCL |
| 1247 | Q9H228\|EDG8_HUMAN | 347 | 352 | GlrrCL |
| 1248 | Q9H252\|KCNH6_HUMAN | 571 | 576 | GfpeCL |
| 1249 | Q9H2D1\|MFTC_HUMAN | 64 | 69 | GilhCL |
| 1250 | Q9H2G2\|SLK_HUMAN | 1208 | 1213 | GeseCL |
| 1251 | Q9H2M9\|RBGPR_HUMAN | 387 | 392 | GesiCL |
| 1252 | Q9H2S1\|KCNN2_HUMAN | 371 | 376 | GkgvCL |
| 1253 | Q9H2X9\|S12A5_HUMAN | 602 | 607 | GmslCL |
| 1254 | Q9H2Y7\|ZF106_HUMAN | 975 | 980 | GegnCL |
| 1255 | Q9H324\|ATS10_HUMAN | 422 | 427 | GlglCL |
| 1256 | Q9H324\|ATS10_HUMAN | 556 | 561 | GgkyCL |
| 1257 | Q9H3D4\|P73L_HUMAN | 557 | 562 | GcssCL |
| 1258 | Q9H3R1\|NDST4_HUMAN | 814 | 819 | GktkCL |
| 1259 | Q9H4F1\|SIA7D_HUMAN | 29 | 34 | GlplCL |
| 1260 | Q9H5U8\|CX045_HUMAN | 403 | 408 | GfdsCL |
| 1261 | Q9H5V8\|CDCP1_HUMAN | 373 | 378 | GcfvCL |
| 1262 | Q9H6E5\|TUT1_HUMAN | 15 | 20 | GfrcCL |
| 1263 | Q9H6R4\|NOL6_HUMAN | 391 | 396 | GislCL |
| 1264 | Q9H792\|SG269_HUMAN | 1661 | 1666 | GilqCL |
| 1265 | Q9H7F0\|AT133_HUMAN | 109 | 114 | GhavCL |
| 1266 | Q9H7M9\|GI24_HUMAN | 142 | 147 | GlycCL |
| 1267 | Q9H808\|TLE6_HUMAN | 315 | 320 | GpdaCL |
| 1268 | Q9H8X2\|IPPK_HUMAN | 110 | 115 | GyamCL |
| 1269 | Q9H9S3\|S61A2_HUMAN | 143 | 148 | GagiCL |
| 1270 | Q9HAF5\|CO028_HUMAN | 120 | 125 | GvrmCL |
| 1271 | Q9HAS0\|NJMU_HUMAN | 123 | 128 | GcyyCL |
| 1272 | Q9HAT1\|LMA1L_HUMAN | 8 | 13 | GplfCL |
| 1273 | Q9HAV4\|XPO5_HUMAN | 266 | 271 | GaaeCL |
| 1274 | Q9HAW7\|UD17_HUMAN | 510 | 515 | GyrkCL |
| 1275 | Q9HAW8\|UD110_HUMAN | 510 | 515 | GyrkCL |
| 1276 | Q9HAW9\|UD18_HUMAN | 510 | 515 | GyrkCL |
| 1277 | Q9HBX8\|LGR6_HUMAN | 550 | 555 | GvlgCL |

TABLE 4-continued

CXCs
Motif: G-X(3)-C-L
Number of Locations: 1337
Number of Different Proteins: 1170

| # | Accession Number\|Protein Name | First Amino acid | Last Amino acid | Sequence |
|---|---|---|---|---|
| 1278 | Q9HBZ2\|ARNT2_HUMAN | 295 | 300 | GskyCL |
| 1279 | Q9HC07\|TM165_HUMAN | 138 | 143 | GlmtCL |
| 1280 | Q9HC84\|MUC5B_HUMAN | 780 | 785 | GklsCL |
| 1281 | Q9HC84\|MUC5B_HUMAN | 1281 | 1286 | GlgaCL |
| 1282 | Q9HCC6\|HES4_HUMAN | 113 | 118 | GfheCL |
| 1283 | Q9HCC9\|ZFY28_HUMAN | 555 | 560 | GatnCL |
| 1284 | Q9HCE9\|TM16H_HUMAN | 541 | 546 | GgrrCL |
| 1285 | Q9HCM2\|PLXA4_HUMAN | 990 | 995 | GkqpCL |
| 1286 | Q9HCM4\|E41L5_HUMAN | 111 | 116 | GspyCL |
| 1287 | Q9HCU4\|CELR2_HUMAN | 1308 | 1313 | GgytCL |
| 1288 | Q9HCU4\|CELR2_HUMAN | 1757 | 1762 | GfrgCL |
| 1289 | Q9HCU4\|CELR2_HUMAN | 1917 | 1922 | GsptCL |
| 1290 | Q9NNW5\|WDR6_HUMAN | 460 | 465 | GvvaCL |
| 1291 | Q9NP73\|GT281_HUMAN | 82 | 87 | GagsCL |
| 1292 | Q9NP90\|RAB9B_HUMAN | 79 | 84 | GadcCL |
| 1293 | Q9NPA1\|KCMB3_HUMAN | 121 | 126 | GkypCL |
| 1294 | Q9NPA3\|M1IP1_HUMAN | 58 | 63 | GsggCL |
| 1295 | Q9NPD7\|NRN1_HUMAN | 37 | 42 | GfsdCL |
| 1296 | Q9NPF8\|CENA2_HUMAN | 41 | 46 | GifiCL |
| 1297 | Q9NPG4\|PCD12_HUMAN | 807 | 812 | GwdpCL |
| 1298 | Q9NPH5\|NOX4_HUMAN | 51 | 56 | GlglCL |
| 1299 | Q9NQ25\|SLAF7_HUMAN | 3 | 8 | GsptCL |
| 1300 | Q9NQ30\|ESM1_HUMAN | 125 | 130 | GtgkCL |
| 1301 | Q9NQ75\|CT032_HUMAN | 50 | 55 | GwwkCL |
| 1302 | Q9NQB0\|TF7L2_HUMAN | 492 | 497 | GegsCL |
| 1303 | Q9NQQ7\|S35C2_HUMAN | 302 | 307 | GfalCL |
| 1304 | Q9NQS5\|GPR84_HUMAN | 195 | 200 | GifyCL |
| 1305 | Q9NQU5\|PAK6_HUMAN | 662 | 667 | GlpeCL |
| 1306 | Q9NR09\|BIRC6_HUMAN | 511 | 516 | GanpCL |
| 1307 | Q9NR61\|DLL4_HUMAN | 204 | 209 | GnlsCL |
| 1308 | Q9NR63\|CP26B_HUMAN | 437 | 442 | GvrtCL |
| 1309 | Q9NR81\|ARHG3_HUMAN | 203 | 208 | GwlpCL |
| 1310 | Q9NR99\|MXRA5_HUMAN | 2414 | 2419 | GnytCL |
| 1311 | Q9NRI5\|DISC1_HUMAN | 23 | 28 | GsrdCL |
| 1312 | Q9NRX5\|SERC1_HUMAN | 19 | 24 | GsapCL |
| 1313 | Q9NS15\|LTBP3_HUMAN | 846 | 851 | GsyrCL |
| 1314 | Q9NS40\|KCNH7_HUMAN | 722 | 727 | GfpeCL |
| 1315 | Q9NS62\|THSD1_HUMAN | 419 | 424 | GislCL |
| 1316 | Q9NSD7\|RL3R1_HUMAN | 243 | 248 | GeelCL |
| 1317 | Q9NSI6\|BRWD1_HUMAN | 204 | 209 | GsddCL |
| 1318 | Q9NSN8\|SNTG1_HUMAN | 242 | 247 | GiiqCL |
| 1319 | Q9NST1\|ADPN_HUMAN | 24 | 29 | GatrCL |
| 1320 | Q9NST1\|ADPN_HUMAN | 97 | 102 | GlckCL |
| 1321 | Q9NT68\|TEN2_HUMAN | 858 | 863 | GlvdCL |
| 1322 | Q9NU22\|MDN1_HUMAN | 427 | 432 | GrgdCL |
| 1323 | Q9NUB4\|CT141_HUMAN | 156 | 161 | GlafCL |
| 1324 | Q9NUP1\|CNO_HUMAN | 67 | 72 | GyaaCL |
| 1325 | Q9NVE7\|PANK4_HUMAN | 304 | 309 | GqlaCL |
| 1326 | Q9NVG8\|TBC13_HUMAN | 38 | 43 | GglrCL |
| 1327 | Q9NVX2\|NLE1_HUMAN | 474 | 479 | GkdkCL |
| 1328 | Q9NW08\|RPC2_HUMAN | 765 | 770 | GfgrCL |
| 1329 | Q9NWT1\|PK1IP_HUMAN | 83 | 88 | GtitCL |
| 1330 | Q9NWU5\|RM22_HUMAN | 142 | 147 | GrgqCL |
| 1331 | Q9NWZ3\|IRAK4_HUMAN | 255 | 260 | GddlCL |
| 1332 | Q9NX02\|NALP2_HUMAN | 139 | 144 | GnviCL |
| 1333 | Q9NXJ0\|M4A12_HUMAN | 106 | 111 | GivlCL |
| 1334 | Q9NXR5\|ANR10_HUMAN | 69 | 74 | GkleCL |
| 1335 | Q9NXR5\|ANR10_HUMAN | 103 | 108 | GhpqCL |
| 1336 | Q9NXS3\|BTBD5_HUMAN | 293 | 298 | GlfaCL |
| 1337 | Q9NXW9\|ALKB4_HUMAN | 19 | 24 | GirtCL |
| 1338 | Q9NY15\|STAB1_HUMAN | 122 | 127 | GhgtCL |
| 1339 | Q9NY15\|STAB1_HUMAN | 177 | 182 | GdgsCL |
| 1340 | Q9NY15\|STAB1_HUMAN | 752 | 757 | GngaCL |
| 1341 | Q9NY15\|STAB1_HUMAN | 1256 | 1261 | GssrCL |
| 1342 | Q9NY15\|STAB1_HUMAN | 1991 | 1996 | GsgqCL |
| 1343 | Q9NY15\|STAB1_HUMAN | 2250 | 2255 | GfhlCL |
| 1344 | Q9NY33\|DPP3_HUMAN | 515 | 520 | GlylCL |
| 1345 | Q9NY35\|CLDND_HUMAN | 213 | 218 | GwsfCL |
| 1346 | Q9NY46\|SCN3A_HUMAN | 956 | 961 | GqtmCL |
| 1347 | Q9NY91\|SC5A4_HUMAN | 507 | 512 | GtgsCL |
| 1348 | Q9NY99\|SNTG2_HUMAN | 14 | 19 | GrqgCL |
| 1349 | Q9NYJ7\|DLL3_HUMAN | 235 | 240 | GecrCL |
| 1350 | Q9NYQ6\|CELR1_HUMAN | 168 | 173 | GrpiCL |
| 1351 | Q9NYQ7\|CELR3_HUMAN | 2070 | 2075 | GsdsCL |
| 1352 | Q9NYQ8\|FAT2_HUMAN | 3908 | 3913 | GfegCL |
| 1353 | Q9NYQ8\|FAT2_HUMAN | 4285 | 4290 | GggpCL |
| 1354 | Q9NYW6\|TA2R3_HUMAN | 104 | 109 | GvlyCL |
| 1355 | Q9NZ56\|FMN2_HUMAN | 1694 | 1699 | GkeqCL |
| 1356 | Q9NZ71\|RTEL1_HUMAN | 47 | 52 | GktlCL |
| 1357 | Q9NZ94\|NLGN3_HUMAN | 19 | 24 | GrslCL |
| 1358 | Q9NZH0\|GPC5B_HUMAN | 164 | 169 | GlalCL |
| 1359 | Q9NZH7\|IL1F8_HUMAN | 68 | 73 | GkdlCL |
| 1360 | Q9NZL3\|ZN224_HUMAN | 550 | 555 | GwasCL |
| 1361 | Q9NZR2\|LRP1B_HUMAN | 866 | 871 | GdddCL |
| 1362 | Q9NZR2\|LRP1B_HUMAN | 2987 | 2992 | GtykCL |
| 1363 | Q9NZV5\|SEPN1_HUMAN | 273 | 278 | GavaCL |
| 1364 | Q9P0K1\|ADA22_HUMAN | 429 | 434 | GggaCL |
| 1365 | Q9P0K7\|RAI14_HUMAN | 64 | 69 | GhveCL |
| 1366 | Q9P0L1\|ZN167_HUMAN | 617 | 622 | GlskCL |
| 1367 | Q9P0M9\|RM27_HUMAN | 84 | 89 | GknkCL |
| 1368 | Q9P0U3\|SENP1_HUMAN | 531 | 536 | GvhwCL |
| 1369 | Q9P0X4\|CAC1I_HUMAN | 290 | 295 | GrecCL |
| 1370 | Q9P203\|BTBD7_HUMAN | 265 | 270 | GnqnCL |
| 1371 | Q9P255\|ZN492_HUMAN | 143 | 148 | GlnqCL |
| 1372 | Q9P273\|TEN3_HUMAN | 142 | 147 | GrssCL |
| 1373 | Q9P273\|TEN3_HUMAN | 1590 | 1595 | GtngCL |
| 1374 | Q9P275\|UBP36_HUMAN | 824 | 829 | GsetCL |
| 1375 | Q9P283\|SEM5B_HUMAN | 589 | 594 | GgldCL |
| 1376 | Q9P283\|SEM5B_HUMAN | 887 | 892 | GediCL |
| 1377 | Q9P298\|HIG1B_HUMAN | 34 | 39 | GlggCL |
| 1378 | Q9P2B2\|FPRP_HUMAN | 844 | 849 | GllsCL |
| 1379 | Q9P2C4\|TM181_HUMAN | 406 | 411 | GerkCL |
| 1380 | Q9P2E3\|ZNFX1_HUMAN | 1162 | 1167 | GqlfCL |
| 1381 | Q9P2I0\|CPSF2_HUMAN | 759 | 764 | GlegCL |
| 1382 | Q9P2J9\|PDP2_HUMAN | 125 | 130 | GvasCL |
| 1383 | Q9P2J9\|PDP2_HUMAN | 298 | 303 | GmwsCL |
| 1384 | Q9P2N4\|ATS9_HUMAN | 490 | 495 | GygeCL |
| 1385 | Q9P2P6\|STAR9_HUMAN | 715 | 720 | GeadCL |
| 1386 | Q9P2R3\|ANFY1_HUMAN | 720 | 725 | GpggCL |
| 1387 | Q9P2R7\|SUCB1_HUMAN | 316 | 321 | GnigCL |
| 1388 | Q9P2S2\|NRX2A_HUMAN | 1061 | 1066 | GfqgCL |
| 1389 | Q9UBD9\|CLCF1_HUMAN | 10 | 15 | GmlaCL |
| 1390 | Q9UBE0\|ULE1A_HUMAN | 338 | 343 | GiveCL |
| 1391 | Q9UBG0\|MRC2_HUMAN | 50 | 55 | GlqgCL |
| 1392 | Q9UBG0\|MRC2_HUMAN | 89 | 94 | GtmqCL |
| 1393 | Q9UBG0\|MRC2_HUMAN | 938 | 943 | GdqrCL |
| 1394 | Q9UBG7\|RBPSL_HUMAN | 56 | 61 | GvrrCL |
| 1395 | Q9UBG7\|RBPSL_HUMAN | 326 | 331 | GtylCL |
| 1396 | Q9UBH0\|IL1F5_HUMAN | 63 | 68 | GgsqCL |
| 1397 | Q9UBM4\|OPT_HUMAN | 124 | 129 | GlptCL |
| 1398 | Q9UBP5\|HEY2_HUMAN | 125 | 130 | GfreCL |
| 1399 | Q9UBS8\|RNF14_HUMAN | 258 | 263 | GqvqCL |
| 1400 | Q9UBY5\|EDG7_HUMAN | 37 | 42 | GtffCL |
| 1401 | Q9UBY8\|CLN8_HUMAN | 145 | 150 | GflgCL |
| 1402 | Q9UDX3\|S14L4_HUMAN | 250 | 255 | GnpkCL |
| 1403 | Q9UDX3\|S14L4_HUMAN | 351 | 356 | GsltCL |
| 1404 | Q9UDX4\|S14L3_HUMAN | 250 | 255 | GnpkCL |
| 1405 | Q9UGF7\|O12D3_HUMAN | 62 | 67 | GnlsCL |
| 1406 | Q9UGI6\|KCNN3_HUMAN | 525 | 530 | GkgvCL |
| 1407 | Q9UGU5\|HM2L1_HUMAN | 567 | 572 | GplaCL |
| 1408 | Q9UHA7\|IL1F6_HUMAN | 69 | 74 | GlnlCL |
| 1409 | Q9UHC6\|CNTP2_HUMAN | 1174 | 1179 | GftgCL |
| 1410 | Q9UHD0\|IL19_HUMAN | 24 | 29 | GlrrCL |
| 1411 | Q9UHI8\|ATS1_HUMAN | 458 | 463 | GhgeCL |
| 1412 | Q9UHW9\|S12A6_HUMAN | 687 | 692 | GmsiCL |
| 1413 | Q9UHX3\|EMR2_HUMAN | 742 | 747 | GctwCL |
| 1414 | Q9UIA9\|XPO7_HUMAN | 933 | 938 | GccsCL |
| 1415 | Q9UIE0\|ZN230_HUMAN | 286 | 291 | GksfCL |
| 1416 | Q9UIF8\|BAZ2B_HUMAN | 627 | 632 | GmqwCL |
| 1417 | Q9UIF9\|BAZ2A_HUMAN | 1006 | 1011 | GpeeCL |
| 1418 | Q9UIH9\|KLF15_HUMAN | 117 | 122 | GehfCL |
| 1419 | Q9UIR0\|BTNL2_HUMAN | 337 | 342 | GqyrCL |

TABLE 4-continued

CXCs
Motif: G-X(3)-C-L
Number of Locations: 1337
Number of Different Proteins: 1170

| # | Accession Number\|Protein Name | First Amino acid | Last Amino acid | Sequence |
|---|---|---|---|---|
| 1420 | Q9UK10\|ZN225_HUMAN | 466 | 471 | GwasCL |
| 1421 | Q9UK11\|ZN223_HUMAN | 294 | 299 | GksfCL |
| 1422 | Q9UK12\|ZN222_HUMAN | 263 | 268 | GksfCL |
| 1423 | Q9UK13\|ZN221_HUMAN | 488 | 493 | GwasCL |
| 1424 | Q9UK13\|ZN221_HUMAN | 572 | 577 | GwasCL |
| 1425 | Q9UK99\|FBX3_HUMAN | 189 | 194 | GlkyCL |
| 1426 | Q9UKB1\|FBW1B_HUMAN | 281 | 286 | GsvlCL |
| 1427 | Q9UKP4\|ATS7_HUMAN | 443 | 448 | GwglCL |
| 1428 | Q9UKP5\|ATS6_HUMAN | 545 | 550 | GgkyCL |
| 1429 | Q9UKQ2\|ADA28_HUMAN | 500 | 505 | GkghCL |
| 1430 | Q9UKU0\|ACSL6_HUMAN | 104 | 109 | GngpCL |
| 1431 | Q9UL25\|RAB21_HUMAN | 121 | 126 | GneiCL |
| 1432 | Q9ULB1\|NRX1A_HUMAN | 1048 | 1053 | GfqgCL |
| 1433 | Q9ULL4\|PLXB3_HUMAN | 1191 | 1196 | GrgeCL |
| 1434 | Q9ULV0\|MYO5B_HUMAN | 1496 | 1501 | GtvpCL |
| 1435 | Q9UM47\|NOTC3_HUMAN | 1228 | 1233 | GgfrCL |
| 1436 | Q9UM82\|SPAT2_HUMAN | 37 | 42 | GsdeCL |
| 1437 | Q9UMF0\|ICAM5_HUMAN | 879 | 884 | GeavCL |
| 1438 | Q9UMW8\|UBP18_HUMAN | 61 | 66 | GqtcCL |
| 1439 | Q9UNA0\|ATS5_HUMAN | 467 | 472 | GhgnCL |
| 1440 | Q9UNA0\|ATS5_HUMAN | 525 | 530 | GqmvCL |
| 1441 | Q9UNI1\|ELA1_HUMAN | 208 | 213 | GplhCL |
| 1442 | Q9UP79\|ATS8_HUMAN | 421 | 426 | GhgdCL |
| 1443 | Q9UP79\|ATS8_HUMAN | 562 | 567 | GgryCL |
| 1444 | Q9UP95\|S12A4_HUMAN | 622 | 627 | GmslCL |
| 1445 | Q9UPA5\|BSN_HUMAN | 1765 | 1770 | GspvCL |
| 1446 | Q9UPZ6\|THS7A_HUMAN | 881 | 886 | GiheCL |
| 1447 | Q9UQ05\|KCNH4_HUMAN | 213 | 218 | GgsrCL |
| 1448 | Q9UQ49\|NEUR3_HUMAN | 380 | 385 | GlfgCL |
| 1449 | Q9UQ52\|CNTN6_HUMAN | 96 | 101 | GmyqCL |
| 1450 | Q9UQD0\|SCN8A_HUMAN | 949 | 954 | GqamCL |
| 1451 | Q9Y219\|JAG2_HUMAN | 907 | 912 | GwkpCL |
| 1452 | Q9Y236\|OSGI2_HUMAN | 480 | 485 | GvtrCL |
| 1453 | Q9Y263\|PLAP_HUMAN | 721 | 726 | GkaqCL |
| 1454 | Q9Y278\|OST2_HUMAN | 51 | 56 | GaprCL |
| 1455 | Q9Y297\|FBW1A_HUMAN | 344 | 349 | GsvlCL |
| 1456 | Q9Y2H6\|FNDC3_HUMAN | 790 | 795 | GivtCL |
| 1457 | Q9Y2L6\|FRM4B_HUMAN | 871 | 876 | GsqrCL |
| 1458 | Q9Y2P5\|S27A5_HUMAN | 345 | 350 | GilgCL |
| 1459 | Q9Y2P5\|S27A5_HUMAN | 452 | 457 | GkmsCL |
| 1460 | Q9Y2Q1\|ZN257_HUMAN | 132 | 137 | GlnqCL |
| 1461 | Q9Y2T5\|GPR52_HUMAN | 205 | 210 | GfivCL |
| 1462 | Q9Y385\|UB2J1_HUMAN | 87 | 92 | GkkiCL |
| 1463 | Q9Y3B6\|CN122_HUMAN | 38 | 43 | GeclCL |
| 1464 | Q9Y3C8\|UFC1_HUMAN | 112 | 117 | GgkiCL |
| 1465 | Q9Y3I1\|FBX7_HUMAN | 71 | 76 | GdliCL |
| 1466 | Q9Y3N9\|OR2W1_HUMAN | 108 | 113 | GsveCL |
| 1467 | Q9Y3R4\|NEUR2_HUMAN | 160 | 165 | GpghCL |
| 1468 | Q9Y3S2\|ZN330_HUMAN | 182 | 187 | GqhsCL |
| 1469 | Q9Y485\|DMXL1_HUMAN | 187 | 192 | GkddCL |
| 1470 | Q9Y485\|DMXL1_HUMAN | 2862 | 2867 | XrnvCL |
| 1471 | Q9Y493\|ZAN_HUMAN | 1152 | 1157 | GtatCL |
| 1472 | Q9Y4C0\|NRX3A_HUMAN | 1014 | 1019 | GfqgCL |
| 1473 | Q9Y4F1\|FARP1_HUMAN | 820 | 825 | GvphCL |
| 1474 | Q9Y4K1\|AIM1_HUMAN | 1473 | 1478 | GhypCL |
| 1475 | Q9Y4W6\|AFG32_HUMAN | 31 | 36 | GeqpCL |
| 1476 | Q9Y535\|RPC8_HUMAN | 43 | 48 | GlciCL |
| 1477 | Q9Y561\|LRP12_HUMAN | 241 | 246 | GnidCL |
| 1478 | Q9Y574\|ASB4_HUMAN | 86 | 91 | GhveCL |
| 1479 | Q9Y575\|ASB3_HUMAN | 291 | 296 | GhedCL |
| 1480 | Q9Y5F7\|PCDGL_HUMAN | 729 | 734 | GtcaCL |
| 1481 | Q9Y5J3\|HEY1_HUMAN | 126 | 131 | GfreCL |
| 1482 | Q9Y5N5\|HEMK2_HUMAN | 45 | 50 | GveiCL |
| 1483 | Q9Y5Q5\|CORIN_HUMAN | 424 | 429 | GdqrCL |
| 1484 | Q9Y5R5\|DMRT2_HUMAN | 130 | 135 | GvvsCL |
| 1485 | Q9Y5R6\|DMRT1_HUMAN | 153 | 158 | GsnpCL |
| 1486 | Q9Y5S2\|MRCKB_HUMAN | 1374 | 1379 | GsvqCL |
| 1487 | Q9Y5W8\|SNX13_HUMAN | 73 | 78 | GvpkCL |
| 1488 | Q9Y616\|IRAK3_HUMAN | 395 | 400 | GldsCL |
| 1489 | Q9Y644\|RFNG_HUMAN | 203 | 208 | GagfCL |
| 1490 | Q9Y662\|OST3B_HUMAN | 7 | 12 | GgrsCL |
| 1491 | Q9Y666\|S12A7_HUMAN | 622 | 627 | GmslCL |
| 1492 | Q9Y6H5\|SNCAP_HUMAN | 361 | 366 | GhaeCL |
| 1493 | Q9Y6I4\|UBP3_HUMAN | 449 | 454 | GpesCL |
| 1494 | Q9Y6N6\|LAMC3_HUMAN | 885 | 890 | GqcsCL |
| 1495 | Q9Y6R1\|S4A4_HUMAN | 512 | 517 | GaifCL |
| 1496 | Q9Y6R7\|FCGBP_HUMAN | 1661 | 1666 | GqgvCL |
| 1497 | Q9Y6R7\|FCGBP_HUMAN | 2388 | 2393 | GqcgCL |
| 1498 | Q9Y6R7\|FCGBP_HUMAN | 2862 | 2867 | GqgvCL |
| 1499 | Q9Y6R7\|FCGBP_HUMAN | 3589 | 3594 | GqcgCL |
| 1500 | Q9Y6R7\|FCGBP_HUMAN | 4063 | 4068 | GqgvCL |
| 1501 | Q9Y6R7\|FCGBP_HUMAN | 4790 | 4795 | GqcgCL |
| 1502 | Q9Y6R7\|FCGBP_HUMAN | 4852 | 4857 | GcgrCL |
| 1503 | Q9Y6R7\|FCGBP_HUMAN | 5032 | 5037 | GcpvCL |

These peptides are likely to have anti-angiogenic activity. Methods for testing for such activity are described herein.

Example 4

Collagen Derived Peptides

Figure 6A:
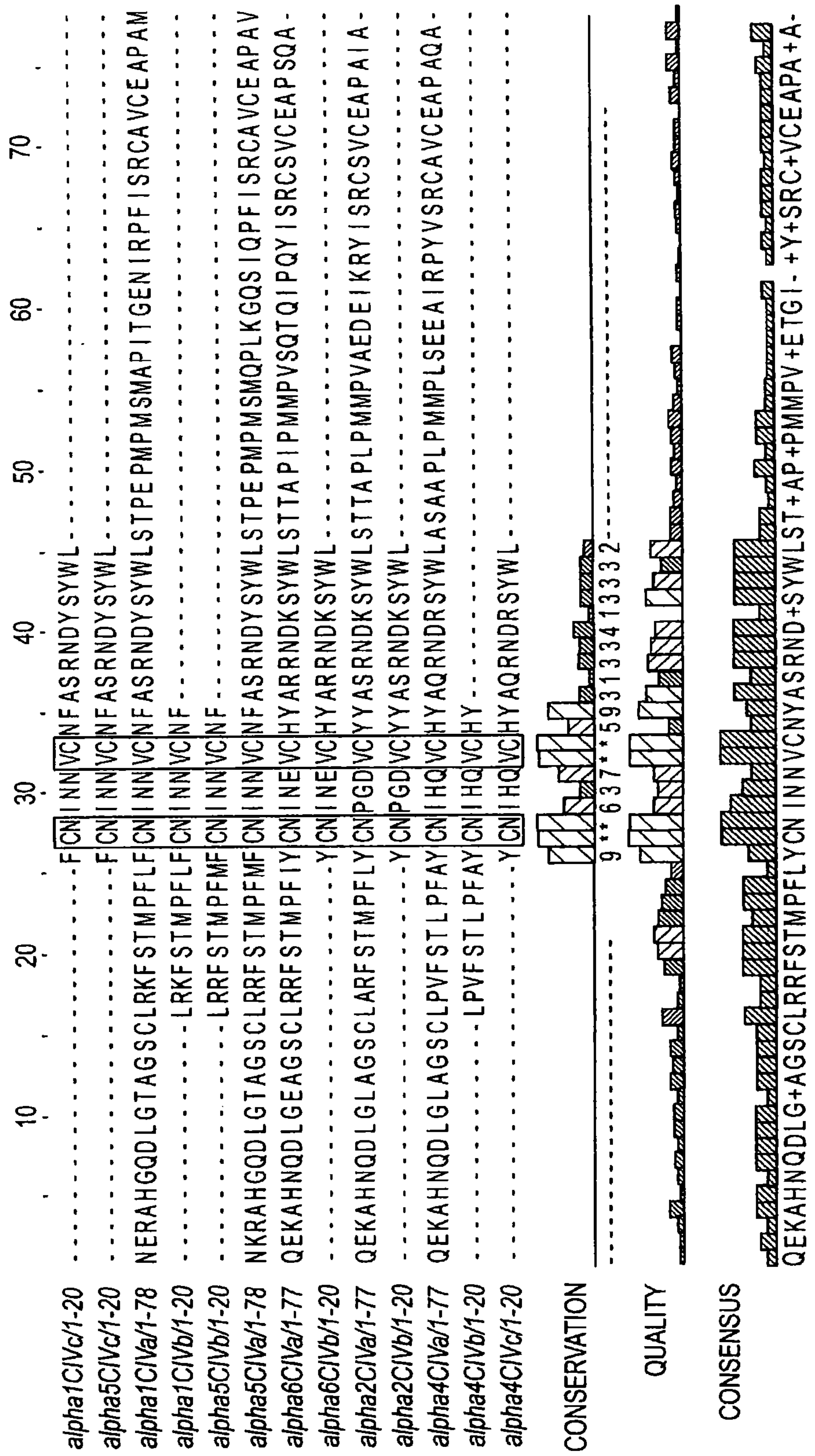
FIGS. 6A-6C show a set of amino acid sequences that include in shading the most abundant motif in the theoretically predicted anti-angiogenic type IV collagen derived peptide fragments (FIG. 6A discloses SEQ ID NOS 2313, 2313, 2408-2409, 2312, 2410-2416 and 2320, respectively, in order of appearance.
Figure 6B:
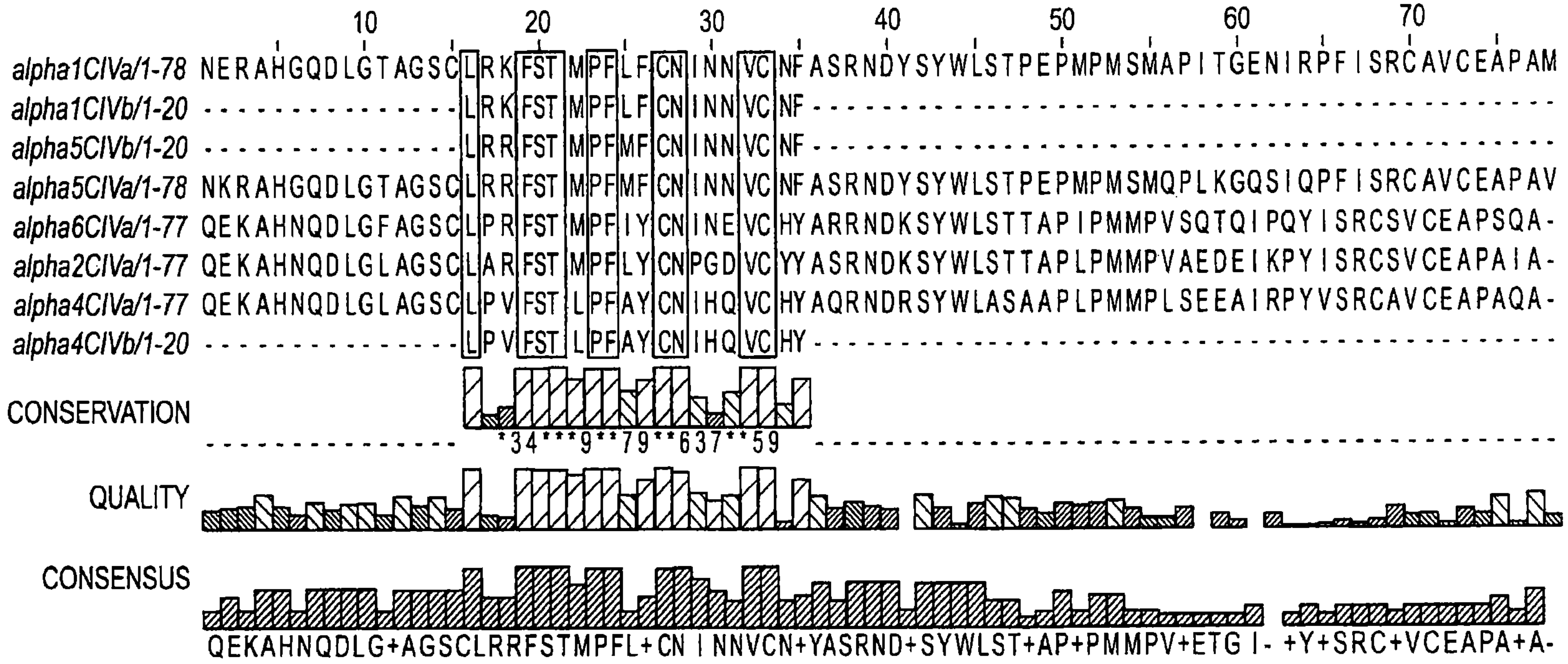
Figure 6C:
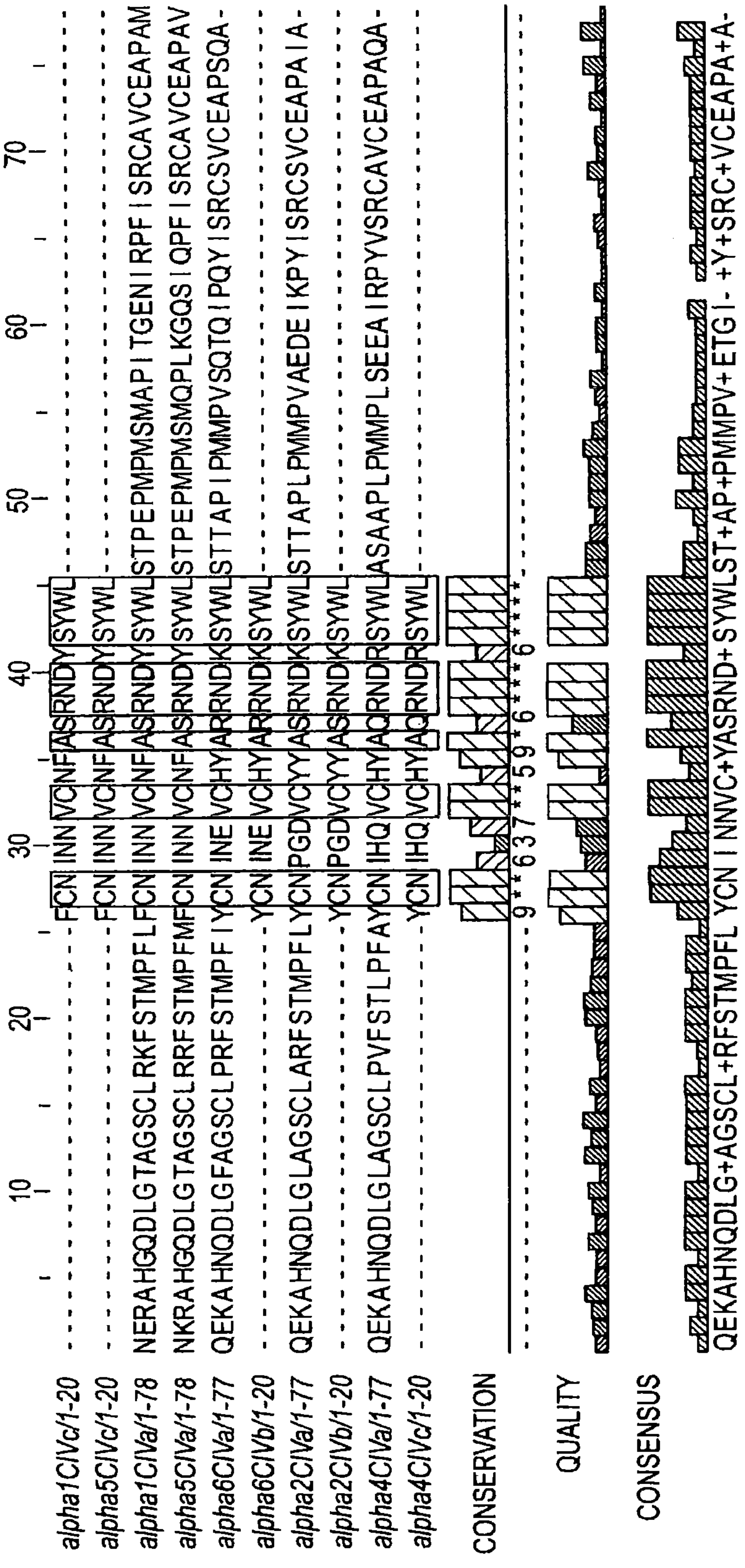

The same procedure as used for the C-X-C chemokines can be repeated for the case of the collagen related fragments. Because the number of the experimentally tested peptides is small in the calculation, all the theoretically predicted fragments are considered. Both the short and long predicted fragments are introduced. Two predominant motifs were calculated. One of them is the most abundant and is characterized by a conserved 4-amino acid repeat. It can be described by the following generic sequence: C-N-X3-V-C (SEQ ID NO: 2288) (FIG. 6A). This motif can be localized either upstream or downstream of the peptide sequence. If the peptides are separated according to the location of the C-N-X3-V-C motif (SEQ ID NO: 2288), it can be either near the amino or carboxy terminal of the peptide. This provides for the identification of a set of two more definitive motifs (FIGS. 6B and 6C). The 4-letter motif appears upstream is the C-N-X3-V-C-X2-A-X-R-N-D-X-S-Y-W-L (SEQ ID NO: 2315) (FIG. 6B), whereas the motif that appears downstream is the L-X2-F-S-T-X-P-F-X2-C-N-X3-V-C (SEQ ID NO: 2316) (FIG. 6C).

Figure 7:
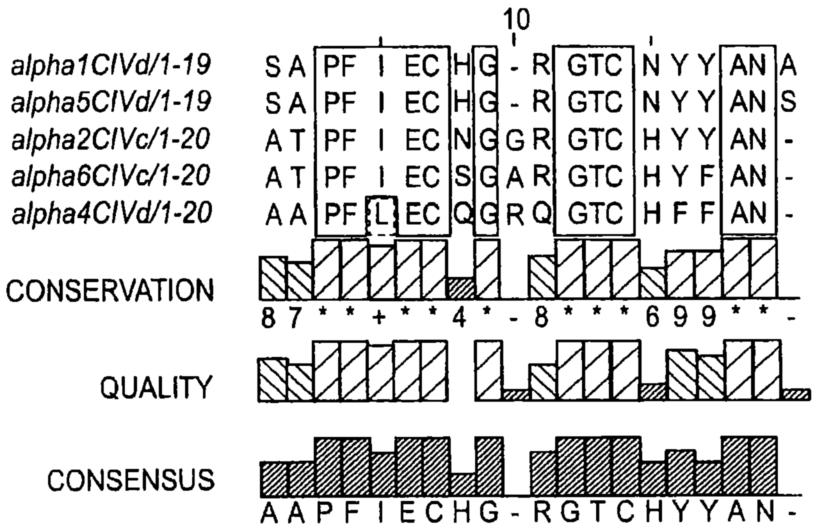
FIG. 7 shows a set of amino acid sequences that include in shading a less common motif within the sequences of type IV collagen derived peptide fragments (SEQ ID NOS 2422-2426, respectively, in order of appearance).

Apart from the aforementioned 7-mer there is another motif that is present in a smaller subset of collagen derived peptides. Those peptides do not include the C-N-X3-V-C (SEQ ID NO: 2288). This motif is described by the generic sequence X2-P-F-X-E-C-X-G-X8-A-N (SEQ ID NO: 2317). Common modifications can be described by the sequence X2-P-F-(I/L)-E-C-X-G-X-(R/G)-X-(Y/F)-(Y/F)-A-N (SEQ ID NO: 2318) (FIG. 7).

Figure 8:
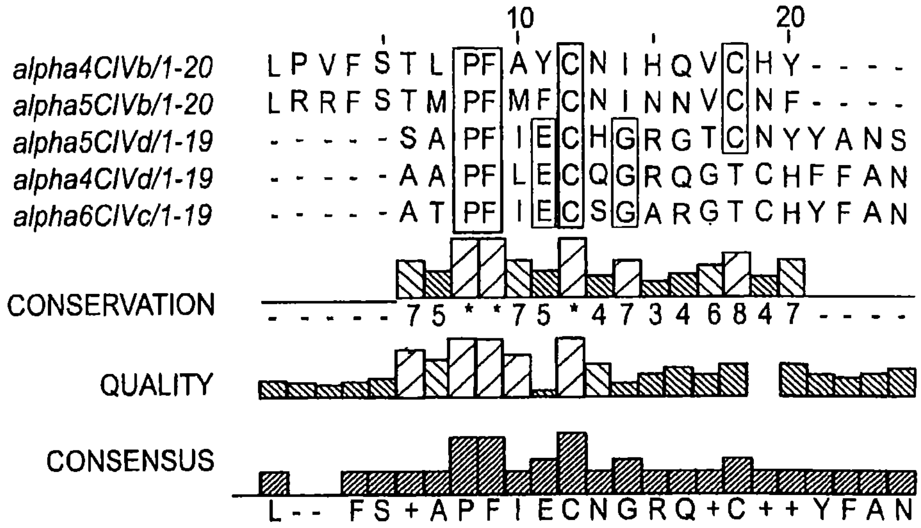
FIG. 8 shows a set of amino acid sequences that include in shading a motif identified within the subset of the of type IV collagen derived short anti-angiogenic peptides (SEQ ID NOS 2416, 2312, 2423, 2426 and 2425, respectively, in order of appearance).

If only the short identified anti-angiogenic fragments are considered then the multiple alignment algorithm may be used to identify motifs present only within this subset of the peptides. The alignment is shown in FIG. 8. These motifs are similar to those identified herein. A more generic 3-common letter motif, the P-F-X2-C motif can be distinguished.

In the case of collagens two generic motifs were identified. The first one is the C-N-X3-V-C (SEQ ID NO: 2288). Using this motif as a query and scanning the Prosite database 24 hits in 24 different proteins were identified. These candidate anti-angiogenic peptides are listed in Table 5 (SEQ ID NO: 1504-1527).

TABLE 5

Collagens
Motif: C-N-X(3)-V-C (SEQ ID NO: 2288)
Number of Locations: 24
Number of Different Proteins: 24

| # | Accession Number\|Protein Name | First Amino acid | Last Amino acid | Sequence |
|---|---|---|---|---|
| 1504 | O14514\|BAI1__HUMAN | 400 | 406 | CNnsaVC |
| 1505 | O75093\|SLIT1__HUMAN | 507 | 513 | CNsdvVC |
| 1506 | O75534\|CSDE1__HUMAN | 733 | 739 | CNvwrVC |
| 1507 | P02462\|CO4A1__HUMAN | 1505 | 1511 | CNinnVC |
| 1508 | P08572\|CO4A2__HUMAN | 1549 | 1555 | CNpgdVC |
| 1509 | P09758\|TACD2__HUMAN | 119 | 125 | CNqtsVC |
| 1510 | P25391\|LAMA1__HUMAN | 751 | 757 | CNvhgVC |
| 1511 | P29400\|CO4A5__HUMAN | 1521 | 1527 | CNinnVC |
| 1512 | P53420\|CO4A4__HUMAN | 1525 | 1531 | CNihqVC |
| 1513 | P83110\|HTRA3__HUMAN | 48 | 54 | CNcclVC |
| 1514 | Q01955\|CO4A3__HUMAN | 1505 | 1511 | CNvndVC |
| 1515 | Q13625\|ASPP2__HUMAN | 1002 | 1008 | CNnvqVC |
| 1516 | Q13751\|LAMB3__HUMAN | 572 | 578 | CNrypVC |
| 1517 | Q14031\|CO4A6__HUMAN | 1527 | 1533 | CNineVC |
| 1518 | Q8WWQ8\|STAB2__HUMAN | 1970 | 1976 | CNnrgVC |
| 1519 | Q96GX1\|TECT2__HUMAN | 642 | 648 | CNrneVC |
| 1520 | Q99965\|ADAM2__HUMAN | 621 | 627 | CNdrgVC |
| 1521 | Q9BX93\|PG12B__HUMAN | 112 | 118 | CNqldVC |
| 1522 | Q9BYD5\|CNFN__HUMAN | 32 | 38 | CNdmpVC |
| 1523 | Q9H013\|ADA19__HUMAN | 659 | 665 | CNghgVC |
| 1524 | Q9HBG6\|IF122__HUMAN | 436 | 442 | CNllvVC |
| 1525 | Q9P2R7\|SUCB1__HUMAN | 152 | 158 | CNqvlVC |
| 1526 | Q9UBX1\|CATF__HUMAN | 89 | 95 | CNdpmVC |
| 1527 | Q9UKF2\|ADA30__HUMAN | 638 | 644 | CNtrgVC |

The second motif is the P-F-X2-C. Again using this motif as a query at the Prosite 306 locations that contain the specific amino acid sequence were identified in 288 different proteins. The hits included peptides shown in Table 6 (SEQ ID Nos: 1528-1833).

TABLE 6

Collagens
Motif: P-F-X2-C
Number of Locations: 306
Number of Different Proteins: 288

| # | Accession Number\|Protein Name | First Amino acid | Last Amino acid | Sequence |
|---|---|---|---|---|
| 1528 | O00116\|ADAS__HUMAN | 561 | 565 | PFstC |
| 1529 | O00182\|LEG9__HUMAN | 98 | 102 | PFdlC |
| 1530 | O00206\|TLR4__HUMAN | 702 | 706 | PFqlC |
| 1531 | O00270\|GPR31__HUMAN | 2 | 6 | PFpnC |
| 1532 | O00398\|P2Y10__HUMAN | 288 | 292 | PFclC |
| 1533 | O00507\|USP9Y__HUMAN | 259 | 263 | PFgqC |
| 1534 | O14646\|CHD1__HUMAN | 450 | 454 | PFkdC |
| 1535 | O14843\|FFAR3__HUMAN | 84 | 88 | PFilC |
| 1536 | O14978\|ZN263__HUMAN | 547 | 551 | PFseC |
| 1537 | O15015\|ZN646__HUMAN | 880 | 884 | PFlcC |
| 1538 | O15031\|PLXB2__HUMAN | 611 | 615 | PFydC |
| 1539 | O15037\|K0323__HUMAN | 423 | 427 | PFtlC |
| 1540 | O15453\|NBR2__HUMAN | 9 | 13 | PFlpC |
| 1541 | O15529\|GPR42__HUMAN | 84 | 88 | PFilC |
| 1542 | O43556\|SGCE__HUMAN | 207 | 211 | PFssC |
| 1543 | O60299\|K0552__HUMAN | 308 | 312 | PFaaC |
| 1544 | O60343\|TBCD4__HUMAN | 89 | 93 | PFlrC |
| 1545 | O60431\|OR1I1__HUMAN | 93 | 97 | PFvgC |
| 1546 | O60449\|LY75__HUMAN | 1250 | 1254 | PFqnC |
| 1547 | O60481\|ZIC3__HUMAN | 331 | 335 | PFpgC |
| 1548 | O60486\|PLXC1__HUMAN | 618 | 622 | PFtaC |
| 1549 | O60494\|CUBN__HUMAN | 3302 | 3306 | PFsiC |
| 1550 | O60603\|TLR2__HUMAN | 669 | 673 | PFklC |
| 1551 | O60656\|UD19__HUMAN | 149 | 153 | PFdnC |
| 1552 | O60706\|ABCC9__HUMAN | 627 | 631 | PFesC |
| 1553 | O75152\|ZC11A__HUMAN | 23 | 27 | PFrhC |

TABLE 6-continued

Collagens
Motif: P-F-X2-C
Number of Locations: 306
Number of Different Proteins: 288

| # | Accession Number\|Protein Name | First Amino acid | Last Amino acid | Sequence |
|---|---|---|---|---|
| 1554 | O75197\|LRP5__HUMAN | 317 | 321 | PFytC |
| 1555 | O75419\|CC45L__HUMAN | 444 | 448 | PFlyC |
| 1556 | O75473\|LGR5__HUMAN | 547 | 551 | PFkpC |
| 1557 | O75478\|TAD2L__HUMAN | 38 | 42 | PFflC |
| 1558 | O75581\|LRP6__HUMAN | 304 | 308 | PFyqC |
| 1559 | O75794\|CD123__HUMAN | 147 | 151 | PFihC |
| 1560 | O75882\|ATRN__HUMAN | 969 | 973 | PFgqC |
| 1561 | O76031\|CLPX__HUMAN | 313 | 317 | PFaiC |
| 1562 | O95006\|OR2F2__HUMAN | 93 | 97 | PFqsC |
| 1563 | O95007\|OR6B1__HUMAN | 285 | 289 | PFiyC |
| 1564 | O95149\|SPN1__HUMAN | 195 | 199 | PFydC |
| 1565 | O95202\|LETM1__HUMAN | 51 | 55 | PFgcC |
| 1566 | O95409\|ZIC2__HUMAN | 336 | 340 | PFpgC |
| 1567 | O95450\|ATS2__HUMAN | 569 | 573 | PFgsC |
| 1568 | O95759\|TBCD8__HUMAN | 67 | 71 | PFsrC |
| 1569 | O95841\|ANGL1__HUMAN | 276 | 280 | PFkdC |
| 1570 | O95886\|DLGP3__HUMAN | 98 | 102 | PFdtC |
| 1571 | P02461\|CO3A1__HUMAN | 80 | 84 | PFgeC |
| 1572 | P02462\|CO4A1__HUMAN | 1501 | 1505 | PFlfC |
| 1573 | P02462\|CO4A1__HUMAN | 1612 | 1616 | PFieC |
| 1574 | P08151\|GLI1__HUMAN | 173 | 177 | PFptC |
| 1575 | P08572\|CO4A2__HUMAN | 1545 | 1549 | PFlyC |
| 1576 | P08572\|CO4A2__HUMAN | 1654 | 1658 | PFieC |
| 1577 | P08581\|MET__HUMAN | 534 | 538 | PFvqC |
| 1578 | P09172\|DOPO__HUMAN | 136 | 140 | PFgtC |
| 1579 | P0C0L4\|CO4A__HUMAN | 731 | 735 | PFlsC |
| 1580 | P0C0L5\|CO4B__HUMAN | 731 | 735 | PFlsC |
| 1581 | P15309\|PPAP__HUMAN | 157 | 161 | PFrnC |
| 1582 | P17021\|ZNF17__HUMAN | 350 | 354 | PFycC |
| 1583 | P18084\|ITB5__HUMAN | 546 | 550 | PFceC |
| 1584 | P20645\|MPRD__HUMAN | 3 | 7 | PFysC |
| 1585 | P20851\|C4BB__HUMAN | 130 | 134 | PFpiC |
| 1586 | P20933\|ASPG__HUMAN | 13 | 17 | PFllC |
| 1587 | P21673\|SAT1__HUMAN | 50 | 54 | PFyhC |
| 1588 | P21854\|CD72__HUMAN | 222 | 226 | PFftC |
| 1589 | P22309\|UD11__HUMAN | 152 | 156 | PFlpC |
| 1590 | P22362\|CCL1__HUMAN | 29 | 33 | PFsrC |
| 1591 | P22681\|CBL__HUMAN | 417 | 421 | PFcrC |
| 1592 | P23942\|RDS__HUMAN | 210 | 214 | PFscC |
| 1593 | P24043\|LAMA2__HUMAN | 2679 | 2683 | PFegC |
| 1594 | P24043\|LAMA2__HUMAN | 3083 | 3087 | PFrgC |
| 1595 | P24903\|CP2F1__HUMAN | 483 | 487 | PFqlC |
| 1596 | P25098\|ARBK1__HUMAN | 252 | 256 | PFivC |
| 1597 | P25490\|TYY1__HUMAN | 386 | 390 | PFdgC |
| 1598 | P25929\|NPY1R__HUMAN | 117 | 121 | PFvqC |
| 1599 | P26718\|NKG2D__HUMAN | 52 | 56 | PFffC |
| 1600 | P26927\|HGFL__HUMAN | 439 | 443 | PFdyC |
| 1601 | P27987\|IP3KB__HUMAN | 869 | 873 | PFfkC |
| 1602 | P29400\|CO4A5__HUMAN | 1517 | 1521 | PFmfC |
| 1603 | P29400\|CO4A5__HUMAN | 1628 | 1632 | PFieC |
| 1604 | P34896\|GLYC__HUMAN | 244 | 248 | PFehC |
| 1605 | P35504\|UD15__HUMAN | 153 | 157 | PFhlC |
| 1606 | P35523\|CLCN1__HUMAN | 26 | 30 | PFehC |
| 1607 | P35626\|ARBK2__HUMAN | 252 | 256 | PFivC |
| 1608 | P36383\|CXA7__HUMAN | 205 | 209 | PFyvC |
| 1609 | P36508\|ZNF76__HUMAN | 258 | 262 | PFegC |
| 1610 | P36509\|UD12__HUMAN | 149 | 153 | PFdnC |
| 1611 | P36894\|BMR1A__HUMAN | 57 | 61 | PFlkC |
| 1612 | P41180\|CASR__HUMAN | 538 | 542 | PFsnC |
| 1613 | P42338\|PK3CB__HUMAN | 650 | 654 | PFldC |
| 1614 | P42575\|CASP2__HUMAN | 141 | 145 | PFpvC |
| 1615 | P45974\|UBP5__HUMAN | 528 | 532 | PFssC |
| 1616 | P46531\|NOTC1__HUMAN | 1411 | 1415 | PFyrC |
| 1617 | P48637\|GSHB__HUMAN | 405 | 409 | PFenC |
| 1618 | P49257\|LMAN1__HUMAN | 471 | 475 | PFpsC |
| 1619 | P49888\|ST1E1__HUMAN | 79 | 83 | PFleC |
| 1620 | P50052\|AGTR2__HUMAN | 315 | 319 | PFlyC |
| 1621 | P50876\|UB7I4__HUMAN | 273 | 277 | PFvlC |
| 1622 | P51606\|RENBP__HUMAN | 376 | 380 | PFkgC |
| 1623 | P51617\|IRAK1__HUMAN | 195 | 199 | PFpfC |
| 1624 | P51689\|ARSD__HUMAN | 581 | 585 | PFcsC |

TABLE 6-continued

Collagens
Motif: P-F-X2-C
Number of Locations: 306
Number of Different Proteins: 288

| # | Accession Number\|Protein Name | First Amino acid | Last Amino acid | Sequence |
|---|---|---|---|---|
| 1625 | P51690\|ARSE_HUMAN | 576 | 580 | PFplC |
| 1626 | P52740\|ZN132_HUMAN | 369 | 373 | PFecC |
| 1627 | P52747\|ZN143_HUMAN | 318 | 322 | PFegC |
| 1628 | P53420\|CO4A4_HUMAN | 1521 | 1525 | PFayC |
| 1629 | P53420\|CO4A4_HUMAN | 1630 | 1634 | PFleC |
| 1630 | P53621\|COPA_HUMAN | 1165 | 1169 | PFdiC |
| 1631 | P54198\|HIRA_HUMAN | 215 | 219 | PFdeC |
| 1632 | P54793\|ARSF_HUMAN | 570 | 574 | PFclC |
| 1633 | P54802\|ANAG_HUMAN | 401 | 405 | PFiwC |
| 1634 | P55157\|MTP_HUMAN | 823 | 827 | PFlvC |
| 1635 | P62079\|TSN5_HUMAN | 183 | 187 | PFscC |
| 1636 | P78357\|CNTP1_HUMAN | 926 | 930 | PFvgC |
| 1637 | P78527\|PRKDC_HUMAN | 2853 | 2857 | PFvsC |
| 1638 | P81133\|SIM1_HUMAN | 200 | 204 | PFdgC |
| 1639 | P98088\|MUC5A_HUMAN | 290 | 294 | PFkmC |
| 1640 | Q01955\|CO4A3_HUMAN | 1501 | 1505 | PFlfC |
| 1641 | Q01955\|CO4A3_HUMAN | 1612 | 1616 | PFleC |
| 1642 | Q02817\|MUC2_HUMAN | 597 | 601 | PFgrC |
| 1643 | Q02817\|MUC2_HUMAN | 1375 | 1379 | PFglC |
| 1644 | Q02817\|MUC2_HUMAN | 4916 | 4920 | PFywC |
| 1645 | Q03395\|ROM1_HUMAN | 213 | 217 | PFscC |
| 1646 | Q07912\|ACK1_HUMAN | 293 | 297 | PFawC |
| 1647 | Q12830\|BPTF_HUMAN | 2873 | 2877 | PFyqC |
| 1648 | Q12836\|ZP4_HUMAN | 238 | 242 | PFtsC |
| 1649 | Q12866\|MERTK_HUMAN | 313 | 317 | PFrnC |
| 1650 | Q12950\|FOXD4_HUMAN | 291 | 295 | PFpcC |
| 1651 | Q12968\|NFAC3_HUMAN | 327 | 331 | PFqyC |
| 1652 | Q13191\|CBLB_HUMAN | 409 | 413 | PFcrC |
| 1653 | Q13258\|PD2R_HUMAN | 4 | 8 | PFyrC |
| 1654 | Q13356\|PPIL2_HUMAN | 38 | 42 | PFdhC |
| 1655 | Q13607\|OR2F1_HUMAN | 93 | 97 | PFqsC |
| 1656 | Q13753\|LAMC2_HUMAN | 409 | 413 | PFgtC |
| 1657 | Q13936\|CAC1C_HUMAN | 2179 | 2183 | PFvnC |
| 1658 | Q14031\|CO4A6_HUMAN | 1523 | 1527 | PFiyC |
| 1659 | Q14031\|CO4A6_HUMAN | 1632 | 1636 | PFieC |
| 1660 | Q14137\|BOP1_HUMAN | 400 | 404 | PFptC |
| 1661 | Q14330\|GPR18_HUMAN | 247 | 251 | PFhiC |
| 1662 | Q14643\|ITPR1_HUMAN | 526 | 530 | PFtdC |
| 1663 | Q15042\|RB3GP_HUMAN | 267 | 271 | PFgaC |
| 1664 | Q15389\|ANGP1_HUMAN | 282 | 286 | PFrdC |
| 1665 | Q15583\|TGIF_HUMAN | 269 | 273 | PFhsC |
| 1666 | Q15583\|TGIF_HUMAN | 314 | 318 | PFslC |
| 1667 | Q15761\|NPY5R_HUMAN | 128 | 132 | PFlqC |
| 1668 | Q15915\|ZIC1_HUMAN | 305 | 309 | PFpgC |
| 1669 | Q16363\|LAMA4_HUMAN | 1788 | 1792 | PFtgC |
| 1670 | Q16572\|VACHT_HUMAN | 517 | 521 | PFdeC |
| 1671 | Q16586\|SGCA_HUMAN | 205 | 209 | PFstC |
| 1672 | Q16773\|KAT1_HUMAN | 123 | 127 | PFfdC |
| 1673 | Q16878\|CDO1_HUMAN | 160 | 164 | PFdtC |
| 1674 | Q2TBC4\|CF049_HUMAN | 298 | 302 | PFstC |
| 1675 | Q49AM1\|MTER3_HUMAN | 28 | 32 | PFlaC |
| 1676 | Q53FE4\|CD017_HUMAN | 77 | 81 | PFanC |
| 1677 | Q53G59\|KLH12_HUMAN | 240 | 244 | PFirC |
| 1678 | Q53T03\|RBP22_HUMAN | 517 | 521 | PFpvC |
| 1679 | Q5IJ48\|CRUM2_HUMAN | 762 | 766 | PFrgC |
| 1680 | Q5T442\|CXA12_HUMAN | 241 | 245 | PFfpC |
| 1681 | Q5VYX0\|RENAL_HUMAN | 310 | 314 | PFlaC |
| 1682 | Q5W0N0\|CI057_HUMAN | 89 | 93 | PFhgC |
| 1683 | Q6NSW7\|NANP8_HUMAN | 239 | 243 | PFynC |
| 1684 | Q6P2Q9\|PRP8_HUMAN | 1892 | 1896 | PFqaC |
| 1685 | Q6PRD1\|GP179_HUMAN | 232 | 236 | PFleC |
| 1686 | Q6TCH4\|PAQR6_HUMAN | 95 | 99 | PFasC |
| 1687 | Q6UB98\|ANR12_HUMAN | 1949 | 1953 | PFsaC |
| 1688 | Q6UB99\|ANR11_HUMAN | 2552 | 2556 | PFsaC |
| 1689 | Q6UXZ4\|UNC5D_HUMAN | 766 | 770 | PFtaC |
| 1690 | Q7Z434\|MAVS_HUMAN | 431 | 435 | PFsgC |
| 1691 | Q7Z6J6\|FRMD5_HUMAN | 87 | 91 | PFtmC |
| 1692 | Q7Z7G8\|VP13B_HUMAN | 441 | 445 | PFfdC |
| 1693 | Q7Z7G8\|VP13B_HUMAN | 1423 | 1427 | PFrnC |
| 1694 | Q7Z7M1\|GP144_HUMAN | 352 | 356 | PFlcC |
| 1695 | Q86SJ6\|DSG4_HUMAN | 523 | 527 | PFtfC |

TABLE 6-continued

Collagens
Motif: P-F-X2-C
Number of Locations: 306
Number of Different Proteins: 288

| # | Accession Number\|Protein Name | First Amino acid | Last Amino acid | Sequence |
|---|---|---|---|---|
| 1696 | Q86SQ6\|GP123_HUMAN | 863 | 867 | PFiiC |
| 1697 | Q86T65\|DAAM2_HUMAN | 548 | 552 | PFacC |
| 1698 | Q86V97\|KBTB6_HUMAN | 355 | 359 | PFlcC |
| 1699 | Q86XI2\|CNDG2_HUMAN | 1043 | 1047 | PFsrC |
| 1700 | Q86YT6\|MIB1_HUMAN | 909 | 913 | PFimC |
| 1701 | Q8IUH2\|CREG2_HUMAN | 152 | 156 | PFgnC |
| 1702 | Q8IWU5\|SULF2_HUMAN | 745 | 749 | PFcaC |
| 1703 | Q8IWV8\|UBR2_HUMAN | 1514 | 1518 | PFlkC |
| 1704 | Q8IWX5\|SGPP2_HUMAN | 257 | 261 | PFflC |
| 1705 | Q8IX07\|FOG1_HUMAN | 293 | 297 | PFpqC |
| 1706 | Q8IX29\|FBX16_HUMAN | 287 | 291 | PFplC |
| 1707 | Q8IXT2\|DMRTD_HUMAN | 224 | 228 | PFttC |
| 1708 | Q8IZF5\|GP113_HUMAN | 62 | 66 | PFpaC |
| 1709 | Q8IZQ8\|MYCD_HUMAN | 403 | 407 | PFqdC |
| 1710 | Q8IZW8\|TENS4_HUMAN | 423 | 427 | PFttC |
| 1711 | Q8N0W3\|FUK_HUMAN | 100 | 104 | PFddC |
| 1712 | Q8N122\|RPTOR_HUMAN | 1033 | 1037 | PFtpC |
| 1713 | Q8N1G1\|REXO1_HUMAN | 278 | 282 | PFgsC |
| 1714 | Q8N1G2\|K0082_HUMAN | 790 | 794 | PFhiC |
| 1715 | Q8N201\|INT1_HUMAN | 1573 | 1577 | PFpaC |
| 1716 | Q8N475\|FSTL5_HUMAN | 61 | 65 | PFgsC |
| 1717 | Q8N567\|ZCHC9_HUMAN | 182 | 186 | PFakC |
| 1718 | Q8N7R0\|NANG2_HUMAN | 166 | 170 | PFynC |
| 1719 | Q8N8U9\|BMPER_HUMAN | 234 | 238 | PFgsC |
| 1720 | Q8N9L1\|ZIC4_HUMAN | 207 | 211 | PFpgC |
| 1721 | Q8NB16\|MLKL_HUMAN | 411 | 415 | PFqgC |
| 1722 | Q8NG11\|TSN14_HUMAN | 183 | 187 | PFscC |
| 1723 | Q8NGC3\|O10G2_HUMAN | 98 | 102 | PFggC |
| 1724 | Q8NGC4\|O10G3_HUMAN | 94 | 98 | PFggC |
| 1725 | Q8NGJ1\|OR4D6_HUMAN | 165 | 169 | PFpfC |
| 1726 | Q8NH69\|OR5W2_HUMAN | 93 | 97 | PFygC |
| 1727 | Q8NH85\|OR5R1_HUMAN | 93 | 97 | PFhaC |
| 1728 | Q8NHU2\|CT026_HUMAN | 442 | 446 | PFntC |
| 1729 | Q8NHY3\|GA2L2_HUMAN | 359 | 363 | PFlrC |
| 1730 | Q8NI51\|BORIS_HUMAN | 369 | 373 | PFqcC |
| 1731 | Q8TCB0\|IFI44_HUMAN | 246 | 250 | PFilC |
| 1732 | Q8TCE9\|PPL13_HUMAN | 88 | 92 | PFelC |
| 1733 | Q8TCT7\|PSL1_HUMAN | 275 | 279 | PFgkC |
| 1734 | Q8TD94\|KLF14_HUMAN | 198 | 202 | PFpgC |
| 1735 | Q8TF76\|HASP_HUMAN | 474 | 478 | PFshC |
| 1736 | Q8WW14\|CJ082_HUMAN | 22 | 26 | PFlsC |
| 1737 | Q8WW38\|FOG2_HUMAN | 299 | 303 | PFpqC |
| 1738 | Q8WWG1\|NRG4_HUMAN | 32 | 36 | PFcrC |
| 1739 | Q8WWZ7\|ABCA5_HUMAN | 361 | 365 | PFchC |
| 1740 | Q8WXT5\|FX4L4_HUMAN | 295 | 299 | PFpcC |
| 1741 | Q8WYR1\|PI3R5_HUMAN | 814 | 818 | PFavC |
| 1742 | Q8WZ42\|TITIN_HUMAN | 31091 | 31095 | PFpiC |
| 1743 | Q8WZ60\|KLHL6_HUMAN | 432 | 436 | PFhnC |
| 1744 | Q92485\|ASM3B_HUMAN | 41 | 45 | PFqvC |
| 1745 | Q92793\|CBP_HUMAN | 1279 | 1283 | PFvdC |
| 1746 | Q92838\|EDA_HUMAN | 328 | 332 | PFlqC |
| 1747 | Q92995\|UBP13_HUMAN | 540 | 544 | PFsaC |
| 1748 | Q93008\|USP9X_HUMAN | 251 | 255 | PFgqC |
| 1749 | Q96F10\|SAT2_HUMAN | 50 | 54 | PFyhC |
| 1750 | Q96FV3\|TSN17_HUMAN | 185 | 189 | PFscC |
| 1751 | Q96IK0\|TM101_HUMAN | 27 | 31 | PFwgC |
| 1752 | Q96L50\|LLR1_HUMAN | 344 | 348 | PFhlC |
| 1753 | Q96L73\|NSD1_HUMAN | 456 | 460 | PFedC |
| 1754 | Q96P88\|GNRR2_HUMAN | 184 | 188 | PFtqC |
| 1755 | Q96PZ7\|CSMD1_HUMAN | 2139 | 2143 | PFprC |
| 1756 | Q96R06\|SPAG5_HUMAN | 378 | 382 | PFstC |
| 1757 | Q96RG2\|PASK_HUMAN | 542 | 546 | PFasC |
| 1758 | Q96RJ0\|TAAR1_HUMAN | 266 | 270 | PFfiC |
| 1759 | Q96RQ9\|OXLA_HUMAN | 32 | 36 | PFekC |
| 1760 | Q96SE7\|ZN347_HUMAN | 798 | 802 | PFsiC |
| 1761 | Q96T25\|ZIC5_HUMAN | 470 | 474 | PFpgC |
| 1762 | Q99666\|RGPD8_HUMAN | 517 | 521 | PFpvC |
| 1763 | Q99698\|LYST_HUMAN | 254 | 258 | PFdlC |
| 1764 | Q99726\|ZNT3_HUMAN | 51 | 55 | PFhhC |
| 1765 | Q9BSE5\|SPEB_HUMAN | 204 | 208 | PFrrC |
| 1766 | Q9BWQ6\|YIPF2_HUMAN | 124 | 128 | PFwiC |

TABLE 6-continued

Collagens
Motif: P-F-X2-C
Number of Locations: 306
Number of Different Proteins: 288

| # | Accession Number\|Protein Name | First Amino acid | Last Amino acid | Sequence |
|---|---|---|---|---|
| 1767 | Q9BXC9\|BBS2_HUMAN | 530 | 534 | PFqvC |
| 1768 | Q9BXJ4\|C1QT3_HUMAN | 18 | 22 | PFclC |
| 1769 | Q9BXK1\|KLF16_HUMAN | 130 | 134 | PFpdC |
| 1770 | Q9BZE2\|PUS3_HUMAN | 261 | 265 | PFqlC |
| 1771 | Q9C0C4\|SEM4C_HUMAN | 719 | 723 | PFrpC |
| 1772 | Q9C0E2\|XPO4_HUMAN | 50 | 54 | PFavC |
| 1773 | Q9C0I4\|THS7B_HUMAN | 1482 | 1486 | PFsyC |
| 1774 | Q9GZN6\|S6A16_HUMAN | 271 | 275 | PFflC |
| 1775 | Q9GZU2\|PEG3_HUMAN | 1330 | 1334 | PFyeC |
| 1776 | Q9GZZ0\|HXD1_HUMAN | 162 | 166 | PFpaC |
| 1777 | Q9H0A6\|RNF32_HUMAN | 344 | 348 | PFhaC |
| 1778 | Q9H0B3\|K1683_HUMAN | 326 | 330 | PFqiC |
| 1779 | Q9H267\|VP33B_HUMAN | 189 | 193 | PFpnC |
| 1780 | Q9H2J1\|CI037_HUMAN | 102 | 106 | PFekC |
| 1781 | Q9H3H5\|GPT_HUMAN | 77 | 81 | PFlnC |
| 1782 | Q9H8V3\|ECT2_HUMAN | 239 | 243 | PFqdC |
| 1783 | Q9H9S0\|NANOG_HUMAN | 239 | 243 | PFynC |
| 1784 | Q9H9V4\|RN122_HUMAN | 3 | 7 | PFqwC |
| 1785 | Q9HAQ2\|KIF9_HUMAN | 291 | 295 | PFrqC |
| 1786 | Q9HAW7\|UD17_HUMAN | 149 | 153 | PFdaC |
| 1787 | Q9HAW8\|UD110_HUMAN | 149 | 153 | PFdtC |
| 1788 | Q9HAW9\|UD18_HUMAN | 149 | 153 | PFdaC |
| 1789 | Q9HBX8\|LGR6_HUMAN | 412 | 416 | PFkpC |
| 1790 | Q9NQW8\|CNGB3_HUMAN | 309 | 313 | PFdiC |
| 1791 | Q9NRZ9\|HELLS_HUMAN | 273 | 277 | PFlvC |
| 1792 | Q9NTG7\|SIRT3_HUMAN | 30 | 34 | PFqaC |
| 1793 | Q9NWZ5\|UCKL1_HUMAN | 370 | 374 | PFqdC |
| 1794 | Q9NY30\|BTG4_HUMAN | 98 | 102 | PFevC |
| 1795 | Q9NYM4\|GPR83_HUMAN | 342 | 346 | PFiyC |
| 1796 | Q9NYV6\|RRN3_HUMAN | 561 | 565 | PFdpC |
| 1797 | Q9NYW1\|TA2R9_HUMAN | 190 | 194 | PFilC |
| 1798 | Q9NYW3\|TA2R7_HUMAN | 193 | 197 | PFcvC |
| 1799 | Q9NZ56\|FMN2_HUMAN | 716 | 720 | PFsdC |
| 1800 | Q9NZ71\|RTEL1_HUMAN | 495 | 499 | PFpvC |
| 1801 | Q9NZD2\|GLTP_HUMAN | 31 | 35 | PFfdC |
| 1802 | Q9P2N4\|ATS9_HUMAN | 596 | 600 | PFgtC |
| 1803 | Q9UBR1\|BUP1_HUMAN | 124 | 128 | PFafC |
| 1804 | Q9UBS0\|KS6B2_HUMAN | 344 | 348 | PFrpC |
| 1805 | Q9UET6\|RRMJ1_HUMAN | 234 | 238 | PFvtC |
| 1806 | Q9UHD4\|CIDEB_HUMAN | 37 | 41 | PFrvC |
| 1807 | Q9UKA4\|AKA11_HUMAN | 917 | 921 | PFshC |
| 1808 | Q9ULC3\|RAB23_HUMAN | 230 | 234 | PFssC |
| 1809 | Q9ULJ3\|ZN295_HUMAN | 125 | 129 | PFptC |
| 1810 | Q9ULK4\|CRSP3_HUMAN | 1086 | 1090 | PFpnC |
| 1811 | Q9ULL4\|PLXB3_HUMAN | 24 | 28 | PFglC |
| 1812 | Q9ULV8\|CBLC_HUMAN | 387 | 391 | PFcrC |
| 1813 | Q9UM47\|NOTC3_HUMAN | 1357 | 1361 | PFfrC |
| 1814 | Q9UNQ2\|DIMT1_HUMAN | 146 | 150 | PFfrC |
| 1815 | Q9Y3D5\|RT18C_HUMAN | 86 | 90 | PFtgC |
| 1816 | Q9Y3F1\|TA6P_HUMAN | 25 | 29 | PFpsC |
| 1817 | Q9Y3R5\|CU005_HUMAN | 255 | 259 | PFytC |
| 1818 | Q9Y450\|HBS1L_HUMAN | 487 | 491 | PFrlC |
| 1819 | Q9Y493\|ZAN_HUMAN | 1364 | 1368 | PFetC |
| 1820 | Q9Y493\|ZAN_HUMAN | 1751 | 1755 | PFsqC |
| 1821 | Q9Y493\|ZAN_HUMAN | 2556 | 2560 | PFaaC |
| 1822 | Q9Y548\|YIPF1_HUMAN | 123 | 127 | PFwiC |
| 1823 | Q9Y5L3\|ENP2_HUMAN | 324 | 328 | PFsrC |
| 1824 | Q9Y5P8\|2ACC_HUMAN | 272 | 276 | PFqdC |
| 1825 | Q9Y664\|KPTN_HUMAN | 143 | 147 | PFqlC |
| 1826 | Q9Y678\|COPG_HUMAN | 226 | 230 | PFayC |
| 1827 | Q9Y6E0\|STK24_HUMAN | 371 | 375 | PFsqC |
| 1828 | Q9Y6R7\|FCGBP_HUMAN | 683 | 687 | PFavC |
| 1829 | Q9Y6R7\|FCGBP_HUMAN | 1074 | 1078 | PFreC |
| 1830 | Q9Y6R7\|FCGBP_HUMAN | 1888 | 1892 | PFttC |
| 1831 | Q9Y6R7\|FCGBP_HUMAN | 3089 | 3093 | PFttC |
| 1832 | Q9Y6R7\|FCGBP_HUMAN | 4290 | 4294 | PFttC |
| 1833 | Q9Y6R7\|FCGBP_HUMAN | 5059 | 5063 | PFatC |

Figure 9:
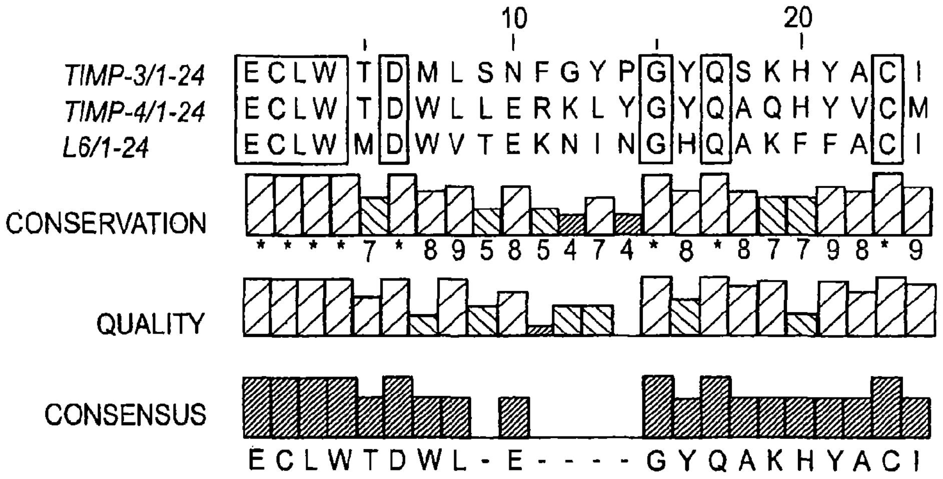
FIG. 9 shows a set of amino acid sequences that include in shading a common motif that occurs in all the predicted anti-angiogenic fragments derived from TIMPs (SEQ ID NOS 2429-2431, respectively, in order of appearance).

Finally the motifs that are found within the predicted peptides that are derived from tissue inhibitors of metalloproteinases were calculated. Because of the small number of peptides present in the peptide pool the loop-6 fragment of TIMP-2 was also included in the calculation. This loop is known to have anti-angiogenic activity. For this case the common motif among the peptide sequences is the E-C-L-W-X-D-X8-G-X-Y-X5-C (SEQ ID NO: 2319) as shown in the FIG. 9.

Example 5

Novel Peptides from the Somatotropin and Serpin Protein Families

Growth Hormone (GH) and prolactin proteins contain a somatotropin conserved domain. Pigment epithelium derived factor (PEDF) contains a serpin conserved domain. There are a number of short peptides, smaller than 25 amino acids, from these two protein families that can be used to identify sequences having similarity to these peptides within the human proteome. Such peptides include the recently identified short fragments of GH and prolactin (Nguyen et al., (2006) *Proc Natl Acad Sci USA* 103, 14319-14324), and short fragments of PEDF (Filleur et al., (2005) *Cancer Res* 65, 5144-5152).

Figure 10A:
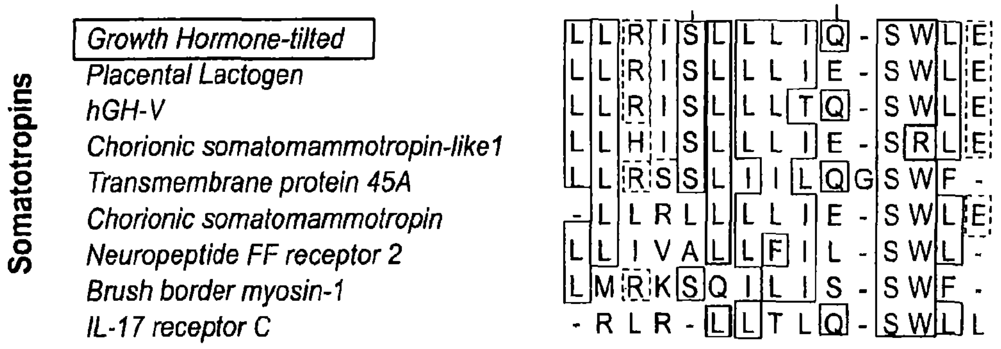
FIGS. 10A and 10B show the amino acid sequences of eleven novel anti-angiogenic peptides. Sequences in FIG. 10A are from the somatotropin family (SEQ ID NOS 2433, 2291-2292, 2295, 2434, 2294, 2298-2299 and 2297, respectively, in order of appearance) and those in FIG. 10B are from the serpin family (SEQ ID NOS 2302-2303, 2435 and 2301, respectively, in order of appearance & 'DEAH' disclosed as SEQ ID NO: 2300).
Figure 10B:
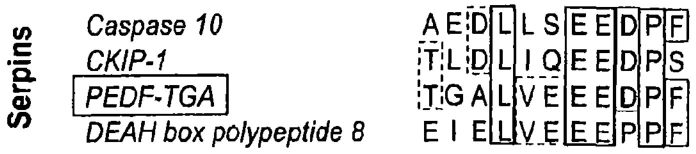

After searching within the human proteome for similar sequences to those of the short peptides and filtering the results for only the statistically significant similarities using a Monte Carlo algorithm eleven novel similar peptides were identified, eight similar to the short fragment derived from growth hormone (FIG. 10A) and three from the short fragment of PEDF (FIG. 10B). These sequences are also included in Tables 7A and 7B.

TABLE 7A

Table of the amino acid sequences of the peptides predicted similar to Growth Hormone

| Protein Name | Peptide Location | Peptide sequence |
|---|---|---|
| Placental Lactogen | AAA98621 (101-114) | LLRISLLLIESWLE (SEQ ID NO: 2291) |
| hGH-V | AAB59548 (101-114) | LLRISLLLTQSWLE (SEQ ID NO: 2292) |
| GH2 | CAG46722 (101-114) | LLHISLLLIQSWLE (SEQ ID NO: 2293) |
| Chorionic somatomammotropin | AAA52116 (101-113) | LLRLLLLIESWLE (SEQ ID NO: 2294) |
| Chorionic somatomammotropin hormone-like 1 | AAI19748 (12-25) | LLHISLLLIESRLE (SEQ ID NO: 2295) |
| Transmembrane protein 45A | NP_060474 (181-194) | LLRSSLILLQGSWF (SEQ ID NO: 2296) |
| IL-17 receptor C | Q8NAC3 (376-387) | RLRLLTLQSWLL (SEQ ID NO: 2297) |
| Neuropeptide FF receptor 2 | Q9Y5X5 (378-390) | LLIVALLFILSWL (SEQ ID NO: 2298) |
| Brush border myosin-I | AAC27437 (719-731) | LMRKSQILIS SWF (SEQ ID NO: 2299) |

TABLE 7B

Table of the amino acid sequences of the peptides predicted similar to PEDF.

| Protein Name | Peptide Location | Peptide sequence |
|---|---|---|
| DEAH | | (SEQ ID NO: 2300) |
| box polypeptide 8 | AAH47327 (438-448) | EIELVEEEPPF (SEQ ID NO: 2301) |
| Caspase 10 | CAD32371(67-77) | AEDLLSEEDPF (SEQ ID NO: 2302) |
| CKIP-1 | CAI14263(66-76) | TLDLIQEEDPS (SEQ ID NO: 2303) |

Example 7

Identification of Motifs within the Somatotropin Derived Peptides

Figure 11:
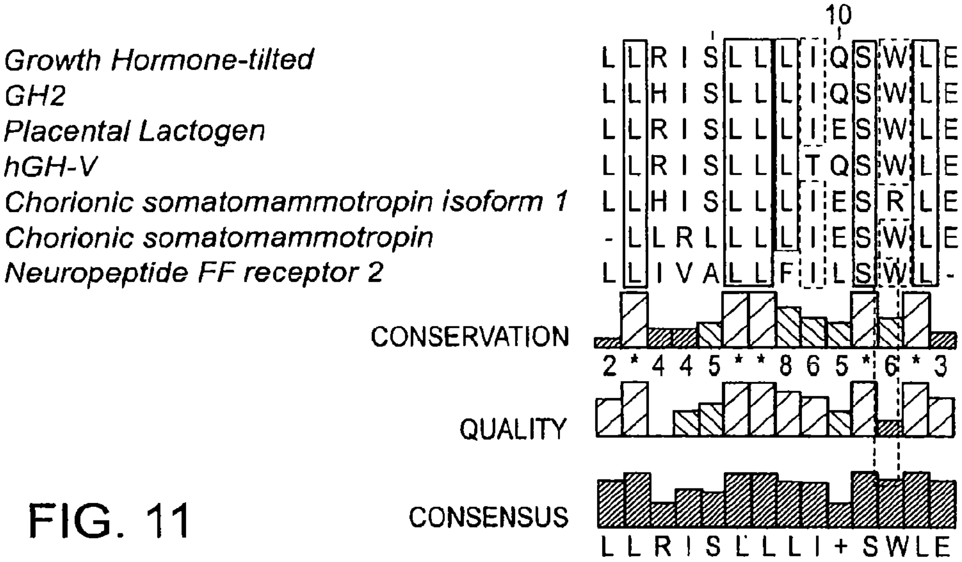
FIG. 11 shows a set of amino acid sequences that include in shading a motif identified within the similarity hits of the Growth Hormone derived anti-angiogenic peptide (SEQ ID NOS 2433, 2293, 2291-2292, 2295, 2294 and 2298, respectively, in order of appearance).

By performing multiple sequence alignment to the sequences of the predicted peptides we can investigate the conservation of specific motifs that are common in most of the sequences. Multiple sequence alignment is performed using the ClustalW algorithm. In order to identify a more robust motif within the peptide sequences, in the case of the somatotropin derived peptides, the lowest similarity hits can be excluded to identify the common amino acids. This process identifies the somatotropin common motif: L-X(3)-L-L-X(3)-S-X-L (SEQ ID NO: 2289) (FIG. 11).

In order to identify the existence of this motif in other protein sequences in the human proteome, the ScanProsite tool was used to search the Prosite database at the Swiss Institute of Bioinformatics. Using the aforementioned motif as a query this motif was identified in 139 locations of 139 different proteins listed in Table 8 (SEQ ID Nos: 1834-1972).

TABLE 8

Amino acid sequences of peptides that contain the somatotropin motif.
Somatotropins
Motif: L-X(3)-L-L-X(3)-S-X-L (SEQ ID NO: 2289)
Number of Locations: 139
Number of Different Proteins: 139

| # | Accession Number\|Protein Name | First Amino acid | Last Amino acid | Sequence |
|---|---|---|---|---|
| 1834 | O14569\|C56D2_HUMAN | 164 | 175 | LvgyLLgsaSlL |
| 1835 | O15287\|FANCG_HUMAN | 416 | 427 | LceeLLsrtSsL |
| 1836 | O15482\|TEX28_HUMAN | 338 | 349 | LatvLLvfvStL |
| 1837 | O43914\|TYOBP_HUMAN | 11 | 22 | LllpLLlavSgL |
| 1838 | O60609\|GFRA3_HUMAN | 15 | 26 | LmllLLlppSpL |
| 1839 | O75844\|FACE1_HUMAN | 279 | 290 | LfdtLLeeySvL |
| 1840 | O95747\|OXSR1_HUMAN | 90 | 101 | LvmkLLsggSvL |
| 1841 | P01241\|SOMA_HUMAN | 102 | 113 | LrisLLliqSwL |
| 1842 | P01242\|SOM2_HUMAN | 102 | 113 | LrisLLliqSwL |
| 1843 | P01243\|CSH_HUMAN | 102 | 113 | LrisLLlieSwL |
| 1844 | P02750\|A2GL_HUMAN | 83 | 94 | LpanLLqgaSkL |
| 1845 | P03891\|NU2M_HUMAN | 149 | 160 | LnvsLLltlSiL |
| 1846 | P04201\|MAS_HUMAN | 151 | 162 | LvcaLLwalScL |
| 1847 | P05783\|K1C18_HUMAN | 338 | 349 | LngiLLhleSeL |
| 1848 | P07359\|GP1BA_HUMAN | 3 | 14 | LlllLLllpSpL |
| 1849 | P09848\|LPH_HUMAN | 35 | 46 | LtndLLhnlSgL |
| 1850 | P11168\|GTR2_HUMAN | 136 | 147 | LvgaLLmgfSkL |
| 1851 | P12034\|FGF5_HUMAN | 3 | 14 | LsflLLlffShL |
| 1852 | P13489\|RINI_HUMAN | 247 | 258 | LcpgLLhpsSrL |
| 1853 | P14902\|I23O_HUMAN | 196 | 207 | LlkaLLeiaScL |
| 1854 | P16278\|BGAL_HUMAN | 135 | 146 | LpawLLekeSiL |

TABLE 8-continued

Amino acid sequences of peptides that contain the somatotropin motif.
Somatotropins
Motif: L-X(3)-L-L-X(3)-S-X-L (SEQ ID NO: 2289)
Number of Locations: 139
Number of Different Proteins: 139

| # | Accession Number\|Protein Name | First Amino acid | Last Amino acid | Sequence |
|---|---|---|---|---|
| 1855 | P19838\|NFKB1_HUMAN | 558 | 569 | LvrdLLevtSgL |
| 1856 | P22079\|PERL_HUMAN | 512 | 523 | LvrgLLakkSkL |
| 1857 | P23276\|KELL_HUMAN | 53 | 64 | LilgLLlcfSvL |
| 1858 | P24394\|IL4RA_HUMAN | 4 | 15 | LcsgLLfpvScL |
| 1859 | P29320\|EPHA3_HUMAN | 5 | 16 | LsilLLlscSvL |
| 1860 | P31512\|FMO4_HUMAN | 524 | 535 | LaslLLickSsL |
| 1861 | P35270\|SPRE_HUMAN | 26 | 37 | LlasLLspgSvL |
| 1862 | P41250\|SYG_HUMAN | 20 | 31 | LpprLLarpSlL |
| 1863 | P42575\|CASP2_HUMAN | 114 | 125 | LedmLLttlSgL |
| 1864 | P46721\|SO1A2_HUMAN | 396 | 407 | LleyLLyflSfL |
| 1865 | P51665\|PSD7_HUMAN | 201 | 212 | LnskLLdirSyL |
| 1866 | P59531\|T2R12_HUMAN | 188 | 199 | LisfLLsliSlL |
| 1867 | P69849\|NOMO3_HUMAN | 1180 | 1191 | LiplLLqltSrL |
| 1868 | P98161\|PKD1_HUMAN | 82 | 93 | LdvgLLanlSaL |
| 1869 | P98171\|RHG04_HUMAN | 153 | 164 | LqdeLLevvSeL |
| 1870 | P98196\|AT11A_HUMAN | 1077 | 1088 | LaivLLvtiSlL |
| 1871 | Q08431\|MFGM_HUMAN | 10 | 21 | LcgaLLcapSlL |
| 1872 | Q08AF3\|SLFN5_HUMAN | 533 | 544 | LvivLLgfkSfL |
| 1873 | Q12952\|FOXL1_HUMAN | 293 | 304 | LgasLLaasSsL |
| 1874 | Q13275\|SEM3F_HUMAN | 2 | 13 | LvagLLlwaSlL |
| 1875 | Q13394\|MB211_HUMAN | 300 | 311 | LngiLLqliScL |
| 1876 | Q13609\|DNSL3_HUMAN | 8 | 19 | LlllLLsihSaL |
| 1877 | Q13619\|CUL4A_HUMAN | 213 | 224 | LlrsLLgmlSdL |
| 1878 | Q13620\|CUL4B_HUMAN | 349 | 360 | LlrsLLsmlSdL |
| 1879 | Q14406\|CSHL_HUMAN | 84 | 95 | LhisLLlieSrL |
| 1880 | Q14667\|K0100_HUMAN | 8 | 19 | LlvlLLvalSaL |
| 1881 | Q15155\|NOMO1_HUMAN | 1180 | 1191 | LiplLLqltSrL |
| 1882 | Q15760\|GPR19_HUMAN | 279 | 290 | LilnLLfllSwL |
| 1883 | Q53RE8\|ANR39_HUMAN | 166 | 177 | LacdLLpcnSdL |
| 1884 | Q5FWE3\|PRRT3_HUMAN | 586 | 597 | LatdLLstwSvL |
| 1885 | Q5GH73\|XKR6_HUMAN | 630 | 641 | LlyeLLqyeSsL |
| 1886 | Q5GH77\|XKR3_HUMAN | 194 | 205 | LnraLLmtfSlL |
| 1887 | Q5JPE7\|NOMO2_HUMAN | 1180 | 1191 | LiplLLqltSrL |
| 1888 | Q5JWR5\|DOP1_HUMAN | 506 | 517 | LpqlLLrmiSaL |
| 1889 | Q5UIP0\|RIF1_HUMAN | 2413 | 2424 | LsknLLaqiSaL |
| 1890 | Q5VTE6\|ANGE2_HUMAN | 175 | 186 | LsqdLLednShL |
| 1891 | Q5VU43\|MYOME_HUMAN | 1932 | 1943 | LreaLLssrShL |
| 1892 | Q5VYK3\|ECM29_HUMAN | 1296 | 1307 | LipaLLeslSvL |
| 1893 | Q68D06\|SLN13_HUMAN | 554 | 565 | LvivLLgfrSlL |
| 1894 | Q6GYQ0\|GRIPE_HUMAN | 641 | 652 | LwddLLsvlSsL |
| 1895 | Q6NTF9\|RHBD2_HUMAN | 166 | 177 | LvpwLLlgaSwL |
| 1896 | Q6ZMH5\|S39A5_HUMAN | 217 | 228 | LavlLLslpSpL |
| 1897 | Q6ZMZ3\|SYNE3_HUMAN | 532 | 543 | LhnsLLqrkSkL |
| 1898 | Q6ZVD8\|PHLPL_HUMAN | 313 | 324 | LfpiLLceiStL |
| 1899 | Q6ZVE7\|GOT1A_HUMAN | 23 | 34 | LfgtLLyfdSvL |
| 1900 | Q70J99\|UN13D_HUMAN | 927 | 938 | LrveLLsasSlL |
| 1901 | Q7Z3Z4\|PIWL4_HUMAN | 139 | 150 | LriaLLyshSeL |
| 1902 | Q7Z6Z7\|HUWE1_HUMAN | 841 | 852 | LqegLLqldSiL |
| 1903 | Q7Z7L1\|SLN11_HUMAN | 554 | 565 | LvivLLgfrSlL |
| 1904 | Q86SM5\|MRGRG_HUMAN | 223 | 234 | LlnfLLpvfSpL |
| 1905 | Q86U44\|MTA70_HUMAN | 78 | 89 | LekkLLhhlSdL |
| 1906 | Q86UQ4\|ABCAD_HUMAN | 3182 | 3193 | LlnsLLdivSsL |
| 1907 | Q86WI3\|NLRC5_HUMAN | 1485 | 1496 | LlqsLLlslSeL |
| 1908 | Q86YC3\|LRC33_HUMAN | 263 | 274 | LffpLLpqySkL |
| 1909 | Q8IYK4\|GT252_HUMAN | 9 | 20 | LawsLLllsSaL |
| 1910 | Q8IYS0\|GRM1C_HUMAN | 485 | 496 | LesdLLieeSvL |
| 1911 | Q8IZL8\|PELP1_HUMAN | 33 | 44 | LrllLLesvSgL |
| 1912 | Q8IZY2\|ABCA7_HUMAN | 1746 | 1757 | LftlLLqhrSqL |
| 1913 | Q8N0X7\|SPG20_HUMAN | 322 | 333 | LfedLLrqmSdL |
| 1914 | Q8N6M3\|CT142_HUMAN | 33 | 44 | LagsLLkelSpL |
| 1915 | Q8N816\|TMM99_HUMAN | 96 | 107 | LlpcLLgvgSwL |
| 1916 | Q8NBM4\|PDHL1_HUMAN | 15 | 26 | LsksLLlvpSaL |
| 1917 | Q8NCG7\|DGLB_HUMAN | 555 | 566 | LtqpLLgeqSlL |
| 1918 | Q8NFR9\|I17RE_HUMAN | 80 | 91 | LcqhLLsggSgL |
| 1919 | Q8NGE3\|O10P1_HUMAN | 9 | 20 | LpefLLlgfSdL |
| 1920 | Q8TCV5\|WFDC5_HUMAN | 8 | 19 | LlgaLLavgSqL |
| 1921 | Q8TDL5\|LPLC1_HUMAN | 165 | 176 | LriqLLhklSfL |
| 1922 | Q8TE82\|S3TC1_HUMAN | 1025 | 1036 | LegqLLetiSqL |
| 1923 | Q8TEQ8\|PIGO_HUMAN | 857 | 868 | LvflLLflqSfL |

TABLE 8-continued

Amino acid sequences of peptides that contain the somatotropin motif.
Somatotropins
Motif: L-X(3)-L-L-X(3)-S-X-L (SEQ ID NO: 2289)
Number of Locations: 139
Number of Different Proteins: 139

| # | Accession Number\|Protein Name | First Amino acid | Last Amino acid | Sequence |
|---|---|---|---|---|
| 1924 | Q8TEZ7\|MPRB__HUMAN | 127 | 138 | LlahLLqskSeL |
| 1925 | Q8WWN8\|CEND3__HUMAN | 1481 | 1492 | LeeqLLqelSsL |
| 1926 | Q8WZ84\|OR8D1__HUMAN | 43 | 54 | LgmiLLiavSpL |
| 1927 | Q92535\|PIGC__HUMAN | 253 | 264 | LfalLLmsiScL |
| 1928 | Q92538\|GBF1__HUMAN | 1224 | 1235 | LrilLLmkpSvL |
| 1929 | Q92743\|HTRA1__HUMAN | 262 | 273 | LpvlLLgrsSeL |
| 1930 | Q92935\|EXTL1__HUMAN | 19 | 30 | LllvLLggfSlL |
| 1931 | Q93074\|MED12__HUMAN | 401 | 412 | LqtiLLccpSaL |
| 1932 | Q96DN6\|MBD6__HUMAN | 740 | 751 | LgasLLgdlSsL |
| 1933 | Q96GR4\|ZDH12__HUMAN | 48 | 59 | LtflLLvlgSlL |
| 1934 | Q96HP8\|T176A__HUMAN | 29 | 40 | LaklLLtccSaL |
| 1935 | Q96K12\|FACR2__HUMAN | 380 | 391 | LmnrLLrtvSmL |
| 1936 | Q96KP1\|EXOC2__HUMAN | 339 | 350 | LldkLLetpStL |
| 1937 | Q96MX0\|CKLF3__HUMAN | 40 | 51 | LkgrLLlaeSgL |
| 1938 | Q96Q45\|AL2S4__HUMAN | 387 | 398 | LvvaLLvglSwL |
| 1939 | Q96QZ0\|PANX3__HUMAN | 136 | 147 | LssdLLfiiSeL |
| 1940 | Q96RQ9\|OXLA__HUMAN | 269 | 280 | LpraLLsslSgL |
| 1941 | Q9BY08\|EBPL__HUMAN | 178 | 189 | LipgLLlwqSwL |
| 1942 | Q9BZ97\|TTY13__HUMAN | 30 | 41 | LclmLLlagScL |
| 1943 | Q9H1Y0\|ATG5__HUMAN | 85 | 96 | LlfdLLassSaL |
| 1944 | Q9H254\|SPTN4__HUMAN | 1422 | 1433 | LdkkLLhmeSqL |
| 1945 | Q9H330\|CI005__HUMAN | 430 | 441 | LgkfLLkvdSkL |
| 1946 | Q9H4I8\|SEHL2__HUMAN | 175 | 186 | LlqrLLksnShL |
| 1947 | Q9HCN3\|TMEM8__HUMAN | 200 | 211 | LpqtLLshpSyL |
| 1948 | Q9NQ34\|TMM9B__HUMAN | 4 | 15 | LwggLLrlgSlL |
| 1949 | Q9NR09\|BIRC6__HUMAN | 1400 | 1411 | LlkaLLdnmSfL |
| 1950 | Q9NRA0\|SPHK2__HUMAN | 296 | 307 | LgldLLlncSlL |
| 1951 | Q9NRU3\|CNNM1__HUMAN | 156 | 167 | LgalLLlalSaL |
| 1952 | Q9NTT1\|U2D3L__HUMAN | 99 | 110 | LskvLLsicSlL |
| 1953 | Q9NVH2\|INT7__HUMAN | 623 | 634 | LridLLqafSqL |
| 1954 | Q9NVM9\|CL011__HUMAN | 350 | 361 | LtnfLLngrSvL |
| 1955 | Q9NZD1\|GPC5D__HUMAN | 60 | 71 | LptqLLflSvL |
| 1956 | Q9P2E9\|RRBP1__HUMAN | 1226 | 1237 | LrqlLLesqSqL |
| 1957 | Q9P2G4\|K1383__HUMAN | 397 | 408 | LlnaLLvelSlL |
| 1958 | Q9P2V4\|LRIT1__HUMAN | 541 | 552 | LpltLLvccSaL |
| 1959 | Q9UDY8\|MALT1__HUMAN | 33 | 44 | LrepLLrrlSeL |
| 1960 | Q9UEW8\|STK39__HUMAN | 138 | 149 | LvmkLLsggSmL |
| 1961 | Q9UGN4\|CM35H__HUMAN | 188 | 199 | LlllLLvgaSlL |
| 1962 | Q9UHD4\|CIDEB__HUMAN | 189 | 200 | LghmLLgisStL |
| 1963 | Q9UIG8\|SO3A1__HUMAN | 270 | 281 | LcgaLLffsSlL |
| 1964 | Q9UPA5\|BSN__HUMAN | 353 | 364 | LgasLLtqaStL |
| 1965 | Q9UPX8\|SHAN2__HUMAN | 609 | 620 | LtgrLLdpsSpL |
| 1966 | Q9Y239\|NOD1__HUMAN | 318 | 329 | LsgkLLkgaSkL |
| 1967 | Q9Y2I2\|NTNG1__HUMAN | 526 | 537 | LlttLLgtaSpL |
| 1968 | Q9Y2U2\|KCNK7__HUMAN | 92 | 103 | LpsaLLfaaSiL |
| 1969 | Q9Y2Y8\|PRG3__HUMAN | 7 | 18 | LpflLLgtvSaL |
| 1970 | Q9Y586\|MB212__HUMAN | 300 | 311 | LngiLLqliScL |
| 1971 | Q9Y5X0\|SNX10__HUMAN | 106 | 117 | LqnaLLlsdSsL |
| 1972 | Q9Y5X5\|NPFF2__HUMAN | 379 | 390 | LivaLLfilSwL |

Example 8

Identification of Motifs within the Serpin Derived Peptides

Figure 12:
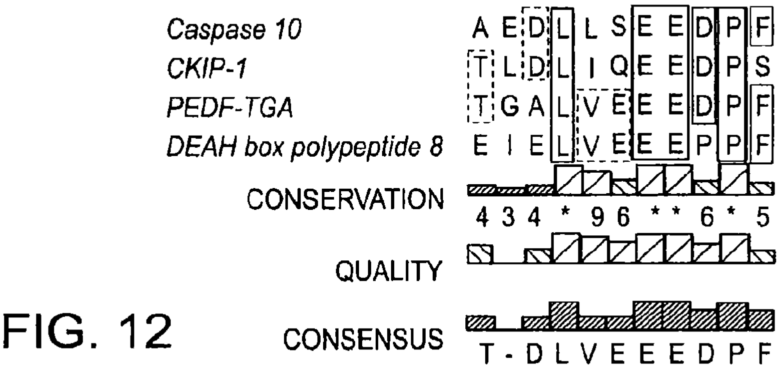
FIG. 12 shows a set of amino acid sequences that include in shading a motif identified within the similarity hits of the PEDF derived short anti-angiogenic peptide (SEQ ID NOS 2302-2303, 2435 and 2301, respectively, in order of appearance & 'DEAH' disclosed as SEQ ID NO: 2300).

The L-X(2)-E-E-X-P (SEQ ID NO: 2290) motif of serpin derived peptides identified the sequences of peptides shown in FIG. 12. Using the ScanProsite tool 314 hits in 302 different proteins were identified. The hits are shown in Table 9 (SEQ ID Nos: 1973-2286).

TABLE 9

Table of the amino acid sequences of the peptides identified to contain the serpin motif.
Serpins
Motif: L-X(2)-E-E-X-P (SEQ ID NO: 2290)
Number of Locations: 314
Number of Different Proteins: 302

| # | Accession Number\|Protein Name | First Amino acid | Last Amino acid | Sequence |
|---|---|---|---|---|
| 1973 | O00160\|MYO1F__HUMAN | 744 | 751 | LglEErPe |
| 1974 | O00507\|USP9Y__HUMAN | 2474 | 2481 | LcpEEePd |
| 1975 | O00625\|PIR__HUMAN | 134 | 141 | LksEEiPk |
| 1976 | O14641\|DVL2__HUMAN | 20 | 27 | LdeEEtPy |
| 1977 | O14686\|MLL2__HUMAN | 2819 | 2826 | LgpEErPp |
| 1978 | O14709\|ZN197__HUMAN | 193 | 200 | LsqEEnPr |
| 1979 | O14795\|UN13B__HUMAN | 1499 | 1506 | LgnEEgPe |
| 1980 | O15013\|ARHGA__HUMAN | 199 | 206 | LssEEpPt |
| 1981 | O15055\|PER2__HUMAN | 994 | 1001 | LqlEEaPe |
| 1982 | O15528\|CP27B__HUMAN | 297 | 304 | LfrEElPa |
| 1983 | O15534\|PER1__HUMAN | 987 | 994 | LqlEElPr |
| 1984 | O43390\|HNRPR__HUMAN | 12 | 19 | LkeEEePm |
| 1985 | O60216\|RAD21__HUMAN | 504 | 511 | LppEEpPn |
| 1986 | O60237\|MYPT2__HUMAN | 339 | 346 | LyeEEtPk |
| 1987 | O60346\|PHLPP__HUMAN | 483 | 490 | LeaEEkPl |
| 1988 | O60779\|S19A2__HUMAN | 259 | 266 | LnmEEpPv |
| 1989 | O60885\|BRD4__HUMAN | 913 | 920 | LedEEpPa |
| 1990 | O75128\|COBL__HUMAN | 1064 | 1071 | LerEEkPs |
| 1991 | O75420\|PERQ1__HUMAN | 334 | 341 | LeeEEePs |
| 1992 | O75787\|RENR__HUMAN | 116 | 123 | LfsEEtPv |
| 1993 | O75914\|PAK3__HUMAN | 5 | 12 | LdnEEkPp |
| 1994 | O94933\|SLIK3__HUMAN | 227 | 234 | LqlEEnPw |
| 1995 | O94966\|UBP19__HUMAN | 1251 | 1258 | LeaEEePv |
| 1996 | O94986\|CE152__HUMAN | 847 | 854 | LknEEvPv |
| 1997 | O94991\|SLIK5__HUMAN | 230 | 237 | LqlEEnPw |
| 1998 | O95153\|RIMB1__HUMAN | 915 | 922 | LngEEcPp |
| 1999 | O95279\|KCNK5__HUMAN | 443 | 450 | LagEEsPq |
| 2000 | O95712\|PA24B__HUMAN | 772 | 779 | LkiEEpPs |
| 2001 | O95881\|TXD12__HUMAN | 94 | 101 | LedEEePk |
| 2002 | O96018\|APBA3__HUMAN | 116 | 123 | LhcEEcPp |
| 2003 | O96024\|B3GT4__HUMAN | 217 | 224 | LhsEEvPl |
| 2004 | P04275\|VWF__HUMAN | 1012 | 1019 | LqvEEdPv |
| 2005 | P05160\|F13B__HUMAN | 18 | 25 | LyaEEkPc |
| 2006 | P06858\|LIPL__HUMAN | 279 | 286 | LlnEEnPs |
| 2007 | P07237\|PDIA1__HUMAN | 307 | 314 | LkkEEcPa |
| 2008 | P07949\|RET__HUMAN | 1033 | 1040 | LseEEtPl |
| 2009 | P08519\|APOA__HUMAN | 3880 | 3887 | LpsEEaPt |
| 2010 | P09769\|FGR__HUMAN | 497 | 504 | LdpEErPt |
| 2011 | P10745\|IRBP__HUMAN | 708 | 715 | LvvEEaPp |
| 2012 | P11532\|DMD__HUMAN | 2255 | 2262 | LlvEElPl |
| 2013 | P14317\|HCLS1__HUMAN | 352 | 359 | LqvEEePv |
| 2014 | P16150\|LEUK__HUMAN | 369 | 376 | LkgEEePl |
| 2015 | P17025\|ZN182__HUMAN | 79 | 86 | LevEEcPa |
| 2016 | P17600\|SYN1__HUMAN | 239 | 246 | LgtEEfPl |
| 2017 | P18583\|SON__HUMAN | 1149 | 1156 | LppEEpPt |
| 2018 | P18583\|SON__HUMAN | 1160 | 1167 | LppEEpPm |
| 2019 | P18583\|SON__HUMAN | 1171 | 1178 | LppEEpPe |
| 2020 | P19484\|TFEB__HUMAN | 350 | 357 | LpsEEgPg |
| 2021 | P21333\|FLNA__HUMAN | 1034 | 1041 | LprEEgPy |
| 2022 | P21802\|FGFR2__HUMAN | 33 | 40 | LepEEpPt |
| 2023 | P22001\|KCNA3__HUMAN | 152 | 159 | LreEErPl |
| 2024 | P31629\|ZEP2__HUMAN | 772 | 779 | LvsEEsPs |
| 2025 | P34925\|RYK__HUMAN | 578 | 585 | LdpEErPk |
| 2026 | P36955\|PEDF__HUMAN | 39 | 46 | LveEEdPf |
| 2027 | P40189\|IL6RB__HUMAN | 787 | 794 | LdsEErPe |
| 2028 | P42898\|MTHR__HUMAN | 598 | 605 | LyeEEsPs |
| 2029 | P48729\|KC1A__HUMAN | 266 | 273 | LrfEEaPd |
| 2030 | P51512\|MMP16__HUMAN | 165 | 172 | LtfEEvPy |
| 2031 | P52746\|ZN142__HUMAN | 750 | 757 | LgaEEnPl |
| 2032 | P53370\|NUDT6__HUMAN | 284 | 291 | LtvEElPa |
| 2033 | P53801\|PTTG__HUMAN | 167 | 174 | LfkEEnPy |
| 2034 | P53804\|TTC3__HUMAN | 2001 | 2008 | LltEEsPs |
| 2035 | P55285\|CADH6__HUMAN | 116 | 123 | LdrEEkPv |
| 2036 | P55289\|CAD12__HUMAN | 117 | 124 | LdrEEkPf |
| 2037 | P56645\|PER3__HUMAN | 929 | 936 | LlqEEmPr |
| 2038 | P59797\|SELV__HUMAN | 163 | 170 | LlpEEdPe |
| 2039 | Q01826\|SATB1__HUMAN | 409 | 416 | LrkEEdPk |
| 2040 | Q04725\|TLE2__HUMAN | 200 | 207 | LveEErPs |
| 2041 | Q06330\|SUH__HUMAN | 7 | 14 | LpaEEpPa |

TABLE 9-continued

Table of the amino acid sequences of the peptides identified to contain the serpin motif.
Serpins
Motif: L-X(2)-E-E-X-P (SEQ ID NO: 2290)
Number of Locations: 314
Number of Different Proteins: 302

| # | Accession Number\|Protein Name | First Amino acid | Last Amino acid | Sequence |
|---|---|---|---|---|
| 2042 | Q06889\|EGR3_HUMAN | 24 | 31 | LypEEiPs |
| 2043 | Q07157\|ZO1_HUMAN | 1155 | 1162 | LrhEEqPa |
| 2044 | Q13072\|BAGE1_HUMAN | 19 | 26 | LmkEEsPv |
| 2045 | Q13087\|PDIA2_HUMAN | 497 | 504 | LptEEpPe |
| 2046 | Q13255\|GRM1_HUMAN | 995 | 1002 | LtaEEtPl |
| 2047 | Q13315\|ATM_HUMAN | 954 | 961 | LpgEEyPl |
| 2048 | Q13439\|GOGA4_HUMAN | 2092 | 2099 | LeqEEnPg |
| 2049 | Q13596\|SNX1_HUMAN | 265 | 272 | LekEElPr |
| 2050 | Q13634\|CAD18_HUMAN | 446 | 453 | LdrEEtPw |
| 2051 | Q14028\|CNGB1_HUMAN | 137 | 144 | LmaEEnPp |
| 2052 | Q14126\|DSG2_HUMAN | 117 | 124 | LdrEEtPf |
| 2053 | Q14204\|DYHC_HUMAN | 3973 | 3980 | LwsEEtPa |
| 2054 | Q14315\|FLNC_HUMAN | 1738 | 1745 | LphEEePs |
| 2055 | Q14524\|SCN5A_HUMAN | 46 | 53 | LpeEEaPr |
| 2056 | Q14554\|PDIA5_HUMAN | 166 | 173 | LkkEEkPl |
| 2057 | Q14562\|DHX8_HUMAN | 411 | 418 | LskEEfPd |
| 2058 | Q14562\|DHX8_HUMAN | 441 | 448 | LveEEpPf |
| 2059 | Q14573\|ITPR3_HUMAN | 315 | 322 | LaaEEnPs |
| 2060 | Q14674\|ESPL1_HUMAN | 613 | 620 | LspEEtPa |
| 2061 | Q14676\|MDC1_HUMAN | 145 | 152 | LtvEEtPr |
| 2062 | Q14684\|RRP1B_HUMAN | 244 | 251 | LsaEEiPe |
| 2063 | Q15021\|CND1_HUMAN | 1179 | 1186 | LgvEEePf |
| 2064 | Q15735\|PI5PA_HUMAN | 189 | 196 | LasEEqPp |
| 2065 | Q15788\|NCOA1_HUMAN | 982 | 989 | LimEErPn |
| 2066 | Q15878\|CAC1E_HUMAN | 797 | 804 | LnrEEaPt |
| 2067 | Q2TAL6\|VWC2_HUMAN | 179 | 186 | LctEEgPl |
| 2068 | Q32MZ4\|LRRF1_HUMAN | 82 | 89 | LrvEErPe |
| 2069 | Q32P28\|P3H1_HUMAN | 215 | 222 | LysEEqPq |
| 2070 | Q3KNS1\|PTHD3_HUMAN | 96 | 103 | LpeEEtPe |
| 2071 | Q3ZCX4\|ZN568_HUMAN | 100 | 107 | LeqEEePw |
| 2072 | Q495W5\|FUT11_HUMAN | 144 | 151 | LlhEEsPl |
| 2073 | Q52LD8\|RFTN2_HUMAN | 123 | 130 | LviEEcPl |
| 2074 | Q53GL0\|PKHO1_HUMAN | 189 | 196 | LiqEEdPs |
| 2075 | Q53GL0\|PKHO1_HUMAN | 289 | 296 | LraEEpPt |
| 2076 | Q53GL7\|PAR10_HUMAN | 693 | 700 | LeaEEpPd |
| 2077 | Q53H47\|SETMR_HUMAN | 499 | 506 | LdqEEaPk |
| 2078 | Q567U6\|CCD93_HUMAN | 300 | 307 | LsaEEsPe |
| 2079 | Q580R0\|CB027_HUMAN | 41 | 48 | LelEEaPe |
| 2080 | Q587I9\|SFT2C_HUMAN | 136 | 143 | LrcEEaPs |
| 2081 | Q5H9T9\|CN155_HUMAN | 427 | 434 | LlpEEaPr |
| 2082 | Q5H9T9\|CN155_HUMAN | 697 | 704 | LpaEEtPi |
| 2083 | Q5H9T9\|CN155_HUMAN | 736 | 743 | LltEEfPi |
| 2084 | Q5JUK9\|GGED1_HUMAN | 38 | 45 | LqqEEpPi |
| 2085 | Q5JXB2\|UE2NL_HUMAN | 58 | 65 | LlaEEyPm |
| 2086 | Q5MCW4\|ZN569_HUMAN | 60 | 67 | LeqEEePw |
| 2087 | Q5SYB0\|FRPD1_HUMAN | 553 | 560 | LikEEqPp |
| 2088 | Q5THJ4\|VP13D_HUMAN | 2943 | 2950 | LtgEEiPf |
| 2089 | Q5VYS4\|CM033_HUMAN | 293 | 300 | LesEEtPn |
| 2090 | Q5VZP5\|DUS27_HUMAN | 942 | 949 | LrtEEkPp |
| 2091 | Q5VZY2\|PPC1A_HUMAN | 247 | 254 | LkkEErPt |
| 2092 | Q63HR2\|TENC1_HUMAN | 564 | 571 | LddEEqPt |
| 2093 | Q66K74\|MAP1S_HUMAN | 777 | 784 | LgaEEtPp |
| 2094 | Q68CZ1\|FTM_HUMAN | 1181 | 1188 | LpaEEtPv |
| 2095 | Q68DD2\|PA24F_HUMAN | 470 | 477 | LyqEEnPa |
| 2096 | Q6BDS2\|URFB1_HUMAN | 1304 | 1311 | LedEEiPv |
| 2097 | Q6DCA0\|AMERL_HUMAN | 183 | 190 | LtrEElPk |
| 2098 | Q6DN90\|IQEC1_HUMAN | 263 | 270 | LhtEEaPa |
| 2099 | Q6DT37\|MRCKG_HUMAN | 1264 | 1271 | LvpEElPp |
| 2100 | Q6HA08\|ASTL_HUMAN | 62 | 69 | LilEEtPe |
| 2101 | Q6IFS5\|HSN2_HUMAN | 298 | 305 | LnqEElPp |
| 2102 | Q6NUN7\|CK063_HUMAN | 74 | 81 | LdeEEsPr |
| 2103 | Q6P2Q9\|PRP8_HUMAN | 1852 | 1859 | LpvEEqPk |
| 2104 | Q6P5W5\|S39A4_HUMAN | 473 | 480 | LvaEEsPe |
| 2105 | Q6P6B1\|CH047_HUMAN | 249 | 256 | LgkEEqPq |
| 2106 | Q6PD74\|P34_HUMAN | 141 | 148 | LspEElPe |
| 2107 | Q6PI48\|SYDM_HUMAN | 488 | 495 | LpkEEnPr |
| 2108 | Q6PJ61\|FBX46_HUMAN | 246 | 253 | LrkEErPg |
| 2109 | Q6S8J7\|POTE8_HUMAN | 307 | 314 | LtsEEePq |
| 2110 | Q6SZW1\|SARM1_HUMAN | 396 | 403 | LlgEEvPr |
| 2111 | Q6UX39\|AMTN_HUMAN | 114 | 121 | LssEElPq |
| 2112 | Q6ZMY3\|SPOC1_HUMAN | 184 | 191 | LskEEpPg |
| 2113 | Q6ZN11\|ZN793_HUMAN | 60 | 67 | LeqEEaPw |
| 2114 | Q6ZNL6\|FGD5_HUMAN | 382 | 389 | LraEEnPm |
| 2115 | Q6ZV29\|PLPL7_HUMAN | 854 | 861 | LhrEEgPa |
| 2116 | Q70CQ4\|UBP31_HUMAN | 527 | 534 | LpqEEqPl |
| 2117 | Q70SY1\|CR3L2_HUMAN | 153 | 160 | LekEEpPl |
| 2118 | Q7L8C5\|SYT13_HUMAN | 229 | 236 | LaeEElPt |
| 2119 | Q7Z3E5\|ARMC9_HUMAN | 570 | 577 | LnsEElPd |
| 2120 | Q7Z410\|TMPS9_HUMAN | 691 | 698 | LacEEaPg |
| 2121 | Q86SP6\|GP149_HUMAN | 217 | 224 | LcsEEpPr |
| 2122 | Q86V87\|RAI16_HUMAN | 496 | 503 | LdlEEdPy |
| 2123 | Q86VQ0\|CF152_HUMAN | 428 | 435 | LerEEkPe |
| 2124 | Q86W50\|MET10_HUMAN | 454 | 461 | LsqEEnPe |
| 2125 | Q86Y13\|DZIP3_HUMAN | 1192 | 1199 | LlpEEfPg |
| 2126 | Q86Y27\|BAGE5_HUMAN | 19 | 26 | LmkEEsPv |
| 2127 | Q86Y28\|BAGE4_HUMAN | 19 | 26 | LmkEEsPv |
| 2128 | Q86Y29\|BAGE3_HUMAN | 19 | 26 | LmkEEsPv |
| 2129 | Q86Y30\|BAGE2_HUMAN | 19 | 26 | LmkEEsPv |
| 2130 | Q8IU99\|FA26C_HUMAN | 315 | 322 | LgqEEpPl |
| 2131 | Q8IUA0\|WFDC8_HUMAN | 217 | 224 | LqdEEcPl |
| 2132 | Q8IV63\|VRK3_HUMAN | 438 | 445 | LtyEEkPp |
| 2133 | Q8IWY9\|CDAN1_HUMAN | 948 | 955 | LlpEEtPa |
| 2134 | Q8IXI1\|MIRO2_HUMAN | 24 | 31 | LvgEEfPe |
| 2135 | Q8IXI2\|MIRO1_HUMAN | 24 | 31 | LvsEEfPe |
| 2136 | Q8IYS5\|OSCAR_HUMAN | 122 | 129 | LvtEElPr |
| 2137 | Q8IZ26\|ZNF34_HUMAN | 251 | 258 | LhtEEkPy |
| 2138 | Q8IZH2\|XRN1_HUMAN | 1143 | 1150 | LfdEEfPg |
| 2139 | Q8IZP0\|ABI1_HUMAN | 7 | 14 | LleEEiPs |
| 2140 | Q8N201\|INT1_HUMAN | 1587 | 1594 | LlqEEePl |
| 2141 | Q8N309\|LRC43_HUMAN | 373 | 380 | LlvEEsPe |
| 2142 | Q8N3C0\|HELC1_HUMAN | 451 | 458 | LsfEEkPv |
| 2143 | Q8N3C0\|HELC1_HUMAN | 1579 | 1586 | LatEEdPk |
| 2144 | Q8N475\|FSTL5_HUMAN | 786 | 793 | LkaEEwPw |
| 2145 | Q8N4L2\|TM55A_HUMAN | 132 | 139 | LisEEqPa |
| 2146 | Q8N752\|KC1AL_HUMAN | 266 | 273 | LrfEEvPd |
| 2147 | Q8NC74\|CT151_HUMAN | 178 | 185 | LrgEEkPa |
| 2148 | Q8NE71\|ABCF1_HUMAN | 701 | 708 | LrmEEtPt |
| 2149 | Q8NEG5\|ZSWM2_HUMAN | 43 | 50 | LlrEEePe |
| 2150 | Q8NEM7\|FA48A_HUMAN | 115 | 122 | LdaEElPp |
| 2151 | Q8NEZ4\|MLL3_HUMAN | 3046 | 3053 | LllEEqPl |
| 2152 | Q8NEZ4\|MLL3_HUMAN | 4023 | 4030 | LvkEEpPe |
| 2153 | Q8NFM7\|I17RD_HUMAN | 702 | 709 | LgeEEpPa |
| 2154 | Q8NFP4\|MDGA1_HUMAN | 489 | 496 | LplEEtPd |
| 2155 | Q8NHJ6\|LIRB4_HUMAN | 60 | 67 | LdkEEsPa |
| 2156 | Q8NI51\|BORIS_HUMAN | 120 | 127 | LwlEEgPr |
| 2157 | Q8TBH0\|ARRD2_HUMAN | 387 | 394 | LysEEdPn |
| 2158 | Q8TDX9\|PK1L1_HUMAN | 1101 | 1108 | LsaEEsPg |
| 2159 | Q8TE68\|ES8L1_HUMAN | 408 | 415 | LspEEgPp |
| 2160 | Q8TER0\|SNED1_HUMAN | 1083 | 1090 | LrgEEhPt |
| 2161 | Q8WU49\|CG033_HUMAN | 8 | 15 | LslEEcPw |
| 2162 | Q8WUA2\|PPIL4_HUMAN | 16 | 23 | LytEErPr |
| 2163 | Q8WUI4\|HDAC7_HUMAN | 943 | 950 | LveEEePm |
| 2164 | Q8WWN8\|CEND3_HUMAN | 1456 | 1463 | LgqEErPp |
| 2165 | Q8WZ42\|TITIN_HUMAN | 12132 | 12139 | LvvEElPv |
| 2166 | Q8WZ42\|TITIN_HUMAN | 13832 | 13839 | LfvEEiPv |
| 2167 | Q92538\|GBF1_HUMAN | 1062 | 1069 | LqrEEtPs |
| 2168 | Q92738\|US6NL_HUMAN | 51 | 58 | LheEElPd |
| 2169 | Q92765\|SFRP3_HUMAN | 134 | 141 | LacEElPv |
| 2170 | Q92851\|CASPA_HUMAN | 70 | 77 | LlsEEdPf |
| 2171 | Q92888\|ARHG1_HUMAN | 390 | 397 | LepEEpPg |
| 2172 | Q93008\|USP9X_HUMAN | 2466 | 2473 | LcpEEePd |
| 2173 | Q969V6\|MKL1_HUMAN | 497 | 504 | LvkEEgPr |
| 2174 | Q96B01\|R51A1_HUMAN | 55 | 62 | LrkEEiPv |
| 2175 | Q96D15\|RCN3_HUMAN | 192 | 199 | LhpEEfPh |
| 2176 | Q96DC7\|TMCO6_HUMAN | 219 | 226 | LqaEEaPe |
| 2177 | Q96FT7\|ACCN4_HUMAN | 90 | 97 | LslEEqPl |
| 2178 | Q96G97\|BSCL2_HUMAN | 326 | 333 | LseEEkPd |
| 2179 | Q96GW7\|PGCB_HUMAN | 880 | 887 | LhpEEdPe |

TABLE 9-continued

Table of the amino acid sequences of the peptides identified to contain the serpin motif.
Serpins
Motif: L-X(2)-E-E-X-P (SEQ ID NO: 2290)
Number of Locations: 314
Number of Different Proteins: 302

| # | Accession Number\|Protein Name | First Amino acid | Last Amino acid | Sequence |
|---|---|---|---|---|
| 2180 | Q96H72\|S39AD_HUMAN | 340 | 347 | LleEEdPw |
| 2181 | Q96H78\|S2544_HUMAN | 265 | 272 | LmaEEgPw |
| 2182 | Q96J42\|TXD15_HUMAN | 42 | 49 | LwsEEqPa |
| 2183 | Q96JI7\|SPTCS_HUMAN | 1940 | 1947 | LleEEaPd |
| 2184 | Q96JL9\|ZN333_HUMAN | 80 | 87 | LkpEElPs |
| 2185 | Q96JQ0\|PCD16_HUMAN | 3106 | 3113 | LyrEEgPp |
| 2186 | Q96MZ0\|GD1L1_HUMAN | 195 | 202 | LdhEEePq |
| 2187 | Q96NZ9\|PRAP1_HUMAN | 71 | 78 | LttEEkPr |
| 2188 | Q96PQ6\|ZN317_HUMAN | 109 | 116 | LeqEEePr |
| 2189 | Q96RE7\|BTB14_HUMAN | 133 | 140 | LhaEEaPs |
| 2190 | Q96RG2\|PASK_HUMAN | 1196 | 1203 | LvfEEnPf |
| 2191 | Q96RL1\|UIMC1_HUMAN | 388 | 395 | LllEEePt |
| 2192 | Q96SB3\|NEB2_HUMAN | 435 | 442 | LseEEdPa |
| 2193 | Q96SJ8\|TSN18_HUMAN | 167 | 174 | LdsEEvPe |
| 2194 | Q99102\|MUC4_HUMAN | 1306 | 1313 | LhrEErPn |
| 2195 | Q99543\|DNJC2_HUMAN | 68 | 75 | LqlEEfPm |
| 2196 | Q9BQS2\|SYT15_HUMAN | 36 | 43 | LtyEElPg |
| 2197 | Q9BVI0\|PHF20_HUMAN | 483 | 490 | LepEEsPg |
| 2198 | Q9BY44\|EIF2A_HUMAN | 461 | 468 | LheEEpPq |
| 2199 | Q9BY78\|RNF26_HUMAN | 356 | 363 | LneEEpPg |
| 2200 | Q9BYD3\|RM04_HUMAN | 221 | 228 | LthEEmPq |
| 2201 | Q9BZA7\|PC11X_HUMAN | 315 | 322 | LdrEEtPn |
| 2202 | Q9BZA8\|PC11Y_HUMAN | 347 | 354 | LdrEEtPn |
| 2203 | Q9C009\|FOXQ1_HUMAN | 227 | 234 | LrpEEaPg |
| 2204 | Q9H095\|IQCG_HUMAN | 122 | 129 | LitEEgPn |
| 2205 | Q9H0D2\|ZN541_HUMAN | 149 | 156 | LggEEpPg |
| 2206 | Q9H2C0\|GAN_HUMAN | 36 | 43 | LdgEEiPv |
| 2207 | Q9H2X9\|S12A5_HUMAN | 681 | 688 | LrlEEgPp |
| 2208 | Q9H334\|FOXP1_HUMAN | 291 | 298 | LshEEhPh |
| 2209 | Q9H3T3\|SEM6B_HUMAN | 26 | 33 | LfpEEpPp |
| 2210 | Q9H579\|CT132_HUMAN | 138 | 145 | LvqEErPh |
| 2211 | Q9H5V8\|CDCP1_HUMAN | 788 | 795 | LatEEpPp |
| 2212 | Q9H6F5\|CCD86_HUMAN | 227 | 234 | LnkEElPv |
| 2213 | Q9H6Z4\|RANB3_HUMAN | 4 | 11 | LanEEkPa |
| 2214 | Q9H7E9\|CH033_HUMAN | 94 | 101 | LapEEvPl |
| 2215 | Q9H8Y1\|CN115_HUMAN | 137 | 144 | LcsEEsPe |
| 2216 | Q9H9E1\|ANRA2_HUMAN | 13 | 20 | LivEEcPs |
| 2217 | Q9H9F9\|ARP5_HUMAN | 415 | 422 | LfsEEtPg |
| 2218 | Q9HAV4\|XPO5_HUMAN | 521 | 528 | LnrEEiPv |
| 2219 | Q9HCE7\|SMUF1_HUMAN | 364 | 371 | LedEElPa |
| 2220 | Q9NPR2\|SEM4B_HUMAN | 47 | 54 | LgsEErPf |
| 2221 | Q9NR50\|EI2BG_HUMAN | 333 | 340 | LcpEEpPv |
| 2222 | Q9NRJ7\|PCDBG_HUMAN | 200 | 207 | LdrEEePq |
| 2223 | Q9NTN9\|SEM4G_HUMAN | 203 | 210 | LrtEEtPm |
| 2224 | Q9NUR3\|CT046_HUMAN | 104 | 111 | LhsEEgPa |
| 2225 | Q9NVR7\|TBCC1_HUMAN | 138 | 145 | LigEEwPs |
| 2226 | Q9NX46\|ARHL2_HUMAN | 235 | 242 | LgmEErPy |
| 2227 | Q9NYB9\|ABI2_HUMAN | 7 | 14 | LleEEiPg |
| 2228 | Q9P1Y5\|K1543_HUMAN | 827 | 834 | LlaEEtPp |
| 2229 | Q9P1Y5\|K1543_HUMAN | 938 | 945 | LaqEEaPg |
| 2230 | Q9P2E7\|PCD10_HUMAN | 316 | 323 | LdyEEsPv |
| 2231 | Q9P2K9\|PTHD2_HUMAN | 673 | 680 | LevEEePv |
| 2232 | Q9UBB4\|ATX10_HUMAN | 289 | 296 | LasEEpPd |
| 2233 | Q9UBN6\|TR10D_HUMAN | 78 | 85 | LkeEEcPa |
| 2234 | Q9UBT6\|POLK_HUMAN | 251 | 258 | LlfEEsPs |
| 2235 | Q9UGF5\|OR5U1_HUMAN | 303 | 310 | LskEElPq |
| 2236 | Q9UGL1\|JAD1B_HUMAN | 879 | 886 | LlsEEtPs |
| 2237 | Q9UHW9\|S12A6_HUMAN | 743 | 750 | LrlEEgPp |
| 2238 | Q9UIF9\|BAZ2A_HUMAN | 609 | 616 | LsaEEiPs |
| 2239 | Q9UIG0\|BAZ1B_HUMAN | 75 | 82 | LlkEEfPa |
| 2240 | Q9ULD6\|PDZD6_HUMAN | 390 | 397 | LpaEEvPl |
| 2241 | Q9ULG1\|INOC1_HUMAN | 235 | 242 | LssEEsPr |
| 2242 | Q9ULI4\|KI26A_HUMAN | 1396 | 1403 | LrgEEePr |
| 2243 | Q9ULQ1\|TPC1_HUMAN | 29 | 36 | LgqEElPs |
| 2244 | Q9UMS0\|NFU1_HUMAN | 93 | 100 | LvtEEtPs |
| 2245 | Q9UN72\|PCDA7_HUMAN | 200 | 207 | LdrEEtPe |
| 2246 | Q9UN73\|PCDA6_HUMAN | 200 | 207 | LdrEEaPa |
| 2247 | Q9UN74\|PCDA4_HUMAN | 200 | 207 | LdrEEaPe |
| 2248 | Q9UNA0\|ATS5_HUMAN | 481 | 488 | LgpEElPg |
| 2249 | Q9UP95\|S12A4_HUMAN | 678 | 685 | LrlEEgPp |
| 2250 | Q9UPQ7\|PZRN3_HUMAN | 385 | 392 | LlpEEhPs |
| 2251 | Q9UPV0\|CE164_HUMAN | 488 | 495 | LatEEePp |
| 2252 | Q9UPW6\|SATB2_HUMAN | 398 | 405 | LrkEEdPr |
| 2253 | Q9UPW8\|UN13A_HUMAN | 332 | 339 | LeeEElPe |
| 2254 | Q9UPX6\|K1024_HUMAN | 371 | 378 | LntEEvPd |
| 2255 | Q9UQ05\|KCNH4_HUMAN | 761 | 768 | LlgEElPp |
| 2256 | Q9UQ26\|RIMS2_HUMAN | 201 | 208 | LrnEEaPq |
| 2257 | Q9UQ26\|RIMS2_HUMAN | 1327 | 1334 | LsfEEsPq |
| 2258 | Q9Y250\|LZTS1_HUMAN | 293 | 300 | LayEErPr |
| 2259 | Q9Y2I6\|NLP_HUMAN | 759 | 766 | LelEEpPq |
| 2260 | Q9Y2K7\|JHD1A_HUMAN | 661 | 668 | LlnEElPn |
| 2261 | Q9Y2L6\|FRM4B_HUMAN | 438 | 445 | LpsEEdPa |
| 2262 | Q9Y2V3\|RX_HUMAN | 126 | 133 | LseEEqPk |
| 2263 | Q9Y343\|SNX24_HUMAN | 87 | 94 | LenEElPk |
| 2264 | Q9Y3I0\|CV028_HUMAN | 466 | 473 | LvmEEaPe |
| 2265 | Q9Y3L3\|3BP1_HUMAN | 130 | 137 | LseEElPa |
| 2266 | Q9Y3L3\|3BP1_HUMAN | 494 | 501 | LasEElPs |
| 2267 | Q9Y3R5\|DOP2_HUMAN | 1084 | 1091 | LseEElPy |
| 2268 | Q9Y426\|CU025_HUMAN | 98 | 105 | LsfEEdPr |
| 2269 | Q9Y566\|SHAN1_HUMAN | 1838 | 1845 | LpwEEgPg |
| 2270 | Q9Y572\|RIPK3_HUMAN | 352 | 359 | LnlEEpPs |
| 2271 | Q9Y5E2\|PCDB7_HUMAN | 200 | 207 | LdrEEiPe |
| 2272 | Q9Y5E3\|PCDB6_HUMAN | 199 | 206 | LdrEEqPq |
| 2273 | Q9Y5E4\|PCDB5_HUMAN | 200 | 207 | LdrEErPe |
| 2274 | Q9Y5E5\|PCDB4_HUMAN | 199 | 206 | LdrEEqPe |
| 2275 | Q9Y5E6\|PCDB3_HUMAN | 200 | 207 | LdrEEqPe |
| 2276 | Q9Y5E7\|PCDB2_HUMAN | 202 | 209 | LdrEEqPe |
| 2277 | Q9Y5F1\|PCDBC_HUMAN | 200 | 207 | LdyEErPe |
| 2278 | Q9Y5F2\|PCDBB_HUMAN | 200 | 207 | LdyEElPe |
| 2279 | Q9Y5F3\|PCDB1_HUMAN | 200 | 207 | LdrEEqPe |
| 2280 | Q9Y5G1\|PCDGF_HUMAN | 200 | 207 | LdrEEqPh |
| 2281 | Q9Y5G2\|PCDGE_HUMAN | 410 | 417 | LdrEEiPe |
| 2282 | Q9Y5H5\|PCDA9_HUMAN | 200 | 207 | LdrEEtPe |
| 2283 | Q9Y5I2\|PCDAA_HUMAN | 199 | 206 | LdrEEnPq |
| 2284 | Q9Y5I3\|PCDA1_HUMAN | 200 | 207 | LdrEEtPe |
| 2285 | Q9Y5Q9\|TF3C3_HUMAN | 42 | 49 | LsaEEnPd |
| 2286 | Q9Y5R2\|MMP24_HUMAN | 201 | 208 | LtfEEvPy |

Example 9

A Novel Peptide Derived from the Alpha6 Fibril of Type 4 Collagen

Figure 13:
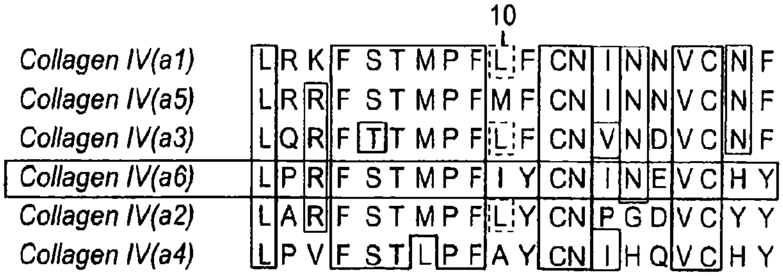
FIG. 13 shows the amino acid sequence of a novel peptide derived from the alpha4 fibril of type IV collagen and its similarities with known peptides (SEQ ID NOS 2409, 2312, 2438, 2304, 2428 and 2416, respectively, in order of appearance). Common amino acids are shaded.

A peptide similar to the short Tumstatin T3 peptide derived from the alpha3 fibril of type IV collagen was identified. This peptide was derived from the alpha6 fibril of type 4 collagen. Its amino acid sequence is LPRFSTMPFIYCNINEVCHY (SEQ ID NO: 2304) as shown in FIG. 13.

TABLE 10

Table containing the amino acid sequence of the peptide predicted similar to Tumstatin/Tum4

| Protein Name | Peptide Location | Peptide sequence |
|---|---|---|
| Collagen type IV, alpha6 fibril | CAI40758.1: 1630-1648 | LPRFSTMPFIYCNINEVCHY (SEQ ID NO: 2304) |

Example 10

Peptide Modifications

One skilled in the art will appreciate that peptides disclosed herein may be modified to increase peptide stability for in vivo administration. To demonstrate the desirability of introducing such modifications, three exemplary peptides were selected where in vivo administration in lung carcinoma xenografts of the naked (unmodified) peptides has shown significant efficacy in suppressing the tumor volume increase.

The three exemplary peptides include a peptide derived from the alpha 5 fibril of type IV collagen, a peptide derived from a TSP1 repeat containing protein properdin, and a peptide derived from a CXC chemokine CXCL1 (FIG. 14). The amino acid sequences of mouse and human peptides are shown in FIG. 14. There are minor differences in the amino acid sequences of the mouse and human sequences for TSP1 derived and CXC derived peptide. These differences do not affect the suggested modifications, as the amino acids that may be associated with peptide instability are common in both the mouse and human sequences. The amino acid sequences of the collagen derived peptides are common in both species.

Amino Acid Modifications Controlling Disulfide Bond Formation

Under oxidizing conditions, the sulfide groups from two cysteines may cross react to form a disulfide bond. If the two cysteines exist in the same molecule, this bond can be formed intra-molecularly producing a hairpin-like tertiary structure in a peptide molecule. If those two cysteines exist either in the same molecule or in two different molecules (one cysteine in the amino acid sequence of the peptide) the disulfide bond formation can cause dimerization or multimerization of the molecules. This can induce possible peptide aggregation, thereby reducing therapeutic efficacy. In addition, albumin contains a free cysteine that can react with the peptides' free cysteines again forming disulfide bonds. These bonds can cause the peptide to non-specifically bind on the albumin's surface. The peptide binding on the albumin's surface can reduce the effective concentration of the circulating peptide.

To promote therapeutic efficacy and reduce the formation of disulfide bonds, cysteines are substituted, for example, by an aminobutyric acid (Abu), serine or alanine. These amino acids have similar physicochemical properties as cysteines, i.e., they include a polar in side chain polarity, neutral in side chain acidity and are largely hydrophobic. However, they are devoid of sulfide groups, which cause them to be non-reactive under oxidizing conditions. Serine and alanine have somewhat different molecular dimensions than cysteine (serine is longer and alanine is shorter). Substitution with these amino acids can cause secondary modifications in the structure of the original peptide. Aminobutyric acid is a favorable modification as it conserves the physicochemical and structural characteristics of the cysteine without the reactive sulfide group.

When two or more cysteines exist per peptide there are two strategies that can be used in order to prevent disulfide bond formation. If the hairpin tertiary structure of the peptide is significant for its activity, the intramolecular disulfide bond formation can be preformed during the solid state synthesis of the molecule if the synthesis is performed under oxidizing conditions. The purification step of the peptide, based on its molecular weight, will eventually obliterate any multimers formed under the oxidizing conditions and can yield a high purity peptide with a hairpin-like tertiary structure. If this structure is not significant or reduces the peptide's activity, then the same strategy as in the case of a single cysteine per molecule can be followed. Both of the cysteines can be substituted by aminobutyric acids, serines or alanines.

Amino Acid Modifications Controlling Pegylation Stability

Pegylation involves the conjugation of polyethylene glycol (PEG) to proteins and peptides. Attaching a PEG increases the molecular weight of a molecule, and yield several significant pharmacological advantages over the unmodified form, which include: improved solubility; reduced dosage frequency without diminished efficacy and potentially reduced toxicity; extended circulating life; and enhanced protection from proteolytic degradation.

The presence of methionines in the amino acid sequence of a peptide may induce a low level oxidation reaction at the sulfur containing chain. This can cause the peptide to be unstable in solution or subject to non-specific interactions. The most important potential problem arising from the presence of methionines is the non-specific interactions of these amino acids with PEG chains. These interactions cause binding of the PEG to the methionines, which may present difficulties in purifying Pegylated peptides (i.e., purifying them to greater than 97% which is required by the U.S. Food and Drug Administration for human administration). The most appropriate strategy for minimizing the effect of the methionines on the Pegylation yield is the substitution of the methionines with isoleucines. Isoleucines have many of the same characteristics as methionines, but no cross-reactivity with the PEG chains.

Another amino acid that may interact non-specifically with PEG chains is lysine. This can reduce the yield of the Pegylation reaction. One strategy to minimize nonspecific interactions with lysine is protecting lysine during chemical synthesis. This extra step may increase the cost of Pegylation. A common modification that can be used in order to avoid lysine protection during Pegylation, is substituting arginine for lysine. Arginine has similar characteristics with lysines and does not affect the Pegylation yield.

Example 11

Receptor Identification and Peptide Combinations

There is growing evidence that anti-angiogenic peptides exert their effects by binding to receptors on endothelial cells. Tumstatin has two binding sites for αvβ3 integrins (Maeshima et al., (2001) *J Biol Chem* 276, 31959-31968), although its anti-angiogenic activity has been connected to the site that is located in the amino-terminal of the fragment. Tumstatin has also been shown to interact with α6β1 integrins (Maeshima et al., (2000) *J Biol Chem* 275, 23745-23750). The major receptor that has been identified for the anti-angiogenic CXC chemokines is CXCR3 (Strieter et al., (2006) *Eur J Cancer* 42, 768-778). CXCR3 exists in three alternative splice isoforms, CXCR3A, CXCR3B, and CXCR3-alt. The CXC chemokine ligands of CXCR3 inhibit the proliferation and migration of human microvascular endothelial cells in response to a variety of angiogenic factors. Extensive studies on the mechanistic details of the anti-angiogenic activity of thrombospondin 1, the prototype type 1 thrombospondin repeat-containing protein, have implicated CD36, a 88-kDa transmembrane glycoprotein, as the cell-surface receptor that mediates its effects on endothelial cells (Dawson et al., (1997) *J Cell Biol* 138, 707-717). CD47 and various integrins have also been mechanistically implicated in the effects of thrombospondin 1 on endothelial cells (Gao et al., (1996) *J Biol Chem* 271, 21-24).

Figure 15A:
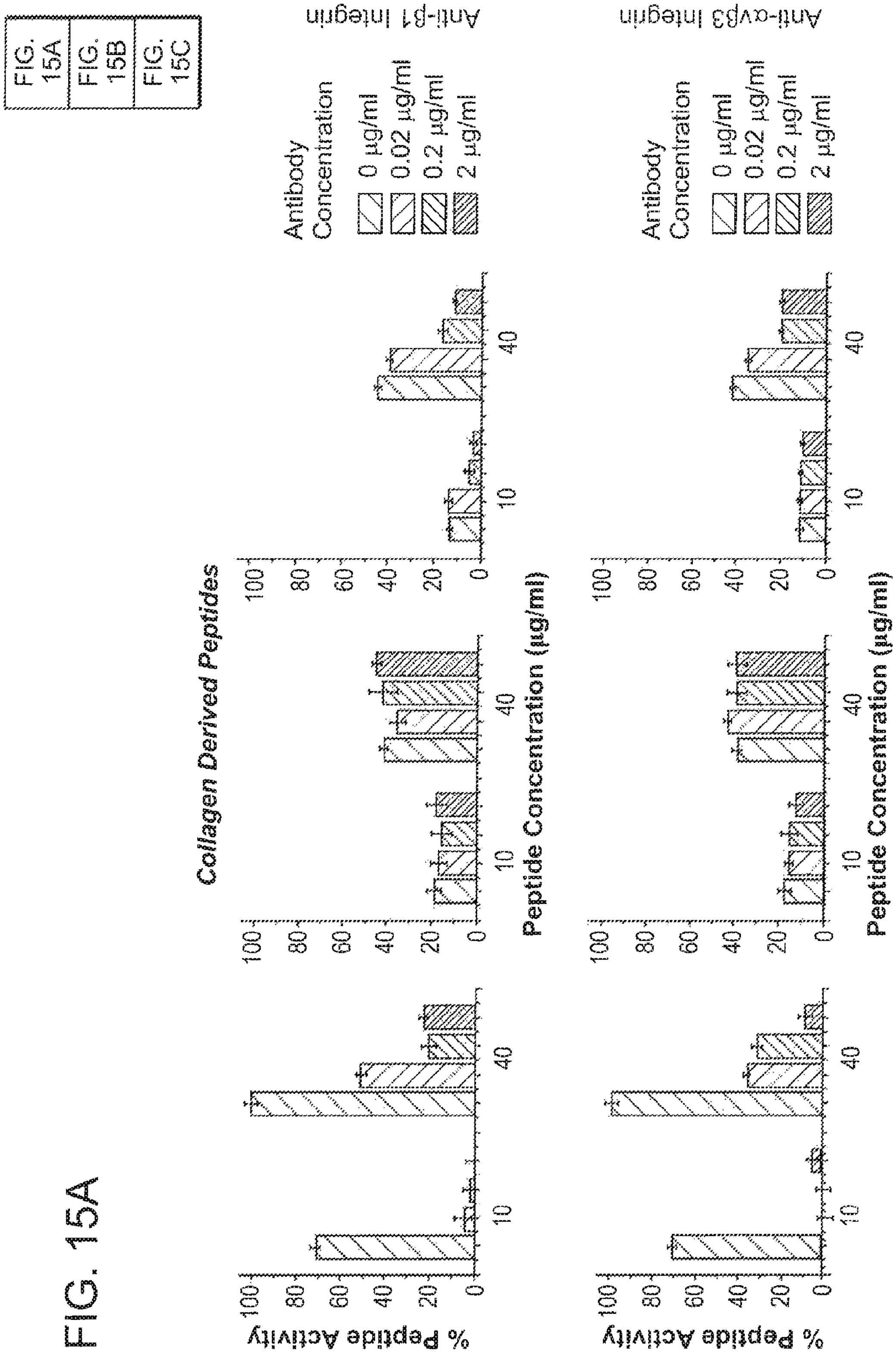
FIGS. 15A-15C includes a set of graphs showing that likely receptors for peptides identified herein were identified in the HUVEC proliferation assay after neutralization of various receptors associated with anti-angiogenic activity.
Figure 15B:
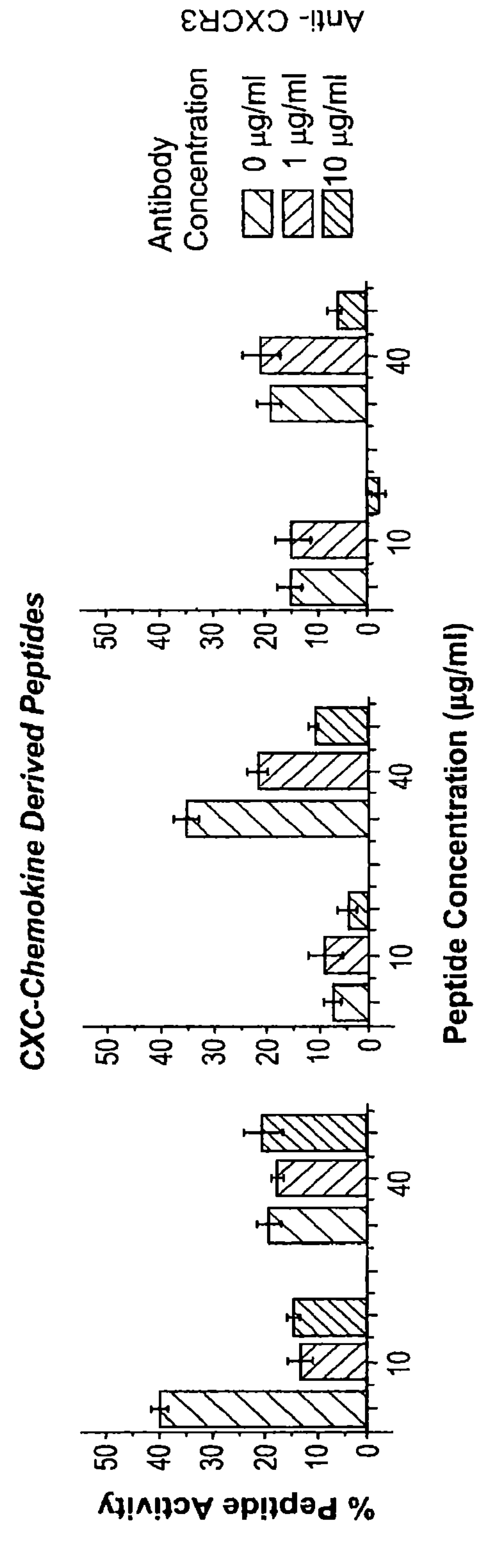
Figure 15C:
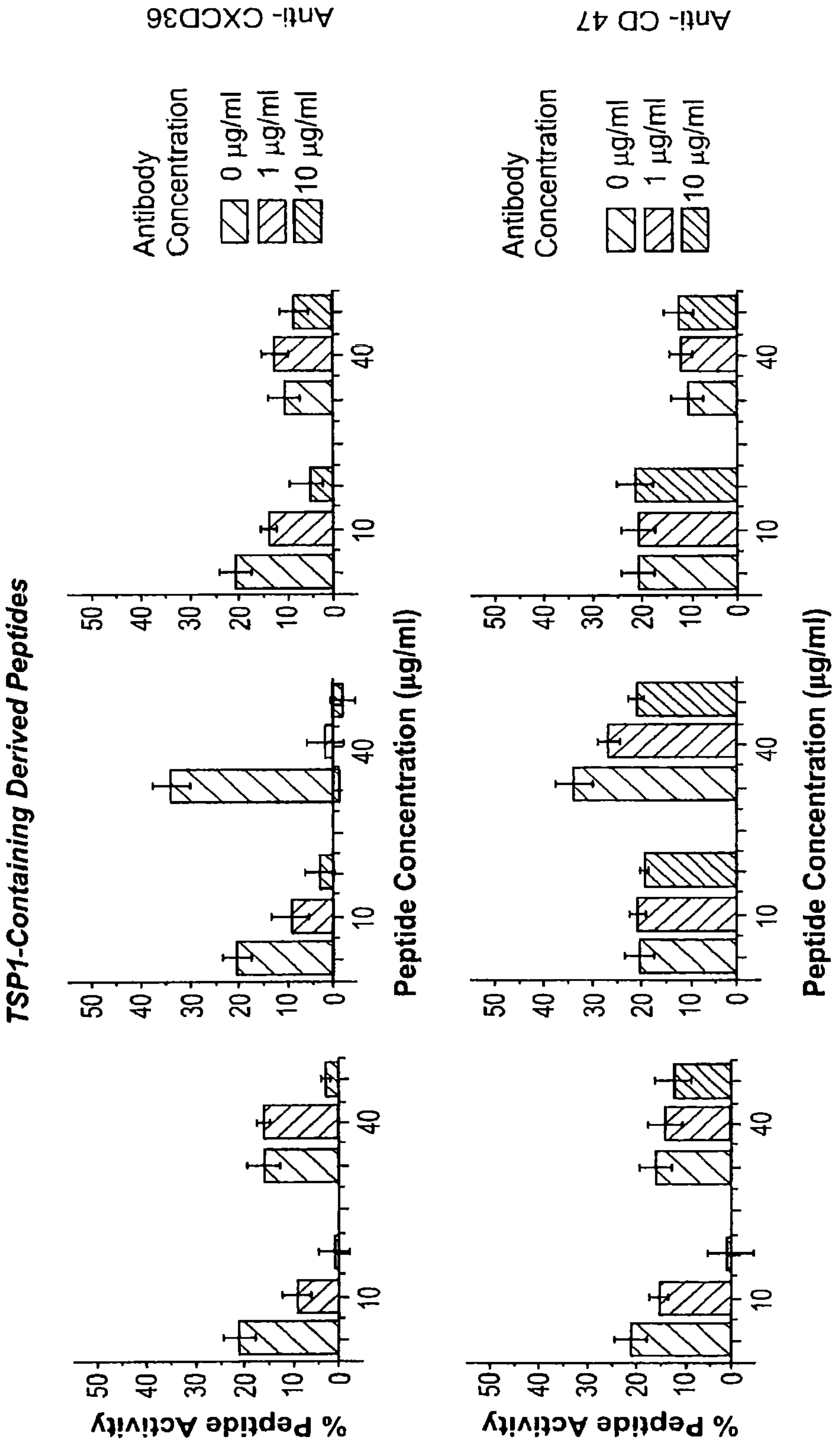

In order to determine whether peptides identified herein share binding partners with previously identified anti-angiogenic peptides, neutralization studies against these receptors were performed. Endothelial cells were pre-incubated with a range of concentrations of neutralizing monoclonal antibodies that target single receptors, and the activity of the peptides in the angiogenesis assay was then compared to that observed in the absence of neutralizing antibody. The results for neutralization studies of the CXC chemokine-derived peptides, the collagen IV-derived peptides, and the TSP1 repeat-containing peptides are presented herein (FIGS. 15A-15C). In each case, a control where the cells were incubated only in the presence of the antibody solutions and without any peptides was carried out. No effect of the antibody alone on the endothelial cells was observed at any concentration.

In order to determine whether CXCR3 is responsible for the binding of the CXC chemokine derived anti-angiogenic peptides, the proliferation experiments were repeated in the presence of different concentrations of a CXCR3-neutralizing antibody. Two concentrations of the antibody were tested, 1 and 10 μg/ml, one below and one above the designated $ED_{50}$. In most cases, the activity of the peptide was abrogated in the presence of an increasing concentration of the neutralizing antibody against the CXCR3 receptor. Interestingly, in the cases in which the peptide exhibited a biphasic dose response, the monoclonal antibody did not entirely neutralize the activity of the peptide. This suggests that more than one receptor or more than one mechanism is responsible for the activity of these peptides. By performing similar neutralization studies using monoclonal antibodies against all the known CXC receptors, including CXCR1, CXCR2, and CXCR4, none of these receptors appeared to mediate the anti-angiogenic activity of the peptides.

Noting that the effects of tumstatins are primarily attributed to peptides binding to β1 and β3 integrins (Maeshima et al., (2001) *J Biol Chem* 276, 31959-31968; Maeshima et al., (2001) *J Biol Chem* 276, 15240-15248), for collagen-derived peptides monoclonal antibodies directed against the β1 and β3 integrins were tested at two antibody concentrations, 1 and 10 ng/ml (FIG. 14). The activity of the highly potent collagen derived peptides was completely abrogated after pre-incubation with either anti-integrin antibody. In the case of the TSP1 repeat-derived peptides, neutralizing CD36, which is the main TSP1 repeat receptor, abolished the peptides' activity. With increasing antibody concentration, increased endothelial cell proliferation was observed relative to the control. It is noteworthy that at these two antibody concentrations for which no direct effect on endothelial cells was observed, the antibodies were potent enough to neutralize the peptide activity. In contrast, blocking CD47, the integrin-associated receptor, only partially neutralized the peptide activity.

Based on the information obtained from the neutralization experiments, a systematic method to create and test the effectiveness of combinations of individual peptides as potent angiogenesis inhibitors was developed. By using combinations of peptides that bind to different receptors, different pathways were targeted to assess whether there was any modulation of the combined activity in our functional assays. In order to evaluate combinations, a sensitive proliferation assay was selected to analyse changes in peptide activity. The use of multiple peptides targeting multiple targets, with different mechanisms or modes of action, creates the possibility for multiple favorable outcomes, including an increased efficacy of the therapeutic effect, the ability to employ a decreased dosage to obtain an analogous or increased level of efficacy (as a strategy to avoid toxicity), as well as a minimization of, or delay in, the development of resistance (Dorrell et al., (2007) *Proceedings of the National Academy of Sciences of the United States of America* 104, 967-972).

Figure 16B:
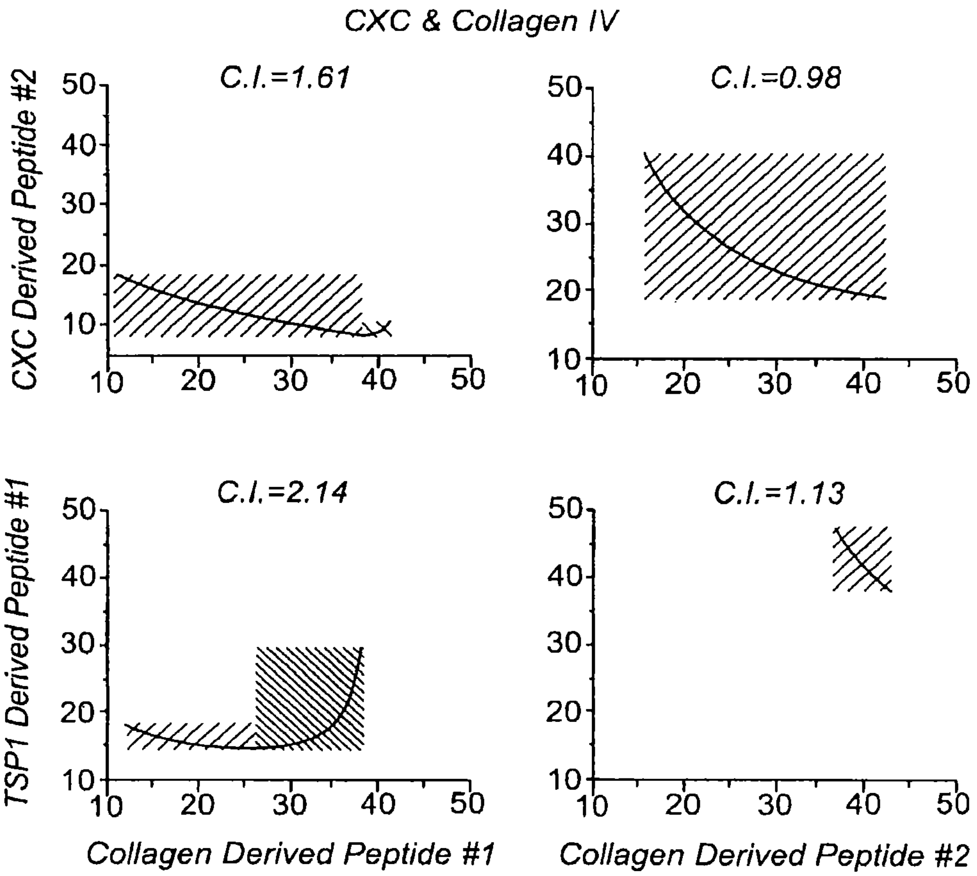
Figure 16C:
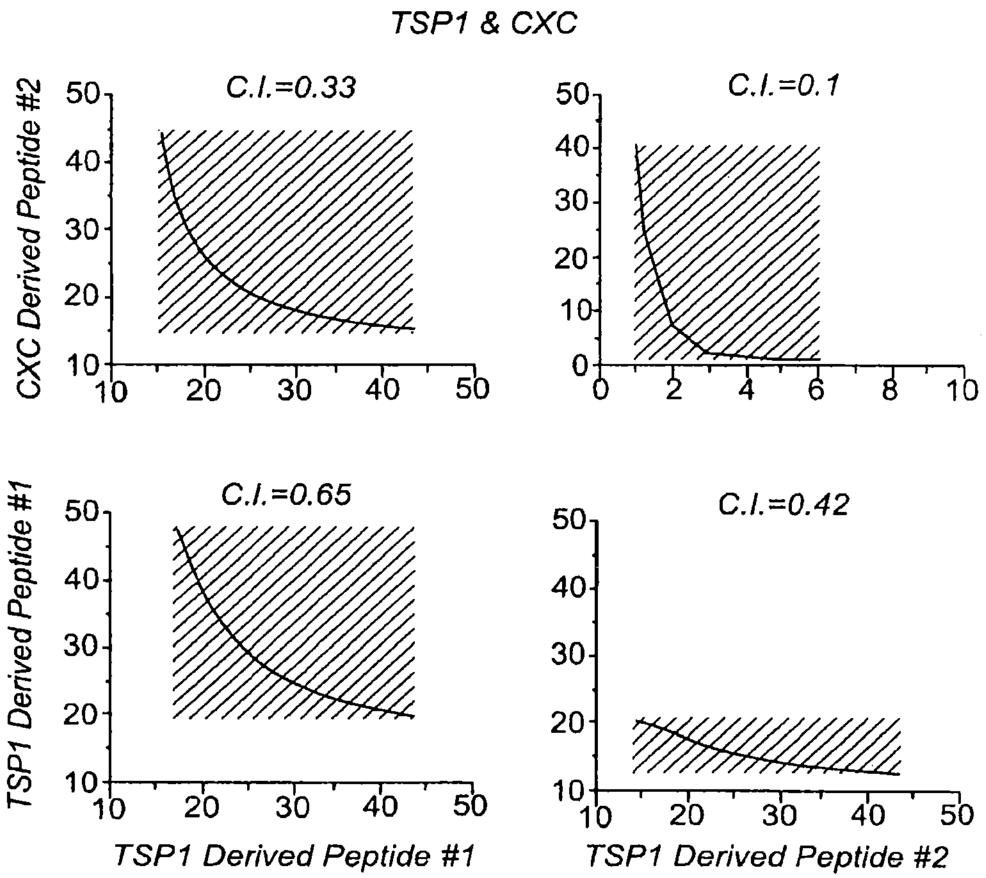
Figure 17:
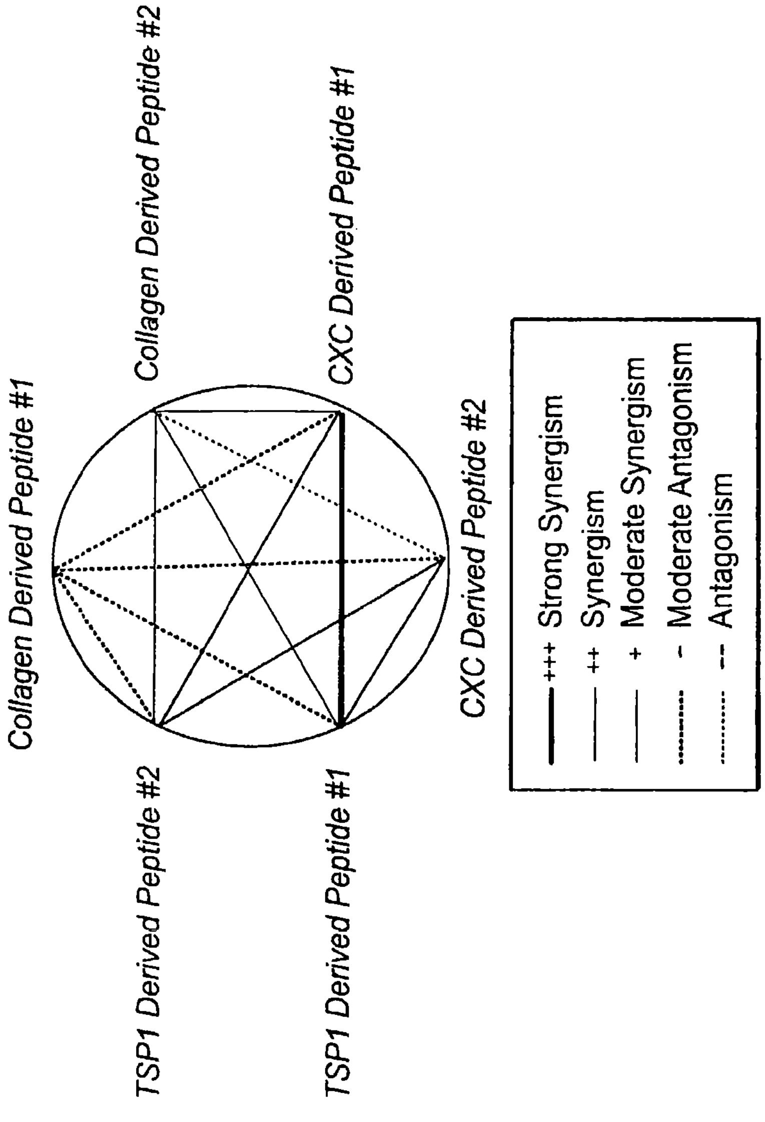
FIG. 17 shows a quantitative description of the peptide combinations. The combinations that induce strong synergism are marked with thicker red lines whereas the combinations that induce antagonism are shown with dotted blue lines.

Combinations of two peptides were tested from each of the three major protein families, the type IV collagen fibrils, CXC chemokines, and TSP1 repeat-containing proteins. The peptides used in the combination experiments are derived from the alpha5 fibril of type IV collagen (LRRFSTMPFMFCNINNVCNF (SEQ ID NO: 2312)), from alpha4 fibril of type IV collagen (YCNIHQVCHYAQRNDRSYWL (SEQ ID NO: 2320)), from a CXC protein GRO-α/CXCL1 (NGRKACLNPASPIVKKIIEKMLNS (SEQ ID NO: 2305)), from a CXC protein ENA-78/CXCL5 (NGKEICLDPEAPFLKKVIQKILD (SEQ ID NO: 2311)), from a TSP1 repeat-containing protein properdin (GPWEPCSVTCSKGTRTRRR (SEQ ID NO: 2306)), and from a TSP1 repeat-containing protein THSD6 (WTRCSSSCGRGVSVRSR (SEQ ID NO: 2321)). One peptide from each family was combined at four different concentrations (0.1, 1, 10, and 30 μg/ml), and the efficacy of these combined peptides was evaluated in a proliferation assay. The peptides were applied in series in order to avoid possible interactions between them, and the viability of the cells was then evaluated. Using the information from the dose-response curves, the data was fit to sigmoidal Hill curves (Chou et al., (2006) Pharmacol Rev 58, 621-681). Based on the estimated Hill curves, isobolograms were calculated to obtain the state space of peptide concentrations with equipotent sums of doses. This data was used to generate graphs of equally effective dose pairs (isoboles) with the same level of effectiveness observed for a single peptide application. In addition to the isobolograms the Combination Indexes (C.I.) for different peptide combinations was also calculated (Chou et al., (1984) Adv Enzyme Regul 22, 27-55) to compare the relative efficacy of the various combinations (FIG. 16).

These analyses indicated a significant synergism between CXC chemokines and TSP1 repeat-containing protein-derived peptides. Thus, it is likely that using specific peptide combinations, provides activity levels similar to those obtained when each of the peptides is used alone, but at significantly lower dosages. In the case of combining a CXC derived peptide with a TSP1 derived peptide, dosage was reduced by one order of magnitude while the same level of efficacy was maintained. Furthermore, when applied at higher concentrations, these two peptides in combination yielded a much higher activity than when either one was applied alone. In the case of the combination of collagen IV-derived peptides with either CXC- or TSP1-derived peptides, a synergism was observed only at lower collagen peptide concentrations. At higher concentrations, the collagen-derived peptides were antagonized by the CXC and TSP1 repeat-derived peptides.

These studies indicated that the peptides bind to receptors on the endothelial cell surface. Based on the information from the receptor binding, combinatorial strategies were designed targeting multiple receptors. This analysis supports the conclusion that targeting CD36 or CD47, the primary thrombospondin receptors, and CXCR3, the receptor responsible for the anti-angiogenic activity of CXC chemokine-derived peptides, provided for the synergistic amplification of the peptides' potency.

Example 12

Anti-Angiogenic Peptides Arrest Tumor Growth

Figure 18A:
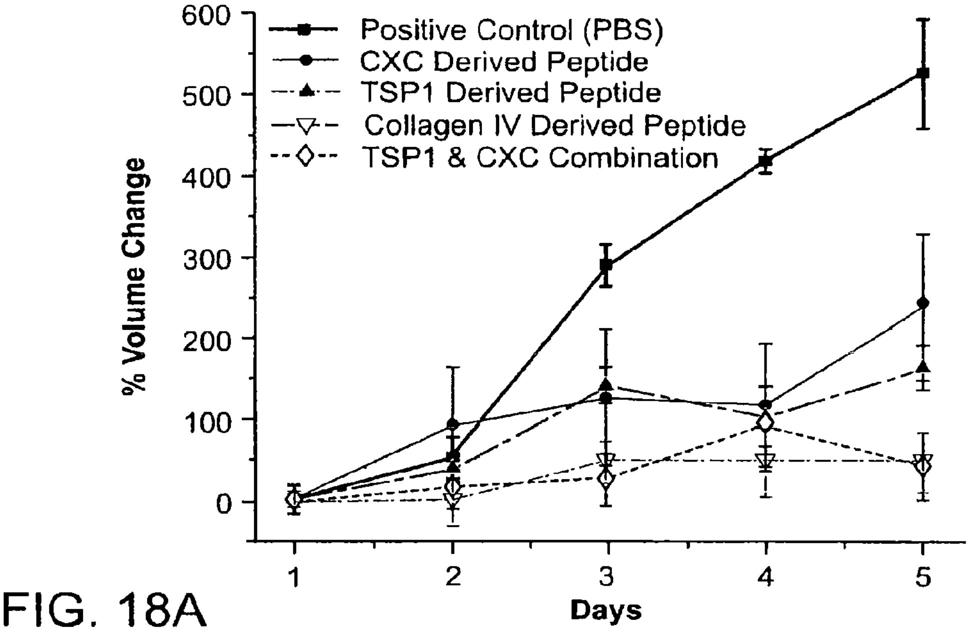
FIGS. 18A-18C are graphs.
Figure 18B:
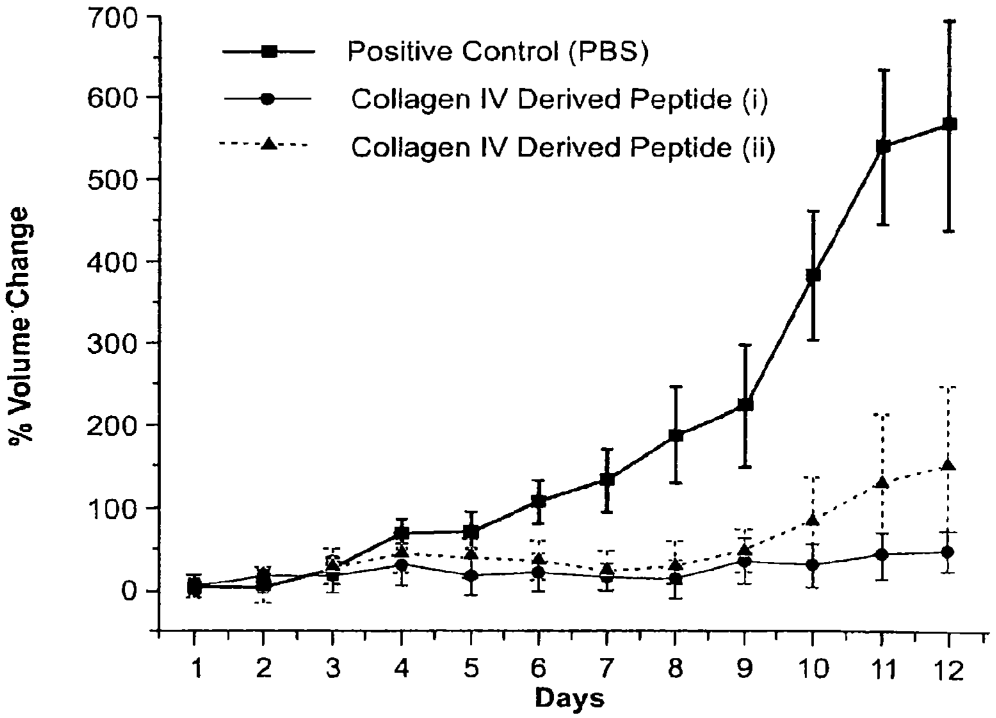
Figure 18C:
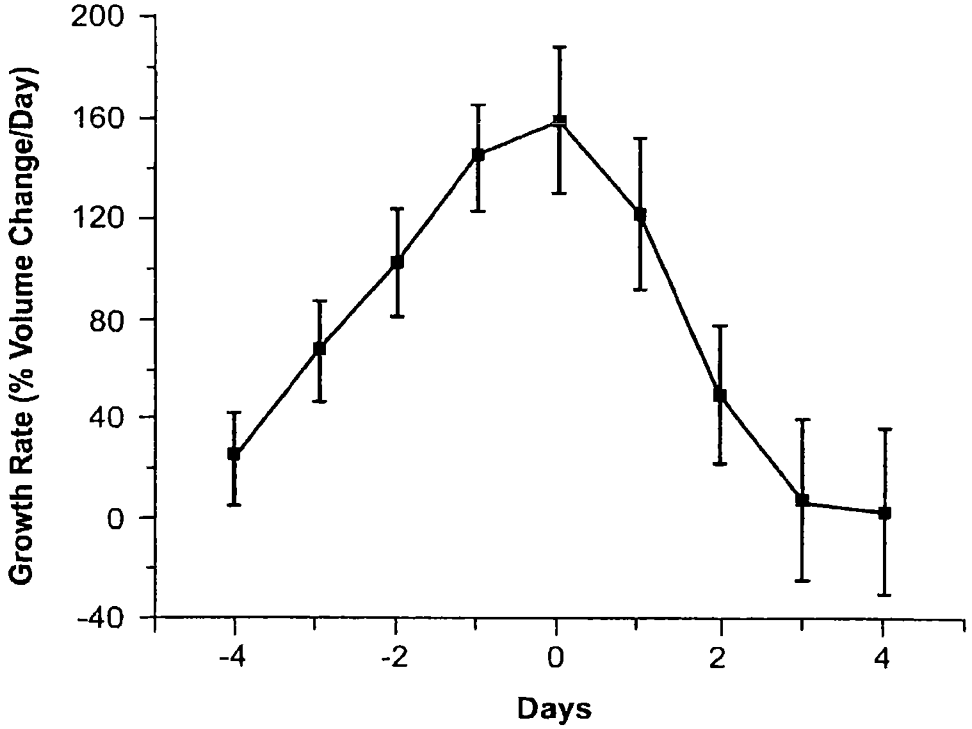

To characterize the functional effects of anti-angiogenic peptides in mouse models, tumor xenografts were generated in female nude mice using the NCI H82 lung carcinoma cell line. This cell line was chosen because its aggressiveness results in rapid tumor growth. Three peptides, a collagen derived, a CXC chemokine derived and a TSP1 containing protein derived peptide were administered once a day, intraperitoneally (i.p.), at doses 10 and 20 mg/kg/day, in a 200 microliter solution injection as individual agents and as a combination. The CXC protein GRO-α/CXCL1 derived peptide (human sequence: NGRKACLNPASPIVKKIIEK-MLNS (SEQ ID NO: 2445); mouse sequence: NGREACLD-PEAPLVQKIVQKMLKG (SEQ ID NO: 2441)), the TSP1 repeat-containing protein WISP-1 derived peptide (human sequence: GPWEPCSVTCSKGTRTRRR (SEQ ID NO: 2444); mouse sequence: GPWGPCSVTCSKGTQIRQR (SEQ ID NO: 2440)), and the type IV collagen alpha5 fibril derived peptide (human sequence: LRRFSTMPFMFCNIN-NVCNF (SEQ ID NO: 2442) is the same as mouse sequence: LRRFSTMPFMFCNINNVCNF (SEQ ID NO: 2443)). An equivalent volume of PBS was injected as control. The injections were repeated for 12 days. At 10 mg/kg/day (FIG. 18A) and 20 mg/kg/day (FIG. 18B) the peptides suppressed the development of tumors as a monotherapy. Injections of the combination of a TSP1 containing protein derived peptide and a CXC chemokine derived peptide in a rapidly developing tumor (Day 14 after inoculation) completely arrested tumor growth within 3 days (FIG. 18C).

The results described in Example 12 were carried out using the following materials and methods.

Cell Culture

Primary human umbilical vein endothelial cells (HUVECs) from a single donor were purchased from Cambrex (Walkersville, Md.). The cells were propagated in EGM-2 medium, consisting of a basal cell medium with 2% FBS, growth factors (hbFGF and VEGF) and antibiotics (gentamicin/amphotericin B). The cells were subcultured according to the supplier's instructions: Once the cells had reached subconfluence, they were washed with HEPES buffer solution and trypsinized. The trypsin was then neutralized with trypsin neutralizing solution (TNS; Cambrex, Walkersville, Md.), and the cells were collected and centrifuged at 1500 rpm for 5 minutes. The supernatant was aspirated, and the cells were resuspended in fresh medium. All the cells used were from passage 3 to passage 6.

In Vitro Cell Viability Assay

To assess the effects of peptides on the proliferation of endothelial cells the viability and metabolic activity of the cells was monitored in the presence of the agent at different concentrations after various periods of time. The colorimetric cell proliferation reagent WST-1 (4-[3-(4-iodophenyl)-2-(4-nitrophenyl)-2H-5-tetrazolio]-1,3-benzene disulphonate) (Roche, Indianapolis, Ind.) was used as the substrate in an assay that measures the metabolic activity of viable cells (Ishiyama et al., (1996) *Biol Pharm Bull* 19, 1518-1520). The assay is based on the reduction of the red tetrazolium salt WST-1 by viable, metabolically active cells to form yellow formazan crystals that are soluble in the cell culture medium.

The cells were cultured as described above and then trypsinized and resuspended in EGM-2 once they had reached 80% confluence. Cell counts were determined using a hemocytometer.

The proliferation assay involved two steps: during the first step, the cells (~$2\times10^3$/well in a 96-well microplate) were seeded without any extracellular matrix substrate onto the microwells overnight (8 hours). The initial cell culture medium was then removed, and the candidate peptides, dissolved in cell culture medium with growth factors and serum, were added to the wells. The viability of the cells was determined after a 3-day exposure to the peptide solution. Each peptide was tested at seven different concentrations: 0.01, 0.1, 1 and 10 μg/ml and 20, 30 and 40 μg/ml. Each of the concentrations was tested simultaneously in quadruplicate, and each of the experiments was repeated two times. As a positive control (i.e., decreasing viability) 100 ng/ml (0.22 μM) TNP-470 (O-(chloro-acetyl-carbamoyl) fumagillol, a synthetic analogue of fumagillin was applied; 0.46 kDa, provided by NCI) along with the full medium. As a negative control (equivalent to normal viability) the cells were cultured without any test agent in full medium, containing growth factors and serum. The cells were then incubated with the WST-1 reagent for approximately 3 hours. During the incubation period, viable cells convert, in their mitochondria, the red WST-1 to yellow formazan crystals that dissolve in the medium. The second step of the assay involved the quantification of the changes in proliferation by measuring the changes in the color of the metabolized substrate. The samples were read at a wavelength of 570 nm in an ELISA plate reader Victor 3V (Perkin Elmer). The amount of color produced was directly proportional to the number of viable cells.

Monoclonal Antibody Neutralization Assay

In the monoclonal antibody neutralization experiments the endothelial cell proliferation assay was repeated in the presence of varying concentrations of monoclonal antibodies against specific receptors. The endothelial cells were seeded overnight in 96 well plates in full growth factor and serum medium. The medium was removed and replaced with medium containing different monoclonal antibody solutions for beta1 integrins (R&D Systems, MAB17781) alphavbeta3 integrins (R&D Systems, MAB3050), CXCR3 (R&D Systems, MAB1685), CD36 (BD Pharmingen, CB38 (NL07)) and CD47 (BD Pharmingen, B6H12). The cells were incubated for two hours with the antibody solutions. After the two hours the peptide solutions at different concentrations were added in the wells. As a control a set of cells was incubated only in the presence of the monoclonal antibody solutions and without any peptides. The cells were incubated for three days and a cell viability estimation was performed similarly to the proliferation assay.

Isobologram and Combination Index Calculation

The proliferation experiments described above were carried out with peptide combinations. In the combination experiments, the cells were seeded in 96-well microplates using the same cell density as described above, i.e., approximately 2000 cells per well. The cells were allowed to attach overnight (6-8 hours) in full growth factor and serum medium. The full medium was withdrawn and a solution of a single peptide was applied in dose response concentrations of 0.1, 1, 10 and 30 μg/ml. These solutions were prepared and applied in growth factor and serum free medium. After two hours the solutions of the first peptide were withdrawn and the solutions of the second peptide were applied in a growth factor and serum free medium. The concentrations at which the second peptide was applied were the same as the concentrations of the first, i.e. in the case that the first peptide was applied at 10 μg/ml, the second was also applied at 10 μg/ml. In addition to the combinations each of the peptides was applied alone for reference. After twenty-four hours the WST-1 dye was applied and the number of live cells was estimated by the optical signal. Dose response sigmoidal curves for a condition "i" were estimated by fitting the data to sigmoidal Hill curves of the type:

$$E_i = E_i^{max} \cdot \frac{D_i^{n_i}}{D_{50,i}^{n_i} + D_i^{n_i}} \rightarrow D_i = D_{50,i} \cdot \sqrt[n_i]{\frac{E_i}{E_i^{max} + E_i}} \quad (1)$$

where E is the effect of the condition "i", in this case the fraction of dead cells, $E^{max}$ is the maximum observed effect, D is the corresponding dose that yields effectiveness E, $D_{50}$ is the dose at which half of the maximum effectiveness $E^{max}$ is observed, and n is the Hill coefficient.

Combining a peptide x with a peptide y and $D_x^{combo}$ is the applied peptide x concentration in the combination experiment and $D_y^{combo}$ is the applied peptide y concentration in combination then due to the set up of the experiment, at each experimental condition $D_x^{combo}=D_y^{combo}=D^{combo}$. In order to construct an isobologram, a graph of equally effective dose pairs (isoboles) for a single peptide effect level (Chou et al., (2006) *Pharmacol Rev* 58, 621-681):

$$\frac{D_x^{combo}}{D_x} + \frac{D_y^{combo}}{D_y} = 1 \quad (2)$$

In the denominator $D_x$ is the dose for $D_x^{combo}$ alone that inhibits the proliferation by effectiveness E and $D_y$ is the dose for $D_y^{combo}$ alone that inhibits the proliferation by the same effectiveness E. Also $D_x^{combo}=D_y^{combo}=D^{combo}$. Solving equation 2 for a single dose:

$$D_x = \frac{D_y \cdot D^{combo}}{D_y - D^{combo}} \quad (3)$$

After substituting the dose response of the combination $D^{combo}$ with the corresponding sigmoidal equation 1 as fitted by the experimental data, equation 3 becomes:

$$D_x = \frac{D_y \cdot D_{50}^{combo} \cdot \sqrt[n_{combo}]{\frac{E_{combo}}{E_{combo}^{max} + E_{combo}}}}{D_y - D_{50}^{combo} \cdot \sqrt[n_{combo}]{\frac{E_{combo}}{E_{combo}^{max} + E_{combo}}}} \quad (4)$$

The isobologram is the plot of these concentrations that the effectiveness of an agent alone is the same as the effectiveness of the same agent in combination, $E_{combo}=E_y$ thus equation 4 becomes:

$$D_x = \frac{D_y \cdot D_{50}^{combo} \cdot \sqrt[n_{combo}]{\frac{E_y}{E_{combo}^{max} + E_y}}}{D_y - D_{50}^{combo} \cdot \sqrt[n_{combo}]{\frac{E_y}{E_{combo}^{max} + E_y}}} \quad (5)$$

But the effectiveness for y alone is defined according to the Hill equation as:

$$E_y = E_y^{max} \cdot \frac{D_y^{n_y}}{D_{50,y}^{n_y} + D_y^{n_y}} \quad (6)$$

Thus after substituting equation 6 into 5:

$$D_x = D_y \cdot D_{50}^{combo} \cdot \frac{\sqrt[n_{combo}]{\frac{E_y^{max} \cdot \frac{D_y^{n_y}}{D_{50,y}^{n_y} + D_y^{n_y}}}{E_{combo}^{max} + E_y^{max} \cdot \frac{D_y^{n_y}}{D_{50,y}^{n_y} + D_y^{n_y}}}}}{D_y - D_{50}^{combo} \cdot \sqrt[n_{combo}]{\frac{E_y^{max} \cdot \frac{D_y^{n_y}}{D_{50,y}^{n_y} + D_y^{n_y}}}{E_{combo}^{max} + E_y^{max} \cdot \frac{D_y^{n_y}}{D_{50,y}^{n_y} + D_y^{n_y}}}}} \quad (7)$$

In order to graph the isobolograms we calculate for each $D_y$ the corresponding $D_x$ and plot the $D_x$ vs. $D_y$ pairs.

The isobolograms are a special case for the combination index equation as introduced by Chou and Talalay (Chou et al., (1984) *Adv Enzyme Regul* 22, 27-55). The generic equation for the combination index calculation is expressed:

$$CI = \frac{D_x^{combo}}{D_x} + \frac{D_y^{combo}}{D_y} \quad (8)$$

If CI<1 the drug combination effect is synergistic; if C.I.=1 the drug combination effect is additive; whereas if CI>1 the drug combination effect is antagonistic.

In Vivo Tumor Xenograft Models

A population of $10^6$ cells were washed twice in PBS and gently resuspended to generate a single cell suspension. The cells were mixed with Matrigel (BD Biosciences) in a final 60% cell solution. Subsequently, the cells were injected into the flank area of immunosuppressed nude mice in a total volume of 100 μl. Following growth incubation of 5 to 6 days, the tumor size volume was calculated by measurements of tumor dimensions with calipers. Tumor growth was monitored to an initial average size of 100 $mm^3$, which developed within 6 days after inoculation. Peptides were administered once a day, intraperitoneally (i.p.), in doses of 10 mg/kg and 20 mg/kg. In the case of testing a combination each peptide was injected in a two day cycle of a different peptide per day. Equivalent volume of PBS solution was injected as control. The injections were continued for up to 14 days. A total of six animals per group were used for the experiments per peptide per concentration.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The following International Patent Application No. PCT/US2006/035580, entitled COMPOSITIONS HAVING ANTIANGIOGENIC ACTIVITY AND USES THEREOF, which was filed on Sep. 12, 2006 may include related subject matter, and is hereby incorporated by reference in its entirety.

All patents and publications mentioned in this specification are herein incorporated by reference to the same extent as if each independent patent and publication was specifically and individually indicated to be incorporated by reference. In particular, the sequence of each of the individual NCBI reference numbers listed in Tables 1-10 is hereby incorporated by reference in its entirety.

What is claimed is:

1. An isolated peptide or analog thereof consisting of a sequence having at least 85% amino acid sequence identity to:

```
                                  (SEQ ID NO: 2294)
Chorionic somatomammotropin   LLRLLLLIESWLE,
or

                                  (SEQ ID NO: 2295)
Chorionic somatomammotropin   LLHISLLLIESRLE
hormone-like 1
```

wherein the peptide reduces blood vessel formation in a cell, tissue, or organ, and comprises at least one modification.

2. The isolated peptide of claim 1, wherein the modification is a sequence alteration or post-translational modification that increases protease resistance, biodistribution, or therapeutic efficacy.

3. A pharmaceutical composition comprising an effective amount of the isolated peptide of claim 1 in a pharmacologically acceptable excipient.

4. A kit comprising an effective amount of the peptide of claim 1, and directions for using the peptide to treat a disease characterized by undesirable or excess angiogenesis.

5. A method of reducing blood vessel formation in a tissue or organ, the method comprising contacting an endothelial cell, or a tissue or organ comprising an endothelial cell, with an effective amount of the peptide of claim 1, thereby reducing blood vessel formation in the tissue or organ.

6. A method of reducing blood vessel formation in a tissue or organ the method comprising:

contacting the tissue, or organ with a vector encoding the peptide of claim 1; and expressing the peptide in a cell of the tissue or organ, thereby reducing blood vessel formation in the tissue or organ.

7. A method for treating a lung carcinoma in a subject in need thereof, the method comprising administering an effective amount of the peptide of claim 1.

* * * * *

SEQUENCE LISTING

<160> NUMBER OF SEQ ID NOS: 2445

<210> SEQ ID NO 1
<211> LENGTH: 11
<212> TYPE: PRT
<213> ORGANISM: Homo sapiens

<400> SEQUENCE: 1

Trp Ser Gln Cys Ser Lys Thr Cys Gly Thr Gly
1 5 10

<210> SEQ ID NO 2
<211> LENGTH: 11
<212> TYPE: PRT
<213> ORGANISM: Homo sapiens

<400> SEQUENCE: 2

Trp Gly Glu Cys Thr Arg Asp Cys Gly Gly Gly
1 5 10

<210> SEQ ID NO 3
<211> LENGTH: 11
<212> TYPE: PRT
<213> ORGANISM: Homo sapiens

<400> SEQUENCE: 3

Trp Ser Val Cys Ser Ser Thr Cys Gly Glu Gly
1 5 10

<210> SEQ ID NO 4
<211> LENGTH: 11
<212> TYPE: PRT
<213> ORGANISM: Homo sapiens

<400> SEQUENCE: 4

Trp Ser Leu Cys Ser Ser Thr Cys Gly Arg Gly
1 5 10

<210> SEQ ID NO 5
<211> LENGTH: 11
<212> TYPE: PRT
<213> ORGANISM: Homo sapiens

<400> SEQUENCE: 5

Trp Ser Ala Cys Ser Ala Ser Cys Ser Gln Gly
1 5 10

<210> SEQ ID NO 6
<211> LENGTH: 11
<212> TYPE: PRT
<213> ORGANISM: Homo sapiens

<400> SEQUENCE: 6

Trp Gly Ser Cys Ser Val Thr Cys Gly Ala Gly
1 5 10

<210> SEQ ID NO 7
<211> LENGTH: 11
<212> TYPE: PRT
<213> ORGANISM: Homo sapiens

<400> SEQUENCE: 7

Trp Ser Glu Cys Ser Val Thr Cys Gly Glu Gly
1 5 10

<210> SEQ ID NO 8
<211> LENGTH: 11
<212> TYPE: PRT
<213> ORGANISM: Homo sapiens

<400> SEQUENCE: 8

Trp Ser Val Cys Ser Leu Thr Cys Gly Gln Gly
1 5 10

<210> SEQ ID NO 9
<211> LENGTH: 11
<212> TYPE: PRT
<213> ORGANISM: Homo sapiens

<400> SEQUENCE: 9

Trp Ser Leu Cys Ser Arg Ser Cys Gly Arg Gly
1 5 10

<210> SEQ ID NO 10
<211> LENGTH: 11
<212> TYPE: PRT
<213> ORGANISM: Homo sapiens

<400> SEQUENCE: 10

Trp Gly Pro Cys Ser Thr Ser Cys Ala Asn Gly
1 5 10

<210> SEQ ID NO 11
<211> LENGTH: 11
<212> TYPE: PRT
<213> ORGANISM: Homo sapiens

<400> SEQUENCE: 11

Trp Ser Leu Cys Ser Lys Thr Cys Asp Thr Gly
1 5 10

<210> SEQ ID NO 12
<211> LENGTH: 11
<212> TYPE: PRT
<213> ORGANISM: Homo sapiens

<400> SEQUENCE: 12

Trp Ser Thr Cys Ser Val Thr Cys Gly Gln Gly
1 5 10

<210> SEQ ID NO 13
<211> LENGTH: 11
<212> TYPE: PRT
<213> ORGANISM: Homo sapiens

<400> SEQUENCE: 13

Trp Ser Leu Cys Ser Phe Thr Cys Gly Arg Gly
1 5 10

<210> SEQ ID NO 14
<211> LENGTH: 11
<212> TYPE: PRT
<213> ORGANISM: Homo sapiens

<400> SEQUENCE: 14

Trp Ser Gln Cys Ser Val Thr Cys Ser Asn Gly
1 5 10

<210> SEQ ID NO 15

<211> LENGTH: 11
<212> TYPE: PRT
<213> ORGANISM: Homo sapiens

<400> SEQUENCE: 15

Trp Ser Gly Cys Ser Lys Ser Cys Asp Gly Gly
1 5 10

<210> SEQ ID NO 16
<211> LENGTH: 11
<212> TYPE: PRT
<213> ORGANISM: Homo sapiens

<400> SEQUENCE: 16

Trp Gly Asp Cys Ser Arg Thr Cys Gly Gly Gly
1 5 10

<210> SEQ ID NO 17
<211> LENGTH: 11
<212> TYPE: PRT
<213> ORGANISM: Homo sapiens

<400> SEQUENCE: 17

Trp Gly Pro Cys Ser Thr Thr Cys Gly Leu Gly
1 5 10

<210> SEQ ID NO 18
<211> LENGTH: 11
<212> TYPE: PRT
<213> ORGANISM: Homo sapiens

<400> SEQUENCE: 18

Trp Ser Val Cys Asn Ser Arg Cys Gly Arg Gly
1 5 10

<210> SEQ ID NO 19
<211> LENGTH: 11
<212> TYPE: PRT
<213> ORGANISM: Homo sapiens

<400> SEQUENCE: 19

Trp Ser Pro Cys Ser Thr Ser Cys Gly Leu Gly
1 5 10

<210> SEQ ID NO 20
<211> LENGTH: 11
<212> TYPE: PRT
<213> ORGANISM: Homo sapiens

<400> SEQUENCE: 20

Trp Thr Pro Cys Ser Arg Thr Cys Gly Met Gly
1 5 10

<210> SEQ ID NO 21
<211> LENGTH: 11
<212> TYPE: PRT
<213> ORGANISM: Homo sapiens

<400> SEQUENCE: 21

Trp Ser Pro Cys Ser Lys Pro Cys Gly Gly Gly
1 5 10

<210> SEQ ID NO 22
<211> LENGTH: 11
<212> TYPE: PRT

<213> ORGANISM: Homo sapiens

<400> SEQUENCE: 22

Trp Ser Gln Cys Ser Val Thr Cys Gly Asn Gly
1 5 10

<210> SEQ ID NO 23
<211> LENGTH: 11
<212> TYPE: PRT
<213> ORGANISM: Homo sapiens

<400> SEQUENCE: 23

Trp Thr Ser Cys Ser Thr Ser Cys Gly Asn Gly
1 5 10

<210> SEQ ID NO 24
<211> LENGTH: 11
<212> TYPE: PRT
<213> ORGANISM: Homo sapiens

<400> SEQUENCE: 24

Trp Ser Ser Cys Ser Val Thr Cys Gly Asp Gly
1 5 10

<210> SEQ ID NO 25
<211> LENGTH: 11
<212> TYPE: PRT
<213> ORGANISM: Homo sapiens

<400> SEQUENCE: 25

Trp Asp Ile Cys Ser Val Thr Cys Gly Gly Gly
1 5 10

<210> SEQ ID NO 26
<211> LENGTH: 11
<212> TYPE: PRT
<213> ORGANISM: Homo sapiens

<400> SEQUENCE: 26

Trp Thr Ser Cys Ser Lys Thr Cys Asn Ser Gly
1 5 10

<210> SEQ ID NO 27
<211> LENGTH: 11
<212> TYPE: PRT
<213> ORGANISM: Homo sapiens

<400> SEQUENCE: 27

Trp Gln Arg Cys Pro Ile Asn Cys Leu Leu Gly
1 5 10

<210> SEQ ID NO 28
<211> LENGTH: 11
<212> TYPE: PRT
<213> ORGANISM: Homo sapiens

<400> SEQUENCE: 28

Trp Arg Asp Cys Ser Arg Pro Cys Pro Pro Gly
1 5 10

<210> SEQ ID NO 29
<211> LENGTH: 11
<212> TYPE: PRT
<213> ORGANISM: Homo sapiens

<400> SEQUENCE: 29

Trp Ala Pro Cys Ser Val Thr Cys Ser Glu Gly
1               5                   10

<210> SEQ ID NO 30
<211> LENGTH: 11
<212> TYPE: PRT
<213> ORGANISM: Homo sapiens

<400> SEQUENCE: 30

Trp Glu Pro Cys Ser Val Thr Cys Ser Lys Gly
1               5                   10

<210> SEQ ID NO 31
<211> LENGTH: 11
<212> TYPE: PRT
<213> ORGANISM: Homo sapiens

<400> SEQUENCE: 31

Trp Thr Pro Cys Ser Ala Ser Cys His Gly Gly
1               5                   10

<210> SEQ ID NO 32
<211> LENGTH: 11
<212> TYPE: PRT
<213> ORGANISM: Homo sapiens

<400> SEQUENCE: 32

Trp Ser Ala Cys Ser Lys Thr Cys Gly Met Gly
1               5                   10

<210> SEQ ID NO 33
<211> LENGTH: 11
<212> TYPE: PRT
<213> ORGANISM: Homo sapiens

<400> SEQUENCE: 33

Trp Thr Gln Cys Ser Val Thr Cys Gly Ser Gly
1               5                   10

<210> SEQ ID NO 34
<211> LENGTH: 11
<212> TYPE: PRT
<213> ORGANISM: Homo sapiens

<400> SEQUENCE: 34

Trp Ser Ser Cys Ser Val Thr Cys Gly Val Gly
1               5                   10

<210> SEQ ID NO 35
<211> LENGTH: 11
<212> TYPE: PRT
<213> ORGANISM: Homo sapiens

<400> SEQUENCE: 35

Trp Ser Ala Cys Thr Val Thr Cys Ala Gly Gly
1               5                   10

<210> SEQ ID NO 36
<211> LENGTH: 11
<212> TYPE: PRT
<213> ORGANISM: Homo sapiens

<400> SEQUENCE: 36

Trp Thr Ala Cys Ser Lys Ser Cys Gly Met Gly
1 5 10

<210> SEQ ID NO 37
<211> LENGTH: 11
<212> TYPE: PRT
<213> ORGANISM: Homo sapiens

<400> SEQUENCE: 37

Trp Glu Glu Cys Lys Gln Arg Cys Pro Pro Gly
1 5 10

<210> SEQ ID NO 38
<211> LENGTH: 11
<212> TYPE: PRT
<213> ORGANISM: Homo sapiens

<400> SEQUENCE: 38

Trp Ser His Cys Ser Arg Thr Cys Gly Ala Gly
1 5 10

<210> SEQ ID NO 39
<211> LENGTH: 11
<212> TYPE: PRT
<213> ORGANISM: Homo sapiens

<400> SEQUENCE: 39

Trp Thr Glu Cys Ser Val Thr Cys Gly Thr Gly
1 5 10

<210> SEQ ID NO 40
<211> LENGTH: 11
<212> TYPE: PRT
<213> ORGANISM: Homo sapiens

<400> SEQUENCE: 40

Trp Ser Glu Cys Ser Val Ser Cys Gly Gly Gly
1 5 10

<210> SEQ ID NO 41
<211> LENGTH: 11
<212> TYPE: PRT
<213> ORGANISM: Homo sapiens

<400> SEQUENCE: 41

Trp Ser Glu Cys Ser Thr Thr Cys Gly Leu Gly
1 5 10

<210> SEQ ID NO 42
<211> LENGTH: 11
<212> TYPE: PRT
<213> ORGANISM: Homo sapiens

<400> SEQUENCE: 42

Trp Ser Lys Cys Ser Arg Asn Cys Ser Gly Gly
1 5 10

<210> SEQ ID NO 43
<211> LENGTH: 11
<212> TYPE: PRT
<213> ORGANISM: Homo sapiens

<400> SEQUENCE: 43

Trp Ser Gln Cys Ser Arg Ser Cys Gly Gly Gly
1 5 10

<210> SEQ ID NO 44
<211> LENGTH: 11
<212> TYPE: PRT
<213> ORGANISM: Homo sapiens

<400> SEQUENCE: 44

Trp Asp Leu Cys Ser Thr Ser Cys Gly Gly Gly
1 5 10

<210> SEQ ID NO 45
<211> LENGTH: 11
<212> TYPE: PRT
<213> ORGANISM: Homo sapiens

<400> SEQUENCE: 45

Trp Ser Gln Cys Ser Arg Ser Cys Gly Gly Gly
1 5 10

<210> SEQ ID NO 46
<211> LENGTH: 11
<212> TYPE: PRT
<213> ORGANISM: Homo sapiens

<400> SEQUENCE: 46

Trp Ser Glu Cys Leu Val Thr Cys Gly Lys Gly
1 5 10

<210> SEQ ID NO 47
<211> LENGTH: 11
<212> TYPE: PRT
<213> ORGANISM: Homo sapiens

<400> SEQUENCE: 47

Trp Gly Pro Cys Thr Thr Thr Cys Gly His Gly
1 5 10

<210> SEQ ID NO 48
<211> LENGTH: 11
<212> TYPE: PRT
<213> ORGANISM: Homo sapiens

<400> SEQUENCE: 48

Trp Thr Pro Cys Ser Val Ser Cys Gly Arg Gly
1 5 10

<210> SEQ ID NO 49
<211> LENGTH: 11
<212> TYPE: PRT
<213> ORGANISM: Homo sapiens

<400> SEQUENCE: 49

Trp Ser Pro Cys Ser Ala Ser Cys Gly His Gly
1 5 10

<210> SEQ ID NO 50
<211> LENGTH: 11
<212> TYPE: PRT
<213> ORGANISM: Homo sapiens

<400> SEQUENCE: 50

Trp Gly Ser Cys Ser Ser Ser Cys Ser Gly Gly
1 5 10

<210> SEQ ID NO 51
<211> LENGTH: 11
<212> TYPE: PRT
<213> ORGANISM: Homo sapiens

<400> SEQUENCE: 51

Trp Gly Glu Cys Ser Gln Thr Cys Gly Gly Gly
1 5 10

<210> SEQ ID NO 52
<211> LENGTH: 11
<212> TYPE: PRT
<213> ORGANISM: Homo sapiens

<400> SEQUENCE: 52

Trp Thr Ser Cys Ser Ala Ser Cys Gly Lys Gly
1 5 10

<210> SEQ ID NO 53
<211> LENGTH: 11
<212> TYPE: PRT
<213> ORGANISM: Homo sapiens

<400> SEQUENCE: 53

Trp Asn Glu Cys Ser Val Thr Cys Gly Ser Gly
1 5 10

<210> SEQ ID NO 54
<211> LENGTH: 11
<212> TYPE: PRT
<213> ORGANISM: Homo sapiens

<400> SEQUENCE: 54

Trp Ser Lys Cys Ser Val Thr Cys Gly Ile Gly
1 5 10

<210> SEQ ID NO 55
<211> LENGTH: 11
<212> TYPE: PRT
<213> ORGANISM: Homo sapiens

<400> SEQUENCE: 55

Trp Ser Asp Cys Ser Arg Thr Cys Gly Gly Gly
1 5 10

<210> SEQ ID NO 56
<211> LENGTH: 11
<212> TYPE: PRT
<213> ORGANISM: Homo sapiens

<400> SEQUENCE: 56

Trp Thr Ala Cys Ser Val Ser Cys Gly Gly Gly
1 5 10

<210> SEQ ID NO 57
<211> LENGTH: 11
<212> TYPE: PRT
<213> ORGANISM: Homo sapiens

<400> SEQUENCE: 57

Trp Ser Gln Cys Thr Val Thr Cys Gly Arg Gly
1 5 10

<210> SEQ ID NO 58
<211> LENGTH: 11

<212> TYPE: PRT
<213> ORGANISM: Homo sapiens

<400> SEQUENCE: 58

Trp Ser Ala Cys Ser Thr Thr Cys Gly Pro Gly
1 5 10

<210> SEQ ID NO 59
<211> LENGTH: 11
<212> TYPE: PRT
<213> ORGANISM: Homo sapiens

<400> SEQUENCE: 59

Trp Gly Pro Cys Ser Ala Thr Cys Gly Val Gly
1 5 10

<210> SEQ ID NO 60
<211> LENGTH: 11
<212> TYPE: PRT
<213> ORGANISM: Homo sapiens

<400> SEQUENCE: 60

Trp Gln Gln Cys Ser Arg Thr Cys Gly Gly Gly
1 5 10

<210> SEQ ID NO 61
<211> LENGTH: 11
<212> TYPE: PRT
<213> ORGANISM: Homo sapiens

<400> SEQUENCE: 61

Trp Ser Lys Cys Ser Val Ser Cys Gly Val Gly
1 5 10

<210> SEQ ID NO 62
<211> LENGTH: 11
<212> TYPE: PRT
<213> ORGANISM: Homo sapiens

<400> SEQUENCE: 62

Trp Ser Gln Cys Ser Val Ser Cys Gly Glu Gly
1 5 10

<210> SEQ ID NO 63
<211> LENGTH: 11
<212> TYPE: PRT
<213> ORGANISM: Homo sapiens

<400> SEQUENCE: 63

Trp Lys Pro Cys Thr Ala Ala Cys Gly Arg Gly
1 5 10

<210> SEQ ID NO 64
<211> LENGTH: 11
<212> TYPE: PRT
<213> ORGANISM: Homo sapiens

<400> SEQUENCE: 64

Trp Ser Pro Cys Ser Thr Thr Cys Gly Ile Gly
1 5 10

<210> SEQ ID NO 65
<211> LENGTH: 11
<212> TYPE: PRT
<213> ORGANISM: Homo sapiens

<400> SEQUENCE: 65

Trp Glu Arg Cys Thr Ala Gln Cys Gly Gly Gly
1 5 10

<210> SEQ ID NO 66
<211> LENGTH: 11
<212> TYPE: PRT
<213> ORGANISM: Homo sapiens

<400> SEQUENCE: 66

Trp Ser Gln Cys Ser Arg Asp Cys Ser Arg Gly
1 5 10

<210> SEQ ID NO 67
<211> LENGTH: 11
<212> TYPE: PRT
<213> ORGANISM: Homo sapiens

<400> SEQUENCE: 67

Trp Thr Lys Cys Ser Ala Thr Cys Gly Gly Gly
1 5 10

<210> SEQ ID NO 68
<211> LENGTH: 11
<212> TYPE: PRT
<213> ORGANISM: Homo sapiens

<400> SEQUENCE: 68

Trp Ser Ala Cys Thr Arg Ser Cys Gly Gly Gly
1 5 10

<210> SEQ ID NO 69
<211> LENGTH: 11
<212> TYPE: PRT
<213> ORGANISM: Homo sapiens

<400> SEQUENCE: 69

Trp Cys Cys Cys Cys Phe Pro Cys Cys Arg Gly
1 5 10

<210> SEQ ID NO 70
<211> LENGTH: 11
<212> TYPE: PRT
<213> ORGANISM: Homo sapiens

<400> SEQUENCE: 70

Trp Ser Ala Cys Asn Val Arg Cys Gly Arg Gly
1 5 10

<210> SEQ ID NO 71
<211> LENGTH: 11
<212> TYPE: PRT
<213> ORGANISM: Homo sapiens

<400> SEQUENCE: 71

Trp Ala Ser Cys Ser Gln Pro Cys Gly Val Gly
1 5 10

<210> SEQ ID NO 72
<211> LENGTH: 11
<212> TYPE: PRT
<213> ORGANISM: Homo sapiens

<400> SEQUENCE: 72

Trp Thr Ser Cys Ser Arg Ser Cys Gly Pro Gly
1 5 10

<210> SEQ ID NO 73
<211> LENGTH: 11
<212> TYPE: PRT
<213> ORGANISM: Homo sapiens

<400> SEQUENCE: 73

Trp Ser Gln Cys Ser Val Arg Cys Gly Arg Gly
1 5 10

<210> SEQ ID NO 74
<211> LENGTH: 11
<212> TYPE: PRT
<213> ORGANISM: Homo sapiens

<400> SEQUENCE: 74

Trp Gly Glu Cys Ser Ser Glu Cys Gly Ser Gly
1 5 10

<210> SEQ ID NO 75
<211> LENGTH: 11
<212> TYPE: PRT
<213> ORGANISM: Homo sapiens

<400> SEQUENCE: 75

Trp Ser Pro Cys Ser Arg Ser Cys Gln Gly Gly
1 5 10

<210> SEQ ID NO 76
<211> LENGTH: 11
<212> TYPE: PRT
<213> ORGANISM: Homo sapiens

<400> SEQUENCE: 76

Trp Thr Arg Cys Ser Ser Ser Cys Gly Arg Gly
1 5 10

<210> SEQ ID NO 77
<211> LENGTH: 11
<212> TYPE: PRT
<213> ORGANISM: Homo sapiens

<400> SEQUENCE: 77

Trp Met Glu Cys Ser Val Ser Cys Gly Asp Gly
1 5 10

<210> SEQ ID NO 78
<211> LENGTH: 11
<212> TYPE: PRT
<213> ORGANISM: Homo sapiens

<400> SEQUENCE: 78

Trp Thr Ala Cys Ser Arg Ser Cys Gly Gly Gly
1 5 10

<210> SEQ ID NO 79
<211> LENGTH: 11
<212> TYPE: PRT
<213> ORGANISM: Homo sapiens

<400> SEQUENCE: 79

Trp Ser Glu Cys Ser Arg Thr Cys Gly Glu Gly 1 5 10

<210> SEQ ID NO 80
<211> LENGTH: 11
<212> TYPE: PRT
<213> ORGANISM: Homo sapiens

<400> SEQUENCE: 80

Trp Gly Pro Cys Ser Gly Ser Cys Gly Gln Gly
1 5 10

<210> SEQ ID NO 81
<211> LENGTH: 11
<212> TYPE: PRT
<213> ORGANISM: Homo sapiens

<400> SEQUENCE: 81

Trp Glu Arg Cys Asn Thr Thr Cys Gly Arg Gly
1 5 10

<210> SEQ ID NO 82
<211> LENGTH: 11
<212> TYPE: PRT
<213> ORGANISM: Homo sapiens

<400> SEQUENCE: 82

Trp Ser Glu Cys Thr Lys Thr Cys Gly Val Gly
1 5 10

<210> SEQ ID NO 83
<211> LENGTH: 11
<212> TYPE: PRT
<213> ORGANISM: Homo sapiens

<400> SEQUENCE: 83

Trp Gly Pro Cys Ser Gly Ser Cys Gly Pro Gly
1 5 10

<210> SEQ ID NO 84
<211> LENGTH: 11
<212> TYPE: PRT
<213> ORGANISM: Homo sapiens

<400> SEQUENCE: 84

Trp Ser Pro Cys Ser Asn Arg Cys Gly Arg Gly
1 5 10

<210> SEQ ID NO 85
<211> LENGTH: 11
<212> TYPE: PRT
<213> ORGANISM: Homo sapiens

<400> SEQUENCE: 85

Trp Ser Glu Cys Ser Arg Thr Cys Gly Gly Gly
1 5 10

<210> SEQ ID NO 86
<211> LENGTH: 11
<212> TYPE: PRT
<213> ORGANISM: Homo sapiens

<400> SEQUENCE: 86

Trp Thr Ala Cys Ser Ser Ser Cys Gly Gly Gly
1 5 10

<210> SEQ ID NO 87
<211> LENGTH: 11
<212> TYPE: PRT
<213> ORGANISM: Homo sapiens

<400> SEQUENCE: 87

Trp Ser Pro Cys Thr Val Thr Cys Gly Gln Gly
1               5                   10

<210> SEQ ID NO 88
<211> LENGTH: 11
<212> TYPE: PRT
<213> ORGANISM: Homo sapiens

<400> SEQUENCE: 88

Trp Ser Met Cys Ser Arg Thr Cys Gly Thr Gly
1               5                   10

<210> SEQ ID NO 89
<211> LENGTH: 11
<212> TYPE: PRT
<213> ORGANISM: Homo sapiens

<400> SEQUENCE: 89

Trp Glu Gly Cys Ser Val Gln Cys Gly Gly Gly
1               5                   10

<210> SEQ ID NO 90
<211> LENGTH: 11
<212> TYPE: PRT
<213> ORGANISM: Homo sapiens

<400> SEQUENCE: 90

Trp Ser Pro Cys Ser Ala Thr Cys Glu Lys Gly
1               5                   10

<210> SEQ ID NO 91
<211> LENGTH: 11
<212> TYPE: PRT
<213> ORGANISM: Homo sapiens

<400> SEQUENCE: 91

Trp Ser Gln Cys Ser Ala Ser Cys Gly Lys Gly
1               5                   10

<210> SEQ ID NO 92
<211> LENGTH: 11
<212> TYPE: PRT
<213> ORGANISM: Homo sapiens

<400> SEQUENCE: 92

Trp Ser Thr Cys Ser Ser Thr Cys Gly Lys Gly
1               5                   10

<210> SEQ ID NO 93
<211> LENGTH: 11
<212> TYPE: PRT
<213> ORGANISM: Homo sapiens

<400> SEQUENCE: 93

Trp Ser Pro Cys Ser Arg Thr Cys Gly Gly Gly
1               5                   10

<210> SEQ ID NO 94

<211> LENGTH: 11
<212> TYPE: PRT
<213> ORGANISM: Homo sapiens

<400> SEQUENCE: 94

Trp Ser Ala Cys Ser Arg Thr Cys Gly Gly Gly
1 5 10

<210> SEQ ID NO 95
<211> LENGTH: 11
<212> TYPE: PRT
<213> ORGANISM: Homo sapiens

<400> SEQUENCE: 95

Trp Ala Glu Cys Ser His Thr Cys Gly Lys Gly
1 5 10

<210> SEQ ID NO 96
<211> LENGTH: 11
<212> TYPE: PRT
<213> ORGANISM: Homo sapiens

<400> SEQUENCE: 96

Trp Ser Gln Cys Ser Val Thr Cys Glu Arg Gly
1 5 10

<210> SEQ ID NO 97
<211> LENGTH: 11
<212> TYPE: PRT
<213> ORGANISM: Homo sapiens

<400> SEQUENCE: 97

Trp Ser Gln Cys Thr Ala Ser Cys Gly Gly Gly
1 5 10

<210> SEQ ID NO 98
<211> LENGTH: 11
<212> TYPE: PRT
<213> ORGANISM: Homo sapiens

<400> SEQUENCE: 98

Trp Gly Pro Cys Ser Ala Ser Cys Gly Ser Gly
1 5 10

<210> SEQ ID NO 99
<211> LENGTH: 11
<212> TYPE: PRT
<213> ORGANISM: Homo sapiens

<400> SEQUENCE: 99

Trp Ser Pro Cys Ser Lys Ser Cys Gly Arg Gly
1 5 10

<210> SEQ ID NO 100
<211> LENGTH: 11
<212> TYPE: PRT
<213> ORGANISM: Homo sapiens

<400> SEQUENCE: 100

Trp Ser Pro Cys Ser Arg Thr Cys Ser Ala Gly
1 5 10

<210> SEQ ID NO 101
<211> LENGTH: 11
<212> TYPE: PRT

<213> ORGANISM: Homo sapiens

<400> SEQUENCE: 101

Trp Glu Asp Cys Asp Ala Thr Cys Gly Gly Gly
1 5 10

<210> SEQ ID NO 102
<211> LENGTH: 11
<212> TYPE: PRT
<213> ORGANISM: Homo sapiens

<400> SEQUENCE: 102

Trp Thr Pro Cys Ser Arg Thr Cys Gly Lys Gly
1 5 10

<210> SEQ ID NO 103
<211> LENGTH: 11
<212> TYPE: PRT
<213> ORGANISM: Homo sapiens

<400> SEQUENCE: 103

Trp Ser Lys Cys Ser Ile Thr Cys Gly Lys Gly
1 5 10

<210> SEQ ID NO 104
<211> LENGTH: 11
<212> TYPE: PRT
<213> ORGANISM: Homo sapiens

<400> SEQUENCE: 104

Trp Ser Glu Cys Ser Arg Thr Cys Gly Gly Gly
1 5 10

<210> SEQ ID NO 105
<211> LENGTH: 11
<212> TYPE: PRT
<213> ORGANISM: Homo sapiens

<400> SEQUENCE: 105

Trp Ser Thr Cys Ser Lys Ala Cys Ala Gly Gly
1 5 10

<210> SEQ ID NO 106
<211> LENGTH: 11
<212> TYPE: PRT
<213> ORGANISM: Homo sapiens

<400> SEQUENCE: 106

Trp Ser Gln Cys Ser Lys Thr Cys Gly Arg Gly
1 5 10

<210> SEQ ID NO 107
<211> LENGTH: 11
<212> TYPE: PRT
<213> ORGANISM: Homo sapiens

<400> SEQUENCE: 107

Trp Ser Glu Cys Ser Ala Thr Cys Gly Leu Gly
1 5 10

<210> SEQ ID NO 108
<211> LENGTH: 11
<212> TYPE: PRT
<213> ORGANISM: Homo sapiens

<400> SEQUENCE: 108

Trp Gln Gln Cys Thr Val Thr Cys Gly Gly Gly
1 5 10

<210> SEQ ID NO 109
<211> LENGTH: 11
<212> TYPE: PRT
<213> ORGANISM: Homo sapiens

<400> SEQUENCE: 109

Trp Ala Pro Cys Ser Lys Ala Cys Gly Gly Gly
1 5 10

<210> SEQ ID NO 110
<211> LENGTH: 11
<212> TYPE: PRT
<213> ORGANISM: Homo sapiens

<400> SEQUENCE: 110

Trp Ser Gln Cys Ser Ala Thr Cys Gly Glu Gly
1 5 10

<210> SEQ ID NO 111
<211> LENGTH: 11
<212> TYPE: PRT
<213> ORGANISM: Homo sapiens

<400> SEQUENCE: 111

Trp Ala Arg Cys Glu Asp Gly Cys Ile Arg Gly
1 5 10

<210> SEQ ID NO 112
<211> LENGTH: 11
<212> TYPE: PRT
<213> ORGANISM: Homo sapiens

<400> SEQUENCE: 112

Trp Arg Ala Cys Ser Val Thr Cys Gly Lys Gly
1 5 10

<210> SEQ ID NO 113
<211> LENGTH: 11
<212> TYPE: PRT
<213> ORGANISM: Homo sapiens

<400> SEQUENCE: 113

Trp Glu Glu Cys Thr Arg Ser Cys Gly Arg Gly
1 5 10

<210> SEQ ID NO 114
<211> LENGTH: 11
<212> TYPE: PRT
<213> ORGANISM: Homo sapiens

<400> SEQUENCE: 114

Trp Gly Thr Cys Ser Glu Ser Cys Gly Lys Gly
1 5 10

<210> SEQ ID NO 115
<211> LENGTH: 11
<212> TYPE: PRT
<213> ORGANISM: Homo sapiens

<400> SEQUENCE: 115

Trp Ser Ala Cys Ser Val Ser Cys Gly Gly Gly
1 5 10

<210> SEQ ID NO 116
<211> LENGTH: 11
<212> TYPE: PRT
<213> ORGANISM: Homo sapiens

<400> SEQUENCE: 116

Trp Gly Thr Cys Ser Arg Thr Cys Asn Gly Gly
1 5 10

<210> SEQ ID NO 117
<211> LENGTH: 11
<212> TYPE: PRT
<213> ORGANISM: Homo sapiens

<400> SEQUENCE: 117

Trp Ser Gln Cys Ser Ala Ser Cys Gly Gly Gly
1 5 10

<210> SEQ ID NO 118
<211> LENGTH: 11
<212> TYPE: PRT
<213> ORGANISM: Homo sapiens

<400> SEQUENCE: 118

Trp Leu Ser Cys Gly Ser Leu Cys Leu Leu Gly
1 5 10

<210> SEQ ID NO 119
<211> LENGTH: 11
<212> TYPE: PRT
<213> ORGANISM: Homo sapiens

<400> SEQUENCE: 119

Trp Gly Arg Cys Thr Gly Asp Cys Gly Pro Gly
1 5 10

<210> SEQ ID NO 120
<211> LENGTH: 11
<212> TYPE: PRT
<213> ORGANISM: Homo sapiens

<400> SEQUENCE: 120

Trp Ser Pro Cys Ser Lys Thr Cys Arg Ser Gly
1 5 10

<210> SEQ ID NO 121
<211> LENGTH: 11
<212> TYPE: PRT
<213> ORGANISM: Homo sapiens

<400> SEQUENCE: 121

Trp Thr Pro Cys Pro Arg Met Cys Gln Ala Gly
1 5 10

<210> SEQ ID NO 122
<211> LENGTH: 11
<212> TYPE: PRT
<213> ORGANISM: Homo sapiens

<400> SEQUENCE: 122

Trp Gly Ser Cys Ser Ser Ser Cys Gly Ile Gly
1 5 10

<210> SEQ ID NO 123
<211> LENGTH: 11
<212> TYPE: PRT
<213> ORGANISM: Homo sapiens

<400> SEQUENCE: 123

Trp Thr Glu Cys Ser Gln Thr Cys Gly His Gly
1 5 10

<210> SEQ ID NO 124
<211> LENGTH: 11
<212> TYPE: PRT
<213> ORGANISM: Homo sapiens

<400> SEQUENCE: 124

Trp Ser Thr Cys Glu Leu Thr Cys Ile Asp Gly
1 5 10

<210> SEQ ID NO 125
<211> LENGTH: 11
<212> TYPE: PRT
<213> ORGANISM: Homo sapiens

<400> SEQUENCE: 125

Trp Gly Asp Cys Ser Arg Thr Cys Gly Gly Gly
1 5 10

<210> SEQ ID NO 126
<211> LENGTH: 11
<212> TYPE: PRT
<213> ORGANISM: Homo sapiens

<400> SEQUENCE: 126

Trp Thr Lys Cys Ser Ala Gln Cys Ala Gly Gly
1 5 10

<210> SEQ ID NO 127
<211> LENGTH: 11
<212> TYPE: PRT
<213> ORGANISM: Homo sapiens

<400> SEQUENCE: 127

Trp Ser Leu Cys Ser Arg Ser Cys Asp Ala Gly
1 5 10

<210> SEQ ID NO 128
<211> LENGTH: 11
<212> TYPE: PRT
<213> ORGANISM: Homo sapiens

<400> SEQUENCE: 128

Trp Ser Glu Cys Thr Pro Ser Cys Gly Pro Gly
1 5 10

<210> SEQ ID NO 129
<211> LENGTH: 11
<212> TYPE: PRT
<213> ORGANISM: Homo sapiens

<400> SEQUENCE: 129

Trp Gly Glu Cys Ser Ala Gln Cys Gly Val Gly
1 5 10

<210> SEQ ID NO 130
<211> LENGTH: 11
<212> TYPE: PRT
<213> ORGANISM: Homo sapiens

<400> SEQUENCE: 130

Trp Ser Pro Cys Ser Ile Ser Cys Gly Met Gly
1 5 10

<210> SEQ ID NO 131
<211> LENGTH: 11
<212> TYPE: PRT
<213> ORGANISM: Homo sapiens

<400> SEQUENCE: 131

Trp Asp Glu Cys Ser Ala Thr Cys Gly Met Gly
1 5 10

<210> SEQ ID NO 132
<211> LENGTH: 11
<212> TYPE: PRT
<213> ORGANISM: Homo sapiens

<400> SEQUENCE: 132

Trp Ser Asp Cys Ser Val Thr Cys Gly Lys Gly
1 5 10

<210> SEQ ID NO 133
<211> LENGTH: 11
<212> TYPE: PRT
<213> ORGANISM: Homo sapiens

<400> SEQUENCE: 133

Trp Ser Glu Cys Asn Lys Ser Cys Gly Lys Gly
1 5 10

<210> SEQ ID NO 134
<211> LENGTH: 11
<212> TYPE: PRT
<213> ORGANISM: Homo sapiens

<400> SEQUENCE: 134

Trp Ser Glu Cys Thr Lys Leu Cys Gly Gly Gly
1 5 10

<210> SEQ ID NO 135
<211> LENGTH: 11
<212> TYPE: PRT
<213> ORGANISM: Homo sapiens

<400> SEQUENCE: 135

Trp Ser Gln Cys Ser Ala Thr Cys Gly Asp Gly
1 5 10

<210> SEQ ID NO 136
<211> LENGTH: 11
<212> TYPE: PRT
<213> ORGANISM: Homo sapiens

<400> SEQUENCE: 136

Trp Ala Leu Cys Ser Thr Ser Cys Gly Ile Gly
1 5 10

<210> SEQ ID NO 137
<211> LENGTH: 11

<212> TYPE: PRT
<213> ORGANISM: Homo sapiens

<400> SEQUENCE: 137

Trp Ser Lys Cys Ser Ser Asn Cys Gly Gly Gly
1 5 10

<210> SEQ ID NO 138
<211> LENGTH: 11
<212> TYPE: PRT
<213> ORGANISM: Homo sapiens

<400> SEQUENCE: 138

Trp Ser Ser Cys Ser Arg Asp Cys Glu Leu Gly
1 5 10

<210> SEQ ID NO 139
<211> LENGTH: 11
<212> TYPE: PRT
<213> ORGANISM: Homo sapiens

<400> SEQUENCE: 139

Trp Ser Pro Cys Ser Ala Ser Cys Gly Gly Gly
1 5 10

<210> SEQ ID NO 140
<211> LENGTH: 11
<212> TYPE: PRT
<213> ORGANISM: Homo sapiens

<400> SEQUENCE: 140

Trp Thr Glu Cys Ser Lys Ser Cys Asp Gly Gly
1 5 10

<210> SEQ ID NO 141
<211> LENGTH: 11
<212> TYPE: PRT
<213> ORGANISM: Homo sapiens

<400> SEQUENCE: 141

Trp Ser Glu Cys Leu Val Thr Cys Gly Lys Gly
1 5 10

<210> SEQ ID NO 142
<211> LENGTH: 11
<212> TYPE: PRT
<213> ORGANISM: Homo sapiens

<400> SEQUENCE: 142

Trp Val Gln Cys Ser Val Thr Cys Gly Gln Gly
1 5 10

<210> SEQ ID NO 143
<211> LENGTH: 11
<212> TYPE: PRT
<213> ORGANISM: Homo sapiens

<400> SEQUENCE: 143

Trp Thr Pro Cys Ser Ala Thr Cys Gly Lys Gly
1 5 10

<210> SEQ ID NO 144
<211> LENGTH: 11
<212> TYPE: PRT
<213> ORGANISM: Homo sapiens

<400> SEQUENCE: 144

Trp Ser Ser Cys Ser Val Thr Cys Gly Gln Gly
1 5 10

<210> SEQ ID NO 145
<211> LENGTH: 11
<212> TYPE: PRT
<213> ORGANISM: Homo sapiens

<400> SEQUENCE: 145

Trp Gly Ala Cys Ser Ser Thr Cys Ala Gly Gly
1 5 10

<210> SEQ ID NO 146
<211> LENGTH: 11
<212> TYPE: PRT
<213> ORGANISM: Homo sapiens

<400> SEQUENCE: 146

Trp Gly Glu Cys Thr Lys Leu Cys Gly Gly Gly
1 5 10

<210> SEQ ID NO 147
<211> LENGTH: 11
<212> TYPE: PRT
<213> ORGANISM: Homo sapiens

<400> SEQUENCE: 147

Trp Ser Ser Cys Ser Val Ser Cys Gly Arg Gly
1 5 10

<210> SEQ ID NO 148
<211> LENGTH: 11
<212> TYPE: PRT
<213> ORGANISM: Homo sapiens

<400> SEQUENCE: 148

Trp Ser Gln Cys Ser Val Ser Cys Gly Arg Gly
1 5 10

<210> SEQ ID NO 149
<211> LENGTH: 11
<212> TYPE: PRT
<213> ORGANISM: Homo sapiens

<400> SEQUENCE: 149

Trp Gln Glu Cys Thr Lys Thr Cys Gly Glu Gly
1 5 10

<210> SEQ ID NO 150
<211> LENGTH: 11
<212> TYPE: PRT
<213> ORGANISM: Homo sapiens

<400> SEQUENCE: 150

Trp Ser Glu Cys Ser Val Thr Cys Gly Lys Gly
1 5 10

<210> SEQ ID NO 151
<211> LENGTH: 11
<212> TYPE: PRT
<213> ORGANISM: Homo sapiens

<400> SEQUENCE: 151

Trp Gly Ser Cys Ser Val Ser Cys Gly Val Gly
1 5 10

<210> SEQ ID NO 152
<211> LENGTH: 11
<212> TYPE: PRT
<213> ORGANISM: Homo sapiens

<400> SEQUENCE: 152

Trp Gly Asp Cys Ser Arg Thr Cys Gly Gly Gly
1 5 10

<210> SEQ ID NO 153
<211> LENGTH: 11
<212> TYPE: PRT
<213> ORGANISM: Homo sapiens

<400> SEQUENCE: 153

Trp Gly Glu Cys Ser Lys Ser Cys Glu Leu Gly
1 5 10

<210> SEQ ID NO 154
<211> LENGTH: 11
<212> TYPE: PRT
<213> ORGANISM: Homo sapiens

<400> SEQUENCE: 154

Trp Ser Ser Cys Ser Lys Thr Cys Gly Lys Gly
1 5 10

<210> SEQ ID NO 155
<211> LENGTH: 11
<212> TYPE: PRT
<213> ORGANISM: Homo sapiens

<400> SEQUENCE: 155

Trp Ser Ile Cys Ser Arg Ser Cys Gly Met Gly
1 5 10

<210> SEQ ID NO 156
<211> LENGTH: 11
<212> TYPE: PRT
<213> ORGANISM: Homo sapiens

<400> SEQUENCE: 156

Trp Thr Lys Cys Thr Val Thr Cys Gly Arg Gly
1 5 10

<210> SEQ ID NO 157
<211> LENGTH: 11
<212> TYPE: PRT
<213> ORGANISM: Homo sapiens

<400> SEQUENCE: 157

Trp Gly Glu Cys Ser Arg Thr Cys Gly Gly Gly
1 5 10

<210> SEQ ID NO 158
<211> LENGTH: 11
<212> TYPE: PRT
<213> ORGANISM: Homo sapiens

<400> SEQUENCE: 158

Trp Ser Glu Cys Ser Ala Thr Cys Ala Gly Gly 1 5 10

<210> SEQ ID NO 159
<211> LENGTH: 11
<212> TYPE: PRT
<213> ORGANISM: Homo sapiens

<400> SEQUENCE: 159

Trp Gly Gln Cys Ser Arg Ser Cys Gly Gly Gly
1 5 10

<210> SEQ ID NO 160
<211> LENGTH: 11
<212> TYPE: PRT
<213> ORGANISM: Homo sapiens

<400> SEQUENCE: 160

Trp Leu Ala Cys Ser Arg Thr Cys Asp Thr Gly
1 5 10

<210> SEQ ID NO 161
<211> LENGTH: 11
<212> TYPE: PRT
<213> ORGANISM: Homo sapiens

<400> SEQUENCE: 161

Trp Gly Glu Cys Ser Arg Thr Cys Gly Gly Gly
1 5 10

<210> SEQ ID NO 162
<211> LENGTH: 11
<212> TYPE: PRT
<213> ORGANISM: Homo sapiens

<400> SEQUENCE: 162

Trp Ser Glu Cys Ser Ser Thr Cys Gly Ala Gly
1 5 10

<210> SEQ ID NO 163
<211> LENGTH: 11
<212> TYPE: PRT
<213> ORGANISM: Homo sapiens

<400> SEQUENCE: 163

Trp Ser Glu Cys Ser Lys Thr Cys Gly Ser Gly
1 5 10

<210> SEQ ID NO 164
<211> LENGTH: 11
<212> TYPE: PRT
<213> ORGANISM: Homo sapiens

<400> SEQUENCE: 164

Trp Thr Ser Cys Pro Ser Ser Cys Lys Glu Gly
1 5 10

<210> SEQ ID NO 165
<211> LENGTH: 11
<212> TYPE: PRT
<213> ORGANISM: Homo sapiens

<400> SEQUENCE: 165

Trp Ser Arg Cys Ser Lys Ser Cys Gly Ser Gly
1 5 10

<210> SEQ ID NO 166
<211> LENGTH: 11
<212> TYPE: PRT
<213> ORGANISM: Homo sapiens

<400> SEQUENCE: 166

```
Trp Ser Leu Cys Gln Leu Thr Cys Val Asn Gly
1               5                   10
```

<210> SEQ ID NO 167
<211> LENGTH: 6
<212> TYPE: PRT
<213> ORGANISM: Homo sapiens

<400> SEQUENCE: 167

```
Gly Lys Thr Thr Cys Leu
1               5
```

<210> SEQ ID NO 168
<211> LENGTH: 6
<212> TYPE: PRT
<213> ORGANISM: Homo sapiens

<400> SEQUENCE: 168

```
Gly Ala Asn Leu Cys Leu
1               5
```

<210> SEQ ID NO 169
<211> LENGTH: 6
<212> TYPE: PRT
<213> ORGANISM: Homo sapiens

<400> SEQUENCE: 169

```
Gly Glu Ala Gln Cys Leu
1               5
```

<210> SEQ ID NO 170
<211> LENGTH: 6
<212> TYPE: PRT
<213> ORGANISM: Homo sapiens

<400> SEQUENCE: 170

```
Gly Ala Thr Thr Cys Leu
1               5
```

<210> SEQ ID NO 171
<211> LENGTH: 6
<212> TYPE: PRT
<213> ORGANISM: Homo sapiens

<400> SEQUENCE: 171

```
Gly Ile Arg Ser Cys Leu
1               5
```

<210> SEQ ID NO 172
<211> LENGTH: 6
<212> TYPE: PRT
<213> ORGANISM: Homo sapiens

<400> SEQUENCE: 172

```
Gly His Arg Ile Cys Leu
1               5
```

<210> SEQ ID NO 173

<211> LENGTH: 6
<212> TYPE: PRT
<213> ORGANISM: Homo sapiens

<400> SEQUENCE: 173

Gly Glu Ala Val Cys Leu
1 5

<210> SEQ ID NO 174
<211> LENGTH: 6
<212> TYPE: PRT
<213> ORGANISM: Homo sapiens

<400> SEQUENCE: 174

Gly Asp His Pro Cys Leu
1 5

<210> SEQ ID NO 175
<211> LENGTH: 6
<212> TYPE: PRT
<213> ORGANISM: Homo sapiens

<400> SEQUENCE: 175

Gly Phe Val Gly Cys Leu
1 5

<210> SEQ ID NO 176
<211> LENGTH: 6
<212> TYPE: PRT
<213> ORGANISM: Homo sapiens

<400> SEQUENCE: 176

Gly Cys Val Cys Cys Leu
1 5

<210> SEQ ID NO 177
<211> LENGTH: 6
<212> TYPE: PRT
<213> ORGANISM: Homo sapiens

<400> SEQUENCE: 177

Gly Leu His Arg Cys Leu
1 5

<210> SEQ ID NO 178
<211> LENGTH: 6
<212> TYPE: PRT
<213> ORGANISM: Homo sapiens

<400> SEQUENCE: 178

Gly Leu Val Leu Cys Leu
1 5

<210> SEQ ID NO 179
<211> LENGTH: 6
<212> TYPE: PRT
<213> ORGANISM: Homo sapiens

<400> SEQUENCE: 179

Gly Cys Val Cys Cys Leu
1 5

<210> SEQ ID NO 180
<211> LENGTH: 6
<212> TYPE: PRT

<213> ORGANISM: Homo sapiens

<400> SEQUENCE: 180

Gly Pro Glu Asn Cys Leu
1 5

<210> SEQ ID NO 181
<211> LENGTH: 6
<212> TYPE: PRT
<213> ORGANISM: Homo sapiens

<400> SEQUENCE: 181

Gly Thr Pro Leu Cys Leu
1 5

<210> SEQ ID NO 182
<211> LENGTH: 6
<212> TYPE: PRT
<213> ORGANISM: Homo sapiens

<400> SEQUENCE: 182

Gly Thr Ile Tyr Cys Leu
1 5

<210> SEQ ID NO 183
<211> LENGTH: 6
<212> TYPE: PRT
<213> ORGANISM: Homo sapiens

<400> SEQUENCE: 183

Gly His His Val Cys Leu
1 5

<210> SEQ ID NO 184
<211> LENGTH: 6
<212> TYPE: PRT
<213> ORGANISM: Homo sapiens

<400> SEQUENCE: 184

Gly Leu Ile Thr Cys Leu
1 5

<210> SEQ ID NO 185
<211> LENGTH: 6
<212> TYPE: PRT
<213> ORGANISM: Homo sapiens

<400> SEQUENCE: 185

Gly Asn Lys Thr Cys Leu
1 5

<210> SEQ ID NO 186
<211> LENGTH: 6
<212> TYPE: PRT
<213> ORGANISM: Homo sapiens

<400> SEQUENCE: 186

Gly Leu Gln Ala Cys Leu
1 5

<210> SEQ ID NO 187
<211> LENGTH: 6
<212> TYPE: PRT
<213> ORGANISM: Homo sapiens

<400> SEQUENCE: 187

Gly Arg Asp Arg Cys Leu
1               5

<210> SEQ ID NO 188
<211> LENGTH: 6
<212> TYPE: PRT
<213> ORGANISM: Homo sapiens

<400> SEQUENCE: 188

Gly Phe Val Gly Cys Leu
1               5

<210> SEQ ID NO 189
<211> LENGTH: 6
<212> TYPE: PRT
<213> ORGANISM: Homo sapiens

<400> SEQUENCE: 189

Gly Asp Val Phe Cys Leu
1               5

<210> SEQ ID NO 190
<211> LENGTH: 6
<212> TYPE: PRT
<213> ORGANISM: Homo sapiens

<400> SEQUENCE: 190

Gly Ser Pro Val Cys Leu
1               5

<210> SEQ ID NO 191
<211> LENGTH: 6
<212> TYPE: PRT
<213> ORGANISM: Homo sapiens

<400> SEQUENCE: 191

Gly Ala Ile Tyr Cys Leu
1               5

<210> SEQ ID NO 192
<211> LENGTH: 6
<212> TYPE: PRT
<213> ORGANISM: Homo sapiens

<400> SEQUENCE: 192

Gly Ala Trp Leu Cys Leu
1               5

<210> SEQ ID NO 193
<211> LENGTH: 6
<212> TYPE: PRT
<213> ORGANISM: Homo sapiens

<400> SEQUENCE: 193

Gly Ser His Glu Cys Leu
1               5

<210> SEQ ID NO 194
<211> LENGTH: 6
<212> TYPE: PRT
<213> ORGANISM: Homo sapiens

<400> SEQUENCE: 194

Gly Ala Gly Leu Cys Leu
1 5

<210> SEQ ID NO 195
<211> LENGTH: 6
<212> TYPE: PRT
<213> ORGANISM: Homo sapiens

<400> SEQUENCE: 195

Gly Arg Asp Asp Cys Leu
1 5

<210> SEQ ID NO 196
<211> LENGTH: 6
<212> TYPE: PRT
<213> ORGANISM: Homo sapiens

<400> SEQUENCE: 196

Gly Thr Asn Ser Cys Leu
1 5

<210> SEQ ID NO 197
<211> LENGTH: 6
<212> TYPE: PRT
<213> ORGANISM: Homo sapiens

<400> SEQUENCE: 197

Gly Cys Asp Gly Cys Leu
1 5

<210> SEQ ID NO 198
<211> LENGTH: 6
<212> TYPE: PRT
<213> ORGANISM: Homo sapiens

<400> SEQUENCE: 198

Gly Leu Val Thr Cys Leu
1 5

<210> SEQ ID NO 199
<211> LENGTH: 6
<212> TYPE: PRT
<213> ORGANISM: Homo sapiens

<400> SEQUENCE: 199

Gly Pro Ser Tyr Cys Leu
1 5

<210> SEQ ID NO 200
<211> LENGTH: 6
<212> TYPE: PRT
<213> ORGANISM: Homo sapiens

<400> SEQUENCE: 200

Gly Asn Leu Glu Cys Leu
1 5

<210> SEQ ID NO 201
<211> LENGTH: 6
<212> TYPE: PRT
<213> ORGANISM: Homo sapiens

<400> SEQUENCE: 201

Gly His Arg Leu Cys Leu
1 5

<210> SEQ ID NO 202
<211> LENGTH: 6
<212> TYPE: PRT
<213> ORGANISM: Homo sapiens

<400> SEQUENCE: 202

Gly His Ser Glu Cys Leu
1 5

<210> SEQ ID NO 203
<211> LENGTH: 6
<212> TYPE: PRT
<213> ORGANISM: Homo sapiens

<400> SEQUENCE: 203

Gly Asn Gly Phe Cys Leu
1 5

<210> SEQ ID NO 204
<211> LENGTH: 6
<212> TYPE: PRT
<213> ORGANISM: Homo sapiens

<400> SEQUENCE: 204

Gly Lys Pro Met Cys Leu
1 5

<210> SEQ ID NO 205
<211> LENGTH: 6
<212> TYPE: PRT
<213> ORGANISM: Homo sapiens

<400> SEQUENCE: 205

Gly Phe Glu Asp Cys Leu
1 5

<210> SEQ ID NO 206
<211> LENGTH: 6
<212> TYPE: PRT
<213> ORGANISM: Homo sapiens

<400> SEQUENCE: 206

Gly Arg Thr Gln Cys Leu
1 5

<210> SEQ ID NO 207
<211> LENGTH: 6
<212> TYPE: PRT
<213> ORGANISM: Homo sapiens

<400> SEQUENCE: 207

Gly Trp Pro His Cys Leu
1 5

<210> SEQ ID NO 208
<211> LENGTH: 6
<212> TYPE: PRT
<213> ORGANISM: Homo sapiens

<400> SEQUENCE: 208

Gly Pro Ala Leu Cys Leu
1 5

<210> SEQ ID NO 209
<211> LENGTH: 6
<212> TYPE: PRT
<213> ORGANISM: Homo sapiens

<400> SEQUENCE: 209

Gly Cys Tyr Phe Cys Leu
1               5

<210> SEQ ID NO 210
<211> LENGTH: 6
<212> TYPE: PRT
<213> ORGANISM: Homo sapiens

<400> SEQUENCE: 210

Gly Arg Tyr Tyr Cys Leu
1               5

<210> SEQ ID NO 211
<211> LENGTH: 6
<212> TYPE: PRT
<213> ORGANISM: Homo sapiens

<400> SEQUENCE: 211

Gly Ser Leu Leu Cys Leu
1               5

<210> SEQ ID NO 212
<211> LENGTH: 6
<212> TYPE: PRT
<213> ORGANISM: Homo sapiens

<400> SEQUENCE: 212

Gly Lys Ile Val Cys Leu
1               5

<210> SEQ ID NO 213
<211> LENGTH: 6
<212> TYPE: PRT
<213> ORGANISM: Homo sapiens

<400> SEQUENCE: 213

Gly Lys Asp Phe Cys Leu
1               5

<210> SEQ ID NO 214
<211> LENGTH: 6
<212> TYPE: PRT
<213> ORGANISM: Homo sapiens

<400> SEQUENCE: 214

Gly Met Ile Met Cys Leu
1               5

<210> SEQ ID NO 215
<211> LENGTH: 6
<212> TYPE: PRT
<213> ORGANISM: Homo sapiens

<400> SEQUENCE: 215

Gly Phe Gly Glu Cys Leu
1               5

<210> SEQ ID NO 216
<211> LENGTH: 6

<212> TYPE: PRT
<213> ORGANISM: Homo sapiens

<400> SEQUENCE: 216

Gly Met Gly Val Cys Leu
1               5

<210> SEQ ID NO 217
<211> LENGTH: 6
<212> TYPE: PRT
<213> ORGANISM: Homo sapiens

<400> SEQUENCE: 217

Gly Leu Phe Gly Cys Leu
1               5

<210> SEQ ID NO 218
<211> LENGTH: 6
<212> TYPE: PRT
<213> ORGANISM: Homo sapiens

<400> SEQUENCE: 218

Gly Cys Gly Pro Cys Leu
1               5

<210> SEQ ID NO 219
<211> LENGTH: 6
<212> TYPE: PRT
<213> ORGANISM: Homo sapiens

<400> SEQUENCE: 219

Gly Phe Asp Asn Cys Leu
1               5

<210> SEQ ID NO 220
<211> LENGTH: 6
<212> TYPE: PRT
<213> ORGANISM: Homo sapiens

<400> SEQUENCE: 220

Gly Leu Gly Val Cys Leu
1               5

<210> SEQ ID NO 221
<211> LENGTH: 6
<212> TYPE: PRT
<213> ORGANISM: Homo sapiens

<400> SEQUENCE: 221

Gly Ser Gly Phe Cys Leu
1               5

<210> SEQ ID NO 222
<211> LENGTH: 6
<212> TYPE: PRT
<213> ORGANISM: Homo sapiens

<400> SEQUENCE: 222

Gly Thr Cys Met Cys Leu
1               5

<210> SEQ ID NO 223
<211> LENGTH: 6
<212> TYPE: PRT
<213> ORGANISM: Homo sapiens

<400> SEQUENCE: 223

Gly Leu Thr Pro Cys Leu
1               5

<210> SEQ ID NO 224
<211> LENGTH: 6
<212> TYPE: PRT
<213> ORGANISM: Homo sapiens

<400> SEQUENCE: 224

Gly Gln Leu Glu Cys Leu
1               5

<210> SEQ ID NO 225
<211> LENGTH: 6
<212> TYPE: PRT
<213> ORGANISM: Homo sapiens

<400> SEQUENCE: 225

Gly Val Ala Leu Cys Leu
1               5

<210> SEQ ID NO 226
<211> LENGTH: 6
<212> TYPE: PRT
<213> ORGANISM: Homo sapiens

<400> SEQUENCE: 226

Gly Val Ile Glu Cys Leu
1               5

<210> SEQ ID NO 227
<211> LENGTH: 6
<212> TYPE: PRT
<213> ORGANISM: Homo sapiens

<400> SEQUENCE: 227

Gly Asn Thr Ser Cys Leu
1               5

<210> SEQ ID NO 228
<211> LENGTH: 6
<212> TYPE: PRT
<213> ORGANISM: Homo sapiens

<400> SEQUENCE: 228

Gly Asn Ser Glu Cys Leu
1               5

<210> SEQ ID NO 229
<211> LENGTH: 6
<212> TYPE: PRT
<213> ORGANISM: Homo sapiens

<400> SEQUENCE: 229

Gly Ser Cys Leu Cys Leu
1               5

<210> SEQ ID NO 230
<211> LENGTH: 6
<212> TYPE: PRT
<213> ORGANISM: Homo sapiens

<400> SEQUENCE: 230

Gly Gly Ile Glu Cys Leu
1 5

<210> SEQ ID NO 231
<211> LENGTH: 6
<212> TYPE: PRT
<213> ORGANISM: Homo sapiens

<400> SEQUENCE: 231

Gly Glu Lys Val Cys Leu
1 5

<210> SEQ ID NO 232
<211> LENGTH: 6
<212> TYPE: PRT
<213> ORGANISM: Homo sapiens

<400> SEQUENCE: 232

Gly Asp Val Val Cys Leu
1 5

<210> SEQ ID NO 233
<211> LENGTH: 6
<212> TYPE: PRT
<213> ORGANISM: Homo sapiens

<400> SEQUENCE: 233

Gly Glu His Ile Cys Leu
1 5

<210> SEQ ID NO 234
<211> LENGTH: 6
<212> TYPE: PRT
<213> ORGANISM: Homo sapiens

<400> SEQUENCE: 234

Gly Glu Arg Arg Cys Leu
1 5

<210> SEQ ID NO 235
<211> LENGTH: 6
<212> TYPE: PRT
<213> ORGANISM: Homo sapiens

<400> SEQUENCE: 235

Gly Pro Ser Gly Cys Leu
1 5

<210> SEQ ID NO 236
<211> LENGTH: 6
<212> TYPE: PRT
<213> ORGANISM: Homo sapiens

<400> SEQUENCE: 236

Gly Tyr Arg Lys Cys Leu
1 5

<210> SEQ ID NO 237
<211> LENGTH: 6
<212> TYPE: PRT
<213> ORGANISM: Homo sapiens

<400> SEQUENCE: 237

Gly Met Ile Tyr Cys Leu 1 5

<210> SEQ ID NO 238
<211> LENGTH: 6
<212> TYPE: PRT
<213> ORGANISM: Homo sapiens

<400> SEQUENCE: 238

Gly Leu Leu Cys Cys Leu
1 5

<210> SEQ ID NO 239
<211> LENGTH: 6
<212> TYPE: PRT
<213> ORGANISM: Homo sapiens

<400> SEQUENCE: 239

Gly Gln Lys Thr Cys Leu
1 5

<210> SEQ ID NO 240
<211> LENGTH: 6
<212> TYPE: PRT
<213> ORGANISM: Homo sapiens

<400> SEQUENCE: 240

Gly Lys Glu Lys Cys Leu
1 5

<210> SEQ ID NO 241
<211> LENGTH: 6
<212> TYPE: PRT
<213> ORGANISM: Homo sapiens

<400> SEQUENCE: 241

Gly Ile Phe Leu Cys Leu
1 5

<210> SEQ ID NO 242
<211> LENGTH: 6
<212> TYPE: PRT
<213> ORGANISM: Homo sapiens

<400> SEQUENCE: 242

Gly Cys Tyr Phe Cys Leu
1 5

<210> SEQ ID NO 243
<211> LENGTH: 6
<212> TYPE: PRT
<213> ORGANISM: Homo sapiens

<400> SEQUENCE: 243

Gly Pro Val Met Cys Leu
1 5

<210> SEQ ID NO 244
<211> LENGTH: 6
<212> TYPE: PRT
<213> ORGANISM: Homo sapiens

<400> SEQUENCE: 244

Gly Leu Thr Pro Cys Leu
1 5

<210> SEQ ID NO 245
<211> LENGTH: 6
<212> TYPE: PRT
<213> ORGANISM: Homo sapiens

<400> SEQUENCE: 245

Gly Arg Arg Asp Cys Leu
1 5

<210> SEQ ID NO 246
<211> LENGTH: 6
<212> TYPE: PRT
<213> ORGANISM: Homo sapiens

<400> SEQUENCE: 246

Gly Gly Gly Ala Cys Leu
1 5

<210> SEQ ID NO 247
<211> LENGTH: 6
<212> TYPE: PRT
<213> ORGANISM: Homo sapiens

<400> SEQUENCE: 247

Gly Gly Gly Ser Cys Leu
1 5

<210> SEQ ID NO 248
<211> LENGTH: 6
<212> TYPE: PRT
<213> ORGANISM: Homo sapiens

<400> SEQUENCE: 248

Gly Glu Pro Tyr Cys Leu
1 5

<210> SEQ ID NO 249
<211> LENGTH: 6
<212> TYPE: PRT
<213> ORGANISM: Homo sapiens

<400> SEQUENCE: 249

Gly Ala Cys Leu Cys Leu
1 5

<210> SEQ ID NO 250
<211> LENGTH: 6
<212> TYPE: PRT
<213> ORGANISM: Homo sapiens

<400> SEQUENCE: 250

Gly Ala Gln Pro Cys Leu
1 5

<210> SEQ ID NO 251
<211> LENGTH: 6
<212> TYPE: PRT
<213> ORGANISM: Homo sapiens

<400> SEQUENCE: 251

Gly Tyr Gly His Cys Leu
1 5

<210> SEQ ID NO 252

<211> LENGTH: 6
<212> TYPE: PRT
<213> ORGANISM: Homo sapiens

<400> SEQUENCE: 252

Gly Met Gly Pro Cys Leu
1 5

<210> SEQ ID NO 253
<211> LENGTH: 6
<212> TYPE: PRT
<213> ORGANISM: Homo sapiens

<400> SEQUENCE: 253

Gly Cys His Gly Cys Leu
1 5

<210> SEQ ID NO 254
<211> LENGTH: 6
<212> TYPE: PRT
<213> ORGANISM: Homo sapiens

<400> SEQUENCE: 254

Gly Glu Gly Thr Cys Leu
1 5

<210> SEQ ID NO 255
<211> LENGTH: 6
<212> TYPE: PRT
<213> ORGANISM: Homo sapiens

<400> SEQUENCE: 255

Gly Phe Pro Arg Cys Leu
1 5

<210> SEQ ID NO 256
<211> LENGTH: 6
<212> TYPE: PRT
<213> ORGANISM: Homo sapiens

<400> SEQUENCE: 256

Gly Leu Asn Gln Cys Leu
1 5

<210> SEQ ID NO 257
<211> LENGTH: 6
<212> TYPE: PRT
<213> ORGANISM: Homo sapiens

<400> SEQUENCE: 257

Gly Arg Arg Arg Cys Leu
1 5

<210> SEQ ID NO 258
<211> LENGTH: 6
<212> TYPE: PRT
<213> ORGANISM: Homo sapiens

<400> SEQUENCE: 258

Gly Ile Glu Asp Cys Leu
1 5

<210> SEQ ID NO 259
<211> LENGTH: 6
<212> TYPE: PRT

<213> ORGANISM: Homo sapiens

<400> SEQUENCE: 259

Gly Asp Gly Tyr Cys Leu
1 5

<210> SEQ ID NO 260
<211> LENGTH: 6
<212> TYPE: PRT
<213> ORGANISM: Homo sapiens

<400> SEQUENCE: 260

Gly Phe Val Gly Cys Leu
1 5

<210> SEQ ID NO 261
<211> LENGTH: 6
<212> TYPE: PRT
<213> ORGANISM: Homo sapiens

<400> SEQUENCE: 261

Gly Gln Gly Leu Cys Leu
1 5

<210> SEQ ID NO 262
<211> LENGTH: 6
<212> TYPE: PRT
<213> ORGANISM: Homo sapiens

<400> SEQUENCE: 262

Gly Gln Leu Cys Cys Leu
1 5

<210> SEQ ID NO 263
<211> LENGTH: 6
<212> TYPE: PRT
<213> ORGANISM: Homo sapiens

<400> SEQUENCE: 263

Gly Ala Val Leu Cys Leu
1 5

<210> SEQ ID NO 264
<211> LENGTH: 6
<212> TYPE: PRT
<213> ORGANISM: Homo sapiens

<400> SEQUENCE: 264

Gly Gln Tyr Gln Cys Leu
1 5

<210> SEQ ID NO 265
<211> LENGTH: 6
<212> TYPE: PRT
<213> ORGANISM: Homo sapiens

<400> SEQUENCE: 265

Gly Phe Gly Val Cys Leu
1 5

<210> SEQ ID NO 266
<211> LENGTH: 6
<212> TYPE: PRT
<213> ORGANISM: Homo sapiens

<400> SEQUENCE: 266

Gly Gly Pro Ala Cys Leu
1               5

<210> SEQ ID NO 267
<211> LENGTH: 6
<212> TYPE: PRT
<213> ORGANISM: Homo sapiens

<400> SEQUENCE: 267

Gly Cys Ala Val Cys Leu
1               5

<210> SEQ ID NO 268
<211> LENGTH: 6
<212> TYPE: PRT
<213> ORGANISM: Homo sapiens

<400> SEQUENCE: 268

Gly Cys Thr Val Cys Leu
1               5

<210> SEQ ID NO 269
<211> LENGTH: 6
<212> TYPE: PRT
<213> ORGANISM: Homo sapiens

<400> SEQUENCE: 269

Gly Val Phe Ile Cys Leu
1               5

<210> SEQ ID NO 270
<211> LENGTH: 6
<212> TYPE: PRT
<213> ORGANISM: Homo sapiens

<400> SEQUENCE: 270

Gly Ala Leu Gln Cys Leu
1               5

<210> SEQ ID NO 271
<211> LENGTH: 6
<212> TYPE: PRT
<213> ORGANISM: Homo sapiens

<400> SEQUENCE: 271

Gly Lys Asp Gly Cys Leu
1               5

<210> SEQ ID NO 272
<211> LENGTH: 6
<212> TYPE: PRT
<213> ORGANISM: Homo sapiens

<400> SEQUENCE: 272

Gly Gln Met Glu Cys Leu
1               5

<210> SEQ ID NO 273
<211> LENGTH: 6
<212> TYPE: PRT
<213> ORGANISM: Homo sapiens

<400> SEQUENCE: 273

Gly Ala Lys Asp Cys Leu
1 5

<210> SEQ ID NO 274
<211> LENGTH: 6
<212> TYPE: PRT
<213> ORGANISM: Homo sapiens

<400> SEQUENCE: 274

Gly His Ile Val Cys Leu
1 5

<210> SEQ ID NO 275
<211> LENGTH: 6
<212> TYPE: PRT
<213> ORGANISM: Homo sapiens

<400> SEQUENCE: 275

Gly Ser Gly Thr Cys Leu
1 5

<210> SEQ ID NO 276
<211> LENGTH: 6
<212> TYPE: PRT
<213> ORGANISM: Homo sapiens

<400> SEQUENCE: 276

Gly Ala His Phe Cys Leu
1 5

<210> SEQ ID NO 277
<211> LENGTH: 6
<212> TYPE: PRT
<213> ORGANISM: Homo sapiens

<400> SEQUENCE: 277

Gly Pro Gln Glu Cys Leu
1 5

<210> SEQ ID NO 278
<211> LENGTH: 6
<212> TYPE: PRT
<213> ORGANISM: Homo sapiens

<400> SEQUENCE: 278

Gly Val Asp Gly Cys Leu
1 5

<210> SEQ ID NO 279
<211> LENGTH: 6
<212> TYPE: PRT
<213> ORGANISM: Homo sapiens

<400> SEQUENCE: 279

Gly Cys Leu Cys Cys Leu
1 5

<210> SEQ ID NO 280
<211> LENGTH: 6
<212> TYPE: PRT
<213> ORGANISM: Homo sapiens

<400> SEQUENCE: 280

Gly Phe Leu Gly Cys Leu
1 5

<210> SEQ ID NO 281
<211> LENGTH: 6
<212> TYPE: PRT
<213> ORGANISM: Homo sapiens

<400> SEQUENCE: 281

Gly Ala Thr Glu Cys Leu
1               5

<210> SEQ ID NO 282
<211> LENGTH: 6
<212> TYPE: PRT
<213> ORGANISM: Homo sapiens

<400> SEQUENCE: 282

Gly Leu Gly Ser Cys Leu
1               5

<210> SEQ ID NO 283
<211> LENGTH: 6
<212> TYPE: PRT
<213> ORGANISM: Homo sapiens

<400> SEQUENCE: 283

Gly Arg Ser Trp Cys Leu
1               5

<210> SEQ ID NO 284
<211> LENGTH: 6
<212> TYPE: PRT
<213> ORGANISM: Homo sapiens

<400> SEQUENCE: 284

Gly Ser Arg Leu Cys Leu
1               5

<210> SEQ ID NO 285
<211> LENGTH: 6
<212> TYPE: PRT
<213> ORGANISM: Homo sapiens

<400> SEQUENCE: 285

Gly Asn Leu Thr Cys Leu
1               5

<210> SEQ ID NO 286
<211> LENGTH: 6
<212> TYPE: PRT
<213> ORGANISM: Homo sapiens

<400> SEQUENCE: 286

Gly Lys Thr Thr Cys Leu
1               5

<210> SEQ ID NO 287
<211> LENGTH: 6
<212> TYPE: PRT
<213> ORGANISM: Homo sapiens

<400> SEQUENCE: 287

Gly Leu Pro Pro Cys Leu
1               5

<210> SEQ ID NO 288
<211> LENGTH: 6
<212> TYPE: PRT
<213> ORGANISM: Homo sapiens

<400> SEQUENCE: 288

Gly His Tyr Gln Cys Leu
1               5

<210> SEQ ID NO 289
<211> LENGTH: 6
<212> TYPE: PRT
<213> ORGANISM: Homo sapiens

<400> SEQUENCE: 289

Gly Ser Tyr Ile Cys Leu
1               5

<210> SEQ ID NO 290
<211> LENGTH: 6
<212> TYPE: PRT
<213> ORGANISM: Homo sapiens

<400> SEQUENCE: 290

Gly Met Tyr Gln Cys Leu
1               5

<210> SEQ ID NO 291
<211> LENGTH: 6
<212> TYPE: PRT
<213> ORGANISM: Homo sapiens

<400> SEQUENCE: 291

Gly Gln Gly Arg Cys Leu
1               5

<210> SEQ ID NO 292
<211> LENGTH: 6
<212> TYPE: PRT
<213> ORGANISM: Homo sapiens

<400> SEQUENCE: 292

Gly Glu Tyr Phe Cys Leu
1               5

<210> SEQ ID NO 293
<211> LENGTH: 6
<212> TYPE: PRT
<213> ORGANISM: Homo sapiens

<400> SEQUENCE: 293

Gly Gln Gln His Cys Leu
1               5

<210> SEQ ID NO 294
<211> LENGTH: 6
<212> TYPE: PRT
<213> ORGANISM: Homo sapiens

<400> SEQUENCE: 294

Gly Pro Ser Pro Cys Leu
1               5

<210> SEQ ID NO 295
<211> LENGTH: 6

<212> TYPE: PRT
<213> ORGANISM: Homo sapiens

<400> SEQUENCE: 295

Gly Val Gln Ile Cys Leu
1 5

<210> SEQ ID NO 296
<211> LENGTH: 6
<212> TYPE: PRT
<213> ORGANISM: Homo sapiens

<400> SEQUENCE: 296

Gly Ile Glu Ser Cys Leu
1 5

<210> SEQ ID NO 297
<211> LENGTH: 6
<212> TYPE: PRT
<213> ORGANISM: Homo sapiens

<400> SEQUENCE: 297

Gly Phe Val Asp Cys Leu
1 5

<210> SEQ ID NO 298
<211> LENGTH: 6
<212> TYPE: PRT
<213> ORGANISM: Homo sapiens

<400> SEQUENCE: 298

Gly Lys Ile Asn Cys Leu
1 5

<210> SEQ ID NO 299
<211> LENGTH: 6
<212> TYPE: PRT
<213> ORGANISM: Homo sapiens

<400> SEQUENCE: 299

Gly Met Leu Leu Cys Leu
1 5

<210> SEQ ID NO 300
<211> LENGTH: 6
<212> TYPE: PRT
<213> ORGANISM: Homo sapiens

<400> SEQUENCE: 300

Gly Thr Gln Val Cys Leu
1 5

<210> SEQ ID NO 301
<211> LENGTH: 6
<212> TYPE: PRT
<213> ORGANISM: Homo sapiens

<400> SEQUENCE: 301

Gly Ala Glu Ala Cys Leu
1 5

<210> SEQ ID NO 302
<211> LENGTH: 6
<212> TYPE: PRT
<213> ORGANISM: Homo sapiens

<400> SEQUENCE: 302

Gly Leu Ala Ser Cys Leu
1               5

<210> SEQ ID NO 303
<211> LENGTH: 6
<212> TYPE: PRT
<213> ORGANISM: Homo sapiens

<400> SEQUENCE: 303

Gly Phe Lys Val Cys Leu
1               5

<210> SEQ ID NO 304
<211> LENGTH: 6
<212> TYPE: PRT
<213> ORGANISM: Homo sapiens

<400> SEQUENCE: 304

Gly Leu Arg Asn Cys Leu
1               5

<210> SEQ ID NO 305
<211> LENGTH: 6
<212> TYPE: PRT
<213> ORGANISM: Homo sapiens

<400> SEQUENCE: 305

Gly Asp His Glu Cys Leu
1               5

<210> SEQ ID NO 306
<211> LENGTH: 6
<212> TYPE: PRT
<213> ORGANISM: Homo sapiens

<400> SEQUENCE: 306

Gly Cys Gln Met Cys Leu
1               5

<210> SEQ ID NO 307
<211> LENGTH: 6
<212> TYPE: PRT
<213> ORGANISM: Homo sapiens

<400> SEQUENCE: 307

Gly Leu Asn Val Cys Leu
1               5

<210> SEQ ID NO 308
<211> LENGTH: 6
<212> TYPE: PRT
<213> ORGANISM: Homo sapiens

<400> SEQUENCE: 308

Gly Tyr Arg Trp Cys Leu
1               5

<210> SEQ ID NO 309
<211> LENGTH: 6
<212> TYPE: PRT
<213> ORGANISM: Homo sapiens

<400> SEQUENCE: 309

Gly Ala Leu Val Cys Leu
1 5

<210> SEQ ID NO 310
<211> LENGTH: 6
<212> TYPE: PRT
<213> ORGANISM: Homo sapiens

<400> SEQUENCE: 310

Gly Thr Pro Leu Cys Leu
1 5

<210> SEQ ID NO 311
<211> LENGTH: 6
<212> TYPE: PRT
<213> ORGANISM: Homo sapiens

<400> SEQUENCE: 311

Gly Leu Leu Gly Cys Leu
1 5

<210> SEQ ID NO 312
<211> LENGTH: 6
<212> TYPE: PRT
<213> ORGANISM: Homo sapiens

<400> SEQUENCE: 312

Gly Tyr Ser Leu Cys Leu
1 5

<210> SEQ ID NO 313
<211> LENGTH: 6
<212> TYPE: PRT
<213> ORGANISM: Homo sapiens

<400> SEQUENCE: 313

Gly Val Pro Leu Cys Leu
1 5

<210> SEQ ID NO 314
<211> LENGTH: 6
<212> TYPE: PRT
<213> ORGANISM: Homo sapiens

<400> SEQUENCE: 314

Gly Gln Gly Arg Cys Leu
1 5

<210> SEQ ID NO 315
<211> LENGTH: 6
<212> TYPE: PRT
<213> ORGANISM: Homo sapiens

<400> SEQUENCE: 315

Gly Phe Val Trp Cys Leu
1 5

<210> SEQ ID NO 316
<211> LENGTH: 6
<212> TYPE: PRT
<213> ORGANISM: Homo sapiens

<400> SEQUENCE: 316

Gly Ile Leu Leu Cys Leu 1 5

<210> SEQ ID NO 317
<211> LENGTH: 6
<212> TYPE: PRT
<213> ORGANISM: Homo sapiens

<400> SEQUENCE: 317

Gly Val Leu Gly Cys Leu
1 5

<210> SEQ ID NO 318
<211> LENGTH: 6
<212> TYPE: PRT
<213> ORGANISM: Homo sapiens

<400> SEQUENCE: 318

Gly Asn Leu Ala Cys Leu
1 5

<210> SEQ ID NO 319
<211> LENGTH: 6
<212> TYPE: PRT
<213> ORGANISM: Homo sapiens

<400> SEQUENCE: 319

Gly Arg Phe Arg Cys Leu
1 5

<210> SEQ ID NO 320
<211> LENGTH: 6
<212> TYPE: PRT
<213> ORGANISM: Homo sapiens

<400> SEQUENCE: 320

Gly Thr Leu Leu Cys Leu
1 5

<210> SEQ ID NO 321
<211> LENGTH: 6
<212> TYPE: PRT
<213> ORGANISM: Homo sapiens

<400> SEQUENCE: 321

Gly Asn Glu Leu Cys Leu
1 5

<210> SEQ ID NO 322
<211> LENGTH: 6
<212> TYPE: PRT
<213> ORGANISM: Homo sapiens

<400> SEQUENCE: 322

Gly Ile Thr Arg Cys Leu
1 5

<210> SEQ ID NO 323
<211> LENGTH: 6
<212> TYPE: PRT
<213> ORGANISM: Homo sapiens

<400> SEQUENCE: 323

Gly Tyr Gly Ala Cys Leu
1 5

<210> SEQ ID NO 324
<211> LENGTH: 6
<212> TYPE: PRT
<213> ORGANISM: Homo sapiens

<400> SEQUENCE: 324

Gly Leu Val His Cys Leu
1               5

<210> SEQ ID NO 325
<211> LENGTH: 6
<212> TYPE: PRT
<213> ORGANISM: Homo sapiens

<400> SEQUENCE: 325

Gly Glu Tyr Gln Cys Leu
1               5

<210> SEQ ID NO 326
<211> LENGTH: 6
<212> TYPE: PRT
<213> ORGANISM: Homo sapiens

<400> SEQUENCE: 326

Gly Ser Thr His Cys Leu
1               5

<210> SEQ ID NO 327
<211> LENGTH: 6
<212> TYPE: PRT
<213> ORGANISM: Homo sapiens

<400> SEQUENCE: 327

Gly Ala Leu His Cys Leu
1               5

<210> SEQ ID NO 328
<211> LENGTH: 6
<212> TYPE: PRT
<213> ORGANISM: Homo sapiens

<400> SEQUENCE: 328

Gly Gly Lys His Cys Leu
1               5

<210> SEQ ID NO 329
<211> LENGTH: 6
<212> TYPE: PRT
<213> ORGANISM: Homo sapiens

<400> SEQUENCE: 329

Gly Gln Glu His Cys Leu
1               5

<210> SEQ ID NO 330
<211> LENGTH: 6
<212> TYPE: PRT
<213> ORGANISM: Homo sapiens

<400> SEQUENCE: 330

Gly Leu Asn Gln Cys Leu
1               5

<210> SEQ ID NO 331

<211> LENGTH: 6
<212> TYPE: PRT
<213> ORGANISM: Homo sapiens

<400> SEQUENCE: 331

Gly Lys Thr Lys Cys Leu
1 5

<210> SEQ ID NO 332
<211> LENGTH: 6
<212> TYPE: PRT
<213> ORGANISM: Homo sapiens

<400> SEQUENCE: 332

Gly Thr Gly Cys Cys Leu
1 5

<210> SEQ ID NO 333
<211> LENGTH: 6
<212> TYPE: PRT
<213> ORGANISM: Homo sapiens

<400> SEQUENCE: 333

Gly Pro Glu Glu Cys Leu
1 5

<210> SEQ ID NO 334
<211> LENGTH: 6
<212> TYPE: PRT
<213> ORGANISM: Homo sapiens

<400> SEQUENCE: 334

Gly Gly Pro Phe Cys Leu
1 5

<210> SEQ ID NO 335
<211> LENGTH: 6
<212> TYPE: PRT
<213> ORGANISM: Homo sapiens

<400> SEQUENCE: 335

Gly Gly Tyr Leu Cys Leu
1 5

<210> SEQ ID NO 336
<211> LENGTH: 6
<212> TYPE: PRT
<213> ORGANISM: Homo sapiens

<400> SEQUENCE: 336

Gly Pro Gly Asp Cys Leu
1 5

<210> SEQ ID NO 337
<211> LENGTH: 6
<212> TYPE: PRT
<213> ORGANISM: Homo sapiens

<400> SEQUENCE: 337

Gly Ala Pro Asn Cys Leu
1 5

<210> SEQ ID NO 338
<211> LENGTH: 6
<212> TYPE: PRT

<213> ORGANISM: Homo sapiens

<400> SEQUENCE: 338

Gly Ala Cys Gly Cys Leu
1 5

<210> SEQ ID NO 339
<211> LENGTH: 6
<212> TYPE: PRT
<213> ORGANISM: Homo sapiens

<400> SEQUENCE: 339

Gly Val Arg Leu Cys Leu
1 5

<210> SEQ ID NO 340
<211> LENGTH: 6
<212> TYPE: PRT
<213> ORGANISM: Homo sapiens

<400> SEQUENCE: 340

Gly Ile Asn Val Cys Leu
1 5

<210> SEQ ID NO 341
<211> LENGTH: 6
<212> TYPE: PRT
<213> ORGANISM: Homo sapiens

<400> SEQUENCE: 341

Gly Pro Leu Val Cys Leu
1 5

<210> SEQ ID NO 342
<211> LENGTH: 6
<212> TYPE: PRT
<213> ORGANISM: Homo sapiens

<400> SEQUENCE: 342

Gly Ala Lys Lys Cys Leu
1 5

<210> SEQ ID NO 343
<211> LENGTH: 6
<212> TYPE: PRT
<213> ORGANISM: Homo sapiens

<400> SEQUENCE: 343

Gly Thr Asn Glu Cys Leu
1 5

<210> SEQ ID NO 344
<211> LENGTH: 6
<212> TYPE: PRT
<213> ORGANISM: Homo sapiens

<400> SEQUENCE: 344

Gly Ala Asp Pro Cys Leu
1 5

<210> SEQ ID NO 345
<211> LENGTH: 6
<212> TYPE: PRT
<213> ORGANISM: Homo sapiens

<400> SEQUENCE: 345

Gly Glu Val Thr Cys Leu
1               5

<210> SEQ ID NO 346
<211> LENGTH: 6
<212> TYPE: PRT
<213> ORGANISM: Homo sapiens

<400> SEQUENCE: 346

Gly Ser Arg Arg Cys Leu
1               5

<210> SEQ ID NO 347
<211> LENGTH: 6
<212> TYPE: PRT
<213> ORGANISM: Homo sapiens

<400> SEQUENCE: 347

Gly Met Trp Gln Cys Leu
1               5

<210> SEQ ID NO 348
<211> LENGTH: 6
<212> TYPE: PRT
<213> ORGANISM: Homo sapiens

<400> SEQUENCE: 348

Gly Phe Tyr Trp Cys Leu
1               5

<210> SEQ ID NO 349
<211> LENGTH: 6
<212> TYPE: PRT
<213> ORGANISM: Homo sapiens

<400> SEQUENCE: 349

Gly Arg Lys Ile Cys Leu
1               5

<210> SEQ ID NO 350
<211> LENGTH: 6
<212> TYPE: PRT
<213> ORGANISM: Homo sapiens

<400> SEQUENCE: 350

Gly Asp Leu Gln Cys Leu
1               5

<210> SEQ ID NO 351
<211> LENGTH: 6
<212> TYPE: PRT
<213> ORGANISM: Homo sapiens

<400> SEQUENCE: 351

Gly Arg Lys Ile Cys Leu
1               5

<210> SEQ ID NO 352
<211> LENGTH: 6
<212> TYPE: PRT
<213> ORGANISM: Homo sapiens

<400> SEQUENCE: 352

Gly Glu Lys Arg Cys Leu
1 5

<210> SEQ ID NO 353
<211> LENGTH: 6
<212> TYPE: PRT
<213> ORGANISM: Homo sapiens

<400> SEQUENCE: 353

Gly Ala Phe Lys Cys Leu
1 5

<210> SEQ ID NO 354
<211> LENGTH: 6
<212> TYPE: PRT
<213> ORGANISM: Homo sapiens

<400> SEQUENCE: 354

Gly Ala Phe Arg Cys Leu
1 5

<210> SEQ ID NO 355
<211> LENGTH: 6
<212> TYPE: PRT
<213> ORGANISM: Homo sapiens

<400> SEQUENCE: 355

Gly Ala Phe Lys Cys Leu
1 5

<210> SEQ ID NO 356
<211> LENGTH: 6
<212> TYPE: PRT
<213> ORGANISM: Homo sapiens

<400> SEQUENCE: 356

Gly Ala Phe Arg Cys Leu
1 5

<210> SEQ ID NO 357
<211> LENGTH: 6
<212> TYPE: PRT
<213> ORGANISM: Homo sapiens

<400> SEQUENCE: 357

Gly Thr Tyr Leu Cys Leu
1 5

<210> SEQ ID NO 358
<211> LENGTH: 6
<212> TYPE: PRT
<213> ORGANISM: Homo sapiens

<400> SEQUENCE: 358

Gly Val Thr Thr Cys Leu
1 5

<210> SEQ ID NO 359
<211> LENGTH: 6
<212> TYPE: PRT
<213> ORGANISM: Homo sapiens

<400> SEQUENCE: 359

Gly Val Val Phe Cys Leu
1 5

<210> SEQ ID NO 360
<211> LENGTH: 6
<212> TYPE: PRT
<213> ORGANISM: Homo sapiens

<400> SEQUENCE: 360

Gly Val Arg Gln Cys Leu
1               5

<210> SEQ ID NO 361
<211> LENGTH: 6
<212> TYPE: PRT
<213> ORGANISM: Homo sapiens

<400> SEQUENCE: 361

Gly Leu Gly Asp Cys Leu
1               5

<210> SEQ ID NO 362
<211> LENGTH: 6
<212> TYPE: PRT
<213> ORGANISM: Homo sapiens

<400> SEQUENCE: 362

Gly Ile Gln Ser Cys Leu
1               5

<210> SEQ ID NO 363
<211> LENGTH: 6
<212> TYPE: PRT
<213> ORGANISM: Homo sapiens

<400> SEQUENCE: 363

Gly Ala Ser Gly Cys Leu
1               5

<210> SEQ ID NO 364
<211> LENGTH: 6
<212> TYPE: PRT
<213> ORGANISM: Homo sapiens

<400> SEQUENCE: 364

Gly Val Ala Gln Cys Leu
1               5

<210> SEQ ID NO 365
<211> LENGTH: 6
<212> TYPE: PRT
<213> ORGANISM: Homo sapiens

<400> SEQUENCE: 365

Gly Gly Phe Gln Cys Leu
1               5

<210> SEQ ID NO 366
<211> LENGTH: 6
<212> TYPE: PRT
<213> ORGANISM: Homo sapiens

<400> SEQUENCE: 366

Gly Lys Thr Leu Cys Leu
1               5

<210> SEQ ID NO 367
<211> LENGTH: 6
<212> TYPE: PRT
<213> ORGANISM: Homo sapiens

<400> SEQUENCE: 367

Gly Asp Gln Asp Cys Leu
1               5

<210> SEQ ID NO 368
<211> LENGTH: 6
<212> TYPE: PRT
<213> ORGANISM: Homo sapiens

<400> SEQUENCE: 368

Gly Val Thr Thr Cys Leu
1               5

<210> SEQ ID NO 369
<211> LENGTH: 6
<212> TYPE: PRT
<213> ORGANISM: Homo sapiens

<400> SEQUENCE: 369

Gly Gly Glu Ala Cys Leu
1               5

<210> SEQ ID NO 370
<211> LENGTH: 6
<212> TYPE: PRT
<213> ORGANISM: Homo sapiens

<400> SEQUENCE: 370

Gly His Ser Cys Cys Leu
1               5

<210> SEQ ID NO 371
<211> LENGTH: 6
<212> TYPE: PRT
<213> ORGANISM: Homo sapiens

<400> SEQUENCE: 371

Gly Gln Cys Leu Cys Leu
1               5

<210> SEQ ID NO 372
<211> LENGTH: 6
<212> TYPE: PRT
<213> ORGANISM: Homo sapiens

<400> SEQUENCE: 372

Gly Ile Cys Gln Cys Leu
1               5

<210> SEQ ID NO 373
<211> LENGTH: 6
<212> TYPE: PRT
<213> ORGANISM: Homo sapiens

<400> SEQUENCE: 373

Gly Glu Pro Cys Cys Leu
1               5

<210> SEQ ID NO 374
<211> LENGTH: 6

<212> TYPE: PRT
<213> ORGANISM: Homo sapiens

<400> SEQUENCE: 374

Gly Leu Ala Pro Cys Leu
1               5

<210> SEQ ID NO 375
<211> LENGTH: 6
<212> TYPE: PRT
<213> ORGANISM: Homo sapiens

<400> SEQUENCE: 375

Gly Ser Asp Asp Cys Leu
1               5

<210> SEQ ID NO 376
<211> LENGTH: 6
<212> TYPE: PRT
<213> ORGANISM: Homo sapiens

<400> SEQUENCE: 376

Gly Ala Thr Asp Cys Leu
1               5

<210> SEQ ID NO 377
<211> LENGTH: 6
<212> TYPE: PRT
<213> ORGANISM: Homo sapiens

<400> SEQUENCE: 377

Gly Ala Phe Arg Cys Leu
1               5

<210> SEQ ID NO 378
<211> LENGTH: 6
<212> TYPE: PRT
<213> ORGANISM: Homo sapiens

<400> SEQUENCE: 378

Gly Ala Phe Arg Cys Leu
1               5

<210> SEQ ID NO 379
<211> LENGTH: 6
<212> TYPE: PRT
<213> ORGANISM: Homo sapiens

<400> SEQUENCE: 379

Gly Ala Arg Val Cys Leu
1               5

<210> SEQ ID NO 380
<211> LENGTH: 6
<212> TYPE: PRT
<213> ORGANISM: Homo sapiens

<400> SEQUENCE: 380

Gly Ser Gly Pro Cys Leu
1               5

<210> SEQ ID NO 381
<211> LENGTH: 6
<212> TYPE: PRT
<213> ORGANISM: Homo sapiens

<400> SEQUENCE: 381

Gly Leu Gln Gly Cys Leu
1 5

<210> SEQ ID NO 382
<211> LENGTH: 6
<212> TYPE: PRT
<213> ORGANISM: Homo sapiens

<400> SEQUENCE: 382

Gly Asp Val Ile Cys Leu
1 5

<210> SEQ ID NO 383
<211> LENGTH: 6
<212> TYPE: PRT
<213> ORGANISM: Homo sapiens

<400> SEQUENCE: 383

Gly His Lys Asn Cys Leu
1 5

<210> SEQ ID NO 384
<211> LENGTH: 6
<212> TYPE: PRT
<213> ORGANISM: Homo sapiens

<400> SEQUENCE: 384

Gly Trp Asp Ser Cys Leu
1 5

<210> SEQ ID NO 385
<211> LENGTH: 6
<212> TYPE: PRT
<213> ORGANISM: Homo sapiens

<400> SEQUENCE: 385

Gly Arg Lys Ala Cys Leu
1 5

<210> SEQ ID NO 386
<211> LENGTH: 6
<212> TYPE: PRT
<213> ORGANISM: Homo sapiens

<400> SEQUENCE: 386

Gly Pro His Ala Cys Leu
1 5

<210> SEQ ID NO 387
<211> LENGTH: 6
<212> TYPE: PRT
<213> ORGANISM: Homo sapiens

<400> SEQUENCE: 387

Gly Pro Glu Ser Cys Leu
1 5

<210> SEQ ID NO 388
<211> LENGTH: 6
<212> TYPE: PRT
<213> ORGANISM: Homo sapiens

<400> SEQUENCE: 388

Gly Cys Gln Ile Cys Leu
1 5

<210> SEQ ID NO 389
<211> LENGTH: 6
<212> TYPE: PRT
<213> ORGANISM: Homo sapiens

<400> SEQUENCE: 389

Gly Arg Glu Leu Cys Leu
1 5

<210> SEQ ID NO 390
<211> LENGTH: 6
<212> TYPE: PRT
<213> ORGANISM: Homo sapiens

<400> SEQUENCE: 390

Gly Arg Arg Ala Cys Leu
1 5

<210> SEQ ID NO 391
<211> LENGTH: 6
<212> TYPE: PRT
<213> ORGANISM: Homo sapiens

<400> SEQUENCE: 391

Gly Pro Ser Trp Cys Leu
1 5

<210> SEQ ID NO 392
<211> LENGTH: 6
<212> TYPE: PRT
<213> ORGANISM: Homo sapiens

<400> SEQUENCE: 392

Gly Asp Leu Gln Cys Leu
1 5

<210> SEQ ID NO 393
<211> LENGTH: 6
<212> TYPE: PRT
<213> ORGANISM: Homo sapiens

<400> SEQUENCE: 393

Gly Arg Lys Ile Cys Leu
1 5

<210> SEQ ID NO 394
<211> LENGTH: 6
<212> TYPE: PRT
<213> ORGANISM: Homo sapiens

<400> SEQUENCE: 394

Gly Val Val His Cys Leu
1 5

<210> SEQ ID NO 395
<211> LENGTH: 6
<212> TYPE: PRT
<213> ORGANISM: Homo sapiens

<400> SEQUENCE: 395

Gly Gln Cys Glu Cys Leu 1 5

<210> SEQ ID NO 396
<211> LENGTH: 6
<212> TYPE: PRT
<213> ORGANISM: Homo sapiens

<400> SEQUENCE: 396

Gly Glu Tyr Thr Cys Leu
1 5

<210> SEQ ID NO 397
<211> LENGTH: 6
<212> TYPE: PRT
<213> ORGANISM: Homo sapiens

<400> SEQUENCE: 397

Gly Thr Ala Ala Cys Leu
1 5

<210> SEQ ID NO 398
<211> LENGTH: 6
<212> TYPE: PRT
<213> ORGANISM: Homo sapiens

<400> SEQUENCE: 398

Gly Leu Gly Asp Cys Leu
1 5

<210> SEQ ID NO 399
<211> LENGTH: 6
<212> TYPE: PRT
<213> ORGANISM: Homo sapiens

<400> SEQUENCE: 399

Gly Asn Asp Thr Cys Leu
1 5

<210> SEQ ID NO 400
<211> LENGTH: 6
<212> TYPE: PRT
<213> ORGANISM: Homo sapiens

<400> SEQUENCE: 400

Gly Val Phe Val Cys Leu
1 5

<210> SEQ ID NO 401
<211> LENGTH: 6
<212> TYPE: PRT
<213> ORGANISM: Homo sapiens

<400> SEQUENCE: 401

Gly Ile Gly Leu Cys Leu
1 5

<210> SEQ ID NO 402
<211> LENGTH: 6
<212> TYPE: PRT
<213> ORGANISM: Homo sapiens

<400> SEQUENCE: 402

Gly Pro Thr His Cys Leu
1 5

<210> SEQ ID NO 403
<211> LENGTH: 6
<212> TYPE: PRT
<213> ORGANISM: Homo sapiens

<400> SEQUENCE: 403

Gly Glu Val Ser Cys Leu
1 5

<210> SEQ ID NO 404
<211> LENGTH: 6
<212> TYPE: PRT
<213> ORGANISM: Homo sapiens

<400> SEQUENCE: 404

Gly Val Gly Leu Cys Leu
1 5

<210> SEQ ID NO 405
<211> LENGTH: 6
<212> TYPE: PRT
<213> ORGANISM: Homo sapiens

<400> SEQUENCE: 405

Gly Asp Val Lys Cys Leu
1 5

<210> SEQ ID NO 406
<211> LENGTH: 6
<212> TYPE: PRT
<213> ORGANISM: Homo sapiens

<400> SEQUENCE: 406

Gly Gly Gly Thr Cys Leu
1 5

<210> SEQ ID NO 407
<211> LENGTH: 6
<212> TYPE: PRT
<213> ORGANISM: Homo sapiens

<400> SEQUENCE: 407

Gly Pro Val Gly Cys Leu
1 5

<210> SEQ ID NO 408
<211> LENGTH: 6
<212> TYPE: PRT
<213> ORGANISM: Homo sapiens

<400> SEQUENCE: 408

Gly Leu Ser Asp Cys Leu
1 5

<210> SEQ ID NO 409
<211> LENGTH: 6
<212> TYPE: PRT
<213> ORGANISM: Homo sapiens

<400> SEQUENCE: 409

Gly Asn Tyr Thr Cys Leu
1 5

<210> SEQ ID NO 410

<211> LENGTH: 6
<212> TYPE: PRT
<213> ORGANISM: Homo sapiens

<400> SEQUENCE: 410

Gly Met Arg Gln Cys Leu
1 5

<210> SEQ ID NO 411
<211> LENGTH: 6
<212> TYPE: PRT
<213> ORGANISM: Homo sapiens

<400> SEQUENCE: 411

Gly Ala Arg Cys Cys Leu
1 5

<210> SEQ ID NO 412
<211> LENGTH: 6
<212> TYPE: PRT
<213> ORGANISM: Homo sapiens

<400> SEQUENCE: 412

Gly Asn Met Ile Cys Leu
1 5

<210> SEQ ID NO 413
<211> LENGTH: 6
<212> TYPE: PRT
<213> ORGANISM: Homo sapiens

<400> SEQUENCE: 413

Gly His Val Ile Cys Leu
1 5

<210> SEQ ID NO 414
<211> LENGTH: 6
<212> TYPE: PRT
<213> ORGANISM: Homo sapiens

<400> SEQUENCE: 414

Gly Tyr Met Asn Cys Leu
1 5

<210> SEQ ID NO 415
<211> LENGTH: 6
<212> TYPE: PRT
<213> ORGANISM: Homo sapiens

<400> SEQUENCE: 415

Gly Phe Asn Gln Cys Leu
1 5

<210> SEQ ID NO 416
<211> LENGTH: 6
<212> TYPE: PRT
<213> ORGANISM: Homo sapiens

<400> SEQUENCE: 416

Gly Asn Ser Val Cys Leu
1 5

<210> SEQ ID NO 417
<211> LENGTH: 6
<212> TYPE: PRT

<213> ORGANISM: Homo sapiens

<400> SEQUENCE: 417

Gly Cys Gly Cys Cys Leu
1 5

<210> SEQ ID NO 418
<211> LENGTH: 6
<212> TYPE: PRT
<213> ORGANISM: Homo sapiens

<400> SEQUENCE: 418

Gly Gly Lys Met Cys Leu
1 5

<210> SEQ ID NO 419
<211> LENGTH: 6
<212> TYPE: PRT
<213> ORGANISM: Homo sapiens

<400> SEQUENCE: 419

Gly Glu Asn Glu Cys Leu
1 5

<210> SEQ ID NO 420
<211> LENGTH: 6
<212> TYPE: PRT
<213> ORGANISM: Homo sapiens

<400> SEQUENCE: 420

Gly Gly Ala Lys Cys Leu
1 5

<210> SEQ ID NO 421
<211> LENGTH: 6
<212> TYPE: PRT
<213> ORGANISM: Homo sapiens

<400> SEQUENCE: 421

Gly Met Arg Gln Cys Leu
1 5

<210> SEQ ID NO 422
<211> LENGTH: 6
<212> TYPE: PRT
<213> ORGANISM: Homo sapiens

<400> SEQUENCE: 422

Gly Tyr Arg Lys Cys Leu
1 5

<210> SEQ ID NO 423
<211> LENGTH: 6
<212> TYPE: PRT
<213> ORGANISM: Homo sapiens

<400> SEQUENCE: 423

Gly Asp Asn Gly Cys Leu
1 5

<210> SEQ ID NO 424
<211> LENGTH: 6
<212> TYPE: PRT
<213> ORGANISM: Homo sapiens

<400> SEQUENCE: 424

Gly Asp Glu Asp Cys Leu
1 5

<210> SEQ ID NO 425
<211> LENGTH: 6
<212> TYPE: PRT
<213> ORGANISM: Homo sapiens

<400> SEQUENCE: 425

Gly Gln Lys Ala Cys Leu
1 5

<210> SEQ ID NO 426
<211> LENGTH: 6
<212> TYPE: PRT
<213> ORGANISM: Homo sapiens

<400> SEQUENCE: 426

Gly Lys Lys Ala Cys Leu
1 5

<210> SEQ ID NO 427
<211> LENGTH: 6
<212> TYPE: PRT
<213> ORGANISM: Homo sapiens

<400> SEQUENCE: 427

Gly Gly Lys Lys Cys Leu
1 5

<210> SEQ ID NO 428
<211> LENGTH: 6
<212> TYPE: PRT
<213> ORGANISM: Homo sapiens

<400> SEQUENCE: 428

Gly Tyr Gln Gln Cys Leu
1 5

<210> SEQ ID NO 429
<211> LENGTH: 6
<212> TYPE: PRT
<213> ORGANISM: Homo sapiens

<400> SEQUENCE: 429

Gly Leu Gly Ser Cys Leu
1 5

<210> SEQ ID NO 430
<211> LENGTH: 6
<212> TYPE: PRT
<213> ORGANISM: Homo sapiens

<400> SEQUENCE: 430

Gly Gly Leu Gln Cys Leu
1 5

<210> SEQ ID NO 431
<211> LENGTH: 6
<212> TYPE: PRT
<213> ORGANISM: Homo sapiens

<400> SEQUENCE: 431

Gly Thr Gly His Cys Leu
1 5

<210> SEQ ID NO 432
<211> LENGTH: 6
<212> TYPE: PRT
<213> ORGANISM: Homo sapiens

<400> SEQUENCE: 432

Gly Asp Pro Gly Cys Leu
1 5

<210> SEQ ID NO 433
<211> LENGTH: 6
<212> TYPE: PRT
<213> ORGANISM: Homo sapiens

<400> SEQUENCE: 433

Gly Lys Arg Ile Cys Leu
1 5

<210> SEQ ID NO 434
<211> LENGTH: 6
<212> TYPE: PRT
<213> ORGANISM: Homo sapiens

<400> SEQUENCE: 434

Gly Val Tyr Ala Cys Leu
1 5

<210> SEQ ID NO 435
<211> LENGTH: 6
<212> TYPE: PRT
<213> ORGANISM: Homo sapiens

<400> SEQUENCE: 435

Gly Val Val His Cys Leu
1 5

<210> SEQ ID NO 436
<211> LENGTH: 6
<212> TYPE: PRT
<213> ORGANISM: Homo sapiens

<400> SEQUENCE: 436

Gly Asp Ser Asp Cys Leu
1 5

<210> SEQ ID NO 437
<211> LENGTH: 6
<212> TYPE: PRT
<213> ORGANISM: Homo sapiens

<400> SEQUENCE: 437

Gly Asp Gly Asn Cys Leu
1 5

<210> SEQ ID NO 438
<211> LENGTH: 6
<212> TYPE: PRT
<213> ORGANISM: Homo sapiens

<400> SEQUENCE: 438

Gly Arg Phe Ile Cys Leu
1 5

<210> SEQ ID NO 439
<211> LENGTH: 6
<212> TYPE: PRT
<213> ORGANISM: Homo sapiens

<400> SEQUENCE: 439

Gly Glu Tyr Thr Cys Leu
1               5

<210> SEQ ID NO 440
<211> LENGTH: 6
<212> TYPE: PRT
<213> ORGANISM: Homo sapiens

<400> SEQUENCE: 440

Gly Pro Ser Arg Cys Leu
1               5

<210> SEQ ID NO 441
<211> LENGTH: 6
<212> TYPE: PRT
<213> ORGANISM: Homo sapiens

<400> SEQUENCE: 441

Gly Pro Gly Gln Cys Leu
1               5

<210> SEQ ID NO 442
<211> LENGTH: 6
<212> TYPE: PRT
<213> ORGANISM: Homo sapiens

<400> SEQUENCE: 442

Gly Trp Gly Leu Cys Leu
1               5

<210> SEQ ID NO 443
<211> LENGTH: 6
<212> TYPE: PRT
<213> ORGANISM: Homo sapiens

<400> SEQUENCE: 443

Gly Ser Phe Arg Cys Leu
1               5

<210> SEQ ID NO 444
<211> LENGTH: 6
<212> TYPE: PRT
<213> ORGANISM: Homo sapiens

<400> SEQUENCE: 444

Gly Ser Tyr Lys Cys Leu
1               5

<210> SEQ ID NO 445
<211> LENGTH: 6
<212> TYPE: PRT
<213> ORGANISM: Homo sapiens

<400> SEQUENCE: 445

Gly Arg Gly Gln Cys Leu
1               5

<210> SEQ ID NO 446
<211> LENGTH: 6
<212> TYPE: PRT
<213> ORGANISM: Homo sapiens

<400> SEQUENCE: 446

Gly Gly Ile Asn Cys Leu
1               5

<210> SEQ ID NO 447
<211> LENGTH: 6
<212> TYPE: PRT
<213> ORGANISM: Homo sapiens

<400> SEQUENCE: 447

Gly Tyr Arg Lys Cys Leu
1               5

<210> SEQ ID NO 448
<211> LENGTH: 6
<212> TYPE: PRT
<213> ORGANISM: Homo sapiens

<400> SEQUENCE: 448

Gly Tyr Arg Lys Cys Leu
1               5

<210> SEQ ID NO 449
<211> LENGTH: 6
<212> TYPE: PRT
<213> ORGANISM: Homo sapiens

<400> SEQUENCE: 449

Gly Val Val Thr Cys Leu
1               5

<210> SEQ ID NO 450
<211> LENGTH: 6
<212> TYPE: PRT
<213> ORGANISM: Homo sapiens

<400> SEQUENCE: 450

Gly Arg Tyr Leu Cys Leu
1               5

<210> SEQ ID NO 451
<211> LENGTH: 6
<212> TYPE: PRT
<213> ORGANISM: Homo sapiens

<400> SEQUENCE: 451

Gly Thr Tyr Thr Cys Leu
1               5

<210> SEQ ID NO 452
<211> LENGTH: 6
<212> TYPE: PRT
<213> ORGANISM: Homo sapiens

<400> SEQUENCE: 452

Gly Glu Tyr Thr Cys Leu
1               5

<210> SEQ ID NO 453
<211> LENGTH: 6

<212> TYPE: PRT
<213> ORGANISM: Homo sapiens

<400> SEQUENCE: 453

Gly Glu Tyr Thr Cys Leu
1 5

<210> SEQ ID NO 454
<211> LENGTH: 6
<212> TYPE: PRT
<213> ORGANISM: Homo sapiens

<400> SEQUENCE: 454

Gly Asn Pro Ile Cys Leu
1 5

<210> SEQ ID NO 455
<211> LENGTH: 6
<212> TYPE: PRT
<213> ORGANISM: Homo sapiens

<400> SEQUENCE: 455

Gly Phe Ser Ile Cys Leu
1 5

<210> SEQ ID NO 456
<211> LENGTH: 6
<212> TYPE: PRT
<213> ORGANISM: Homo sapiens

<400> SEQUENCE: 456

Gly Ile His Asn Cys Leu
1 5

<210> SEQ ID NO 457
<211> LENGTH: 6
<212> TYPE: PRT
<213> ORGANISM: Homo sapiens

<400> SEQUENCE: 457

Gly Gly Phe Arg Cys Leu
1 5

<210> SEQ ID NO 458
<211> LENGTH: 6
<212> TYPE: PRT
<213> ORGANISM: Homo sapiens

<400> SEQUENCE: 458

Gly Met Gly His Cys Leu
1 5

<210> SEQ ID NO 459
<211> LENGTH: 6
<212> TYPE: PRT
<213> ORGANISM: Homo sapiens

<400> SEQUENCE: 459

Gly Gln Ser Glu Cys Leu
1 5

<210> SEQ ID NO 460
<211> LENGTH: 6
<212> TYPE: PRT
<213> ORGANISM: Homo sapiens

<400> SEQUENCE: 460

Gly Gly Ile Tyr Cys Leu
1 5

<210> SEQ ID NO 461
<211> LENGTH: 6
<212> TYPE: PRT
<213> ORGANISM: Homo sapiens

<400> SEQUENCE: 461

Gly Pro Arg Ser Cys Leu
1 5

<210> SEQ ID NO 462
<211> LENGTH: 6
<212> TYPE: PRT
<213> ORGANISM: Homo sapiens

<400> SEQUENCE: 462

Gly Arg Gly Arg Cys Leu
1 5

<210> SEQ ID NO 463
<211> LENGTH: 6
<212> TYPE: PRT
<213> ORGANISM: Homo sapiens

<400> SEQUENCE: 463

Gly Arg Gly Val Cys Leu
1 5

<210> SEQ ID NO 464
<211> LENGTH: 6
<212> TYPE: PRT
<213> ORGANISM: Homo sapiens

<400> SEQUENCE: 464

Gly Ala Gly Cys Cys Leu
1 5

<210> SEQ ID NO 465
<211> LENGTH: 6
<212> TYPE: PRT
<213> ORGANISM: Homo sapiens

<400> SEQUENCE: 465

Gly Arg Arg Leu Cys Leu
1 5

<210> SEQ ID NO 466
<211> LENGTH: 6
<212> TYPE: PRT
<213> ORGANISM: Homo sapiens

<400> SEQUENCE: 466

Gly Thr Tyr Arg Cys Leu
1 5

<210> SEQ ID NO 467
<211> LENGTH: 6
<212> TYPE: PRT
<213> ORGANISM: Homo sapiens

<400> SEQUENCE: 467

Gly Ile Ala Ala Cys Leu
1 5

<210> SEQ ID NO 468
<211> LENGTH: 6
<212> TYPE: PRT
<213> ORGANISM: Homo sapiens

<400> SEQUENCE: 468

Gly Gly Glu Thr Cys Leu
1 5

<210> SEQ ID NO 469
<211> LENGTH: 6
<212> TYPE: PRT
<213> ORGANISM: Homo sapiens

<400> SEQUENCE: 469

Gly Gly Ile Tyr Cys Leu
1 5

<210> SEQ ID NO 470
<211> LENGTH: 6
<212> TYPE: PRT
<213> ORGANISM: Homo sapiens

<400> SEQUENCE: 470

Gly Leu Glu Glu Cys Leu
1 5

<210> SEQ ID NO 471
<211> LENGTH: 6
<212> TYPE: PRT
<213> ORGANISM: Homo sapiens

<400> SEQUENCE: 471

Gly Arg Trp Asn Cys Leu
1 5

<210> SEQ ID NO 472
<211> LENGTH: 6
<212> TYPE: PRT
<213> ORGANISM: Homo sapiens

<400> SEQUENCE: 472

Gly Ser Lys Phe Cys Leu
1 5

<210> SEQ ID NO 473
<211> LENGTH: 6
<212> TYPE: PRT
<213> ORGANISM: Homo sapiens

<400> SEQUENCE: 473

Gly Thr Arg Ser Cys Leu
1 5

<210> SEQ ID NO 474
<211> LENGTH: 6
<212> TYPE: PRT
<213> ORGANISM: Homo sapiens

<400> SEQUENCE: 474

Gly Ala Thr Glu Cys Leu 1 5

<210> SEQ ID NO 475
<211> LENGTH: 6
<212> TYPE: PRT
<213> ORGANISM: Homo sapiens

<400> SEQUENCE: 475

Gly Lys Leu Pro Cys Leu
1 5

<210> SEQ ID NO 476
<211> LENGTH: 6
<212> TYPE: PRT
<213> ORGANISM: Homo sapiens

<400> SEQUENCE: 476

Gly Gln Val Ala Cys Leu
1 5

<210> SEQ ID NO 477
<211> LENGTH: 6
<212> TYPE: PRT
<213> ORGANISM: Homo sapiens

<400> SEQUENCE: 477

Gly Ser Glu Leu Cys Leu
1 5

<210> SEQ ID NO 478
<211> LENGTH: 6
<212> TYPE: PRT
<213> ORGANISM: Homo sapiens

<400> SEQUENCE: 478

Gly Met Phe Pro Cys Leu
1 5

<210> SEQ ID NO 479
<211> LENGTH: 6
<212> TYPE: PRT
<213> ORGANISM: Homo sapiens

<400> SEQUENCE: 479

Gly Met Pro Gly Cys Leu
1 5

<210> SEQ ID NO 480
<211> LENGTH: 6
<212> TYPE: PRT
<213> ORGANISM: Homo sapiens

<400> SEQUENCE: 480

Gly Gln Tyr Gln Cys Leu
1 5

<210> SEQ ID NO 481
<211> LENGTH: 6
<212> TYPE: PRT
<213> ORGANISM: Homo sapiens

<400> SEQUENCE: 481

Gly Glu Lys Ile Cys Leu
1 5

<210> SEQ ID NO 482
<211> LENGTH: 6
<212> TYPE: PRT
<213> ORGANISM: Homo sapiens

<400> SEQUENCE: 482

Gly Lys Arg Cys Cys Leu
1               5

<210> SEQ ID NO 483
<211> LENGTH: 6
<212> TYPE: PRT
<213> ORGANISM: Homo sapiens

<400> SEQUENCE: 483

Gly Thr Val Lys Cys Leu
1               5

<210> SEQ ID NO 484
<211> LENGTH: 6
<212> TYPE: PRT
<213> ORGANISM: Homo sapiens

<400> SEQUENCE: 484

Gly Glu Tyr Arg Cys Leu
1               5

<210> SEQ ID NO 485
<211> LENGTH: 6
<212> TYPE: PRT
<213> ORGANISM: Homo sapiens

<400> SEQUENCE: 485

Gly Arg Tyr Phe Cys Leu
1               5

<210> SEQ ID NO 486
<211> LENGTH: 6
<212> TYPE: PRT
<213> ORGANISM: Homo sapiens

<400> SEQUENCE: 486

Gly Ile Arg Thr Cys Leu
1               5

<210> SEQ ID NO 487
<211> LENGTH: 6
<212> TYPE: PRT
<213> ORGANISM: Homo sapiens

<400> SEQUENCE: 487

Gly Thr Tyr Gln Cys Leu
1               5

<210> SEQ ID NO 488
<211> LENGTH: 6
<212> TYPE: PRT
<213> ORGANISM: Homo sapiens

<400> SEQUENCE: 488

Gly Ala Lys Tyr Cys Leu
1               5

<210> SEQ ID NO 489

<211> LENGTH: 6
<212> TYPE: PRT
<213> ORGANISM: Homo sapiens

<400> SEQUENCE: 489

Gly Leu Val Ile Cys Leu
1 5

<210> SEQ ID NO 490
<211> LENGTH: 6
<212> TYPE: PRT
<213> ORGANISM: Homo sapiens

<400> SEQUENCE: 490

Gly Asn Cys Ser Cys Leu
1 5

<210> SEQ ID NO 491
<211> LENGTH: 6
<212> TYPE: PRT
<213> ORGANISM: Homo sapiens

<400> SEQUENCE: 491

Gly Pro Ala Val Cys Leu
1 5

<210> SEQ ID NO 492
<211> LENGTH: 6
<212> TYPE: PRT
<213> ORGANISM: Homo sapiens

<400> SEQUENCE: 492

Gly Tyr Val Gly Cys Leu
1 5

<210> SEQ ID NO 493
<211> LENGTH: 6
<212> TYPE: PRT
<213> ORGANISM: Homo sapiens

<400> SEQUENCE: 493

Gly Tyr Arg Glu Cys Leu
1 5

<210> SEQ ID NO 494
<211> LENGTH: 6
<212> TYPE: PRT
<213> ORGANISM: Homo sapiens

<400> SEQUENCE: 494

Gly Ser Leu Asn Cys Leu
1 5

<210> SEQ ID NO 495
<211> LENGTH: 6
<212> TYPE: PRT
<213> ORGANISM: Homo sapiens

<400> SEQUENCE: 495

Gly Ala Glu Asn Cys Leu
1 5

<210> SEQ ID NO 496
<211> LENGTH: 6
<212> TYPE: PRT

<213> ORGANISM: Homo sapiens

<400> SEQUENCE: 496

Gly Arg Ala Val Cys Leu
1 5

<210> SEQ ID NO 497
<211> LENGTH: 6
<212> TYPE: PRT
<213> ORGANISM: Homo sapiens

<400> SEQUENCE: 497

Gly Arg Pro Leu Cys Leu
1 5

<210> SEQ ID NO 498
<211> LENGTH: 6
<212> TYPE: PRT
<213> ORGANISM: Homo sapiens

<400> SEQUENCE: 498

Gly Val Ala Ser Cys Leu
1 5

<210> SEQ ID NO 499
<211> LENGTH: 6
<212> TYPE: PRT
<213> ORGANISM: Homo sapiens

<400> SEQUENCE: 499

Gly Gln Ala Met Cys Leu
1 5

<210> SEQ ID NO 500
<211> LENGTH: 6
<212> TYPE: PRT
<213> ORGANISM: Homo sapiens

<400> SEQUENCE: 500

Gly Gln Ala Met Cys Leu
1 5

<210> SEQ ID NO 501
<211> LENGTH: 6
<212> TYPE: PRT
<213> ORGANISM: Homo sapiens

<400> SEQUENCE: 501

Gly Tyr Arg Lys Cys Leu
1 5

<210> SEQ ID NO 502
<211> LENGTH: 6
<212> TYPE: PRT
<213> ORGANISM: Homo sapiens

<400> SEQUENCE: 502

Gly Tyr Arg Lys Cys Leu
1 5

<210> SEQ ID NO 503
<211> LENGTH: 6
<212> TYPE: PRT
<213> ORGANISM: Homo sapiens

<400> SEQUENCE: 503

Gly Glu Tyr Arg Cys Leu
1               5

<210> SEQ ID NO 504
<211> LENGTH: 6
<212> TYPE: PRT
<213> ORGANISM: Homo sapiens

<400> SEQUENCE: 504

Gly Ser Tyr Arg Cys Leu
1               5

<210> SEQ ID NO 505
<211> LENGTH: 6
<212> TYPE: PRT
<213> ORGANISM: Homo sapiens

<400> SEQUENCE: 505

Gly Asn Gly Gln Cys Leu
1               5

<210> SEQ ID NO 506
<211> LENGTH: 6
<212> TYPE: PRT
<213> ORGANISM: Homo sapiens

<400> SEQUENCE: 506

Gly Ser Phe Tyr Cys Leu
1               5

<210> SEQ ID NO 507
<211> LENGTH: 6
<212> TYPE: PRT
<213> ORGANISM: Homo sapiens

<400> SEQUENCE: 507

Gly Ser Phe Lys Cys Leu
1               5

<210> SEQ ID NO 508
<211> LENGTH: 6
<212> TYPE: PRT
<213> ORGANISM: Homo sapiens

<400> SEQUENCE: 508

Gly Glu Tyr Arg Cys Leu
1               5

<210> SEQ ID NO 509
<211> LENGTH: 6
<212> TYPE: PRT
<213> ORGANISM: Homo sapiens

<400> SEQUENCE: 509

Gly Ser Tyr Asn Cys Leu
1               5

<210> SEQ ID NO 510
<211> LENGTH: 6
<212> TYPE: PRT
<213> ORGANISM: Homo sapiens

<400> SEQUENCE: 510

Gly Ser Phe Lys Cys Leu
1 5

<210> SEQ ID NO 511
<211> LENGTH: 6
<212> TYPE: PRT
<213> ORGANISM: Homo sapiens

<400> SEQUENCE: 511

Gly Gly Phe Gln Cys Leu
1 5

<210> SEQ ID NO 512
<211> LENGTH: 6
<212> TYPE: PRT
<213> ORGANISM: Homo sapiens

<400> SEQUENCE: 512

Gly Leu Thr Phe Cys Leu
1 5

<210> SEQ ID NO 513
<211> LENGTH: 6
<212> TYPE: PRT
<213> ORGANISM: Homo sapiens

<400> SEQUENCE: 513

Gly Ala Ala Leu Cys Leu
1 5

<210> SEQ ID NO 514
<211> LENGTH: 6
<212> TYPE: PRT
<213> ORGANISM: Homo sapiens

<400> SEQUENCE: 514

Gly Asp Tyr Val Cys Leu
1 5

<210> SEQ ID NO 515
<211> LENGTH: 6
<212> TYPE: PRT
<213> ORGANISM: Homo sapiens

<400> SEQUENCE: 515

Gly Tyr Arg Lys Cys Leu
1 5

<210> SEQ ID NO 516
<211> LENGTH: 6
<212> TYPE: PRT
<213> ORGANISM: Homo sapiens

<400> SEQUENCE: 516

Gly Asn Ile Ser Cys Leu
1 5

<210> SEQ ID NO 517
<211> LENGTH: 6
<212> TYPE: PRT
<213> ORGANISM: Homo sapiens

<400> SEQUENCE: 517

Gly Leu Leu Val Cys Leu
1 5

<210> SEQ ID NO 518
<211> LENGTH: 6
<212> TYPE: PRT
<213> ORGANISM: Homo sapiens

<400> SEQUENCE: 518

Gly Ser Arg Phe Cys Leu
1               5

<210> SEQ ID NO 519
<211> LENGTH: 6
<212> TYPE: PRT
<213> ORGANISM: Homo sapiens

<400> SEQUENCE: 519

Gly Leu Val Val Cys Leu
1               5

<210> SEQ ID NO 520
<211> LENGTH: 6
<212> TYPE: PRT
<213> ORGANISM: Homo sapiens

<400> SEQUENCE: 520

Gly Tyr Ile Leu Cys Leu
1               5

<210> SEQ ID NO 521
<211> LENGTH: 6
<212> TYPE: PRT
<213> ORGANISM: Homo sapiens

<400> SEQUENCE: 521

Gly Arg Val Lys Cys Leu
1               5

<210> SEQ ID NO 522
<211> LENGTH: 6
<212> TYPE: PRT
<213> ORGANISM: Homo sapiens

<400> SEQUENCE: 522

Gly Arg Val Lys Cys Leu
1               5

<210> SEQ ID NO 523
<211> LENGTH: 6
<212> TYPE: PRT
<213> ORGANISM: Homo sapiens

<400> SEQUENCE: 523

Gly Gln Cys Trp Cys Leu
1               5

<210> SEQ ID NO 524
<211> LENGTH: 6
<212> TYPE: PRT
<213> ORGANISM: Homo sapiens

<400> SEQUENCE: 524

Gly Arg Pro Pro Cys Leu
1               5

<210> SEQ ID NO 525
<211> LENGTH: 6
<212> TYPE: PRT
<213> ORGANISM: Homo sapiens

<400> SEQUENCE: 525

Gly Phe Pro Pro Cys Leu
1 5

<210> SEQ ID NO 526
<211> LENGTH: 6
<212> TYPE: PRT
<213> ORGANISM: Homo sapiens

<400> SEQUENCE: 526

Gly Cys Tyr Met Cys Leu
1 5

<210> SEQ ID NO 527
<211> LENGTH: 6
<212> TYPE: PRT
<213> ORGANISM: Homo sapiens

<400> SEQUENCE: 527

Gly Gln Ser Ala Cys Leu
1 5

<210> SEQ ID NO 528
<211> LENGTH: 6
<212> TYPE: PRT
<213> ORGANISM: Homo sapiens

<400> SEQUENCE: 528

Gly Arg Met Arg Cys Leu
1 5

<210> SEQ ID NO 529
<211> LENGTH: 6
<212> TYPE: PRT
<213> ORGANISM: Homo sapiens

<400> SEQUENCE: 529

Gly Gln Val Lys Cys Leu
1 5

<210> SEQ ID NO 530
<211> LENGTH: 6
<212> TYPE: PRT
<213> ORGANISM: Homo sapiens

<400> SEQUENCE: 530

Gly Lys Glu Ile Cys Leu
1 5

<210> SEQ ID NO 531
<211> LENGTH: 6
<212> TYPE: PRT
<213> ORGANISM: Homo sapiens

<400> SEQUENCE: 531

Gly Leu Val Ala Cys Leu
1 5

<210> SEQ ID NO 532
<211> LENGTH: 6

<212> TYPE: PRT
<213> ORGANISM: Homo sapiens

<400> SEQUENCE: 532

Gly Asp Val Pro Cys Leu
1 5

<210> SEQ ID NO 533
<211> LENGTH: 6
<212> TYPE: PRT
<213> ORGANISM: Homo sapiens

<400> SEQUENCE: 533

Gly Val Phe Asp Cys Leu
1 5

<210> SEQ ID NO 534
<211> LENGTH: 6
<212> TYPE: PRT
<213> ORGANISM: Homo sapiens

<400> SEQUENCE: 534

Gly Leu Ile Tyr Cys Leu
1 5

<210> SEQ ID NO 535
<211> LENGTH: 6
<212> TYPE: PRT
<213> ORGANISM: Homo sapiens

<400> SEQUENCE: 535

Gly Leu Phe Glu Cys Leu
1 5

<210> SEQ ID NO 536
<211> LENGTH: 6
<212> TYPE: PRT
<213> ORGANISM: Homo sapiens

<400> SEQUENCE: 536

Gly Ser Leu Arg Cys Leu
1 5

<210> SEQ ID NO 537
<211> LENGTH: 6
<212> TYPE: PRT
<213> ORGANISM: Homo sapiens

<400> SEQUENCE: 537

Gly Thr Ser Ile Cys Leu
1 5

<210> SEQ ID NO 538
<211> LENGTH: 6
<212> TYPE: PRT
<213> ORGANISM: Homo sapiens

<400> SEQUENCE: 538

Gly Ile Trp Gln Cys Leu
1 5

<210> SEQ ID NO 539
<211> LENGTH: 6
<212> TYPE: PRT
<213> ORGANISM: Homo sapiens

<400> SEQUENCE: 539

Gly Gly Lys Leu Cys Leu
1 5

<210> SEQ ID NO 540
<211> LENGTH: 6
<212> TYPE: PRT
<213> ORGANISM: Homo sapiens

<400> SEQUENCE: 540

Gly His Ile Tyr Cys Leu
1 5

<210> SEQ ID NO 541
<211> LENGTH: 6
<212> TYPE: PRT
<213> ORGANISM: Homo sapiens

<400> SEQUENCE: 541

Gly Glu Leu Tyr Cys Leu
1 5

<210> SEQ ID NO 542
<211> LENGTH: 6
<212> TYPE: PRT
<213> ORGANISM: Homo sapiens

<400> SEQUENCE: 542

Gly Thr Gln Phe Cys Leu
1 5

<210> SEQ ID NO 543
<211> LENGTH: 6
<212> TYPE: PRT
<213> ORGANISM: Homo sapiens

<400> SEQUENCE: 543

Gly Cys Ala Arg Cys Leu
1 5

<210> SEQ ID NO 544
<211> LENGTH: 6
<212> TYPE: PRT
<213> ORGANISM: Homo sapiens

<400> SEQUENCE: 544

Gly Cys Ser Cys Cys Leu
1 5

<210> SEQ ID NO 545
<211> LENGTH: 6
<212> TYPE: PRT
<213> ORGANISM: Homo sapiens

<400> SEQUENCE: 545

Gly Gly Gly Gly Cys Leu
1 5

<210> SEQ ID NO 546
<211> LENGTH: 6
<212> TYPE: PRT
<213> ORGANISM: Homo sapiens

<400> SEQUENCE: 546

Gly Leu Val Asn Cys Leu
1 5

<210> SEQ ID NO 547
<211> LENGTH: 6
<212> TYPE: PRT
<213> ORGANISM: Homo sapiens

<400> SEQUENCE: 547

Gly Lys Ile Thr Cys Leu
1 5

<210> SEQ ID NO 548
<211> LENGTH: 6
<212> TYPE: PRT
<213> ORGANISM: Homo sapiens

<400> SEQUENCE: 548

Gly Pro Cys Ser Cys Leu
1 5

<210> SEQ ID NO 549
<211> LENGTH: 6
<212> TYPE: PRT
<213> ORGANISM: Homo sapiens

<400> SEQUENCE: 549

Gly Trp Arg Gly Cys Leu
1 5

<210> SEQ ID NO 550
<211> LENGTH: 6
<212> TYPE: PRT
<213> ORGANISM: Homo sapiens

<400> SEQUENCE: 550

Gly Glu Thr Pro Cys Leu
1 5

<210> SEQ ID NO 551
<211> LENGTH: 6
<212> TYPE: PRT
<213> ORGANISM: Homo sapiens

<400> SEQUENCE: 551

Gly Gly Glu Leu Cys Leu
1 5

<210> SEQ ID NO 552
<211> LENGTH: 6
<212> TYPE: PRT
<213> ORGANISM: Homo sapiens

<400> SEQUENCE: 552

Gly Leu Leu Ile Cys Leu
1 5

<210> SEQ ID NO 553
<211> LENGTH: 6
<212> TYPE: PRT
<213> ORGANISM: Homo sapiens

<400> SEQUENCE: 553

Gly Gln Asp Thr Cys Leu 1 5

<210> SEQ ID NO 554
<211> LENGTH: 6
<212> TYPE: PRT
<213> ORGANISM: Homo sapiens

<400> SEQUENCE: 554

Gly Pro Glu Asn Cys Leu
1 5

<210> SEQ ID NO 555
<211> LENGTH: 6
<212> TYPE: PRT
<213> ORGANISM: Homo sapiens

<400> SEQUENCE: 555

Gly Ser Asp Cys Cys Leu
1 5

<210> SEQ ID NO 556
<211> LENGTH: 6
<212> TYPE: PRT
<213> ORGANISM: Homo sapiens

<400> SEQUENCE: 556

Gly Ser Val Leu Cys Leu
1 5

<210> SEQ ID NO 557
<211> LENGTH: 6
<212> TYPE: PRT
<213> ORGANISM: Homo sapiens

<400> SEQUENCE: 557

Gly Lys Arg Ala Cys Leu
1 5

<210> SEQ ID NO 558
<211> LENGTH: 6
<212> TYPE: PRT
<213> ORGANISM: Homo sapiens

<400> SEQUENCE: 558

Gly Phe Phe Thr Cys Leu
1 5

<210> SEQ ID NO 559
<211> LENGTH: 6
<212> TYPE: PRT
<213> ORGANISM: Homo sapiens

<400> SEQUENCE: 559

Gly Ala Asn Leu Cys Leu
1 5

<210> SEQ ID NO 560
<211> LENGTH: 6
<212> TYPE: PRT
<213> ORGANISM: Homo sapiens

<400> SEQUENCE: 560

Gly Thr Thr Leu Cys Leu
1 5

<210> SEQ ID NO 561
<211> LENGTH: 6
<212> TYPE: PRT
<213> ORGANISM: Homo sapiens

<400> SEQUENCE: 561

Gly Ala Ala Ala Cys Leu
1               5

<210> SEQ ID NO 562
<211> LENGTH: 6
<212> TYPE: PRT
<213> ORGANISM: Homo sapiens

<400> SEQUENCE: 562

Gly Leu Arg Gln Cys Leu
1               5

<210> SEQ ID NO 563
<211> LENGTH: 6
<212> TYPE: PRT
<213> ORGANISM: Homo sapiens

<400> SEQUENCE: 563

Gly Ala Ala Ala Cys Leu
1               5

<210> SEQ ID NO 564
<211> LENGTH: 6
<212> TYPE: PRT
<213> ORGANISM: Homo sapiens

<400> SEQUENCE: 564

Gly Leu Arg Gln Cys Leu
1               5

<210> SEQ ID NO 565
<211> LENGTH: 6
<212> TYPE: PRT
<213> ORGANISM: Homo sapiens

<400> SEQUENCE: 565

Gly Ala Ala Ala Cys Leu
1               5

<210> SEQ ID NO 566
<211> LENGTH: 6
<212> TYPE: PRT
<213> ORGANISM: Homo sapiens

<400> SEQUENCE: 566

Gly Leu Arg Gln Cys Leu
1               5

<210> SEQ ID NO 567
<211> LENGTH: 6
<212> TYPE: PRT
<213> ORGANISM: Homo sapiens

<400> SEQUENCE: 567

Gly His Gln Gln Cys Leu
1               5

<210> SEQ ID NO 568

<211> LENGTH: 6
<212> TYPE: PRT
<213> ORGANISM: Homo sapiens

<400> SEQUENCE: 568

Gly His Gln Gln Cys Leu
1 5

<210> SEQ ID NO 569
<211> LENGTH: 6
<212> TYPE: PRT
<213> ORGANISM: Homo sapiens

<400> SEQUENCE: 569

Gly Glu Gly Lys Cys Leu
1 5

<210> SEQ ID NO 570
<211> LENGTH: 6
<212> TYPE: PRT
<213> ORGANISM: Homo sapiens

<400> SEQUENCE: 570

Gly Cys Leu Asp Cys Leu
1 5

<210> SEQ ID NO 571
<211> LENGTH: 6
<212> TYPE: PRT
<213> ORGANISM: Homo sapiens

<400> SEQUENCE: 571

Gly Leu Val Glu Cys Leu
1 5

<210> SEQ ID NO 572
<211> LENGTH: 6
<212> TYPE: PRT
<213> ORGANISM: Homo sapiens

<400> SEQUENCE: 572

Gly Thr Lys Asp Cys Leu
1 5

<210> SEQ ID NO 573
<211> LENGTH: 6
<212> TYPE: PRT
<213> ORGANISM: Homo sapiens

<400> SEQUENCE: 573

Gly Leu Asn Gln Cys Leu
1 5

<210> SEQ ID NO 574
<211> LENGTH: 6
<212> TYPE: PRT
<213> ORGANISM: Homo sapiens

<400> SEQUENCE: 574

Gly Asp Asn Gly Cys Leu
1 5

<210> SEQ ID NO 575
<211> LENGTH: 6
<212> TYPE: PRT

<213> ORGANISM: Homo sapiens

<400> SEQUENCE: 575

Gly Arg Arg Ser Cys Leu
1 5

<210> SEQ ID NO 576
<211> LENGTH: 6
<212> TYPE: PRT
<213> ORGANISM: Homo sapiens

<400> SEQUENCE: 576

Gly Ala Phe Ala Cys Leu
1 5

<210> SEQ ID NO 577
<211> LENGTH: 6
<212> TYPE: PRT
<213> ORGANISM: Homo sapiens

<400> SEQUENCE: 577

Gly Lys Thr Lys Cys Leu
1 5

<210> SEQ ID NO 578
<211> LENGTH: 6
<212> TYPE: PRT
<213> ORGANISM: Homo sapiens

<400> SEQUENCE: 578

Gly Lys Arg Leu Cys Leu
1 5

<210> SEQ ID NO 579
<211> LENGTH: 6
<212> TYPE: PRT
<213> ORGANISM: Homo sapiens

<400> SEQUENCE: 579

Gly Lys Thr Arg Cys Leu
1 5

<210> SEQ ID NO 580
<211> LENGTH: 6
<212> TYPE: PRT
<213> ORGANISM: Homo sapiens

<400> SEQUENCE: 580

Gly Ile Trp Thr Cys Leu
1 5

<210> SEQ ID NO 581
<211> LENGTH: 6
<212> TYPE: PRT
<213> ORGANISM: Homo sapiens

<400> SEQUENCE: 581

Gly Lys Asp Trp Cys Leu
1 5

<210> SEQ ID NO 582
<211> LENGTH: 6
<212> TYPE: PRT
<213> ORGANISM: Homo sapiens

<400> SEQUENCE: 582

Gly Ile Ile Tyr Cys Leu
1               5

<210> SEQ ID NO 583
<211> LENGTH: 6
<212> TYPE: PRT
<213> ORGANISM: Homo sapiens

<400> SEQUENCE: 583

Gly Met Ala Asn Cys Leu
1               5

<210> SEQ ID NO 584
<211> LENGTH: 6
<212> TYPE: PRT
<213> ORGANISM: Homo sapiens

<400> SEQUENCE: 584

Gly Ile Leu Arg Cys Leu
1               5

<210> SEQ ID NO 585
<211> LENGTH: 6
<212> TYPE: PRT
<213> ORGANISM: Homo sapiens

<400> SEQUENCE: 585

Gly Glu Gly Pro Cys Leu
1               5

<210> SEQ ID NO 586
<211> LENGTH: 6
<212> TYPE: PRT
<213> ORGANISM: Homo sapiens

<400> SEQUENCE: 586

Gly Ala Trp Leu Cys Leu
1               5

<210> SEQ ID NO 587
<211> LENGTH: 6
<212> TYPE: PRT
<213> ORGANISM: Homo sapiens

<400> SEQUENCE: 587

Gly Pro Ile Glu Cys Leu
1               5

<210> SEQ ID NO 588
<211> LENGTH: 6
<212> TYPE: PRT
<213> ORGANISM: Homo sapiens

<400> SEQUENCE: 588

Gly Cys Asp Arg Cys Leu
1               5

<210> SEQ ID NO 589
<211> LENGTH: 6
<212> TYPE: PRT
<213> ORGANISM: Homo sapiens

<400> SEQUENCE: 589

Gly Gln Cys Pro Cys Leu
1 5

<210> SEQ ID NO 590
<211> LENGTH: 6
<212> TYPE: PRT
<213> ORGANISM: Homo sapiens

<400> SEQUENCE: 590

Gly Val Pro Gly Cys Leu
1 5

<210> SEQ ID NO 591
<211> LENGTH: 6
<212> TYPE: PRT
<213> ORGANISM: Homo sapiens

<400> SEQUENCE: 591

Gly Ser Ser Asp Cys Leu
1 5

<210> SEQ ID NO 592
<211> LENGTH: 6
<212> TYPE: PRT
<213> ORGANISM: Homo sapiens

<400> SEQUENCE: 592

Gly Phe Leu Lys Cys Leu
1 5

<210> SEQ ID NO 593
<211> LENGTH: 6
<212> TYPE: PRT
<213> ORGANISM: Homo sapiens

<400> SEQUENCE: 593

Gly Ser Ser Gln Cys Leu
1 5

<210> SEQ ID NO 594
<211> LENGTH: 6
<212> TYPE: PRT
<213> ORGANISM: Homo sapiens

<400> SEQUENCE: 594

Gly Leu Leu Leu Cys Leu
1 5

<210> SEQ ID NO 595
<211> LENGTH: 6
<212> TYPE: PRT
<213> ORGANISM: Homo sapiens

<400> SEQUENCE: 595

Gly Trp Gly Phe Cys Leu
1 5

<210> SEQ ID NO 596
<211> LENGTH: 6
<212> TYPE: PRT
<213> ORGANISM: Homo sapiens

<400> SEQUENCE: 596

Gly Ser Cys Gly Cys Leu
1 5

<210> SEQ ID NO 597
<211> LENGTH: 6
<212> TYPE: PRT
<213> ORGANISM: Homo sapiens

<400> SEQUENCE: 597

Gly Phe Pro Ala Cys Leu
1               5

<210> SEQ ID NO 598
<211> LENGTH: 6
<212> TYPE: PRT
<213> ORGANISM: Homo sapiens

<400> SEQUENCE: 598

Gly Leu Gln Trp Cys Leu
1               5

<210> SEQ ID NO 599
<211> LENGTH: 6
<212> TYPE: PRT
<213> ORGANISM: Homo sapiens

<400> SEQUENCE: 599

Gly Tyr Gly Glu Cys Leu
1               5

<210> SEQ ID NO 600
<211> LENGTH: 6
<212> TYPE: PRT
<213> ORGANISM: Homo sapiens

<400> SEQUENCE: 600

Gly Thr Ala Pro Cys Leu
1               5

<210> SEQ ID NO 601
<211> LENGTH: 6
<212> TYPE: PRT
<213> ORGANISM: Homo sapiens

<400> SEQUENCE: 601

Gly Ser Arg Val Cys Leu
1               5

<210> SEQ ID NO 602
<211> LENGTH: 6
<212> TYPE: PRT
<213> ORGANISM: Homo sapiens

<400> SEQUENCE: 602

Gly Ser Arg Val Cys Leu
1               5

<210> SEQ ID NO 603
<211> LENGTH: 6
<212> TYPE: PRT
<213> ORGANISM: Homo sapiens

<400> SEQUENCE: 603

Gly Ser Arg Val Cys Leu
1               5

<210> SEQ ID NO 604
<211> LENGTH: 6
<212> TYPE: PRT
<213> ORGANISM: Homo sapiens

<400> SEQUENCE: 604

Gly Thr Phe Ser Cys Leu
1               5

<210> SEQ ID NO 605
<211> LENGTH: 6
<212> TYPE: PRT
<213> ORGANISM: Homo sapiens

<400> SEQUENCE: 605

Gly Trp Lys Thr Cys Leu
1               5

<210> SEQ ID NO 606
<211> LENGTH: 6
<212> TYPE: PRT
<213> ORGANISM: Homo sapiens

<400> SEQUENCE: 606

Gly Asn Ala Ser Cys Leu
1               5

<210> SEQ ID NO 607
<211> LENGTH: 6
<212> TYPE: PRT
<213> ORGANISM: Homo sapiens

<400> SEQUENCE: 607

Gly Ala Gly Ile Cys Leu
1               5

<210> SEQ ID NO 608
<211> LENGTH: 6
<212> TYPE: PRT
<213> ORGANISM: Homo sapiens

<400> SEQUENCE: 608

Gly Glu Ser Val Cys Leu
1               5

<210> SEQ ID NO 609
<211> LENGTH: 6
<212> TYPE: PRT
<213> ORGANISM: Homo sapiens

<400> SEQUENCE: 609

Gly Val Leu Ala Cys Leu
1               5

<210> SEQ ID NO 610
<211> LENGTH: 6
<212> TYPE: PRT
<213> ORGANISM: Homo sapiens

<400> SEQUENCE: 610

Gly Gln Ile Phe Cys Leu
1               5

<210> SEQ ID NO 611
<211> LENGTH: 6

<212> TYPE: PRT
<213> ORGANISM: Homo sapiens

<400> SEQUENCE: 611

Gly Gln Ile Phe Cys Leu
1 5

<210> SEQ ID NO 612
<211> LENGTH: 6
<212> TYPE: PRT
<213> ORGANISM: Homo sapiens

<400> SEQUENCE: 612

Gly Val Thr Thr Cys Leu
1 5

<210> SEQ ID NO 613
<211> LENGTH: 6
<212> TYPE: PRT
<213> ORGANISM: Homo sapiens

<400> SEQUENCE: 613

Gly Lys Val Ser Cys Leu
1 5

<210> SEQ ID NO 614
<211> LENGTH: 6
<212> TYPE: PRT
<213> ORGANISM: Homo sapiens

<400> SEQUENCE: 614

Gly Ser Asp Gln Cys Leu
1 5

<210> SEQ ID NO 615
<211> LENGTH: 6
<212> TYPE: PRT
<213> ORGANISM: Homo sapiens

<400> SEQUENCE: 615

Gly Pro Leu Leu Cys Leu
1 5

<210> SEQ ID NO 616
<211> LENGTH: 6
<212> TYPE: PRT
<213> ORGANISM: Homo sapiens

<400> SEQUENCE: 616

Gly Gln Asp His Cys Leu
1 5

<210> SEQ ID NO 617
<211> LENGTH: 6
<212> TYPE: PRT
<213> ORGANISM: Homo sapiens

<400> SEQUENCE: 617

Gly Asp Glu Asp Cys Leu
1 5

<210> SEQ ID NO 618
<211> LENGTH: 6
<212> TYPE: PRT
<213> ORGANISM: Homo sapiens

<400> SEQUENCE: 618

Gly Phe Ser Gly Cys Leu
1 5

<210> SEQ ID NO 619
<211> LENGTH: 6
<212> TYPE: PRT
<213> ORGANISM: Homo sapiens

<400> SEQUENCE: 619

Gly Leu Leu Phe Cys Leu
1 5

<210> SEQ ID NO 620
<211> LENGTH: 6
<212> TYPE: PRT
<213> ORGANISM: Homo sapiens

<400> SEQUENCE: 620

Gly Pro Arg Pro Cys Leu
1 5

<210> SEQ ID NO 621
<211> LENGTH: 6
<212> TYPE: PRT
<213> ORGANISM: Homo sapiens

<400> SEQUENCE: 621

Gly His Gly Asp Cys Leu
1 5

<210> SEQ ID NO 622
<211> LENGTH: 6
<212> TYPE: PRT
<213> ORGANISM: Homo sapiens

<400> SEQUENCE: 622

Gly Val Ala Ala Cys Leu
1 5

<210> SEQ ID NO 623
<211> LENGTH: 6
<212> TYPE: PRT
<213> ORGANISM: Homo sapiens

<400> SEQUENCE: 623

Gly Gln Gln Thr Cys Leu
1 5

<210> SEQ ID NO 624
<211> LENGTH: 6
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Any amino acid

<400> SEQUENCE: 624

Gly Pro Gln Gly Cys Xaa
1 5

<210> SEQ ID NO 625
<211> LENGTH: 6

<212> TYPE: PRT
<213> ORGANISM: Homo sapiens

<400> SEQUENCE: 625

Gly Lys Gln Val Cys Leu
1               5

<210> SEQ ID NO 626
<211> LENGTH: 6
<212> TYPE: PRT
<213> ORGANISM: Homo sapiens

<400> SEQUENCE: 626

Gly Leu Gln Gly Cys Leu
1               5

<210> SEQ ID NO 627
<211> LENGTH: 6
<212> TYPE: PRT
<213> ORGANISM: Homo sapiens

<400> SEQUENCE: 627

Gly Leu Gly Arg Cys Leu
1               5

<210> SEQ ID NO 628
<211> LENGTH: 6
<212> TYPE: PRT
<213> ORGANISM: Homo sapiens

<400> SEQUENCE: 628

Gly Cys Pro Arg Cys Leu
1               5

<210> SEQ ID NO 629
<211> LENGTH: 6
<212> TYPE: PRT
<213> ORGANISM: Homo sapiens

<400> SEQUENCE: 629

Gly Ser Phe Arg Cys Leu
1               5

<210> SEQ ID NO 630
<211> LENGTH: 6
<212> TYPE: PRT
<213> ORGANISM: Homo sapiens

<400> SEQUENCE: 630

Gly Asp Asp Pro Cys Leu
1               5

<210> SEQ ID NO 631
<211> LENGTH: 6
<212> TYPE: PRT
<213> ORGANISM: Homo sapiens

<400> SEQUENCE: 631

Gly Thr Tyr Val Cys Leu
1               5

<210> SEQ ID NO 632
<211> LENGTH: 6
<212> TYPE: PRT
<213> ORGANISM: Homo sapiens

<400> SEQUENCE: 632

Gly Ala Asn Ile Cys Leu
1               5

<210> SEQ ID NO 633
<211> LENGTH: 6
<212> TYPE: PRT
<213> ORGANISM: Homo sapiens

<400> SEQUENCE: 633

Gly His Pro Asp Cys Leu
1               5

<210> SEQ ID NO 634
<211> LENGTH: 6
<212> TYPE: PRT
<213> ORGANISM: Homo sapiens

<400> SEQUENCE: 634

Gly Ser Ala Asp Cys Leu
1               5

<210> SEQ ID NO 635
<211> LENGTH: 6
<212> TYPE: PRT
<213> ORGANISM: Homo sapiens

<400> SEQUENCE: 635

Gly Pro Lys Ile Cys Leu
1               5

<210> SEQ ID NO 636
<211> LENGTH: 6
<212> TYPE: PRT
<213> ORGANISM: Homo sapiens

<400> SEQUENCE: 636

Gly Asp Thr Val Cys Leu
1               5

<210> SEQ ID NO 637
<211> LENGTH: 6
<212> TYPE: PRT
<213> ORGANISM: Homo sapiens

<400> SEQUENCE: 637

Gly Lys Glu Ile Cys Leu
1               5

<210> SEQ ID NO 638
<211> LENGTH: 6
<212> TYPE: PRT
<213> ORGANISM: Homo sapiens

<400> SEQUENCE: 638

Gly Leu Gly Asn Cys Leu
1               5

<210> SEQ ID NO 639
<211> LENGTH: 6
<212> TYPE: PRT
<213> ORGANISM: Homo sapiens

<400> SEQUENCE: 639

Gly Met Val His Cys Leu
1 5

<210> SEQ ID NO 640
<211> LENGTH: 6
<212> TYPE: PRT
<213> ORGANISM: Homo sapiens

<400> SEQUENCE: 640

Gly Pro Ala Pro Cys Leu
1 5

<210> SEQ ID NO 641
<211> LENGTH: 6
<212> TYPE: PRT
<213> ORGANISM: Homo sapiens

<400> SEQUENCE: 641

Gly Val Tyr Gln Cys Leu
1 5

<210> SEQ ID NO 642
<211> LENGTH: 6
<212> TYPE: PRT
<213> ORGANISM: Homo sapiens

<400> SEQUENCE: 642

Gly Asn Tyr Ser Cys Leu
1 5

<210> SEQ ID NO 643
<211> LENGTH: 6
<212> TYPE: PRT
<213> ORGANISM: Homo sapiens

<400> SEQUENCE: 643

Gly Val Arg Ala Cys Leu
1 5

<210> SEQ ID NO 644
<211> LENGTH: 6
<212> TYPE: PRT
<213> ORGANISM: Homo sapiens

<400> SEQUENCE: 644

Gly Ser Ile Thr Cys Leu
1 5

<210> SEQ ID NO 645
<211> LENGTH: 6
<212> TYPE: PRT
<213> ORGANISM: Homo sapiens

<400> SEQUENCE: 645

Gly Leu Asn Gln Cys Leu
1 5

<210> SEQ ID NO 646
<211> LENGTH: 6
<212> TYPE: PRT
<213> ORGANISM: Homo sapiens

<400> SEQUENCE: 646

Gly Met Ile Ser Cys Leu 1 5

<210> SEQ ID NO 647
<211> LENGTH: 6
<212> TYPE: PRT
<213> ORGANISM: Homo sapiens

<400> SEQUENCE: 647

Gly Leu Asn Gln Cys Leu
1 5

<210> SEQ ID NO 648
<211> LENGTH: 6
<212> TYPE: PRT
<213> ORGANISM: Homo sapiens

<400> SEQUENCE: 648

Gly Leu Asn Gln Cys Leu
1 5

<210> SEQ ID NO 649
<211> LENGTH: 6
<212> TYPE: PRT
<213> ORGANISM: Homo sapiens

<400> SEQUENCE: 649

Gly Leu Asn Gln Cys Leu
1 5

<210> SEQ ID NO 650
<211> LENGTH: 6
<212> TYPE: PRT
<213> ORGANISM: Homo sapiens

<400> SEQUENCE: 650

Gly Gly Phe Thr Cys Leu
1 5

<210> SEQ ID NO 651
<211> LENGTH: 6
<212> TYPE: PRT
<213> ORGANISM: Homo sapiens

<400> SEQUENCE: 651

Gly Glu Arg Ile Cys Leu
1 5

<210> SEQ ID NO 652
<211> LENGTH: 6
<212> TYPE: PRT
<213> ORGANISM: Homo sapiens

<400> SEQUENCE: 652

Gly Lys Thr Phe Cys Leu
1 5

<210> SEQ ID NO 653
<211> LENGTH: 6
<212> TYPE: PRT
<213> ORGANISM: Homo sapiens

<400> SEQUENCE: 653

Gly Lys Thr Phe Cys Leu
1 5

<210> SEQ ID NO 654
<211> LENGTH: 6
<212> TYPE: PRT
<213> ORGANISM: Homo sapiens

<400> SEQUENCE: 654

Gly Val Gln Thr Cys Leu
1               5

<210> SEQ ID NO 655
<211> LENGTH: 6
<212> TYPE: PRT
<213> ORGANISM: Homo sapiens

<400> SEQUENCE: 655

Gly Ser Asn Ser Cys Leu
1               5

<210> SEQ ID NO 656
<211> LENGTH: 6
<212> TYPE: PRT
<213> ORGANISM: Homo sapiens

<400> SEQUENCE: 656

Gly Asp Asn Asp Cys Leu
1               5

<210> SEQ ID NO 657
<211> LENGTH: 6
<212> TYPE: PRT
<213> ORGANISM: Homo sapiens

<400> SEQUENCE: 657

Gly Ser Tyr Lys Cys Leu
1               5

<210> SEQ ID NO 658
<211> LENGTH: 6
<212> TYPE: PRT
<213> ORGANISM: Homo sapiens

<400> SEQUENCE: 658

Gly Pro Cys Pro Cys Leu
1               5

<210> SEQ ID NO 659
<211> LENGTH: 6
<212> TYPE: PRT
<213> ORGANISM: Homo sapiens

<400> SEQUENCE: 659

Gly Ile Val Leu Cys Leu
1               5

<210> SEQ ID NO 660
<211> LENGTH: 6
<212> TYPE: PRT
<213> ORGANISM: Homo sapiens

<400> SEQUENCE: 660

Gly Ser Asn Leu Cys Leu
1               5

<210> SEQ ID NO 661

<211> LENGTH: 6
<212> TYPE: PRT
<213> ORGANISM: Homo sapiens

<400> SEQUENCE: 661

Gly Asp Gly Pro Cys Leu
1 5

<210> SEQ ID NO 662
<211> LENGTH: 6
<212> TYPE: PRT
<213> ORGANISM: Homo sapiens

<400> SEQUENCE: 662

Gly Gly Tyr Leu Cys Leu
1 5

<210> SEQ ID NO 663
<211> LENGTH: 6
<212> TYPE: PRT
<213> ORGANISM: Homo sapiens

<400> SEQUENCE: 663

Gly Phe Pro Glu Cys Leu
1 5

<210> SEQ ID NO 664
<211> LENGTH: 6
<212> TYPE: PRT
<213> ORGANISM: Homo sapiens

<400> SEQUENCE: 664

Gly Glu Pro Thr Cys Leu
1 5

<210> SEQ ID NO 665
<211> LENGTH: 6
<212> TYPE: PRT
<213> ORGANISM: Homo sapiens

<400> SEQUENCE: 665

Gly Leu Phe Gly Cys Leu
1 5

<210> SEQ ID NO 666
<211> LENGTH: 6
<212> TYPE: PRT
<213> ORGANISM: Homo sapiens

<400> SEQUENCE: 666

Gly Ile Tyr Tyr Cys Leu
1 5

<210> SEQ ID NO 667
<211> LENGTH: 6
<212> TYPE: PRT
<213> ORGANISM: Homo sapiens

<400> SEQUENCE: 667

Gly Cys Thr Leu Cys Leu
1 5

<210> SEQ ID NO 668
<211> LENGTH: 6
<212> TYPE: PRT

<213> ORGANISM: Homo sapiens

<400> SEQUENCE: 668

Gly Tyr Lys Met Cys Leu
1 5

<210> SEQ ID NO 669
<211> LENGTH: 6
<212> TYPE: PRT
<213> ORGANISM: Homo sapiens

<400> SEQUENCE: 669

Gly Asp Phe Ser Cys Leu
1 5

<210> SEQ ID NO 670
<211> LENGTH: 6
<212> TYPE: PRT
<213> ORGANISM: Homo sapiens

<400> SEQUENCE: 670

Gly Tyr Lys Leu Cys Leu
1 5

<210> SEQ ID NO 671
<211> LENGTH: 6
<212> TYPE: PRT
<213> ORGANISM: Homo sapiens

<400> SEQUENCE: 671

Gly Leu Arg Pro Cys Leu
1 5

<210> SEQ ID NO 672
<211> LENGTH: 6
<212> TYPE: PRT
<213> ORGANISM: Homo sapiens

<400> SEQUENCE: 672

Gly Glu Arg Glu Cys Leu
1 5

<210> SEQ ID NO 673
<211> LENGTH: 6
<212> TYPE: PRT
<213> ORGANISM: Homo sapiens

<400> SEQUENCE: 673

Gly Tyr Asn Arg Cys Leu
1 5

<210> SEQ ID NO 674
<211> LENGTH: 6
<212> TYPE: PRT
<213> ORGANISM: Homo sapiens

<400> SEQUENCE: 674

Gly Asp Asp Gln Cys Leu
1 5

<210> SEQ ID NO 675
<211> LENGTH: 6
<212> TYPE: PRT
<213> ORGANISM: Homo sapiens

<400> SEQUENCE: 675

Gly Ile Asn Arg Cys Leu
1               5

<210> SEQ ID NO 676
<211> LENGTH: 6
<212> TYPE: PRT
<213> ORGANISM: Homo sapiens

<400> SEQUENCE: 676

Gly Gly His Cys Cys Leu
1               5

<210> SEQ ID NO 677
<211> LENGTH: 6
<212> TYPE: PRT
<213> ORGANISM: Homo sapiens

<400> SEQUENCE: 677

Gly Tyr Leu Asp Cys Leu
1               5

<210> SEQ ID NO 678
<211> LENGTH: 6
<212> TYPE: PRT
<213> ORGANISM: Homo sapiens

<400> SEQUENCE: 678

Gly Ile Phe Ser Cys Leu
1               5

<210> SEQ ID NO 679
<211> LENGTH: 6
<212> TYPE: PRT
<213> ORGANISM: Homo sapiens

<400> SEQUENCE: 679

Gly Leu Glu Arg Cys Leu
1               5

<210> SEQ ID NO 680
<211> LENGTH: 6
<212> TYPE: PRT
<213> ORGANISM: Homo sapiens

<400> SEQUENCE: 680

Gly Gly Ala Gly Cys Leu
1               5

<210> SEQ ID NO 681
<211> LENGTH: 6
<212> TYPE: PRT
<213> ORGANISM: Homo sapiens

<400> SEQUENCE: 681

Gly Cys Met Ile Cys Leu
1               5

<210> SEQ ID NO 682
<211> LENGTH: 6
<212> TYPE: PRT
<213> ORGANISM: Homo sapiens

<400> SEQUENCE: 682

Gly Leu Phe Ser Cys Leu
1 5

<210> SEQ ID NO 683
<211> LENGTH: 6
<212> TYPE: PRT
<213> ORGANISM: Homo sapiens

<400> SEQUENCE: 683

Gly Leu Pro Arg Cys Leu
1 5

<210> SEQ ID NO 684
<211> LENGTH: 6
<212> TYPE: PRT
<213> ORGANISM: Homo sapiens

<400> SEQUENCE: 684

Gly Met Gly Ser Cys Leu
1 5

<210> SEQ ID NO 685
<211> LENGTH: 6
<212> TYPE: PRT
<213> ORGANISM: Homo sapiens

<400> SEQUENCE: 685

Gly Gly Leu Lys Cys Leu
1 5

<210> SEQ ID NO 686
<211> LENGTH: 6
<212> TYPE: PRT
<213> ORGANISM: Homo sapiens

<400> SEQUENCE: 686

Gly Asp Arg Phe Cys Leu
1 5

<210> SEQ ID NO 687
<211> LENGTH: 6
<212> TYPE: PRT
<213> ORGANISM: Homo sapiens

<400> SEQUENCE: 687

Gly Pro Pro Pro Cys Leu
1 5

<210> SEQ ID NO 688
<211> LENGTH: 6
<212> TYPE: PRT
<213> ORGANISM: Homo sapiens

<400> SEQUENCE: 688

Gly Gly Met Pro Cys Leu
1 5

<210> SEQ ID NO 689
<211> LENGTH: 6
<212> TYPE: PRT
<213> ORGANISM: Homo sapiens

<400> SEQUENCE: 689

Gly Gly Asp Ile Cys Leu
1 5

<210> SEQ ID NO 690
<211> LENGTH: 6
<212> TYPE: PRT
<213> ORGANISM: Homo sapiens

<400> SEQUENCE: 690

Gly Glu Val Phe Cys Leu
1               5

<210> SEQ ID NO 691
<211> LENGTH: 6
<212> TYPE: PRT
<213> ORGANISM: Homo sapiens

<400> SEQUENCE: 691

Gly His His Cys Cys Leu
1               5

<210> SEQ ID NO 692
<211> LENGTH: 6
<212> TYPE: PRT
<213> ORGANISM: Homo sapiens

<400> SEQUENCE: 692

Gly Leu Pro His Cys Leu
1               5

<210> SEQ ID NO 693
<211> LENGTH: 6
<212> TYPE: PRT
<213> ORGANISM: Homo sapiens

<400> SEQUENCE: 693

Gly Gly Leu Tyr Cys Leu
1               5

<210> SEQ ID NO 694
<211> LENGTH: 6
<212> TYPE: PRT
<213> ORGANISM: Homo sapiens

<400> SEQUENCE: 694

Gly Arg Cys Leu Cys Leu
1               5

<210> SEQ ID NO 695
<211> LENGTH: 6
<212> TYPE: PRT
<213> ORGANISM: Homo sapiens

<400> SEQUENCE: 695

Gly Gln Phe Asn Cys Leu
1               5

<210> SEQ ID NO 696
<211> LENGTH: 6
<212> TYPE: PRT
<213> ORGANISM: Homo sapiens

<400> SEQUENCE: 696

Gly Asn Leu Lys Cys Leu
1               5

<210> SEQ ID NO 697
<211> LENGTH: 6
<212> TYPE: PRT
<213> ORGANISM: Homo sapiens

<400> SEQUENCE: 697

Gly Arg Arg Asp Cys Leu
1               5

<210> SEQ ID NO 698
<211> LENGTH: 6
<212> TYPE: PRT
<213> ORGANISM: Homo sapiens

<400> SEQUENCE: 698

Gly Val Asn Ile Cys Leu
1               5

<210> SEQ ID NO 699
<211> LENGTH: 6
<212> TYPE: PRT
<213> ORGANISM: Homo sapiens

<400> SEQUENCE: 699

Gly Val Thr Thr Cys Leu
1               5

<210> SEQ ID NO 700
<211> LENGTH: 6
<212> TYPE: PRT
<213> ORGANISM: Homo sapiens

<400> SEQUENCE: 700

Gly Ile Glu Ile Cys Leu
1               5

<210> SEQ ID NO 701
<211> LENGTH: 6
<212> TYPE: PRT
<213> ORGANISM: Homo sapiens

<400> SEQUENCE: 701

Gly Val Ile Gly Cys Leu
1               5

<210> SEQ ID NO 702
<211> LENGTH: 6
<212> TYPE: PRT
<213> ORGANISM: Homo sapiens

<400> SEQUENCE: 702

Gly Asn Arg Ser Cys Leu
1               5

<210> SEQ ID NO 703
<211> LENGTH: 6
<212> TYPE: PRT
<213> ORGANISM: Homo sapiens

<400> SEQUENCE: 703

Gly Leu Asn Glu Cys Leu
1               5

<210> SEQ ID NO 704
<211> LENGTH: 6

<212> TYPE: PRT
<213> ORGANISM: Homo sapiens

<400> SEQUENCE: 704

Gly Thr Arg Ala Cys Leu
1 5

<210> SEQ ID NO 705
<211> LENGTH: 6
<212> TYPE: PRT
<213> ORGANISM: Homo sapiens

<400> SEQUENCE: 705

Gly Glu Leu Thr Cys Leu
1 5

<210> SEQ ID NO 706
<211> LENGTH: 6
<212> TYPE: PRT
<213> ORGANISM: Homo sapiens

<400> SEQUENCE: 706

Gly Leu Gly Ala Cys Leu
1 5

<210> SEQ ID NO 707
<211> LENGTH: 6
<212> TYPE: PRT
<213> ORGANISM: Homo sapiens

<400> SEQUENCE: 707

Gly Asp Pro His Cys Leu
1 5

<210> SEQ ID NO 708
<211> LENGTH: 6
<212> TYPE: PRT
<213> ORGANISM: Homo sapiens

<400> SEQUENCE: 708

Gly Ser Leu Pro Cys Leu
1 5

<210> SEQ ID NO 709
<211> LENGTH: 6
<212> TYPE: PRT
<213> ORGANISM: Homo sapiens

<400> SEQUENCE: 709

Gly Asn Phe Phe Cys Leu
1 5

<210> SEQ ID NO 710
<211> LENGTH: 6
<212> TYPE: PRT
<213> ORGANISM: Homo sapiens

<400> SEQUENCE: 710

Gly Ser Tyr Ser Cys Leu
1 5

<210> SEQ ID NO 711
<211> LENGTH: 6
<212> TYPE: PRT
<213> ORGANISM: Homo sapiens

<400> SEQUENCE: 711

Gly Glu Arg Pro Cys Leu
1               5

<210> SEQ ID NO 712
<211> LENGTH: 6
<212> TYPE: PRT
<213> ORGANISM: Homo sapiens

<400> SEQUENCE: 712

Gly Gln Pro Leu Cys Leu
1               5

<210> SEQ ID NO 713
<211> LENGTH: 6
<212> TYPE: PRT
<213> ORGANISM: Homo sapiens

<400> SEQUENCE: 713

Gly Ile Leu Pro Cys Leu
1               5

<210> SEQ ID NO 714
<211> LENGTH: 6
<212> TYPE: PRT
<213> ORGANISM: Homo sapiens

<400> SEQUENCE: 714

Gly Arg Gly Gln Cys Leu
1               5

<210> SEQ ID NO 715
<211> LENGTH: 6
<212> TYPE: PRT
<213> ORGANISM: Homo sapiens

<400> SEQUENCE: 715

Gly Gln Ser Leu Cys Leu
1               5

<210> SEQ ID NO 716
<211> LENGTH: 6
<212> TYPE: PRT
<213> ORGANISM: Homo sapiens

<400> SEQUENCE: 716

Gly Thr Phe Leu Cys Leu
1               5

<210> SEQ ID NO 717
<211> LENGTH: 6
<212> TYPE: PRT
<213> ORGANISM: Homo sapiens

<400> SEQUENCE: 717

Gly Leu Asn Gln Cys Leu
1               5

<210> SEQ ID NO 718
<211> LENGTH: 6
<212> TYPE: PRT
<213> ORGANISM: Homo sapiens

<400> SEQUENCE: 718

Gly Val Leu Ser Cys Leu
1 5

<210> SEQ ID NO 719
<211> LENGTH: 6
<212> TYPE: PRT
<213> ORGANISM: Homo sapiens

<400> SEQUENCE: 719

Gly Leu Ala Asp Cys Leu
1 5

<210> SEQ ID NO 720
<211> LENGTH: 6
<212> TYPE: PRT
<213> ORGANISM: Homo sapiens

<400> SEQUENCE: 720

Gly Gly Ala Glu Cys Leu
1 5

<210> SEQ ID NO 721
<211> LENGTH: 6
<212> TYPE: PRT
<213> ORGANISM: Homo sapiens

<400> SEQUENCE: 721

Gly Asp Ser Asn Cys Leu
1 5

<210> SEQ ID NO 722
<211> LENGTH: 6
<212> TYPE: PRT
<213> ORGANISM: Homo sapiens

<400> SEQUENCE: 722

Gly Ile Ile Val Cys Leu
1 5

<210> SEQ ID NO 723
<211> LENGTH: 6
<212> TYPE: PRT
<213> ORGANISM: Homo sapiens

<400> SEQUENCE: 723

Gly Ser Phe Arg Cys Leu
1 5

<210> SEQ ID NO 724
<211> LENGTH: 6
<212> TYPE: PRT
<213> ORGANISM: Homo sapiens

<400> SEQUENCE: 724

Gly Ser Tyr Lys Cys Leu
1 5

<210> SEQ ID NO 725
<211> LENGTH: 6
<212> TYPE: PRT
<213> ORGANISM: Homo sapiens

<400> SEQUENCE: 725

Gly Ser Tyr Thr Cys Leu 1 5

<210> SEQ ID NO 726
<211> LENGTH: 6
<212> TYPE: PRT
<213> ORGANISM: Homo sapiens

<400> SEQUENCE: 726

Gly Ser Tyr Gln Cys Leu
1 5

<210> SEQ ID NO 727
<211> LENGTH: 6
<212> TYPE: PRT
<213> ORGANISM: Homo sapiens

<400> SEQUENCE: 727

Gly Ser Phe Phe Cys Leu
1 5

<210> SEQ ID NO 728
<211> LENGTH: 6
<212> TYPE: PRT
<213> ORGANISM: Homo sapiens

<400> SEQUENCE: 728

Gly Ser Phe Asn Cys Leu
1 5

<210> SEQ ID NO 729
<211> LENGTH: 6
<212> TYPE: PRT
<213> ORGANISM: Homo sapiens

<400> SEQUENCE: 729

Gly Ser Phe Arg Cys Leu
1 5

<210> SEQ ID NO 730
<211> LENGTH: 6
<212> TYPE: PRT
<213> ORGANISM: Homo sapiens

<400> SEQUENCE: 730

Gly Ser Phe Leu Cys Leu
1 5

<210> SEQ ID NO 731
<211> LENGTH: 6
<212> TYPE: PRT
<213> ORGANISM: Homo sapiens

<400> SEQUENCE: 731

Gly Ala Leu Gly Cys Leu
1 5

<210> SEQ ID NO 732
<211> LENGTH: 6
<212> TYPE: PRT
<213> ORGANISM: Homo sapiens

<400> SEQUENCE: 732

Gly Phe Ala Leu Cys Leu
1 5

<210> SEQ ID NO 733
<211> LENGTH: 6
<212> TYPE: PRT
<213> ORGANISM: Homo sapiens

<400> SEQUENCE: 733

Gly Cys Ala Val Cys Leu
1               5

<210> SEQ ID NO 734
<211> LENGTH: 6
<212> TYPE: PRT
<213> ORGANISM: Homo sapiens

<400> SEQUENCE: 734

Gly Ser Gly Ala Cys Leu
1               5

<210> SEQ ID NO 735
<211> LENGTH: 6
<212> TYPE: PRT
<213> ORGANISM: Homo sapiens

<400> SEQUENCE: 735

Gly Pro Ser Pro Cys Leu
1               5

<210> SEQ ID NO 736
<211> LENGTH: 6
<212> TYPE: PRT
<213> ORGANISM: Homo sapiens

<400> SEQUENCE: 736

Gly Thr Ile Gln Cys Leu
1               5

<210> SEQ ID NO 737
<211> LENGTH: 6
<212> TYPE: PRT
<213> ORGANISM: Homo sapiens

<400> SEQUENCE: 737

Gly Asn Trp His Cys Leu
1               5

<210> SEQ ID NO 738
<211> LENGTH: 6
<212> TYPE: PRT
<213> ORGANISM: Homo sapiens

<400> SEQUENCE: 738

Gly Arg Phe Thr Cys Leu
1               5

<210> SEQ ID NO 739
<211> LENGTH: 6
<212> TYPE: PRT
<213> ORGANISM: Homo sapiens

<400> SEQUENCE: 739

Gly Phe Asn Thr Cys Leu
1               5

<210> SEQ ID NO 740

<211> LENGTH: 6
<212> TYPE: PRT
<213> ORGANISM: Homo sapiens

<400> SEQUENCE: 740

Gly Thr Cys Thr Cys Leu
1 5

<210> SEQ ID NO 741
<211> LENGTH: 6
<212> TYPE: PRT
<213> ORGANISM: Homo sapiens

<400> SEQUENCE: 741

Gly Gly Ser Asn Cys Leu
1 5

<210> SEQ ID NO 742
<211> LENGTH: 6
<212> TYPE: PRT
<213> ORGANISM: Homo sapiens

<400> SEQUENCE: 742

Gly Lys Val Ser Cys Leu
1 5

<210> SEQ ID NO 743
<211> LENGTH: 6
<212> TYPE: PRT
<213> ORGANISM: Homo sapiens

<400> SEQUENCE: 743

Gly Pro Ala His Cys Leu
1 5

<210> SEQ ID NO 744
<211> LENGTH: 6
<212> TYPE: PRT
<213> ORGANISM: Homo sapiens

<400> SEQUENCE: 744

Gly Pro Asp Gln Cys Leu
1 5

<210> SEQ ID NO 745
<211> LENGTH: 6
<212> TYPE: PRT
<213> ORGANISM: Homo sapiens

<400> SEQUENCE: 745

Gly Val Val Arg Cys Leu
1 5

<210> SEQ ID NO 746
<211> LENGTH: 6
<212> TYPE: PRT
<213> ORGANISM: Homo sapiens

<400> SEQUENCE: 746

Gly Met Gln Ile Cys Leu
1 5

<210> SEQ ID NO 747
<211> LENGTH: 6
<212> TYPE: PRT

<213> ORGANISM: Homo sapiens

<400> SEQUENCE: 747

Gly His Asp Glu Cys Leu
1 5

<210> SEQ ID NO 748
<211> LENGTH: 6
<212> TYPE: PRT
<213> ORGANISM: Homo sapiens

<400> SEQUENCE: 748

Gly Leu Arg Thr Cys Leu
1 5

<210> SEQ ID NO 749
<211> LENGTH: 6
<212> TYPE: PRT
<213> ORGANISM: Homo sapiens

<400> SEQUENCE: 749

Gly Asn Pro Glu Cys Leu
1 5

<210> SEQ ID NO 750
<211> LENGTH: 6
<212> TYPE: PRT
<213> ORGANISM: Homo sapiens

<400> SEQUENCE: 750

Gly Leu Ile Tyr Cys Leu
1 5

<210> SEQ ID NO 751
<211> LENGTH: 6
<212> TYPE: PRT
<213> ORGANISM: Homo sapiens

<400> SEQUENCE: 751

Gly Leu Cys Gln Cys Leu
1 5

<210> SEQ ID NO 752
<211> LENGTH: 6
<212> TYPE: PRT
<213> ORGANISM: Homo sapiens

<400> SEQUENCE: 752

Gly Ser Gly Pro Cys Leu
1 5

<210> SEQ ID NO 753
<211> LENGTH: 6
<212> TYPE: PRT
<213> ORGANISM: Homo sapiens

<400> SEQUENCE: 753

Gly Phe Val Val Cys Leu
1 5

<210> SEQ ID NO 754
<211> LENGTH: 6
<212> TYPE: PRT
<213> ORGANISM: Homo sapiens

<400> SEQUENCE: 754

Gly Pro Gly Arg Cys Leu
1               5

<210> SEQ ID NO 755
<211> LENGTH: 6
<212> TYPE: PRT
<213> ORGANISM: Homo sapiens

<400> SEQUENCE: 755

Gly Val Tyr Thr Cys Leu
1               5

<210> SEQ ID NO 756
<211> LENGTH: 6
<212> TYPE: PRT
<213> ORGANISM: Homo sapiens

<400> SEQUENCE: 756

Gly Thr Tyr Thr Cys Leu
1               5

<210> SEQ ID NO 757
<211> LENGTH: 6
<212> TYPE: PRT
<213> ORGANISM: Homo sapiens

<400> SEQUENCE: 757

Gly Gln Ala Met Cys Leu
1               5

<210> SEQ ID NO 758
<211> LENGTH: 6
<212> TYPE: PRT
<213> ORGANISM: Homo sapiens

<400> SEQUENCE: 758

Gly Ser Tyr His Cys Leu
1               5

<210> SEQ ID NO 759
<211> LENGTH: 6
<212> TYPE: PRT
<213> ORGANISM: Homo sapiens

<400> SEQUENCE: 759

Gly Glu Ser Val Cys Leu
1               5

<210> SEQ ID NO 760
<211> LENGTH: 6
<212> TYPE: PRT
<213> ORGANISM: Homo sapiens

<400> SEQUENCE: 760

Gly Phe Val Gly Cys Leu
1               5

<210> SEQ ID NO 761
<211> LENGTH: 6
<212> TYPE: PRT
<213> ORGANISM: Homo sapiens

<400> SEQUENCE: 761

Gly Leu Pro Thr Cys Leu
1 5

<210> SEQ ID NO 762
<211> LENGTH: 6
<212> TYPE: PRT
<213> ORGANISM: Homo sapiens

<400> SEQUENCE: 762

Gly Leu Met Phe Cys Leu
1 5

<210> SEQ ID NO 763
<211> LENGTH: 6
<212> TYPE: PRT
<213> ORGANISM: Homo sapiens

<400> SEQUENCE: 763

Gly His Asn His Cys Leu
1 5

<210> SEQ ID NO 764
<211> LENGTH: 6
<212> TYPE: PRT
<213> ORGANISM: Homo sapiens

<400> SEQUENCE: 764

Gly Val Ser Ser Cys Leu
1 5

<210> SEQ ID NO 765
<211> LENGTH: 6
<212> TYPE: PRT
<213> ORGANISM: Homo sapiens

<400> SEQUENCE: 765

Gly Thr His Cys Cys Leu
1 5

<210> SEQ ID NO 766
<211> LENGTH: 6
<212> TYPE: PRT
<213> ORGANISM: Homo sapiens

<400> SEQUENCE: 766

Gly Thr His Arg Cys Leu
1 5

<210> SEQ ID NO 767
<211> LENGTH: 6
<212> TYPE: PRT
<213> ORGANISM: Homo sapiens

<400> SEQUENCE: 767

Gly Ala Glu His Cys Leu
1 5

<210> SEQ ID NO 768
<211> LENGTH: 6
<212> TYPE: PRT
<213> ORGANISM: Homo sapiens

<400> SEQUENCE: 768

Gly Gln Leu Asn Cys Leu
1 5

<210> SEQ ID NO 769
<211> LENGTH: 6
<212> TYPE: PRT
<213> ORGANISM: Homo sapiens

<400> SEQUENCE: 769

Gly Gly Arg Leu Cys Leu
1               5

<210> SEQ ID NO 770
<211> LENGTH: 6
<212> TYPE: PRT
<213> ORGANISM: Homo sapiens

<400> SEQUENCE: 770

Gly Cys Ala Asp Cys Leu
1               5

<210> SEQ ID NO 771
<211> LENGTH: 6
<212> TYPE: PRT
<213> ORGANISM: Homo sapiens

<400> SEQUENCE: 771

Gly His Leu His Cys Leu
1               5

<210> SEQ ID NO 772
<211> LENGTH: 6
<212> TYPE: PRT
<213> ORGANISM: Homo sapiens

<400> SEQUENCE: 772

Gly Glu Phe Ser Cys Leu
1               5

<210> SEQ ID NO 773
<211> LENGTH: 6
<212> TYPE: PRT
<213> ORGANISM: Homo sapiens

<400> SEQUENCE: 773

Gly Arg Phe Arg Cys Leu
1               5

<210> SEQ ID NO 774
<211> LENGTH: 6
<212> TYPE: PRT
<213> ORGANISM: Homo sapiens

<400> SEQUENCE: 774

Gly Ile Glu Asp Cys Leu
1               5

<210> SEQ ID NO 775
<211> LENGTH: 6
<212> TYPE: PRT
<213> ORGANISM: Homo sapiens

<400> SEQUENCE: 775

Gly Tyr Tyr Gln Cys Leu
1               5

<210> SEQ ID NO 776
<211> LENGTH: 6
<212> TYPE: PRT
<213> ORGANISM: Homo sapiens

<400> SEQUENCE: 776

Gly Val Ile Tyr Cys Leu
1 5

<210> SEQ ID NO 777
<211> LENGTH: 6
<212> TYPE: PRT
<213> ORGANISM: Homo sapiens

<400> SEQUENCE: 777

Gly Thr Cys Ser Cys Leu
1 5

<210> SEQ ID NO 778
<211> LENGTH: 6
<212> TYPE: PRT
<213> ORGANISM: Homo sapiens

<400> SEQUENCE: 778

Gly Phe Leu Gly Cys Leu
1 5

<210> SEQ ID NO 779
<211> LENGTH: 6
<212> TYPE: PRT
<213> ORGANISM: Homo sapiens

<400> SEQUENCE: 779

Gly Thr Tyr Thr Cys Leu
1 5

<210> SEQ ID NO 780
<211> LENGTH: 6
<212> TYPE: PRT
<213> ORGANISM: Homo sapiens

<400> SEQUENCE: 780

Gly Arg Phe Leu Cys Leu
1 5

<210> SEQ ID NO 781
<211> LENGTH: 6
<212> TYPE: PRT
<213> ORGANISM: Homo sapiens

<400> SEQUENCE: 781

Gly Ser Phe Arg Cys Leu
1 5

<210> SEQ ID NO 782
<211> LENGTH: 6
<212> TYPE: PRT
<213> ORGANISM: Homo sapiens

<400> SEQUENCE: 782

Gly Lys Val Ser Cys Leu
1 5

<210> SEQ ID NO 783
<211> LENGTH: 6

<212> TYPE: PRT
<213> ORGANISM: Homo sapiens

<400> SEQUENCE: 783

Gly Lys Ser Lys Cys Leu
1               5

<210> SEQ ID NO 784
<211> LENGTH: 6
<212> TYPE: PRT
<213> ORGANISM: Homo sapiens

<400> SEQUENCE: 784

Gly Leu Lys Gln Cys Leu
1               5

<210> SEQ ID NO 785
<211> LENGTH: 6
<212> TYPE: PRT
<213> ORGANISM: Homo sapiens

<400> SEQUENCE: 785

Gly Val Arg Asn Cys Leu
1               5

<210> SEQ ID NO 786
<211> LENGTH: 6
<212> TYPE: PRT
<213> ORGANISM: Homo sapiens

<400> SEQUENCE: 786

Gly Thr Ser Gly Cys Leu
1               5

<210> SEQ ID NO 787
<211> LENGTH: 6
<212> TYPE: PRT
<213> ORGANISM: Homo sapiens

<400> SEQUENCE: 787

Gly Cys Cys Val Cys Leu
1               5

<210> SEQ ID NO 788
<211> LENGTH: 6
<212> TYPE: PRT
<213> ORGANISM: Homo sapiens

<400> SEQUENCE: 788

Gly Lys Asp Trp Cys Leu
1               5

<210> SEQ ID NO 789
<211> LENGTH: 6
<212> TYPE: PRT
<213> ORGANISM: Homo sapiens

<400> SEQUENCE: 789

Gly Ala Thr Ala Cys Leu
1               5

<210> SEQ ID NO 790
<211> LENGTH: 6
<212> TYPE: PRT
<213> ORGANISM: Homo sapiens

<400> SEQUENCE: 790

Gly Ser Ile Lys Cys Leu
1               5

<210> SEQ ID NO 791
<211> LENGTH: 6
<212> TYPE: PRT
<213> ORGANISM: Homo sapiens

<400> SEQUENCE: 791

Gly Asp Gly Asn Cys Leu
1               5

<210> SEQ ID NO 792
<211> LENGTH: 6
<212> TYPE: PRT
<213> ORGANISM: Homo sapiens

<400> SEQUENCE: 792

Gly Arg Arg Pro Cys Leu
1               5

<210> SEQ ID NO 793
<211> LENGTH: 6
<212> TYPE: PRT
<213> ORGANISM: Homo sapiens

<400> SEQUENCE: 793

Gly Gly Gly Cys Cys Leu
1               5

<210> SEQ ID NO 794
<211> LENGTH: 6
<212> TYPE: PRT
<213> ORGANISM: Homo sapiens

<400> SEQUENCE: 794

Gly Gly Gly Cys Cys Leu
1               5

<210> SEQ ID NO 795
<211> LENGTH: 6
<212> TYPE: PRT
<213> ORGANISM: Homo sapiens

<400> SEQUENCE: 795

Gly Gly Gly Cys Cys Leu
1               5

<210> SEQ ID NO 796
<211> LENGTH: 6
<212> TYPE: PRT
<213> ORGANISM: Homo sapiens

<400> SEQUENCE: 796

Gly Gly Gly Cys Cys Leu
1               5

<210> SEQ ID NO 797
<211> LENGTH: 6
<212> TYPE: PRT
<213> ORGANISM: Homo sapiens

<400> SEQUENCE: 797

Gly Gly Gly Cys Cys Leu
1               5

<210> SEQ ID NO 798
<211> LENGTH: 6
<212> TYPE: PRT
<213> ORGANISM: Homo sapiens

<400> SEQUENCE: 798

Gly Gly Gly Cys Cys Leu
1               5

<210> SEQ ID NO 799
<211> LENGTH: 6
<212> TYPE: PRT
<213> ORGANISM: Homo sapiens

<400> SEQUENCE: 799

Gly Gly Gly Cys Cys Leu
1               5

<210> SEQ ID NO 800
<211> LENGTH: 6
<212> TYPE: PRT
<213> ORGANISM: Homo sapiens

<400> SEQUENCE: 800

Gly Gly Gly Cys Cys Leu
1               5

<210> SEQ ID NO 801
<211> LENGTH: 6
<212> TYPE: PRT
<213> ORGANISM: Homo sapiens

<400> SEQUENCE: 801

Gly Gly Gly Cys Cys Leu
1               5

<210> SEQ ID NO 802
<211> LENGTH: 6
<212> TYPE: PRT
<213> ORGANISM: Homo sapiens

<400> SEQUENCE: 802

Gly Gly Gly Cys Cys Leu
1               5

<210> SEQ ID NO 803
<211> LENGTH: 6
<212> TYPE: PRT
<213> ORGANISM: Homo sapiens

<400> SEQUENCE: 803

Gly Gly Asn Gly Cys Leu
1               5

<210> SEQ ID NO 804
<211> LENGTH: 6
<212> TYPE: PRT
<213> ORGANISM: Homo sapiens

<400> SEQUENCE: 804

Gly Asn Glu Cys Cys Leu 1 5

<210> SEQ ID NO 805
<211> LENGTH: 6
<212> TYPE: PRT
<213> ORGANISM: Homo sapiens

<400> SEQUENCE: 805

Gly Ser Leu Gly Cys Leu
1 5

<210> SEQ ID NO 806
<211> LENGTH: 6
<212> TYPE: PRT
<213> ORGANISM: Homo sapiens

<400> SEQUENCE: 806

Gly Asp Arg Tyr Cys Leu
1 5

<210> SEQ ID NO 807
<211> LENGTH: 6
<212> TYPE: PRT
<213> ORGANISM: Homo sapiens

<400> SEQUENCE: 807

Gly Val Gln Trp Cys Leu
1 5

<210> SEQ ID NO 808
<211> LENGTH: 6
<212> TYPE: PRT
<213> ORGANISM: Homo sapiens

<400> SEQUENCE: 808

Gly Val Tyr Arg Cys Leu
1 5

<210> SEQ ID NO 809
<211> LENGTH: 6
<212> TYPE: PRT
<213> ORGANISM: Homo sapiens

<400> SEQUENCE: 809

Gly Val Tyr Thr Cys Leu
1 5

<210> SEQ ID NO 810
<211> LENGTH: 6
<212> TYPE: PRT
<213> ORGANISM: Homo sapiens

<400> SEQUENCE: 810

Gly Ala Leu Thr Cys Leu
1 5

<210> SEQ ID NO 811
<211> LENGTH: 6
<212> TYPE: PRT
<213> ORGANISM: Homo sapiens

<400> SEQUENCE: 811

Gly Pro Ser Pro Cys Leu
1 5

<210> SEQ ID NO 812
<211> LENGTH: 6
<212> TYPE: PRT
<213> ORGANISM: Homo sapiens

<400> SEQUENCE: 812

Gly Ala Ser Ala Cys Leu
1               5

<210> SEQ ID NO 813
<211> LENGTH: 6
<212> TYPE: PRT
<213> ORGANISM: Homo sapiens

<400> SEQUENCE: 813

Gly Pro Lys Gln Cys Leu
1               5

<210> SEQ ID NO 814
<211> LENGTH: 6
<212> TYPE: PRT
<213> ORGANISM: Homo sapiens

<400> SEQUENCE: 814

Gly Thr Gly Gly Cys Leu
1               5

<210> SEQ ID NO 815
<211> LENGTH: 6
<212> TYPE: PRT
<213> ORGANISM: Homo sapiens

<400> SEQUENCE: 815

Gly Gly Ser Leu Cys Leu
1               5

<210> SEQ ID NO 816
<211> LENGTH: 6
<212> TYPE: PRT
<213> ORGANISM: Homo sapiens

<400> SEQUENCE: 816

Gly Thr Tyr Ser Cys Leu
1               5

<210> SEQ ID NO 817
<211> LENGTH: 6
<212> TYPE: PRT
<213> ORGANISM: Homo sapiens

<400> SEQUENCE: 817

Gly Thr Tyr Ser Cys Leu
1               5

<210> SEQ ID NO 818
<211> LENGTH: 6
<212> TYPE: PRT
<213> ORGANISM: Homo sapiens

<400> SEQUENCE: 818

Gly Leu Ser Val Cys Leu
1               5

<210> SEQ ID NO 819

<211> LENGTH: 6
<212> TYPE: PRT
<213> ORGANISM: Homo sapiens

<400> SEQUENCE: 819

Gly Ala Glu His Cys Leu
1 5

<210> SEQ ID NO 820
<211> LENGTH: 6
<212> TYPE: PRT
<213> ORGANISM: Homo sapiens

<400> SEQUENCE: 820

Gly Lys Gly Arg Cys Leu
1 5

<210> SEQ ID NO 821
<211> LENGTH: 6
<212> TYPE: PRT
<213> ORGANISM: Homo sapiens

<400> SEQUENCE: 821

Gly Phe Tyr Lys Cys Leu
1 5

<210> SEQ ID NO 822
<211> LENGTH: 6
<212> TYPE: PRT
<213> ORGANISM: Homo sapiens

<400> SEQUENCE: 822

Gly Asn Leu Phe Cys Leu
1 5

<210> SEQ ID NO 823
<211> LENGTH: 6
<212> TYPE: PRT
<213> ORGANISM: Homo sapiens

<400> SEQUENCE: 823

Gly Asp Gly Asn Cys Leu
1 5

<210> SEQ ID NO 824
<211> LENGTH: 6
<212> TYPE: PRT
<213> ORGANISM: Homo sapiens

<400> SEQUENCE: 824

Gly Leu Val Leu Cys Leu
1 5

<210> SEQ ID NO 825
<211> LENGTH: 6
<212> TYPE: PRT
<213> ORGANISM: Homo sapiens

<400> SEQUENCE: 825

Gly Thr Gly Arg Cys Leu
1 5

<210> SEQ ID NO 826
<211> LENGTH: 6
<212> TYPE: PRT

<213> ORGANISM: Homo sapiens

<400> SEQUENCE: 826

Gly Leu Val Leu Cys Leu
1               5

<210> SEQ ID NO 827
<211> LENGTH: 6
<212> TYPE: PRT
<213> ORGANISM: Homo sapiens

<400> SEQUENCE: 827

Gly Leu Tyr Arg Cys Leu
1               5

<210> SEQ ID NO 828
<211> LENGTH: 6
<212> TYPE: PRT
<213> ORGANISM: Homo sapiens

<400> SEQUENCE: 828

Gly Arg Ser Ser Cys Leu
1               5

<210> SEQ ID NO 829
<211> LENGTH: 6
<212> TYPE: PRT
<213> ORGANISM: Homo sapiens

<400> SEQUENCE: 829

Gly Asn Ala Arg Cys Leu
1               5

<210> SEQ ID NO 830
<211> LENGTH: 6
<212> TYPE: PRT
<213> ORGANISM: Homo sapiens

<400> SEQUENCE: 830

Gly Ile Gly Gln Cys Leu
1               5

<210> SEQ ID NO 831
<211> LENGTH: 6
<212> TYPE: PRT
<213> ORGANISM: Homo sapiens

<400> SEQUENCE: 831

Gly Asn Ile Gln Cys Leu
1               5

<210> SEQ ID NO 832
<211> LENGTH: 6
<212> TYPE: PRT
<213> ORGANISM: Homo sapiens

<400> SEQUENCE: 832

Gly Tyr Ala Leu Cys Leu
1               5

<210> SEQ ID NO 833
<211> LENGTH: 6
<212> TYPE: PRT
<213> ORGANISM: Homo sapiens

<400> SEQUENCE: 833

Gly Gln Asp Phe Cys Leu
1               5

<210> SEQ ID NO 834
<211> LENGTH: 6
<212> TYPE: PRT
<213> ORGANISM: Homo sapiens

<400> SEQUENCE: 834

Gly Val Gly Gln Cys Leu
1               5

<210> SEQ ID NO 835
<211> LENGTH: 6
<212> TYPE: PRT
<213> ORGANISM: Homo sapiens

<400> SEQUENCE: 835

Gly Gly Asp Ala Cys Leu
1               5

<210> SEQ ID NO 836
<211> LENGTH: 6
<212> TYPE: PRT
<213> ORGANISM: Homo sapiens

<400> SEQUENCE: 836

Gly Pro Val Trp Cys Leu
1               5

<210> SEQ ID NO 837
<211> LENGTH: 6
<212> TYPE: PRT
<213> ORGANISM: Homo sapiens

<400> SEQUENCE: 837

Gly Leu Glu Asp Cys Leu
1               5

<210> SEQ ID NO 838
<211> LENGTH: 6
<212> TYPE: PRT
<213> ORGANISM: Homo sapiens

<400> SEQUENCE: 838

Gly Thr Glu Ile Cys Leu
1               5

<210> SEQ ID NO 839
<211> LENGTH: 6
<212> TYPE: PRT
<213> ORGANISM: Homo sapiens

<400> SEQUENCE: 839

Gly Ser Ser Gly Cys Leu
1               5

<210> SEQ ID NO 840
<211> LENGTH: 6
<212> TYPE: PRT
<213> ORGANISM: Homo sapiens

<400> SEQUENCE: 840

Gly Gly Cys Cys Cys Leu
1 5

<210> SEQ ID NO 841
<211> LENGTH: 6
<212> TYPE: PRT
<213> ORGANISM: Homo sapiens

<400> SEQUENCE: 841

Gly Ala Ala Leu Cys Leu
1 5

<210> SEQ ID NO 842
<211> LENGTH: 6
<212> TYPE: PRT
<213> ORGANISM: Homo sapiens

<400> SEQUENCE: 842

Gly Asn Cys Val Cys Leu
1 5

<210> SEQ ID NO 843
<211> LENGTH: 6
<212> TYPE: PRT
<213> ORGANISM: Homo sapiens

<400> SEQUENCE: 843

Gly Asp Gly Cys Cys Leu
1 5

<210> SEQ ID NO 844
<211> LENGTH: 6
<212> TYPE: PRT
<213> ORGANISM: Homo sapiens

<400> SEQUENCE: 844

Gly Ile Leu Ser Cys Leu
1 5

<210> SEQ ID NO 845
<211> LENGTH: 6
<212> TYPE: PRT
<213> ORGANISM: Homo sapiens

<400> SEQUENCE: 845

Gly Met Trp Ser Cys Leu
1 5

<210> SEQ ID NO 846
<211> LENGTH: 6
<212> TYPE: PRT
<213> ORGANISM: Homo sapiens

<400> SEQUENCE: 846

Gly Leu Tyr Arg Cys Leu
1 5

<210> SEQ ID NO 847
<211> LENGTH: 6
<212> TYPE: PRT
<213> ORGANISM: Homo sapiens

<400> SEQUENCE: 847

Gly Ala Arg Ser Cys Leu
1 5

<210> SEQ ID NO 848
<211> LENGTH: 6
<212> TYPE: PRT
<213> ORGANISM: Homo sapiens

<400> SEQUENCE: 848

Gly Asn Gly Leu Cys Leu
1               5

<210> SEQ ID NO 849
<211> LENGTH: 6
<212> TYPE: PRT
<213> ORGANISM: Homo sapiens

<400> SEQUENCE: 849

Gly His Val Val Cys Leu
1               5

<210> SEQ ID NO 850
<211> LENGTH: 6
<212> TYPE: PRT
<213> ORGANISM: Homo sapiens

<400> SEQUENCE: 850

Gly Arg Arg His Cys Leu
1               5

<210> SEQ ID NO 851
<211> LENGTH: 6
<212> TYPE: PRT
<213> ORGANISM: Homo sapiens

<400> SEQUENCE: 851

Gly Asp Cys Glu Cys Leu
1               5

<210> SEQ ID NO 852
<211> LENGTH: 6
<212> TYPE: PRT
<213> ORGANISM: Homo sapiens

<400> SEQUENCE: 852

Gly Leu Met Tyr Cys Leu
1               5

<210> SEQ ID NO 853
<211> LENGTH: 6
<212> TYPE: PRT
<213> ORGANISM: Homo sapiens

<400> SEQUENCE: 853

Gly Ala Arg Gln Cys Leu
1               5

<210> SEQ ID NO 854
<211> LENGTH: 6
<212> TYPE: PRT
<213> ORGANISM: Homo sapiens

<400> SEQUENCE: 854

Gly Gly Ser Pro Cys Leu
1               5

<210> SEQ ID NO 855
<211> LENGTH: 6
<212> TYPE: PRT
<213> ORGANISM: Homo sapiens

<400> SEQUENCE: 855

Gly Leu Ser Thr Cys Leu
1               5

<210> SEQ ID NO 856
<211> LENGTH: 6
<212> TYPE: PRT
<213> ORGANISM: Homo sapiens

<400> SEQUENCE: 856

Gly Ile Leu Lys Cys Leu
1               5

<210> SEQ ID NO 857
<211> LENGTH: 6
<212> TYPE: PRT
<213> ORGANISM: Homo sapiens

<400> SEQUENCE: 857

Gly Ala Glu Val Cys Leu
1               5

<210> SEQ ID NO 858
<211> LENGTH: 6
<212> TYPE: PRT
<213> ORGANISM: Homo sapiens

<400> SEQUENCE: 858

Gly Gly His Ser Cys Leu
1               5

<210> SEQ ID NO 859
<211> LENGTH: 6
<212> TYPE: PRT
<213> ORGANISM: Homo sapiens

<400> SEQUENCE: 859

Gly Ser Arg Asn Cys Leu
1               5

<210> SEQ ID NO 860
<211> LENGTH: 6
<212> TYPE: PRT
<213> ORGANISM: Homo sapiens

<400> SEQUENCE: 860

Gly Gln Ala Leu Cys Leu
1               5

<210> SEQ ID NO 861
<211> LENGTH: 6
<212> TYPE: PRT
<213> ORGANISM: Homo sapiens

<400> SEQUENCE: 861

Gly Ser Phe Ser Cys Leu
1               5

<210> SEQ ID NO 862
<211> LENGTH: 6

<212> TYPE: PRT
<213> ORGANISM: Homo sapiens

<400> SEQUENCE: 862

Gly Gly His Arg Cys Leu
1 5

<210> SEQ ID NO 863
<211> LENGTH: 6
<212> TYPE: PRT
<213> ORGANISM: Homo sapiens

<400> SEQUENCE: 863

Gly Ser Tyr Met Cys Leu
1 5

<210> SEQ ID NO 864
<211> LENGTH: 6
<212> TYPE: PRT
<213> ORGANISM: Homo sapiens

<400> SEQUENCE: 864

Gly Ser Tyr Asn Cys Leu
1 5

<210> SEQ ID NO 865
<211> LENGTH: 6
<212> TYPE: PRT
<213> ORGANISM: Homo sapiens

<400> SEQUENCE: 865

Gly Ser Phe His Cys Leu
1 5

<210> SEQ ID NO 866
<211> LENGTH: 6
<212> TYPE: PRT
<213> ORGANISM: Homo sapiens

<400> SEQUENCE: 866

Gly Ser Phe Gln Cys Leu
1 5

<210> SEQ ID NO 867
<211> LENGTH: 6
<212> TYPE: PRT
<213> ORGANISM: Homo sapiens

<400> SEQUENCE: 867

Gly Glu Trp Leu Cys Leu
1 5

<210> SEQ ID NO 868
<211> LENGTH: 6
<212> TYPE: PRT
<213> ORGANISM: Homo sapiens

<400> SEQUENCE: 868

Gly Arg Arg Gln Cys Leu
1 5

<210> SEQ ID NO 869
<211> LENGTH: 6
<212> TYPE: PRT
<213> ORGANISM: Homo sapiens

<400> SEQUENCE: 869

Gly Lys Glu Tyr Cys Leu
1               5

<210> SEQ ID NO 870
<211> LENGTH: 6
<212> TYPE: PRT
<213> ORGANISM: Homo sapiens

<400> SEQUENCE: 870

Gly Ile Thr Asp Cys Leu
1               5

<210> SEQ ID NO 871
<211> LENGTH: 6
<212> TYPE: PRT
<213> ORGANISM: Homo sapiens

<400> SEQUENCE: 871

Gly Phe Gly Val Cys Leu
1               5

<210> SEQ ID NO 872
<211> LENGTH: 6
<212> TYPE: PRT
<213> ORGANISM: Homo sapiens

<400> SEQUENCE: 872

Gly Arg Leu Leu Cys Leu
1               5

<210> SEQ ID NO 873
<211> LENGTH: 6
<212> TYPE: PRT
<213> ORGANISM: Homo sapiens

<400> SEQUENCE: 873

Gly Thr Val Pro Cys Leu
1               5

<210> SEQ ID NO 874
<211> LENGTH: 6
<212> TYPE: PRT
<213> ORGANISM: Homo sapiens

<400> SEQUENCE: 874

Gly Lys Leu Gly Cys Leu
1               5

<210> SEQ ID NO 875
<211> LENGTH: 6
<212> TYPE: PRT
<213> ORGANISM: Homo sapiens

<400> SEQUENCE: 875

Gly Ala Cys Ser Cys Leu
1               5

<210> SEQ ID NO 876
<211> LENGTH: 6
<212> TYPE: PRT
<213> ORGANISM: Homo sapiens

<400> SEQUENCE: 876

Gly Ala Pro Leu Cys Leu
1 5

<210> SEQ ID NO 877
<211> LENGTH: 6
<212> TYPE: PRT
<213> ORGANISM: Homo sapiens

<400> SEQUENCE: 877

Gly Gly Ser Asn Cys Leu
1 5

<210> SEQ ID NO 878
<211> LENGTH: 6
<212> TYPE: PRT
<213> ORGANISM: Homo sapiens

<400> SEQUENCE: 878

Gly Glu Lys Lys Cys Leu
1 5

<210> SEQ ID NO 879
<211> LENGTH: 6
<212> TYPE: PRT
<213> ORGANISM: Homo sapiens

<400> SEQUENCE: 879

Gly Arg Gln Thr Cys Leu
1 5

<210> SEQ ID NO 880
<211> LENGTH: 6
<212> TYPE: PRT
<213> ORGANISM: Homo sapiens

<400> SEQUENCE: 880

Gly Gly Val Glu Cys Leu
1 5

<210> SEQ ID NO 881
<211> LENGTH: 6
<212> TYPE: PRT
<213> ORGANISM: Homo sapiens

<400> SEQUENCE: 881

Gly Ser Ala Asp Cys Leu
1 5

<210> SEQ ID NO 882
<211> LENGTH: 6
<212> TYPE: PRT
<213> ORGANISM: Homo sapiens

<400> SEQUENCE: 882

Gly Ile Cys Leu Cys Leu
1 5

<210> SEQ ID NO 883
<211> LENGTH: 6
<212> TYPE: PRT
<213> ORGANISM: Homo sapiens

<400> SEQUENCE: 883

Gly Pro Val Met Cys Leu 1 5

<210> SEQ ID NO 884
<211> LENGTH: 6
<212> TYPE: PRT
<213> ORGANISM: Homo sapiens

<400> SEQUENCE: 884

Gly Cys Leu Ala Cys Leu
1 5

<210> SEQ ID NO 885
<211> LENGTH: 6
<212> TYPE: PRT
<213> ORGANISM: Homo sapiens

<400> SEQUENCE: 885

Gly Ala Glu Arg Cys Leu
1 5

<210> SEQ ID NO 886
<211> LENGTH: 6
<212> TYPE: PRT
<213> ORGANISM: Homo sapiens

<400> SEQUENCE: 886

Gly Ser Leu Glu Cys Leu
1 5

<210> SEQ ID NO 887
<211> LENGTH: 6
<212> TYPE: PRT
<213> ORGANISM: Homo sapiens

<400> SEQUENCE: 887

Gly Pro Gly Pro Cys Leu
1 5

<210> SEQ ID NO 888
<211> LENGTH: 6
<212> TYPE: PRT
<213> ORGANISM: Homo sapiens

<400> SEQUENCE: 888

Gly Cys Gly Trp Cys Leu
1 5

<210> SEQ ID NO 889
<211> LENGTH: 6
<212> TYPE: PRT
<213> ORGANISM: Homo sapiens

<400> SEQUENCE: 889

Gly Ser Glu Leu Cys Leu
1 5

<210> SEQ ID NO 890
<211> LENGTH: 6
<212> TYPE: PRT
<213> ORGANISM: Homo sapiens

<400> SEQUENCE: 890

Gly Ser Asn Gly Cys Leu
1 5

<210> SEQ ID NO 891
<211> LENGTH: 6
<212> TYPE: PRT
<213> ORGANISM: Homo sapiens

<400> SEQUENCE: 891

Gly Arg Ala Ala Cys Leu
1 5

<210> SEQ ID NO 892
<211> LENGTH: 6
<212> TYPE: PRT
<213> ORGANISM: Homo sapiens

<400> SEQUENCE: 892

Gly His Ala Ser Cys Leu
1 5

<210> SEQ ID NO 893
<211> LENGTH: 6
<212> TYPE: PRT
<213> ORGANISM: Homo sapiens

<400> SEQUENCE: 893

Gly Val Leu Asp Cys Leu
1 5

<210> SEQ ID NO 894
<211> LENGTH: 6
<212> TYPE: PRT
<213> ORGANISM: Homo sapiens

<400> SEQUENCE: 894

Gly Ala Pro Pro Cys Leu
1 5

<210> SEQ ID NO 895
<211> LENGTH: 6
<212> TYPE: PRT
<213> ORGANISM: Homo sapiens

<400> SEQUENCE: 895

Gly Gly Glu Leu Cys Leu
1 5

<210> SEQ ID NO 896
<211> LENGTH: 6
<212> TYPE: PRT
<213> ORGANISM: Homo sapiens

<400> SEQUENCE: 896

Gly Lys Glu His Cys Leu
1 5

<210> SEQ ID NO 897
<211> LENGTH: 6
<212> TYPE: PRT
<213> ORGANISM: Homo sapiens

<400> SEQUENCE: 897

Gly Val Val Leu Cys Leu
1 5

<210> SEQ ID NO 898

<211> LENGTH: 6
<212> TYPE: PRT
<213> ORGANISM: Homo sapiens

<400> SEQUENCE: 898

Gly Trp Leu Cys Cys Leu
1 5

<210> SEQ ID NO 899
<211> LENGTH: 6
<212> TYPE: PRT
<213> ORGANISM: Homo sapiens

<400> SEQUENCE: 899

Gly Gly Arg Gly Cys Leu
1 5

<210> SEQ ID NO 900
<211> LENGTH: 6
<212> TYPE: PRT
<213> ORGANISM: Homo sapiens

<400> SEQUENCE: 900

Gly Pro Pro Phe Cys Leu
1 5

<210> SEQ ID NO 901
<211> LENGTH: 6
<212> TYPE: PRT
<213> ORGANISM: Homo sapiens

<400> SEQUENCE: 901

Gly Ser Phe Lys Cys Leu
1 5

<210> SEQ ID NO 902
<211> LENGTH: 6
<212> TYPE: PRT
<213> ORGANISM: Homo sapiens

<400> SEQUENCE: 902

Gly Cys Met Leu Cys Leu
1 5

<210> SEQ ID NO 903
<211> LENGTH: 6
<212> TYPE: PRT
<213> ORGANISM: Homo sapiens

<400> SEQUENCE: 903

Gly Val Asp Thr Cys Leu
1 5

<210> SEQ ID NO 904
<211> LENGTH: 6
<212> TYPE: PRT
<213> ORGANISM: Homo sapiens

<400> SEQUENCE: 904

Gly Asn Pro Asn Cys Leu
1 5

<210> SEQ ID NO 905
<211> LENGTH: 6
<212> TYPE: PRT

<213> ORGANISM: Homo sapiens

<400> SEQUENCE: 905

Gly Leu Pro Val Cys Leu
1 5

<210> SEQ ID NO 906
<211> LENGTH: 6
<212> TYPE: PRT
<213> ORGANISM: Homo sapiens

<400> SEQUENCE: 906

Gly Ala Ile Leu Cys Leu
1 5

<210> SEQ ID NO 907
<211> LENGTH: 6
<212> TYPE: PRT
<213> ORGANISM: Homo sapiens

<400> SEQUENCE: 907

Gly Leu Asn Gln Cys Leu
1 5

<210> SEQ ID NO 908
<211> LENGTH: 6
<212> TYPE: PRT
<213> ORGANISM: Homo sapiens

<400> SEQUENCE: 908

Gly Thr Phe Lys Cys Leu
1 5

<210> SEQ ID NO 909
<211> LENGTH: 6
<212> TYPE: PRT
<213> ORGANISM: Homo sapiens

<400> SEQUENCE: 909

Gly Ala Ser Asp Cys Leu
1 5

<210> SEQ ID NO 910
<211> LENGTH: 6
<212> TYPE: PRT
<213> ORGANISM: Homo sapiens

<400> SEQUENCE: 910

Gly Tyr Arg Ser Cys Leu
1 5

<210> SEQ ID NO 911
<211> LENGTH: 6
<212> TYPE: PRT
<213> ORGANISM: Homo sapiens

<400> SEQUENCE: 911

Gly Leu Phe Val Cys Leu
1 5

<210> SEQ ID NO 912
<211> LENGTH: 6
<212> TYPE: PRT
<213> ORGANISM: Homo sapiens

<400> SEQUENCE: 912

Gly Gly Val Cys Cys Leu
1 5

<210> SEQ ID NO 913
<211> LENGTH: 6
<212> TYPE: PRT
<213> ORGANISM: Homo sapiens

<400> SEQUENCE: 913

Gly Pro Gly Leu Cys Leu
1 5

<210> SEQ ID NO 914
<211> LENGTH: 6
<212> TYPE: PRT
<213> ORGANISM: Homo sapiens

<400> SEQUENCE: 914

Gly Thr Asp Val Cys Leu
1 5

<210> SEQ ID NO 915
<211> LENGTH: 6
<212> TYPE: PRT
<213> ORGANISM: Homo sapiens

<400> SEQUENCE: 915

Gly Leu Pro Val Cys Leu
1 5

<210> SEQ ID NO 916
<211> LENGTH: 6
<212> TYPE: PRT
<213> ORGANISM: Homo sapiens

<400> SEQUENCE: 916

Gly Trp Leu Leu Cys Leu
1 5

<210> SEQ ID NO 917
<211> LENGTH: 6
<212> TYPE: PRT
<213> ORGANISM: Homo sapiens

<400> SEQUENCE: 917

Gly Leu Ala Ser Cys Leu
1 5

<210> SEQ ID NO 918
<211> LENGTH: 6
<212> TYPE: PRT
<213> ORGANISM: Homo sapiens

<400> SEQUENCE: 918

Gly Gln Pro Asp Cys Leu
1 5

<210> SEQ ID NO 919
<211> LENGTH: 6
<212> TYPE: PRT
<213> ORGANISM: Homo sapiens

<400> SEQUENCE: 919

Gly Cys Gly Ser Cys Leu
1 5

<210> SEQ ID NO 920
<211> LENGTH: 6
<212> TYPE: PRT
<213> ORGANISM: Homo sapiens

<400> SEQUENCE: 920

Gly Cys Gln Lys Cys Leu
1 5

<210> SEQ ID NO 921
<211> LENGTH: 6
<212> TYPE: PRT
<213> ORGANISM: Homo sapiens

<400> SEQUENCE: 921

Gly Tyr Lys Lys Cys Leu
1 5

<210> SEQ ID NO 922
<211> LENGTH: 6
<212> TYPE: PRT
<213> ORGANISM: Homo sapiens

<400> SEQUENCE: 922

Gly Gln Arg Ala Cys Leu
1 5

<210> SEQ ID NO 923
<211> LENGTH: 6
<212> TYPE: PRT
<213> ORGANISM: Homo sapiens

<400> SEQUENCE: 923

Gly Ser Val Ala Cys Leu
1 5

<210> SEQ ID NO 924
<211> LENGTH: 6
<212> TYPE: PRT
<213> ORGANISM: Homo sapiens

<400> SEQUENCE: 924

Gly Ser Lys Arg Cys Leu
1 5

<210> SEQ ID NO 925
<211> LENGTH: 6
<212> TYPE: PRT
<213> ORGANISM: Homo sapiens

<400> SEQUENCE: 925

Gly Met Tyr Gln Cys Leu
1 5

<210> SEQ ID NO 926
<211> LENGTH: 6
<212> TYPE: PRT
<213> ORGANISM: Homo sapiens

<400> SEQUENCE: 926

Gly Ser Phe Gln Cys Leu
1 5

<210> SEQ ID NO 927
<211> LENGTH: 6
<212> TYPE: PRT
<213> ORGANISM: Homo sapiens

<400> SEQUENCE: 927

Gly Ser Phe Gln Cys Leu
1               5

<210> SEQ ID NO 928
<211> LENGTH: 6
<212> TYPE: PRT
<213> ORGANISM: Homo sapiens

<400> SEQUENCE: 928

Gly Gln Thr Pro Cys Leu
1               5

<210> SEQ ID NO 929
<211> LENGTH: 6
<212> TYPE: PRT
<213> ORGANISM: Homo sapiens

<400> SEQUENCE: 929

Gly Ser Leu Pro Cys Leu
1               5

<210> SEQ ID NO 930
<211> LENGTH: 6
<212> TYPE: PRT
<213> ORGANISM: Homo sapiens

<400> SEQUENCE: 930

Gly Thr Leu Tyr Cys Leu
1               5

<210> SEQ ID NO 931
<211> LENGTH: 6
<212> TYPE: PRT
<213> ORGANISM: Homo sapiens

<400> SEQUENCE: 931

Gly Val Phe Tyr Cys Leu
1               5

<210> SEQ ID NO 932
<211> LENGTH: 6
<212> TYPE: PRT
<213> ORGANISM: Homo sapiens

<400> SEQUENCE: 932

Gly Val Tyr Gln Cys Leu
1               5

<210> SEQ ID NO 933
<211> LENGTH: 6
<212> TYPE: PRT
<213> ORGANISM: Homo sapiens

<400> SEQUENCE: 933

Gly Asn Leu Val Cys Leu
1               5

<210> SEQ ID NO 934
<211> LENGTH: 6
<212> TYPE: PRT
<213> ORGANISM: Homo sapiens

<400> SEQUENCE: 934

Gly Gly Ser Leu Cys Leu
1 5

<210> SEQ ID NO 935
<211> LENGTH: 6
<212> TYPE: PRT
<213> ORGANISM: Homo sapiens

<400> SEQUENCE: 935

Gly Gly Ser Phe Cys Leu
1 5

<210> SEQ ID NO 936
<211> LENGTH: 6
<212> TYPE: PRT
<213> ORGANISM: Homo sapiens

<400> SEQUENCE: 936

Gly Glu Thr Pro Cys Leu
1 5

<210> SEQ ID NO 937
<211> LENGTH: 6
<212> TYPE: PRT
<213> ORGANISM: Homo sapiens

<400> SEQUENCE: 937

Gly Lys Leu Leu Cys Leu
1 5

<210> SEQ ID NO 938
<211> LENGTH: 6
<212> TYPE: PRT
<213> ORGANISM: Homo sapiens

<400> SEQUENCE: 938

Gly Thr Phe Gly Cys Leu
1 5

<210> SEQ ID NO 939
<211> LENGTH: 6
<212> TYPE: PRT
<213> ORGANISM: Homo sapiens

<400> SEQUENCE: 939

Gly Leu Ala Arg Cys Leu
1 5

<210> SEQ ID NO 940
<211> LENGTH: 6
<212> TYPE: PRT
<213> ORGANISM: Homo sapiens

<400> SEQUENCE: 940

Gly Arg Phe Arg Cys Leu
1 5

<210> SEQ ID NO 941
<211> LENGTH: 6

<212> TYPE: PRT
<213> ORGANISM: Homo sapiens

<400> SEQUENCE: 941

Gly Gln Glu Ala Cys Leu
1 5

<210> SEQ ID NO 942
<211> LENGTH: 6
<212> TYPE: PRT
<213> ORGANISM: Homo sapiens

<400> SEQUENCE: 942

Gly Ala Ile Ser Cys Leu
1 5

<210> SEQ ID NO 943
<211> LENGTH: 6
<212> TYPE: PRT
<213> ORGANISM: Homo sapiens

<400> SEQUENCE: 943

Gly Asp Pro Pro Cys Leu
1 5

<210> SEQ ID NO 944
<211> LENGTH: 6
<212> TYPE: PRT
<213> ORGANISM: Homo sapiens

<400> SEQUENCE: 944

Gly Ala Gln Gln Cys Leu
1 5

<210> SEQ ID NO 945
<211> LENGTH: 6
<212> TYPE: PRT
<213> ORGANISM: Homo sapiens

<400> SEQUENCE: 945

Gly Leu Thr Glu Cys Leu
1 5

<210> SEQ ID NO 946
<211> LENGTH: 6
<212> TYPE: PRT
<213> ORGANISM: Homo sapiens

<400> SEQUENCE: 946

Gly Leu Trp Asp Cys Leu
1 5

<210> SEQ ID NO 947
<211> LENGTH: 6
<212> TYPE: PRT
<213> ORGANISM: Homo sapiens

<400> SEQUENCE: 947

Gly Glu Phe Ser Cys Leu
1 5

<210> SEQ ID NO 948
<211> LENGTH: 6
<212> TYPE: PRT
<213> ORGANISM: Homo sapiens

<400> SEQUENCE: 948

Gly Ala Val Lys Cys Leu
1               5

<210> SEQ ID NO 949
<211> LENGTH: 6
<212> TYPE: PRT
<213> ORGANISM: Homo sapiens

<400> SEQUENCE: 949

Gly Ser Tyr Arg Cys Leu
1               5

<210> SEQ ID NO 950
<211> LENGTH: 6
<212> TYPE: PRT
<213> ORGANISM: Homo sapiens

<400> SEQUENCE: 950

Gly Met Tyr Ile Cys Leu
1               5

<210> SEQ ID NO 951
<211> LENGTH: 6
<212> TYPE: PRT
<213> ORGANISM: Homo sapiens

<400> SEQUENCE: 951

Gly Asp Thr Leu Cys Leu
1               5

<210> SEQ ID NO 952
<211> LENGTH: 6
<212> TYPE: PRT
<213> ORGANISM: Homo sapiens

<400> SEQUENCE: 952

Gly Leu Leu Ser Cys Leu
1               5

<210> SEQ ID NO 953
<211> LENGTH: 6
<212> TYPE: PRT
<213> ORGANISM: Homo sapiens

<400> SEQUENCE: 953

Gly Cys Val Asn Cys Leu
1               5

<210> SEQ ID NO 954
<211> LENGTH: 6
<212> TYPE: PRT
<213> ORGANISM: Homo sapiens

<400> SEQUENCE: 954

Gly Leu Gly Phe Cys Leu
1               5

<210> SEQ ID NO 955
<211> LENGTH: 6
<212> TYPE: PRT
<213> ORGANISM: Homo sapiens

<400> SEQUENCE: 955

Gly Asp Val Lys Cys Leu
1 5

<210> SEQ ID NO 956
<211> LENGTH: 6
<212> TYPE: PRT
<213> ORGANISM: Homo sapiens

<400> SEQUENCE: 956

Gly Gly Leu Val Cys Leu
1 5

<210> SEQ ID NO 957
<211> LENGTH: 6
<212> TYPE: PRT
<213> ORGANISM: Homo sapiens

<400> SEQUENCE: 957

Gly Ile Trp Ile Cys Leu
1 5

<210> SEQ ID NO 958
<211> LENGTH: 6
<212> TYPE: PRT
<213> ORGANISM: Homo sapiens

<400> SEQUENCE: 958

Gly Arg Ser Leu Cys Leu
1 5

<210> SEQ ID NO 959
<211> LENGTH: 6
<212> TYPE: PRT
<213> ORGANISM: Homo sapiens

<400> SEQUENCE: 959

Gly Pro Phe Ser Cys Leu
1 5

<210> SEQ ID NO 960
<211> LENGTH: 6
<212> TYPE: PRT
<213> ORGANISM: Homo sapiens

<400> SEQUENCE: 960

Gly Ile Tyr Ile Cys Leu
1 5

<210> SEQ ID NO 961
<211> LENGTH: 6
<212> TYPE: PRT
<213> ORGANISM: Homo sapiens

<400> SEQUENCE: 961

Gly Arg Ala Arg Cys Leu
1 5

<210> SEQ ID NO 962
<211> LENGTH: 6
<212> TYPE: PRT
<213> ORGANISM: Homo sapiens

<400> SEQUENCE: 962

Gly Ser Cys Thr Cys Leu 1 5

<210> SEQ ID NO 963
<211> LENGTH: 6
<212> TYPE: PRT
<213> ORGANISM: Homo sapiens

<400> SEQUENCE: 963

Gly Arg Asp Glu Cys Leu
1 5

<210> SEQ ID NO 964
<211> LENGTH: 6
<212> TYPE: PRT
<213> ORGANISM: Homo sapiens

<400> SEQUENCE: 964

Gly His Arg Gln Cys Leu
1 5

<210> SEQ ID NO 965
<211> LENGTH: 6
<212> TYPE: PRT
<213> ORGANISM: Homo sapiens

<400> SEQUENCE: 965

Gly His Thr Leu Cys Leu
1 5

<210> SEQ ID NO 966
<211> LENGTH: 6
<212> TYPE: PRT
<213> ORGANISM: Homo sapiens

<400> SEQUENCE: 966

Gly Lys Ile Gly Cys Leu
1 5

<210> SEQ ID NO 967
<211> LENGTH: 6
<212> TYPE: PRT
<213> ORGANISM: Homo sapiens

<400> SEQUENCE: 967

Gly Ser Leu Asp Cys Leu
1 5

<210> SEQ ID NO 968
<211> LENGTH: 6
<212> TYPE: PRT
<213> ORGANISM: Homo sapiens

<400> SEQUENCE: 968

Gly Arg Leu Gly Cys Leu
1 5

<210> SEQ ID NO 969
<211> LENGTH: 6
<212> TYPE: PRT
<213> ORGANISM: Homo sapiens

<400> SEQUENCE: 969

Gly His Ile Glu Cys Leu
1 5

<210> SEQ ID NO 970
<211> LENGTH: 6
<212> TYPE: PRT
<213> ORGANISM: Homo sapiens

<400> SEQUENCE: 970

Gly Ala Asp Ile Cys Leu
1               5

<210> SEQ ID NO 971
<211> LENGTH: 6
<212> TYPE: PRT
<213> ORGANISM: Homo sapiens

<400> SEQUENCE: 971

Gly Asn Val Glu Cys Leu
1               5

<210> SEQ ID NO 972
<211> LENGTH: 6
<212> TYPE: PRT
<213> ORGANISM: Homo sapiens

<400> SEQUENCE: 972

Gly Cys Glu Asp Cys Leu
1               5

<210> SEQ ID NO 973
<211> LENGTH: 6
<212> TYPE: PRT
<213> ORGANISM: Homo sapiens

<400> SEQUENCE: 973

Gly His Glu Asp Cys Leu
1               5

<210> SEQ ID NO 974
<211> LENGTH: 6
<212> TYPE: PRT
<213> ORGANISM: Homo sapiens

<400> SEQUENCE: 974

Gly Tyr Glu Asp Cys Leu
1               5

<210> SEQ ID NO 975
<211> LENGTH: 6
<212> TYPE: PRT
<213> ORGANISM: Homo sapiens

<400> SEQUENCE: 975

Gly Met Leu Phe Cys Leu
1               5

<210> SEQ ID NO 976
<211> LENGTH: 6
<212> TYPE: PRT
<213> ORGANISM: Homo sapiens

<400> SEQUENCE: 976

Gly Thr Ile Leu Cys Leu
1               5

<210> SEQ ID NO 977

<211> LENGTH: 6
<212> TYPE: PRT
<213> ORGANISM: Homo sapiens

<400> SEQUENCE: 977

Gly Thr Asn Gln Cys Leu
1 5

<210> SEQ ID NO 978
<211> LENGTH: 6
<212> TYPE: PRT
<213> ORGANISM: Homo sapiens

<400> SEQUENCE: 978

Gly Ser Gly Thr Cys Leu
1 5

<210> SEQ ID NO 979
<211> LENGTH: 6
<212> TYPE: PRT
<213> ORGANISM: Homo sapiens

<400> SEQUENCE: 979

Gly Cys Ala Gly Cys Leu
1 5

<210> SEQ ID NO 980
<211> LENGTH: 6
<212> TYPE: PRT
<213> ORGANISM: Homo sapiens

<400> SEQUENCE: 980

Gly Leu Lys Cys Cys Leu
1 5

<210> SEQ ID NO 981
<211> LENGTH: 6
<212> TYPE: PRT
<213> ORGANISM: Homo sapiens

<400> SEQUENCE: 981

Gly Glu Asp His Cys Leu
1 5

<210> SEQ ID NO 982
<211> LENGTH: 6
<212> TYPE: PRT
<213> ORGANISM: Homo sapiens

<400> SEQUENCE: 982

Gly Gly Leu Ile Cys Leu
1 5

<210> SEQ ID NO 983
<211> LENGTH: 6
<212> TYPE: PRT
<213> ORGANISM: Homo sapiens

<400> SEQUENCE: 983

Gly Ser Ala Ala Cys Leu
1 5

<210> SEQ ID NO 984
<211> LENGTH: 6
<212> TYPE: PRT

<213> ORGANISM: Homo sapiens

<400> SEQUENCE: 984

Gly Pro Glu Asn Cys Leu
1 5

<210> SEQ ID NO 985
<211> LENGTH: 6
<212> TYPE: PRT
<213> ORGANISM: Homo sapiens

<400> SEQUENCE: 985

Gly Val Thr Ala Cys Leu
1 5

<210> SEQ ID NO 986
<211> LENGTH: 6
<212> TYPE: PRT
<213> ORGANISM: Homo sapiens

<400> SEQUENCE: 986

Gly Thr Ser Glu Cys Leu
1 5

<210> SEQ ID NO 987
<211> LENGTH: 6
<212> TYPE: PRT
<213> ORGANISM: Homo sapiens

<400> SEQUENCE: 987

Gly Leu Glu Asn Cys Leu
1 5

<210> SEQ ID NO 988
<211> LENGTH: 6
<212> TYPE: PRT
<213> ORGANISM: Homo sapiens

<400> SEQUENCE: 988

Gly Thr Thr Glu Cys Leu
1 5

<210> SEQ ID NO 989
<211> LENGTH: 6
<212> TYPE: PRT
<213> ORGANISM: Homo sapiens

<400> SEQUENCE: 989

Gly Tyr Thr Val Cys Leu
1 5

<210> SEQ ID NO 990
<211> LENGTH: 6
<212> TYPE: PRT
<213> ORGANISM: Homo sapiens

<400> SEQUENCE: 990

Gly Tyr Ile Val Cys Leu
1 5

<210> SEQ ID NO 991
<211> LENGTH: 6
<212> TYPE: PRT
<213> ORGANISM: Homo sapiens

<400> SEQUENCE: 991

Gly Phe Asp Glu Cys Leu
1               5

<210> SEQ ID NO 992
<211> LENGTH: 6
<212> TYPE: PRT
<213> ORGANISM: Homo sapiens

<400> SEQUENCE: 992

Gly Leu Ser Glu Cys Leu
1               5

<210> SEQ ID NO 993
<211> LENGTH: 6
<212> TYPE: PRT
<213> ORGANISM: Homo sapiens

<400> SEQUENCE: 993

Gly Leu Asp Ala Cys Leu
1               5

<210> SEQ ID NO 994
<211> LENGTH: 6
<212> TYPE: PRT
<213> ORGANISM: Homo sapiens

<400> SEQUENCE: 994

Gly Leu Asp Asn Cys Leu
1               5

<210> SEQ ID NO 995
<211> LENGTH: 6
<212> TYPE: PRT
<213> ORGANISM: Homo sapiens

<400> SEQUENCE: 995

Gly Ser Thr Glu Cys Leu
1               5

<210> SEQ ID NO 996
<211> LENGTH: 6
<212> TYPE: PRT
<213> ORGANISM: Homo sapiens

<400> SEQUENCE: 996

Gly Ser Thr Glu Cys Leu
1               5

<210> SEQ ID NO 997
<211> LENGTH: 6
<212> TYPE: PRT
<213> ORGANISM: Homo sapiens

<400> SEQUENCE: 997

Gly Tyr Gly Ser Cys Leu
1               5

<210> SEQ ID NO 998
<211> LENGTH: 6
<212> TYPE: PRT
<213> ORGANISM: Homo sapiens

<400> SEQUENCE: 998

Gly His Ser Glu Cys Leu
1 5

<210> SEQ ID NO 999
<211> LENGTH: 6
<212> TYPE: PRT
<213> ORGANISM: Homo sapiens

<400> SEQUENCE: 999

Gly Tyr Gly Ser Cys Leu
1 5

<210> SEQ ID NO 1000
<211> LENGTH: 6
<212> TYPE: PRT
<213> ORGANISM: Homo sapiens

<400> SEQUENCE: 1000

Gly Ala Glu Cys Cys Leu
1 5

<210> SEQ ID NO 1001
<211> LENGTH: 6
<212> TYPE: PRT
<213> ORGANISM: Homo sapiens

<400> SEQUENCE: 1001

Gly Thr Glu Ala Cys Leu
1 5

<210> SEQ ID NO 1002
<211> LENGTH: 6
<212> TYPE: PRT
<213> ORGANISM: Homo sapiens

<400> SEQUENCE: 1002

Gly Gly Thr Glu Cys Leu
1 5

<210> SEQ ID NO 1003
<211> LENGTH: 6
<212> TYPE: PRT
<213> ORGANISM: Homo sapiens

<400> SEQUENCE: 1003

Gly Asn Leu Ser Cys Leu
1 5

<210> SEQ ID NO 1004
<211> LENGTH: 6
<212> TYPE: PRT
<213> ORGANISM: Homo sapiens

<400> SEQUENCE: 1004

Gly Ser Asp His Cys Leu
1 5

<210> SEQ ID NO 1005
<211> LENGTH: 6
<212> TYPE: PRT
<213> ORGANISM: Homo sapiens

<400> SEQUENCE: 1005

Gly Asn Ile Pro Cys Leu
1 5

<210> SEQ ID NO 1006
<211> LENGTH: 6
<212> TYPE: PRT
<213> ORGANISM: Homo sapiens

<400> SEQUENCE: 1006

Gly Phe Lys Ser Cys Leu
1               5

<210> SEQ ID NO 1007
<211> LENGTH: 6
<212> TYPE: PRT
<213> ORGANISM: Homo sapiens

<400> SEQUENCE: 1007

Gly Leu Ala Leu Cys Leu
1               5

<210> SEQ ID NO 1008
<211> LENGTH: 6
<212> TYPE: PRT
<213> ORGANISM: Homo sapiens

<400> SEQUENCE: 1008

Gly Ser Arg Ser Cys Leu
1               5

<210> SEQ ID NO 1009
<211> LENGTH: 6
<212> TYPE: PRT
<213> ORGANISM: Homo sapiens

<400> SEQUENCE: 1009

Gly Lys Pro Tyr Cys Leu
1               5

<210> SEQ ID NO 1010
<211> LENGTH: 6
<212> TYPE: PRT
<213> ORGANISM: Homo sapiens

<400> SEQUENCE: 1010

Gly Pro Ala Glu Cys Leu
1               5

<210> SEQ ID NO 1011
<211> LENGTH: 6
<212> TYPE: PRT
<213> ORGANISM: Homo sapiens

<400> SEQUENCE: 1011

Gly Met Arg Leu Cys Leu
1               5

<210> SEQ ID NO 1012
<211> LENGTH: 6
<212> TYPE: PRT
<213> ORGANISM: Homo sapiens

<400> SEQUENCE: 1012

Gly Ser Pro Pro Cys Leu
1               5

<210> SEQ ID NO 1013
<211> LENGTH: 6
<212> TYPE: PRT
<213> ORGANISM: Homo sapiens

<400> SEQUENCE: 1013

Gly Val Gly Asn Cys Leu
1 5

<210> SEQ ID NO 1014
<211> LENGTH: 6
<212> TYPE: PRT
<213> ORGANISM: Homo sapiens

<400> SEQUENCE: 1014

Gly Met Tyr Arg Cys Leu
1 5

<210> SEQ ID NO 1015
<211> LENGTH: 6
<212> TYPE: PRT
<213> ORGANISM: Homo sapiens

<400> SEQUENCE: 1015

Gly Leu Tyr Ser Cys Leu
1 5

<210> SEQ ID NO 1016
<211> LENGTH: 6
<212> TYPE: PRT
<213> ORGANISM: Homo sapiens

<400> SEQUENCE: 1016

Gly Ile Ala Phe Cys Leu
1 5

<210> SEQ ID NO 1017
<211> LENGTH: 6
<212> TYPE: PRT
<213> ORGANISM: Homo sapiens

<400> SEQUENCE: 1017

Gly Ile Ala Phe Cys Leu
1 5

<210> SEQ ID NO 1018
<211> LENGTH: 6
<212> TYPE: PRT
<213> ORGANISM: Homo sapiens

<400> SEQUENCE: 1018

Gly Asn Leu Cys Cys Leu
1 5

<210> SEQ ID NO 1019
<211> LENGTH: 6
<212> TYPE: PRT
<213> ORGANISM: Homo sapiens

<400> SEQUENCE: 1019

Gly Thr His Gly Cys Leu
1 5

<210> SEQ ID NO 1020
<211> LENGTH: 6

<212> TYPE: PRT
<213> ORGANISM: Homo sapiens

<400> SEQUENCE: 1020

Gly Ala Ala Asp Cys Leu
1 5

<210> SEQ ID NO 1021
<211> LENGTH: 6
<212> TYPE: PRT
<213> ORGANISM: Homo sapiens

<400> SEQUENCE: 1021

Gly Asp Ala Thr Cys Leu
1 5

<210> SEQ ID NO 1022
<211> LENGTH: 6
<212> TYPE: PRT
<213> ORGANISM: Homo sapiens

<400> SEQUENCE: 1022

Gly Gly Arg Arg Cys Leu
1 5

<210> SEQ ID NO 1023
<211> LENGTH: 6
<212> TYPE: PRT
<213> ORGANISM: Homo sapiens

<400> SEQUENCE: 1023

Gly Lys Asp Asp Cys Leu
1 5

<210> SEQ ID NO 1024
<211> LENGTH: 6
<212> TYPE: PRT
<213> ORGANISM: Homo sapiens

<400> SEQUENCE: 1024

Gly Val Lys Asp Cys Leu
1 5

<210> SEQ ID NO 1025
<211> LENGTH: 6
<212> TYPE: PRT
<213> ORGANISM: Homo sapiens

<400> SEQUENCE: 1025

Gly Ser Gly Pro Cys Leu
1 5

<210> SEQ ID NO 1026
<211> LENGTH: 6
<212> TYPE: PRT
<213> ORGANISM: Homo sapiens

<400> SEQUENCE: 1026

Gly Tyr Trp Ser Cys Leu
1 5

<210> SEQ ID NO 1027
<211> LENGTH: 6
<212> TYPE: PRT
<213> ORGANISM: Homo sapiens

<400> SEQUENCE: 1027

Gly Val Arg Leu Cys Leu
1 5

<210> SEQ ID NO 1028
<211> LENGTH: 6
<212> TYPE: PRT
<213> ORGANISM: Homo sapiens

<400> SEQUENCE: 1028

Gly Val Glu Met Cys Leu
1 5

<210> SEQ ID NO 1029
<211> LENGTH: 6
<212> TYPE: PRT
<213> ORGANISM: Homo sapiens

<400> SEQUENCE: 1029

Gly Glu Ala Leu Cys Leu
1 5

<210> SEQ ID NO 1030
<211> LENGTH: 6
<212> TYPE: PRT
<213> ORGANISM: Homo sapiens

<400> SEQUENCE: 1030

Gly Glu Leu Val Cys Leu
1 5

<210> SEQ ID NO 1031
<211> LENGTH: 6
<212> TYPE: PRT
<213> ORGANISM: Homo sapiens

<400> SEQUENCE: 1031

Gly His Phe Tyr Cys Leu
1 5

<210> SEQ ID NO 1032
<211> LENGTH: 6
<212> TYPE: PRT
<213> ORGANISM: Homo sapiens

<400> SEQUENCE: 1032

Gly Asp Gly Asn Cys Leu
1 5

<210> SEQ ID NO 1033
<211> LENGTH: 6
<212> TYPE: PRT
<213> ORGANISM: Homo sapiens

<400> SEQUENCE: 1033

Gly His Gly Asp Cys Leu
1 5

<210> SEQ ID NO 1034
<211> LENGTH: 6
<212> TYPE: PRT
<213> ORGANISM: Homo sapiens

<400> SEQUENCE: 1034

Gly Val Lys Gly Cys Leu
1 5

<210> SEQ ID NO 1035
<211> LENGTH: 6
<212> TYPE: PRT
<213> ORGANISM: Homo sapiens

<400> SEQUENCE: 1035

Gly Asp Val Leu Cys Leu
1 5

<210> SEQ ID NO 1036
<211> LENGTH: 6
<212> TYPE: PRT
<213> ORGANISM: Homo sapiens

<400> SEQUENCE: 1036

Gly Phe Leu Ile Cys Leu
1 5

<210> SEQ ID NO 1037
<211> LENGTH: 6
<212> TYPE: PRT
<213> ORGANISM: Homo sapiens

<400> SEQUENCE: 1037

Gly Thr Ser Ala Cys Leu
1 5

<210> SEQ ID NO 1038
<211> LENGTH: 6
<212> TYPE: PRT
<213> ORGANISM: Homo sapiens

<400> SEQUENCE: 1038

Gly Phe Cys Pro Cys Leu
1 5

<210> SEQ ID NO 1039
<211> LENGTH: 6
<212> TYPE: PRT
<213> ORGANISM: Homo sapiens

<400> SEQUENCE: 1039

Gly His Pro Ser Cys Leu
1 5

<210> SEQ ID NO 1040
<211> LENGTH: 6
<212> TYPE: PRT
<213> ORGANISM: Homo sapiens

<400> SEQUENCE: 1040

Gly Gly Trp Ala Cys Leu
1 5

<210> SEQ ID NO 1041
<211> LENGTH: 6
<212> TYPE: PRT
<213> ORGANISM: Homo sapiens

<400> SEQUENCE: 1041

Gly Asn Gly Ile Cys Leu 1 5

<210> SEQ ID NO 1042
<211> LENGTH: 6
<212> TYPE: PRT
<213> ORGANISM: Homo sapiens

<400> SEQUENCE: 1042

Gly Ser Gly Gln Cys Leu
1 5

<210> SEQ ID NO 1043
<211> LENGTH: 6
<212> TYPE: PRT
<213> ORGANISM: Homo sapiens

<400> SEQUENCE: 1043

Gly His His Glu Cys Leu
1 5

<210> SEQ ID NO 1044
<211> LENGTH: 6
<212> TYPE: PRT
<213> ORGANISM: Homo sapiens

<400> SEQUENCE: 1044

Gly Gly Ser Arg Cys Leu
1 5

<210> SEQ ID NO 1045
<211> LENGTH: 6
<212> TYPE: PRT
<213> ORGANISM: Homo sapiens

<400> SEQUENCE: 1045

Gly Leu Asp Asp Cys Leu
1 5

<210> SEQ ID NO 1046
<211> LENGTH: 6
<212> TYPE: PRT
<213> ORGANISM: Homo sapiens

<400> SEQUENCE: 1046

Gly Leu Ile Thr Cys Leu
1 5

<210> SEQ ID NO 1047
<211> LENGTH: 6
<212> TYPE: PRT
<213> ORGANISM: Homo sapiens

<400> SEQUENCE: 1047

Gly His Leu Ser Cys Leu
1 5

<210> SEQ ID NO 1048
<211> LENGTH: 6
<212> TYPE: PRT
<213> ORGANISM: Homo sapiens

<400> SEQUENCE: 1048

Gly Tyr Gln Thr Cys Leu
1 5

<210> SEQ ID NO 1049
<211> LENGTH: 6
<212> TYPE: PRT
<213> ORGANISM: Homo sapiens

<400> SEQUENCE: 1049

Gly Gly Arg Pro Cys Leu
1 5

<210> SEQ ID NO 1050
<211> LENGTH: 6
<212> TYPE: PRT
<213> ORGANISM: Homo sapiens

<400> SEQUENCE: 1050

Gly His Pro Ser Cys Leu
1 5

<210> SEQ ID NO 1051
<211> LENGTH: 6
<212> TYPE: PRT
<213> ORGANISM: Homo sapiens

<400> SEQUENCE: 1051

Gly Ser Val Leu Cys Leu
1 5

<210> SEQ ID NO 1052
<211> LENGTH: 6
<212> TYPE: PRT
<213> ORGANISM: Homo sapiens

<400> SEQUENCE: 1052

Gly Asn Arg Lys Cys Leu
1 5

<210> SEQ ID NO 1053
<211> LENGTH: 6
<212> TYPE: PRT
<213> ORGANISM: Homo sapiens

<400> SEQUENCE: 1053

Gly Tyr Asn Arg Cys Leu
1 5

<210> SEQ ID NO 1054
<211> LENGTH: 6
<212> TYPE: PRT
<213> ORGANISM: Homo sapiens

<400> SEQUENCE: 1054

Gly Lys Tyr Thr Cys Leu
1 5

<210> SEQ ID NO 1055
<211> LENGTH: 6
<212> TYPE: PRT
<213> ORGANISM: Homo sapiens

<400> SEQUENCE: 1055

Gly Ser Ala Val Cys Leu
1 5

<210> SEQ ID NO 1056

<211> LENGTH: 6
<212> TYPE: PRT
<213> ORGANISM: Homo sapiens

<400> SEQUENCE: 1056

Gly Asp Tyr Ser Cys Leu
1 5

<210> SEQ ID NO 1057
<211> LENGTH: 6
<212> TYPE: PRT
<213> ORGANISM: Homo sapiens

<400> SEQUENCE: 1057

Gly Ala Gln Asp Cys Leu
1 5

<210> SEQ ID NO 1058
<211> LENGTH: 6
<212> TYPE: PRT
<213> ORGANISM: Homo sapiens

<400> SEQUENCE: 1058

Gly Thr Asn Val Cys Leu
1 5

<210> SEQ ID NO 1059
<211> LENGTH: 6
<212> TYPE: PRT
<213> ORGANISM: Homo sapiens

<400> SEQUENCE: 1059

Gly Pro Arg Leu Cys Leu
1 5

<210> SEQ ID NO 1060
<211> LENGTH: 6
<212> TYPE: PRT
<213> ORGANISM: Homo sapiens

<400> SEQUENCE: 1060

Gly Phe Lys Asn Cys Leu
1 5

<210> SEQ ID NO 1061
<211> LENGTH: 6
<212> TYPE: PRT
<213> ORGANISM: Homo sapiens

<400> SEQUENCE: 1061

Gly Ile Gln Ser Cys Leu
1 5

<210> SEQ ID NO 1062
<211> LENGTH: 6
<212> TYPE: PRT
<213> ORGANISM: Homo sapiens

<400> SEQUENCE: 1062

Gly Ser Ile Thr Cys Leu
1 5

<210> SEQ ID NO 1063
<211> LENGTH: 6
<212> TYPE: PRT

<213> ORGANISM: Homo sapiens

<400> SEQUENCE: 1063

Gly Pro Lys Ile Cys Leu
1               5

<210> SEQ ID NO 1064
<211> LENGTH: 6
<212> TYPE: PRT
<213> ORGANISM: Homo sapiens

<400> SEQUENCE: 1064

Gly Glu Pro Pro Cys Leu
1               5

<210> SEQ ID NO 1065
<211> LENGTH: 6
<212> TYPE: PRT
<213> ORGANISM: Homo sapiens

<400> SEQUENCE: 1065

Gly Ser Glu Leu Cys Leu
1               5

<210> SEQ ID NO 1066
<211> LENGTH: 6
<212> TYPE: PRT
<213> ORGANISM: Homo sapiens

<400> SEQUENCE: 1066

Gly Thr Val Ala Cys Leu
1               5

<210> SEQ ID NO 1067
<211> LENGTH: 6
<212> TYPE: PRT
<213> ORGANISM: Homo sapiens

<400> SEQUENCE: 1067

Gly Arg Glu Cys Cys Leu
1               5

<210> SEQ ID NO 1068
<211> LENGTH: 6
<212> TYPE: PRT
<213> ORGANISM: Homo sapiens

<400> SEQUENCE: 1068

Gly Phe Val Glu Cys Leu
1               5

<210> SEQ ID NO 1069
<211> LENGTH: 6
<212> TYPE: PRT
<213> ORGANISM: Homo sapiens

<400> SEQUENCE: 1069

Gly Thr Asp Gly Cys Leu
1               5

<210> SEQ ID NO 1070
<211> LENGTH: 6
<212> TYPE: PRT
<213> ORGANISM: Homo sapiens

<400> SEQUENCE: 1070

Gly Pro Ser Thr Cys Leu
1               5

<210> SEQ ID NO 1071
<211> LENGTH: 6
<212> TYPE: PRT
<213> ORGANISM: Homo sapiens

<400> SEQUENCE: 1071

Gly Ala Ala Ile Cys Leu
1               5

<210> SEQ ID NO 1072
<211> LENGTH: 6
<212> TYPE: PRT
<213> ORGANISM: Homo sapiens

<400> SEQUENCE: 1072

Gly Gln Arg Gln Cys Leu
1               5

<210> SEQ ID NO 1073
<211> LENGTH: 6
<212> TYPE: PRT
<213> ORGANISM: Homo sapiens

<400> SEQUENCE: 1073

Gly His Pro Ser Cys Leu
1               5

<210> SEQ ID NO 1074
<211> LENGTH: 6
<212> TYPE: PRT
<213> ORGANISM: Homo sapiens

<400> SEQUENCE: 1074

Gly Pro Lys Asp Cys Leu
1               5

<210> SEQ ID NO 1075
<211> LENGTH: 6
<212> TYPE: PRT
<213> ORGANISM: Homo sapiens

<400> SEQUENCE: 1075

Gly His Pro Ser Cys Leu
1               5

<210> SEQ ID NO 1076
<211> LENGTH: 6
<212> TYPE: PRT
<213> ORGANISM: Homo sapiens

<400> SEQUENCE: 1076

Gly His Pro Ser Cys Leu
1               5

<210> SEQ ID NO 1077
<211> LENGTH: 6
<212> TYPE: PRT
<213> ORGANISM: Homo sapiens

<400> SEQUENCE: 1077

Gly Gly Phe Asp Cys Leu
1 5

<210> SEQ ID NO 1078
<211> LENGTH: 6
<212> TYPE: PRT
<213> ORGANISM: Homo sapiens

<400> SEQUENCE: 1078

Gly Val Tyr Gln Cys Leu
1 5

<210> SEQ ID NO 1079
<211> LENGTH: 6
<212> TYPE: PRT
<213> ORGANISM: Homo sapiens

<400> SEQUENCE: 1079

Gly Asp Glu Ile Cys Leu
1 5

<210> SEQ ID NO 1080
<211> LENGTH: 6
<212> TYPE: PRT
<213> ORGANISM: Homo sapiens

<400> SEQUENCE: 1080

Gly Arg Leu Gly Cys Leu
1 5

<210> SEQ ID NO 1081
<211> LENGTH: 6
<212> TYPE: PRT
<213> ORGANISM: Homo sapiens

<400> SEQUENCE: 1081

Gly Leu Ile Tyr Cys Leu
1 5

<210> SEQ ID NO 1082
<211> LENGTH: 6
<212> TYPE: PRT
<213> ORGANISM: Homo sapiens

<400> SEQUENCE: 1082

Gly Pro Phe Gly Cys Leu
1 5

<210> SEQ ID NO 1083
<211> LENGTH: 6
<212> TYPE: PRT
<213> ORGANISM: Homo sapiens

<400> SEQUENCE: 1083

Gly Leu His Ala Cys Leu
1 5

<210> SEQ ID NO 1084
<211> LENGTH: 6
<212> TYPE: PRT
<213> ORGANISM: Homo sapiens

<400> SEQUENCE: 1084

Gly Lys Gly Val Cys Leu
1 5

<210> SEQ ID NO 1085
<211> LENGTH: 6
<212> TYPE: PRT
<213> ORGANISM: Homo sapiens

<400> SEQUENCE: 1085

Gly Leu Ser Lys Cys Leu
1               5

<210> SEQ ID NO 1086
<211> LENGTH: 6
<212> TYPE: PRT
<213> ORGANISM: Homo sapiens

<400> SEQUENCE: 1086

Gly Thr Val Ala Cys Leu
1               5

<210> SEQ ID NO 1087
<211> LENGTH: 6
<212> TYPE: PRT
<213> ORGANISM: Homo sapiens

<400> SEQUENCE: 1087

Gly Asn Ser Thr Cys Leu
1               5

<210> SEQ ID NO 1088
<211> LENGTH: 6
<212> TYPE: PRT
<213> ORGANISM: Homo sapiens

<400> SEQUENCE: 1088

Gly Ala Phe Val Cys Leu
1               5

<210> SEQ ID NO 1089
<211> LENGTH: 6
<212> TYPE: PRT
<213> ORGANISM: Homo sapiens

<400> SEQUENCE: 1089

Gly Thr Tyr Arg Cys Leu
1               5

<210> SEQ ID NO 1090
<211> LENGTH: 6
<212> TYPE: PRT
<213> ORGANISM: Homo sapiens

<400> SEQUENCE: 1090

Gly Ala Val Leu Cys Leu
1               5

<210> SEQ ID NO 1091
<211> LENGTH: 6
<212> TYPE: PRT
<213> ORGANISM: Homo sapiens

<400> SEQUENCE: 1091

Gly Ala Leu Val Cys Leu
1               5

<210> SEQ ID NO 1092
<211> LENGTH: 6
<212> TYPE: PRT
<213> ORGANISM: Homo sapiens

<400> SEQUENCE: 1092

Gly Thr Val Leu Cys Leu
1 5

<210> SEQ ID NO 1093
<211> LENGTH: 6
<212> TYPE: PRT
<213> ORGANISM: Homo sapiens

<400> SEQUENCE: 1093

Gly Lys Leu Cys Cys Leu
1 5

<210> SEQ ID NO 1094
<211> LENGTH: 6
<212> TYPE: PRT
<213> ORGANISM: Homo sapiens

<400> SEQUENCE: 1094

Gly Leu Tyr Leu Cys Leu
1 5

<210> SEQ ID NO 1095
<211> LENGTH: 6
<212> TYPE: PRT
<213> ORGANISM: Homo sapiens

<400> SEQUENCE: 1095

Gly Leu Glu Thr Cys Leu
1 5

<210> SEQ ID NO 1096
<211> LENGTH: 6
<212> TYPE: PRT
<213> ORGANISM: Homo sapiens

<400> SEQUENCE: 1096

Gly Cys Leu Ser Cys Leu
1 5

<210> SEQ ID NO 1097
<211> LENGTH: 6
<212> TYPE: PRT
<213> ORGANISM: Homo sapiens

<400> SEQUENCE: 1097

Gly Val Gly Asp Cys Leu
1 5

<210> SEQ ID NO 1098
<211> LENGTH: 6
<212> TYPE: PRT
<213> ORGANISM: Homo sapiens

<400> SEQUENCE: 1098

Gly His Gln Leu Cys Leu
1 5

<210> SEQ ID NO 1099
<211> LENGTH: 6

<212> TYPE: PRT
<213> ORGANISM: Homo sapiens

<400> SEQUENCE: 1099

Gly Thr Gly Asp Cys Leu
1               5

<210> SEQ ID NO 1100
<211> LENGTH: 6
<212> TYPE: PRT
<213> ORGANISM: Homo sapiens

<400> SEQUENCE: 1100

Gly Ala Ala Lys Cys Leu
1               5

<210> SEQ ID NO 1101
<211> LENGTH: 6
<212> TYPE: PRT
<213> ORGANISM: Homo sapiens

<400> SEQUENCE: 1101

Gly Cys Tyr Gly Cys Leu
1               5

<210> SEQ ID NO 1102
<211> LENGTH: 6
<212> TYPE: PRT
<213> ORGANISM: Homo sapiens

<400> SEQUENCE: 1102

Gly Tyr Phe Leu Cys Leu
1               5

<210> SEQ ID NO 1103
<211> LENGTH: 6
<212> TYPE: PRT
<213> ORGANISM: Homo sapiens

<400> SEQUENCE: 1103

Gly Arg Arg Ala Cys Leu
1               5

<210> SEQ ID NO 1104
<211> LENGTH: 6
<212> TYPE: PRT
<213> ORGANISM: Homo sapiens

<400> SEQUENCE: 1104

Gly Ser Gln Ala Cys Leu
1               5

<210> SEQ ID NO 1105
<211> LENGTH: 6
<212> TYPE: PRT
<213> ORGANISM: Homo sapiens

<400> SEQUENCE: 1105

Gly Thr Thr Cys Cys Leu
1               5

<210> SEQ ID NO 1106
<211> LENGTH: 6
<212> TYPE: PRT
<213> ORGANISM: Homo sapiens

<400> SEQUENCE: 1106

Gly Leu Asn Gln Cys Leu
1 5

<210> SEQ ID NO 1107
<211> LENGTH: 6
<212> TYPE: PRT
<213> ORGANISM: Homo sapiens

<400> SEQUENCE: 1107

Gly Val Leu Leu Cys Leu
1 5

<210> SEQ ID NO 1108
<211> LENGTH: 6
<212> TYPE: PRT
<213> ORGANISM: Homo sapiens

<400> SEQUENCE: 1108

Gly Thr Tyr Arg Cys Leu
1 5

<210> SEQ ID NO 1109
<211> LENGTH: 6
<212> TYPE: PRT
<213> ORGANISM: Homo sapiens

<400> SEQUENCE: 1109

Gly Ala Val Glu Cys Leu
1 5

<210> SEQ ID NO 1110
<211> LENGTH: 6
<212> TYPE: PRT
<213> ORGANISM: Homo sapiens

<400> SEQUENCE: 1110

Gly Thr Ala Ala Cys Leu
1 5

<210> SEQ ID NO 1111
<211> LENGTH: 6
<212> TYPE: PRT
<213> ORGANISM: Homo sapiens

<400> SEQUENCE: 1111

Gly Val Ser Leu Cys Leu
1 5

<210> SEQ ID NO 1112
<211> LENGTH: 6
<212> TYPE: PRT
<213> ORGANISM: Homo sapiens

<400> SEQUENCE: 1112

Gly Leu Lys Val Cys Leu
1 5

<210> SEQ ID NO 1113
<211> LENGTH: 6
<212> TYPE: PRT
<213> ORGANISM: Homo sapiens

<400> SEQUENCE: 1113

Gly Asp Gly His Cys Leu
1 5

<210> SEQ ID NO 1114
<211> LENGTH: 6
<212> TYPE: PRT
<213> ORGANISM: Homo sapiens

<400> SEQUENCE: 1114

Gly Glu Pro Phe Cys Leu
1 5

<210> SEQ ID NO 1115
<211> LENGTH: 6
<212> TYPE: PRT
<213> ORGANISM: Homo sapiens

<400> SEQUENCE: 1115

Gly Leu Glu Val Cys Leu
1 5

<210> SEQ ID NO 1116
<211> LENGTH: 6
<212> TYPE: PRT
<213> ORGANISM: Homo sapiens

<400> SEQUENCE: 1116

Gly Arg Gly Ile Cys Leu
1 5

<210> SEQ ID NO 1117
<211> LENGTH: 6
<212> TYPE: PRT
<213> ORGANISM: Homo sapiens

<400> SEQUENCE: 1117

Gly Gln Ala Arg Cys Leu
1 5

<210> SEQ ID NO 1118
<211> LENGTH: 6
<212> TYPE: PRT
<213> ORGANISM: Homo sapiens

<400> SEQUENCE: 1118

Gly Ile Trp Phe Cys Leu
1 5

<210> SEQ ID NO 1119
<211> LENGTH: 6
<212> TYPE: PRT
<213> ORGANISM: Homo sapiens

<400> SEQUENCE: 1119

Gly Lys Tyr Arg Cys Leu
1 5

<210> SEQ ID NO 1120
<211> LENGTH: 6
<212> TYPE: PRT
<213> ORGANISM: Homo sapiens

<400> SEQUENCE: 1120

Gly Gln Ser Leu Cys Leu 1 5

<210> SEQ ID NO 1121
<211> LENGTH: 6
<212> TYPE: PRT
<213> ORGANISM: Homo sapiens

<400> SEQUENCE: 1121

Gly His Asn Phe Cys Leu
1 5

<210> SEQ ID NO 1122
<211> LENGTH: 6
<212> TYPE: PRT
<213> ORGANISM: Homo sapiens

<400> SEQUENCE: 1122

Gly Glu Pro Arg Cys Leu
1 5

<210> SEQ ID NO 1123
<211> LENGTH: 6
<212> TYPE: PRT
<213> ORGANISM: Homo sapiens

<400> SEQUENCE: 1123

Gly Cys Val His Cys Leu
1 5

<210> SEQ ID NO 1124
<211> LENGTH: 6
<212> TYPE: PRT
<213> ORGANISM: Homo sapiens

<400> SEQUENCE: 1124

Gly Gln Pro Glu Cys Leu
1 5

<210> SEQ ID NO 1125
<211> LENGTH: 6
<212> TYPE: PRT
<213> ORGANISM: Homo sapiens

<400> SEQUENCE: 1125

Gly Lys Tyr Lys Cys Leu
1 5

<210> SEQ ID NO 1126
<211> LENGTH: 6
<212> TYPE: PRT
<213> ORGANISM: Homo sapiens

<400> SEQUENCE: 1126

Gly Thr Gln Leu Cys Leu
1 5

<210> SEQ ID NO 1127
<211> LENGTH: 6
<212> TYPE: PRT
<213> ORGANISM: Homo sapiens

<400> SEQUENCE: 1127

Gly Gly Lys Pro Cys Leu
1 5

<210> SEQ ID NO 1128
<211> LENGTH: 6
<212> TYPE: PRT
<213> ORGANISM: Homo sapiens

<400> SEQUENCE: 1128

Gly Lys Thr Phe Cys Leu
1 5

<210> SEQ ID NO 1129
<211> LENGTH: 6
<212> TYPE: PRT
<213> ORGANISM: Homo sapiens

<400> SEQUENCE: 1129

Gly Asn Tyr Tyr Cys Leu
1 5

<210> SEQ ID NO 1130
<211> LENGTH: 6
<212> TYPE: PRT
<213> ORGANISM: Homo sapiens

<400> SEQUENCE: 1130

Gly Ala Glu His Cys Leu
1 5

<210> SEQ ID NO 1131
<211> LENGTH: 6
<212> TYPE: PRT
<213> ORGANISM: Homo sapiens

<400> SEQUENCE: 1131

Gly Cys Gly Gln Cys Leu
1 5

<210> SEQ ID NO 1132
<211> LENGTH: 6
<212> TYPE: PRT
<213> ORGANISM: Homo sapiens

<400> SEQUENCE: 1132

Gly Ser Tyr Arg Cys Leu
1 5

<210> SEQ ID NO 1133
<211> LENGTH: 6
<212> TYPE: PRT
<213> ORGANISM: Homo sapiens

<400> SEQUENCE: 1133

Gly Ala Val Pro Cys Leu
1 5

<210> SEQ ID NO 1134
<211> LENGTH: 6
<212> TYPE: PRT
<213> ORGANISM: Homo sapiens

<400> SEQUENCE: 1134

Gly Ala Cys Ser Cys Leu
1 5

<210> SEQ ID NO 1135

<211> LENGTH: 6
<212> TYPE: PRT
<213> ORGANISM: Homo sapiens

<400> SEQUENCE: 1135

Gly Asn Val Thr Cys Leu
1 5

<210> SEQ ID NO 1136
<211> LENGTH: 6
<212> TYPE: PRT
<213> ORGANISM: Homo sapiens

<400> SEQUENCE: 1136

Gly Gln Val Gly Cys Leu
1 5

<210> SEQ ID NO 1137
<211> LENGTH: 6
<212> TYPE: PRT
<213> ORGANISM: Homo sapiens

<400> SEQUENCE: 1137

Gly His Leu Asp Cys Leu
1 5

<210> SEQ ID NO 1138
<211> LENGTH: 6
<212> TYPE: PRT
<213> ORGANISM: Homo sapiens

<400> SEQUENCE: 1138

Gly Ala Ala Phe Cys Leu
1 5

<210> SEQ ID NO 1139
<211> LENGTH: 6
<212> TYPE: PRT
<213> ORGANISM: Homo sapiens

<400> SEQUENCE: 1139

Gly Met Glu Glu Cys Leu
1 5

<210> SEQ ID NO 1140
<211> LENGTH: 6
<212> TYPE: PRT
<213> ORGANISM: Homo sapiens

<400> SEQUENCE: 1140

Gly Pro Thr His Cys Leu
1 5

<210> SEQ ID NO 1141
<211> LENGTH: 6
<212> TYPE: PRT
<213> ORGANISM: Homo sapiens

<400> SEQUENCE: 1141

Gly Tyr Phe Ser Cys Leu
1 5

<210> SEQ ID NO 1142
<211> LENGTH: 6
<212> TYPE: PRT

<213> ORGANISM: Homo sapiens

<400> SEQUENCE: 1142

Gly Leu Phe Val Cys Leu
1               5

<210> SEQ ID NO 1143
<211> LENGTH: 6
<212> TYPE: PRT
<213> ORGANISM: Homo sapiens

<400> SEQUENCE: 1143

Gly Thr Val Ala Cys Leu
1               5

<210> SEQ ID NO 1144
<211> LENGTH: 6
<212> TYPE: PRT
<213> ORGANISM: Homo sapiens

<400> SEQUENCE: 1144

Gly Ile Tyr Gly Cys Leu
1               5

<210> SEQ ID NO 1145
<211> LENGTH: 6
<212> TYPE: PRT
<213> ORGANISM: Homo sapiens

<400> SEQUENCE: 1145

Gly Arg Tyr Thr Cys Leu
1               5

<210> SEQ ID NO 1146
<211> LENGTH: 6
<212> TYPE: PRT
<213> ORGANISM: Homo sapiens

<400> SEQUENCE: 1146

Gly Arg Tyr Thr Cys Leu
1               5

<210> SEQ ID NO 1147
<211> LENGTH: 6
<212> TYPE: PRT
<213> ORGANISM: Homo sapiens

<400> SEQUENCE: 1147

Gly Gly Ala Pro Cys Leu
1               5

<210> SEQ ID NO 1148
<211> LENGTH: 6
<212> TYPE: PRT
<213> ORGANISM: Homo sapiens

<400> SEQUENCE: 1148

Gly Lys Arg Val Cys Leu
1               5

<210> SEQ ID NO 1149
<211> LENGTH: 6
<212> TYPE: PRT
<213> ORGANISM: Homo sapiens

<400> SEQUENCE: 1149

Gly Cys Val Ser Cys Leu
1 5

<210> SEQ ID NO 1150
<211> LENGTH: 6
<212> TYPE: PRT
<213> ORGANISM: Homo sapiens

<400> SEQUENCE: 1150

Gly Gln Thr Met Cys Leu
1 5

<210> SEQ ID NO 1151
<211> LENGTH: 6
<212> TYPE: PRT
<213> ORGANISM: Homo sapiens

<400> SEQUENCE: 1151

Gly Ser Phe Gln Cys Leu
1 5

<210> SEQ ID NO 1152
<211> LENGTH: 6
<212> TYPE: PRT
<213> ORGANISM: Homo sapiens

<400> SEQUENCE: 1152

Gly Ser Phe Ser Cys Leu
1 5

<210> SEQ ID NO 1153
<211> LENGTH: 6
<212> TYPE: PRT
<213> ORGANISM: Homo sapiens

<400> SEQUENCE: 1153

Gly Ser Thr Leu Cys Leu
1 5

<210> SEQ ID NO 1154
<211> LENGTH: 6
<212> TYPE: PRT
<213> ORGANISM: Homo sapiens

<400> SEQUENCE: 1154

Gly Ser Phe Asn Cys Leu
1 5

<210> SEQ ID NO 1155
<211> LENGTH: 6
<212> TYPE: PRT
<213> ORGANISM: Homo sapiens

<400> SEQUENCE: 1155

Gly Ala Phe Phe Cys Leu
1 5

<210> SEQ ID NO 1156
<211> LENGTH: 6
<212> TYPE: PRT
<213> ORGANISM: Homo sapiens

<400> SEQUENCE: 1156

Gly Thr Phe Ser Cys Leu
1 5

<210> SEQ ID NO 1157
<211> LENGTH: 6
<212> TYPE: PRT
<213> ORGANISM: Homo sapiens

<400> SEQUENCE: 1157

Gly Gly Pro Asp Cys Leu
1 5

<210> SEQ ID NO 1158
<211> LENGTH: 6
<212> TYPE: PRT
<213> ORGANISM: Homo sapiens

<400> SEQUENCE: 1158

Gly Gly Gly Ala Cys Leu
1 5

<210> SEQ ID NO 1159
<211> LENGTH: 6
<212> TYPE: PRT
<213> ORGANISM: Homo sapiens

<400> SEQUENCE: 1159

Gly His Ala Val Cys Leu
1 5

<210> SEQ ID NO 1160
<211> LENGTH: 6
<212> TYPE: PRT
<213> ORGANISM: Homo sapiens

<400> SEQUENCE: 1160

Gly Leu Leu Ile Cys Leu
1 5

<210> SEQ ID NO 1161
<211> LENGTH: 6
<212> TYPE: PRT
<213> ORGANISM: Homo sapiens

<400> SEQUENCE: 1161

Gly Ala Arg Gly Cys Leu
1 5

<210> SEQ ID NO 1162
<211> LENGTH: 6
<212> TYPE: PRT
<213> ORGANISM: Homo sapiens

<400> SEQUENCE: 1162

Gly Lys Thr Ala Cys Leu
1 5

<210> SEQ ID NO 1163
<211> LENGTH: 6
<212> TYPE: PRT
<213> ORGANISM: Homo sapiens

<400> SEQUENCE: 1163

Gly Gln Phe Lys Cys Leu
1 5

<210> SEQ ID NO 1164
<211> LENGTH: 6
<212> TYPE: PRT
<213> ORGANISM: Homo sapiens

<400> SEQUENCE: 1164

Gly Gln Leu Lys Cys Leu
1               5

<210> SEQ ID NO 1165
<211> LENGTH: 6
<212> TYPE: PRT
<213> ORGANISM: Homo sapiens

<400> SEQUENCE: 1165

Gly Leu Lys Gln Cys Leu
1               5

<210> SEQ ID NO 1166
<211> LENGTH: 6
<212> TYPE: PRT
<213> ORGANISM: Homo sapiens

<400> SEQUENCE: 1166

Gly Val Thr Thr Cys Leu
1               5

<210> SEQ ID NO 1167
<211> LENGTH: 6
<212> TYPE: PRT
<213> ORGANISM: Homo sapiens

<400> SEQUENCE: 1167

Gly Leu Leu Ser Cys Leu
1               5

<210> SEQ ID NO 1168
<211> LENGTH: 6
<212> TYPE: PRT
<213> ORGANISM: Homo sapiens

<400> SEQUENCE: 1168

Gly Pro Phe Ala Cys Leu
1               5

<210> SEQ ID NO 1169
<211> LENGTH: 6
<212> TYPE: PRT
<213> ORGANISM: Homo sapiens

<400> SEQUENCE: 1169

Gly Ala Arg Leu Cys Leu
1               5

<210> SEQ ID NO 1170
<211> LENGTH: 6
<212> TYPE: PRT
<213> ORGANISM: Homo sapiens

<400> SEQUENCE: 1170

Gly Ile Ser Ala Cys Leu
1               5

<210> SEQ ID NO 1171
<211> LENGTH: 6
<212> TYPE: PRT
<213> ORGANISM: Homo sapiens

<400> SEQUENCE: 1171

Gly Ser Val Ser Cys Leu
1               5

<210> SEQ ID NO 1172
<211> LENGTH: 6
<212> TYPE: PRT
<213> ORGANISM: Homo sapiens

<400> SEQUENCE: 1172

Gly Leu Leu Asn Cys Leu
1               5

<210> SEQ ID NO 1173
<211> LENGTH: 6
<212> TYPE: PRT
<213> ORGANISM: Homo sapiens

<400> SEQUENCE: 1173

Gly Pro Ser Ser Cys Leu
1               5

<210> SEQ ID NO 1174
<211> LENGTH: 6
<212> TYPE: PRT
<213> ORGANISM: Homo sapiens

<400> SEQUENCE: 1174

Gly Met Phe Thr Cys Leu
1               5

<210> SEQ ID NO 1175
<211> LENGTH: 6
<212> TYPE: PRT
<213> ORGANISM: Homo sapiens

<400> SEQUENCE: 1175

Gly Pro Leu Val Cys Leu
1               5

<210> SEQ ID NO 1176
<211> LENGTH: 6
<212> TYPE: PRT
<213> ORGANISM: Homo sapiens

<400> SEQUENCE: 1176

Gly Ala Ser Cys Cys Leu
1               5

<210> SEQ ID NO 1177
<211> LENGTH: 6
<212> TYPE: PRT
<213> ORGANISM: Homo sapiens

<400> SEQUENCE: 1177

Gly Leu Ser Ala Cys Leu
1               5

<210> SEQ ID NO 1178
<211> LENGTH: 6

<212> TYPE: PRT
<213> ORGANISM: Homo sapiens

<400> SEQUENCE: 1178

Gly Arg Ser Ala Cys Leu
1 5

<210> SEQ ID NO 1179
<211> LENGTH: 6
<212> TYPE: PRT
<213> ORGANISM: Homo sapiens

<400> SEQUENCE: 1179

Gly Pro Ala Pro Cys Leu
1 5

<210> SEQ ID NO 1180
<211> LENGTH: 6
<212> TYPE: PRT
<213> ORGANISM: Homo sapiens

<400> SEQUENCE: 1180

Gly Ala Lys Thr Cys Leu
1 5

<210> SEQ ID NO 1181
<211> LENGTH: 6
<212> TYPE: PRT
<213> ORGANISM: Homo sapiens

<400> SEQUENCE: 1181

Gly Val Asn Ile Cys Leu
1 5

<210> SEQ ID NO 1182
<211> LENGTH: 6
<212> TYPE: PRT
<213> ORGANISM: Homo sapiens

<400> SEQUENCE: 1182

Gly Phe Ser His Cys Leu
1 5

<210> SEQ ID NO 1183
<211> LENGTH: 6
<212> TYPE: PRT
<213> ORGANISM: Homo sapiens

<400> SEQUENCE: 1183

Gly Ile Lys Lys Cys Leu
1 5

<210> SEQ ID NO 1184
<211> LENGTH: 6
<212> TYPE: PRT
<213> ORGANISM: Homo sapiens

<400> SEQUENCE: 1184

Gly Ser Asp Glu Cys Leu
1 5

<210> SEQ ID NO 1185
<211> LENGTH: 6
<212> TYPE: PRT
<213> ORGANISM: Homo sapiens

<400> SEQUENCE: 1185

Gly Asp Pro Val Cys Leu
1               5

<210> SEQ ID NO 1186
<211> LENGTH: 6
<212> TYPE: PRT
<213> ORGANISM: Homo sapiens

<400> SEQUENCE: 1186

Gly Tyr Pro Ser Cys Leu
1               5

<210> SEQ ID NO 1187
<211> LENGTH: 6
<212> TYPE: PRT
<213> ORGANISM: Homo sapiens

<400> SEQUENCE: 1187

Gly Pro Val Thr Cys Leu
1               5

<210> SEQ ID NO 1188
<211> LENGTH: 6
<212> TYPE: PRT
<213> ORGANISM: Homo sapiens

<400> SEQUENCE: 1188

Gly Gly Lys Asp Cys Leu
1               5

<210> SEQ ID NO 1189
<211> LENGTH: 6
<212> TYPE: PRT
<213> ORGANISM: Homo sapiens

<400> SEQUENCE: 1189

Gly Glu Val Arg Cys Leu
1               5

<210> SEQ ID NO 1190
<211> LENGTH: 6
<212> TYPE: PRT
<213> ORGANISM: Homo sapiens

<400> SEQUENCE: 1190

Gly Gln Leu Gln Cys Leu
1               5

<210> SEQ ID NO 1191
<211> LENGTH: 6
<212> TYPE: PRT
<213> ORGANISM: Homo sapiens

<400> SEQUENCE: 1191

Gly Val Thr Thr Cys Leu
1               5

<210> SEQ ID NO 1192
<211> LENGTH: 6
<212> TYPE: PRT
<213> ORGANISM: Homo sapiens

<400> SEQUENCE: 1192

Gly Leu Ala Val Cys Leu
1 5

<210> SEQ ID NO 1193
<211> LENGTH: 6
<212> TYPE: PRT
<213> ORGANISM: Homo sapiens

<400> SEQUENCE: 1193

Gly Phe Leu Arg Cys Leu
1 5

<210> SEQ ID NO 1194
<211> LENGTH: 6
<212> TYPE: PRT
<213> ORGANISM: Homo sapiens

<400> SEQUENCE: 1194

Gly Lys Lys His Cys Leu
1 5

<210> SEQ ID NO 1195
<211> LENGTH: 6
<212> TYPE: PRT
<213> ORGANISM: Homo sapiens

<400> SEQUENCE: 1195

Gly Thr Ser Tyr Cys Leu
1 5

<210> SEQ ID NO 1196
<211> LENGTH: 6
<212> TYPE: PRT
<213> ORGANISM: Homo sapiens

<400> SEQUENCE: 1196

Gly Cys Asp Val Cys Leu
1 5

<210> SEQ ID NO 1197
<211> LENGTH: 6
<212> TYPE: PRT
<213> ORGANISM: Homo sapiens

<400> SEQUENCE: 1197

Gly Pro Pro Cys Cys Leu
1 5

<210> SEQ ID NO 1198
<211> LENGTH: 6
<212> TYPE: PRT
<213> ORGANISM: Homo sapiens

<400> SEQUENCE: 1198

Gly Thr His Pro Cys Leu
1 5

<210> SEQ ID NO 1199
<211> LENGTH: 6
<212> TYPE: PRT
<213> ORGANISM: Homo sapiens

<400> SEQUENCE: 1199

Gly Phe Lys Lys Cys Leu 1 5

<210> SEQ ID NO 1200
<211> LENGTH: 6
<212> TYPE: PRT
<213> ORGANISM: Homo sapiens

<400> SEQUENCE: 1200

Gly Gly Asn Gly Cys Leu
1 5

<210> SEQ ID NO 1201
<211> LENGTH: 6
<212> TYPE: PRT
<213> ORGANISM: Homo sapiens

<400> SEQUENCE: 1201

Gly Cys Arg Ile Cys Leu
1 5

<210> SEQ ID NO 1202
<211> LENGTH: 6
<212> TYPE: PRT
<213> ORGANISM: Homo sapiens

<400> SEQUENCE: 1202

Gly Phe Leu Arg Cys Leu
1 5

<210> SEQ ID NO 1203
<211> LENGTH: 6
<212> TYPE: PRT
<213> ORGANISM: Homo sapiens

<400> SEQUENCE: 1203

Gly Glu Lys Lys Cys Leu
1 5

<210> SEQ ID NO 1204
<211> LENGTH: 6
<212> TYPE: PRT
<213> ORGANISM: Homo sapiens

<400> SEQUENCE: 1204

Gly Gly His Ile Cys Leu
1 5

<210> SEQ ID NO 1205
<211> LENGTH: 6
<212> TYPE: PRT
<213> ORGANISM: Homo sapiens

<400> SEQUENCE: 1205

Gly Cys Thr Trp Cys Leu
1 5

<210> SEQ ID NO 1206
<211> LENGTH: 6
<212> TYPE: PRT
<213> ORGANISM: Homo sapiens

<400> SEQUENCE: 1206

Gly Ile Gly Lys Cys Leu
1 5

<210> SEQ ID NO 1207
<211> LENGTH: 6
<212> TYPE: PRT
<213> ORGANISM: Homo sapiens

<400> SEQUENCE: 1207

Gly Met Pro Met Cys Leu
1 5

<210> SEQ ID NO 1208
<211> LENGTH: 6
<212> TYPE: PRT
<213> ORGANISM: Homo sapiens

<400> SEQUENCE: 1208

Gly Phe Arg Glu Cys Leu
1 5

<210> SEQ ID NO 1209
<211> LENGTH: 6
<212> TYPE: PRT
<213> ORGANISM: Homo sapiens

<400> SEQUENCE: 1209

Gly Gln Asp Thr Cys Leu
1 5

<210> SEQ ID NO 1210
<211> LENGTH: 6
<212> TYPE: PRT
<213> ORGANISM: Homo sapiens

<400> SEQUENCE: 1210

Gly Phe Ser Leu Cys Leu
1 5

<210> SEQ ID NO 1211
<211> LENGTH: 6
<212> TYPE: PRT
<213> ORGANISM: Homo sapiens

<400> SEQUENCE: 1211

Gly Ser Trp Thr Cys Leu
1 5

<210> SEQ ID NO 1212
<211> LENGTH: 6
<212> TYPE: PRT
<213> ORGANISM: Homo sapiens

<400> SEQUENCE: 1212

Gly Ser Val Ser Cys Leu
1 5

<210> SEQ ID NO 1213
<211> LENGTH: 6
<212> TYPE: PRT
<213> ORGANISM: Homo sapiens

<400> SEQUENCE: 1213

Gly Gly Gly Ala Cys Leu
1 5

<210> SEQ ID NO 1214

<211> LENGTH: 6
<212> TYPE: PRT
<213> ORGANISM: Homo sapiens

<400> SEQUENCE: 1214

Gly Phe Gln Gly Cys Leu
1               5

<210> SEQ ID NO 1215
<211> LENGTH: 6
<212> TYPE: PRT
<213> ORGANISM: Homo sapiens

<400> SEQUENCE: 1215

Gly Phe Thr Gly Cys Leu
1               5

<210> SEQ ID NO 1216
<211> LENGTH: 6
<212> TYPE: PRT
<213> ORGANISM: Homo sapiens

<400> SEQUENCE: 1216

Gly Arg Leu Arg Cys Leu
1               5

<210> SEQ ID NO 1217
<211> LENGTH: 6
<212> TYPE: PRT
<213> ORGANISM: Homo sapiens

<400> SEQUENCE: 1217

Gly Arg Arg Ala Cys Leu
1               5

<210> SEQ ID NO 1218
<211> LENGTH: 6
<212> TYPE: PRT
<213> ORGANISM: Homo sapiens

<400> SEQUENCE: 1218

Gly Asn Leu Glu Cys Leu
1               5

<210> SEQ ID NO 1219
<211> LENGTH: 6
<212> TYPE: PRT
<213> ORGANISM: Homo sapiens

<400> SEQUENCE: 1219

Gly His Ala Leu Cys Leu
1               5

<210> SEQ ID NO 1220
<211> LENGTH: 6
<212> TYPE: PRT
<213> ORGANISM: Homo sapiens

<400> SEQUENCE: 1220

Gly Ser Pro Tyr Cys Leu
1               5

<210> SEQ ID NO 1221
<211> LENGTH: 6
<212> TYPE: PRT

<213> ORGANISM: Homo sapiens

<400> SEQUENCE: 1221

Gly Arg Ala Gln Cys Leu
1 5

<210> SEQ ID NO 1222
<211> LENGTH: 6
<212> TYPE: PRT
<213> ORGANISM: Homo sapiens

<400> SEQUENCE: 1222

Gly His Asn Phe Cys Leu
1 5

<210> SEQ ID NO 1223
<211> LENGTH: 6
<212> TYPE: PRT
<213> ORGANISM: Homo sapiens

<400> SEQUENCE: 1223

Gly Met Tyr His Cys Leu
1 5

<210> SEQ ID NO 1224
<211> LENGTH: 6
<212> TYPE: PRT
<213> ORGANISM: Homo sapiens

<400> SEQUENCE: 1224

Gly Thr Cys Met Cys Leu
1 5

<210> SEQ ID NO 1225
<211> LENGTH: 6
<212> TYPE: PRT
<213> ORGANISM: Homo sapiens

<400> SEQUENCE: 1225

Gly Phe Thr Gly Cys Leu
1 5

<210> SEQ ID NO 1226
<211> LENGTH: 6
<212> TYPE: PRT
<213> ORGANISM: Homo sapiens

<400> SEQUENCE: 1226

Gly Ser Ser Glu Cys Leu
1 5

<210> SEQ ID NO 1227
<211> LENGTH: 6
<212> TYPE: PRT
<213> ORGANISM: Homo sapiens

<400> SEQUENCE: 1227

Gly Ser Thr Glu Cys Leu
1 5

<210> SEQ ID NO 1228
<211> LENGTH: 6
<212> TYPE: PRT
<213> ORGANISM: Homo sapiens

<400> SEQUENCE: 1228

Gly Ala Leu His Cys Leu
1               5

<210> SEQ ID NO 1229
<211> LENGTH: 6
<212> TYPE: PRT
<213> ORGANISM: Homo sapiens

<400> SEQUENCE: 1229

Gly Leu Glu Cys Cys Leu
1               5

<210> SEQ ID NO 1230
<211> LENGTH: 6
<212> TYPE: PRT
<213> ORGANISM: Homo sapiens

<400> SEQUENCE: 1230

Gly Gly Gly Met Cys Leu
1               5

<210> SEQ ID NO 1231
<211> LENGTH: 6
<212> TYPE: PRT
<213> ORGANISM: Homo sapiens

<400> SEQUENCE: 1231

Gly Pro Gly Ser Cys Leu
1               5

<210> SEQ ID NO 1232
<211> LENGTH: 6
<212> TYPE: PRT
<213> ORGANISM: Homo sapiens

<400> SEQUENCE: 1232

Gly Arg Phe Pro Cys Leu
1               5

<210> SEQ ID NO 1233
<211> LENGTH: 6
<212> TYPE: PRT
<213> ORGANISM: Homo sapiens

<400> SEQUENCE: 1233

Gly Lys Ile Arg Cys Leu
1               5

<210> SEQ ID NO 1234
<211> LENGTH: 6
<212> TYPE: PRT
<213> ORGANISM: Homo sapiens

<400> SEQUENCE: 1234

Gly Asp Gln Ile Cys Leu
1               5

<210> SEQ ID NO 1235
<211> LENGTH: 6
<212> TYPE: PRT
<213> ORGANISM: Homo sapiens

<400> SEQUENCE: 1235

Gly Phe Gly Gln Cys Leu
1 5

<210> SEQ ID NO 1236
<211> LENGTH: 6
<212> TYPE: PRT
<213> ORGANISM: Homo sapiens

<400> SEQUENCE: 1236

Gly Asp Leu Thr Cys Leu
1 5

<210> SEQ ID NO 1237
<211> LENGTH: 6
<212> TYPE: PRT
<213> ORGANISM: Homo sapiens

<400> SEQUENCE: 1237

Gly Gln Cys Ala Cys Leu
1 5

<210> SEQ ID NO 1238
<211> LENGTH: 6
<212> TYPE: PRT
<213> ORGANISM: Homo sapiens

<400> SEQUENCE: 1238

Gly Gly Pro Ala Cys Leu
1 5

<210> SEQ ID NO 1239
<211> LENGTH: 6
<212> TYPE: PRT
<213> ORGANISM: Homo sapiens

<400> SEQUENCE: 1239

Gly Leu Ile Leu Cys Leu
1 5

<210> SEQ ID NO 1240
<211> LENGTH: 6
<212> TYPE: PRT
<213> ORGANISM: Homo sapiens

<400> SEQUENCE: 1240

Gly Met Ile Asp Cys Leu
1 5

<210> SEQ ID NO 1241
<211> LENGTH: 6
<212> TYPE: PRT
<213> ORGANISM: Homo sapiens

<400> SEQUENCE: 1241

Gly Leu Arg Arg Cys Leu
1 5

<210> SEQ ID NO 1242
<211> LENGTH: 6
<212> TYPE: PRT
<213> ORGANISM: Homo sapiens

<400> SEQUENCE: 1242

Gly Arg Tyr Cys Cys Leu
1 5

<210> SEQ ID NO 1243
<211> LENGTH: 6
<212> TYPE: PRT
<213> ORGANISM: Homo sapiens

<400> SEQUENCE: 1243

Gly Leu Asn Lys Cys Leu
1 5

<210> SEQ ID NO 1244
<211> LENGTH: 6
<212> TYPE: PRT
<213> ORGANISM: Homo sapiens

<400> SEQUENCE: 1244

Gly Gln Ala Leu Cys Leu
1 5

<210> SEQ ID NO 1245
<211> LENGTH: 6
<212> TYPE: PRT
<213> ORGANISM: Homo sapiens

<400> SEQUENCE: 1245

Gly Leu Asp Pro Cys Leu
1 5

<210> SEQ ID NO 1246
<211> LENGTH: 6
<212> TYPE: PRT
<213> ORGANISM: Homo sapiens

<400> SEQUENCE: 1246

Gly Ala Glu Ala Cys Leu
1 5

<210> SEQ ID NO 1247
<211> LENGTH: 6
<212> TYPE: PRT
<213> ORGANISM: Homo sapiens

<400> SEQUENCE: 1247

Gly Leu Arg Arg Cys Leu
1 5

<210> SEQ ID NO 1248
<211> LENGTH: 6
<212> TYPE: PRT
<213> ORGANISM: Homo sapiens

<400> SEQUENCE: 1248

Gly Phe Pro Glu Cys Leu
1 5

<210> SEQ ID NO 1249
<211> LENGTH: 6
<212> TYPE: PRT
<213> ORGANISM: Homo sapiens

<400> SEQUENCE: 1249

Gly Ile Leu His Cys Leu
1 5

<210> SEQ ID NO 1250
<211> LENGTH: 6
<212> TYPE: PRT
<213> ORGANISM: Homo sapiens

<400> SEQUENCE: 1250

Gly Glu Ser Glu Cys Leu
1 5

<210> SEQ ID NO 1251
<211> LENGTH: 6
<212> TYPE: PRT
<213> ORGANISM: Homo sapiens

<400> SEQUENCE: 1251

Gly Glu Ser Ile Cys Leu
1 5

<210> SEQ ID NO 1252
<211> LENGTH: 6
<212> TYPE: PRT
<213> ORGANISM: Homo sapiens

<400> SEQUENCE: 1252

Gly Lys Gly Val Cys Leu
1 5

<210> SEQ ID NO 1253
<211> LENGTH: 6
<212> TYPE: PRT
<213> ORGANISM: Homo sapiens

<400> SEQUENCE: 1253

Gly Met Ser Leu Cys Leu
1 5

<210> SEQ ID NO 1254
<211> LENGTH: 6
<212> TYPE: PRT
<213> ORGANISM: Homo sapiens

<400> SEQUENCE: 1254

Gly Glu Gly Asn Cys Leu
1 5

<210> SEQ ID NO 1255
<211> LENGTH: 6
<212> TYPE: PRT
<213> ORGANISM: Homo sapiens

<400> SEQUENCE: 1255

Gly Leu Gly Leu Cys Leu
1 5

<210> SEQ ID NO 1256
<211> LENGTH: 6
<212> TYPE: PRT
<213> ORGANISM: Homo sapiens

<400> SEQUENCE: 1256

Gly Gly Lys Tyr Cys Leu
1 5

<210> SEQ ID NO 1257
<211> LENGTH: 6

<212> TYPE: PRT
<213> ORGANISM: Homo sapiens

<400> SEQUENCE: 1257

Gly Cys Ser Ser Cys Leu
1 5

<210> SEQ ID NO 1258
<211> LENGTH: 6
<212> TYPE: PRT
<213> ORGANISM: Homo sapiens

<400> SEQUENCE: 1258

Gly Lys Thr Lys Cys Leu
1 5

<210> SEQ ID NO 1259
<211> LENGTH: 6
<212> TYPE: PRT
<213> ORGANISM: Homo sapiens

<400> SEQUENCE: 1259

Gly Leu Pro Leu Cys Leu
1 5

<210> SEQ ID NO 1260
<211> LENGTH: 6
<212> TYPE: PRT
<213> ORGANISM: Homo sapiens

<400> SEQUENCE: 1260

Gly Phe Asp Ser Cys Leu
1 5

<210> SEQ ID NO 1261
<211> LENGTH: 6
<212> TYPE: PRT
<213> ORGANISM: Homo sapiens

<400> SEQUENCE: 1261

Gly Cys Phe Val Cys Leu
1 5

<210> SEQ ID NO 1262
<211> LENGTH: 6
<212> TYPE: PRT
<213> ORGANISM: Homo sapiens

<400> SEQUENCE: 1262

Gly Phe Arg Cys Cys Leu
1 5

<210> SEQ ID NO 1263
<211> LENGTH: 6
<212> TYPE: PRT
<213> ORGANISM: Homo sapiens

<400> SEQUENCE: 1263

Gly Ile Ser Leu Cys Leu
1 5

<210> SEQ ID NO 1264
<211> LENGTH: 6
<212> TYPE: PRT
<213> ORGANISM: Homo sapiens

<400> SEQUENCE: 1264

Gly Ile Leu Gln Cys Leu
1 5

<210> SEQ ID NO 1265
<211> LENGTH: 6
<212> TYPE: PRT
<213> ORGANISM: Homo sapiens

<400> SEQUENCE: 1265

Gly His Ala Val Cys Leu
1 5

<210> SEQ ID NO 1266
<211> LENGTH: 6
<212> TYPE: PRT
<213> ORGANISM: Homo sapiens

<400> SEQUENCE: 1266

Gly Leu Tyr Cys Cys Leu
1 5

<210> SEQ ID NO 1267
<211> LENGTH: 6
<212> TYPE: PRT
<213> ORGANISM: Homo sapiens

<400> SEQUENCE: 1267

Gly Pro Asp Ala Cys Leu
1 5

<210> SEQ ID NO 1268
<211> LENGTH: 6
<212> TYPE: PRT
<213> ORGANISM: Homo sapiens

<400> SEQUENCE: 1268

Gly Tyr Ala Met Cys Leu
1 5

<210> SEQ ID NO 1269
<211> LENGTH: 6
<212> TYPE: PRT
<213> ORGANISM: Homo sapiens

<400> SEQUENCE: 1269

Gly Ala Gly Ile Cys Leu
1 5

<210> SEQ ID NO 1270
<211> LENGTH: 6
<212> TYPE: PRT
<213> ORGANISM: Homo sapiens

<400> SEQUENCE: 1270

Gly Val Arg Met Cys Leu
1 5

<210> SEQ ID NO 1271
<211> LENGTH: 6
<212> TYPE: PRT
<213> ORGANISM: Homo sapiens

<400> SEQUENCE: 1271

Gly Cys Tyr Tyr Cys Leu
1               5

<210> SEQ ID NO 1272
<211> LENGTH: 6
<212> TYPE: PRT
<213> ORGANISM: Homo sapiens

<400> SEQUENCE: 1272

Gly Pro Leu Phe Cys Leu
1               5

<210> SEQ ID NO 1273
<211> LENGTH: 6
<212> TYPE: PRT
<213> ORGANISM: Homo sapiens

<400> SEQUENCE: 1273

Gly Ala Ala Glu Cys Leu
1               5

<210> SEQ ID NO 1274
<211> LENGTH: 6
<212> TYPE: PRT
<213> ORGANISM: Homo sapiens

<400> SEQUENCE: 1274

Gly Tyr Arg Lys Cys Leu
1               5

<210> SEQ ID NO 1275
<211> LENGTH: 6
<212> TYPE: PRT
<213> ORGANISM: Homo sapiens

<400> SEQUENCE: 1275

Gly Tyr Arg Lys Cys Leu
1               5

<210> SEQ ID NO 1276
<211> LENGTH: 6
<212> TYPE: PRT
<213> ORGANISM: Homo sapiens

<400> SEQUENCE: 1276

Gly Tyr Arg Lys Cys Leu
1               5

<210> SEQ ID NO 1277
<211> LENGTH: 6
<212> TYPE: PRT
<213> ORGANISM: Homo sapiens

<400> SEQUENCE: 1277

Gly Val Leu Gly Cys Leu
1               5

<210> SEQ ID NO 1278
<211> LENGTH: 6
<212> TYPE: PRT
<213> ORGANISM: Homo sapiens

<400> SEQUENCE: 1278

Gly Ser Lys Tyr Cys Leu 1 5

<210> SEQ ID NO 1279
<211> LENGTH: 6
<212> TYPE: PRT
<213> ORGANISM: Homo sapiens

<400> SEQUENCE: 1279

Gly Leu Met Thr Cys Leu
1 5

<210> SEQ ID NO 1280
<211> LENGTH: 6
<212> TYPE: PRT
<213> ORGANISM: Homo sapiens

<400> SEQUENCE: 1280

Gly Lys Leu Ser Cys Leu
1 5

<210> SEQ ID NO 1281
<211> LENGTH: 6
<212> TYPE: PRT
<213> ORGANISM: Homo sapiens

<400> SEQUENCE: 1281

Gly Leu Gly Ala Cys Leu
1 5

<210> SEQ ID NO 1282
<211> LENGTH: 6
<212> TYPE: PRT
<213> ORGANISM: Homo sapiens

<400> SEQUENCE: 1282

Gly Phe His Glu Cys Leu
1 5

<210> SEQ ID NO 1283
<211> LENGTH: 6
<212> TYPE: PRT
<213> ORGANISM: Homo sapiens

<400> SEQUENCE: 1283

Gly Ala Thr Asn Cys Leu
1 5

<210> SEQ ID NO 1284
<211> LENGTH: 6
<212> TYPE: PRT
<213> ORGANISM: Homo sapiens

<400> SEQUENCE: 1284

Gly Gly Arg Arg Cys Leu
1 5

<210> SEQ ID NO 1285
<211> LENGTH: 6
<212> TYPE: PRT
<213> ORGANISM: Homo sapiens

<400> SEQUENCE: 1285

Gly Lys Gln Pro Cys Leu
1 5

<210> SEQ ID NO 1286
<211> LENGTH: 6
<212> TYPE: PRT
<213> ORGANISM: Homo sapiens

<400> SEQUENCE: 1286

Gly Ser Pro Tyr Cys Leu
1 5

<210> SEQ ID NO 1287
<211> LENGTH: 6
<212> TYPE: PRT
<213> ORGANISM: Homo sapiens

<400> SEQUENCE: 1287

Gly Gly Tyr Thr Cys Leu
1 5

<210> SEQ ID NO 1288
<211> LENGTH: 6
<212> TYPE: PRT
<213> ORGANISM: Homo sapiens

<400> SEQUENCE: 1288

Gly Phe Arg Gly Cys Leu
1 5

<210> SEQ ID NO 1289
<211> LENGTH: 6
<212> TYPE: PRT
<213> ORGANISM: Homo sapiens

<400> SEQUENCE: 1289

Gly Ser Pro Thr Cys Leu
1 5

<210> SEQ ID NO 1290
<211> LENGTH: 6
<212> TYPE: PRT
<213> ORGANISM: Homo sapiens

<400> SEQUENCE: 1290

Gly Val Val Ala Cys Leu
1 5

<210> SEQ ID NO 1291
<211> LENGTH: 6
<212> TYPE: PRT
<213> ORGANISM: Homo sapiens

<400> SEQUENCE: 1291

Gly Ala Gly Ser Cys Leu
1 5

<210> SEQ ID NO 1292
<211> LENGTH: 6
<212> TYPE: PRT
<213> ORGANISM: Homo sapiens

<400> SEQUENCE: 1292

Gly Ala Asp Cys Cys Leu
1 5

<210> SEQ ID NO 1293

<211> LENGTH: 6
<212> TYPE: PRT
<213> ORGANISM: Homo sapiens

<400> SEQUENCE: 1293

Gly Lys Tyr Pro Cys Leu
1 5

<210> SEQ ID NO 1294
<211> LENGTH: 6
<212> TYPE: PRT
<213> ORGANISM: Homo sapiens

<400> SEQUENCE: 1294

Gly Ser Gly Gly Cys Leu
1 5

<210> SEQ ID NO 1295
<211> LENGTH: 6
<212> TYPE: PRT
<213> ORGANISM: Homo sapiens

<400> SEQUENCE: 1295

Gly Phe Ser Asp Cys Leu
1 5

<210> SEQ ID NO 1296
<211> LENGTH: 6
<212> TYPE: PRT
<213> ORGANISM: Homo sapiens

<400> SEQUENCE: 1296

Gly Ile Phe Ile Cys Leu
1 5

<210> SEQ ID NO 1297
<211> LENGTH: 6
<212> TYPE: PRT
<213> ORGANISM: Homo sapiens

<400> SEQUENCE: 1297

Gly Trp Asp Pro Cys Leu
1 5

<210> SEQ ID NO 1298
<211> LENGTH: 6
<212> TYPE: PRT
<213> ORGANISM: Homo sapiens

<400> SEQUENCE: 1298

Gly Leu Gly Leu Cys Leu
1 5

<210> SEQ ID NO 1299
<211> LENGTH: 6
<212> TYPE: PRT
<213> ORGANISM: Homo sapiens

<400> SEQUENCE: 1299

Gly Ser Pro Thr Cys Leu
1 5

<210> SEQ ID NO 1300
<211> LENGTH: 6
<212> TYPE: PRT

<213> ORGANISM: Homo sapiens

<400> SEQUENCE: 1300

Gly Thr Gly Lys Cys Leu
1               5

<210> SEQ ID NO 1301
<211> LENGTH: 6
<212> TYPE: PRT
<213> ORGANISM: Homo sapiens

<400> SEQUENCE: 1301

Gly Trp Trp Lys Cys Leu
1               5

<210> SEQ ID NO 1302
<211> LENGTH: 6
<212> TYPE: PRT
<213> ORGANISM: Homo sapiens

<400> SEQUENCE: 1302

Gly Glu Gly Ser Cys Leu
1               5

<210> SEQ ID NO 1303
<211> LENGTH: 6
<212> TYPE: PRT
<213> ORGANISM: Homo sapiens

<400> SEQUENCE: 1303

Gly Phe Ala Leu Cys Leu
1               5

<210> SEQ ID NO 1304
<211> LENGTH: 6
<212> TYPE: PRT
<213> ORGANISM: Homo sapiens

<400> SEQUENCE: 1304

Gly Ile Phe Tyr Cys Leu
1               5

<210> SEQ ID NO 1305
<211> LENGTH: 6
<212> TYPE: PRT
<213> ORGANISM: Homo sapiens

<400> SEQUENCE: 1305

Gly Leu Pro Glu Cys Leu
1               5

<210> SEQ ID NO 1306
<211> LENGTH: 6
<212> TYPE: PRT
<213> ORGANISM: Homo sapiens

<400> SEQUENCE: 1306

Gly Ala Asn Pro Cys Leu
1               5

<210> SEQ ID NO 1307
<211> LENGTH: 6
<212> TYPE: PRT
<213> ORGANISM: Homo sapiens

<400> SEQUENCE: 1307

Gly Asn Leu Ser Cys Leu
1 5

<210> SEQ ID NO 1308
<211> LENGTH: 6
<212> TYPE: PRT
<213> ORGANISM: Homo sapiens

<400> SEQUENCE: 1308

Gly Val Arg Thr Cys Leu
1 5

<210> SEQ ID NO 1309
<211> LENGTH: 6
<212> TYPE: PRT
<213> ORGANISM: Homo sapiens

<400> SEQUENCE: 1309

Gly Trp Leu Pro Cys Leu
1 5

<210> SEQ ID NO 1310
<211> LENGTH: 6
<212> TYPE: PRT
<213> ORGANISM: Homo sapiens

<400> SEQUENCE: 1310

Gly Asn Tyr Thr Cys Leu
1 5

<210> SEQ ID NO 1311
<211> LENGTH: 6
<212> TYPE: PRT
<213> ORGANISM: Homo sapiens

<400> SEQUENCE: 1311

Gly Ser Arg Asp Cys Leu
1 5

<210> SEQ ID NO 1312
<211> LENGTH: 6
<212> TYPE: PRT
<213> ORGANISM: Homo sapiens

<400> SEQUENCE: 1312

Gly Ser Ala Pro Cys Leu
1 5

<210> SEQ ID NO 1313
<211> LENGTH: 6
<212> TYPE: PRT
<213> ORGANISM: Homo sapiens

<400> SEQUENCE: 1313

Gly Ser Tyr Arg Cys Leu
1 5

<210> SEQ ID NO 1314
<211> LENGTH: 6
<212> TYPE: PRT
<213> ORGANISM: Homo sapiens

<400> SEQUENCE: 1314

Gly Phe Pro Glu Cys Leu
1 5

<210> SEQ ID NO 1315
<211> LENGTH: 6
<212> TYPE: PRT
<213> ORGANISM: Homo sapiens

<400> SEQUENCE: 1315

Gly Ile Ser Leu Cys Leu
1 5

<210> SEQ ID NO 1316
<211> LENGTH: 6
<212> TYPE: PRT
<213> ORGANISM: Homo sapiens

<400> SEQUENCE: 1316

Gly Glu Glu Leu Cys Leu
1 5

<210> SEQ ID NO 1317
<211> LENGTH: 6
<212> TYPE: PRT
<213> ORGANISM: Homo sapiens

<400> SEQUENCE: 1317

Gly Ser Asp Asp Cys Leu
1 5

<210> SEQ ID NO 1318
<211> LENGTH: 6
<212> TYPE: PRT
<213> ORGANISM: Homo sapiens

<400> SEQUENCE: 1318

Gly Ile Ile Gln Cys Leu
1 5

<210> SEQ ID NO 1319
<211> LENGTH: 6
<212> TYPE: PRT
<213> ORGANISM: Homo sapiens

<400> SEQUENCE: 1319

Gly Ala Thr Arg Cys Leu
1 5

<210> SEQ ID NO 1320
<211> LENGTH: 6
<212> TYPE: PRT
<213> ORGANISM: Homo sapiens

<400> SEQUENCE: 1320

Gly Leu Cys Lys Cys Leu
1 5

<210> SEQ ID NO 1321
<211> LENGTH: 6
<212> TYPE: PRT
<213> ORGANISM: Homo sapiens

<400> SEQUENCE: 1321

Gly Leu Val Asp Cys Leu
1 5

<210> SEQ ID NO 1322
<211> LENGTH: 6
<212> TYPE: PRT
<213> ORGANISM: Homo sapiens

<400> SEQUENCE: 1322

Gly Arg Gly Asp Cys Leu
1 5

<210> SEQ ID NO 1323
<211> LENGTH: 6
<212> TYPE: PRT
<213> ORGANISM: Homo sapiens

<400> SEQUENCE: 1323

Gly Leu Ala Phe Cys Leu
1 5

<210> SEQ ID NO 1324
<211> LENGTH: 6
<212> TYPE: PRT
<213> ORGANISM: Homo sapiens

<400> SEQUENCE: 1324

Gly Tyr Ala Ala Cys Leu
1 5

<210> SEQ ID NO 1325
<211> LENGTH: 6
<212> TYPE: PRT
<213> ORGANISM: Homo sapiens

<400> SEQUENCE: 1325

Gly Gln Leu Ala Cys Leu
1 5

<210> SEQ ID NO 1326
<211> LENGTH: 6
<212> TYPE: PRT
<213> ORGANISM: Homo sapiens

<400> SEQUENCE: 1326

Gly Gly Leu Arg Cys Leu
1 5

<210> SEQ ID NO 1327
<211> LENGTH: 6
<212> TYPE: PRT
<213> ORGANISM: Homo sapiens

<400> SEQUENCE: 1327

Gly Lys Asp Lys Cys Leu
1 5

<210> SEQ ID NO 1328
<211> LENGTH: 6
<212> TYPE: PRT
<213> ORGANISM: Homo sapiens

<400> SEQUENCE: 1328

Gly Phe Gly Arg Cys Leu
1 5

<210> SEQ ID NO 1329
<211> LENGTH: 6
<212> TYPE: PRT
<213> ORGANISM: Homo sapiens

<400> SEQUENCE: 1329

Gly Thr Ile Thr Cys Leu
1               5

<210> SEQ ID NO 1330
<211> LENGTH: 6
<212> TYPE: PRT
<213> ORGANISM: Homo sapiens

<400> SEQUENCE: 1330

Gly Arg Gly Gln Cys Leu
1               5

<210> SEQ ID NO 1331
<211> LENGTH: 6
<212> TYPE: PRT
<213> ORGANISM: Homo sapiens

<400> SEQUENCE: 1331

Gly Asp Asp Leu Cys Leu
1               5

<210> SEQ ID NO 1332
<211> LENGTH: 6
<212> TYPE: PRT
<213> ORGANISM: Homo sapiens

<400> SEQUENCE: 1332

Gly Asn Val Ile Cys Leu
1               5

<210> SEQ ID NO 1333
<211> LENGTH: 6
<212> TYPE: PRT
<213> ORGANISM: Homo sapiens

<400> SEQUENCE: 1333

Gly Ile Val Leu Cys Leu
1               5

<210> SEQ ID NO 1334
<211> LENGTH: 6
<212> TYPE: PRT
<213> ORGANISM: Homo sapiens

<400> SEQUENCE: 1334

Gly Lys Leu Glu Cys Leu
1               5

<210> SEQ ID NO 1335
<211> LENGTH: 6
<212> TYPE: PRT
<213> ORGANISM: Homo sapiens

<400> SEQUENCE: 1335

Gly His Pro Gln Cys Leu
1               5

<210> SEQ ID NO 1336
<211> LENGTH: 6

<212> TYPE: PRT
<213> ORGANISM: Homo sapiens

<400> SEQUENCE: 1336

Gly Leu Phe Ala Cys Leu
1               5

<210> SEQ ID NO 1337
<211> LENGTH: 6
<212> TYPE: PRT
<213> ORGANISM: Homo sapiens

<400> SEQUENCE: 1337

Gly Ile Arg Thr Cys Leu
1               5

<210> SEQ ID NO 1338
<211> LENGTH: 6
<212> TYPE: PRT
<213> ORGANISM: Homo sapiens

<400> SEQUENCE: 1338

Gly His Gly Thr Cys Leu
1               5

<210> SEQ ID NO 1339
<211> LENGTH: 6
<212> TYPE: PRT
<213> ORGANISM: Homo sapiens

<400> SEQUENCE: 1339

Gly Asp Gly Ser Cys Leu
1               5

<210> SEQ ID NO 1340
<211> LENGTH: 6
<212> TYPE: PRT
<213> ORGANISM: Homo sapiens

<400> SEQUENCE: 1340

Gly Asn Gly Ala Cys Leu
1               5

<210> SEQ ID NO 1341
<211> LENGTH: 6
<212> TYPE: PRT
<213> ORGANISM: Homo sapiens

<400> SEQUENCE: 1341

Gly Ser Ser Arg Cys Leu
1               5

<210> SEQ ID NO 1342
<211> LENGTH: 6
<212> TYPE: PRT
<213> ORGANISM: Homo sapiens

<400> SEQUENCE: 1342

Gly Ser Gly Gln Cys Leu
1               5

<210> SEQ ID NO 1343
<211> LENGTH: 6
<212> TYPE: PRT
<213> ORGANISM: Homo sapiens

<400> SEQUENCE: 1343

Gly Phe His Leu Cys Leu
1 5

<210> SEQ ID NO 1344
<211> LENGTH: 6
<212> TYPE: PRT
<213> ORGANISM: Homo sapiens

<400> SEQUENCE: 1344

Gly Leu Tyr Leu Cys Leu
1 5

<210> SEQ ID NO 1345
<211> LENGTH: 6
<212> TYPE: PRT
<213> ORGANISM: Homo sapiens

<400> SEQUENCE: 1345

Gly Trp Ser Phe Cys Leu
1 5

<210> SEQ ID NO 1346
<211> LENGTH: 6
<212> TYPE: PRT
<213> ORGANISM: Homo sapiens

<400> SEQUENCE: 1346

Gly Gln Thr Met Cys Leu
1 5

<210> SEQ ID NO 1347
<211> LENGTH: 6
<212> TYPE: PRT
<213> ORGANISM: Homo sapiens

<400> SEQUENCE: 1347

Gly Thr Gly Ser Cys Leu
1 5

<210> SEQ ID NO 1348
<211> LENGTH: 6
<212> TYPE: PRT
<213> ORGANISM: Homo sapiens

<400> SEQUENCE: 1348

Gly Arg Gln Gly Cys Leu
1 5

<210> SEQ ID NO 1349
<211> LENGTH: 6
<212> TYPE: PRT
<213> ORGANISM: Homo sapiens

<400> SEQUENCE: 1349

Gly Glu Cys Arg Cys Leu
1 5

<210> SEQ ID NO 1350
<211> LENGTH: 6
<212> TYPE: PRT
<213> ORGANISM: Homo sapiens

<400> SEQUENCE: 1350

Gly Arg Pro Ile Cys Leu
1               5

<210> SEQ ID NO 1351
<211> LENGTH: 6
<212> TYPE: PRT
<213> ORGANISM: Homo sapiens

<400> SEQUENCE: 1351

Gly Ser Asp Ser Cys Leu
1               5

<210> SEQ ID NO 1352
<211> LENGTH: 6
<212> TYPE: PRT
<213> ORGANISM: Homo sapiens

<400> SEQUENCE: 1352

Gly Phe Glu Gly Cys Leu
1               5

<210> SEQ ID NO 1353
<211> LENGTH: 6
<212> TYPE: PRT
<213> ORGANISM: Homo sapiens

<400> SEQUENCE: 1353

Gly Gly Gly Pro Cys Leu
1               5

<210> SEQ ID NO 1354
<211> LENGTH: 6
<212> TYPE: PRT
<213> ORGANISM: Homo sapiens

<400> SEQUENCE: 1354

Gly Val Leu Tyr Cys Leu
1               5

<210> SEQ ID NO 1355
<211> LENGTH: 6
<212> TYPE: PRT
<213> ORGANISM: Homo sapiens

<400> SEQUENCE: 1355

Gly Lys Glu Gln Cys Leu
1               5

<210> SEQ ID NO 1356
<211> LENGTH: 6
<212> TYPE: PRT
<213> ORGANISM: Homo sapiens

<400> SEQUENCE: 1356

Gly Lys Thr Leu Cys Leu
1               5

<210> SEQ ID NO 1357
<211> LENGTH: 6
<212> TYPE: PRT
<213> ORGANISM: Homo sapiens

<400> SEQUENCE: 1357

Gly Arg Ser Leu Cys Leu 1 5

<210> SEQ ID NO 1358
<211> LENGTH: 6
<212> TYPE: PRT
<213> ORGANISM: Homo sapiens

<400> SEQUENCE: 1358

Gly Leu Ala Leu Cys Leu
1 5

<210> SEQ ID NO 1359
<211> LENGTH: 6
<212> TYPE: PRT
<213> ORGANISM: Homo sapiens

<400> SEQUENCE: 1359

Gly Lys Asp Leu Cys Leu
1 5

<210> SEQ ID NO 1360
<211> LENGTH: 6
<212> TYPE: PRT
<213> ORGANISM: Homo sapiens

<400> SEQUENCE: 1360

Gly Trp Ala Ser Cys Leu
1 5

<210> SEQ ID NO 1361
<211> LENGTH: 6
<212> TYPE: PRT
<213> ORGANISM: Homo sapiens

<400> SEQUENCE: 1361

Gly Asp Asp Asp Cys Leu
1 5

<210> SEQ ID NO 1362
<211> LENGTH: 6
<212> TYPE: PRT
<213> ORGANISM: Homo sapiens

<400> SEQUENCE: 1362

Gly Thr Tyr Lys Cys Leu
1 5

<210> SEQ ID NO 1363
<211> LENGTH: 6
<212> TYPE: PRT
<213> ORGANISM: Homo sapiens

<400> SEQUENCE: 1363

Gly Ala Val Ala Cys Leu
1 5

<210> SEQ ID NO 1364
<211> LENGTH: 6
<212> TYPE: PRT
<213> ORGANISM: Homo sapiens

<400> SEQUENCE: 1364

Gly Gly Gly Ala Cys Leu
1 5

<210> SEQ ID NO 1365
<211> LENGTH: 6
<212> TYPE: PRT
<213> ORGANISM: Homo sapiens

<400> SEQUENCE: 1365

Gly His Val Glu Cys Leu
1               5

<210> SEQ ID NO 1366
<211> LENGTH: 6
<212> TYPE: PRT
<213> ORGANISM: Homo sapiens

<400> SEQUENCE: 1366

Gly Leu Ser Lys Cys Leu
1               5

<210> SEQ ID NO 1367
<211> LENGTH: 6
<212> TYPE: PRT
<213> ORGANISM: Homo sapiens

<400> SEQUENCE: 1367

Gly Lys Asn Lys Cys Leu
1               5

<210> SEQ ID NO 1368
<211> LENGTH: 6
<212> TYPE: PRT
<213> ORGANISM: Homo sapiens

<400> SEQUENCE: 1368

Gly Val His Trp Cys Leu
1               5

<210> SEQ ID NO 1369
<211> LENGTH: 6
<212> TYPE: PRT
<213> ORGANISM: Homo sapiens

<400> SEQUENCE: 1369

Gly Arg Glu Cys Cys Leu
1               5

<210> SEQ ID NO 1370
<211> LENGTH: 6
<212> TYPE: PRT
<213> ORGANISM: Homo sapiens

<400> SEQUENCE: 1370

Gly Asn Gln Asn Cys Leu
1               5

<210> SEQ ID NO 1371
<211> LENGTH: 6
<212> TYPE: PRT
<213> ORGANISM: Homo sapiens

<400> SEQUENCE: 1371

Gly Leu Asn Gln Cys Leu
1               5

<210> SEQ ID NO 1372

<211> LENGTH: 6
<212> TYPE: PRT
<213> ORGANISM: Homo sapiens

<400> SEQUENCE: 1372

Gly Arg Ser Ser Cys Leu
1 5

<210> SEQ ID NO 1373
<211> LENGTH: 6
<212> TYPE: PRT
<213> ORGANISM: Homo sapiens

<400> SEQUENCE: 1373

Gly Thr Asn Gly Cys Leu
1 5

<210> SEQ ID NO 1374
<211> LENGTH: 6
<212> TYPE: PRT
<213> ORGANISM: Homo sapiens

<400> SEQUENCE: 1374

Gly Ser Glu Thr Cys Leu
1 5

<210> SEQ ID NO 1375
<211> LENGTH: 6
<212> TYPE: PRT
<213> ORGANISM: Homo sapiens

<400> SEQUENCE: 1375

Gly Gly Leu Asp Cys Leu
1 5

<210> SEQ ID NO 1376
<211> LENGTH: 6
<212> TYPE: PRT
<213> ORGANISM: Homo sapiens

<400> SEQUENCE: 1376

Gly Glu Asp Ile Cys Leu
1 5

<210> SEQ ID NO 1377
<211> LENGTH: 6
<212> TYPE: PRT
<213> ORGANISM: Homo sapiens

<400> SEQUENCE: 1377

Gly Leu Gly Gly Cys Leu
1 5

<210> SEQ ID NO 1378
<211> LENGTH: 6
<212> TYPE: PRT
<213> ORGANISM: Homo sapiens

<400> SEQUENCE: 1378

Gly Leu Leu Ser Cys Leu
1 5

<210> SEQ ID NO 1379
<211> LENGTH: 6
<212> TYPE: PRT

<213> ORGANISM: Homo sapiens

<400> SEQUENCE: 1379

Gly Glu Arg Lys Cys Leu
1 5

<210> SEQ ID NO 1380
<211> LENGTH: 6
<212> TYPE: PRT
<213> ORGANISM: Homo sapiens

<400> SEQUENCE: 1380

Gly Gln Leu Phe Cys Leu
1 5

<210> SEQ ID NO 1381
<211> LENGTH: 6
<212> TYPE: PRT
<213> ORGANISM: Homo sapiens

<400> SEQUENCE: 1381

Gly Leu Glu Gly Cys Leu
1 5

<210> SEQ ID NO 1382
<211> LENGTH: 6
<212> TYPE: PRT
<213> ORGANISM: Homo sapiens

<400> SEQUENCE: 1382

Gly Val Ala Ser Cys Leu
1 5

<210> SEQ ID NO 1383
<211> LENGTH: 6
<212> TYPE: PRT
<213> ORGANISM: Homo sapiens

<400> SEQUENCE: 1383

Gly Met Trp Ser Cys Leu
1 5

<210> SEQ ID NO 1384
<211> LENGTH: 6
<212> TYPE: PRT
<213> ORGANISM: Homo sapiens

<400> SEQUENCE: 1384

Gly Tyr Gly Glu Cys Leu
1 5

<210> SEQ ID NO 1385
<211> LENGTH: 6
<212> TYPE: PRT
<213> ORGANISM: Homo sapiens

<400> SEQUENCE: 1385

Gly Glu Ala Asp Cys Leu
1 5

<210> SEQ ID NO 1386
<211> LENGTH: 6
<212> TYPE: PRT
<213> ORGANISM: Homo sapiens

<400> SEQUENCE: 1386

Gly Pro Gly Gly Cys Leu
1 5

<210> SEQ ID NO 1387
<211> LENGTH: 6
<212> TYPE: PRT
<213> ORGANISM: Homo sapiens

<400> SEQUENCE: 1387

Gly Asn Ile Gly Cys Leu
1 5

<210> SEQ ID NO 1388
<211> LENGTH: 6
<212> TYPE: PRT
<213> ORGANISM: Homo sapiens

<400> SEQUENCE: 1388

Gly Phe Gln Gly Cys Leu
1 5

<210> SEQ ID NO 1389
<211> LENGTH: 6
<212> TYPE: PRT
<213> ORGANISM: Homo sapiens

<400> SEQUENCE: 1389

Gly Met Leu Ala Cys Leu
1 5

<210> SEQ ID NO 1390
<211> LENGTH: 6
<212> TYPE: PRT
<213> ORGANISM: Homo sapiens

<400> SEQUENCE: 1390

Gly Ile Val Glu Cys Leu
1 5

<210> SEQ ID NO 1391
<211> LENGTH: 6
<212> TYPE: PRT
<213> ORGANISM: Homo sapiens

<400> SEQUENCE: 1391

Gly Leu Gln Gly Cys Leu
1 5

<210> SEQ ID NO 1392
<211> LENGTH: 6
<212> TYPE: PRT
<213> ORGANISM: Homo sapiens

<400> SEQUENCE: 1392

Gly Thr Met Gln Cys Leu
1 5

<210> SEQ ID NO 1393
<211> LENGTH: 6
<212> TYPE: PRT
<213> ORGANISM: Homo sapiens

<400> SEQUENCE: 1393

Gly Asp Gln Arg Cys Leu
1 5

<210> SEQ ID NO 1394
<211> LENGTH: 6
<212> TYPE: PRT
<213> ORGANISM: Homo sapiens

<400> SEQUENCE: 1394

Gly Val Arg Arg Cys Leu
1 5

<210> SEQ ID NO 1395
<211> LENGTH: 6
<212> TYPE: PRT
<213> ORGANISM: Homo sapiens

<400> SEQUENCE: 1395

Gly Thr Tyr Leu Cys Leu
1 5

<210> SEQ ID NO 1396
<211> LENGTH: 6
<212> TYPE: PRT
<213> ORGANISM: Homo sapiens

<400> SEQUENCE: 1396

Gly Gly Ser Gln Cys Leu
1 5

<210> SEQ ID NO 1397
<211> LENGTH: 6
<212> TYPE: PRT
<213> ORGANISM: Homo sapiens

<400> SEQUENCE: 1397

Gly Leu Pro Thr Cys Leu
1 5

<210> SEQ ID NO 1398
<211> LENGTH: 6
<212> TYPE: PRT
<213> ORGANISM: Homo sapiens

<400> SEQUENCE: 1398

Gly Phe Arg Glu Cys Leu
1 5

<210> SEQ ID NO 1399
<211> LENGTH: 6
<212> TYPE: PRT
<213> ORGANISM: Homo sapiens

<400> SEQUENCE: 1399

Gly Gln Val Gln Cys Leu
1 5

<210> SEQ ID NO 1400
<211> LENGTH: 6
<212> TYPE: PRT
<213> ORGANISM: Homo sapiens

<400> SEQUENCE: 1400

Gly Thr Phe Phe Cys Leu
1 5

<210> SEQ ID NO 1401
<211> LENGTH: 6
<212> TYPE: PRT
<213> ORGANISM: Homo sapiens

<400> SEQUENCE: 1401

Gly Phe Leu Gly Cys Leu
1               5

<210> SEQ ID NO 1402
<211> LENGTH: 6
<212> TYPE: PRT
<213> ORGANISM: Homo sapiens

<400> SEQUENCE: 1402

Gly Asn Pro Lys Cys Leu
1               5

<210> SEQ ID NO 1403
<211> LENGTH: 6
<212> TYPE: PRT
<213> ORGANISM: Homo sapiens

<400> SEQUENCE: 1403

Gly Ser Leu Thr Cys Leu
1               5

<210> SEQ ID NO 1404
<211> LENGTH: 6
<212> TYPE: PRT
<213> ORGANISM: Homo sapiens

<400> SEQUENCE: 1404

Gly Asn Pro Lys Cys Leu
1               5

<210> SEQ ID NO 1405
<211> LENGTH: 6
<212> TYPE: PRT
<213> ORGANISM: Homo sapiens

<400> SEQUENCE: 1405

Gly Asn Leu Ser Cys Leu
1               5

<210> SEQ ID NO 1406
<211> LENGTH: 6
<212> TYPE: PRT
<213> ORGANISM: Homo sapiens

<400> SEQUENCE: 1406

Gly Lys Gly Val Cys Leu
1               5

<210> SEQ ID NO 1407
<211> LENGTH: 6
<212> TYPE: PRT
<213> ORGANISM: Homo sapiens

<400> SEQUENCE: 1407

Gly Pro Leu Ala Cys Leu
1               5

<210> SEQ ID NO 1408
<211> LENGTH: 6
<212> TYPE: PRT
<213> ORGANISM: Homo sapiens

<400> SEQUENCE: 1408

Gly Leu Asn Leu Cys Leu
1 5

<210> SEQ ID NO 1409
<211> LENGTH: 6
<212> TYPE: PRT
<213> ORGANISM: Homo sapiens

<400> SEQUENCE: 1409

Gly Phe Thr Gly Cys Leu
1 5

<210> SEQ ID NO 1410
<211> LENGTH: 6
<212> TYPE: PRT
<213> ORGANISM: Homo sapiens

<400> SEQUENCE: 1410

Gly Leu Arg Arg Cys Leu
1 5

<210> SEQ ID NO 1411
<211> LENGTH: 6
<212> TYPE: PRT
<213> ORGANISM: Homo sapiens

<400> SEQUENCE: 1411

Gly His Gly Glu Cys Leu
1 5

<210> SEQ ID NO 1412
<211> LENGTH: 6
<212> TYPE: PRT
<213> ORGANISM: Homo sapiens

<400> SEQUENCE: 1412

Gly Met Ser Ile Cys Leu
1 5

<210> SEQ ID NO 1413
<211> LENGTH: 6
<212> TYPE: PRT
<213> ORGANISM: Homo sapiens

<400> SEQUENCE: 1413

Gly Cys Thr Trp Cys Leu
1 5

<210> SEQ ID NO 1414
<211> LENGTH: 6
<212> TYPE: PRT
<213> ORGANISM: Homo sapiens

<400> SEQUENCE: 1414

Gly Cys Cys Ser Cys Leu
1 5

<210> SEQ ID NO 1415
<211> LENGTH: 6

<212> TYPE: PRT
<213> ORGANISM: Homo sapiens

<400> SEQUENCE: 1415

Gly Lys Ser Phe Cys Leu
1 5

<210> SEQ ID NO 1416
<211> LENGTH: 6
<212> TYPE: PRT
<213> ORGANISM: Homo sapiens

<400> SEQUENCE: 1416

Gly Met Gln Trp Cys Leu
1 5

<210> SEQ ID NO 1417
<211> LENGTH: 6
<212> TYPE: PRT
<213> ORGANISM: Homo sapiens

<400> SEQUENCE: 1417

Gly Pro Glu Glu Cys Leu
1 5

<210> SEQ ID NO 1418
<211> LENGTH: 6
<212> TYPE: PRT
<213> ORGANISM: Homo sapiens

<400> SEQUENCE: 1418

Gly Glu His Phe Cys Leu
1 5

<210> SEQ ID NO 1419
<211> LENGTH: 6
<212> TYPE: PRT
<213> ORGANISM: Homo sapiens

<400> SEQUENCE: 1419

Gly Gln Tyr Arg Cys Leu
1 5

<210> SEQ ID NO 1420
<211> LENGTH: 6
<212> TYPE: PRT
<213> ORGANISM: Homo sapiens

<400> SEQUENCE: 1420

Gly Trp Ala Ser Cys Leu
1 5

<210> SEQ ID NO 1421
<211> LENGTH: 6
<212> TYPE: PRT
<213> ORGANISM: Homo sapiens

<400> SEQUENCE: 1421

Gly Lys Ser Phe Cys Leu
1 5

<210> SEQ ID NO 1422
<211> LENGTH: 6
<212> TYPE: PRT
<213> ORGANISM: Homo sapiens

<400> SEQUENCE: 1422

Gly Lys Ser Phe Cys Leu
1 5

<210> SEQ ID NO 1423
<211> LENGTH: 6
<212> TYPE: PRT
<213> ORGANISM: Homo sapiens

<400> SEQUENCE: 1423

Gly Trp Ala Ser Cys Leu
1 5

<210> SEQ ID NO 1424
<211> LENGTH: 6
<212> TYPE: PRT
<213> ORGANISM: Homo sapiens

<400> SEQUENCE: 1424

Gly Trp Ala Ser Cys Leu
1 5

<210> SEQ ID NO 1425
<211> LENGTH: 6
<212> TYPE: PRT
<213> ORGANISM: Homo sapiens

<400> SEQUENCE: 1425

Gly Leu Lys Tyr Cys Leu
1 5

<210> SEQ ID NO 1426
<211> LENGTH: 6
<212> TYPE: PRT
<213> ORGANISM: Homo sapiens

<400> SEQUENCE: 1426

Gly Ser Val Leu Cys Leu
1 5

<210> SEQ ID NO 1427
<211> LENGTH: 6
<212> TYPE: PRT
<213> ORGANISM: Homo sapiens

<400> SEQUENCE: 1427

Gly Trp Gly Leu Cys Leu
1 5

<210> SEQ ID NO 1428
<211> LENGTH: 6
<212> TYPE: PRT
<213> ORGANISM: Homo sapiens

<400> SEQUENCE: 1428

Gly Gly Lys Tyr Cys Leu
1 5

<210> SEQ ID NO 1429
<211> LENGTH: 6
<212> TYPE: PRT
<213> ORGANISM: Homo sapiens

<400> SEQUENCE: 1429

Gly Lys Gly His Cys Leu
1 5

<210> SEQ ID NO 1430
<211> LENGTH: 6
<212> TYPE: PRT
<213> ORGANISM: Homo sapiens

<400> SEQUENCE: 1430

Gly Asn Gly Pro Cys Leu
1 5

<210> SEQ ID NO 1431
<211> LENGTH: 6
<212> TYPE: PRT
<213> ORGANISM: Homo sapiens

<400> SEQUENCE: 1431

Gly Asn Glu Ile Cys Leu
1 5

<210> SEQ ID NO 1432
<211> LENGTH: 6
<212> TYPE: PRT
<213> ORGANISM: Homo sapiens

<400> SEQUENCE: 1432

Gly Phe Gln Gly Cys Leu
1 5

<210> SEQ ID NO 1433
<211> LENGTH: 6
<212> TYPE: PRT
<213> ORGANISM: Homo sapiens

<400> SEQUENCE: 1433

Gly Arg Gly Glu Cys Leu
1 5

<210> SEQ ID NO 1434
<211> LENGTH: 6
<212> TYPE: PRT
<213> ORGANISM: Homo sapiens

<400> SEQUENCE: 1434

Gly Thr Val Pro Cys Leu
1 5

<210> SEQ ID NO 1435
<211> LENGTH: 6
<212> TYPE: PRT
<213> ORGANISM: Homo sapiens

<400> SEQUENCE: 1435

Gly Gly Phe Arg Cys Leu
1 5

<210> SEQ ID NO 1436
<211> LENGTH: 6
<212> TYPE: PRT
<213> ORGANISM: Homo sapiens

<400> SEQUENCE: 1436

Gly Ser Asp Glu Cys Leu 1 5

<210> SEQ ID NO 1437
<211> LENGTH: 6
<212> TYPE: PRT
<213> ORGANISM: Homo sapiens

<400> SEQUENCE: 1437

Gly Glu Ala Val Cys Leu
1 5

<210> SEQ ID NO 1438
<211> LENGTH: 6
<212> TYPE: PRT
<213> ORGANISM: Homo sapiens

<400> SEQUENCE: 1438

Gly Gln Thr Cys Cys Leu
1 5

<210> SEQ ID NO 1439
<211> LENGTH: 6
<212> TYPE: PRT
<213> ORGANISM: Homo sapiens

<400> SEQUENCE: 1439

Gly His Gly Asn Cys Leu
1 5

<210> SEQ ID NO 1440
<211> LENGTH: 6
<212> TYPE: PRT
<213> ORGANISM: Homo sapiens

<400> SEQUENCE: 1440

Gly Gln Met Val Cys Leu
1 5

<210> SEQ ID NO 1441
<211> LENGTH: 6
<212> TYPE: PRT
<213> ORGANISM: Homo sapiens

<400> SEQUENCE: 1441

Gly Pro Leu His Cys Leu
1 5

<210> SEQ ID NO 1442
<211> LENGTH: 6
<212> TYPE: PRT
<213> ORGANISM: Homo sapiens

<400> SEQUENCE: 1442

Gly His Gly Asp Cys Leu
1 5

<210> SEQ ID NO 1443
<211> LENGTH: 6
<212> TYPE: PRT
<213> ORGANISM: Homo sapiens

<400> SEQUENCE: 1443

Gly Gly Arg Tyr Cys Leu
1 5

<210> SEQ ID NO 1444
<211> LENGTH: 6
<212> TYPE: PRT
<213> ORGANISM: Homo sapiens

<400> SEQUENCE: 1444

Gly Met Ser Leu Cys Leu
1 5

<210> SEQ ID NO 1445
<211> LENGTH: 6
<212> TYPE: PRT
<213> ORGANISM: Homo sapiens

<400> SEQUENCE: 1445

Gly Ser Pro Val Cys Leu
1 5

<210> SEQ ID NO 1446
<211> LENGTH: 6
<212> TYPE: PRT
<213> ORGANISM: Homo sapiens

<400> SEQUENCE: 1446

Gly Ile His Glu Cys Leu
1 5

<210> SEQ ID NO 1447
<211> LENGTH: 6
<212> TYPE: PRT
<213> ORGANISM: Homo sapiens

<400> SEQUENCE: 1447

Gly Gly Ser Arg Cys Leu
1 5

<210> SEQ ID NO 1448
<211> LENGTH: 6
<212> TYPE: PRT
<213> ORGANISM: Homo sapiens

<400> SEQUENCE: 1448

Gly Leu Phe Gly Cys Leu
1 5

<210> SEQ ID NO 1449
<211> LENGTH: 6
<212> TYPE: PRT
<213> ORGANISM: Homo sapiens

<400> SEQUENCE: 1449

Gly Met Tyr Gln Cys Leu
1 5

<210> SEQ ID NO 1450
<211> LENGTH: 6
<212> TYPE: PRT
<213> ORGANISM: Homo sapiens

<400> SEQUENCE: 1450

Gly Gln Ala Met Cys Leu
1 5

<210> SEQ ID NO 1451

<211> LENGTH: 6
<212> TYPE: PRT
<213> ORGANISM: Homo sapiens

<400> SEQUENCE: 1451

Gly Trp Lys Pro Cys Leu
1 5

<210> SEQ ID NO 1452
<211> LENGTH: 6
<212> TYPE: PRT
<213> ORGANISM: Homo sapiens

<400> SEQUENCE: 1452

Gly Val Thr Arg Cys Leu
1 5

<210> SEQ ID NO 1453
<211> LENGTH: 6
<212> TYPE: PRT
<213> ORGANISM: Homo sapiens

<400> SEQUENCE: 1453

Gly Lys Ala Gln Cys Leu
1 5

<210> SEQ ID NO 1454
<211> LENGTH: 6
<212> TYPE: PRT
<213> ORGANISM: Homo sapiens

<400> SEQUENCE: 1454

Gly Ala Pro Arg Cys Leu
1 5

<210> SEQ ID NO 1455
<211> LENGTH: 6
<212> TYPE: PRT
<213> ORGANISM: Homo sapiens

<400> SEQUENCE: 1455

Gly Ser Val Leu Cys Leu
1 5

<210> SEQ ID NO 1456
<211> LENGTH: 6
<212> TYPE: PRT
<213> ORGANISM: Homo sapiens

<400> SEQUENCE: 1456

Gly Ile Val Thr Cys Leu
1 5

<210> SEQ ID NO 1457
<211> LENGTH: 6
<212> TYPE: PRT
<213> ORGANISM: Homo sapiens

<400> SEQUENCE: 1457

Gly Ser Gln Arg Cys Leu
1 5

<210> SEQ ID NO 1458
<211> LENGTH: 6
<212> TYPE: PRT

<213> ORGANISM: Homo sapiens

<400> SEQUENCE: 1458

Gly Ile Leu Gly Cys Leu
1 5

<210> SEQ ID NO 1459
<211> LENGTH: 6
<212> TYPE: PRT
<213> ORGANISM: Homo sapiens

<400> SEQUENCE: 1459

Gly Lys Met Ser Cys Leu
1 5

<210> SEQ ID NO 1460
<211> LENGTH: 6
<212> TYPE: PRT
<213> ORGANISM: Homo sapiens

<400> SEQUENCE: 1460

Gly Leu Asn Gln Cys Leu
1 5

<210> SEQ ID NO 1461
<211> LENGTH: 6
<212> TYPE: PRT
<213> ORGANISM: Homo sapiens

<400> SEQUENCE: 1461

Gly Phe Ile Val Cys Leu
1 5

<210> SEQ ID NO 1462
<211> LENGTH: 6
<212> TYPE: PRT
<213> ORGANISM: Homo sapiens

<400> SEQUENCE: 1462

Gly Lys Lys Ile Cys Leu
1 5

<210> SEQ ID NO 1463
<211> LENGTH: 6
<212> TYPE: PRT
<213> ORGANISM: Homo sapiens

<400> SEQUENCE: 1463

Gly Glu Cys Leu Cys Leu
1 5

<210> SEQ ID NO 1464
<211> LENGTH: 6
<212> TYPE: PRT
<213> ORGANISM: Homo sapiens

<400> SEQUENCE: 1464

Gly Gly Lys Ile Cys Leu
1 5

<210> SEQ ID NO 1465
<211> LENGTH: 6
<212> TYPE: PRT
<213> ORGANISM: Homo sapiens

<400> SEQUENCE: 1465

Gly Asp Leu Ile Cys Leu
1 5

<210> SEQ ID NO 1466
<211> LENGTH: 6
<212> TYPE: PRT
<213> ORGANISM: Homo sapiens

<400> SEQUENCE: 1466

Gly Ser Val Glu Cys Leu
1 5

<210> SEQ ID NO 1467
<211> LENGTH: 6
<212> TYPE: PRT
<213> ORGANISM: Homo sapiens

<400> SEQUENCE: 1467

Gly Pro Gly His Cys Leu
1 5

<210> SEQ ID NO 1468
<211> LENGTH: 6
<212> TYPE: PRT
<213> ORGANISM: Homo sapiens

<400> SEQUENCE: 1468

Gly Gln His Ser Cys Leu
1 5

<210> SEQ ID NO 1469
<211> LENGTH: 6
<212> TYPE: PRT
<213> ORGANISM: Homo sapiens

<400> SEQUENCE: 1469

Gly Lys Asp Asp Cys Leu
1 5

<210> SEQ ID NO 1470
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Any amino acid

<400> SEQUENCE: 1470

Xaa Arg Asn Val Cys Leu
1 5

<210> SEQ ID NO 1471
<211> LENGTH: 6
<212> TYPE: PRT
<213> ORGANISM: Homo sapiens

<400> SEQUENCE: 1471

Gly Thr Ala Thr Cys Leu
1 5

<210> SEQ ID NO 1472
<211> LENGTH: 6
<212> TYPE: PRT

<213> ORGANISM: Homo sapiens

<400> SEQUENCE: 1472

Gly Phe Gln Gly Cys Leu
1 5

<210> SEQ ID NO 1473
<211> LENGTH: 6
<212> TYPE: PRT
<213> ORGANISM: Homo sapiens

<400> SEQUENCE: 1473

Gly Val Pro His Cys Leu
1 5

<210> SEQ ID NO 1474
<211> LENGTH: 6
<212> TYPE: PRT
<213> ORGANISM: Homo sapiens

<400> SEQUENCE: 1474

Gly His Tyr Pro Cys Leu
1 5

<210> SEQ ID NO 1475
<211> LENGTH: 6
<212> TYPE: PRT
<213> ORGANISM: Homo sapiens

<400> SEQUENCE: 1475

Gly Glu Gln Pro Cys Leu
1 5

<210> SEQ ID NO 1476
<211> LENGTH: 6
<212> TYPE: PRT
<213> ORGANISM: Homo sapiens

<400> SEQUENCE: 1476

Gly Leu Cys Ile Cys Leu
1 5

<210> SEQ ID NO 1477
<211> LENGTH: 6
<212> TYPE: PRT
<213> ORGANISM: Homo sapiens

<400> SEQUENCE: 1477

Gly Asn Ile Asp Cys Leu
1 5

<210> SEQ ID NO 1478
<211> LENGTH: 6
<212> TYPE: PRT
<213> ORGANISM: Homo sapiens

<400> SEQUENCE: 1478

Gly His Val Glu Cys Leu
1 5

<210> SEQ ID NO 1479
<211> LENGTH: 6
<212> TYPE: PRT
<213> ORGANISM: Homo sapiens

<400> SEQUENCE: 1479

Gly His Glu Asp Cys Leu
1 5

<210> SEQ ID NO 1480
<211> LENGTH: 6
<212> TYPE: PRT
<213> ORGANISM: Homo sapiens

<400> SEQUENCE: 1480

Gly Thr Cys Ala Cys Leu
1 5

<210> SEQ ID NO 1481
<211> LENGTH: 6
<212> TYPE: PRT
<213> ORGANISM: Homo sapiens

<400> SEQUENCE: 1481

Gly Phe Arg Glu Cys Leu
1 5

<210> SEQ ID NO 1482
<211> LENGTH: 6
<212> TYPE: PRT
<213> ORGANISM: Homo sapiens

<400> SEQUENCE: 1482

Gly Val Glu Ile Cys Leu
1 5

<210> SEQ ID NO 1483
<211> LENGTH: 6
<212> TYPE: PRT
<213> ORGANISM: Homo sapiens

<400> SEQUENCE: 1483

Gly Asp Gln Arg Cys Leu
1 5

<210> SEQ ID NO 1484
<211> LENGTH: 6
<212> TYPE: PRT
<213> ORGANISM: Homo sapiens

<400> SEQUENCE: 1484

Gly Val Val Ser Cys Leu
1 5

<210> SEQ ID NO 1485
<211> LENGTH: 6
<212> TYPE: PRT
<213> ORGANISM: Homo sapiens

<400> SEQUENCE: 1485

Gly Ser Asn Pro Cys Leu
1 5

<210> SEQ ID NO 1486
<211> LENGTH: 6
<212> TYPE: PRT
<213> ORGANISM: Homo sapiens

<400> SEQUENCE: 1486

Gly Ser Val Gln Cys Leu
1 5

<210> SEQ ID NO 1487
<211> LENGTH: 6
<212> TYPE: PRT
<213> ORGANISM: Homo sapiens

<400> SEQUENCE: 1487

Gly Val Pro Lys Cys Leu
1 5

<210> SEQ ID NO 1488
<211> LENGTH: 6
<212> TYPE: PRT
<213> ORGANISM: Homo sapiens

<400> SEQUENCE: 1488

Gly Leu Asp Ser Cys Leu
1 5

<210> SEQ ID NO 1489
<211> LENGTH: 6
<212> TYPE: PRT
<213> ORGANISM: Homo sapiens

<400> SEQUENCE: 1489

Gly Ala Gly Phe Cys Leu
1 5

<210> SEQ ID NO 1490
<211> LENGTH: 6
<212> TYPE: PRT
<213> ORGANISM: Homo sapiens

<400> SEQUENCE: 1490

Gly Gly Arg Ser Cys Leu
1 5

<210> SEQ ID NO 1491
<211> LENGTH: 6
<212> TYPE: PRT
<213> ORGANISM: Homo sapiens

<400> SEQUENCE: 1491

Gly Met Ser Leu Cys Leu
1 5

<210> SEQ ID NO 1492
<211> LENGTH: 6
<212> TYPE: PRT
<213> ORGANISM: Homo sapiens

<400> SEQUENCE: 1492

Gly His Ala Glu Cys Leu
1 5

<210> SEQ ID NO 1493
<211> LENGTH: 6
<212> TYPE: PRT
<213> ORGANISM: Homo sapiens

<400> SEQUENCE: 1493

Gly Pro Glu Ser Cys Leu
1 5

<210> SEQ ID NO 1494
<211> LENGTH: 6
<212> TYPE: PRT
<213> ORGANISM: Homo sapiens

<400> SEQUENCE: 1494

Gly Gln Cys Ser Cys Leu
1               5

<210> SEQ ID NO 1495
<211> LENGTH: 6
<212> TYPE: PRT
<213> ORGANISM: Homo sapiens

<400> SEQUENCE: 1495

Gly Ala Ile Phe Cys Leu
1               5

<210> SEQ ID NO 1496
<211> LENGTH: 6
<212> TYPE: PRT
<213> ORGANISM: Homo sapiens

<400> SEQUENCE: 1496

Gly Gln Gly Val Cys Leu
1               5

<210> SEQ ID NO 1497
<211> LENGTH: 6
<212> TYPE: PRT
<213> ORGANISM: Homo sapiens

<400> SEQUENCE: 1497

Gly Gln Cys Gly Cys Leu
1               5

<210> SEQ ID NO 1498
<211> LENGTH: 6
<212> TYPE: PRT
<213> ORGANISM: Homo sapiens

<400> SEQUENCE: 1498

Gly Gln Gly Val Cys Leu
1               5

<210> SEQ ID NO 1499
<211> LENGTH: 6
<212> TYPE: PRT
<213> ORGANISM: Homo sapiens

<400> SEQUENCE: 1499

Gly Gln Cys Gly Cys Leu
1               5

<210> SEQ ID NO 1500
<211> LENGTH: 6
<212> TYPE: PRT
<213> ORGANISM: Homo sapiens

<400> SEQUENCE: 1500

Gly Gln Gly Val Cys Leu
1               5

<210> SEQ ID NO 1501
<211> LENGTH: 6
<212> TYPE: PRT
<213> ORGANISM: Homo sapiens

<400> SEQUENCE: 1501

Gly Gln Cys Gly Cys Leu
1               5

<210> SEQ ID NO 1502
<211> LENGTH: 6
<212> TYPE: PRT
<213> ORGANISM: Homo sapiens

<400> SEQUENCE: 1502

Gly Cys Gly Arg Cys Leu
1               5

<210> SEQ ID NO 1503
<211> LENGTH: 6
<212> TYPE: PRT
<213> ORGANISM: Homo sapiens

<400> SEQUENCE: 1503

Gly Cys Pro Val Cys Leu
1               5

<210> SEQ ID NO 1504
<211> LENGTH: 7
<212> TYPE: PRT
<213> ORGANISM: Homo sapiens

<400> SEQUENCE: 1504

Cys Asn Asn Ser Ala Val Cys
1               5

<210> SEQ ID NO 1505
<211> LENGTH: 7
<212> TYPE: PRT
<213> ORGANISM: Homo sapiens

<400> SEQUENCE: 1505

Cys Asn Ser Asp Val Val Cys
1               5

<210> SEQ ID NO 1506
<211> LENGTH: 7
<212> TYPE: PRT
<213> ORGANISM: Homo sapiens

<400> SEQUENCE: 1506

Cys Asn Val Trp Arg Val Cys
1               5

<210> SEQ ID NO 1507
<211> LENGTH: 7
<212> TYPE: PRT
<213> ORGANISM: Homo sapiens

<400> SEQUENCE: 1507

Cys Asn Ile Asn Asn Val Cys
1               5

<210> SEQ ID NO 1508
<211> LENGTH: 7

<212> TYPE: PRT
<213> ORGANISM: Homo sapiens

<400> SEQUENCE: 1508

Cys Asn Pro Gly Asp Val Cys
1 5

<210> SEQ ID NO 1509
<211> LENGTH: 7
<212> TYPE: PRT
<213> ORGANISM: Homo sapiens

<400> SEQUENCE: 1509

Cys Asn Gln Thr Ser Val Cys
1 5

<210> SEQ ID NO 1510
<211> LENGTH: 7
<212> TYPE: PRT
<213> ORGANISM: Homo sapiens

<400> SEQUENCE: 1510

Cys Asn Val His Gly Val Cys
1 5

<210> SEQ ID NO 1511
<211> LENGTH: 7
<212> TYPE: PRT
<213> ORGANISM: Homo sapiens

<400> SEQUENCE: 1511

Cys Asn Ile Asn Asn Val Cys
1 5

<210> SEQ ID NO 1512
<211> LENGTH: 7
<212> TYPE: PRT
<213> ORGANISM: Homo sapiens

<400> SEQUENCE: 1512

Cys Asn Ile His Gln Val Cys
1 5

<210> SEQ ID NO 1513
<211> LENGTH: 7
<212> TYPE: PRT
<213> ORGANISM: Homo sapiens

<400> SEQUENCE: 1513

Cys Asn Cys Cys Leu Val Cys
1 5

<210> SEQ ID NO 1514
<211> LENGTH: 7
<212> TYPE: PRT
<213> ORGANISM: Homo sapiens

<400> SEQUENCE: 1514

Cys Asn Val Asn Asp Val Cys
1 5

<210> SEQ ID NO 1515
<211> LENGTH: 7
<212> TYPE: PRT
<213> ORGANISM: Homo sapiens

<400> SEQUENCE: 1515

Cys Asn Asn Val Gln Val Cys
1               5

<210> SEQ ID NO 1516
<211> LENGTH: 7
<212> TYPE: PRT
<213> ORGANISM: Homo sapiens

<400> SEQUENCE: 1516

Cys Asn Arg Tyr Pro Val Cys
1               5

<210> SEQ ID NO 1517
<211> LENGTH: 7
<212> TYPE: PRT
<213> ORGANISM: Homo sapiens

<400> SEQUENCE: 1517

Cys Asn Ile Asn Glu Val Cys
1               5

<210> SEQ ID NO 1518
<211> LENGTH: 7
<212> TYPE: PRT
<213> ORGANISM: Homo sapiens

<400> SEQUENCE: 1518

Cys Asn Asn Arg Gly Val Cys
1               5

<210> SEQ ID NO 1519
<211> LENGTH: 7
<212> TYPE: PRT
<213> ORGANISM: Homo sapiens

<400> SEQUENCE: 1519

Cys Asn Arg Asn Glu Val Cys
1               5

<210> SEQ ID NO 1520
<211> LENGTH: 7
<212> TYPE: PRT
<213> ORGANISM: Homo sapiens

<400> SEQUENCE: 1520

Cys Asn Asp Arg Gly Val Cys
1               5

<210> SEQ ID NO 1521
<211> LENGTH: 7
<212> TYPE: PRT
<213> ORGANISM: Homo sapiens

<400> SEQUENCE: 1521

Cys Asn Gln Leu Asp Val Cys
1               5

<210> SEQ ID NO 1522
<211> LENGTH: 7
<212> TYPE: PRT
<213> ORGANISM: Homo sapiens

<400> SEQUENCE: 1522

Cys Asn Asp Met Pro Val Cys
1 5

<210> SEQ ID NO 1523
<211> LENGTH: 7
<212> TYPE: PRT
<213> ORGANISM: Homo sapiens

<400> SEQUENCE: 1523

Cys Asn Gly His Gly Val Cys
1 5

<210> SEQ ID NO 1524
<211> LENGTH: 7
<212> TYPE: PRT
<213> ORGANISM: Homo sapiens

<400> SEQUENCE: 1524

Cys Asn Leu Leu Val Val Cys
1 5

<210> SEQ ID NO 1525
<211> LENGTH: 7
<212> TYPE: PRT
<213> ORGANISM: Homo sapiens

<400> SEQUENCE: 1525

Cys Asn Gln Val Leu Val Cys
1 5

<210> SEQ ID NO 1526
<211> LENGTH: 7
<212> TYPE: PRT
<213> ORGANISM: Homo sapiens

<400> SEQUENCE: 1526

Cys Asn Asp Pro Met Val Cys
1 5

<210> SEQ ID NO 1527
<211> LENGTH: 7
<212> TYPE: PRT
<213> ORGANISM: Homo sapiens

<400> SEQUENCE: 1527

Cys Asn Thr Arg Gly Val Cys
1 5

<210> SEQ ID NO 1528
<211> LENGTH: 5
<212> TYPE: PRT
<213> ORGANISM: Homo sapiens

<400> SEQUENCE: 1528

Pro Phe Ser Thr Cys
1 5

<210> SEQ ID NO 1529
<211> LENGTH: 5
<212> TYPE: PRT
<213> ORGANISM: Homo sapiens

<400> SEQUENCE: 1529

Pro Phe Asp Leu Cys 1 5

<210> SEQ ID NO 1530
<211> LENGTH: 5
<212> TYPE: PRT
<213> ORGANISM: Homo sapiens

<400> SEQUENCE: 1530

Pro Phe Gln Leu Cys
1 5

<210> SEQ ID NO 1531
<211> LENGTH: 5
<212> TYPE: PRT
<213> ORGANISM: Homo sapiens

<400> SEQUENCE: 1531

Pro Phe Pro Asn Cys
1 5

<210> SEQ ID NO 1532
<211> LENGTH: 5
<212> TYPE: PRT
<213> ORGANISM: Homo sapiens

<400> SEQUENCE: 1532

Pro Phe Cys Leu Cys
1 5

<210> SEQ ID NO 1533
<211> LENGTH: 5
<212> TYPE: PRT
<213> ORGANISM: Homo sapiens

<400> SEQUENCE: 1533

Pro Phe Gly Gln Cys
1 5

<210> SEQ ID NO 1534
<211> LENGTH: 5
<212> TYPE: PRT
<213> ORGANISM: Homo sapiens

<400> SEQUENCE: 1534

Pro Phe Lys Asp Cys
1 5

<210> SEQ ID NO 1535
<211> LENGTH: 5
<212> TYPE: PRT
<213> ORGANISM: Homo sapiens

<400> SEQUENCE: 1535

Pro Phe Ile Leu Cys
1 5

<210> SEQ ID NO 1536
<211> LENGTH: 5
<212> TYPE: PRT
<213> ORGANISM: Homo sapiens

<400> SEQUENCE: 1536

Pro Phe Ser Glu Cys
1 5

<210> SEQ ID NO 1537
<211> LENGTH: 5
<212> TYPE: PRT
<213> ORGANISM: Homo sapiens

<400> SEQUENCE: 1537

Pro Phe Leu Cys Cys
1 5

<210> SEQ ID NO 1538
<211> LENGTH: 5
<212> TYPE: PRT
<213> ORGANISM: Homo sapiens

<400> SEQUENCE: 1538

Pro Phe Tyr Asp Cys
1 5

<210> SEQ ID NO 1539
<211> LENGTH: 5
<212> TYPE: PRT
<213> ORGANISM: Homo sapiens

<400> SEQUENCE: 1539

Pro Phe Thr Leu Cys
1 5

<210> SEQ ID NO 1540
<211> LENGTH: 5
<212> TYPE: PRT
<213> ORGANISM: Homo sapiens

<400> SEQUENCE: 1540

Pro Phe Leu Pro Cys
1 5

<210> SEQ ID NO 1541
<211> LENGTH: 5
<212> TYPE: PRT
<213> ORGANISM: Homo sapiens

<400> SEQUENCE: 1541

Pro Phe Ile Leu Cys
1 5

<210> SEQ ID NO 1542
<211> LENGTH: 5
<212> TYPE: PRT
<213> ORGANISM: Homo sapiens

<400> SEQUENCE: 1542

Pro Phe Ser Ser Cys
1 5

<210> SEQ ID NO 1543
<211> LENGTH: 5
<212> TYPE: PRT
<213> ORGANISM: Homo sapiens

<400> SEQUENCE: 1543

Pro Phe Ala Ala Cys
1 5

<210> SEQ ID NO 1544

<211> LENGTH: 5
<212> TYPE: PRT
<213> ORGANISM: Homo sapiens

<400> SEQUENCE: 1544

Pro Phe Leu Arg Cys
1 5

<210> SEQ ID NO 1545
<211> LENGTH: 5
<212> TYPE: PRT
<213> ORGANISM: Homo sapiens

<400> SEQUENCE: 1545

Pro Phe Val Gly Cys
1 5

<210> SEQ ID NO 1546
<211> LENGTH: 5
<212> TYPE: PRT
<213> ORGANISM: Homo sapiens

<400> SEQUENCE: 1546

Pro Phe Gln Asn Cys
1 5

<210> SEQ ID NO 1547
<211> LENGTH: 5
<212> TYPE: PRT
<213> ORGANISM: Homo sapiens

<400> SEQUENCE: 1547

Pro Phe Pro Gly Cys
1 5

<210> SEQ ID NO 1548
<211> LENGTH: 5
<212> TYPE: PRT
<213> ORGANISM: Homo sapiens

<400> SEQUENCE: 1548

Pro Phe Thr Ala Cys
1 5

<210> SEQ ID NO 1549
<211> LENGTH: 5
<212> TYPE: PRT
<213> ORGANISM: Homo sapiens

<400> SEQUENCE: 1549

Pro Phe Ser Ile Cys
1 5

<210> SEQ ID NO 1550
<211> LENGTH: 5
<212> TYPE: PRT
<213> ORGANISM: Homo sapiens

<400> SEQUENCE: 1550

Pro Phe Lys Leu Cys
1 5

<210> SEQ ID NO 1551
<211> LENGTH: 5
<212> TYPE: PRT

<213> ORGANISM: Homo sapiens

<400> SEQUENCE: 1551

Pro Phe Asp Asn Cys
1 5

<210> SEQ ID NO 1552
<211> LENGTH: 5
<212> TYPE: PRT
<213> ORGANISM: Homo sapiens

<400> SEQUENCE: 1552

Pro Phe Glu Ser Cys
1 5

<210> SEQ ID NO 1553
<211> LENGTH: 5
<212> TYPE: PRT
<213> ORGANISM: Homo sapiens

<400> SEQUENCE: 1553

Pro Phe Arg His Cys
1 5

<210> SEQ ID NO 1554
<211> LENGTH: 5
<212> TYPE: PRT
<213> ORGANISM: Homo sapiens

<400> SEQUENCE: 1554

Pro Phe Tyr Thr Cys
1 5

<210> SEQ ID NO 1555
<211> LENGTH: 5
<212> TYPE: PRT
<213> ORGANISM: Homo sapiens

<400> SEQUENCE: 1555

Pro Phe Leu Tyr Cys
1 5

<210> SEQ ID NO 1556
<211> LENGTH: 5
<212> TYPE: PRT
<213> ORGANISM: Homo sapiens

<400> SEQUENCE: 1556

Pro Phe Lys Pro Cys
1 5

<210> SEQ ID NO 1557
<211> LENGTH: 5
<212> TYPE: PRT
<213> ORGANISM: Homo sapiens

<400> SEQUENCE: 1557

Pro Phe Phe Leu Cys
1 5

<210> SEQ ID NO 1558
<211> LENGTH: 5
<212> TYPE: PRT
<213> ORGANISM: Homo sapiens

<400> SEQUENCE: 1558

Pro Phe Tyr Gln Cys
1 5

<210> SEQ ID NO 1559
<211> LENGTH: 5
<212> TYPE: PRT
<213> ORGANISM: Homo sapiens

<400> SEQUENCE: 1559

Pro Phe Ile His Cys
1 5

<210> SEQ ID NO 1560
<211> LENGTH: 5
<212> TYPE: PRT
<213> ORGANISM: Homo sapiens

<400> SEQUENCE: 1560

Pro Phe Gly Gln Cys
1 5

<210> SEQ ID NO 1561
<211> LENGTH: 5
<212> TYPE: PRT
<213> ORGANISM: Homo sapiens

<400> SEQUENCE: 1561

Pro Phe Ala Ile Cys
1 5

<210> SEQ ID NO 1562
<211> LENGTH: 5
<212> TYPE: PRT
<213> ORGANISM: Homo sapiens

<400> SEQUENCE: 1562

Pro Phe Gln Ser Cys
1 5

<210> SEQ ID NO 1563
<211> LENGTH: 5
<212> TYPE: PRT
<213> ORGANISM: Homo sapiens

<400> SEQUENCE: 1563

Pro Phe Ile Tyr Cys
1 5

<210> SEQ ID NO 1564
<211> LENGTH: 5
<212> TYPE: PRT
<213> ORGANISM: Homo sapiens

<400> SEQUENCE: 1564

Pro Phe Tyr Asp Cys
1 5

<210> SEQ ID NO 1565
<211> LENGTH: 5
<212> TYPE: PRT
<213> ORGANISM: Homo sapiens

<400> SEQUENCE: 1565

```
Pro Phe Gly Cys Cys
1               5


<210> SEQ ID NO 1566
<211> LENGTH: 5
<212> TYPE: PRT
<213> ORGANISM: Homo sapiens

<400> SEQUENCE: 1566

Pro Phe Pro Gly Cys
1               5


<210> SEQ ID NO 1567
<211> LENGTH: 5
<212> TYPE: PRT
<213> ORGANISM: Homo sapiens

<400> SEQUENCE: 1567

Pro Phe Gly Ser Cys
1               5


<210> SEQ ID NO 1568
<211> LENGTH: 5
<212> TYPE: PRT
<213> ORGANISM: Homo sapiens

<400> SEQUENCE: 1568

Pro Phe Ser Arg Cys
1               5


<210> SEQ ID NO 1569
<211> LENGTH: 5
<212> TYPE: PRT
<213> ORGANISM: Homo sapiens

<400> SEQUENCE: 1569

Pro Phe Lys Asp Cys
1               5


<210> SEQ ID NO 1570
<211> LENGTH: 5
<212> TYPE: PRT
<213> ORGANISM: Homo sapiens

<400> SEQUENCE: 1570

Pro Phe Asp Thr Cys
1               5


<210> SEQ ID NO 1571
<211> LENGTH: 5
<212> TYPE: PRT
<213> ORGANISM: Homo sapiens

<400> SEQUENCE: 1571

Pro Phe Gly Glu Cys
1               5


<210> SEQ ID NO 1572
<211> LENGTH: 5
<212> TYPE: PRT
<213> ORGANISM: Homo sapiens

<400> SEQUENCE: 1572

Pro Phe Leu Phe Cys
1               5
```

<210> SEQ ID NO 1573
<211> LENGTH: 5
<212> TYPE: PRT
<213> ORGANISM: Homo sapiens

<400> SEQUENCE: 1573

Pro Phe Ile Glu Cys
1 5

<210> SEQ ID NO 1574
<211> LENGTH: 5
<212> TYPE: PRT
<213> ORGANISM: Homo sapiens

<400> SEQUENCE: 1574

Pro Phe Pro Thr Cys
1 5

<210> SEQ ID NO 1575
<211> LENGTH: 5
<212> TYPE: PRT
<213> ORGANISM: Homo sapiens

<400> SEQUENCE: 1575

Pro Phe Leu Tyr Cys
1 5

<210> SEQ ID NO 1576
<211> LENGTH: 5
<212> TYPE: PRT
<213> ORGANISM: Homo sapiens

<400> SEQUENCE: 1576

Pro Phe Ile Glu Cys
1 5

<210> SEQ ID NO 1577
<211> LENGTH: 5
<212> TYPE: PRT
<213> ORGANISM: Homo sapiens

<400> SEQUENCE: 1577

Pro Phe Val Gln Cys
1 5

<210> SEQ ID NO 1578
<211> LENGTH: 5
<212> TYPE: PRT
<213> ORGANISM: Homo sapiens

<400> SEQUENCE: 1578

Pro Phe Gly Thr Cys
1 5

<210> SEQ ID NO 1579
<211> LENGTH: 5
<212> TYPE: PRT
<213> ORGANISM: Homo sapiens

<400> SEQUENCE: 1579

Pro Phe Leu Ser Cys
1 5

<210> SEQ ID NO 1580
<211> LENGTH: 5
<212> TYPE: PRT
<213> ORGANISM: Homo sapiens

<400> SEQUENCE: 1580

Pro Phe Leu Ser Cys
1 5

<210> SEQ ID NO 1581
<211> LENGTH: 5
<212> TYPE: PRT
<213> ORGANISM: Homo sapiens

<400> SEQUENCE: 1581

Pro Phe Arg Asn Cys
1 5

<210> SEQ ID NO 1582
<211> LENGTH: 5
<212> TYPE: PRT
<213> ORGANISM: Homo sapiens

<400> SEQUENCE: 1582

Pro Phe Tyr Cys Cys
1 5

<210> SEQ ID NO 1583
<211> LENGTH: 5
<212> TYPE: PRT
<213> ORGANISM: Homo sapiens

<400> SEQUENCE: 1583

Pro Phe Cys Glu Cys
1 5

<210> SEQ ID NO 1584
<211> LENGTH: 5
<212> TYPE: PRT
<213> ORGANISM: Homo sapiens

<400> SEQUENCE: 1584

Pro Phe Tyr Ser Cys
1 5

<210> SEQ ID NO 1585
<211> LENGTH: 5
<212> TYPE: PRT
<213> ORGANISM: Homo sapiens

<400> SEQUENCE: 1585

Pro Phe Pro Ile Cys
1 5

<210> SEQ ID NO 1586
<211> LENGTH: 5
<212> TYPE: PRT
<213> ORGANISM: Homo sapiens

<400> SEQUENCE: 1586

Pro Phe Leu Leu Cys
1 5

<210> SEQ ID NO 1587
<211> LENGTH: 5

<212> TYPE: PRT
<213> ORGANISM: Homo sapiens

<400> SEQUENCE: 1587

Pro Phe Tyr His Cys
1 5

<210> SEQ ID NO 1588
<211> LENGTH: 5
<212> TYPE: PRT
<213> ORGANISM: Homo sapiens

<400> SEQUENCE: 1588

Pro Phe Phe Thr Cys
1 5

<210> SEQ ID NO 1589
<211> LENGTH: 5
<212> TYPE: PRT
<213> ORGANISM: Homo sapiens

<400> SEQUENCE: 1589

Pro Phe Leu Pro Cys
1 5

<210> SEQ ID NO 1590
<211> LENGTH: 5
<212> TYPE: PRT
<213> ORGANISM: Homo sapiens

<400> SEQUENCE: 1590

Pro Phe Ser Arg Cys
1 5

<210> SEQ ID NO 1591
<211> LENGTH: 5
<212> TYPE: PRT
<213> ORGANISM: Homo sapiens

<400> SEQUENCE: 1591

Pro Phe Cys Arg Cys
1 5

<210> SEQ ID NO 1592
<211> LENGTH: 5
<212> TYPE: PRT
<213> ORGANISM: Homo sapiens

<400> SEQUENCE: 1592

Pro Phe Ser Cys Cys
1 5

<210> SEQ ID NO 1593
<211> LENGTH: 5
<212> TYPE: PRT
<213> ORGANISM: Homo sapiens

<400> SEQUENCE: 1593

Pro Phe Glu Gly Cys
1 5

<210> SEQ ID NO 1594
<211> LENGTH: 5
<212> TYPE: PRT
<213> ORGANISM: Homo sapiens

<400> SEQUENCE: 1594

Pro Phe Arg Gly Cys
1 5

<210> SEQ ID NO 1595
<211> LENGTH: 5
<212> TYPE: PRT
<213> ORGANISM: Homo sapiens

<400> SEQUENCE: 1595

Pro Phe Gln Leu Cys
1 5

<210> SEQ ID NO 1596
<211> LENGTH: 5
<212> TYPE: PRT
<213> ORGANISM: Homo sapiens

<400> SEQUENCE: 1596

Pro Phe Ile Val Cys
1 5

<210> SEQ ID NO 1597
<211> LENGTH: 5
<212> TYPE: PRT
<213> ORGANISM: Homo sapiens

<400> SEQUENCE: 1597

Pro Phe Asp Gly Cys
1 5

<210> SEQ ID NO 1598
<211> LENGTH: 5
<212> TYPE: PRT
<213> ORGANISM: Homo sapiens

<400> SEQUENCE: 1598

Pro Phe Val Gln Cys
1 5

<210> SEQ ID NO 1599
<211> LENGTH: 5
<212> TYPE: PRT
<213> ORGANISM: Homo sapiens

<400> SEQUENCE: 1599

Pro Phe Phe Phe Cys
1 5

<210> SEQ ID NO 1600
<211> LENGTH: 5
<212> TYPE: PRT
<213> ORGANISM: Homo sapiens

<400> SEQUENCE: 1600

Pro Phe Asp Tyr Cys
1 5

<210> SEQ ID NO 1601
<211> LENGTH: 5
<212> TYPE: PRT
<213> ORGANISM: Homo sapiens

<400> SEQUENCE: 1601

Pro Phe Phe Lys Cys
1 5

<210> SEQ ID NO 1602
<211> LENGTH: 5
<212> TYPE: PRT
<213> ORGANISM: Homo sapiens

<400> SEQUENCE: 1602

Pro Phe Met Phe Cys
1 5

<210> SEQ ID NO 1603
<211> LENGTH: 5
<212> TYPE: PRT
<213> ORGANISM: Homo sapiens

<400> SEQUENCE: 1603

Pro Phe Ile Glu Cys
1 5

<210> SEQ ID NO 1604
<211> LENGTH: 5
<212> TYPE: PRT
<213> ORGANISM: Homo sapiens

<400> SEQUENCE: 1604

Pro Phe Glu His Cys
1 5

<210> SEQ ID NO 1605
<211> LENGTH: 5
<212> TYPE: PRT
<213> ORGANISM: Homo sapiens

<400> SEQUENCE: 1605

Pro Phe His Leu Cys
1 5

<210> SEQ ID NO 1606
<211> LENGTH: 5
<212> TYPE: PRT
<213> ORGANISM: Homo sapiens

<400> SEQUENCE: 1606

Pro Phe Glu His Cys
1 5

<210> SEQ ID NO 1607
<211> LENGTH: 5
<212> TYPE: PRT
<213> ORGANISM: Homo sapiens

<400> SEQUENCE: 1607

Pro Phe Ile Val Cys
1 5

<210> SEQ ID NO 1608
<211> LENGTH: 5
<212> TYPE: PRT
<213> ORGANISM: Homo sapiens

<400> SEQUENCE: 1608

Pro Phe Tyr Val Cys 1 5

<210> SEQ ID NO 1609
<211> LENGTH: 5
<212> TYPE: PRT
<213> ORGANISM: Homo sapiens

<400> SEQUENCE: 1609

Pro Phe Glu Gly Cys
1 5

<210> SEQ ID NO 1610
<211> LENGTH: 5
<212> TYPE: PRT
<213> ORGANISM: Homo sapiens

<400> SEQUENCE: 1610

Pro Phe Asp Asn Cys
1 5

<210> SEQ ID NO 1611
<211> LENGTH: 5
<212> TYPE: PRT
<213> ORGANISM: Homo sapiens

<400> SEQUENCE: 1611

Pro Phe Leu Lys Cys
1 5

<210> SEQ ID NO 1612
<211> LENGTH: 5
<212> TYPE: PRT
<213> ORGANISM: Homo sapiens

<400> SEQUENCE: 1612

Pro Phe Ser Asn Cys
1 5

<210> SEQ ID NO 1613
<211> LENGTH: 5
<212> TYPE: PRT
<213> ORGANISM: Homo sapiens

<400> SEQUENCE: 1613

Pro Phe Leu Asp Cys
1 5

<210> SEQ ID NO 1614
<211> LENGTH: 5
<212> TYPE: PRT
<213> ORGANISM: Homo sapiens

<400> SEQUENCE: 1614

Pro Phe Pro Val Cys
1 5

<210> SEQ ID NO 1615
<211> LENGTH: 5
<212> TYPE: PRT
<213> ORGANISM: Homo sapiens

<400> SEQUENCE: 1615

Pro Phe Ser Ser Cys
1 5

<210> SEQ ID NO 1616
<211> LENGTH: 5
<212> TYPE: PRT
<213> ORGANISM: Homo sapiens

<400> SEQUENCE: 1616

Pro Phe Tyr Arg Cys
1 5

<210> SEQ ID NO 1617
<211> LENGTH: 5
<212> TYPE: PRT
<213> ORGANISM: Homo sapiens

<400> SEQUENCE: 1617

Pro Phe Glu Asn Cys
1 5

<210> SEQ ID NO 1618
<211> LENGTH: 5
<212> TYPE: PRT
<213> ORGANISM: Homo sapiens

<400> SEQUENCE: 1618

Pro Phe Pro Ser Cys
1 5

<210> SEQ ID NO 1619
<211> LENGTH: 5
<212> TYPE: PRT
<213> ORGANISM: Homo sapiens

<400> SEQUENCE: 1619

Pro Phe Leu Glu Cys
1 5

<210> SEQ ID NO 1620
<211> LENGTH: 5
<212> TYPE: PRT
<213> ORGANISM: Homo sapiens

<400> SEQUENCE: 1620

Pro Phe Leu Tyr Cys
1 5

<210> SEQ ID NO 1621
<211> LENGTH: 5
<212> TYPE: PRT
<213> ORGANISM: Homo sapiens

<400> SEQUENCE: 1621

Pro Phe Val Leu Cys
1 5

<210> SEQ ID NO 1622
<211> LENGTH: 5
<212> TYPE: PRT
<213> ORGANISM: Homo sapiens

<400> SEQUENCE: 1622

Pro Phe Lys Gly Cys
1 5

<210> SEQ ID NO 1623

<211> LENGTH: 5
<212> TYPE: PRT
<213> ORGANISM: Homo sapiens

<400> SEQUENCE: 1623

Pro Phe Pro Phe Cys
1 5

<210> SEQ ID NO 1624
<211> LENGTH: 5
<212> TYPE: PRT
<213> ORGANISM: Homo sapiens

<400> SEQUENCE: 1624

Pro Phe Cys Ser Cys
1 5

<210> SEQ ID NO 1625
<211> LENGTH: 5
<212> TYPE: PRT
<213> ORGANISM: Homo sapiens

<400> SEQUENCE: 1625

Pro Phe Pro Leu Cys
1 5

<210> SEQ ID NO 1626
<211> LENGTH: 5
<212> TYPE: PRT
<213> ORGANISM: Homo sapiens

<400> SEQUENCE: 1626

Pro Phe Glu Cys Cys
1 5

<210> SEQ ID NO 1627
<211> LENGTH: 5
<212> TYPE: PRT
<213> ORGANISM: Homo sapiens

<400> SEQUENCE: 1627

Pro Phe Glu Gly Cys
1 5

<210> SEQ ID NO 1628
<211> LENGTH: 5
<212> TYPE: PRT
<213> ORGANISM: Homo sapiens

<400> SEQUENCE: 1628

Pro Phe Ala Tyr Cys
1 5

<210> SEQ ID NO 1629
<211> LENGTH: 5
<212> TYPE: PRT
<213> ORGANISM: Homo sapiens

<400> SEQUENCE: 1629

Pro Phe Leu Glu Cys
1 5

<210> SEQ ID NO 1630
<211> LENGTH: 5
<212> TYPE: PRT

<213> ORGANISM: Homo sapiens

<400> SEQUENCE: 1630

Pro Phe Asp Ile Cys
1 5

<210> SEQ ID NO 1631
<211> LENGTH: 5
<212> TYPE: PRT
<213> ORGANISM: Homo sapiens

<400> SEQUENCE: 1631

Pro Phe Asp Glu Cys
1 5

<210> SEQ ID NO 1632
<211> LENGTH: 5
<212> TYPE: PRT
<213> ORGANISM: Homo sapiens

<400> SEQUENCE: 1632

Pro Phe Cys Leu Cys
1 5

<210> SEQ ID NO 1633
<211> LENGTH: 5
<212> TYPE: PRT
<213> ORGANISM: Homo sapiens

<400> SEQUENCE: 1633

Pro Phe Ile Trp Cys
1 5

<210> SEQ ID NO 1634
<211> LENGTH: 5
<212> TYPE: PRT
<213> ORGANISM: Homo sapiens

<400> SEQUENCE: 1634

Pro Phe Leu Val Cys
1 5

<210> SEQ ID NO 1635
<211> LENGTH: 5
<212> TYPE: PRT
<213> ORGANISM: Homo sapiens

<400> SEQUENCE: 1635

Pro Phe Ser Cys Cys
1 5

<210> SEQ ID NO 1636
<211> LENGTH: 5
<212> TYPE: PRT
<213> ORGANISM: Homo sapiens

<400> SEQUENCE: 1636

Pro Phe Val Gly Cys
1 5

<210> SEQ ID NO 1637
<211> LENGTH: 5
<212> TYPE: PRT
<213> ORGANISM: Homo sapiens

<400> SEQUENCE: 1637

Pro Phe Val Ser Cys
1 5

<210> SEQ ID NO 1638
<211> LENGTH: 5
<212> TYPE: PRT
<213> ORGANISM: Homo sapiens

<400> SEQUENCE: 1638

Pro Phe Asp Gly Cys
1 5

<210> SEQ ID NO 1639
<211> LENGTH: 5
<212> TYPE: PRT
<213> ORGANISM: Homo sapiens

<400> SEQUENCE: 1639

Pro Phe Lys Met Cys
1 5

<210> SEQ ID NO 1640
<211> LENGTH: 5
<212> TYPE: PRT
<213> ORGANISM: Homo sapiens

<400> SEQUENCE: 1640

Pro Phe Leu Phe Cys
1 5

<210> SEQ ID NO 1641
<211> LENGTH: 5
<212> TYPE: PRT
<213> ORGANISM: Homo sapiens

<400> SEQUENCE: 1641

Pro Phe Leu Glu Cys
1 5

<210> SEQ ID NO 1642
<211> LENGTH: 5
<212> TYPE: PRT
<213> ORGANISM: Homo sapiens

<400> SEQUENCE: 1642

Pro Phe Gly Arg Cys
1 5

<210> SEQ ID NO 1643
<211> LENGTH: 5
<212> TYPE: PRT
<213> ORGANISM: Homo sapiens

<400> SEQUENCE: 1643

Pro Phe Gly Leu Cys
1 5

<210> SEQ ID NO 1644
<211> LENGTH: 5
<212> TYPE: PRT
<213> ORGANISM: Homo sapiens

<400> SEQUENCE: 1644

Pro Phe Tyr Trp Cys
1 5

<210> SEQ ID NO 1645
<211> LENGTH: 5
<212> TYPE: PRT
<213> ORGANISM: Homo sapiens

<400> SEQUENCE: 1645

Pro Phe Ser Cys Cys
1 5

<210> SEQ ID NO 1646
<211> LENGTH: 5
<212> TYPE: PRT
<213> ORGANISM: Homo sapiens

<400> SEQUENCE: 1646

Pro Phe Ala Trp Cys
1 5

<210> SEQ ID NO 1647
<211> LENGTH: 5
<212> TYPE: PRT
<213> ORGANISM: Homo sapiens

<400> SEQUENCE: 1647

Pro Phe Tyr Gln Cys
1 5

<210> SEQ ID NO 1648
<211> LENGTH: 5
<212> TYPE: PRT
<213> ORGANISM: Homo sapiens

<400> SEQUENCE: 1648

Pro Phe Thr Ser Cys
1 5

<210> SEQ ID NO 1649
<211> LENGTH: 5
<212> TYPE: PRT
<213> ORGANISM: Homo sapiens

<400> SEQUENCE: 1649

Pro Phe Arg Asn Cys
1 5

<210> SEQ ID NO 1650
<211> LENGTH: 5
<212> TYPE: PRT
<213> ORGANISM: Homo sapiens

<400> SEQUENCE: 1650

Pro Phe Pro Cys Cys
1 5

<210> SEQ ID NO 1651
<211> LENGTH: 5
<212> TYPE: PRT
<213> ORGANISM: Homo sapiens

<400> SEQUENCE: 1651

Pro Phe Gln Tyr Cys
1 5

<210> SEQ ID NO 1652
<211> LENGTH: 5
<212> TYPE: PRT
<213> ORGANISM: Homo sapiens

<400> SEQUENCE: 1652

Pro Phe Cys Arg Cys
1 5

<210> SEQ ID NO 1653
<211> LENGTH: 5
<212> TYPE: PRT
<213> ORGANISM: Homo sapiens

<400> SEQUENCE: 1653

Pro Phe Tyr Arg Cys
1 5

<210> SEQ ID NO 1654
<211> LENGTH: 5
<212> TYPE: PRT
<213> ORGANISM: Homo sapiens

<400> SEQUENCE: 1654

Pro Phe Asp His Cys
1 5

<210> SEQ ID NO 1655
<211> LENGTH: 5
<212> TYPE: PRT
<213> ORGANISM: Homo sapiens

<400> SEQUENCE: 1655

Pro Phe Gln Ser Cys
1 5

<210> SEQ ID NO 1656
<211> LENGTH: 5
<212> TYPE: PRT
<213> ORGANISM: Homo sapiens

<400> SEQUENCE: 1656

Pro Phe Gly Thr Cys
1 5

<210> SEQ ID NO 1657
<211> LENGTH: 5
<212> TYPE: PRT
<213> ORGANISM: Homo sapiens

<400> SEQUENCE: 1657

Pro Phe Val Asn Cys
1 5

<210> SEQ ID NO 1658
<211> LENGTH: 5
<212> TYPE: PRT
<213> ORGANISM: Homo sapiens

<400> SEQUENCE: 1658

Pro Phe Ile Tyr Cys
1 5

<210> SEQ ID NO 1659
<211> LENGTH: 5
<212> TYPE: PRT
<213> ORGANISM: Homo sapiens

<400> SEQUENCE: 1659

Pro Phe Ile Glu Cys
1               5

<210> SEQ ID NO 1660
<211> LENGTH: 5
<212> TYPE: PRT
<213> ORGANISM: Homo sapiens

<400> SEQUENCE: 1660

Pro Phe Pro Thr Cys
1               5

<210> SEQ ID NO 1661
<211> LENGTH: 5
<212> TYPE: PRT
<213> ORGANISM: Homo sapiens

<400> SEQUENCE: 1661

Pro Phe His Ile Cys
1               5

<210> SEQ ID NO 1662
<211> LENGTH: 5
<212> TYPE: PRT
<213> ORGANISM: Homo sapiens

<400> SEQUENCE: 1662

Pro Phe Thr Asp Cys
1               5

<210> SEQ ID NO 1663
<211> LENGTH: 5
<212> TYPE: PRT
<213> ORGANISM: Homo sapiens

<400> SEQUENCE: 1663

Pro Phe Gly Ala Cys
1               5

<210> SEQ ID NO 1664
<211> LENGTH: 5
<212> TYPE: PRT
<213> ORGANISM: Homo sapiens

<400> SEQUENCE: 1664

Pro Phe Arg Asp Cys
1               5

<210> SEQ ID NO 1665
<211> LENGTH: 5
<212> TYPE: PRT
<213> ORGANISM: Homo sapiens

<400> SEQUENCE: 1665

Pro Phe His Ser Cys
1               5

<210> SEQ ID NO 1666
<211> LENGTH: 5

<212> TYPE: PRT
<213> ORGANISM: Homo sapiens

<400> SEQUENCE: 1666

Pro Phe Ser Leu Cys
1 5

<210> SEQ ID NO 1667
<211> LENGTH: 5
<212> TYPE: PRT
<213> ORGANISM: Homo sapiens

<400> SEQUENCE: 1667

Pro Phe Leu Gln Cys
1 5

<210> SEQ ID NO 1668
<211> LENGTH: 5
<212> TYPE: PRT
<213> ORGANISM: Homo sapiens

<400> SEQUENCE: 1668

Pro Phe Pro Gly Cys
1 5

<210> SEQ ID NO 1669
<211> LENGTH: 5
<212> TYPE: PRT
<213> ORGANISM: Homo sapiens

<400> SEQUENCE: 1669

Pro Phe Thr Gly Cys
1 5

<210> SEQ ID NO 1670
<211> LENGTH: 5
<212> TYPE: PRT
<213> ORGANISM: Homo sapiens

<400> SEQUENCE: 1670

Pro Phe Asp Glu Cys
1 5

<210> SEQ ID NO 1671
<211> LENGTH: 5
<212> TYPE: PRT
<213> ORGANISM: Homo sapiens

<400> SEQUENCE: 1671

Pro Phe Ser Thr Cys
1 5

<210> SEQ ID NO 1672
<211> LENGTH: 5
<212> TYPE: PRT
<213> ORGANISM: Homo sapiens

<400> SEQUENCE: 1672

Pro Phe Phe Asp Cys
1 5

<210> SEQ ID NO 1673
<211> LENGTH: 5
<212> TYPE: PRT
<213> ORGANISM: Homo sapiens

<400> SEQUENCE: 1673

Pro Phe Asp Thr Cys
1 5

<210> SEQ ID NO 1674
<211> LENGTH: 5
<212> TYPE: PRT
<213> ORGANISM: Homo sapiens

<400> SEQUENCE: 1674

Pro Phe Ser Thr Cys
1 5

<210> SEQ ID NO 1675
<211> LENGTH: 5
<212> TYPE: PRT
<213> ORGANISM: Homo sapiens

<400> SEQUENCE: 1675

Pro Phe Leu Ala Cys
1 5

<210> SEQ ID NO 1676
<211> LENGTH: 5
<212> TYPE: PRT
<213> ORGANISM: Homo sapiens

<400> SEQUENCE: 1676

Pro Phe Ala Asn Cys
1 5

<210> SEQ ID NO 1677
<211> LENGTH: 5
<212> TYPE: PRT
<213> ORGANISM: Homo sapiens

<400> SEQUENCE: 1677

Pro Phe Ile Arg Cys
1 5

<210> SEQ ID NO 1678
<211> LENGTH: 5
<212> TYPE: PRT
<213> ORGANISM: Homo sapiens

<400> SEQUENCE: 1678

Pro Phe Pro Val Cys
1 5

<210> SEQ ID NO 1679
<211> LENGTH: 5
<212> TYPE: PRT
<213> ORGANISM: Homo sapiens

<400> SEQUENCE: 1679

Pro Phe Arg Gly Cys
1 5

<210> SEQ ID NO 1680
<211> LENGTH: 5
<212> TYPE: PRT
<213> ORGANISM: Homo sapiens

<400> SEQUENCE: 1680

Pro Phe Phe Pro Cys
1 5

<210> SEQ ID NO 1681
<211> LENGTH: 5
<212> TYPE: PRT
<213> ORGANISM: Homo sapiens

<400> SEQUENCE: 1681

Pro Phe Leu Ala Cys
1 5

<210> SEQ ID NO 1682
<211> LENGTH: 5
<212> TYPE: PRT
<213> ORGANISM: Homo sapiens

<400> SEQUENCE: 1682

Pro Phe His Gly Cys
1 5

<210> SEQ ID NO 1683
<211> LENGTH: 5
<212> TYPE: PRT
<213> ORGANISM: Homo sapiens

<400> SEQUENCE: 1683

Pro Phe Tyr Asn Cys
1 5

<210> SEQ ID NO 1684
<211> LENGTH: 5
<212> TYPE: PRT
<213> ORGANISM: Homo sapiens

<400> SEQUENCE: 1684

Pro Phe Gln Ala Cys
1 5

<210> SEQ ID NO 1685
<211> LENGTH: 5
<212> TYPE: PRT
<213> ORGANISM: Homo sapiens

<400> SEQUENCE: 1685

Pro Phe Leu Glu Cys
1 5

<210> SEQ ID NO 1686
<211> LENGTH: 5
<212> TYPE: PRT
<213> ORGANISM: Homo sapiens

<400> SEQUENCE: 1686

Pro Phe Ala Ser Cys
1 5

<210> SEQ ID NO 1687
<211> LENGTH: 5
<212> TYPE: PRT
<213> ORGANISM: Homo sapiens

<400> SEQUENCE: 1687

Pro Phe Ser Ala Cys 1 5

<210> SEQ ID NO 1688
<211> LENGTH: 5
<212> TYPE: PRT
<213> ORGANISM: Homo sapiens

<400> SEQUENCE: 1688

Pro Phe Ser Ala Cys
1 5

<210> SEQ ID NO 1689
<211> LENGTH: 5
<212> TYPE: PRT
<213> ORGANISM: Homo sapiens

<400> SEQUENCE: 1689

Pro Phe Thr Ala Cys
1 5

<210> SEQ ID NO 1690
<211> LENGTH: 5
<212> TYPE: PRT
<213> ORGANISM: Homo sapiens

<400> SEQUENCE: 1690

Pro Phe Ser Gly Cys
1 5

<210> SEQ ID NO 1691
<211> LENGTH: 5
<212> TYPE: PRT
<213> ORGANISM: Homo sapiens

<400> SEQUENCE: 1691

Pro Phe Thr Met Cys
1 5

<210> SEQ ID NO 1692
<211> LENGTH: 5
<212> TYPE: PRT
<213> ORGANISM: Homo sapiens

<400> SEQUENCE: 1692

Pro Phe Phe Asp Cys
1 5

<210> SEQ ID NO 1693
<211> LENGTH: 5
<212> TYPE: PRT
<213> ORGANISM: Homo sapiens

<400> SEQUENCE: 1693

Pro Phe Arg Asn Cys
1 5

<210> SEQ ID NO 1694
<211> LENGTH: 5
<212> TYPE: PRT
<213> ORGANISM: Homo sapiens

<400> SEQUENCE: 1694

Pro Phe Leu Cys Cys
1 5

<210> SEQ ID NO 1695
<211> LENGTH: 5
<212> TYPE: PRT
<213> ORGANISM: Homo sapiens

<400> SEQUENCE: 1695

Pro Phe Thr Phe Cys
1 5

<210> SEQ ID NO 1696
<211> LENGTH: 5
<212> TYPE: PRT
<213> ORGANISM: Homo sapiens

<400> SEQUENCE: 1696

Pro Phe Ile Ile Cys
1 5

<210> SEQ ID NO 1697
<211> LENGTH: 5
<212> TYPE: PRT
<213> ORGANISM: Homo sapiens

<400> SEQUENCE: 1697

Pro Phe Ala Cys Cys
1 5

<210> SEQ ID NO 1698
<211> LENGTH: 5
<212> TYPE: PRT
<213> ORGANISM: Homo sapiens

<400> SEQUENCE: 1698

Pro Phe Leu Cys Cys
1 5

<210> SEQ ID NO 1699
<211> LENGTH: 5
<212> TYPE: PRT
<213> ORGANISM: Homo sapiens

<400> SEQUENCE: 1699

Pro Phe Ser Arg Cys
1 5

<210> SEQ ID NO 1700
<211> LENGTH: 5
<212> TYPE: PRT
<213> ORGANISM: Homo sapiens

<400> SEQUENCE: 1700

Pro Phe Ile Met Cys
1 5

<210> SEQ ID NO 1701
<211> LENGTH: 5
<212> TYPE: PRT
<213> ORGANISM: Homo sapiens

<400> SEQUENCE: 1701

Pro Phe Gly Asn Cys
1 5

<210> SEQ ID NO 1702

<211> LENGTH: 5
<212> TYPE: PRT
<213> ORGANISM: Homo sapiens

<400> SEQUENCE: 1702

Pro Phe Cys Ala Cys
1 5

<210> SEQ ID NO 1703
<211> LENGTH: 5
<212> TYPE: PRT
<213> ORGANISM: Homo sapiens

<400> SEQUENCE: 1703

Pro Phe Leu Lys Cys
1 5

<210> SEQ ID NO 1704
<211> LENGTH: 5
<212> TYPE: PRT
<213> ORGANISM: Homo sapiens

<400> SEQUENCE: 1704

Pro Phe Phe Leu Cys
1 5

<210> SEQ ID NO 1705
<211> LENGTH: 5
<212> TYPE: PRT
<213> ORGANISM: Homo sapiens

<400> SEQUENCE: 1705

Pro Phe Pro Gln Cys
1 5

<210> SEQ ID NO 1706
<211> LENGTH: 5
<212> TYPE: PRT
<213> ORGANISM: Homo sapiens

<400> SEQUENCE: 1706

Pro Phe Pro Leu Cys
1 5

<210> SEQ ID NO 1707
<211> LENGTH: 5
<212> TYPE: PRT
<213> ORGANISM: Homo sapiens

<400> SEQUENCE: 1707

Pro Phe Thr Thr Cys
1 5

<210> SEQ ID NO 1708
<211> LENGTH: 5
<212> TYPE: PRT
<213> ORGANISM: Homo sapiens

<400> SEQUENCE: 1708

Pro Phe Pro Ala Cys
1 5

<210> SEQ ID NO 1709
<211> LENGTH: 5
<212> TYPE: PRT

<213> ORGANISM: Homo sapiens

<400> SEQUENCE: 1709

Pro Phe Gln Asp Cys
1 5

<210> SEQ ID NO 1710
<211> LENGTH: 5
<212> TYPE: PRT
<213> ORGANISM: Homo sapiens

<400> SEQUENCE: 1710

Pro Phe Thr Thr Cys
1 5

<210> SEQ ID NO 1711
<211> LENGTH: 5
<212> TYPE: PRT
<213> ORGANISM: Homo sapiens

<400> SEQUENCE: 1711

Pro Phe Asp Asp Cys
1 5

<210> SEQ ID NO 1712
<211> LENGTH: 5
<212> TYPE: PRT
<213> ORGANISM: Homo sapiens

<400> SEQUENCE: 1712

Pro Phe Thr Pro Cys
1 5

<210> SEQ ID NO 1713
<211> LENGTH: 5
<212> TYPE: PRT
<213> ORGANISM: Homo sapiens

<400> SEQUENCE: 1713

Pro Phe Gly Ser Cys
1 5

<210> SEQ ID NO 1714
<211> LENGTH: 5
<212> TYPE: PRT
<213> ORGANISM: Homo sapiens

<400> SEQUENCE: 1714

Pro Phe His Ile Cys
1 5

<210> SEQ ID NO 1715
<211> LENGTH: 5
<212> TYPE: PRT
<213> ORGANISM: Homo sapiens

<400> SEQUENCE: 1715

Pro Phe Pro Ala Cys
1 5

<210> SEQ ID NO 1716
<211> LENGTH: 5
<212> TYPE: PRT
<213> ORGANISM: Homo sapiens

<400> SEQUENCE: 1716

Pro Phe Gly Ser Cys
1 5

<210> SEQ ID NO 1717
<211> LENGTH: 5
<212> TYPE: PRT
<213> ORGANISM: Homo sapiens

<400> SEQUENCE: 1717

Pro Phe Ala Lys Cys
1 5

<210> SEQ ID NO 1718
<211> LENGTH: 5
<212> TYPE: PRT
<213> ORGANISM: Homo sapiens

<400> SEQUENCE: 1718

Pro Phe Tyr Asn Cys
1 5

<210> SEQ ID NO 1719
<211> LENGTH: 5
<212> TYPE: PRT
<213> ORGANISM: Homo sapiens

<400> SEQUENCE: 1719

Pro Phe Gly Ser Cys
1 5

<210> SEQ ID NO 1720
<211> LENGTH: 5
<212> TYPE: PRT
<213> ORGANISM: Homo sapiens

<400> SEQUENCE: 1720

Pro Phe Pro Gly Cys
1 5

<210> SEQ ID NO 1721
<211> LENGTH: 5
<212> TYPE: PRT
<213> ORGANISM: Homo sapiens

<400> SEQUENCE: 1721

Pro Phe Gln Gly Cys
1 5

<210> SEQ ID NO 1722
<211> LENGTH: 5
<212> TYPE: PRT
<213> ORGANISM: Homo sapiens

<400> SEQUENCE: 1722

Pro Phe Ser Cys Cys
1 5

<210> SEQ ID NO 1723
<211> LENGTH: 5
<212> TYPE: PRT
<213> ORGANISM: Homo sapiens

<400> SEQUENCE: 1723

Pro Phe Gly Gly Cys
1 5

<210> SEQ ID NO 1724
<211> LENGTH: 5
<212> TYPE: PRT
<213> ORGANISM: Homo sapiens

<400> SEQUENCE: 1724

Pro Phe Gly Gly Cys
1 5

<210> SEQ ID NO 1725
<211> LENGTH: 5
<212> TYPE: PRT
<213> ORGANISM: Homo sapiens

<400> SEQUENCE: 1725

Pro Phe Pro Phe Cys
1 5

<210> SEQ ID NO 1726
<211> LENGTH: 5
<212> TYPE: PRT
<213> ORGANISM: Homo sapiens

<400> SEQUENCE: 1726

Pro Phe Tyr Gly Cys
1 5

<210> SEQ ID NO 1727
<211> LENGTH: 5
<212> TYPE: PRT
<213> ORGANISM: Homo sapiens

<400> SEQUENCE: 1727

Pro Phe His Ala Cys
1 5

<210> SEQ ID NO 1728
<211> LENGTH: 5
<212> TYPE: PRT
<213> ORGANISM: Homo sapiens

<400> SEQUENCE: 1728

Pro Phe Asn Thr Cys
1 5

<210> SEQ ID NO 1729
<211> LENGTH: 5
<212> TYPE: PRT
<213> ORGANISM: Homo sapiens

<400> SEQUENCE: 1729

Pro Phe Leu Arg Cys
1 5

<210> SEQ ID NO 1730
<211> LENGTH: 5
<212> TYPE: PRT
<213> ORGANISM: Homo sapiens

<400> SEQUENCE: 1730

Pro Phe Gln Cys Cys
1 5

<210> SEQ ID NO 1731
<211> LENGTH: 5
<212> TYPE: PRT
<213> ORGANISM: Homo sapiens

<400> SEQUENCE: 1731

Pro Phe Ile Leu Cys
1 5

<210> SEQ ID NO 1732
<211> LENGTH: 5
<212> TYPE: PRT
<213> ORGANISM: Homo sapiens

<400> SEQUENCE: 1732

Pro Phe Glu Leu Cys
1 5

<210> SEQ ID NO 1733
<211> LENGTH: 5
<212> TYPE: PRT
<213> ORGANISM: Homo sapiens

<400> SEQUENCE: 1733

Pro Phe Gly Lys Cys
1 5

<210> SEQ ID NO 1734
<211> LENGTH: 5
<212> TYPE: PRT
<213> ORGANISM: Homo sapiens

<400> SEQUENCE: 1734

Pro Phe Pro Gly Cys
1 5

<210> SEQ ID NO 1735
<211> LENGTH: 5
<212> TYPE: PRT
<213> ORGANISM: Homo sapiens

<400> SEQUENCE: 1735

Pro Phe Ser His Cys
1 5

<210> SEQ ID NO 1736
<211> LENGTH: 5
<212> TYPE: PRT
<213> ORGANISM: Homo sapiens

<400> SEQUENCE: 1736

Pro Phe Leu Ser Cys
1 5

<210> SEQ ID NO 1737
<211> LENGTH: 5
<212> TYPE: PRT
<213> ORGANISM: Homo sapiens

<400> SEQUENCE: 1737

Pro Phe Pro Gln Cys
1 5

<210> SEQ ID NO 1738
<211> LENGTH: 5
<212> TYPE: PRT
<213> ORGANISM: Homo sapiens

<400> SEQUENCE: 1738

Pro Phe Cys Arg Cys
1               5

<210> SEQ ID NO 1739
<211> LENGTH: 5
<212> TYPE: PRT
<213> ORGANISM: Homo sapiens

<400> SEQUENCE: 1739

Pro Phe Cys His Cys
1               5

<210> SEQ ID NO 1740
<211> LENGTH: 5
<212> TYPE: PRT
<213> ORGANISM: Homo sapiens

<400> SEQUENCE: 1740

Pro Phe Pro Cys Cys
1               5

<210> SEQ ID NO 1741
<211> LENGTH: 5
<212> TYPE: PRT
<213> ORGANISM: Homo sapiens

<400> SEQUENCE: 1741

Pro Phe Ala Val Cys
1               5

<210> SEQ ID NO 1742
<211> LENGTH: 5
<212> TYPE: PRT
<213> ORGANISM: Homo sapiens

<400> SEQUENCE: 1742

Pro Phe Pro Ile Cys
1               5

<210> SEQ ID NO 1743
<211> LENGTH: 5
<212> TYPE: PRT
<213> ORGANISM: Homo sapiens

<400> SEQUENCE: 1743

Pro Phe His Asn Cys
1               5

<210> SEQ ID NO 1744
<211> LENGTH: 5
<212> TYPE: PRT
<213> ORGANISM: Homo sapiens

<400> SEQUENCE: 1744

Pro Phe Gln Val Cys
1               5

<210> SEQ ID NO 1745
<211> LENGTH: 5

<212> TYPE: PRT
<213> ORGANISM: Homo sapiens

<400> SEQUENCE: 1745

Pro Phe Val Asp Cys
1 5

<210> SEQ ID NO 1746
<211> LENGTH: 5
<212> TYPE: PRT
<213> ORGANISM: Homo sapiens

<400> SEQUENCE: 1746

Pro Phe Leu Gln Cys
1 5

<210> SEQ ID NO 1747
<211> LENGTH: 5
<212> TYPE: PRT
<213> ORGANISM: Homo sapiens

<400> SEQUENCE: 1747

Pro Phe Ser Ala Cys
1 5

<210> SEQ ID NO 1748
<211> LENGTH: 5
<212> TYPE: PRT
<213> ORGANISM: Homo sapiens

<400> SEQUENCE: 1748

Pro Phe Gly Gln Cys
1 5

<210> SEQ ID NO 1749
<211> LENGTH: 5
<212> TYPE: PRT
<213> ORGANISM: Homo sapiens

<400> SEQUENCE: 1749

Pro Phe Tyr His Cys
1 5

<210> SEQ ID NO 1750
<211> LENGTH: 5
<212> TYPE: PRT
<213> ORGANISM: Homo sapiens

<400> SEQUENCE: 1750

Pro Phe Ser Cys Cys
1 5

<210> SEQ ID NO 1751
<211> LENGTH: 5
<212> TYPE: PRT
<213> ORGANISM: Homo sapiens

<400> SEQUENCE: 1751

Pro Phe Trp Gly Cys
1 5

<210> SEQ ID NO 1752
<211> LENGTH: 5
<212> TYPE: PRT
<213> ORGANISM: Homo sapiens

<400> SEQUENCE: 1752

Pro Phe His Leu Cys
1 5

<210> SEQ ID NO 1753
<211> LENGTH: 5
<212> TYPE: PRT
<213> ORGANISM: Homo sapiens

<400> SEQUENCE: 1753

Pro Phe Glu Asp Cys
1 5

<210> SEQ ID NO 1754
<211> LENGTH: 5
<212> TYPE: PRT
<213> ORGANISM: Homo sapiens

<400> SEQUENCE: 1754

Pro Phe Thr Gln Cys
1 5

<210> SEQ ID NO 1755
<211> LENGTH: 5
<212> TYPE: PRT
<213> ORGANISM: Homo sapiens

<400> SEQUENCE: 1755

Pro Phe Pro Arg Cys
1 5

<210> SEQ ID NO 1756
<211> LENGTH: 5
<212> TYPE: PRT
<213> ORGANISM: Homo sapiens

<400> SEQUENCE: 1756

Pro Phe Ser Thr Cys
1 5

<210> SEQ ID NO 1757
<211> LENGTH: 5
<212> TYPE: PRT
<213> ORGANISM: Homo sapiens

<400> SEQUENCE: 1757

Pro Phe Ala Ser Cys
1 5

<210> SEQ ID NO 1758
<211> LENGTH: 5
<212> TYPE: PRT
<213> ORGANISM: Homo sapiens

<400> SEQUENCE: 1758

Pro Phe Phe Ile Cys
1 5

<210> SEQ ID NO 1759
<211> LENGTH: 5
<212> TYPE: PRT
<213> ORGANISM: Homo sapiens

<400> SEQUENCE: 1759

Pro Phe Glu Lys Cys
1 5

<210> SEQ ID NO 1760
<211> LENGTH: 5
<212> TYPE: PRT
<213> ORGANISM: Homo sapiens

<400> SEQUENCE: 1760

Pro Phe Ser Ile Cys
1 5

<210> SEQ ID NO 1761
<211> LENGTH: 5
<212> TYPE: PRT
<213> ORGANISM: Homo sapiens

<400> SEQUENCE: 1761

Pro Phe Pro Gly Cys
1 5

<210> SEQ ID NO 1762
<211> LENGTH: 5
<212> TYPE: PRT
<213> ORGANISM: Homo sapiens

<400> SEQUENCE: 1762

Pro Phe Pro Val Cys
1 5

<210> SEQ ID NO 1763
<211> LENGTH: 5
<212> TYPE: PRT
<213> ORGANISM: Homo sapiens

<400> SEQUENCE: 1763

Pro Phe Asp Leu Cys
1 5

<210> SEQ ID NO 1764
<211> LENGTH: 5
<212> TYPE: PRT
<213> ORGANISM: Homo sapiens

<400> SEQUENCE: 1764

Pro Phe His His Cys
1 5

<210> SEQ ID NO 1765
<211> LENGTH: 5
<212> TYPE: PRT
<213> ORGANISM: Homo sapiens

<400> SEQUENCE: 1765

Pro Phe Arg Arg Cys
1 5

<210> SEQ ID NO 1766
<211> LENGTH: 5
<212> TYPE: PRT
<213> ORGANISM: Homo sapiens

<400> SEQUENCE: 1766

Pro Phe Trp Ile Cys 1 5

<210> SEQ ID NO 1767
<211> LENGTH: 5
<212> TYPE: PRT
<213> ORGANISM: Homo sapiens

<400> SEQUENCE: 1767

Pro Phe Gln Val Cys
1 5

<210> SEQ ID NO 1768
<211> LENGTH: 5
<212> TYPE: PRT
<213> ORGANISM: Homo sapiens

<400> SEQUENCE: 1768

Pro Phe Cys Leu Cys
1 5

<210> SEQ ID NO 1769
<211> LENGTH: 5
<212> TYPE: PRT
<213> ORGANISM: Homo sapiens

<400> SEQUENCE: 1769

Pro Phe Pro Asp Cys
1 5

<210> SEQ ID NO 1770
<211> LENGTH: 5
<212> TYPE: PRT
<213> ORGANISM: Homo sapiens

<400> SEQUENCE: 1770

Pro Phe Gln Leu Cys
1 5

<210> SEQ ID NO 1771
<211> LENGTH: 5
<212> TYPE: PRT
<213> ORGANISM: Homo sapiens

<400> SEQUENCE: 1771

Pro Phe Arg Pro Cys
1 5

<210> SEQ ID NO 1772
<211> LENGTH: 5
<212> TYPE: PRT
<213> ORGANISM: Homo sapiens

<400> SEQUENCE: 1772

Pro Phe Ala Val Cys
1 5

<210> SEQ ID NO 1773
<211> LENGTH: 5
<212> TYPE: PRT
<213> ORGANISM: Homo sapiens

<400> SEQUENCE: 1773

Pro Phe Ser Tyr Cys
1 5

<210> SEQ ID NO 1774
<211> LENGTH: 5
<212> TYPE: PRT
<213> ORGANISM: Homo sapiens

<400> SEQUENCE: 1774

Pro Phe Phe Leu Cys
1 5

<210> SEQ ID NO 1775
<211> LENGTH: 5
<212> TYPE: PRT
<213> ORGANISM: Homo sapiens

<400> SEQUENCE: 1775

Pro Phe Tyr Glu Cys
1 5

<210> SEQ ID NO 1776
<211> LENGTH: 5
<212> TYPE: PRT
<213> ORGANISM: Homo sapiens

<400> SEQUENCE: 1776

Pro Phe Pro Ala Cys
1 5

<210> SEQ ID NO 1777
<211> LENGTH: 5
<212> TYPE: PRT
<213> ORGANISM: Homo sapiens

<400> SEQUENCE: 1777

Pro Phe His Ala Cys
1 5

<210> SEQ ID NO 1778
<211> LENGTH: 5
<212> TYPE: PRT
<213> ORGANISM: Homo sapiens

<400> SEQUENCE: 1778

Pro Phe Gln Ile Cys
1 5

<210> SEQ ID NO 1779
<211> LENGTH: 5
<212> TYPE: PRT
<213> ORGANISM: Homo sapiens

<400> SEQUENCE: 1779

Pro Phe Pro Asn Cys
1 5

<210> SEQ ID NO 1780
<211> LENGTH: 5
<212> TYPE: PRT
<213> ORGANISM: Homo sapiens

<400> SEQUENCE: 1780

Pro Phe Glu Lys Cys
1 5

<210> SEQ ID NO 1781

<211> LENGTH: 5
<212> TYPE: PRT
<213> ORGANISM: Homo sapiens

<400> SEQUENCE: 1781

Pro Phe Leu Asn Cys
1 5

<210> SEQ ID NO 1782
<211> LENGTH: 5
<212> TYPE: PRT
<213> ORGANISM: Homo sapiens

<400> SEQUENCE: 1782

Pro Phe Gln Asp Cys
1 5

<210> SEQ ID NO 1783
<211> LENGTH: 5
<212> TYPE: PRT
<213> ORGANISM: Homo sapiens

<400> SEQUENCE: 1783

Pro Phe Tyr Asn Cys
1 5

<210> SEQ ID NO 1784
<211> LENGTH: 5
<212> TYPE: PRT
<213> ORGANISM: Homo sapiens

<400> SEQUENCE: 1784

Pro Phe Gln Trp Cys
1 5

<210> SEQ ID NO 1785
<211> LENGTH: 5
<212> TYPE: PRT
<213> ORGANISM: Homo sapiens

<400> SEQUENCE: 1785

Pro Phe Arg Gln Cys
1 5

<210> SEQ ID NO 1786
<211> LENGTH: 5
<212> TYPE: PRT
<213> ORGANISM: Homo sapiens

<400> SEQUENCE: 1786

Pro Phe Asp Ala Cys
1 5

<210> SEQ ID NO 1787
<211> LENGTH: 5
<212> TYPE: PRT
<213> ORGANISM: Homo sapiens

<400> SEQUENCE: 1787

Pro Phe Asp Thr Cys
1 5

<210> SEQ ID NO 1788
<211> LENGTH: 5
<212> TYPE: PRT

<213> ORGANISM: Homo sapiens

<400> SEQUENCE: 1788

Pro Phe Asp Ala Cys
1 5

<210> SEQ ID NO 1789
<211> LENGTH: 5
<212> TYPE: PRT
<213> ORGANISM: Homo sapiens

<400> SEQUENCE: 1789

Pro Phe Lys Pro Cys
1 5

<210> SEQ ID NO 1790
<211> LENGTH: 5
<212> TYPE: PRT
<213> ORGANISM: Homo sapiens

<400> SEQUENCE: 1790

Pro Phe Asp Ile Cys
1 5

<210> SEQ ID NO 1791
<211> LENGTH: 5
<212> TYPE: PRT
<213> ORGANISM: Homo sapiens

<400> SEQUENCE: 1791

Pro Phe Leu Val Cys
1 5

<210> SEQ ID NO 1792
<211> LENGTH: 5
<212> TYPE: PRT
<213> ORGANISM: Homo sapiens

<400> SEQUENCE: 1792

Pro Phe Gln Ala Cys
1 5

<210> SEQ ID NO 1793
<211> LENGTH: 5
<212> TYPE: PRT
<213> ORGANISM: Homo sapiens

<400> SEQUENCE: 1793

Pro Phe Gln Asp Cys
1 5

<210> SEQ ID NO 1794
<211> LENGTH: 5
<212> TYPE: PRT
<213> ORGANISM: Homo sapiens

<400> SEQUENCE: 1794

Pro Phe Glu Val Cys
1 5

<210> SEQ ID NO 1795
<211> LENGTH: 5
<212> TYPE: PRT
<213> ORGANISM: Homo sapiens

<400> SEQUENCE: 1795

Pro Phe Ile Tyr Cys
1 5

<210> SEQ ID NO 1796
<211> LENGTH: 5
<212> TYPE: PRT
<213> ORGANISM: Homo sapiens

<400> SEQUENCE: 1796

Pro Phe Asp Pro Cys
1 5

<210> SEQ ID NO 1797
<211> LENGTH: 5
<212> TYPE: PRT
<213> ORGANISM: Homo sapiens

<400> SEQUENCE: 1797

Pro Phe Ile Leu Cys
1 5

<210> SEQ ID NO 1798
<211> LENGTH: 5
<212> TYPE: PRT
<213> ORGANISM: Homo sapiens

<400> SEQUENCE: 1798

Pro Phe Cys Val Cys
1 5

<210> SEQ ID NO 1799
<211> LENGTH: 5
<212> TYPE: PRT
<213> ORGANISM: Homo sapiens

<400> SEQUENCE: 1799

Pro Phe Ser Asp Cys
1 5

<210> SEQ ID NO 1800
<211> LENGTH: 5
<212> TYPE: PRT
<213> ORGANISM: Homo sapiens

<400> SEQUENCE: 1800

Pro Phe Pro Val Cys
1 5

<210> SEQ ID NO 1801
<211> LENGTH: 5
<212> TYPE: PRT
<213> ORGANISM: Homo sapiens

<400> SEQUENCE: 1801

Pro Phe Phe Asp Cys
1 5

<210> SEQ ID NO 1802
<211> LENGTH: 5
<212> TYPE: PRT
<213> ORGANISM: Homo sapiens

<400> SEQUENCE: 1802

Pro Phe Gly Thr Cys
1 5

<210> SEQ ID NO 1803
<211> LENGTH: 5
<212> TYPE: PRT
<213> ORGANISM: Homo sapiens

<400> SEQUENCE: 1803

Pro Phe Ala Phe Cys
1 5

<210> SEQ ID NO 1804
<211> LENGTH: 5
<212> TYPE: PRT
<213> ORGANISM: Homo sapiens

<400> SEQUENCE: 1804

Pro Phe Arg Pro Cys
1 5

<210> SEQ ID NO 1805
<211> LENGTH: 5
<212> TYPE: PRT
<213> ORGANISM: Homo sapiens

<400> SEQUENCE: 1805

Pro Phe Val Thr Cys
1 5

<210> SEQ ID NO 1806
<211> LENGTH: 5
<212> TYPE: PRT
<213> ORGANISM: Homo sapiens

<400> SEQUENCE: 1806

Pro Phe Arg Val Cys
1 5

<210> SEQ ID NO 1807
<211> LENGTH: 5
<212> TYPE: PRT
<213> ORGANISM: Homo sapiens

<400> SEQUENCE: 1807

Pro Phe Ser His Cys
1 5

<210> SEQ ID NO 1808
<211> LENGTH: 5
<212> TYPE: PRT
<213> ORGANISM: Homo sapiens

<400> SEQUENCE: 1808

Pro Phe Ser Ser Cys
1 5

<210> SEQ ID NO 1809
<211> LENGTH: 5
<212> TYPE: PRT
<213> ORGANISM: Homo sapiens

<400> SEQUENCE: 1809

Pro Phe Pro Thr Cys
1 5

<210> SEQ ID NO 1810
<211> LENGTH: 5
<212> TYPE: PRT
<213> ORGANISM: Homo sapiens

<400> SEQUENCE: 1810

Pro Phe Pro Asn Cys
1 5

<210> SEQ ID NO 1811
<211> LENGTH: 5
<212> TYPE: PRT
<213> ORGANISM: Homo sapiens

<400> SEQUENCE: 1811

Pro Phe Gly Leu Cys
1 5

<210> SEQ ID NO 1812
<211> LENGTH: 5
<212> TYPE: PRT
<213> ORGANISM: Homo sapiens

<400> SEQUENCE: 1812

Pro Phe Cys Arg Cys
1 5

<210> SEQ ID NO 1813
<211> LENGTH: 5
<212> TYPE: PRT
<213> ORGANISM: Homo sapiens

<400> SEQUENCE: 1813

Pro Phe Phe Arg Cys
1 5

<210> SEQ ID NO 1814
<211> LENGTH: 5
<212> TYPE: PRT
<213> ORGANISM: Homo sapiens

<400> SEQUENCE: 1814

Pro Phe Phe Arg Cys
1 5

<210> SEQ ID NO 1815
<211> LENGTH: 5
<212> TYPE: PRT
<213> ORGANISM: Homo sapiens

<400> SEQUENCE: 1815

Pro Phe Thr Gly Cys
1 5

<210> SEQ ID NO 1816
<211> LENGTH: 5
<212> TYPE: PRT
<213> ORGANISM: Homo sapiens

<400> SEQUENCE: 1816

Pro Phe Pro Ser Cys
1 5

<210> SEQ ID NO 1817
<211> LENGTH: 5
<212> TYPE: PRT
<213> ORGANISM: Homo sapiens

<400> SEQUENCE: 1817

Pro Phe Tyr Thr Cys
1               5

<210> SEQ ID NO 1818
<211> LENGTH: 5
<212> TYPE: PRT
<213> ORGANISM: Homo sapiens

<400> SEQUENCE: 1818

Pro Phe Arg Leu Cys
1               5

<210> SEQ ID NO 1819
<211> LENGTH: 5
<212> TYPE: PRT
<213> ORGANISM: Homo sapiens

<400> SEQUENCE: 1819

Pro Phe Glu Thr Cys
1               5

<210> SEQ ID NO 1820
<211> LENGTH: 5
<212> TYPE: PRT
<213> ORGANISM: Homo sapiens

<400> SEQUENCE: 1820

Pro Phe Ser Gln Cys
1               5

<210> SEQ ID NO 1821
<211> LENGTH: 5
<212> TYPE: PRT
<213> ORGANISM: Homo sapiens

<400> SEQUENCE: 1821

Pro Phe Ala Ala Cys
1               5

<210> SEQ ID NO 1822
<211> LENGTH: 5
<212> TYPE: PRT
<213> ORGANISM: Homo sapiens

<400> SEQUENCE: 1822

Pro Phe Trp Ile Cys
1               5

<210> SEQ ID NO 1823
<211> LENGTH: 5
<212> TYPE: PRT
<213> ORGANISM: Homo sapiens

<400> SEQUENCE: 1823

Pro Phe Ser Arg Cys
1               5

<210> SEQ ID NO 1824
<211> LENGTH: 5

<212> TYPE: PRT
<213> ORGANISM: Homo sapiens

<400> SEQUENCE: 1824

Pro Phe Gln Asp Cys
1 5

<210> SEQ ID NO 1825
<211> LENGTH: 5
<212> TYPE: PRT
<213> ORGANISM: Homo sapiens

<400> SEQUENCE: 1825

Pro Phe Gln Leu Cys
1 5

<210> SEQ ID NO 1826
<211> LENGTH: 5
<212> TYPE: PRT
<213> ORGANISM: Homo sapiens

<400> SEQUENCE: 1826

Pro Phe Ala Tyr Cys
1 5

<210> SEQ ID NO 1827
<211> LENGTH: 5
<212> TYPE: PRT
<213> ORGANISM: Homo sapiens

<400> SEQUENCE: 1827

Pro Phe Ser Gln Cys
1 5

<210> SEQ ID NO 1828
<211> LENGTH: 5
<212> TYPE: PRT
<213> ORGANISM: Homo sapiens

<400> SEQUENCE: 1828

Pro Phe Ala Val Cys
1 5

<210> SEQ ID NO 1829
<211> LENGTH: 5
<212> TYPE: PRT
<213> ORGANISM: Homo sapiens

<400> SEQUENCE: 1829

Pro Phe Arg Glu Cys
1 5

<210> SEQ ID NO 1830
<211> LENGTH: 5
<212> TYPE: PRT
<213> ORGANISM: Homo sapiens

<400> SEQUENCE: 1830

Pro Phe Thr Thr Cys
1 5

<210> SEQ ID NO 1831
<211> LENGTH: 5
<212> TYPE: PRT
<213> ORGANISM: Homo sapiens

<400> SEQUENCE: 1831

Pro Phe Thr Thr Cys
1 5

<210> SEQ ID NO 1832
<211> LENGTH: 5
<212> TYPE: PRT
<213> ORGANISM: Homo sapiens

<400> SEQUENCE: 1832

Pro Phe Thr Thr Cys
1 5

<210> SEQ ID NO 1833
<211> LENGTH: 5
<212> TYPE: PRT
<213> ORGANISM: Homo sapiens

<400> SEQUENCE: 1833

Pro Phe Ala Thr Cys
1 5

<210> SEQ ID NO 1834
<211> LENGTH: 12
<212> TYPE: PRT
<213> ORGANISM: Homo sapiens

<400> SEQUENCE: 1834

Leu Val Gly Tyr Leu Leu Gly Ser Ala Ser Leu Leu
1 5 10

<210> SEQ ID NO 1835
<211> LENGTH: 12
<212> TYPE: PRT
<213> ORGANISM: Homo sapiens

<400> SEQUENCE: 1835

Leu Cys Glu Glu Leu Leu Ser Arg Thr Ser Ser Leu
1 5 10

<210> SEQ ID NO 1836
<211> LENGTH: 12
<212> TYPE: PRT
<213> ORGANISM: Homo sapiens

<400> SEQUENCE: 1836

Leu Ala Thr Val Leu Leu Val Phe Val Ser Thr Leu
1 5 10

<210> SEQ ID NO 1837
<211> LENGTH: 12
<212> TYPE: PRT
<213> ORGANISM: Homo sapiens

<400> SEQUENCE: 1837

Leu Leu Leu Pro Leu Leu Leu Ala Val Ser Gly Leu
1 5 10

<210> SEQ ID NO 1838
<211> LENGTH: 12
<212> TYPE: PRT
<213> ORGANISM: Homo sapiens

<400> SEQUENCE: 1838

Leu Met Leu Leu Leu Leu Leu Pro Pro Ser Pro Leu
1 5 10

<210> SEQ ID NO 1839
<211> LENGTH: 12
<212> TYPE: PRT
<213> ORGANISM: Homo sapiens

<400> SEQUENCE: 1839

Leu Phe Asp Thr Leu Leu Glu Glu Tyr Ser Val Leu
1 5 10

<210> SEQ ID NO 1840
<211> LENGTH: 12
<212> TYPE: PRT
<213> ORGANISM: Homo sapiens

<400> SEQUENCE: 1840

Leu Val Met Lys Leu Leu Ser Gly Gly Ser Val Leu
1 5 10

<210> SEQ ID NO 1841
<211> LENGTH: 12
<212> TYPE: PRT
<213> ORGANISM: Homo sapiens

<400> SEQUENCE: 1841

Leu Arg Ile Ser Leu Leu Leu Ile Gln Ser Trp Leu
1 5 10

<210> SEQ ID NO 1842
<211> LENGTH: 12
<212> TYPE: PRT
<213> ORGANISM: Homo sapiens

<400> SEQUENCE: 1842

Leu Arg Ile Ser Leu Leu Leu Ile Gln Ser Trp Leu
1 5 10

<210> SEQ ID NO 1843
<211> LENGTH: 12
<212> TYPE: PRT
<213> ORGANISM: Homo sapiens

<400> SEQUENCE: 1843

Leu Arg Ile Ser Leu Leu Leu Ile Glu Ser Trp Leu
1 5 10

<210> SEQ ID NO 1844
<211> LENGTH: 12
<212> TYPE: PRT
<213> ORGANISM: Homo sapiens

<400> SEQUENCE: 1844

Leu Pro Ala Asn Leu Leu Gln Gly Ala Ser Lys Leu
1 5 10

<210> SEQ ID NO 1845
<211> LENGTH: 12
<212> TYPE: PRT
<213> ORGANISM: Homo sapiens

<400> SEQUENCE: 1845

Leu Asn Val Ser Leu Leu Leu Thr Leu Ser Ile Leu 1 5 10

<210> SEQ ID NO 1846
<211> LENGTH: 12
<212> TYPE: PRT
<213> ORGANISM: Homo sapiens

<400> SEQUENCE: 1846

Leu Val Cys Ala Leu Leu Trp Ala Leu Ser Cys Leu
1 5 10

<210> SEQ ID NO 1847
<211> LENGTH: 12
<212> TYPE: PRT
<213> ORGANISM: Homo sapiens

<400> SEQUENCE: 1847

Leu Asn Gly Ile Leu Leu His Leu Glu Ser Glu Leu
1 5 10

<210> SEQ ID NO 1848
<211> LENGTH: 12
<212> TYPE: PRT
<213> ORGANISM: Homo sapiens

<400> SEQUENCE: 1848

Leu Leu Leu Leu Leu Leu Leu Leu Pro Ser Pro Leu
1 5 10

<210> SEQ ID NO 1849
<211> LENGTH: 12
<212> TYPE: PRT
<213> ORGANISM: Homo sapiens

<400> SEQUENCE: 1849

Leu Thr Asn Asp Leu Leu His Asn Leu Ser Gly Leu
1 5 10

<210> SEQ ID NO 1850
<211> LENGTH: 12
<212> TYPE: PRT
<213> ORGANISM: Homo sapiens

<400> SEQUENCE: 1850

Leu Val Gly Ala Leu Leu Met Gly Phe Ser Lys Leu
1 5 10

<210> SEQ ID NO 1851
<211> LENGTH: 12
<212> TYPE: PRT
<213> ORGANISM: Homo sapiens

<400> SEQUENCE: 1851

Leu Ser Phe Leu Leu Leu Leu Phe Phe Ser His Leu
1 5 10

<210> SEQ ID NO 1852
<211> LENGTH: 12
<212> TYPE: PRT
<213> ORGANISM: Homo sapiens

<400> SEQUENCE: 1852

Leu Cys Pro Gly Leu Leu His Pro Ser Ser Arg Leu
1 5 10

<210> SEQ ID NO 1853
<211> LENGTH: 12
<212> TYPE: PRT
<213> ORGANISM: Homo sapiens

<400> SEQUENCE: 1853

Leu Leu Lys Ala Leu Leu Glu Ile Ala Ser Cys Leu
1 5 10

<210> SEQ ID NO 1854
<211> LENGTH: 12
<212> TYPE: PRT
<213> ORGANISM: Homo sapiens

<400> SEQUENCE: 1854

Leu Pro Ala Trp Leu Leu Glu Lys Glu Ser Ile Leu
1 5 10

<210> SEQ ID NO 1855
<211> LENGTH: 12
<212> TYPE: PRT
<213> ORGANISM: Homo sapiens

<400> SEQUENCE: 1855

Leu Val Arg Asp Leu Leu Glu Val Thr Ser Gly Leu
1 5 10

<210> SEQ ID NO 1856
<211> LENGTH: 12
<212> TYPE: PRT
<213> ORGANISM: Homo sapiens

<400> SEQUENCE: 1856

Leu Val Arg Gly Leu Leu Ala Lys Lys Ser Lys Leu
1 5 10

<210> SEQ ID NO 1857
<211> LENGTH: 12
<212> TYPE: PRT
<213> ORGANISM: Homo sapiens

<400> SEQUENCE: 1857

Leu Ile Leu Gly Leu Leu Leu Cys Phe Ser Val Leu
1 5 10

<210> SEQ ID NO 1858
<211> LENGTH: 12
<212> TYPE: PRT
<213> ORGANISM: Homo sapiens

<400> SEQUENCE: 1858

Leu Cys Ser Gly Leu Leu Phe Pro Val Ser Cys Leu
1 5 10

<210> SEQ ID NO 1859
<211> LENGTH: 12
<212> TYPE: PRT
<213> ORGANISM: Homo sapiens

<400> SEQUENCE: 1859

Leu Ser Ile Leu Leu Leu Leu Ser Cys Ser Val Leu
1 5 10

<210> SEQ ID NO 1860

<211> LENGTH: 12
<212> TYPE: PRT
<213> ORGANISM: Homo sapiens

<400> SEQUENCE: 1860

Leu Ala Ser Leu Leu Leu Ile Cys Lys Ser Ser Leu
1 5 10

<210> SEQ ID NO 1861
<211> LENGTH: 12
<212> TYPE: PRT
<213> ORGANISM: Homo sapiens

<400> SEQUENCE: 1861

Leu Leu Ala Ser Leu Leu Ser Pro Gly Ser Val Leu
1 5 10

<210> SEQ ID NO 1862
<211> LENGTH: 12
<212> TYPE: PRT
<213> ORGANISM: Homo sapiens

<400> SEQUENCE: 1862

Leu Pro Pro Arg Leu Leu Ala Arg Pro Ser Leu Leu
1 5 10

<210> SEQ ID NO 1863
<211> LENGTH: 12
<212> TYPE: PRT
<213> ORGANISM: Homo sapiens

<400> SEQUENCE: 1863

Leu Glu Asp Met Leu Leu Thr Thr Leu Ser Gly Leu
1 5 10

<210> SEQ ID NO 1864
<211> LENGTH: 12
<212> TYPE: PRT
<213> ORGANISM: Homo sapiens

<400> SEQUENCE: 1864

Leu Leu Glu Tyr Leu Leu Tyr Phe Leu Ser Phe Leu
1 5 10

<210> SEQ ID NO 1865
<211> LENGTH: 12
<212> TYPE: PRT
<213> ORGANISM: Homo sapiens

<400> SEQUENCE: 1865

Leu Asn Ser Lys Leu Leu Asp Ile Arg Ser Tyr Leu
1 5 10

<210> SEQ ID NO 1866
<211> LENGTH: 12
<212> TYPE: PRT
<213> ORGANISM: Homo sapiens

<400> SEQUENCE: 1866

Leu Ile Ser Phe Leu Leu Ser Leu Ile Ser Leu Leu
1 5 10

<210> SEQ ID NO 1867
<211> LENGTH: 12
<212> TYPE: PRT

<213> ORGANISM: Homo sapiens

<400> SEQUENCE: 1867

Leu Ile Pro Leu Leu Leu Gln Leu Thr Ser Arg Leu
1 5 10

<210> SEQ ID NO 1868
<211> LENGTH: 12
<212> TYPE: PRT
<213> ORGANISM: Homo sapiens

<400> SEQUENCE: 1868

Leu Asp Val Gly Leu Leu Ala Asn Leu Ser Ala Leu
1 5 10

<210> SEQ ID NO 1869
<211> LENGTH: 12
<212> TYPE: PRT
<213> ORGANISM: Homo sapiens

<400> SEQUENCE: 1869

Leu Gln Asp Glu Leu Leu Glu Val Val Ser Glu Leu
1 5 10

<210> SEQ ID NO 1870
<211> LENGTH: 12
<212> TYPE: PRT
<213> ORGANISM: Homo sapiens

<400> SEQUENCE: 1870

Leu Ala Ile Val Leu Leu Val Thr Ile Ser Leu Leu
1 5 10

<210> SEQ ID NO 1871
<211> LENGTH: 12
<212> TYPE: PRT
<213> ORGANISM: Homo sapiens

<400> SEQUENCE: 1871

Leu Cys Gly Ala Leu Leu Cys Ala Pro Ser Leu Leu
1 5 10

<210> SEQ ID NO 1872
<211> LENGTH: 12
<212> TYPE: PRT
<213> ORGANISM: Homo sapiens

<400> SEQUENCE: 1872

Leu Val Ile Val Leu Leu Gly Phe Lys Ser Phe Leu
1 5 10

<210> SEQ ID NO 1873
<211> LENGTH: 12
<212> TYPE: PRT
<213> ORGANISM: Homo sapiens

<400> SEQUENCE: 1873

Leu Gly Ala Ser Leu Leu Ala Ala Ser Ser Ser Leu
1 5 10

<210> SEQ ID NO 1874
<211> LENGTH: 12
<212> TYPE: PRT
<213> ORGANISM: Homo sapiens

<400> SEQUENCE: 1874

Leu Val Ala Gly Leu Leu Leu Trp Ala Ser Leu Leu
1 5 10

<210> SEQ ID NO 1875
<211> LENGTH: 12
<212> TYPE: PRT
<213> ORGANISM: Homo sapiens

<400> SEQUENCE: 1875

Leu Asn Gly Ile Leu Leu Gln Leu Ile Ser Cys Leu
1 5 10

<210> SEQ ID NO 1876
<211> LENGTH: 12
<212> TYPE: PRT
<213> ORGANISM: Homo sapiens

<400> SEQUENCE: 1876

Leu Leu Leu Leu Leu Leu Ser Ile His Ser Ala Leu
1 5 10

<210> SEQ ID NO 1877
<211> LENGTH: 12
<212> TYPE: PRT
<213> ORGANISM: Homo sapiens

<400> SEQUENCE: 1877

Leu Leu Arg Ser Leu Leu Gly Met Leu Ser Asp Leu
1 5 10

<210> SEQ ID NO 1878
<211> LENGTH: 12
<212> TYPE: PRT
<213> ORGANISM: Homo sapiens

<400> SEQUENCE: 1878

Leu Leu Arg Ser Leu Leu Ser Met Leu Ser Asp Leu
1 5 10

<210> SEQ ID NO 1879
<211> LENGTH: 12
<212> TYPE: PRT
<213> ORGANISM: Homo sapiens

<400> SEQUENCE: 1879

Leu His Ile Ser Leu Leu Leu Ile Glu Ser Arg Leu
1 5 10

<210> SEQ ID NO 1880
<211> LENGTH: 12
<212> TYPE: PRT
<213> ORGANISM: Homo sapiens

<400> SEQUENCE: 1880

Leu Leu Val Leu Leu Leu Val Ala Leu Ser Ala Leu
1 5 10

<210> SEQ ID NO 1881
<211> LENGTH: 12
<212> TYPE: PRT
<213> ORGANISM: Homo sapiens

<400> SEQUENCE: 1881

Leu Ile Pro Leu Leu Leu Gln Leu Thr Ser Arg Leu
1 5 10

<210> SEQ ID NO 1882
<211> LENGTH: 12
<212> TYPE: PRT
<213> ORGANISM: Homo sapiens

<400> SEQUENCE: 1882

Leu Ile Leu Asn Leu Leu Phe Leu Leu Ser Trp Leu
1 5 10

<210> SEQ ID NO 1883
<211> LENGTH: 12
<212> TYPE: PRT
<213> ORGANISM: Homo sapiens

<400> SEQUENCE: 1883

Leu Ala Cys Asp Leu Leu Pro Cys Asn Ser Asp Leu
1 5 10

<210> SEQ ID NO 1884
<211> LENGTH: 12
<212> TYPE: PRT
<213> ORGANISM: Homo sapiens

<400> SEQUENCE: 1884

Leu Ala Thr Asp Leu Leu Ser Thr Trp Ser Val Leu
1 5 10

<210> SEQ ID NO 1885
<211> LENGTH: 12
<212> TYPE: PRT
<213> ORGANISM: Homo sapiens

<400> SEQUENCE: 1885

Leu Leu Tyr Glu Leu Leu Gln Tyr Glu Ser Ser Leu
1 5 10

<210> SEQ ID NO 1886
<211> LENGTH: 12
<212> TYPE: PRT
<213> ORGANISM: Homo sapiens

<400> SEQUENCE: 1886

Leu Asn Arg Ala Leu Leu Met Thr Phe Ser Leu Leu
1 5 10

<210> SEQ ID NO 1887
<211> LENGTH: 12
<212> TYPE: PRT
<213> ORGANISM: Homo sapiens

<400> SEQUENCE: 1887

Leu Ile Pro Leu Leu Leu Gln Leu Thr Ser Arg Leu
1 5 10

<210> SEQ ID NO 1888
<211> LENGTH: 12
<212> TYPE: PRT
<213> ORGANISM: Homo sapiens

<400> SEQUENCE: 1888

Leu Pro Gln Leu Leu Leu Arg Met Ile Ser Ala Leu
1 5 10

<210> SEQ ID NO 1889
<211> LENGTH: 12
<212> TYPE: PRT
<213> ORGANISM: Homo sapiens

<400> SEQUENCE: 1889

Leu Ser Lys Asn Leu Leu Ala Gln Ile Ser Ala Leu
1 5 10

<210> SEQ ID NO 1890
<211> LENGTH: 12
<212> TYPE: PRT
<213> ORGANISM: Homo sapiens

<400> SEQUENCE: 1890

Leu Ser Gln Asp Leu Leu Glu Asp Asn Ser His Leu
1 5 10

<210> SEQ ID NO 1891
<211> LENGTH: 12
<212> TYPE: PRT
<213> ORGANISM: Homo sapiens

<400> SEQUENCE: 1891

Leu Arg Glu Ala Leu Leu Ser Ser Arg Ser His Leu
1 5 10

<210> SEQ ID NO 1892
<211> LENGTH: 12
<212> TYPE: PRT
<213> ORGANISM: Homo sapiens

<400> SEQUENCE: 1892

Leu Ile Pro Ala Leu Leu Glu Ser Leu Ser Val Leu
1 5 10

<210> SEQ ID NO 1893
<211> LENGTH: 12
<212> TYPE: PRT
<213> ORGANISM: Homo sapiens

<400> SEQUENCE: 1893

Leu Val Ile Val Leu Leu Gly Phe Arg Ser Leu Leu
1 5 10

<210> SEQ ID NO 1894
<211> LENGTH: 12
<212> TYPE: PRT
<213> ORGANISM: Homo sapiens

<400> SEQUENCE: 1894

Leu Trp Asp Asp Leu Leu Ser Val Leu Ser Ser Leu
1 5 10

<210> SEQ ID NO 1895
<211> LENGTH: 12
<212> TYPE: PRT
<213> ORGANISM: Homo sapiens

<400> SEQUENCE: 1895

Leu Val Pro Trp Leu Leu Leu Gly Ala Ser Trp Leu
1 5 10

<210> SEQ ID NO 1896
<211> LENGTH: 12
<212> TYPE: PRT
<213> ORGANISM: Homo sapiens

<400> SEQUENCE: 1896

Leu Ala Val Leu Leu Leu Ser Leu Pro Ser Pro Leu
1 5 10

<210> SEQ ID NO 1897
<211> LENGTH: 12
<212> TYPE: PRT
<213> ORGANISM: Homo sapiens

<400> SEQUENCE: 1897

Leu His Asn Ser Leu Leu Gln Arg Lys Ser Lys Leu
1 5 10

<210> SEQ ID NO 1898
<211> LENGTH: 12
<212> TYPE: PRT
<213> ORGANISM: Homo sapiens

<400> SEQUENCE: 1898

Leu Phe Pro Ile Leu Leu Cys Glu Ile Ser Thr Leu
1 5 10

<210> SEQ ID NO 1899
<211> LENGTH: 12
<212> TYPE: PRT
<213> ORGANISM: Homo sapiens

<400> SEQUENCE: 1899

Leu Phe Gly Thr Leu Leu Tyr Phe Asp Ser Val Leu
1 5 10

<210> SEQ ID NO 1900
<211> LENGTH: 12
<212> TYPE: PRT
<213> ORGANISM: Homo sapiens

<400> SEQUENCE: 1900

Leu Arg Val Glu Leu Leu Ser Ala Ser Ser Leu Leu
1 5 10

<210> SEQ ID NO 1901
<211> LENGTH: 12
<212> TYPE: PRT
<213> ORGANISM: Homo sapiens

<400> SEQUENCE: 1901

Leu Arg Ile Ala Leu Leu Tyr Ser His Ser Glu Leu
1 5 10

<210> SEQ ID NO 1902
<211> LENGTH: 12
<212> TYPE: PRT
<213> ORGANISM: Homo sapiens

<400> SEQUENCE: 1902

Leu Gln Glu Gly Leu Leu Gln Leu Asp Ser Ile Leu
1 5 10

<210> SEQ ID NO 1903
<211> LENGTH: 12

<212> TYPE: PRT
<213> ORGANISM: Homo sapiens

<400> SEQUENCE: 1903

Leu Val Ile Val Leu Leu Gly Phe Arg Ser Leu Leu
1 5 10

<210> SEQ ID NO 1904
<211> LENGTH: 12
<212> TYPE: PRT
<213> ORGANISM: Homo sapiens

<400> SEQUENCE: 1904

Leu Leu Asn Phe Leu Leu Pro Val Phe Ser Pro Leu
1 5 10

<210> SEQ ID NO 1905
<211> LENGTH: 12
<212> TYPE: PRT
<213> ORGANISM: Homo sapiens

<400> SEQUENCE: 1905

Leu Glu Lys Lys Leu Leu His His Leu Ser Asp Leu
1 5 10

<210> SEQ ID NO 1906
<211> LENGTH: 12
<212> TYPE: PRT
<213> ORGANISM: Homo sapiens

<400> SEQUENCE: 1906

Leu Leu Asn Ser Leu Leu Asp Ile Val Ser Ser Leu
1 5 10

<210> SEQ ID NO 1907
<211> LENGTH: 12
<212> TYPE: PRT
<213> ORGANISM: Homo sapiens

<400> SEQUENCE: 1907

Leu Leu Gln Ser Leu Leu Leu Ser Leu Ser Glu Leu
1 5 10

<210> SEQ ID NO 1908
<211> LENGTH: 12
<212> TYPE: PRT
<213> ORGANISM: Homo sapiens

<400> SEQUENCE: 1908

Leu Phe Phe Pro Leu Leu Pro Gln Tyr Ser Lys Leu
1 5 10

<210> SEQ ID NO 1909
<211> LENGTH: 12
<212> TYPE: PRT
<213> ORGANISM: Homo sapiens

<400> SEQUENCE: 1909

Leu Ala Trp Ser Leu Leu Leu Leu Ser Ser Ala Leu
1 5 10

<210> SEQ ID NO 1910
<211> LENGTH: 12
<212> TYPE: PRT
<213> ORGANISM: Homo sapiens

<400> SEQUENCE: 1910

Leu Glu Ser Asp Leu Leu Ile Glu Glu Ser Val Leu
1 5 10

<210> SEQ ID NO 1911
<211> LENGTH: 12
<212> TYPE: PRT
<213> ORGANISM: Homo sapiens

<400> SEQUENCE: 1911

Leu Arg Leu Leu Leu Leu Glu Ser Val Ser Gly Leu
1 5 10

<210> SEQ ID NO 1912
<211> LENGTH: 12
<212> TYPE: PRT
<213> ORGANISM: Homo sapiens

<400> SEQUENCE: 1912

Leu Phe Thr Leu Leu Leu Gln His Arg Ser Gln Leu
1 5 10

<210> SEQ ID NO 1913
<211> LENGTH: 12
<212> TYPE: PRT
<213> ORGANISM: Homo sapiens

<400> SEQUENCE: 1913

Leu Phe Glu Asp Leu Leu Arg Gln Met Ser Asp Leu
1 5 10

<210> SEQ ID NO 1914
<211> LENGTH: 12
<212> TYPE: PRT
<213> ORGANISM: Homo sapiens

<400> SEQUENCE: 1914

Leu Ala Gly Ser Leu Leu Lys Glu Leu Ser Pro Leu
1 5 10

<210> SEQ ID NO 1915
<211> LENGTH: 12
<212> TYPE: PRT
<213> ORGANISM: Homo sapiens

<400> SEQUENCE: 1915

Leu Leu Pro Cys Leu Leu Gly Val Gly Ser Trp Leu
1 5 10

<210> SEQ ID NO 1916
<211> LENGTH: 12
<212> TYPE: PRT
<213> ORGANISM: Homo sapiens

<400> SEQUENCE: 1916

Leu Ser Lys Ser Leu Leu Leu Val Pro Ser Ala Leu
1 5 10

<210> SEQ ID NO 1917
<211> LENGTH: 12
<212> TYPE: PRT
<213> ORGANISM: Homo sapiens

<400> SEQUENCE: 1917

-continued

Leu Thr Gln Pro Leu Leu Gly Glu Gln Ser Leu Leu
1 5 10

<210> SEQ ID NO 1918
<211> LENGTH: 12
<212> TYPE: PRT
<213> ORGANISM: Homo sapiens

<400> SEQUENCE: 1918

Leu Cys Gln His Leu Leu Ser Gly Gly Ser Gly Leu
1 5 10

<210> SEQ ID NO 1919
<211> LENGTH: 12
<212> TYPE: PRT
<213> ORGANISM: Homo sapiens

<400> SEQUENCE: 1919

Leu Pro Glu Phe Leu Leu Leu Gly Phe Ser Asp Leu
1 5 10

<210> SEQ ID NO 1920
<211> LENGTH: 12
<212> TYPE: PRT
<213> ORGANISM: Homo sapiens

<400> SEQUENCE: 1920

Leu Leu Gly Ala Leu Leu Ala Val Gly Ser Gln Leu
1 5 10

<210> SEQ ID NO 1921
<211> LENGTH: 12
<212> TYPE: PRT
<213> ORGANISM: Homo sapiens

<400> SEQUENCE: 1921

Leu Arg Ile Gln Leu Leu His Lys Leu Ser Phe Leu
1 5 10

<210> SEQ ID NO 1922
<211> LENGTH: 12
<212> TYPE: PRT
<213> ORGANISM: Homo sapiens

<400> SEQUENCE: 1922

Leu Glu Gly Gln Leu Leu Glu Thr Ile Ser Gln Leu
1 5 10

<210> SEQ ID NO 1923
<211> LENGTH: 12
<212> TYPE: PRT
<213> ORGANISM: Homo sapiens

<400> SEQUENCE: 1923

Leu Val Phe Leu Leu Leu Phe Leu Gln Ser Phe Leu
1 5 10

<210> SEQ ID NO 1924
<211> LENGTH: 12
<212> TYPE: PRT
<213> ORGANISM: Homo sapiens

<400> SEQUENCE: 1924

Leu Leu Ala His Leu Leu Gln Ser Lys Ser Glu Leu 1 5 10

<210> SEQ ID NO 1925
<211> LENGTH: 12
<212> TYPE: PRT
<213> ORGANISM: Homo sapiens

<400> SEQUENCE: 1925

Leu Glu Glu Gln Leu Leu Gln Glu Leu Ser Ser Leu
1 5 10

<210> SEQ ID NO 1926
<211> LENGTH: 12
<212> TYPE: PRT
<213> ORGANISM: Homo sapiens

<400> SEQUENCE: 1926

Leu Gly Met Ile Leu Leu Ile Ala Val Ser Pro Leu
1 5 10

<210> SEQ ID NO 1927
<211> LENGTH: 12
<212> TYPE: PRT
<213> ORGANISM: Homo sapiens

<400> SEQUENCE: 1927

Leu Phe Ala Leu Leu Leu Met Ser Ile Ser Cys Leu
1 5 10

<210> SEQ ID NO 1928
<211> LENGTH: 12
<212> TYPE: PRT
<213> ORGANISM: Homo sapiens

<400> SEQUENCE: 1928

Leu Arg Ile Leu Leu Leu Met Lys Pro Ser Val Leu
1 5 10

<210> SEQ ID NO 1929
<211> LENGTH: 12
<212> TYPE: PRT
<213> ORGANISM: Homo sapiens

<400> SEQUENCE: 1929

Leu Pro Val Leu Leu Leu Gly Arg Ser Ser Glu Leu
1 5 10

<210> SEQ ID NO 1930
<211> LENGTH: 12
<212> TYPE: PRT
<213> ORGANISM: Homo sapiens

<400> SEQUENCE: 1930

Leu Leu Leu Val Leu Leu Gly Gly Phe Ser Leu Leu
1 5 10

<210> SEQ ID NO 1931
<211> LENGTH: 12
<212> TYPE: PRT
<213> ORGANISM: Homo sapiens

<400> SEQUENCE: 1931

Leu Gln Thr Ile Leu Leu Cys Cys Pro Ser Ala Leu
1 5 10

<210> SEQ ID NO 1932
<211> LENGTH: 12
<212> TYPE: PRT
<213> ORGANISM: Homo sapiens

<400> SEQUENCE: 1932

Leu Gly Ala Ser Leu Leu Gly Asp Leu Ser Ser Leu
1 5 10

<210> SEQ ID NO 1933
<211> LENGTH: 12
<212> TYPE: PRT
<213> ORGANISM: Homo sapiens

<400> SEQUENCE: 1933

Leu Thr Phe Leu Leu Leu Val Leu Gly Ser Leu Leu
1 5 10

<210> SEQ ID NO 1934
<211> LENGTH: 12
<212> TYPE: PRT
<213> ORGANISM: Homo sapiens

<400> SEQUENCE: 1934

Leu Ala Lys Leu Leu Leu Thr Cys Cys Ser Ala Leu
1 5 10

<210> SEQ ID NO 1935
<211> LENGTH: 12
<212> TYPE: PRT
<213> ORGANISM: Homo sapiens

<400> SEQUENCE: 1935

Leu Met Asn Arg Leu Leu Arg Thr Val Ser Met Leu
1 5 10

<210> SEQ ID NO 1936
<211> LENGTH: 12
<212> TYPE: PRT
<213> ORGANISM: Homo sapiens

<400> SEQUENCE: 1936

Leu Leu Asp Lys Leu Leu Glu Thr Pro Ser Thr Leu
1 5 10

<210> SEQ ID NO 1937
<211> LENGTH: 12
<212> TYPE: PRT
<213> ORGANISM: Homo sapiens

<400> SEQUENCE: 1937

Leu Lys Gly Arg Leu Leu Leu Ala Glu Ser Gly Leu
1 5 10

<210> SEQ ID NO 1938
<211> LENGTH: 12
<212> TYPE: PRT
<213> ORGANISM: Homo sapiens

<400> SEQUENCE: 1938

Leu Val Val Ala Leu Leu Val Gly Leu Ser Trp Leu
1 5 10

<210> SEQ ID NO 1939

<211> LENGTH: 12
<212> TYPE: PRT
<213> ORGANISM: Homo sapiens

<400> SEQUENCE: 1939

Leu Ser Ser Asp Leu Leu Phe Ile Ile Ser Glu Leu
1 5 10

<210> SEQ ID NO 1940
<211> LENGTH: 12
<212> TYPE: PRT
<213> ORGANISM: Homo sapiens

<400> SEQUENCE: 1940

Leu Pro Arg Ala Leu Leu Ser Ser Leu Ser Gly Leu
1 5 10

<210> SEQ ID NO 1941
<211> LENGTH: 12
<212> TYPE: PRT
<213> ORGANISM: Homo sapiens

<400> SEQUENCE: 1941

Leu Ile Pro Gly Leu Leu Leu Trp Gln Ser Trp Leu
1 5 10

<210> SEQ ID NO 1942
<211> LENGTH: 12
<212> TYPE: PRT
<213> ORGANISM: Homo sapiens

<400> SEQUENCE: 1942

Leu Cys Leu Met Leu Leu Leu Ala Gly Ser Cys Leu
1 5 10

<210> SEQ ID NO 1943
<211> LENGTH: 12
<212> TYPE: PRT
<213> ORGANISM: Homo sapiens

<400> SEQUENCE: 1943

Leu Leu Phe Asp Leu Leu Ala Ser Ser Ser Ala Leu
1 5 10

<210> SEQ ID NO 1944
<211> LENGTH: 12
<212> TYPE: PRT
<213> ORGANISM: Homo sapiens

<400> SEQUENCE: 1944

Leu Asp Lys Lys Leu Leu His Met Glu Ser Gln Leu
1 5 10

<210> SEQ ID NO 1945
<211> LENGTH: 12
<212> TYPE: PRT
<213> ORGANISM: Homo sapiens

<400> SEQUENCE: 1945

Leu Gly Lys Phe Leu Leu Lys Val Asp Ser Lys Leu
1 5 10

<210> SEQ ID NO 1946
<211> LENGTH: 12
<212> TYPE: PRT

<213> ORGANISM: Homo sapiens

<400> SEQUENCE: 1946

Leu Leu Gln Arg Leu Leu Lys Ser Asn Ser His Leu
1 5 10

<210> SEQ ID NO 1947
<211> LENGTH: 12
<212> TYPE: PRT
<213> ORGANISM: Homo sapiens

<400> SEQUENCE: 1947

Leu Pro Gln Thr Leu Leu Ser His Pro Ser Tyr Leu
1 5 10

<210> SEQ ID NO 1948
<211> LENGTH: 12
<212> TYPE: PRT
<213> ORGANISM: Homo sapiens

<400> SEQUENCE: 1948

Leu Trp Gly Gly Leu Leu Arg Leu Gly Ser Leu Leu
1 5 10

<210> SEQ ID NO 1949
<211> LENGTH: 12
<212> TYPE: PRT
<213> ORGANISM: Homo sapiens

<400> SEQUENCE: 1949

Leu Leu Lys Ala Leu Leu Asp Asn Met Ser Phe Leu
1 5 10

<210> SEQ ID NO 1950
<211> LENGTH: 12
<212> TYPE: PRT
<213> ORGANISM: Homo sapiens

<400> SEQUENCE: 1950

Leu Gly Leu Asp Leu Leu Leu Asn Cys Ser Leu Leu
1 5 10

<210> SEQ ID NO 1951
<211> LENGTH: 12
<212> TYPE: PRT
<213> ORGANISM: Homo sapiens

<400> SEQUENCE: 1951

Leu Gly Ala Leu Leu Leu Leu Ala Leu Ser Ala Leu
1 5 10

<210> SEQ ID NO 1952
<211> LENGTH: 12
<212> TYPE: PRT
<213> ORGANISM: Homo sapiens

<400> SEQUENCE: 1952

Leu Ser Lys Val Leu Leu Ser Ile Cys Ser Leu Leu
1 5 10

<210> SEQ ID NO 1953
<211> LENGTH: 12
<212> TYPE: PRT
<213> ORGANISM: Homo sapiens

<400> SEQUENCE: 1953

Leu Arg Ile Asp Leu Leu Gln Ala Phe Ser Gln Leu
1 5 10

<210> SEQ ID NO 1954
<211> LENGTH: 12
<212> TYPE: PRT
<213> ORGANISM: Homo sapiens

<400> SEQUENCE: 1954

Leu Thr Asn Phe Leu Leu Asn Gly Arg Ser Val Leu
1 5 10

<210> SEQ ID NO 1955
<211> LENGTH: 12
<212> TYPE: PRT
<213> ORGANISM: Homo sapiens

<400> SEQUENCE: 1955

Leu Pro Thr Gln Leu Leu Phe Leu Leu Ser Val Leu
1 5 10

<210> SEQ ID NO 1956
<211> LENGTH: 12
<212> TYPE: PRT
<213> ORGANISM: Homo sapiens

<400> SEQUENCE: 1956

Leu Arg Gln Leu Leu Leu Glu Ser Gln Ser Gln Leu
1 5 10

<210> SEQ ID NO 1957
<211> LENGTH: 12
<212> TYPE: PRT
<213> ORGANISM: Homo sapiens

<400> SEQUENCE: 1957

Leu Leu Asn Ala Leu Leu Val Glu Leu Ser Leu Leu
1 5 10

<210> SEQ ID NO 1958
<211> LENGTH: 12
<212> TYPE: PRT
<213> ORGANISM: Homo sapiens

<400> SEQUENCE: 1958

Leu Pro Leu Thr Leu Leu Val Cys Cys Ser Ala Leu
1 5 10

<210> SEQ ID NO 1959
<211> LENGTH: 12
<212> TYPE: PRT
<213> ORGANISM: Homo sapiens

<400> SEQUENCE: 1959

Leu Arg Glu Pro Leu Leu Arg Arg Leu Ser Glu Leu
1 5 10

<210> SEQ ID NO 1960
<211> LENGTH: 12
<212> TYPE: PRT
<213> ORGANISM: Homo sapiens

<400> SEQUENCE: 1960

Leu Val Met Lys Leu Leu Ser Gly Gly Ser Met Leu
1 5 10

<210> SEQ ID NO 1961
<211> LENGTH: 12
<212> TYPE: PRT
<213> ORGANISM: Homo sapiens

<400> SEQUENCE: 1961

Leu Leu Leu Leu Leu Leu Val Gly Ala Ser Leu Leu
1 5 10

<210> SEQ ID NO 1962
<211> LENGTH: 12
<212> TYPE: PRT
<213> ORGANISM: Homo sapiens

<400> SEQUENCE: 1962

Leu Gly His Met Leu Leu Gly Ile Ser Ser Thr Leu
1 5 10

<210> SEQ ID NO 1963
<211> LENGTH: 12
<212> TYPE: PRT
<213> ORGANISM: Homo sapiens

<400> SEQUENCE: 1963

Leu Cys Gly Ala Leu Leu Phe Phe Ser Ser Leu Leu
1 5 10

<210> SEQ ID NO 1964
<211> LENGTH: 12
<212> TYPE: PRT
<213> ORGANISM: Homo sapiens

<400> SEQUENCE: 1964

Leu Gly Ala Ser Leu Leu Thr Gln Ala Ser Thr Leu
1 5 10

<210> SEQ ID NO 1965
<211> LENGTH: 12
<212> TYPE: PRT
<213> ORGANISM: Homo sapiens

<400> SEQUENCE: 1965

Leu Thr Gly Arg Leu Leu Asp Pro Ser Ser Pro Leu
1 5 10

<210> SEQ ID NO 1966
<211> LENGTH: 12
<212> TYPE: PRT
<213> ORGANISM: Homo sapiens

<400> SEQUENCE: 1966

Leu Ser Gly Lys Leu Leu Lys Gly Ala Ser Lys Leu
1 5 10

<210> SEQ ID NO 1967
<211> LENGTH: 12
<212> TYPE: PRT
<213> ORGANISM: Homo sapiens

<400> SEQUENCE: 1967

Leu Leu Thr Thr Leu Leu Gly Thr Ala Ser Pro Leu
1 5 10

<210> SEQ ID NO 1968
<211> LENGTH: 12
<212> TYPE: PRT
<213> ORGANISM: Homo sapiens

<400> SEQUENCE: 1968

Leu Pro Ser Ala Leu Leu Phe Ala Ala Ser Ile Leu
1 5 10

<210> SEQ ID NO 1969
<211> LENGTH: 12
<212> TYPE: PRT
<213> ORGANISM: Homo sapiens

<400> SEQUENCE: 1969

Leu Pro Phe Leu Leu Leu Gly Thr Val Ser Ala Leu
1 5 10

<210> SEQ ID NO 1970
<211> LENGTH: 12
<212> TYPE: PRT
<213> ORGANISM: Homo sapiens

<400> SEQUENCE: 1970

Leu Asn Gly Ile Leu Leu Gln Leu Ile Ser Cys Leu
1 5 10

<210> SEQ ID NO 1971
<211> LENGTH: 12
<212> TYPE: PRT
<213> ORGANISM: Homo sapiens

<400> SEQUENCE: 1971

Leu Gln Asn Ala Leu Leu Leu Ser Asp Ser Ser Leu
1 5 10

<210> SEQ ID NO 1972
<211> LENGTH: 12
<212> TYPE: PRT
<213> ORGANISM: Homo sapiens

<400> SEQUENCE: 1972

Leu Ile Val Ala Leu Leu Phe Ile Leu Ser Trp Leu
1 5 10

<210> SEQ ID NO 1973
<211> LENGTH: 8
<212> TYPE: PRT
<213> ORGANISM: Homo sapiens

<400> SEQUENCE: 1973

Leu Gly Leu Glu Glu Arg Pro Glu
1 5

<210> SEQ ID NO 1974
<211> LENGTH: 8
<212> TYPE: PRT
<213> ORGANISM: Homo sapiens

<400> SEQUENCE: 1974

Leu Cys Pro Glu Glu Glu Pro Asp
1 5

<210> SEQ ID NO 1975
<211> LENGTH: 8
<212> TYPE: PRT
<213> ORGANISM: Homo sapiens

<400> SEQUENCE: 1975

Leu Lys Ser Glu Glu Ile Pro Lys
1 5

<210> SEQ ID NO 1976
<211> LENGTH: 8
<212> TYPE: PRT
<213> ORGANISM: Homo sapiens

<400> SEQUENCE: 1976

Leu Asp Glu Glu Glu Thr Pro Tyr
1 5

<210> SEQ ID NO 1977
<211> LENGTH: 8
<212> TYPE: PRT
<213> ORGANISM: Homo sapiens

<400> SEQUENCE: 1977

Leu Gly Pro Glu Glu Arg Pro Pro
1 5

<210> SEQ ID NO 1978
<211> LENGTH: 8
<212> TYPE: PRT
<213> ORGANISM: Homo sapiens

<400> SEQUENCE: 1978

Leu Ser Gln Glu Glu Asn Pro Arg
1 5

<210> SEQ ID NO 1979
<211> LENGTH: 8
<212> TYPE: PRT
<213> ORGANISM: Homo sapiens

<400> SEQUENCE: 1979

Leu Gly Asn Glu Glu Gly Pro Glu
1 5

<210> SEQ ID NO 1980
<211> LENGTH: 8
<212> TYPE: PRT
<213> ORGANISM: Homo sapiens

<400> SEQUENCE: 1980

Leu Ser Ser Glu Glu Pro Pro Thr
1 5

<210> SEQ ID NO 1981
<211> LENGTH: 8
<212> TYPE: PRT
<213> ORGANISM: Homo sapiens

<400> SEQUENCE: 1981

Leu Gln Leu Glu Glu Ala Pro Glu
1 5

<210> SEQ ID NO 1982
<211> LENGTH: 8

<212> TYPE: PRT
<213> ORGANISM: Homo sapiens

<400> SEQUENCE: 1982

Leu Phe Arg Glu Glu Leu Pro Ala
1 5

<210> SEQ ID NO 1983
<211> LENGTH: 8
<212> TYPE: PRT
<213> ORGANISM: Homo sapiens

<400> SEQUENCE: 1983

Leu Gln Leu Glu Glu Leu Pro Arg
1 5

<210> SEQ ID NO 1984
<211> LENGTH: 8
<212> TYPE: PRT
<213> ORGANISM: Homo sapiens

<400> SEQUENCE: 1984

Leu Lys Glu Glu Glu Glu Pro Met
1 5

<210> SEQ ID NO 1985
<211> LENGTH: 8
<212> TYPE: PRT
<213> ORGANISM: Homo sapiens

<400> SEQUENCE: 1985

Leu Pro Pro Glu Glu Pro Pro Asn
1 5

<210> SEQ ID NO 1986
<211> LENGTH: 8
<212> TYPE: PRT
<213> ORGANISM: Homo sapiens

<400> SEQUENCE: 1986

Leu Tyr Glu Glu Glu Thr Pro Lys
1 5

<210> SEQ ID NO 1987
<211> LENGTH: 8
<212> TYPE: PRT
<213> ORGANISM: Homo sapiens

<400> SEQUENCE: 1987

Leu Glu Ala Glu Glu Lys Pro Leu
1 5

<210> SEQ ID NO 1988
<211> LENGTH: 8
<212> TYPE: PRT
<213> ORGANISM: Homo sapiens

<400> SEQUENCE: 1988

Leu Asn Met Glu Glu Pro Pro Val
1 5

<210> SEQ ID NO 1989
<211> LENGTH: 8
<212> TYPE: PRT
<213> ORGANISM: Homo sapiens

<400> SEQUENCE: 1989

Leu Glu Asp Glu Glu Pro Pro Ala
1               5

<210> SEQ ID NO 1990
<211> LENGTH: 8
<212> TYPE: PRT
<213> ORGANISM: Homo sapiens

<400> SEQUENCE: 1990

Leu Glu Arg Glu Glu Lys Pro Ser
1               5

<210> SEQ ID NO 1991
<211> LENGTH: 8
<212> TYPE: PRT
<213> ORGANISM: Homo sapiens

<400> SEQUENCE: 1991

Leu Glu Glu Glu Glu Glu Pro Ser
1               5

<210> SEQ ID NO 1992
<211> LENGTH: 8
<212> TYPE: PRT
<213> ORGANISM: Homo sapiens

<400> SEQUENCE: 1992

Leu Phe Ser Glu Glu Thr Pro Val
1               5

<210> SEQ ID NO 1993
<211> LENGTH: 8
<212> TYPE: PRT
<213> ORGANISM: Homo sapiens

<400> SEQUENCE: 1993

Leu Asp Asn Glu Glu Lys Pro Pro
1               5

<210> SEQ ID NO 1994
<211> LENGTH: 8
<212> TYPE: PRT
<213> ORGANISM: Homo sapiens

<400> SEQUENCE: 1994

Leu Gln Leu Glu Glu Asn Pro Trp
1               5

<210> SEQ ID NO 1995
<211> LENGTH: 8
<212> TYPE: PRT
<213> ORGANISM: Homo sapiens

<400> SEQUENCE: 1995

Leu Glu Ala Glu Glu Glu Pro Val
1               5

<210> SEQ ID NO 1996
<211> LENGTH: 8
<212> TYPE: PRT
<213> ORGANISM: Homo sapiens

<400> SEQUENCE: 1996

Leu Lys Asn Glu Glu Val Pro Val
1 5

<210> SEQ ID NO 1997
<211> LENGTH: 8
<212> TYPE: PRT
<213> ORGANISM: Homo sapiens

<400> SEQUENCE: 1997

Leu Gln Leu Glu Glu Asn Pro Trp
1 5

<210> SEQ ID NO 1998
<211> LENGTH: 8
<212> TYPE: PRT
<213> ORGANISM: Homo sapiens

<400> SEQUENCE: 1998

Leu Asn Gly Glu Glu Cys Pro Pro
1 5

<210> SEQ ID NO 1999
<211> LENGTH: 8
<212> TYPE: PRT
<213> ORGANISM: Homo sapiens

<400> SEQUENCE: 1999

Leu Ala Gly Glu Glu Ser Pro Gln
1 5

<210> SEQ ID NO 2000
<211> LENGTH: 8
<212> TYPE: PRT
<213> ORGANISM: Homo sapiens

<400> SEQUENCE: 2000

Leu Lys Ile Glu Glu Pro Pro Ser
1 5

<210> SEQ ID NO 2001
<211> LENGTH: 8
<212> TYPE: PRT
<213> ORGANISM: Homo sapiens

<400> SEQUENCE: 2001

Leu Glu Asp Glu Glu Glu Pro Lys
1 5

<210> SEQ ID NO 2002
<211> LENGTH: 8
<212> TYPE: PRT
<213> ORGANISM: Homo sapiens

<400> SEQUENCE: 2002

Leu His Cys Glu Glu Cys Pro Pro
1 5

<210> SEQ ID NO 2003
<211> LENGTH: 8
<212> TYPE: PRT
<213> ORGANISM: Homo sapiens

<400> SEQUENCE: 2003

Leu His Ser Glu Glu Val Pro Leu 1 5

<210> SEQ ID NO 2004
<211> LENGTH: 8
<212> TYPE: PRT
<213> ORGANISM: Homo sapiens

<400> SEQUENCE: 2004

Leu Gln Val Glu Glu Asp Pro Val
1 5

<210> SEQ ID NO 2005
<211> LENGTH: 8
<212> TYPE: PRT
<213> ORGANISM: Homo sapiens

<400> SEQUENCE: 2005

Leu Tyr Ala Glu Glu Lys Pro Cys
1 5

<210> SEQ ID NO 2006
<211> LENGTH: 8
<212> TYPE: PRT
<213> ORGANISM: Homo sapiens

<400> SEQUENCE: 2006

Leu Leu Asn Glu Glu Asn Pro Ser
1 5

<210> SEQ ID NO 2007
<211> LENGTH: 8
<212> TYPE: PRT
<213> ORGANISM: Homo sapiens

<400> SEQUENCE: 2007

Leu Lys Lys Glu Glu Cys Pro Ala
1 5

<210> SEQ ID NO 2008
<211> LENGTH: 8
<212> TYPE: PRT
<213> ORGANISM: Homo sapiens

<400> SEQUENCE: 2008

Leu Ser Glu Glu Glu Thr Pro Leu
1 5

<210> SEQ ID NO 2009
<211> LENGTH: 8
<212> TYPE: PRT
<213> ORGANISM: Homo sapiens

<400> SEQUENCE: 2009

Leu Pro Ser Glu Glu Ala Pro Thr
1 5

<210> SEQ ID NO 2010
<211> LENGTH: 8
<212> TYPE: PRT
<213> ORGANISM: Homo sapiens

<400> SEQUENCE: 2010

Leu Asp Pro Glu Glu Arg Pro Thr
1 5

<210> SEQ ID NO 2011
<211> LENGTH: 8
<212> TYPE: PRT
<213> ORGANISM: Homo sapiens

<400> SEQUENCE: 2011

Leu Val Val Glu Glu Ala Pro Pro
1 5

<210> SEQ ID NO 2012
<211> LENGTH: 8
<212> TYPE: PRT
<213> ORGANISM: Homo sapiens

<400> SEQUENCE: 2012

Leu Leu Val Glu Glu Leu Pro Leu
1 5

<210> SEQ ID NO 2013
<211> LENGTH: 8
<212> TYPE: PRT
<213> ORGANISM: Homo sapiens

<400> SEQUENCE: 2013

Leu Gln Val Glu Glu Glu Pro Val
1 5

<210> SEQ ID NO 2014
<211> LENGTH: 8
<212> TYPE: PRT
<213> ORGANISM: Homo sapiens

<400> SEQUENCE: 2014

Leu Lys Gly Glu Glu Glu Pro Leu
1 5

<210> SEQ ID NO 2015
<211> LENGTH: 8
<212> TYPE: PRT
<213> ORGANISM: Homo sapiens

<400> SEQUENCE: 2015

Leu Glu Val Glu Glu Cys Pro Ala
1 5

<210> SEQ ID NO 2016
<211> LENGTH: 8
<212> TYPE: PRT
<213> ORGANISM: Homo sapiens

<400> SEQUENCE: 2016

Leu Gly Thr Glu Glu Phe Pro Leu
1 5

<210> SEQ ID NO 2017
<211> LENGTH: 8
<212> TYPE: PRT
<213> ORGANISM: Homo sapiens

<400> SEQUENCE: 2017

Leu Pro Pro Glu Glu Pro Pro Thr
1 5

<210> SEQ ID NO 2018

<211> LENGTH: 8
<212> TYPE: PRT
<213> ORGANISM: Homo sapiens

<400> SEQUENCE: 2018

Leu Pro Pro Glu Glu Pro Pro Met
1 5

<210> SEQ ID NO 2019
<211> LENGTH: 8
<212> TYPE: PRT
<213> ORGANISM: Homo sapiens

<400> SEQUENCE: 2019

Leu Pro Pro Glu Glu Pro Pro Glu
1 5

<210> SEQ ID NO 2020
<211> LENGTH: 8
<212> TYPE: PRT
<213> ORGANISM: Homo sapiens

<400> SEQUENCE: 2020

Leu Pro Ser Glu Glu Gly Pro Gly
1 5

<210> SEQ ID NO 2021
<211> LENGTH: 8
<212> TYPE: PRT
<213> ORGANISM: Homo sapiens

<400> SEQUENCE: 2021

Leu Pro Arg Glu Glu Gly Pro Tyr
1 5

<210> SEQ ID NO 2022
<211> LENGTH: 8
<212> TYPE: PRT
<213> ORGANISM: Homo sapiens

<400> SEQUENCE: 2022

Leu Glu Pro Glu Glu Pro Pro Thr
1 5

<210> SEQ ID NO 2023
<211> LENGTH: 8
<212> TYPE: PRT
<213> ORGANISM: Homo sapiens

<400> SEQUENCE: 2023

Leu Arg Glu Glu Glu Arg Pro Leu
1 5

<210> SEQ ID NO 2024
<211> LENGTH: 8
<212> TYPE: PRT
<213> ORGANISM: Homo sapiens

<400> SEQUENCE: 2024

Leu Val Ser Glu Glu Ser Pro Ser
1 5

<210> SEQ ID NO 2025
<211> LENGTH: 8
<212> TYPE: PRT

<213> ORGANISM: Homo sapiens

<400> SEQUENCE: 2025

Leu Asp Pro Glu Glu Arg Pro Lys
1 5

<210> SEQ ID NO 2026
<211> LENGTH: 8
<212> TYPE: PRT
<213> ORGANISM: Homo sapiens

<400> SEQUENCE: 2026

Leu Val Glu Glu Glu Asp Pro Phe
1 5

<210> SEQ ID NO 2027
<211> LENGTH: 8
<212> TYPE: PRT
<213> ORGANISM: Homo sapiens

<400> SEQUENCE: 2027

Leu Asp Ser Glu Glu Arg Pro Glu
1 5

<210> SEQ ID NO 2028
<211> LENGTH: 8
<212> TYPE: PRT
<213> ORGANISM: Homo sapiens

<400> SEQUENCE: 2028

Leu Tyr Glu Glu Glu Ser Pro Ser
1 5

<210> SEQ ID NO 2029
<211> LENGTH: 8
<212> TYPE: PRT
<213> ORGANISM: Homo sapiens

<400> SEQUENCE: 2029

Leu Arg Phe Glu Glu Ala Pro Asp
1 5

<210> SEQ ID NO 2030
<211> LENGTH: 8
<212> TYPE: PRT
<213> ORGANISM: Homo sapiens

<400> SEQUENCE: 2030

Leu Thr Phe Glu Glu Val Pro Tyr
1 5

<210> SEQ ID NO 2031
<211> LENGTH: 8
<212> TYPE: PRT
<213> ORGANISM: Homo sapiens

<400> SEQUENCE: 2031

Leu Gly Ala Glu Glu Asn Pro Leu
1 5

<210> SEQ ID NO 2032
<211> LENGTH: 8
<212> TYPE: PRT
<213> ORGANISM: Homo sapiens

<400> SEQUENCE: 2032

Leu Thr Val Glu Glu Leu Pro Ala
1               5

<210> SEQ ID NO 2033
<211> LENGTH: 8
<212> TYPE: PRT
<213> ORGANISM: Homo sapiens

<400> SEQUENCE: 2033

Leu Phe Lys Glu Glu Asn Pro Tyr
1               5

<210> SEQ ID NO 2034
<211> LENGTH: 8
<212> TYPE: PRT
<213> ORGANISM: Homo sapiens

<400> SEQUENCE: 2034

Leu Leu Thr Glu Glu Ser Pro Ser
1               5

<210> SEQ ID NO 2035
<211> LENGTH: 8
<212> TYPE: PRT
<213> ORGANISM: Homo sapiens

<400> SEQUENCE: 2035

Leu Asp Arg Glu Glu Lys Pro Val
1               5

<210> SEQ ID NO 2036
<211> LENGTH: 8
<212> TYPE: PRT
<213> ORGANISM: Homo sapiens

<400> SEQUENCE: 2036

Leu Asp Arg Glu Glu Lys Pro Phe
1               5

<210> SEQ ID NO 2037
<211> LENGTH: 8
<212> TYPE: PRT
<213> ORGANISM: Homo sapiens

<400> SEQUENCE: 2037

Leu Leu Gln Glu Glu Met Pro Arg
1               5

<210> SEQ ID NO 2038
<211> LENGTH: 8
<212> TYPE: PRT
<213> ORGANISM: Homo sapiens

<400> SEQUENCE: 2038

Leu Leu Pro Glu Glu Asp Pro Glu
1               5

<210> SEQ ID NO 2039
<211> LENGTH: 8
<212> TYPE: PRT
<213> ORGANISM: Homo sapiens

<400> SEQUENCE: 2039

Leu Arg Lys Glu Glu Asp Pro Lys
1 5

<210> SEQ ID NO 2040
<211> LENGTH: 8
<212> TYPE: PRT
<213> ORGANISM: Homo sapiens

<400> SEQUENCE: 2040

Leu Val Glu Glu Glu Arg Pro Ser
1 5

<210> SEQ ID NO 2041
<211> LENGTH: 8
<212> TYPE: PRT
<213> ORGANISM: Homo sapiens

<400> SEQUENCE: 2041

Leu Pro Ala Glu Glu Pro Pro Ala
1 5

<210> SEQ ID NO 2042
<211> LENGTH: 8
<212> TYPE: PRT
<213> ORGANISM: Homo sapiens

<400> SEQUENCE: 2042

Leu Tyr Pro Glu Glu Ile Pro Ser
1 5

<210> SEQ ID NO 2043
<211> LENGTH: 8
<212> TYPE: PRT
<213> ORGANISM: Homo sapiens

<400> SEQUENCE: 2043

Leu Arg His Glu Glu Gln Pro Ala
1 5

<210> SEQ ID NO 2044
<211> LENGTH: 8
<212> TYPE: PRT
<213> ORGANISM: Homo sapiens

<400> SEQUENCE: 2044

Leu Met Lys Glu Glu Ser Pro Val
1 5

<210> SEQ ID NO 2045
<211> LENGTH: 8
<212> TYPE: PRT
<213> ORGANISM: Homo sapiens

<400> SEQUENCE: 2045

Leu Pro Thr Glu Glu Pro Pro Glu
1 5

<210> SEQ ID NO 2046
<211> LENGTH: 8
<212> TYPE: PRT
<213> ORGANISM: Homo sapiens

<400> SEQUENCE: 2046

Leu Thr Ala Glu Glu Thr Pro Leu
1 5

<210> SEQ ID NO 2047
<211> LENGTH: 8
<212> TYPE: PRT
<213> ORGANISM: Homo sapiens

<400> SEQUENCE: 2047

Leu Pro Gly Glu Glu Tyr Pro Leu
1               5

<210> SEQ ID NO 2048
<211> LENGTH: 8
<212> TYPE: PRT
<213> ORGANISM: Homo sapiens

<400> SEQUENCE: 2048

Leu Glu Gln Glu Glu Asn Pro Gly
1               5

<210> SEQ ID NO 2049
<211> LENGTH: 8
<212> TYPE: PRT
<213> ORGANISM: Homo sapiens

<400> SEQUENCE: 2049

Leu Glu Lys Glu Glu Leu Pro Arg
1               5

<210> SEQ ID NO 2050
<211> LENGTH: 8
<212> TYPE: PRT
<213> ORGANISM: Homo sapiens

<400> SEQUENCE: 2050

Leu Asp Arg Glu Glu Thr Pro Trp
1               5

<210> SEQ ID NO 2051
<211> LENGTH: 8
<212> TYPE: PRT
<213> ORGANISM: Homo sapiens

<400> SEQUENCE: 2051

Leu Met Ala Glu Glu Asn Pro Pro
1               5

<210> SEQ ID NO 2052
<211> LENGTH: 8
<212> TYPE: PRT
<213> ORGANISM: Homo sapiens

<400> SEQUENCE: 2052

Leu Asp Arg Glu Glu Thr Pro Phe
1               5

<210> SEQ ID NO 2053
<211> LENGTH: 8
<212> TYPE: PRT
<213> ORGANISM: Homo sapiens

<400> SEQUENCE: 2053

Leu Trp Ser Glu Glu Thr Pro Ala
1               5

<210> SEQ ID NO 2054
<211> LENGTH: 8
<212> TYPE: PRT
<213> ORGANISM: Homo sapiens

<400> SEQUENCE: 2054

Leu Pro His Glu Glu Glu Pro Ser
1               5

<210> SEQ ID NO 2055
<211> LENGTH: 8
<212> TYPE: PRT
<213> ORGANISM: Homo sapiens

<400> SEQUENCE: 2055

Leu Pro Glu Glu Glu Ala Pro Arg
1               5

<210> SEQ ID NO 2056
<211> LENGTH: 8
<212> TYPE: PRT
<213> ORGANISM: Homo sapiens

<400> SEQUENCE: 2056

Leu Lys Lys Glu Glu Lys Pro Leu
1               5

<210> SEQ ID NO 2057
<211> LENGTH: 8
<212> TYPE: PRT
<213> ORGANISM: Homo sapiens

<400> SEQUENCE: 2057

Leu Ser Lys Glu Glu Phe Pro Asp
1               5

<210> SEQ ID NO 2058
<211> LENGTH: 8
<212> TYPE: PRT
<213> ORGANISM: Homo sapiens

<400> SEQUENCE: 2058

Leu Val Glu Glu Glu Pro Pro Phe
1               5

<210> SEQ ID NO 2059
<211> LENGTH: 8
<212> TYPE: PRT
<213> ORGANISM: Homo sapiens

<400> SEQUENCE: 2059

Leu Ala Ala Glu Glu Asn Pro Ser
1               5

<210> SEQ ID NO 2060
<211> LENGTH: 8
<212> TYPE: PRT
<213> ORGANISM: Homo sapiens

<400> SEQUENCE: 2060

Leu Ser Pro Glu Glu Thr Pro Ala
1               5

<210> SEQ ID NO 2061
<211> LENGTH: 8

<212> TYPE: PRT
<213> ORGANISM: Homo sapiens

<400> SEQUENCE: 2061

Leu Thr Val Glu Glu Thr Pro Arg
1 5

<210> SEQ ID NO 2062
<211> LENGTH: 8
<212> TYPE: PRT
<213> ORGANISM: Homo sapiens

<400> SEQUENCE: 2062

Leu Ser Ala Glu Glu Ile Pro Glu
1 5

<210> SEQ ID NO 2063
<211> LENGTH: 8
<212> TYPE: PRT
<213> ORGANISM: Homo sapiens

<400> SEQUENCE: 2063

Leu Gly Val Glu Glu Glu Pro Phe
1 5

<210> SEQ ID NO 2064
<211> LENGTH: 8
<212> TYPE: PRT
<213> ORGANISM: Homo sapiens

<400> SEQUENCE: 2064

Leu Ala Ser Glu Glu Gln Pro Pro
1 5

<210> SEQ ID NO 2065
<211> LENGTH: 8
<212> TYPE: PRT
<213> ORGANISM: Homo sapiens

<400> SEQUENCE: 2065

Leu Ile Met Glu Glu Arg Pro Asn
1 5

<210> SEQ ID NO 2066
<211> LENGTH: 8
<212> TYPE: PRT
<213> ORGANISM: Homo sapiens

<400> SEQUENCE: 2066

Leu Asn Arg Glu Glu Ala Pro Thr
1 5

<210> SEQ ID NO 2067
<211> LENGTH: 8
<212> TYPE: PRT
<213> ORGANISM: Homo sapiens

<400> SEQUENCE: 2067

Leu Cys Thr Glu Glu Gly Pro Leu
1 5

<210> SEQ ID NO 2068
<211> LENGTH: 8
<212> TYPE: PRT
<213> ORGANISM: Homo sapiens

<400> SEQUENCE: 2068

Leu Arg Val Glu Glu Arg Pro Glu
1               5

<210> SEQ ID NO 2069
<211> LENGTH: 8
<212> TYPE: PRT
<213> ORGANISM: Homo sapiens

<400> SEQUENCE: 2069

Leu Tyr Ser Glu Glu Gln Pro Gln
1               5

<210> SEQ ID NO 2070
<211> LENGTH: 8
<212> TYPE: PRT
<213> ORGANISM: Homo sapiens

<400> SEQUENCE: 2070

Leu Pro Glu Glu Glu Thr Pro Glu
1               5

<210> SEQ ID NO 2071
<211> LENGTH: 8
<212> TYPE: PRT
<213> ORGANISM: Homo sapiens

<400> SEQUENCE: 2071

Leu Glu Gln Glu Glu Glu Pro Trp
1               5

<210> SEQ ID NO 2072
<211> LENGTH: 8
<212> TYPE: PRT
<213> ORGANISM: Homo sapiens

<400> SEQUENCE: 2072

Leu Leu His Glu Glu Ser Pro Leu
1               5

<210> SEQ ID NO 2073
<211> LENGTH: 8
<212> TYPE: PRT
<213> ORGANISM: Homo sapiens

<400> SEQUENCE: 2073

Leu Val Ile Glu Glu Cys Pro Leu
1               5

<210> SEQ ID NO 2074
<211> LENGTH: 8
<212> TYPE: PRT
<213> ORGANISM: Homo sapiens

<400> SEQUENCE: 2074

Leu Ile Gln Glu Glu Asp Pro Ser
1               5

<210> SEQ ID NO 2075
<211> LENGTH: 8
<212> TYPE: PRT
<213> ORGANISM: Homo sapiens

<400> SEQUENCE: 2075

Leu Arg Ala Glu Glu Pro Pro Thr
1 5

<210> SEQ ID NO 2076
<211> LENGTH: 8
<212> TYPE: PRT
<213> ORGANISM: Homo sapiens

<400> SEQUENCE: 2076

Leu Glu Ala Glu Glu Pro Pro Asp
1 5

<210> SEQ ID NO 2077
<211> LENGTH: 8
<212> TYPE: PRT
<213> ORGANISM: Homo sapiens

<400> SEQUENCE: 2077

Leu Asp Gln Glu Glu Ala Pro Lys
1 5

<210> SEQ ID NO 2078
<211> LENGTH: 8
<212> TYPE: PRT
<213> ORGANISM: Homo sapiens

<400> SEQUENCE: 2078

Leu Ser Ala Glu Glu Ser Pro Glu
1 5

<210> SEQ ID NO 2079
<211> LENGTH: 8
<212> TYPE: PRT
<213> ORGANISM: Homo sapiens

<400> SEQUENCE: 2079

Leu Glu Leu Glu Glu Ala Pro Glu
1 5

<210> SEQ ID NO 2080
<211> LENGTH: 8
<212> TYPE: PRT
<213> ORGANISM: Homo sapiens

<400> SEQUENCE: 2080

Leu Arg Cys Glu Glu Ala Pro Ser
1 5

<210> SEQ ID NO 2081
<211> LENGTH: 8
<212> TYPE: PRT
<213> ORGANISM: Homo sapiens

<400> SEQUENCE: 2081

Leu Leu Pro Glu Glu Ala Pro Arg
1 5

<210> SEQ ID NO 2082
<211> LENGTH: 8
<212> TYPE: PRT
<213> ORGANISM: Homo sapiens

<400> SEQUENCE: 2082

Leu Pro Ala Glu Glu Thr Pro Ile 1 5

<210> SEQ ID NO 2083
<211> LENGTH: 8
<212> TYPE: PRT
<213> ORGANISM: Homo sapiens

<400> SEQUENCE: 2083

Leu Leu Thr Glu Glu Phe Pro Ile
1 5

<210> SEQ ID NO 2084
<211> LENGTH: 8
<212> TYPE: PRT
<213> ORGANISM: Homo sapiens

<400> SEQUENCE: 2084

Leu Gln Gln Glu Glu Pro Pro Ile
1 5

<210> SEQ ID NO 2085
<211> LENGTH: 8
<212> TYPE: PRT
<213> ORGANISM: Homo sapiens

<400> SEQUENCE: 2085

Leu Leu Ala Glu Glu Tyr Pro Met
1 5

<210> SEQ ID NO 2086
<211> LENGTH: 8
<212> TYPE: PRT
<213> ORGANISM: Homo sapiens

<400> SEQUENCE: 2086

Leu Glu Gln Glu Glu Glu Pro Trp
1 5

<210> SEQ ID NO 2087
<211> LENGTH: 8
<212> TYPE: PRT
<213> ORGANISM: Homo sapiens

<400> SEQUENCE: 2087

Leu Ile Lys Glu Glu Gln Pro Pro
1 5

<210> SEQ ID NO 2088
<211> LENGTH: 8
<212> TYPE: PRT
<213> ORGANISM: Homo sapiens

<400> SEQUENCE: 2088

Leu Thr Gly Glu Glu Ile Pro Phe
1 5

<210> SEQ ID NO 2089
<211> LENGTH: 8
<212> TYPE: PRT
<213> ORGANISM: Homo sapiens

<400> SEQUENCE: 2089

Leu Glu Ser Glu Glu Thr Pro Asn
1 5

<210> SEQ ID NO 2090
<211> LENGTH: 8
<212> TYPE: PRT
<213> ORGANISM: Homo sapiens

<400> SEQUENCE: 2090

Leu Arg Thr Glu Glu Lys Pro Pro
1 5

<210> SEQ ID NO 2091
<211> LENGTH: 8
<212> TYPE: PRT
<213> ORGANISM: Homo sapiens

<400> SEQUENCE: 2091

Leu Lys Lys Glu Glu Arg Pro Thr
1 5

<210> SEQ ID NO 2092
<211> LENGTH: 8
<212> TYPE: PRT
<213> ORGANISM: Homo sapiens

<400> SEQUENCE: 2092

Leu Asp Asp Glu Glu Gln Pro Thr
1 5

<210> SEQ ID NO 2093
<211> LENGTH: 8
<212> TYPE: PRT
<213> ORGANISM: Homo sapiens

<400> SEQUENCE: 2093

Leu Gly Ala Glu Glu Thr Pro Pro
1 5

<210> SEQ ID NO 2094
<211> LENGTH: 8
<212> TYPE: PRT
<213> ORGANISM: Homo sapiens

<400> SEQUENCE: 2094

Leu Pro Ala Glu Glu Thr Pro Val
1 5

<210> SEQ ID NO 2095
<211> LENGTH: 8
<212> TYPE: PRT
<213> ORGANISM: Homo sapiens

<400> SEQUENCE: 2095

Leu Tyr Gln Glu Glu Asn Pro Ala
1 5

<210> SEQ ID NO 2096
<211> LENGTH: 8
<212> TYPE: PRT
<213> ORGANISM: Homo sapiens

<400> SEQUENCE: 2096

Leu Glu Asp Glu Glu Ile Pro Val
1 5

<210> SEQ ID NO 2097

<211> LENGTH: 8
<212> TYPE: PRT
<213> ORGANISM: Homo sapiens

<400> SEQUENCE: 2097

Leu Thr Arg Glu Glu Leu Pro Lys
1 5

<210> SEQ ID NO 2098
<211> LENGTH: 8
<212> TYPE: PRT
<213> ORGANISM: Homo sapiens

<400> SEQUENCE: 2098

Leu His Thr Glu Glu Ala Pro Ala
1 5

<210> SEQ ID NO 2099
<211> LENGTH: 8
<212> TYPE: PRT
<213> ORGANISM: Homo sapiens

<400> SEQUENCE: 2099

Leu Val Pro Glu Glu Leu Pro Pro
1 5

<210> SEQ ID NO 2100
<211> LENGTH: 8
<212> TYPE: PRT
<213> ORGANISM: Homo sapiens

<400> SEQUENCE: 2100

Leu Ile Leu Glu Glu Thr Pro Glu
1 5

<210> SEQ ID NO 2101
<211> LENGTH: 8
<212> TYPE: PRT
<213> ORGANISM: Homo sapiens

<400> SEQUENCE: 2101

Leu Asn Gln Glu Glu Leu Pro Pro
1 5

<210> SEQ ID NO 2102
<211> LENGTH: 8
<212> TYPE: PRT
<213> ORGANISM: Homo sapiens

<400> SEQUENCE: 2102

Leu Asp Glu Glu Glu Ser Pro Arg
1 5

<210> SEQ ID NO 2103
<211> LENGTH: 8
<212> TYPE: PRT
<213> ORGANISM: Homo sapiens

<400> SEQUENCE: 2103

Leu Pro Val Glu Glu Gln Pro Lys
1 5

<210> SEQ ID NO 2104
<211> LENGTH: 8
<212> TYPE: PRT

<213> ORGANISM: Homo sapiens

<400> SEQUENCE: 2104

Leu Val Ala Glu Glu Ser Pro Glu
1               5

<210> SEQ ID NO 2105
<211> LENGTH: 8
<212> TYPE: PRT
<213> ORGANISM: Homo sapiens

<400> SEQUENCE: 2105

Leu Gly Lys Glu Glu Gln Pro Gln
1               5

<210> SEQ ID NO 2106
<211> LENGTH: 8
<212> TYPE: PRT
<213> ORGANISM: Homo sapiens

<400> SEQUENCE: 2106

Leu Ser Pro Glu Glu Leu Pro Glu
1               5

<210> SEQ ID NO 2107
<211> LENGTH: 8
<212> TYPE: PRT
<213> ORGANISM: Homo sapiens

<400> SEQUENCE: 2107

Leu Pro Lys Glu Glu Asn Pro Arg
1               5

<210> SEQ ID NO 2108
<211> LENGTH: 8
<212> TYPE: PRT
<213> ORGANISM: Homo sapiens

<400> SEQUENCE: 2108

Leu Arg Lys Glu Glu Arg Pro Gly
1               5

<210> SEQ ID NO 2109
<211> LENGTH: 8
<212> TYPE: PRT
<213> ORGANISM: Homo sapiens

<400> SEQUENCE: 2109

Leu Thr Ser Glu Glu Glu Pro Gln
1               5

<210> SEQ ID NO 2110
<211> LENGTH: 8
<212> TYPE: PRT
<213> ORGANISM: Homo sapiens

<400> SEQUENCE: 2110

Leu Leu Gly Glu Glu Val Pro Arg
1               5

<210> SEQ ID NO 2111
<211> LENGTH: 8
<212> TYPE: PRT
<213> ORGANISM: Homo sapiens

<400> SEQUENCE: 2111

Leu Ser Ser Glu Glu Leu Pro Gln
1               5

<210> SEQ ID NO 2112
<211> LENGTH: 8
<212> TYPE: PRT
<213> ORGANISM: Homo sapiens

<400> SEQUENCE: 2112

Leu Ser Lys Glu Glu Pro Pro Gly
1               5

<210> SEQ ID NO 2113
<211> LENGTH: 8
<212> TYPE: PRT
<213> ORGANISM: Homo sapiens

<400> SEQUENCE: 2113

Leu Glu Gln Glu Glu Ala Pro Trp
1               5

<210> SEQ ID NO 2114
<211> LENGTH: 8
<212> TYPE: PRT
<213> ORGANISM: Homo sapiens

<400> SEQUENCE: 2114

Leu Arg Ala Glu Glu Asn Pro Met
1               5

<210> SEQ ID NO 2115
<211> LENGTH: 8
<212> TYPE: PRT
<213> ORGANISM: Homo sapiens

<400> SEQUENCE: 2115

Leu His Arg Glu Glu Gly Pro Ala
1               5

<210> SEQ ID NO 2116
<211> LENGTH: 8
<212> TYPE: PRT
<213> ORGANISM: Homo sapiens

<400> SEQUENCE: 2116

Leu Pro Gln Glu Glu Gln Pro Leu
1               5

<210> SEQ ID NO 2117
<211> LENGTH: 8
<212> TYPE: PRT
<213> ORGANISM: Homo sapiens

<400> SEQUENCE: 2117

Leu Glu Lys Glu Glu Pro Pro Leu
1               5

<210> SEQ ID NO 2118
<211> LENGTH: 8
<212> TYPE: PRT
<213> ORGANISM: Homo sapiens

<400> SEQUENCE: 2118

Leu Ala Glu Glu Glu Leu Pro Thr
1               5

<210> SEQ ID NO 2119
<211> LENGTH: 8
<212> TYPE: PRT
<213> ORGANISM: Homo sapiens

<400> SEQUENCE: 2119

Leu Asn Ser Glu Glu Leu Pro Asp
1               5

<210> SEQ ID NO 2120
<211> LENGTH: 8
<212> TYPE: PRT
<213> ORGANISM: Homo sapiens

<400> SEQUENCE: 2120

Leu Ala Cys Glu Glu Ala Pro Gly
1               5

<210> SEQ ID NO 2121
<211> LENGTH: 8
<212> TYPE: PRT
<213> ORGANISM: Homo sapiens

<400> SEQUENCE: 2121

Leu Cys Ser Glu Glu Pro Pro Arg
1               5

<210> SEQ ID NO 2122
<211> LENGTH: 8
<212> TYPE: PRT
<213> ORGANISM: Homo sapiens

<400> SEQUENCE: 2122

Leu Asp Leu Glu Glu Asp Pro Tyr
1               5

<210> SEQ ID NO 2123
<211> LENGTH: 8
<212> TYPE: PRT
<213> ORGANISM: Homo sapiens

<400> SEQUENCE: 2123

Leu Glu Arg Glu Glu Lys Pro Glu
1               5

<210> SEQ ID NO 2124
<211> LENGTH: 8
<212> TYPE: PRT
<213> ORGANISM: Homo sapiens

<400> SEQUENCE: 2124

Leu Ser Gln Glu Glu Asn Pro Glu
1               5

<210> SEQ ID NO 2125
<211> LENGTH: 8
<212> TYPE: PRT
<213> ORGANISM: Homo sapiens

<400> SEQUENCE: 2125

Leu Leu Pro Glu Glu Phe Pro Gly
1               5

<210> SEQ ID NO 2126
<211> LENGTH: 8
<212> TYPE: PRT
<213> ORGANISM: Homo sapiens

<400> SEQUENCE: 2126

Leu Met Lys Glu Glu Ser Pro Val
1               5

<210> SEQ ID NO 2127
<211> LENGTH: 8
<212> TYPE: PRT
<213> ORGANISM: Homo sapiens

<400> SEQUENCE: 2127

Leu Met Lys Glu Glu Ser Pro Val
1               5

<210> SEQ ID NO 2128
<211> LENGTH: 8
<212> TYPE: PRT
<213> ORGANISM: Homo sapiens

<400> SEQUENCE: 2128

Leu Met Lys Glu Glu Ser Pro Val
1               5

<210> SEQ ID NO 2129
<211> LENGTH: 8
<212> TYPE: PRT
<213> ORGANISM: Homo sapiens

<400> SEQUENCE: 2129

Leu Met Lys Glu Glu Ser Pro Val
1               5

<210> SEQ ID NO 2130
<211> LENGTH: 8
<212> TYPE: PRT
<213> ORGANISM: Homo sapiens

<400> SEQUENCE: 2130

Leu Gly Gln Glu Glu Pro Pro Leu
1               5

<210> SEQ ID NO 2131
<211> LENGTH: 8
<212> TYPE: PRT
<213> ORGANISM: Homo sapiens

<400> SEQUENCE: 2131

Leu Gln Asp Glu Glu Cys Pro Leu
1               5

<210> SEQ ID NO 2132
<211> LENGTH: 8
<212> TYPE: PRT
<213> ORGANISM: Homo sapiens

<400> SEQUENCE: 2132

Leu Thr Tyr Glu Glu Lys Pro Pro
1               5

<210> SEQ ID NO 2133
<211> LENGTH: 8
<212> TYPE: PRT
<213> ORGANISM: Homo sapiens

<400> SEQUENCE: 2133

Leu Leu Pro Glu Glu Thr Pro Ala
1               5

<210> SEQ ID NO 2134
<211> LENGTH: 8
<212> TYPE: PRT
<213> ORGANISM: Homo sapiens

<400> SEQUENCE: 2134

Leu Val Gly Glu Glu Phe Pro Glu
1               5

<210> SEQ ID NO 2135
<211> LENGTH: 8
<212> TYPE: PRT
<213> ORGANISM: Homo sapiens

<400> SEQUENCE: 2135

Leu Val Ser Glu Glu Phe Pro Glu
1               5

<210> SEQ ID NO 2136
<211> LENGTH: 8
<212> TYPE: PRT
<213> ORGANISM: Homo sapiens

<400> SEQUENCE: 2136

Leu Val Thr Glu Glu Leu Pro Arg
1               5

<210> SEQ ID NO 2137
<211> LENGTH: 8
<212> TYPE: PRT
<213> ORGANISM: Homo sapiens

<400> SEQUENCE: 2137

Leu His Thr Glu Glu Lys Pro Tyr
1               5

<210> SEQ ID NO 2138
<211> LENGTH: 8
<212> TYPE: PRT
<213> ORGANISM: Homo sapiens

<400> SEQUENCE: 2138

Leu Phe Asp Glu Glu Phe Pro Gly
1               5

<210> SEQ ID NO 2139
<211> LENGTH: 8
<212> TYPE: PRT
<213> ORGANISM: Homo sapiens

<400> SEQUENCE: 2139

Leu Leu Glu Glu Glu Ile Pro Ser
1               5

<210> SEQ ID NO 2140
<211> LENGTH: 8

<212> TYPE: PRT
<213> ORGANISM: Homo sapiens

<400> SEQUENCE: 2140

Leu Leu Gln Glu Glu Glu Pro Leu
1 5

<210> SEQ ID NO 2141
<211> LENGTH: 8
<212> TYPE: PRT
<213> ORGANISM: Homo sapiens

<400> SEQUENCE: 2141

Leu Leu Val Glu Glu Ser Pro Glu
1 5

<210> SEQ ID NO 2142
<211> LENGTH: 8
<212> TYPE: PRT
<213> ORGANISM: Homo sapiens

<400> SEQUENCE: 2142

Leu Ser Phe Glu Glu Lys Pro Val
1 5

<210> SEQ ID NO 2143
<211> LENGTH: 8
<212> TYPE: PRT
<213> ORGANISM: Homo sapiens

<400> SEQUENCE: 2143

Leu Ala Thr Glu Glu Asp Pro Lys
1 5

<210> SEQ ID NO 2144
<211> LENGTH: 8
<212> TYPE: PRT
<213> ORGANISM: Homo sapiens

<400> SEQUENCE: 2144

Leu Lys Ala Glu Glu Trp Pro Trp
1 5

<210> SEQ ID NO 2145
<211> LENGTH: 8
<212> TYPE: PRT
<213> ORGANISM: Homo sapiens

<400> SEQUENCE: 2145

Leu Ile Ser Glu Glu Gln Pro Ala
1 5

<210> SEQ ID NO 2146
<211> LENGTH: 8
<212> TYPE: PRT
<213> ORGANISM: Homo sapiens

<400> SEQUENCE: 2146

Leu Arg Phe Glu Glu Val Pro Asp
1 5

<210> SEQ ID NO 2147
<211> LENGTH: 8
<212> TYPE: PRT
<213> ORGANISM: Homo sapiens

<400> SEQUENCE: 2147

Leu Arg Gly Glu Glu Lys Pro Ala
1               5

<210> SEQ ID NO 2148
<211> LENGTH: 8
<212> TYPE: PRT
<213> ORGANISM: Homo sapiens

<400> SEQUENCE: 2148

Leu Arg Met Glu Glu Thr Pro Thr
1               5

<210> SEQ ID NO 2149
<211> LENGTH: 8
<212> TYPE: PRT
<213> ORGANISM: Homo sapiens

<400> SEQUENCE: 2149

Leu Leu Arg Glu Glu Glu Pro Glu
1               5

<210> SEQ ID NO 2150
<211> LENGTH: 8
<212> TYPE: PRT
<213> ORGANISM: Homo sapiens

<400> SEQUENCE: 2150

Leu Asp Ala Glu Glu Leu Pro Pro
1               5

<210> SEQ ID NO 2151
<211> LENGTH: 8
<212> TYPE: PRT
<213> ORGANISM: Homo sapiens

<400> SEQUENCE: 2151

Leu Leu Leu Glu Glu Gln Pro Leu
1               5

<210> SEQ ID NO 2152
<211> LENGTH: 8
<212> TYPE: PRT
<213> ORGANISM: Homo sapiens

<400> SEQUENCE: 2152

Leu Val Lys Glu Glu Pro Pro Glu
1               5

<210> SEQ ID NO 2153
<211> LENGTH: 8
<212> TYPE: PRT
<213> ORGANISM: Homo sapiens

<400> SEQUENCE: 2153

Leu Gly Glu Glu Glu Pro Pro Ala
1               5

<210> SEQ ID NO 2154
<211> LENGTH: 8
<212> TYPE: PRT
<213> ORGANISM: Homo sapiens

<400> SEQUENCE: 2154

Leu Pro Leu Glu Glu Thr Pro Asp
1 5

<210> SEQ ID NO 2155
<211> LENGTH: 8
<212> TYPE: PRT
<213> ORGANISM: Homo sapiens

<400> SEQUENCE: 2155

Leu Asp Lys Glu Glu Ser Pro Ala
1 5

<210> SEQ ID NO 2156
<211> LENGTH: 8
<212> TYPE: PRT
<213> ORGANISM: Homo sapiens

<400> SEQUENCE: 2156

Leu Trp Leu Glu Glu Gly Pro Arg
1 5

<210> SEQ ID NO 2157
<211> LENGTH: 8
<212> TYPE: PRT
<213> ORGANISM: Homo sapiens

<400> SEQUENCE: 2157

Leu Tyr Ser Glu Glu Asp Pro Asn
1 5

<210> SEQ ID NO 2158
<211> LENGTH: 8
<212> TYPE: PRT
<213> ORGANISM: Homo sapiens

<400> SEQUENCE: 2158

Leu Ser Ala Glu Glu Ser Pro Gly
1 5

<210> SEQ ID NO 2159
<211> LENGTH: 8
<212> TYPE: PRT
<213> ORGANISM: Homo sapiens

<400> SEQUENCE: 2159

Leu Ser Pro Glu Glu Gly Pro Pro
1 5

<210> SEQ ID NO 2160
<211> LENGTH: 8
<212> TYPE: PRT
<213> ORGANISM: Homo sapiens

<400> SEQUENCE: 2160

Leu Arg Gly Glu Glu His Pro Thr
1 5

<210> SEQ ID NO 2161
<211> LENGTH: 8
<212> TYPE: PRT
<213> ORGANISM: Homo sapiens

<400> SEQUENCE: 2161

Leu Ser Leu Glu Glu Cys Pro Trp 1 5

<210> SEQ ID NO 2162
<211> LENGTH: 8
<212> TYPE: PRT
<213> ORGANISM: Homo sapiens

<400> SEQUENCE: 2162

Leu Tyr Thr Glu Glu Arg Pro Arg
1 5

<210> SEQ ID NO 2163
<211> LENGTH: 8
<212> TYPE: PRT
<213> ORGANISM: Homo sapiens

<400> SEQUENCE: 2163

Leu Val Glu Glu Glu Glu Pro Met
1 5

<210> SEQ ID NO 2164
<211> LENGTH: 8
<212> TYPE: PRT
<213> ORGANISM: Homo sapiens

<400> SEQUENCE: 2164

Leu Gly Gln Glu Glu Arg Pro Pro
1 5

<210> SEQ ID NO 2165
<211> LENGTH: 8
<212> TYPE: PRT
<213> ORGANISM: Homo sapiens

<400> SEQUENCE: 2165

Leu Val Val Glu Glu Leu Pro Val
1 5

<210> SEQ ID NO 2166
<211> LENGTH: 8
<212> TYPE: PRT
<213> ORGANISM: Homo sapiens

<400> SEQUENCE: 2166

Leu Phe Val Glu Glu Ile Pro Val
1 5

<210> SEQ ID NO 2167
<211> LENGTH: 8
<212> TYPE: PRT
<213> ORGANISM: Homo sapiens

<400> SEQUENCE: 2167

Leu Gln Arg Glu Glu Thr Pro Ser
1 5

<210> SEQ ID NO 2168
<211> LENGTH: 8
<212> TYPE: PRT
<213> ORGANISM: Homo sapiens

<400> SEQUENCE: 2168

Leu His Glu Glu Glu Leu Pro Asp
1 5

<210> SEQ ID NO 2169
<211> LENGTH: 8
<212> TYPE: PRT
<213> ORGANISM: Homo sapiens

<400> SEQUENCE: 2169

Leu Ala Cys Glu Glu Leu Pro Val
1               5

<210> SEQ ID NO 2170
<211> LENGTH: 8
<212> TYPE: PRT
<213> ORGANISM: Homo sapiens

<400> SEQUENCE: 2170

Leu Leu Ser Glu Glu Asp Pro Phe
1               5

<210> SEQ ID NO 2171
<211> LENGTH: 8
<212> TYPE: PRT
<213> ORGANISM: Homo sapiens

<400> SEQUENCE: 2171

Leu Glu Pro Glu Glu Pro Pro Gly
1               5

<210> SEQ ID NO 2172
<211> LENGTH: 8
<212> TYPE: PRT
<213> ORGANISM: Homo sapiens

<400> SEQUENCE: 2172

Leu Cys Pro Glu Glu Glu Pro Asp
1               5

<210> SEQ ID NO 2173
<211> LENGTH: 8
<212> TYPE: PRT
<213> ORGANISM: Homo sapiens

<400> SEQUENCE: 2173

Leu Val Lys Glu Glu Gly Pro Arg
1               5

<210> SEQ ID NO 2174
<211> LENGTH: 8
<212> TYPE: PRT
<213> ORGANISM: Homo sapiens

<400> SEQUENCE: 2174

Leu Arg Lys Glu Glu Ile Pro Val
1               5

<210> SEQ ID NO 2175
<211> LENGTH: 8
<212> TYPE: PRT
<213> ORGANISM: Homo sapiens

<400> SEQUENCE: 2175

Leu His Pro Glu Glu Phe Pro His
1               5

<210> SEQ ID NO 2176

<211> LENGTH: 8
<212> TYPE: PRT
<213> ORGANISM: Homo sapiens

<400> SEQUENCE: 2176

Leu Gln Ala Glu Glu Ala Pro Glu
1 5

<210> SEQ ID NO 2177
<211> LENGTH: 8
<212> TYPE: PRT
<213> ORGANISM: Homo sapiens

<400> SEQUENCE: 2177

Leu Ser Leu Glu Glu Gln Pro Leu
1 5

<210> SEQ ID NO 2178
<211> LENGTH: 8
<212> TYPE: PRT
<213> ORGANISM: Homo sapiens

<400> SEQUENCE: 2178

Leu Ser Glu Glu Glu Lys Pro Asp
1 5

<210> SEQ ID NO 2179
<211> LENGTH: 8
<212> TYPE: PRT
<213> ORGANISM: Homo sapiens

<400> SEQUENCE: 2179

Leu His Pro Glu Glu Asp Pro Glu
1 5

<210> SEQ ID NO 2180
<211> LENGTH: 8
<212> TYPE: PRT
<213> ORGANISM: Homo sapiens

<400> SEQUENCE: 2180

Leu Leu Glu Glu Glu Asp Pro Trp
1 5

<210> SEQ ID NO 2181
<211> LENGTH: 8
<212> TYPE: PRT
<213> ORGANISM: Homo sapiens

<400> SEQUENCE: 2181

Leu Met Ala Glu Glu Gly Pro Trp
1 5

<210> SEQ ID NO 2182
<211> LENGTH: 8
<212> TYPE: PRT
<213> ORGANISM: Homo sapiens

<400> SEQUENCE: 2182

Leu Trp Ser Glu Glu Gln Pro Ala
1 5

<210> SEQ ID NO 2183
<211> LENGTH: 8
<212> TYPE: PRT

<213> ORGANISM: Homo sapiens

<400> SEQUENCE: 2183

Leu Leu Glu Glu Glu Ala Pro Asp
1 5

<210> SEQ ID NO 2184
<211> LENGTH: 8
<212> TYPE: PRT
<213> ORGANISM: Homo sapiens

<400> SEQUENCE: 2184

Leu Lys Pro Glu Glu Leu Pro Ser
1 5

<210> SEQ ID NO 2185
<211> LENGTH: 8
<212> TYPE: PRT
<213> ORGANISM: Homo sapiens

<400> SEQUENCE: 2185

Leu Tyr Arg Glu Glu Gly Pro Pro
1 5

<210> SEQ ID NO 2186
<211> LENGTH: 8
<212> TYPE: PRT
<213> ORGANISM: Homo sapiens

<400> SEQUENCE: 2186

Leu Asp His Glu Glu Glu Pro Gln
1 5

<210> SEQ ID NO 2187
<211> LENGTH: 8
<212> TYPE: PRT
<213> ORGANISM: Homo sapiens

<400> SEQUENCE: 2187

Leu Thr Thr Glu Glu Lys Pro Arg
1 5

<210> SEQ ID NO 2188
<211> LENGTH: 8
<212> TYPE: PRT
<213> ORGANISM: Homo sapiens

<400> SEQUENCE: 2188

Leu Glu Gln Glu Glu Glu Pro Arg
1 5

<210> SEQ ID NO 2189
<211> LENGTH: 8
<212> TYPE: PRT
<213> ORGANISM: Homo sapiens

<400> SEQUENCE: 2189

Leu His Ala Glu Glu Ala Pro Ser
1 5

<210> SEQ ID NO 2190
<211> LENGTH: 8
<212> TYPE: PRT
<213> ORGANISM: Homo sapiens

<400> SEQUENCE: 2190

Leu Val Phe Glu Glu Asn Pro Phe
1               5

<210> SEQ ID NO 2191
<211> LENGTH: 8
<212> TYPE: PRT
<213> ORGANISM: Homo sapiens

<400> SEQUENCE: 2191

Leu Leu Leu Glu Glu Glu Pro Thr
1               5

<210> SEQ ID NO 2192
<211> LENGTH: 8
<212> TYPE: PRT
<213> ORGANISM: Homo sapiens

<400> SEQUENCE: 2192

Leu Ser Glu Glu Glu Asp Pro Ala
1               5

<210> SEQ ID NO 2193
<211> LENGTH: 8
<212> TYPE: PRT
<213> ORGANISM: Homo sapiens

<400> SEQUENCE: 2193

Leu Asp Ser Glu Glu Val Pro Glu
1               5

<210> SEQ ID NO 2194
<211> LENGTH: 8
<212> TYPE: PRT
<213> ORGANISM: Homo sapiens

<400> SEQUENCE: 2194

Leu His Arg Glu Glu Arg Pro Asn
1               5

<210> SEQ ID NO 2195
<211> LENGTH: 8
<212> TYPE: PRT
<213> ORGANISM: Homo sapiens

<400> SEQUENCE: 2195

Leu Gln Leu Glu Glu Phe Pro Met
1               5

<210> SEQ ID NO 2196
<211> LENGTH: 8
<212> TYPE: PRT
<213> ORGANISM: Homo sapiens

<400> SEQUENCE: 2196

Leu Thr Tyr Glu Glu Leu Pro Gly
1               5

<210> SEQ ID NO 2197
<211> LENGTH: 8
<212> TYPE: PRT
<213> ORGANISM: Homo sapiens

<400> SEQUENCE: 2197

Leu Glu Pro Glu Glu Ser Pro Gly
1 5

<210> SEQ ID NO 2198
<211> LENGTH: 8
<212> TYPE: PRT
<213> ORGANISM: Homo sapiens

<400> SEQUENCE: 2198

Leu His Glu Glu Glu Pro Pro Gln
1 5

<210> SEQ ID NO 2199
<211> LENGTH: 8
<212> TYPE: PRT
<213> ORGANISM: Homo sapiens

<400> SEQUENCE: 2199

Leu Asn Glu Glu Glu Pro Pro Gly
1 5

<210> SEQ ID NO 2200
<211> LENGTH: 8
<212> TYPE: PRT
<213> ORGANISM: Homo sapiens

<400> SEQUENCE: 2200

Leu Thr His Glu Glu Met Pro Gln
1 5

<210> SEQ ID NO 2201
<211> LENGTH: 8
<212> TYPE: PRT
<213> ORGANISM: Homo sapiens

<400> SEQUENCE: 2201

Leu Asp Arg Glu Glu Thr Pro Asn
1 5

<210> SEQ ID NO 2202
<211> LENGTH: 8
<212> TYPE: PRT
<213> ORGANISM: Homo sapiens

<400> SEQUENCE: 2202

Leu Asp Arg Glu Glu Thr Pro Asn
1 5

<210> SEQ ID NO 2203
<211> LENGTH: 8
<212> TYPE: PRT
<213> ORGANISM: Homo sapiens

<400> SEQUENCE: 2203

Leu Arg Pro Glu Glu Ala Pro Gly
1 5

<210> SEQ ID NO 2204
<211> LENGTH: 8
<212> TYPE: PRT
<213> ORGANISM: Homo sapiens

<400> SEQUENCE: 2204

Leu Ile Thr Glu Glu Gly Pro Asn
1 5

<210> SEQ ID NO 2205
<211> LENGTH: 8
<212> TYPE: PRT
<213> ORGANISM: Homo sapiens

<400> SEQUENCE: 2205

Leu Gly Gly Glu Glu Pro Pro Gly
1               5

<210> SEQ ID NO 2206
<211> LENGTH: 8
<212> TYPE: PRT
<213> ORGANISM: Homo sapiens

<400> SEQUENCE: 2206

Leu Asp Gly Glu Glu Ile Pro Val
1               5

<210> SEQ ID NO 2207
<211> LENGTH: 8
<212> TYPE: PRT
<213> ORGANISM: Homo sapiens

<400> SEQUENCE: 2207

Leu Arg Leu Glu Glu Gly Pro Pro
1               5

<210> SEQ ID NO 2208
<211> LENGTH: 8
<212> TYPE: PRT
<213> ORGANISM: Homo sapiens

<400> SEQUENCE: 2208

Leu Ser His Glu Glu His Pro His
1               5

<210> SEQ ID NO 2209
<211> LENGTH: 8
<212> TYPE: PRT
<213> ORGANISM: Homo sapiens

<400> SEQUENCE: 2209

Leu Phe Pro Glu Glu Pro Pro Pro
1               5

<210> SEQ ID NO 2210
<211> LENGTH: 8
<212> TYPE: PRT
<213> ORGANISM: Homo sapiens

<400> SEQUENCE: 2210

Leu Val Gln Glu Glu Arg Pro His
1               5

<210> SEQ ID NO 2211
<211> LENGTH: 8
<212> TYPE: PRT
<213> ORGANISM: Homo sapiens

<400> SEQUENCE: 2211

Leu Ala Thr Glu Glu Pro Pro Pro
1               5

<210> SEQ ID NO 2212
<211> LENGTH: 8
<212> TYPE: PRT
<213> ORGANISM: Homo sapiens

<400> SEQUENCE: 2212

Leu Asn Lys Glu Glu Leu Pro Val
1               5

<210> SEQ ID NO 2213
<211> LENGTH: 8
<212> TYPE: PRT
<213> ORGANISM: Homo sapiens

<400> SEQUENCE: 2213

Leu Ala Asn Glu Glu Lys Pro Ala
1               5

<210> SEQ ID NO 2214
<211> LENGTH: 8
<212> TYPE: PRT
<213> ORGANISM: Homo sapiens

<400> SEQUENCE: 2214

Leu Ala Pro Glu Glu Val Pro Leu
1               5

<210> SEQ ID NO 2215
<211> LENGTH: 8
<212> TYPE: PRT
<213> ORGANISM: Homo sapiens

<400> SEQUENCE: 2215

Leu Cys Ser Glu Glu Ser Pro Glu
1               5

<210> SEQ ID NO 2216
<211> LENGTH: 8
<212> TYPE: PRT
<213> ORGANISM: Homo sapiens

<400> SEQUENCE: 2216

Leu Ile Val Glu Glu Cys Pro Ser
1               5

<210> SEQ ID NO 2217
<211> LENGTH: 8
<212> TYPE: PRT
<213> ORGANISM: Homo sapiens

<400> SEQUENCE: 2217

Leu Phe Ser Glu Glu Thr Pro Gly
1               5

<210> SEQ ID NO 2218
<211> LENGTH: 8
<212> TYPE: PRT
<213> ORGANISM: Homo sapiens

<400> SEQUENCE: 2218

Leu Asn Arg Glu Glu Ile Pro Val
1               5

<210> SEQ ID NO 2219
<211> LENGTH: 8

<212> TYPE: PRT
<213> ORGANISM: Homo sapiens

<400> SEQUENCE: 2219

Leu Glu Asp Glu Glu Leu Pro Ala
1 5

<210> SEQ ID NO 2220
<211> LENGTH: 8
<212> TYPE: PRT
<213> ORGANISM: Homo sapiens

<400> SEQUENCE: 2220

Leu Gly Ser Glu Glu Arg Pro Phe
1 5

<210> SEQ ID NO 2221
<211> LENGTH: 8
<212> TYPE: PRT
<213> ORGANISM: Homo sapiens

<400> SEQUENCE: 2221

Leu Cys Pro Glu Glu Pro Pro Val
1 5

<210> SEQ ID NO 2222
<211> LENGTH: 8
<212> TYPE: PRT
<213> ORGANISM: Homo sapiens

<400> SEQUENCE: 2222

Leu Asp Arg Glu Glu Glu Pro Gln
1 5

<210> SEQ ID NO 2223
<211> LENGTH: 8
<212> TYPE: PRT
<213> ORGANISM: Homo sapiens

<400> SEQUENCE: 2223

Leu Arg Thr Glu Glu Thr Pro Met
1 5

<210> SEQ ID NO 2224
<211> LENGTH: 8
<212> TYPE: PRT
<213> ORGANISM: Homo sapiens

<400> SEQUENCE: 2224

Leu His Ser Glu Glu Gly Pro Ala
1 5

<210> SEQ ID NO 2225
<211> LENGTH: 8
<212> TYPE: PRT
<213> ORGANISM: Homo sapiens

<400> SEQUENCE: 2225

Leu Ile Gly Glu Glu Trp Pro Ser
1 5

<210> SEQ ID NO 2226
<211> LENGTH: 8
<212> TYPE: PRT
<213> ORGANISM: Homo sapiens

<400> SEQUENCE: 2226

Leu Gly Met Glu Glu Arg Pro Tyr
1               5

<210> SEQ ID NO 2227
<211> LENGTH: 8
<212> TYPE: PRT
<213> ORGANISM: Homo sapiens

<400> SEQUENCE: 2227

Leu Leu Glu Glu Glu Ile Pro Gly
1               5

<210> SEQ ID NO 2228
<211> LENGTH: 8
<212> TYPE: PRT
<213> ORGANISM: Homo sapiens

<400> SEQUENCE: 2228

Leu Leu Ala Glu Glu Thr Pro Pro
1               5

<210> SEQ ID NO 2229
<211> LENGTH: 8
<212> TYPE: PRT
<213> ORGANISM: Homo sapiens

<400> SEQUENCE: 2229

Leu Ala Gln Glu Glu Ala Pro Gly
1               5

<210> SEQ ID NO 2230
<211> LENGTH: 8
<212> TYPE: PRT
<213> ORGANISM: Homo sapiens

<400> SEQUENCE: 2230

Leu Asp Tyr Glu Glu Ser Pro Val
1               5

<210> SEQ ID NO 2231
<211> LENGTH: 8
<212> TYPE: PRT
<213> ORGANISM: Homo sapiens

<400> SEQUENCE: 2231

Leu Glu Val Glu Glu Glu Pro Val
1               5

<210> SEQ ID NO 2232
<211> LENGTH: 8
<212> TYPE: PRT
<213> ORGANISM: Homo sapiens

<400> SEQUENCE: 2232

Leu Ala Ser Glu Glu Pro Pro Asp
1               5

<210> SEQ ID NO 2233
<211> LENGTH: 8
<212> TYPE: PRT
<213> ORGANISM: Homo sapiens

<400> SEQUENCE: 2233

Leu Lys Glu Glu Glu Cys Pro Ala
1 5

<210> SEQ ID NO 2234
<211> LENGTH: 8
<212> TYPE: PRT
<213> ORGANISM: Homo sapiens

<400> SEQUENCE: 2234

Leu Leu Phe Glu Glu Ser Pro Ser
1 5

<210> SEQ ID NO 2235
<211> LENGTH: 8
<212> TYPE: PRT
<213> ORGANISM: Homo sapiens

<400> SEQUENCE: 2235

Leu Ser Lys Glu Glu Leu Pro Gln
1 5

<210> SEQ ID NO 2236
<211> LENGTH: 8
<212> TYPE: PRT
<213> ORGANISM: Homo sapiens

<400> SEQUENCE: 2236

Leu Leu Ser Glu Glu Thr Pro Ser
1 5

<210> SEQ ID NO 2237
<211> LENGTH: 8
<212> TYPE: PRT
<213> ORGANISM: Homo sapiens

<400> SEQUENCE: 2237

Leu Arg Leu Glu Glu Gly Pro Pro
1 5

<210> SEQ ID NO 2238
<211> LENGTH: 8
<212> TYPE: PRT
<213> ORGANISM: Homo sapiens

<400> SEQUENCE: 2238

Leu Ser Ala Glu Glu Ile Pro Ser
1 5

<210> SEQ ID NO 2239
<211> LENGTH: 8
<212> TYPE: PRT
<213> ORGANISM: Homo sapiens

<400> SEQUENCE: 2239

Leu Leu Lys Glu Glu Phe Pro Ala
1 5

<210> SEQ ID NO 2240
<211> LENGTH: 8
<212> TYPE: PRT
<213> ORGANISM: Homo sapiens

<400> SEQUENCE: 2240

Leu Pro Ala Glu Glu Val Pro Leu 1 5

<210> SEQ ID NO 2241
<211> LENGTH: 8
<212> TYPE: PRT
<213> ORGANISM: Homo sapiens

<400> SEQUENCE: 2241

Leu Ser Ser Glu Glu Ser Pro Arg
1 5

<210> SEQ ID NO 2242
<211> LENGTH: 8
<212> TYPE: PRT
<213> ORGANISM: Homo sapiens

<400> SEQUENCE: 2242

Leu Arg Gly Glu Glu Glu Pro Arg
1 5

<210> SEQ ID NO 2243
<211> LENGTH: 8
<212> TYPE: PRT
<213> ORGANISM: Homo sapiens

<400> SEQUENCE: 2243

Leu Gly Gln Glu Glu Leu Pro Ser
1 5

<210> SEQ ID NO 2244
<211> LENGTH: 8
<212> TYPE: PRT
<213> ORGANISM: Homo sapiens

<400> SEQUENCE: 2244

Leu Val Thr Glu Glu Thr Pro Ser
1 5

<210> SEQ ID NO 2245
<211> LENGTH: 8
<212> TYPE: PRT
<213> ORGANISM: Homo sapiens

<400> SEQUENCE: 2245

Leu Asp Arg Glu Glu Thr Pro Glu
1 5

<210> SEQ ID NO 2246
<211> LENGTH: 8
<212> TYPE: PRT
<213> ORGANISM: Homo sapiens

<400> SEQUENCE: 2246

Leu Asp Arg Glu Glu Ala Pro Ala
1 5

<210> SEQ ID NO 2247
<211> LENGTH: 8
<212> TYPE: PRT
<213> ORGANISM: Homo sapiens

<400> SEQUENCE: 2247

Leu Asp Arg Glu Glu Ala Pro Glu
1 5

<210> SEQ ID NO 2248
<211> LENGTH: 8
<212> TYPE: PRT
<213> ORGANISM: Homo sapiens

<400> SEQUENCE: 2248

Leu Gly Pro Glu Glu Leu Pro Gly
1               5

<210> SEQ ID NO 2249
<211> LENGTH: 8
<212> TYPE: PRT
<213> ORGANISM: Homo sapiens

<400> SEQUENCE: 2249

Leu Arg Leu Glu Glu Gly Pro Pro
1               5

<210> SEQ ID NO 2250
<211> LENGTH: 8
<212> TYPE: PRT
<213> ORGANISM: Homo sapiens

<400> SEQUENCE: 2250

Leu Leu Pro Glu Glu His Pro Ser
1               5

<210> SEQ ID NO 2251
<211> LENGTH: 8
<212> TYPE: PRT
<213> ORGANISM: Homo sapiens

<400> SEQUENCE: 2251

Leu Ala Thr Glu Glu Glu Pro Pro
1               5

<210> SEQ ID NO 2252
<211> LENGTH: 8
<212> TYPE: PRT
<213> ORGANISM: Homo sapiens

<400> SEQUENCE: 2252

Leu Arg Lys Glu Glu Asp Pro Arg
1               5

<210> SEQ ID NO 2253
<211> LENGTH: 8
<212> TYPE: PRT
<213> ORGANISM: Homo sapiens

<400> SEQUENCE: 2253

Leu Glu Glu Glu Glu Leu Pro Glu
1               5

<210> SEQ ID NO 2254
<211> LENGTH: 8
<212> TYPE: PRT
<213> ORGANISM: Homo sapiens

<400> SEQUENCE: 2254

Leu Asn Thr Glu Glu Val Pro Asp
1               5

<210> SEQ ID NO 2255

<211> LENGTH: 8
<212> TYPE: PRT
<213> ORGANISM: Homo sapiens

<400> SEQUENCE: 2255

Leu Leu Gly Glu Glu Leu Pro Pro
1               5

<210> SEQ ID NO 2256
<211> LENGTH: 8
<212> TYPE: PRT
<213> ORGANISM: Homo sapiens

<400> SEQUENCE: 2256

Leu Arg Asn Glu Glu Ala Pro Gln
1               5

<210> SEQ ID NO 2257
<211> LENGTH: 8
<212> TYPE: PRT
<213> ORGANISM: Homo sapiens

<400> SEQUENCE: 2257

Leu Ser Phe Glu Glu Ser Pro Gln
1               5

<210> SEQ ID NO 2258
<211> LENGTH: 8
<212> TYPE: PRT
<213> ORGANISM: Homo sapiens

<400> SEQUENCE: 2258

Leu Ala Tyr Glu Glu Arg Pro Arg
1               5

<210> SEQ ID NO 2259
<211> LENGTH: 8
<212> TYPE: PRT
<213> ORGANISM: Homo sapiens

<400> SEQUENCE: 2259

Leu Glu Leu Glu Glu Pro Pro Gln
1               5

<210> SEQ ID NO 2260
<211> LENGTH: 8
<212> TYPE: PRT
<213> ORGANISM: Homo sapiens

<400> SEQUENCE: 2260

Leu Leu Asn Glu Glu Leu Pro Asn
1               5

<210> SEQ ID NO 2261
<211> LENGTH: 8
<212> TYPE: PRT
<213> ORGANISM: Homo sapiens

<400> SEQUENCE: 2261

Leu Pro Ser Glu Glu Asp Pro Ala
1               5

<210> SEQ ID NO 2262
<211> LENGTH: 8
<212> TYPE: PRT

<213> ORGANISM: Homo sapiens

<400> SEQUENCE: 2262

Leu Ser Glu Glu Glu Gln Pro Lys
1               5

<210> SEQ ID NO 2263
<211> LENGTH: 8
<212> TYPE: PRT
<213> ORGANISM: Homo sapiens

<400> SEQUENCE: 2263

Leu Glu Asn Glu Glu Leu Pro Lys
1               5

<210> SEQ ID NO 2264
<211> LENGTH: 8
<212> TYPE: PRT
<213> ORGANISM: Homo sapiens

<400> SEQUENCE: 2264

Leu Val Met Glu Glu Ala Pro Glu
1               5

<210> SEQ ID NO 2265
<211> LENGTH: 8
<212> TYPE: PRT
<213> ORGANISM: Homo sapiens

<400> SEQUENCE: 2265

Leu Ser Glu Glu Glu Leu Pro Ala
1               5

<210> SEQ ID NO 2266
<211> LENGTH: 8
<212> TYPE: PRT
<213> ORGANISM: Homo sapiens

<400> SEQUENCE: 2266

Leu Ala Ser Glu Glu Leu Pro Ser
1               5

<210> SEQ ID NO 2267
<211> LENGTH: 8
<212> TYPE: PRT
<213> ORGANISM: Homo sapiens

<400> SEQUENCE: 2267

Leu Ser Glu Glu Glu Leu Pro Tyr
1               5

<210> SEQ ID NO 2268
<211> LENGTH: 8
<212> TYPE: PRT
<213> ORGANISM: Homo sapiens

<400> SEQUENCE: 2268

Leu Ser Phe Glu Glu Asp Pro Arg
1               5

<210> SEQ ID NO 2269
<211> LENGTH: 8
<212> TYPE: PRT
<213> ORGANISM: Homo sapiens

<400> SEQUENCE: 2269

Leu Pro Trp Glu Glu Gly Pro Gly
1               5

<210> SEQ ID NO 2270
<211> LENGTH: 8
<212> TYPE: PRT
<213> ORGANISM: Homo sapiens

<400> SEQUENCE: 2270

Leu Asn Leu Glu Glu Pro Pro Ser
1               5

<210> SEQ ID NO 2271
<211> LENGTH: 8
<212> TYPE: PRT
<213> ORGANISM: Homo sapiens

<400> SEQUENCE: 2271

Leu Asp Arg Glu Glu Ile Pro Glu
1               5

<210> SEQ ID NO 2272
<211> LENGTH: 8
<212> TYPE: PRT
<213> ORGANISM: Homo sapiens

<400> SEQUENCE: 2272

Leu Asp Arg Glu Glu Gln Pro Gln
1               5

<210> SEQ ID NO 2273
<211> LENGTH: 8
<212> TYPE: PRT
<213> ORGANISM: Homo sapiens

<400> SEQUENCE: 2273

Leu Asp Arg Glu Glu Arg Pro Glu
1               5

<210> SEQ ID NO 2274
<211> LENGTH: 8
<212> TYPE: PRT
<213> ORGANISM: Homo sapiens

<400> SEQUENCE: 2274

Leu Asp Arg Glu Glu Gln Pro Glu
1               5

<210> SEQ ID NO 2275
<211> LENGTH: 8
<212> TYPE: PRT
<213> ORGANISM: Homo sapiens

<400> SEQUENCE: 2275

Leu Asp Arg Glu Glu Gln Pro Glu
1               5

<210> SEQ ID NO 2276
<211> LENGTH: 8
<212> TYPE: PRT
<213> ORGANISM: Homo sapiens

<400> SEQUENCE: 2276

Leu Asp Arg Glu Glu Gln Pro Glu
1 5

<210> SEQ ID NO 2277
<211> LENGTH: 8
<212> TYPE: PRT
<213> ORGANISM: Homo sapiens

<400> SEQUENCE: 2277

Leu Asp Tyr Glu Glu Arg Pro Glu
1 5

<210> SEQ ID NO 2278
<211> LENGTH: 8
<212> TYPE: PRT
<213> ORGANISM: Homo sapiens

<400> SEQUENCE: 2278

Leu Asp Tyr Glu Glu Leu Pro Glu
1 5

<210> SEQ ID NO 2279
<211> LENGTH: 8
<212> TYPE: PRT
<213> ORGANISM: Homo sapiens

<400> SEQUENCE: 2279

Leu Asp Arg Glu Glu Gln Pro Glu
1 5

<210> SEQ ID NO 2280
<211> LENGTH: 8
<212> TYPE: PRT
<213> ORGANISM: Homo sapiens

<400> SEQUENCE: 2280

Leu Asp Arg Glu Glu Gln Pro His
1 5

<210> SEQ ID NO 2281
<211> LENGTH: 8
<212> TYPE: PRT
<213> ORGANISM: Homo sapiens

<400> SEQUENCE: 2281

Leu Asp Arg Glu Glu Ile Pro Glu
1 5

<210> SEQ ID NO 2282
<211> LENGTH: 8
<212> TYPE: PRT
<213> ORGANISM: Homo sapiens

<400> SEQUENCE: 2282

Leu Asp Arg Glu Glu Thr Pro Glu
1 5

<210> SEQ ID NO 2283
<211> LENGTH: 8
<212> TYPE: PRT
<213> ORGANISM: Homo sapiens

<400> SEQUENCE: 2283

Leu Asp Arg Glu Glu Asn Pro Gln
1 5

<210> SEQ ID NO 2284
<211> LENGTH: 8
<212> TYPE: PRT
<213> ORGANISM: Homo sapiens

<400> SEQUENCE: 2284

Leu Asp Arg Glu Glu Thr Pro Glu
1               5

<210> SEQ ID NO 2285
<211> LENGTH: 8
<212> TYPE: PRT
<213> ORGANISM: Homo sapiens

<400> SEQUENCE: 2285

Leu Ser Ala Glu Glu Asn Pro Asp
1               5

<210> SEQ ID NO 2286
<211> LENGTH: 8
<212> TYPE: PRT
<213> ORGANISM: Homo sapiens

<400> SEQUENCE: 2286

Leu Thr Phe Glu Glu Val Pro Tyr
1               5

<210> SEQ ID NO 2287
<211> LENGTH: 11
<212> TYPE: PRT
<213> ORGANISM: Artificial Sequence
<220> FEATURE:
<223> OTHER INFORMATION: Description of Artificial Sequence: Synthetic
      TSP motif
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (9)..(10)
<223> OTHER INFORMATION: Any amino acid

<400> SEQUENCE: 2287

Trp Xaa Xaa Cys Xaa Xaa Xaa Cys Xaa Xaa Gly
1               5                   10

<210> SEQ ID NO 2288
<211> LENGTH: 7
<212> TYPE: PRT
<213> ORGANISM: Artificial Sequence
<220> FEATURE:
<223> OTHER INFORMATION: Description of Artificial Sequence: Synthetic
      collagen motif
<220> FEATURE:
<221> NAME/KEY: MOD_RES
<222> LOCATION: (3)..(5)
<223> OTHER INFORMATION: Any amino acid

<400> SEQUENCE: 2288

Cys Asn Xaa Xaa Xaa Val Cys
1               5

<210> SEQ ID NO 2289
<211> LENGTH: 12
<212> TYPE: PRT
<213> ORGANISM: Artificial Sequence
<220> FEATURE:
<223> OTHER INFORMATION: Description of Artificial Sequence: Synthetic somatotropin motif
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (7)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid

<400> SEQUENCE: 2289

Leu Xaa Xaa Xaa Leu Leu Xaa Xaa Xaa Ser Xaa Leu
1 5 10

<210> SEQ ID NO 2290
<211> LENGTH: 7
<212> TYPE: PRT
<213> ORGANISM: Artificial Sequence
<220> FEATURE:
<223> OTHER INFORMATION: Description of Artificial Sequence: Synthetic serpin motif
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 2290

Leu Xaa Xaa Glu Glu Xaa Pro
1 5

<210> SEQ ID NO 2291
<211> LENGTH: 14
<212> TYPE: PRT
<213> ORGANISM: Homo sapiens

<400> SEQUENCE: 2291

Leu Leu Arg Ile Ser Leu Leu Leu Ile Glu Ser Trp Leu Glu
1 5 10

<210> SEQ ID NO 2292
<211> LENGTH: 14
<212> TYPE: PRT
<213> ORGANISM: Homo sapiens

<400> SEQUENCE: 2292

Leu Leu Arg Ile Ser Leu Leu Leu Thr Gln Ser Trp Leu Glu
1 5 10

<210> SEQ ID NO 2293
<211> LENGTH: 14
<212> TYPE: PRT
<213> ORGANISM: Unknown
<220> FEATURE:
<223> OTHER INFORMATION: Description of Unknown: GH2 peptide

<400> SEQUENCE: 2293

-continued

Leu Leu His Ile Ser Leu Leu Leu Ile Gln Ser Trp Leu Glu
1 5 10

<210> SEQ ID NO 2294
<211> LENGTH: 13
<212> TYPE: PRT
<213> ORGANISM: Unknown
<220> FEATURE:
<223> OTHER INFORMATION: Description of Unknown: Chorionic somatomammotropin peptide

<400> SEQUENCE: 2294

Leu Leu Arg Leu Leu Leu Leu Ile Glu Ser Trp Leu Glu
1 5 10

<210> SEQ ID NO 2295
<211> LENGTH: 14
<212> TYPE: PRT
<213> ORGANISM: Unknown
<220> FEATURE:
<223> OTHER INFORMATION: Description of Unknown: Chorionic somatomammotropin hormone-like peptide

<400> SEQUENCE: 2295

Leu Leu His Ile Ser Leu Leu Leu Ile Glu Ser Arg Leu Glu
1 5 10

<210> SEQ ID NO 2296
<211> LENGTH: 14
<212> TYPE: PRT
<213> ORGANISM: Unknown
<220> FEATURE:
<223> OTHER INFORMATION: Description of Unknown: Transmembrane protein 45A peptide

<400> SEQUENCE: 2296

Leu Leu Arg Ser Ser Leu Ile Leu Leu Gln Gly Ser Trp Phe
1 5 10

<210> SEQ ID NO 2297
<211> LENGTH: 12
<212> TYPE: PRT
<213> ORGANISM: Unknown
<220> FEATURE:
<223> OTHER INFORMATION: Description of Unknown: IL-17 receptor C peptide

<400> SEQUENCE: 2297

Arg Leu Arg Leu Leu Thr Leu Gln Ser Trp Leu Leu
1 5 10

<210> SEQ ID NO 2298
<211> LENGTH: 13
<212> TYPE: PRT
<213> ORGANISM: Unknown
<220> FEATURE:
<223> OTHER INFORMATION: Description of Unknown: Neuropeptide FF receptor 2 peptide

<400> SEQUENCE: 2298

Leu Leu Ile Val Ala Leu Leu Phe Ile Leu Ser Trp Leu
1 5 10

<210> SEQ ID NO 2299
<211> LENGTH: 13
<212> TYPE: PRT
<213> ORGANISM: Unknown
<220> FEATURE:

<223> OTHER INFORMATION: Description of Unknown: Brush border myosin-I peptide

<400> SEQUENCE: 2299

Leu Met Arg Lys Ser Gln Ile Leu Ile Ser Ser Trp Phe
1               5                   10

<210> SEQ ID NO 2300
<211> LENGTH: 4
<212> TYPE: PRT
<213> ORGANISM: Unknown
<220> FEATURE:
<223> OTHER INFORMATION: Description of Unknown: Motif peptide

<400> SEQUENCE: 2300

Asp Glu Ala His
1

<210> SEQ ID NO 2301
<211> LENGTH: 11
<212> TYPE: PRT
<213> ORGANISM: Unknown
<220> FEATURE:
<223> OTHER INFORMATION: Description of Unknown: DEAH box polypeptide peptide

<400> SEQUENCE: 2301

Glu Ile Glu Leu Val Glu Glu Glu Pro Pro Phe
1               5                   10

<210> SEQ ID NO 2302
<211> LENGTH: 11
<212> TYPE: PRT
<213> ORGANISM: Unknown
<220> FEATURE:
<223> OTHER INFORMATION: Description of Unknown: Caspase 10 peptide

<400> SEQUENCE: 2302

Ala Glu Asp Leu Leu Ser Glu Glu Asp Pro Phe
1               5                   10

<210> SEQ ID NO 2303
<211> LENGTH: 11
<212> TYPE: PRT
<213> ORGANISM: Unknown
<220> FEATURE:
<223> OTHER INFORMATION: Description of Unknown: CKIP-1 peptide

<400> SEQUENCE: 2303

Thr Leu Asp Leu Ile Gln Glu Glu Asp Pro Ser
1               5                   10

<210> SEQ ID NO 2304
<211> LENGTH: 20
<212> TYPE: PRT
<213> ORGANISM: Unknown
<220> FEATURE:
<223> OTHER INFORMATION: Description of Unknown: Collagen type IV, alpha6 fibril peptide

<400> SEQUENCE: 2304

Leu Pro Arg Phe Ser Thr Met Pro Phe Ile Tyr Cys Asn Ile Asn Glu
1               5                   10                  15

Val Cys His Tyr
            20

<210> SEQ ID NO 2305
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2305

Asn Gly Arg Lys Ala Cys Leu Asn Pro Ala Ser Pro Ile Val Lys Lys
1 5 10 15

Ile Ile Glu Lys Met Leu Asn Ser
20

<210> SEQ ID NO 2306
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2306

Gly Pro Trp Glu Pro Cys Ser Val Thr Cys Ser Lys Gly Thr Arg Thr
1 5 10 15

Arg Arg Arg

<210> SEQ ID NO 2307
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2307

Ser Pro Trp Ser Pro Cys Ser Thr Ser Cys Gly Leu Gly Val Ser Thr
1 5 10 15

Arg Ile

<210> SEQ ID NO 2308
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2308

Thr Glu Trp Thr Ala Cys Ser Lys Ser Cys Gly Met Gly Phe Ser Thr
1 5 10 15

Arg Val

<210> SEQ ID NO 2309
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2309

Thr Glu Trp Ser Val Cys Asn Ser Arg Cys Gly Arg Gly Tyr Gln Lys
1 5 10 15

Arg Thr Arg

<210> SEQ ID NO 2310
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2310

```
Asn Gly Lys Lys Ala Cys Leu Asn Pro Ala Ser Pro Met Val Gln Lys
1               5                   10                  15

Ile Ile Glu Lys Ile Leu
            20
```

<210> SEQ ID NO 2311
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2311

```
Asn Gly Lys Glu Ile Cys Leu Asp Pro Glu Ala Pro Phe Leu Lys Lys
1               5                   10                  15

Val Ile Gln Lys Ile Leu Asp
            20
```

<210> SEQ ID NO 2312
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2312

```
Leu Arg Arg Phe Ser Thr Met Pro Phe Met Phe Cys Asn Ile Asn Asn
1               5                   10                  15

Val Cys Asn Phe
            20
```

<210> SEQ ID NO 2313
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2313

```
Phe Cys Asn Ile Asn Asn Val Cys Asn Phe Ala Ser Arg Asn Asp Tyr
1               5                   10                  15

Ser Tyr Trp Leu
            20
```

<210> SEQ ID NO 2314
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 2314

His His His His His His
1 5

<210> SEQ ID NO 2315
<211> LENGTH: 19
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (15)..(15)
<223> OTHER INFORMATION: Any amino acid

<400> SEQUENCE: 2315

Cys Asn Xaa Xaa Xaa Val Cys Xaa Xaa Ala Xaa Arg Asn Asp Xaa Ser
1 5 10 15

Tyr Trp Leu

<210> SEQ ID NO 2316
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (10)..(11)
<223> OTHER INFORMATION: Any amino acid
<220> FEATURE:
<221> NAME/KEY: MOD_RES
<222> LOCATION: (14)..(16)
<223> OTHER INFORMATION: Any amino acid

<400> SEQUENCE: 2316

Leu Xaa Xaa Phe Ser Thr Xaa Pro Phe Xaa Xaa Cys Asn Xaa Xaa Xaa
1 5 10 15

Val Cys

<210> SEQ ID NO 2317
<211> LENGTH: 19
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(2)

<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (10)..(17)
<223> OTHER INFORMATION: Any amino acid

<400> SEQUENCE: 2317

Xaa Xaa Pro Phe Xaa Glu Cys Xaa Gly Xaa Xaa Xaa Xaa Xaa Xaa Xaa
1 5 10 15

Xaa Ala Asn

<210> SEQ ID NO 2318
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (5)..(5)
<223> OTHER INFORMATION: Ile or Leu
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Arg or Gly
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (13)..(14)
<223> OTHER INFORMATION: Tyr or Phe

<400> SEQUENCE: 2318

Xaa Xaa Pro Phe Xaa Glu Cys Xaa Gly Xaa Xaa Xaa Xaa Xaa Ala Asn
1 5 10 15

<210> SEQ ID NO 2319
<211> LENGTH: 23
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (18)..(22)
<223> OTHER INFORMATION: Any amino acid

<400> SEQUENCE: 2319

Glu Cys Leu Trp Xaa Asp Xaa Xaa Xaa Xaa Xaa Xaa Xaa Xaa Gly Xaa
1 5 10 15

Tyr Xaa Xaa Xaa Xaa Xaa Cys
20

<210> SEQ ID NO 2320
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2320

Tyr Cys Asn Ile His Gln Val Cys His Tyr Ala Gln Arg Asn Asp Arg
1 5 10 15

Ser Tyr Trp Leu
20

<210> SEQ ID NO 2321
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2321

Trp Thr Arg Cys Ser Ser Ser Cys Gly Arg Gly Val Ser Val Arg Ser
1 5 10 15

Arg

<210> SEQ ID NO 2322
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2322

Asn Gly Arg Glu Ala Cys Leu Asp Pro Glu Ala Pro Leu Val Gln Lys
1 5 10 15

Ile Val Gln Lys Met Leu Lys Gly
20

<210> SEQ ID NO 2323
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2323

Gly Pro Trp Gly Pro Cys Ser Val Thr Cys Ser Lys Gly Thr Gln Ile 1 5 10 15

Arg Gln Arg

<210> SEQ ID NO 2324
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2324

Gly Pro Trp Gly Asp Cys Ser Arg Thr Cys Gly Gly Gly Val Gln Phe
1 5 10 15

Ser Ser Arg

<210> SEQ ID NO 2325
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2325

Gly Pro Trp Gly Glu Cys Ser Arg Thr Cys Gly Gly Gly Val Gln Phe
1 5 10 15

Ser His Arg

<210> SEQ ID NO 2326
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2326

Ser Pro Trp Ser Gln Cys Thr Ala Ser Cys Gly Gly Gly Val Gln Thr
1 5 10 15

Arg

<210> SEQ ID NO 2327
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2327

Ser Lys Trp Ser Glu Cys Ser Arg Thr Cys Gly Gly Gly Val Lys Phe
1 5 10 15

Gln Glu Arg

<210> SEQ ID NO 2328
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2328

Thr Gln Trp Thr Ser Cys Ser Lys Thr Cys Asn Ser Gly Thr Gln Ser
1 5 10 15

Arg His Arg

<210> SEQ ID NO 2329
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2329

Gly Pro Trp Gly Pro Cys Ser Gly Ser Cys Gly Pro Gly Arg Arg Leu
1 5 10 15

Arg Arg Arg

<210> SEQ ID NO 2330
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2330

Thr Glu Trp Ser Ala Cys Ser Lys Thr Cys Gly Met Gly Ile Ser Thr
1 5 10 15

Arg Val

<210> SEQ ID NO 2331
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2331

Thr Ser Trp Ser Gln Cys Ser Lys Thr Cys Gly Thr Gly Ile Ser Thr
1 5 10 15

Arg Val

<210> SEQ ID NO 2332
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2332

Trp Asp Glu Cys Ser Ala Thr Cys Gly Met Gly Met Lys Lys Arg His
1 5 10 15

Arg

<210> SEQ ID NO 2333
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2333

Ser Glu Trp Ser Asp Cys Ser Val Thr Cys Gly Lys Gly Met Arg Thr
1 5 10 15

Arg Gln Arg

<210> SEQ ID NO 2334
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2334

Gln Pro Trp Gly Thr Cys Ser Glu Ser Cys Gly Lys Gly Thr Gln Thr
1 5 10 15

Arg Ala Arg

<210> SEQ ID NO 2335
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2335

Ser Ala Trp Arg Ala Cys Ser Val Thr Cys Gly Lys Gly Ile Gln Lys
1 5 10 15

Arg Ser Arg

<210> SEQ ID NO 2336
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2336

Ala Ser Trp Ser Ala Cys Ser Val Ser Cys Gly Gly Gly Ala Arg Gln
1 5 10 15

Arg Thr Arg

<210> SEQ ID NO 2337
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2337

Thr Glu Trp Thr Ala Cys Ser Lys Ser Cys Gly Met Gly Phe Ser Thr
1 5 10 15

Arg Val

<210> SEQ ID NO 2338
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2338

Ser Gln Trp Ser Pro Cys Ser Arg Thr Cys Gly Gly Gly Val Ser Phe
1 5 10 15

Arg Glu Arg

<210> SEQ ID NO 2339
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2339

Gly Pro Trp Ala Pro Cys Ser Ala Ser Cys Gly Gly Gly Ser Gln Ser
1 5 10 15

Arg Ser

<210> SEQ ID NO 2340
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2340

Gly Pro Trp Glu Pro Cys Ser Val Thr Cys Ser Lys Gly Thr Arg Thr
1 5 10 15

Arg Arg Arg

<210> SEQ ID NO 2341
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2341

Gly Pro Trp Glu Asp Cys Ser Val Ser Cys Gly Gly Gly Glu Gln Leu
1 5 10 15

Arg Ser Arg

<210> SEQ ID NO 2342
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2342

Ser Pro Trp Thr Lys Cys Ser Ala Thr Cys Gly Gly Gly His Tyr Met
1 5 10 15

Arg Thr Arg

<210> SEQ ID NO 2343
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2343

Thr Ser Trp Ser Pro Cys Ser Ala Ser Cys Gly Gly Gly His Tyr Gln
1 5 10 15

Arg Thr Arg

<210> SEQ ID NO 2344
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2344

Gln Pro Trp Ser Gln Cys Ser Ala Thr Cys Gly Asp Gly Val Arg Glu
1 5 10 15

Arg Arg Arg

<210> SEQ ID NO 2345
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2345

Ser Pro Trp Ser Pro Cys Ser Gly Asn Cys Ser Thr Gly Lys Gln Gln
1 5 10 15

Arg Thr Arg

<210> SEQ ID NO 2346
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2346

Trp Thr Arg Cys Ser Ser Ser Cys Gly Arg Gly Val Ser Val Arg Ser
1 5 10 15

Arg

<210> SEQ ID NO 2347
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2347

Ser Pro Trp Ser Gln Cys Ser Val Arg Cys Gly Arg Gly Gln Arg Ser
1 5 10 15

Arg Gln Val Arg
20

<210> SEQ ID NO 2348
<211> LENGTH: 19
<212> TYPE: PRT
<213> ORGANISM: Artificial Sequence
<220> FEATURE:

<223> OTHER INFORMATION: Description of Artificial Sequence: Synthetic peptide

<400> SEQUENCE: 2348

Thr Glu Trp Ser Val Cys Asn Ser Arg Cys Gly Arg Gly Tyr Gln Lys
1 5 10 15

Arg Thr Arg

<210> SEQ ID NO 2349
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2349

Thr Glu Trp Ser Ala Cys Asn Val Arg Cys Gly Arg Gly Trp Gln Lys
1 5 10 15

Arg Ser Arg

<210> SEQ ID NO 2350
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2350

Ser Pro Trp Ser Pro Cys Ser Thr Ser Cys Gly Leu Gly Val Ser Thr
1 5 10 15

Arg Ile

<210> SEQ ID NO 2351
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2351

Thr Ala Trp Gly Pro Cys Ser Thr Thr Cys Gly Leu Gly Met Ala Thr
1 5 10 15

Arg Val

<210> SEQ ID NO 2352
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2352

Thr Lys Trp Thr Pro Cys Ser Arg Thr Cys Gly Met Gly Ile Ser Asn
1 5 10 15

Arg Val

<210> SEQ ID NO 2353
<211> LENGTH: 19
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (7)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(19)
<223> OTHER INFORMATION: Any amino acid

<400> SEQUENCE: 2353

```
Xaa Xaa Trp Xaa Xaa Cys Xaa Xaa Xaa Cys Xaa Xaa Gly Xaa Xaa Xaa
1               5                   10                  15

Xaa Xaa Xaa
```

<210> SEQ ID NO 2354
<211> LENGTH: 20
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (7)..(7)
<223> OTHER INFORMATION: Thr, Ser or Asn
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(20)
<223> OTHER INFORMATION: Any amino acid

<400> SEQUENCE: 2354

```
Xaa Xaa Trp Xaa Xaa Cys Xaa Xaa Xaa Cys Xaa Xaa Gly Xaa Xaa Xaa
1               5                   10                  15

Xaa Xaa Xaa Xaa
            20
```

<210> SEQ ID NO 2355
<211> LENGTH: 20
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(16)
<223> OTHER INFORMATION: Any amino acid
<220> FEATURE:
<221> NAME/KEY: MOD_RES
<222> LOCATION: (18)..(20)
<223> OTHER INFORMATION: Any amino acid

<400> SEQUENCE: 2355

Xaa Xaa Trp Xaa Xaa Cys Ser Xaa Xaa Cys Gly Xaa Gly Xaa Xaa Xaa
1 5 10 15

Arg Xaa Xaa Xaa
20

<210> SEQ ID NO 2356
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2356

Gly Pro Trp Gly Asp Cys Ser Arg Thr Cys Gly Gly Gly Val Gln Tyr
1 5 10 15

Thr Met Arg

<210> SEQ ID NO 2357
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2357

Gly Pro Trp Ser Gln Cys Ser Val Thr Cys Gly Asn Gly Thr Gln Glu
1 5 10 15

Arg

<210> SEQ ID NO 2358
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2358

Gly Pro Trp Ser Glu Cys Ser Val Thr Cys Gly Glu Gly Thr Glu Val
1 5 10 15

Arg

<210> SEQ ID NO 2359
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2359

Gly Pro Trp Gly Asp Cys Ser Arg Thr Cys Gly Gly Gly Val
1 5 10

<210> SEQ ID NO 2360
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2360

Gly Pro Trp Leu Ala Cys Ser Arg Thr Cys Asp Thr Gly Trp His Thr
1 5 10 15

Arg

<210> SEQ ID NO 2361
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2361

Gln Pro Trp Ser Glu Cys Ser Ala Thr Cys Ala Gly Gly Val
1 5 10

<210> SEQ ID NO 2362
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2362

Gln Pro Trp Ser Glu Cys Ser Ala Thr Cys Ala Gly Gly Val Gln Arg
1 5 10 15

Gln

<210> SEQ ID NO 2363
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2363

Gly Pro Trp Gly Gln Cys Ser Gly Pro Cys Gly Gly Gly Val Gln Arg
1 5 10 15

Arg

<210> SEQ ID NO 2364
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2364

Gly Pro Trp Thr Lys Cys Thr Val Thr Cys Gly Arg Gly Val
1 5 10

<210> SEQ ID NO 2365
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2365

Gly Pro Trp Gly Glu Cys Ser Arg Thr Cys Gly Gly Gly Val
1 5 10

<210> SEQ ID NO 2366
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2366

Trp Ser Ser Cys Ser Val Thr Cys Gly Gln Gly Arg Ala Thr Arg
1 5 10 15

<210> SEQ ID NO 2367
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2367

Gly Pro Trp Gly Ala Cys Ser Ser Thr Cys Ala Gly Gly Ser Gln Arg
1 5 10 15

Arg

<210> SEQ ID NO 2368
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2368

Thr Pro Trp Gly Asp Cys Ser Arg Thr Cys Gly Gly Gly Val Ser Ser
1 5 10 15

Ser Ser Arg

<210> SEQ ID NO 2369
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2369

Trp Asp Leu Cys Ser Thr Ser Cys Gly Gly Gly Phe Gln Lys Arg
1 5 10 15

<210> SEQ ID NO 2370
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2370

Ser Pro Trp Ser His Cys Ser Arg Thr Cys Gly Ala Gly Val
1 5 10

<210> SEQ ID NO 2371
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2371

Trp Met Glu Cys Ser Val Ser Cys Gly Asp Gly Ile Gln Arg Arg
1 5 10 15

<210> SEQ ID NO 2372
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2372

Trp Ser Gln Cys Ser Ala Thr Cys Gly Glu Gly Ile Gln Gln Arg
1 5 10 15

<210> SEQ ID NO 2373
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2373

Ser Ala Trp Ser Pro Cys Ser Lys Ser Cys Gly Arg Gly Phe Gln Arg
1 5 10 15

Arg

<210> SEQ ID NO 2374
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2374

Ser Pro Trp Ser Gln Cys Thr Ala Ser Cys Gly Gly Gly Val Gln Thr 1 5 10 15

Arg Ser

<210> SEQ ID NO 2375
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2375

Pro Trp Gln Gln Cys Thr Val Thr Cys Gly Gly Gly Val Gln Thr Arg
1 5 10 15

<210> SEQ ID NO 2376
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2376

Pro Trp Gln Gln Cys Thr Val Thr Cys Gly Gly Gly Val Gln Thr Arg
1 5 10 15

Ser

<210> SEQ ID NO 2377
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2377

Gly Pro Trp Ser Gln Cys Ser Lys Thr Cys Gly Arg Gly Val Arg Lys
1 5 10 15

Arg

<210> SEQ ID NO 2378
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2378

Trp Ser Lys Cys Ser Ile Thr Cys Gly Lys Gly Met Gln Ser Arg Val
1 5 10 15

<210> SEQ ID NO 2379
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2379

Asn Ser Trp Asn Glu Cys Ser Val Thr Cys Gly Ser Gly Val Gln Gln
1 5 10 15

Arg

<210> SEQ ID NO 2380
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2380

Gly Pro Trp Gly Gln Cys Ser Ser Ser Cys Ser Gly Gly Leu Gln His
1 5 10 15

Arg Ala

<210> SEQ ID NO 2381
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2381

Trp Ser Lys Cys Ser Val Thr Cys Gly Ile Gly Ile Met Lys Arg
1 5 10 15

<210> SEQ ID NO 2382
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2382

Ser Pro Trp Ser Val Cys Ser Ser Thr Cys Gly Glu Gly Trp Gln Thr
1 5 10 15

Arg Thr Arg

<210> SEQ ID NO 2383
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2383

Ser Pro Trp Ser Val Cys Ser Leu Thr Cys Gly Gln Gly Leu Gln Val
1 5 10 15

Arg Thr Arg

<210> SEQ ID NO 2384
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2384

Ser Pro Trp Ser Leu Cys Ser Phe Thr Cys Gly Arg Gly Gln Arg Thr
1 5 10 15

Arg Thr Arg

<210> SEQ ID NO 2385
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2385

Ser Pro Trp Ser Ser Cys Ser Val Thr Cys Gly Val Gly Asn Ile Thr
1 5 10 15

Arg Ile Arg

<210> SEQ ID NO 2386
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2386

Ser Pro Trp Ser Ala Cys Thr Val Thr Cys Ala Gly Gly Ile Arg Glu
1 5 10 15

Arg Thr Arg

<210> SEQ ID NO 2387
<211> LENGTH: 20
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(16)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (19)..(19)
<223> OTHER INFORMATION: Arg or Val
<220> FEATURE:
<221> NAME/KEY: MOD_RES
<222> LOCATION: (20)..(20)
<223> OTHER INFORMATION: Any amino acid

<400> SEQUENCE: 2387

Xaa Xaa Trp Xaa Xaa Cys Ser Xaa Xaa Cys Gly Xaa Gly Xaa Xaa Xaa
1 5 10 15

Arg Xaa Xaa Xaa

20

<210> SEQ ID NO 2388
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2388

Asn Gly Lys Gln Val Cys Leu Asp Pro Glu Ala Pro Phe Leu Lys Lys
1 5 10 15

Val Ile Gln Lys Ile Leu Asp Ser
20

<210> SEQ ID NO 2389
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2389

Asp Gly Arg Lys Ile Cys Leu Asp Pro Asp Ala Pro Arg Ile Lys Lys
1 5 10 15

Ile Val Gln Lys Lys Leu
20

<210> SEQ ID NO 2390
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2390

Asp Gly Arg Glu Leu Cys Leu Asp Pro Lys Glu Asn Trp Val Gln Arg
1 5 10 15

Val Val Glu Lys Phe Leu Lys
20

<210> SEQ ID NO 2391
<211> LENGTH: 20
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Ser, Arg or Thr
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(16)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (19)..(19)
<223> OTHER INFORMATION: Arg or Val
<220> FEATURE:
<221> NAME/KEY: MOD_RES
<222> LOCATION: (20)..(20)
<223> OTHER INFORMATION: Any amino acid

<400> SEQUENCE: 2391

```
Xaa Xaa Trp Xaa Xaa Cys Ser Xaa Xaa Cys Gly Xaa Gly Xaa Xaa Xaa
1               5                   10                  15

Arg Xaa Xaa Xaa
            20
```

<210> SEQ ID NO 2392
<211> LENGTH: 60
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 2392

```
Gln Cys Ile Lys Thr Tyr Ser Lys Pro Phe His Pro Lys Phe Ile Lys
1               5                   10                  15

Glu Leu Arg Val Ile Glu Ser Gly Pro His Cys Ala Asn Thr Glu Ile
            20                  25                  30

Ile Val Lys Leu Ser Asp Gly Arg Glu Leu Cys Leu Asp Pro Lys Glu
        35                  40                  45

Asn Trp Val Gln Arg Val Val Glu Lys Phe Leu Lys
    50                  55                  60
```

<210> SEQ ID NO 2393
<211> LENGTH: 60
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 2393

```
Leu Arg Cys Thr Cys Leu Arg Val Thr Leu Arg Val Asn Pro Lys Thr
1               5                   10                  15

Ile Gly Lys Leu Gln Val Phe Pro Ala Gly Pro Gln Cys Ser Lys Val
            20                  25                  30

Glu Val Val Ala Ser Leu Lys Asn Gly Lys Gln Val Cys Leu Asp Pro
        35                  40                  45

Glu Ala Pro Phe Leu Lys Lys Val Ile Gln Lys Ile
    50                  55                  60
```

<210> SEQ ID NO 2394
<211> LENGTH: 56
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 2394

Arg Cys Thr Cys Leu Arg Val Thr Leu Arg Val Asn Pro Lys Thr Ile
1 5 10 15

Gly Lys Leu Gln Val Phe Pro Ala Gly Pro Gln Cys Ser Lys Val Glu
20 25 30

Val Val Ala Ser Leu Lys Asn Gly Lys Gln Val Cys Leu Asp Pro Glu
35 40 45

Ala Pro Phe Leu Lys Lys Val Ile
50 55

<210> SEQ ID NO 2395
<211> LENGTH: 57
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 2395

Cys Leu Arg Val Thr Leu Arg Val Asn Pro Lys Thr Ile Gly Lys Leu
1 5 10 15

Gln Val Phe Pro Ala Gly Pro Gln Cys Ser Lys Val Glu Val Val Ala
20 25 30

Ser Leu Lys Asn Gly Lys Gln Val Cys Leu Asp Pro Glu Ala Pro Phe
35 40 45

Leu Lys Lys Val Ile Gln Lys Ile Leu
50 55

<210> SEQ ID NO 2396
<211> LENGTH: 56
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 2396

Arg Cys Val Cys Leu Gln Thr Thr Gln Gly Val His Pro Lys Met Ile
1 5 10 15

Ser Asn Leu Gln Val Phe Ala Ile Gly Pro Gln Cys Ser Lys Val Glu
20 25 30

Val Val Ala Ser Leu Lys Asn Gly Lys Glu Ile Cys Leu Asp Pro Glu
35 40 45

Ala Pro Phe Leu Lys Lys Val Ile
50 55

<210> SEQ ID NO 2397
<211> LENGTH: 57
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 2397

Cys Leu Gln Thr Thr Gln Gly Val His Pro Lys Met Ile Ser Asn Leu
1 5 10 15

Gln Val Phe Ala Ile Gly Pro Gln Cys Ser Lys Val Glu Val Val Ala
20 25 30

Ser Leu Lys Asn Gly Lys Glu Ile Cys Leu Asp Pro Glu Ala Pro Phe
35 40 45

Leu Lys Lys Val Ile Gln Lys Ile Leu
50 55

<210> SEQ ID NO 2398
<211> LENGTH: 58
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2398

Met Cys Ile Lys Thr Thr Ser Gly Ile His Pro Lys Asn Ile Gln Ser
1 5 10 15

Leu Glu Val Ile Gly Lys Gly Thr His Cys Asn Gln Val Glu Val Ile
20 25 30

Ala Thr Leu Lys Asp Gly Arg Lys Ile Cys Leu Asp Pro Asp Ala Pro
35 40 45

Arg Ile Lys Lys Ile Val Gln Lys Lys Leu
50 55

<210> SEQ ID NO 2399
<211> LENGTH: 56
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2399

Arg Cys Met Cys Ile Lys Thr Thr Ser Gly Ile His Pro Lys Asn Ile
1 5 10 15

Gln Ser Leu Glu Val Ile Gly Lys Gly Thr His Cys Asn Gln Val Glu
20 25 30

Val Ile Ala Thr Leu Lys Asp Gly Arg Lys Ile Cys Leu Asp Pro Asp
35 40 45

Ala Pro Arg Ile Lys Lys Ile Val
50 55

<210> SEQ ID NO 2400
<211> LENGTH: 58
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2400

Cys Val Lys Thr Thr Ser Gln Val Arg Pro Arg His Ile Thr Ser Leu
1 5 10 15

Glu Val Ile Lys Ala Gly Pro His Cys Pro Thr Ala Gln Leu Ile Ala
20 25 30

Thr Leu Lys Asn Gly Arg Lys Ile Cys Leu Asp Leu Gln Ala Pro Leu
35 40 45

Tyr Lys Lys Ile Ile Lys Lys Leu Leu Glu
50 55

<210> SEQ ID NO 2401
<211> LENGTH: 56

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 2401

```
Arg Cys Gln Cys Leu Gln Thr Leu Gln Gly Ile His Leu Lys Asn Ile
1               5                   10                  15

Gln Ser Val Lys Val Lys Ser Pro Gly Pro His Cys Ala Gln Thr Glu
            20                  25                  30

Val Ile Ala Thr Leu Lys Asn Gly Gln Lys Ala Cys Leu Asn Pro Ala
        35                  40                  45

Ser Pro Met Val Lys Lys Ile Ile
    50                  55
```

<210> SEQ ID NO 2402
<211> LENGTH: 56
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 2402

```
Arg Cys Gln Cys Leu Gln Thr Leu Gln Gly Ile His Leu Lys Asn Ile
1               5                   10                  15

Gln Ser Val Asn Val Arg Ser Pro Gly Pro His Cys Ala Gln Thr Glu
            20                  25                  30

Val Ile Ala Thr Leu Lys Asn Gly Lys Lys Ala Cys Leu Asn Pro Ala
        35                  40                  45

Ser Pro Met Val Gln Lys Ile Ile
    50                  55
```

<210> SEQ ID NO 2403
<211> LENGTH: 56
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 2403

```
Arg Cys Gln Cys Leu Gln Thr Leu Gln Gly Ile His Pro Lys Asn Ile
1               5                   10                  15

Gln Ser Val Asn Val Lys Ser Pro Gly Pro His Cys Ala Gln Thr Glu
            20                  25                  30

Val Ile Ala Thr Leu Lys Asn Gly Arg Lys Ala Cys Leu Asn Pro Ala
        35                  40                  45

Ser Pro Ile Val Lys Lys Ile Ile
    50                  55
```

<210> SEQ ID NO 2404
<211> LENGTH: 58
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 2404

```
Gln Cys Leu Gln Thr Leu Gln Gly Ile His Pro Lys Asn Ile Gln Ser
1               5                   10                  15
```

Val Asn Val Lys Ser Pro Gly Pro His Cys Ala Gln Thr Glu Val Ile
20 25 30

Ala Thr Leu Lys Asn Gly Arg Lys Ala Cys Leu Asn Pro Ala Ser Pro
35 40 45

Ile Val Lys Lys Ile Ile Glu Lys Met Leu
50 55

<210> SEQ ID NO 2405
<211> LENGTH: 58
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2405

Gln Cys Leu Gln Thr Leu Gln Gly Ile His Leu Lys Asn Ile Gln Ser
1 5 10 15

Val Asn Val Arg Ser Pro Gly Pro His Cys Ala Gln Thr Glu Val Ile
20 25 30

Ala Thr Leu Lys Asn Gly Lys Lys Ala Cys Leu Asn Pro Ala Ser Pro
35 40 45

Met Val Gln Lys Ile Ile Glu Lys Ile Leu
50 55

<210> SEQ ID NO 2406
<211> LENGTH: 57
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2406

Arg Cys Thr Cys Ile Ser Ile Ser Asn Gln Pro Val Asn Pro Arg Ser
1 5 10 15

Leu Glu Lys Leu Glu Ile Ile Pro Ala Ser Gln Phe Cys Pro Arg Val
20 25 30

Glu Ile Ile Ala Thr Met Lys Lys Gly Glu Lys Arg Cys Leu Asn Pro
35 40 45

Glu Ser Lys Ala Ile Lys Asn Leu Leu
50 55

<210> SEQ ID NO 2407
<211> LENGTH: 20
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (7)..(9)
<223> OTHER INFORMATION: Any amino acid
<220> FEATURE:
<221> NAME/KEY: MOD_RES
<222> LOCATION: (11)..(12)

<223> OTHER INFORMATION: Any amino acid
<220> FEATURE:
<221> NAME/KEY: MOD_RES
<222> LOCATION: (14)..(20)
<223> OTHER INFORMATION: Any amino acid

<400> SEQUENCE: 2407

Xaa Pro Trp Xaa Xaa Cys Xaa Xaa Xaa Cys Xaa Xaa Gly Xaa Xaa Xaa
1 5 10 15

Xaa Xaa Xaa Xaa
20

<210> SEQ ID NO 2408
<211> LENGTH: 78
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 2408

Asn Glu Arg Ala His Gly Gln Asp Leu Gly Thr Ala Gly Ser Cys Leu
1 5 10 15

Arg Lys Phe Ser Thr Met Pro Phe Leu Phe Cys Asn Ile Asn Asn Val
20 25 30

Cys Asn Phe Ala Ser Arg Asn Asp Tyr Ser Tyr Trp Leu Ser Thr Pro
35 40 45

Glu Pro Met Pro Met Ser Met Ala Pro Ile Thr Gly Glu Asn Ile Arg
50 55 60

Pro Phe Ile Ser Arg Cys Ala Val Cys Glu Ala Pro Ala Met
65 70 75

<210> SEQ ID NO 2409
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2409

Leu Arg Lys Phe Ser Thr Met Pro Phe Leu Phe Cys Asn Ile Asn Asn
1 5 10 15

Val Cys Asn Phe
20

<210> SEQ ID NO 2410
<211> LENGTH: 78
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 2410

Asn Lys Arg Ala His Gly Gln Asp Leu Gly Thr Ala Gly Ser Cys Leu
1 5 10 15

Arg Arg Phe Ser Thr Met Pro Phe Met Phe Cys Asn Ile Asn Asn Val
20 25 30

Cys Asn Phe Ala Ser Arg Asn Asp Tyr Ser Tyr Trp Leu Ser Thr Pro
35 40 45

Glu Pro Met Pro Met Ser Met Gln Pro Leu Lys Gly Gln Ser Ile Gln
50 55 60

Pro Phe Ile Ser Arg Cys Ala Val Cys Glu Ala Pro Ala Val
65 70 75

<210> SEQ ID NO 2411
<211> LENGTH: 77
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2411

Gln Glu Lys Ala His Asn Gln Asp Leu Gly Glu Ala Gly Ser Cys Leu
1 5 10 15

Arg Arg Phe Ser Thr Met Pro Phe Ile Tyr Cys Asn Ile Asn Glu Val
20 25 30

Cys His Tyr Ala Arg Arg Asn Asp Lys Ser Tyr Trp Leu Ser Thr Thr
35 40 45

Ala Pro Ile Pro Met Met Pro Val Ser Gln Thr Gln Ile Pro Gln Tyr
50 55 60

Ile Ser Arg Cys Ser Val Cys Glu Ala Pro Ser Gln Ala
65 70 75

<210> SEQ ID NO 2412
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2412

Tyr Cys Asn Ile Asn Glu Val Cys His Tyr Ala Arg Arg Asn Asp Lys
1 5 10 15

Ser Tyr Trp Leu
20

<210> SEQ ID NO 2413
<211> LENGTH: 77
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2413

Gln Glu Lys Ala His Asn Gln Asp Leu Gly Leu Ala Gly Ser Cys Leu
1 5 10 15

Ala Arg Phe Ser Thr Met Pro Phe Leu Tyr Cys Asn Pro Gly Asp Val
20 25 30

Cys Tyr Tyr Ala Ser Arg Asn Asp Lys Ser Tyr Trp Leu Ser Thr Thr
35 40 45

Ala Pro Leu Pro Met Met Pro Val Ala Glu Asp Glu Ile Lys Arg Tyr
50 55 60

Ile Ser Arg Cys Ser Val Cys Glu Ala Pro Ala Ile Ala
65 70 75

<210> SEQ ID NO 2414
<211> LENGTH: 20
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 2414

Tyr Cys Asn Pro Gly Asp Val Cys Tyr Tyr Ala Ser Arg Asn Asp Lys
1               5                   10                  15

Ser Tyr Trp Leu
            20

<210> SEQ ID NO 2415
<211> LENGTH: 77
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2415

Gln Glu Lys Ala His Asn Gln Asp Leu Gly Leu Ala Gly Ser Cys Leu
1               5                   10                  15

Pro Val Phe Ser Thr Leu Pro Phe Ala Tyr Cys Asn Ile His Gln Val
            20                  25                  30

Cys His Tyr Ala Gln Arg Asn Asp Arg Ser Tyr Trp Leu Ala Ser Ala
        35                  40                  45

Ala Pro Leu Pro Met Met Pro Leu Ser Glu Glu Ala Ile Arg Pro Tyr
    50                  55                  60

Val Ser Arg Cys Ala Val Cys Glu Ala Pro Ala Gln Ala
65                  70                  75

<210> SEQ ID NO 2416
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2416

Leu Pro Val Phe Ser Thr Leu Pro Phe Ala Tyr Cys Asn Ile His Gln
1               5                   10                  15

Val Cys His Tyr
            20

<210> SEQ ID NO 2417
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Gly or Gln
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (8)..(9)
<223> OTHER INFORMATION: Any amino acid
<220> FEATURE:

```
<221> NAME/KEY: MOD_RES
<222> LOCATION: (11)..(11)
<223> OTHER INFORMATION: Gly or Ser
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(16)
<223> OTHER INFORMATION: Any amino acid
<220> FEATURE:
<221> NAME/KEY: MOD_RES
<222> LOCATION: (17)..(17)
<223> OTHER INFORMATION: Arg or Ser
<220> FEATURE:
<221> NAME/KEY: MOD_RES
<222> LOCATION: (18)..(20)
<223> OTHER INFORMATION: Any amino acid

<400> SEQUENCE: 2417

Xaa Pro Trp Xaa Xaa Cys Xaa Xaa Xaa Cys Xaa Xaa Gly Xaa Xaa Xaa
1               5                   10                  15

Xaa Xaa Xaa Xaa
            20


<210> SEQ ID NO 2418
<211> LENGTH: 77
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2418

Gln Glu Lys Ala His Asn Gln Asp Leu Gly Phe Ala Gly Ser Cys Leu
1               5                   10                  15

Pro Arg Phe Ser Thr Met Pro Phe Ile Tyr Cys Asn Ile Asn Glu Val
            20                  25                  30

Cys His Tyr Ala Arg Arg Asn Asp Lys Ser Tyr Trp Leu Ser Thr Thr
        35                  40                  45

Ala Pro Ile Pro Met Met Pro Val Ser Gln Thr Gln Ile Pro Gln Tyr
    50                  55                  60

Ile Ser Arg Cys Ser Val Cys Glu Ala Pro Ser Gln Ala
65                  70                  75


<210> SEQ ID NO 2419
<211> LENGTH: 77
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2419

Gln Glu Lys Ala His Asn Gln Asp Leu Gly Leu Ala Gly Ser Cys Leu
1               5                   10                  15

Ala Arg Phe Ser Thr Met Pro Phe Leu Tyr Cys Asn Pro Gly Asp Val
            20                  25                  30

Cys Tyr Tyr Ala Ser Arg Asn Asp Lys Ser Tyr Trp Leu Ser Thr Thr
        35                  40                  45

Ala Pro Leu Pro Met Met Pro Val Ala Glu Asp Glu Ile Lys Pro Tyr
    50                  55                  60

Ile Ser Arg Cys Ser Val Cys Glu Ala Pro Ala Ile Ala
65                  70                  75
```

<210> SEQ ID NO 2420
<211> LENGTH: 20
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Ser, Thr, Gly, Gln or Ala
<220> FEATURE:
<221> NAME/KEY: MOD_RES
<222> LOCATION: (2)..(2)
<223> OTHER INFORMATION: Pro, Glu, Ser, Ala, Gln or Lys
<220> FEATURE:
<221> NAME/KEY: MOD_RES
<222> LOCATION: (4)..(4)
<223> OTHER INFORMATION: Ser, Thr, Gly, Glu, Asp, Arg or Ala
<220> FEATURE:
<221> NAME/KEY: MOD_RES
<222> LOCATION: (5)..(5)
<223> OTHER INFORMATION: Pro, Ala, Gln, Asp, Glu, Lys, Arg or Val
<220> FEATURE:
<221> NAME/KEY: MOD_RES
<222> LOCATION: (7)..(7)
<223> OTHER INFORMATION: Ser, Asn or Thr
<220> FEATURE:
<221> NAME/KEY: MOD_RES
<222> LOCATION: (8)..(8)
<223> OTHER INFORMATION: Val, Ala, Arg, Lys, Gly, Ser, Thr or Glu
<220> FEATURE:
<221> NAME/KEY: MOD_RES
<222> LOCATION: (9)..(9)
<223> OTHER INFORMATION: Thr, Ser, Arg or Asn
<220> FEATURE:
<221> NAME/KEY: MOD_RES
<222> LOCATION: (11)..(11)
<223> OTHER INFORMATION: Gly, Ser or Asn
<220> FEATURE:
<221> NAME/KEY: MOD_RES
<222> LOCATION: (12)..(12)
<223> OTHER INFORMATION: Gly, Lys, Arg, Met, Thr, Leu, Asp, Ser or Pro
<220> FEATURE:
<221> NAME/KEY: MOD_RES
<222> LOCATION: (14)..(14)
<223> OTHER INFORMATION: Val, Ile, Met, Thr, His, Ala, Glu, Phe, Lys, Arg, Ser, Gln, Trp or Tyr
<220> FEATURE:
<221> NAME/KEY: MOD_RES
<222> LOCATION: (15)..(15)
<223> OTHER INFORMATION: Gln, Ser, Arg, Lys, Tyr or Ala
<220> FEATURE:
<221> NAME/KEY: MOD_RES
<222> LOCATION: (16)..(16)
<223> OTHER INFORMATION: Thr, Phe, Lys, Gln, Ser, Leu, Glu, Met, Asn or Val
<220> FEATURE:
<221> NAME/KEY: MOD_RES
<222> LOCATION: (17)..(17)
<223> OTHER INFORMATION: Arg, Ser or Gln
<220> FEATURE:
<221> NAME/KEY: MOD_RES
<222> LOCATION: (18)..(18)
<223> OTHER INFORMATION: Ser, Thr, Val, Arg, His, Glu, Gln, Ala or Ile
<220> FEATURE:
<221> NAME/KEY: MOD_RES
<222> LOCATION: (19)..(19)
<223> OTHER INFORMATION: Arg or Val

<400> SEQUENCE: 2420

```
Xaa Xaa Trp Xaa Xaa Cys Xaa Xaa Xaa Cys Xaa Xaa Gly Xaa Xaa Xaa
1               5                   10                  15

Xaa Xaa Xaa Arg
            20
```

<210> SEQ ID NO 2421
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(5)
<223> OTHER INFORMATION: Thr, Ser or Asn
<220> FEATURE:
<221> NAME/KEY: MOD_RES
<222> LOCATION: (6)..(7)
<223> OTHER INFORMATION: Any amino acid
<220> FEATURE:
<221> NAME/KEY: MOD_RES
<222> LOCATION: (9)..(10)
<223> OTHER INFORMATION: Any amino acid

<400> SEQUENCE: 2421

Trp Xaa Xaa Cys Xaa Xaa Xaa Cys Xaa Xaa Gly
1               5                   10

<210> SEQ ID NO 2422
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2422

Ser Ala Pro Phe Ile Glu Cys His Gly Arg Gly Thr Cys Asn Tyr Tyr
1               5                   10                  15

Ala Asn Ala

<210> SEQ ID NO 2423
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2423

Ser Ala Pro Phe Ile Glu Cys His Gly Arg Gly Thr Cys Asn Tyr Tyr
1               5                   10                  15

Ala Asn Ser

<210> SEQ ID NO 2424
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2424

Ala Thr Pro Phe Ile Glu Cys Asn Gly Gly Arg Gly Thr Cys His Tyr
1               5                   10                  15

Tyr Ala Asn

<210> SEQ ID NO 2425
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2425

Ala Thr Pro Phe Ile Glu Cys Ser Gly Ala Arg Gly Thr Cys His Tyr
1 5 10 15

Phe Ala Asn

<210> SEQ ID NO 2426
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2426

Ala Ala Pro Phe Leu Glu Cys Gln Gly Arg Gln Gly Thr Cys His Phe
1 5 10 15

Phe Ala Asn

<210> SEQ ID NO 2427
<211> LENGTH: 20
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (7)..(7)
<223> OTHER INFORMATION: Thr, Ser or Asn
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(18)
<223> OTHER INFORMATION: Any amino acid
<220> FEATURE:
<221> NAME/KEY: MOD_RES
<222> LOCATION: (19)..(19)
<223> OTHER INFORMATION: Arg or Val
<220> FEATURE:
<221> NAME/KEY: MOD_RES
<222> LOCATION: (20)..(20)
<223> OTHER INFORMATION: Any amino acid

<400> SEQUENCE: 2427

Xaa Xaa Trp Xaa Xaa Cys Xaa Xaa Xaa Cys Xaa Xaa Gly Xaa Xaa Xaa
1 5 10 15

Xaa Xaa Xaa Xaa

20

<210> SEQ ID NO 2428
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2428

Leu Ala Arg Phe Ser Thr Met Pro Phe Leu Tyr Cys Asn Pro Gly Asp
1 5 10 15

Val Cys Tyr Tyr
20

<210> SEQ ID NO 2429
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2429

Glu Cys Leu Trp Thr Asp Met Leu Ser Asn Phe Gly Tyr Pro Gly Tyr
1 5 10 15

Gln Ser Lys His Tyr Ala Cys Ile
20

<210> SEQ ID NO 2430
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2430

Glu Cys Leu Trp Thr Asp Trp Leu Leu Glu Arg Lys Leu Tyr Gly Tyr
1 5 10 15

Gln Ala Gln His Tyr Val Cys Met
20

<210> SEQ ID NO 2431
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2431

Glu Cys Leu Trp Met Asp Trp Val Thr Glu Lys Asn Ile Asn Gly His
1 5 10 15

Gln Ala Lys Phe Phe Ala Cys Ile
20

<210> SEQ ID NO 2432
<211> LENGTH: 22
<212> TYPE: PRT
<213> ORGANISM: Artificial Sequence
<220> FEATURE:
<223> OTHER INFORMATION: Description of Artificial Sequence: Synthetic
peptide
<220> FEATURE:

<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(5)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (10)..(19)
<223> OTHER INFORMATION: Any amino acid
<220> FEATURE:
<221> NAME/KEY: MOD_RES
<222> LOCATION: (21)..(21)
<223> OTHER INFORMATION: Any amino acid

<400> SEQUENCE: 2432

```
Xaa Gly Xaa Xaa Xaa Cys Leu Xaa Pro Xaa Xaa Xaa Xaa Xaa Xaa Xaa
1               5                   10                  15

Xaa Xaa Xaa Lys Xaa Leu
            20
```

<210> SEQ ID NO 2433
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2433

```
Leu Leu Arg Ile Ser Leu Leu Leu Ile Gln Ser Trp Leu Glu
1               5                   10
```

<210> SEQ ID NO 2434
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2434

```
Leu Leu Arg Ser Ser Leu Ile Ile Leu Gln Gly Ser Trp Phe
1               5                   10
```

<210> SEQ ID NO 2435
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2435

```
Thr Gly Ala Leu Val Glu Glu Glu Asp Pro Phe
1               5                   10
```

<210> SEQ ID NO 2436
<211> LENGTH: 22
<212> TYPE: PRT
<213> ORGANISM: Artificial Sequence
<220> FEATURE:
<223> OTHER INFORMATION: Description of Artificial Sequence: Synthetic
peptide
<220> FEATURE:

<221> NAME/KEY: MOD_RES
<222> LOCATION: (1)..(1)
<223> OTHER INFORMATION: Asn or Asp
<220> FEATURE:
<221> NAME/KEY: MOD_RES
<222> LOCATION: (3)..(3)
<223> OTHER INFORMATION: Arg or Lys
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (8)..(8)
<223> OTHER INFORMATION: Asn or Asp
<220> FEATURE:
<221> NAME/KEY: MOD_RES
<222> LOCATION: (10)..(11)
<223> OTHER INFORMATION: Any amino acid
<220> FEATURE:
<221> NAME/KEY: MOD_RES
<222> LOCATION: (12)..(12)
<223> OTHER INFORMATION: Pro or Asn
<220> FEATURE:
<221> NAME/KEY: MOD_RES
<222> LOCATION: (13)..(14)
<223> OTHER INFORMATION: Any amino acid
<220> FEATURE:
<221> NAME/KEY: MOD_RES
<222> LOCATION: (15)..(16)
<223> OTHER INFORMATION: Lys or Gln
<220> FEATURE:
<221> NAME/KEY: MOD_RES
<222> LOCATION: (17)..(18)
<223> OTHER INFORMATION: Ile or Val
<220> FEATURE:
<221> NAME/KEY: MOD_RES
<222> LOCATION: (19)..(19)
<223> OTHER INFORMATION: Glu or Gln
<220> FEATURE:
<221> NAME/KEY: MOD_RES
<222> LOCATION: (21)..(21)
<223> OTHER INFORMATION: Any amino acid

<400> SEQUENCE: 2436

```
Xaa Gly Xaa Xaa Xaa Cys Leu Xaa Pro Xaa Xaa Xaa Xaa Xaa Xaa Xaa
1               5                   10                  15

Xaa Xaa Xaa Lys Xaa Leu
            20
```

<210> SEQ ID NO 2437
<211> LENGTH: 22
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Asn or Asp
<220> FEATURE:
<221> NAME/KEY: MOD_RES
<222> LOCATION: (3)..(3)
<223> OTHER INFORMATION: Arg or Lys
<220> FEATURE:
<221> NAME/KEY: MOD_RES
<222> LOCATION: (4)..(4)
<223> OTHER INFORMATION: Lys, Glu or Gln
<220> FEATURE:
<221> NAME/KEY: MOD_RES
<222> LOCATION: (5)..(5)
<223> OTHER INFORMATION: Ala, Ile, Leu or Val
<220> FEATURE:
<221> NAME/KEY: MOD_RES
<222> LOCATION: (8)..(8)

<223> OTHER INFORMATION: Asp or Asn
<220> FEATURE:
<221> NAME/KEY: MOD_RES
<222> LOCATION: (10)..(10)
<223> OTHER INFORMATION: Ala, Glu, Asp or Lys
<220> FEATURE:
<221> NAME/KEY: MOD_RES
<222> LOCATION: (11)..(11)
<223> OTHER INFORMATION: Ala, Ser or Glu
<220> FEATURE:
<221> NAME/KEY: MOD_RES
<222> LOCATION: (13)..(13)
<223> OTHER INFORMATION: Phe, Ile, Met, Arg or Trp
<220> FEATURE:
<221> NAME/KEY: MOD_RES
<222> LOCATION: (14)..(14)
<223> OTHER INFORMATION: Val, Leu or Ile
<220> FEATURE:
<221> NAME/KEY: MOD_RES
<222> LOCATION: (15)..(15)
<223> OTHER INFORMATION: Lys or Gln
<220> FEATURE:
<221> NAME/KEY: MOD_RES
<222> LOCATION: (16)..(16)
<223> OTHER INFORMATION: Lys or Arg
<220> FEATURE:
<221> NAME/KEY: MOD_RES
<222> LOCATION: (17)..(18)
<223> OTHER INFORMATION: Ile or Val
<220> FEATURE:
<221> NAME/KEY: MOD_RES
<222> LOCATION: (19)..(19)
<223> OTHER INFORMATION: Glu or Gln
<220> FEATURE:
<221> NAME/KEY: MOD_RES
<222> LOCATION: (21)..(21)
<223> OTHER INFORMATION: Ile, Phe, Lys or Met

<400> SEQUENCE: 2437

```
Xaa Gly Xaa Xaa Xaa Cys Leu Xaa Pro Xaa Xaa Pro Xaa Xaa Xaa Xaa
1               5                   10                  15

Xaa Xaa Xaa Lys Xaa Leu
            20
```

<210> SEQ ID NO 2438
<211> LENGTH: 20
<212> TYPE: PRT
<213> ORGANISM: Homo sapiens

<400> SEQUENCE: 2438

```
Leu Gln Arg Phe Thr Thr Met Pro Phe Leu Phe Cys Asn Val Asn Asp
1               5                   10                  15

Val Cys Asn Phe
            20
```

<210> SEQ ID NO 2439
<211> LENGTH: 20
<212> TYPE: PRT
<213> ORGANISM: Mus sp.

<400> SEQUENCE: 2439

```
Leu Arg Arg Phe Ser Thr Met Pro Phe Met Phe Cys Asn Ile Asn Asn
1               5                   10                  15

Val Cys Asn Phe
            20
```

<210> SEQ ID NO 2440
<211> LENGTH: 19
<212> TYPE: PRT
<213> ORGANISM: Mus sp.

<400> SEQUENCE: 2440

Gly Pro Trp Gly Pro Cys Ser Val Thr Cys Ser Lys Gly Thr Gln Ile
1 5 10 15

Arg Gln Arg

<210> SEQ ID NO 2441
<211> LENGTH: 24
<212> TYPE: PRT
<213> ORGANISM: Mus sp.

<400> SEQUENCE: 2441

Asn Gly Arg Glu Ala Cys Leu Asp Pro Glu Ala Pro Leu Val Gln Lys
1 5 10 15

Ile Val Gln Lys Met Leu Lys Gly
20

<210> SEQ ID NO 2442
<211> LENGTH: 20
<212> TYPE: PRT
<213> ORGANISM: Homo sapiens

<400> SEQUENCE: 2442

Leu Arg Arg Phe Ser Thr Met Pro Phe Met Phe Cys Asn Ile Asn Asn
1 5 10 15

Val Cys Asn Phe
20

<210> SEQ ID NO 2443
<211> LENGTH: 20
<212> TYPE: PRT
<213> ORGANISM: Mus sp.

<400> SEQUENCE: 2443

Leu Arg Arg Phe Ser Thr Met Pro Phe Met Phe Cys Asn Ile Asn Asn
1 5 10 15

Val Cys Asn Phe
20

<210> SEQ ID NO 2444
<211> LENGTH: 19
<212> TYPE: PRT
<213> ORGANISM: Homo sapiens

<400> SEQUENCE: 2444

Gly Pro Trp Glu Pro Cys Ser Val Thr Cys Ser Lys Gly Thr Arg Thr
1 5 10 15

Arg Arg Arg

<210> SEQ ID NO 2445
<211> LENGTH: 24
<212> TYPE: PRT
<213> ORGANISM: Homo sapiens

<400> SEQUENCE: 2445

Asn Gly Arg Lys Ala Cys Leu Asn Pro Ala Ser Pro Ile Val Lys Lys
1 5 10 15

Ile Ile Glu Lys Met Leu Asn Ser
20